United States Patent
Kuhne et al.

(10) Patent No.: US 11,242,393 B2
(45) Date of Patent: Feb. 8, 2022

(54) ANTIBODIES AGAINST MICA AND/OR MICB AND USES THEREOF

(71) Applicant: Bristol-Myers Squibb Company, Princeton, NJ (US)

(72) Inventors: Michelle Renee Kuhne, San Francisco, CA (US); Alan J. Korman, Piedmont, CA (US); Haichun Huang, Fremont, CA (US); Yiming Yin, Andover, MA (US); Robert F. Graziano, Frenchtown, NJ (US); Natalie A. Bezman, Foster City, CA (US); Pavel Strop, San Mateo, CA (US); Richard Y. Huang, Bridgewater, NJ (US); Guodong Chen, East Brunswick, NJ (US); Mohan Srinivasan, Cupertino, CA (US); Peter Sung Keun Lee, Millbrae, CA (US); Gamze Ozlem Camdere, Camarillo, CA (US)

(73) Assignee: Bristol-Myers Squibb Company, Princeton, NJ (US)

( * ) Notice: Subject to any disclaimer, the term of this patent is extended or adjusted under 35 U.S.C. 154(b) by 251 days.

(21) Appl. No.: 16/362,411

(22) Filed: Mar. 22, 2019

(65) Prior Publication Data
US 2019/0315870 A1 Oct. 17, 2019

Related U.S. Application Data

(60) Provisional application No. 62/647,556, filed on Mar. 23, 2018, provisional application No. 62/667,170, filed on May 4, 2018.

(51) Int. Cl.
*C07K 16/28* (2006.01)
*A61P 35/00* (2006.01)
*C12N 15/85* (2006.01)

(52) U.S. Cl.
CPC .......... *C07K 16/2833* (2013.01); *A61P 35/00* (2018.01); *C12N 15/85* (2013.01)

(58) Field of Classification Search
CPC ................................................. C07K 16/2833
USPC .......................................... 424/133.1, 178.1
See application file for complete search history.

(56) References Cited

U.S. PATENT DOCUMENTS

| | | | |
|---|---|---|---|
| 4,399,216 A | 8/1983 | Axel et al. | |
| 4,439,196 A | 3/1984 | Higuchi | |
| 4,447,224 A | 5/1984 | DeCant, Jr. et al. | |
| 4,447,233 A | 5/1984 | Mayfield | |
| 4,475,196 A | 10/1984 | La Zor | |
| 4,486,194 A | 12/1984 | Ferrara | |
| 4,487,603 A | 12/1984 | Harris | |
| 4,522,811 A | 6/1985 | Eppstein et al. | |
| 4,596,556 A | 6/1986 | Morrow et al. | |
| 4,634,665 A | 1/1987 | Axel et al. | |
| 4,683,195 A | 7/1987 | Mullis et al. | |
| 4,790,824 A | 12/1988 | Morrow et al. | |
| 4,816,567 A | 3/1989 | Cabilly et al. | |
| 4,881,175 A | 11/1989 | Ladner | |
| 4,941,880 A | 7/1990 | Burns | |
| 4,946,778 A | 8/1990 | Ladner et al. | |
| 5,013,653 A | 5/1991 | Huston et al. | |
| 5,064,413 A | 11/1991 | McKinnon et al. | |
| 5,091,513 A | 2/1992 | Huston et al. | |
| 5,132,405 A | 7/1992 | Huston et al. | |
| 5,179,017 A | 1/1993 | Axel et al. | |
| 5,223,409 A | 6/1993 | Ladner et al. | |
| 5,225,539 A | 7/1993 | Winter | |
| 5,258,498 A | 11/1993 | Huston et al. | |
| 5,260,203 A | 11/1993 | Ladner et al. | |
| 5,312,335 A | 5/1994 | McKinnon et al. | |
| 5,374,548 A | 12/1994 | Caras | |
| 5,383,851 A | 1/1995 | McKinnon, Jr. et al. | |
| 5,399,163 A | 3/1995 | Peterson et al. | |
| 5,399,331 A | 3/1995 | Loughrey et al. | |
| 5,403,484 A | 4/1995 | Ladner et al. | |
| 5,416,016 A | 5/1995 | Low et al. | |
| 5,427,908 A | 6/1995 | Dower et al. | |
| 5,455,030 A | 10/1995 | Ladner et al. | |
| 5,476,786 A | 12/1995 | Huston | |
| 5,476,996 A | 12/1995 | Wilson et al. | |
| 5,482,858 A | 1/1996 | Huston et al. | |
| 5,530,101 A | 6/1996 | Queen et al. | |
| 5,545,806 A | 8/1996 | Lonberg et al. | |
| 5,545,807 A | 8/1996 | Surani et al. | |
| 5,569,825 A | 10/1996 | Lonberg et al. | |
| 5,571,698 A | 11/1996 | Ladner et al. | |
| 5,580,717 A | 12/1996 | Dower et al. | |

(Continued)

FOREIGN PATENT DOCUMENTS

EP 0154316 A2 9/1985
EP 0401384 A1 12/1990
(Continued)

OTHER PUBLICATIONS

Biotechnology, Chemical, Pharmaceutical (BCP) Partnership Meeting (SPE Dan Kolker, Sep. 17, 2020; pp. 1-36).*
Huang et al. (Analytical and Bioanalytical Chemistry (2020) 412:1693-1700).*
Bonnafous, C., et al., "Targeting MICA with Therapeutic Antibodies for the Treatment of Cancer", Journal for Immunotherapy of Cancer, Biomed Central Ltd, United Kingdom, Nov. 7, 2013, vol. 1 (1), pp. P41, XP021167251.
Bordusa, F, "F C_N Protease Catalyzed Bond Formation Using," Highlights in Bioorganic Chemistry 389-403, (2004).
(Continued)

*Primary Examiner* — Lynn A Bristol
(74) *Attorney, Agent, or Firm* — Sterne, Kessler, Goldstein & Fox P.L.L.C.

(57) ABSTRACT

The disclosure provides antibodies that specifically bind human MICA/B and methods of use thereof. In some aspects, the disclosure is directed to methods of treating a cancer in a subject, comprising administering to the subject an anti-MICA/B antibody.

19 Claims, 85 Drawing Sheets

Specification includes a Sequence Listing.

(56) References Cited

U.S. PATENT DOCUMENTS

| | | |
|---|---|---|
| 5,585,089 A | 12/1996 | Queen et al. |
| 5,624,821 A | 4/1997 | Winter et al. |
| 5,625,126 A | 4/1997 | Lonberg et al. |
| 5,633,425 A | 5/1997 | Lonberg et al. |
| 5,648,260 A | 7/1997 | Winter et al. |
| 5,661,016 A | 8/1997 | Lonberg et al. |
| 5,677,425 A | 10/1997 | Bodmer et al. |
| 5,693,762 A | 12/1997 | Queen et al. |
| 5,698,767 A | 12/1997 | Wilson et al. |
| 5,714,350 A | 2/1998 | Co et al. |
| 5,770,429 A | 6/1998 | Lonberg et al. |
| 5,789,650 A | 8/1998 | Lonberg et al. |
| 5,811,097 A | 9/1998 | Allison et al. |
| 5,814,318 A | 9/1998 | Lonberg et al. |
| 5,821,337 A | 10/1998 | Carter et al. |
| 5,837,243 A | 11/1998 | Deo et al. |
| 5,869,046 A | 2/1999 | Presta et al. |
| 5,874,299 A | 2/1999 | Lonberg et al. |
| 5,877,397 A | 3/1999 | Lonberg et al. |
| 5,885,793 A | 3/1999 | Griffiths et al. |
| 5,922,845 A | 7/1999 | Deo et al. |
| 5,939,598 A | 8/1999 | Kucherlapati et al. |
| 5,969,108 A | 10/1999 | McCafferty et al. |
| 5,977,318 A | 11/1999 | Linsley et al. |
| 6,051,227 A | 4/2000 | Allison et al. |
| 6,075,181 A | 6/2000 | Kucherlapati et al. |
| 6,114,598 A | 9/2000 | Kucherlapati et al. |
| 6,121,022 A | 9/2000 | Presta et al. |
| 6,150,584 A | 11/2000 | Kucherlapati et al. |
| 6,162,963 A | 12/2000 | Kucherlapati et al. |
| 6,165,745 A | 12/2000 | Ward et al. |
| 6,172,197 B1 | 1/2001 | McCafferty et al. |
| 6,180,370 B1 | 1/2001 | Queen et al. |
| 6,194,551 B1 | 2/2001 | Idusogie et al. |
| 6,210,669 B1 | 4/2001 | Aruffo et al. |
| 6,277,375 B1 | 8/2001 | Ward |
| 6,303,121 B1 | 10/2001 | Kwon |
| 6,350,861 B1 | 2/2002 | Co et al. |
| 6,355,476 B1 | 3/2002 | Kwon et al. |
| 6,362,325 B1 | 3/2002 | Kwon |
| 6,437,095 B1 | 8/2002 | Lilie et al. |
| 6,521,404 B1 | 2/2003 | Griffiths et al. |
| 6,528,624 B1 | 3/2003 | Idusogie et al. |
| 6,544,731 B1 | 4/2003 | Griffiths et al. |
| 6,555,313 B1 | 4/2003 | Griffiths et al. |
| 6,569,997 B1 | 5/2003 | Kwon |
| 6,582,915 B1 | 6/2003 | Griffiths et al. |
| 6,593,081 B1 | 7/2003 | Griffiths et al. |
| 6,682,736 B1 | 1/2004 | Hanson et al. |
| 6,737,056 B1 | 5/2004 | Presta |
| 6,808,710 B1 | 10/2004 | Wood et al. |
| 6,887,673 B2 | 5/2005 | Kunkel et al. |
| 6,905,685 B2 | 6/2005 | Kwon |
| 6,974,863 B2 | 12/2005 | Kwon |
| 6,984,720 B1 | 1/2006 | Korman et al. |
| 6,989,452 B2 | 1/2006 | Ng et al. |
| 7,034,121 B2 | 4/2006 | Carreno et al. |
| 7,045,615 B2 | 5/2006 | Tamatani et al. |
| 7,087,600 B2 | 8/2006 | Ng et al. |
| 7,112,655 B1 | 9/2006 | Tamatani et al. |
| 7,129,261 B2 | 10/2006 | Ng et al. |
| 7,214,493 B2 | 5/2007 | Kunkel et al. |
| 7,214,775 B2 | 5/2007 | Hanai et al. |
| 7,259,247 B1 | 8/2007 | Kroczek |
| 7,288,638 B2 | 10/2007 | Jure-Kunkel et al. |
| 7,317,091 B2 | 1/2008 | Lazar et al. |
| 7,355,008 B2 | 4/2008 | Stavenhagen et al. |
| 7,488,802 B2 | 2/2009 | Collins et al. |
| 7,722,872 B2 | 5/2010 | Kroczek |
| 7,767,429 B2 | 8/2010 | Bookbinder et al. |
| 7,771,718 B2 | 8/2010 | Spies et al. |
| 7,812,135 B2 | 10/2010 | Smith et al. |
| 7,943,743 B2 | 5/2011 | Korman et al. |
| 7,959,916 B2 | 6/2011 | Spies et al. |
| 7,960,512 B2 | 6/2011 | Stavenhagen et al. |
| 8,008,449 B2 | 8/2011 | Korman et al. |
| 8,101,720 B2 | 1/2012 | Lazar et al. |
| 8,163,551 B2 | 4/2012 | Alley et al. |
| 8,168,757 B2 | 5/2012 | Finnefrock et al. |
| 8,182,809 B1 | 5/2012 | Wu |
| 8,206,709 B2 | 6/2012 | Spee et al. |
| 8,217,149 B2 | 7/2012 | Irving et al. |
| 8,252,275 B2 | 8/2012 | Bentley et al. |
| 8,354,509 B2 | 1/2013 | Carven et al. |
| 8,388,967 B2 | 3/2013 | Smith et al. |
| 8,389,690 B2 | 3/2013 | Tamatani et al. |
| 8,399,623 B2 | 3/2013 | Terrett et al. |
| 8,642,292 B2 | 2/2014 | Sandig et al. |
| 8,709,424 B2 | 4/2014 | Schebye et al. |
| 8,753,640 B2 | 6/2014 | Wu |
| 8,779,105 B2 | 7/2014 | Korman et al. |
| 8,796,427 B2 | 8/2014 | Spee et al. |
| 8,900,587 B2 | 12/2014 | Carven et al. |
| 8,901,283 B2 | 12/2014 | Spee et al. |
| 8,993,319 B2 | 3/2015 | Moretta et al. |
| 9,040,041 B2 | 5/2015 | Desjarlais et al. |
| 9,169,325 B2 | 10/2015 | Keler et al. |
| 9,402,905 B2 | 8/2016 | Wucherpfennig et al. |
| 9,422,368 B2 | 8/2016 | Spee et al. |
| 9,447,185 B2 | 9/2016 | Romagne et al. |
| 9,556,270 B2 | 1/2017 | Takayanagi |
| 9,580,507 B2 | 2/2017 | Korman et al. |
| 9,683,041 B2 | 6/2017 | Spee et al. |
| 9,738,718 B2 | 8/2017 | Liu et al. |
| 9,771,424 B2 | 9/2017 | Liu et al. |
| 9,803,017 B2 | 10/2017 | Wu |
| 10,106,611 B2 | 10/2018 | Wucherpfennig et al. |
| 2003/0153043 A1 | 8/2003 | Carr et al. |
| 2003/0165835 A1 | 9/2003 | Spies et al. |
| 2004/0002587 A1 | 1/2004 | Watkins et al. |
| 2004/0110704 A1 | 6/2004 | Yamane et al. |
| 2005/0095244 A1 | 5/2005 | Jure-Kunkel et al. |
| 2006/0004081 A1 | 1/2006 | Chen et al. |
| 2006/0024317 A1 | 2/2006 | Boyd et al. |
| 2006/0247295 A1 | 11/2006 | Gangwar et al. |
| 2007/0248607 A1 | 10/2007 | Spies et al. |
| 2008/0118513 A1 | 5/2008 | Kroczek |
| 2009/0136494 A1 | 5/2009 | Ponath et al. |
| 2010/0069614 A1 | 3/2010 | Houtzager et al. |
| 2011/0150892 A1 | 6/2011 | Thudium et al. |
| 2012/0070861 A1 | 3/2012 | Macdonald et al. |
| 2012/0073004 A1 | 3/2012 | Macdonald et al. |
| 2012/0276086 A1 | 11/2012 | Black et al. |
| 2012/0315287 A1 | 12/2012 | Wu |
| 2013/0183321 A1 | 7/2013 | Smith et al. |
| 2014/0037630 A1 | 2/2014 | Dranoff et al. |
| 2014/0065152 A1 | 3/2014 | Kwon |
| 2014/0072565 A1 | 3/2014 | Kwon |
| 2014/0072566 A1 | 3/2014 | Kwon |
| 2014/0093511 A1 | 4/2014 | Lonberg et al. |
| 2014/0220002 A1 | 8/2014 | Ponte et al. |
| 2014/0322208 A1 | 10/2014 | Kuhne et al. |
| 2014/0348841 A1 | 11/2014 | Schebye et al. |
| 2015/0079109 A1 | 3/2015 | Li et al. |
| 2015/0191542 A1 | 7/2015 | Blery et al. |
| 2016/0030659 A1 | 2/2016 | Cheney |
| 2016/0046689 A1 | 2/2016 | Cheney |
| 2016/0046716 A1 | 2/2016 | Wucherpfennig et al. |
| 2016/0272708 A1 | 9/2016 | Chen |
| 2016/0376367 A1 | 12/2016 | Yuan et al. |
| 2017/0022275 A1 | 1/2017 | Wucherpfennig et al. |
| 2017/0267764 A1 | 9/2017 | Blery et al. |
| 2018/0339059 A1 | 11/2018 | Xu et al. |
| 2019/0023782 A1 | 1/2019 | Chen et al. |
| 2020/0239577 A1* | 7/2020 | Bhagavatheeswaran ............ A61P 35/00 |
| 2021/0032344 A1* | 2/2021 | Bhagavatheeswaran ............ A61P 35/00 |

(56) References Cited

U.S. PATENT DOCUMENTS

2021/0101980 A1* 4/2021 Bhagavatheeswaran ............ A61P 35/00

FOREIGN PATENT DOCUMENTS

| | | |
|---|---|---|
| EP | 0338841 B1 | 3/1995 |
| EP | 1176195 A1 | 1/2002 |
| EP | 2482849 B1 | 6/2018 |
| EP | 3147297 B1 | 12/2018 |
| JP | 2008278814 A | 11/2008 |
| WO | WO-8704462 A1 | 7/1987 |
| WO | WO-8901036 A1 | 2/1989 |
| WO | WO-9203918 A1 | 3/1992 |
| WO | WO-9312227 A1 | 6/1993 |
| WO | WO-9425585 A1 | 11/1994 |
| WO | WO-9429351 A2 | 12/1994 |
| WO | WO-9512673 A1 | 5/1995 |
| WO | WO-9517886 A1 | 7/1995 |
| WO | WO-9632478 A1 | 10/1996 |
| WO | WO-9713852 A1 | 4/1997 |
| WO | WO-9734631 A1 | 9/1997 |
| WO | WO-9819167 A2 | 5/1998 |
| WO | WO-9824884 A1 | 6/1998 |
| WO | WO-9838216 A1 | 9/1998 |
| WO | WO-9915553 A2 | 4/1999 |
| WO | WO-9942585 A1 | 8/1999 |
| WO | WO-9945962 A1 | 9/1999 |
| WO | WO-9954342 A1 | 10/1999 |
| WO | WO-0037504 A2 | 6/2000 |
| WO | WO-0042072 A2 | 7/2000 |
| WO | WO-0100244 A2 | 1/2001 |
| WO | WO-0114424 A2 | 3/2001 |
| WO | WO-0158957 A2 | 8/2001 |
| WO | WO-0206919 A2 | 1/2002 |
| WO | WO-0243478 A2 | 6/2002 |
| WO | WO-02092780 A2 | 11/2002 |
| WO | WO-02096910 A1 | 12/2002 |
| WO | WO-03035835 A2 | 5/2003 |
| WO | WO-03074679 A2 | 9/2003 |
| WO | WO-03089616 A2 | 10/2003 |
| WO | WO-03106498 A2 | 12/2003 |
| WO | WO-2004016750 A2 | 2/2004 |
| WO | WO-2004029207 A2 | 4/2004 |
| WO | WO-2004035752 A2 | 4/2004 |
| WO | WO-2004063351 A2 | 7/2004 |
| WO | WO-2004074455 A2 | 9/2004 |
| WO | WO-2004099249 A2 | 11/2004 |
| WO | WO-2005003168 A2 | 1/2005 |
| WO | WO-2005009465 A1 | 2/2005 |
| WO | WO-2005040217 A2 | 5/2005 |
| WO | WO-2005070963 A1 | 8/2005 |
| WO | WO-2005092925 A2 | 10/2005 |
| WO | WO-2006003179 A2 | 1/2006 |
| WO | WO-2006020114 A2 | 2/2006 |
| WO | WO-2006070286 A2 | 7/2006 |
| WO | WO-2006072625 A2 | 7/2006 |
| WO | WO-2006072626 A1 | 7/2006 |
| WO | WO-2006089231 A2 | 8/2006 |
| WO | WO-2006105021 A2 | 10/2006 |
| WO | WO-2006122150 A1 | 11/2006 |
| WO | WO-2007038658 A2 | 4/2007 |
| WO | WO-2007041635 A2 | 4/2007 |
| WO | WO-2007042573 A2 | 4/2007 |
| WO | WO-2007051081 A1 | 5/2007 |
| WO | WO-2007055926 A1 | 5/2007 |
| WO | WO-2007059404 A2 | 5/2007 |
| WO | WO-2007075598 A2 | 7/2007 |
| WO | WO-2007113648 A2 | 10/2007 |
| WO | WO-2008009545 A1 | 1/2008 |
| WO | WO-2008036642 A2 | 3/2008 |
| WO | WO-2008036653 A2 | 3/2008 |
| WO | WO-2008036981 A1 | 3/2008 |
| WO | WO-2008083312 A2 | 7/2008 |
| WO | WO-2008084106 A1 | 7/2008 |
| WO | WO-2008103693 A2 | 8/2008 |
| WO | WO-2008131406 A2 | 10/2008 |
| WO | WO-2008137915 A2 | 11/2008 |
| WO | WO-2008156712 A1 | 12/2008 |
| WO | WO-2009009116 A2 | 1/2009 |
| WO | WO-2009015777 A1 | 2/2009 |
| WO | WO-2009059278 A1 | 5/2009 |
| WO | WO-2009073533 A2 | 6/2009 |
| WO | WO-2009073620 A2 | 6/2009 |
| WO | WO-2009092805 A1 | 7/2009 |
| WO | WO-2009135181 A2 | 11/2009 |
| WO | WO-2010065939 A1 | 6/2010 |
| WO | WO-2011028683 A1 | 3/2011 |
| WO | WO-2011041613 A2 | 4/2011 |
| WO | WO-2011056652 A1 | 5/2011 |
| WO | WO-2011066389 A1 | 6/2011 |
| WO | WO-2011070024 A1 | 6/2011 |
| WO | WO-2011072204 A1 | 6/2011 |
| WO | WO-2011097603 A1 | 8/2011 |
| WO | WO-2011107553 A1 | 9/2011 |
| WO | WO-2011131407 A1 | 10/2011 |
| WO | WO-2011140249 A2 | 11/2011 |
| WO | WO-2011155607 A1 | 12/2011 |
| WO | WO-2011159877 A2 | 12/2011 |
| WO | WO-2011163311 A2 | 12/2011 |
| WO | WO-2011163314 A1 | 12/2011 |
| WO | WO-2012027328 A2 | 3/2012 |
| WO | WO-2012065086 A1 | 5/2012 |
| WO | WO-2012071411 A2 | 5/2012 |
| WO | WO-2012122444 A2 | 9/2012 |
| WO | WO-2012131004 A2 | 10/2012 |
| WO | WO-2012142237 A1 | 10/2012 |
| WO | WO-2012145493 A1 | 10/2012 |
| WO | WO-2012148873 A2 | 11/2012 |
| WO | WO-2012160448 A2 | 11/2012 |
| WO | WO-2013006490 A2 | 1/2013 |
| WO | WO-2013028231 A1 | 2/2013 |
| WO | WO-2013038191 A2 | 3/2013 |
| WO | WO-2013039954 A1 | 3/2013 |
| WO | WO-2013049517 A2 | 4/2013 |
| WO | WO-2013079174 A1 | 6/2013 |
| WO | WO-2013087699 A1 | 6/2013 |
| WO | WO-2013117647 A1 | 8/2013 |
| WO | WO-2013119716 A1 | 8/2013 |
| WO | WO-2013132044 A1 | 9/2013 |
| WO | WO-2013169264 A1 | 11/2013 |
| WO | WO-2013173223 A1 | 11/2013 |
| WO | WO-2013181634 A2 | 12/2013 |
| WO | WO-2014036357 A1 | 3/2014 |
| WO | WO-2014055648 A1 | 4/2014 |
| WO | WO-2014144791 A2 | 9/2014 |
| WO | WO-2014148895 A1 | 9/2014 |
| WO | WO-2014179664 A2 | 11/2014 |
| WO | WO-2014194302 A2 | 12/2014 |
| WO | WO-2014206107 A1 | 12/2014 |
| WO | WO-2015003114 A1 | 1/2015 |
| WO | WO-2015026684 A1 | 2/2015 |
| WO | WO-2015031667 A2 | 3/2015 |
| WO | WO-2015035606 A1 | 3/2015 |
| WO | WO-2015042246 A1 | 3/2015 |
| WO | WO-2015085210 A1 | 6/2015 |
| WO | WO-2015085847 A1 | 6/2015 |
| WO | WO-2015112800 A1 | 7/2015 |
| WO | WO-2015112900 A1 | 7/2015 |
| WO | WO-2015117002 A1 | 8/2015 |
| WO | WO-2015125159 A1 | 8/2015 |
| WO | WO-2015153513 A1 | 10/2015 |
| WO | WO-2015153514 A1 | 10/2015 |
| WO | WO-2015184099 A1 | 12/2015 |
| WO | WO-2015187835 A2 | 12/2015 |
| WO | WO-2016032334 A1 | 3/2016 |
| WO | WO-2016041945 A1 | 3/2016 |
| WO | WO-2016041947 A1 | 3/2016 |
| WO | WO-2016057667 A1 | 4/2016 |
| WO | WO-2016068802 A1 | 5/2016 |
| WO | WO-2016068803 A1 | 5/2016 |
| WO | WO-2016071448 A1 | 5/2016 |
| WO | WO-2016106159 A1 | 6/2016 |
| WO | WO-2016106302 A1 | 6/2016 |

(56) References Cited

FOREIGN PATENT DOCUMENTS

| | | |
|---|---|---|
| WO | WO-2016111947 A2 | 7/2016 |
| WO | WO-2016134371 A2 | 8/2016 |
| WO | WO-2016144803 A2 | 9/2016 |
| WO | WO-2016149201 A2 | 9/2016 |
| WO | WO-2016154177 A2 | 9/2016 |
| WO | WO-2016154585 A1 | 9/2016 |
| WO | WO-2016161270 A1 | 10/2016 |
| WO | WO-2016196228 A1 | 12/2016 |
| WO | WO-2016196237 A1 | 12/2016 |
| WO | WO-2016197367 A1 | 12/2016 |
| WO | WO-2016200836 A1 | 12/2016 |
| WO | WO-2017019846 A1 | 2/2017 |
| WO | WO-2017020291 A1 | 2/2017 |
| WO | WO-2017020858 A1 | 2/2017 |
| WO | WO-2017024465 A1 | 2/2017 |
| WO | WO-2017024515 A1 | 2/2017 |
| WO | WO-2017025016 A1 | 2/2017 |
| WO | WO-2017025051 A1 | 2/2017 |
| WO | WO-2017031242 A1 | 2/2017 |
| WO | WO-2017034916 A1 | 3/2017 |
| WO | WO-2017040790 A1 | 3/2017 |
| WO | WO-2017053748 A2 | 3/2017 |
| WO | WO-2017055399 A1 | 4/2017 |
| WO | WO-2017055404 A1 | 4/2017 |
| WO | WO-2017063162 A1 | 4/2017 |
| WO | WO-2017079112 A1 | 5/2017 |
| WO | WO-2017079115 A1 | 5/2017 |
| WO | WO-2017079116 A2 | 5/2017 |
| WO | WO-2017096179 A1 | 6/2017 |
| WO | WO-2017096182 A1 | 6/2017 |
| WO | WO-2017096281 A1 | 6/2017 |
| WO | WO-2017106061 A1 | 6/2017 |
| WO | WO-2017123557 A1 | 7/2017 |
| WO | WO-2017132825 A1 | 8/2017 |
| WO | WO-2017132827 A1 | 8/2017 |
| WO | WO-2017133540 A1 | 8/2017 |
| WO | WO-2017134292 A1 | 8/2017 |
| WO | WO-2017157895 A1 | 9/2017 |
| WO | WO-2017178493 A1 | 10/2017 |
| WO | WO-2017205721 A1 | 11/2017 |
| WO | WO-2017220988 A1 | 12/2017 |
| WO | WO-2018013818 A2 | 1/2018 |
| WO | WO-2018036561 A1 | 3/2018 |
| WO | WO-2018039020 A1 | 3/2018 |
| WO | WO-2018081648 A2 | 5/2018 |
| WO | WO-2018160536 A1 | 9/2018 |
| WO | WO-2019147863 A2 | 8/2019 |

OTHER PUBLICATIONS

Duquesnoy, R.J., et al., "Structurally Based Epitope Analysis of Major Histocompatibility Complex Class I-related Chain a (MICA) Antibody Specificity Patterns," Human Immunology, 69(12):826-832, Elsevier/North-Holland, United States (Dec. 2008).

Girlanda, S., et al., "MICA Expressed by Multiple Myeloma and Monoclonal Gammopathy of Undetermined Significance Plasma Cells Costimulates Pamidronate-activated Gammadelta Lymphocytes," Cancer Research, 65(16):7502-7508, American Association for Cancer Research, United States (Aug. 2005).

Groh, V., et al., "Broad Tumor-associated Expression and Recognition by Tumor-derived Gamma Delta T Cells of MICA and MICB," Proceedings of the National Academy of Sciences of the United States of America, 96(12):6879-6884, National Academy of Sciences, United States (Jun. 1999).

Groh, V., et al., "Cell Stress-regulated Human Major Histocompatibility Complex Class 1 Gene Expressed in Gastrointestinal Epithelium," Proceedings of the National Academy of Sciences of the United States of America, 93(22):12445-12450, National Academy of Sciences, United States (Oct. 1996).

Groh, V., et al., "Recognition of Stress-induced MHC Molecules by Intestinal Epithelial Gammadelta T Cells," Science, 279(5357):1737-1740, American Association for the Advancement of Science, United States (Mar. 1998).

Hue, S., et al., "Potential Role of NKG2D/MHC Class I-related Chain a Interaction in Intrathymic Maturation of Single-positive CD8 T Cells," Journal of Immunology, 171(4):1909-1917, American Association of Immunologists, United States (Aug. 2003).

Jordan, P.A., et al., "A role for the Thiol Isomerase Protein ERP5 in Platelet Function," Blood, 105(4):1500-1507, American Society of Hematology, United States (Feb. 2005).

Marten, A., et al., "Soluble MIC is Elevated in the Serum of Patients with Pancreatic Carcinoma Diminishing γδ T Cell Cytotoxicity," International Journal of Cancer, 119(10):2359-2365, Wiley-Liss, Inc, United States (Nov. 2006).

Norberto, W., et al., "Identification of MICA as a New Polymorphic Alloantigen Recognized by Antibodies in Sera of Organ Transplant Recipients," Human Immunology, 61(9): 917-924,Elsevier Science INC, United States (Sep. 2000).

Ranade. V,V., "Drug Delivery Systems. 1. Site-specific Drug Delivery Using Liposomes as Carriers," Journal of Clinical Pharmacology 29(8):685-694, Wiley, England (1989).

Salih, H.R., et al., "Functional Expression and Release of Ligands for the Activating Immunoreceptor NKG2D in Leukemia," Blood, 102(4):1389-1396, American Society of Hematology, United States (Aug. 2003).

Steinle, A., et al., "Diversification, Expression, and γδ T Cell Recognition of Evolutionarily Distant Members of the MIC Family of Major Histocompatibility Complex Class I-related Molecules," Immunology and Proceedings of the National Academy of Sciences of the United States of America, 95(21):12510-12515, National Academy of Sciences,United States (Oct. 1998).

Steinle, A., et al., "Interactions of Human NKG2D with its Ligands MICA, MICB, and Homologs of the Mouse RAE-1 Protein Family," Immunogenetics, 53(4):279-287, Springer-Verlag, United States (May-Jun. 2001).

Liu, G., et al., "Perturbation of NK Cell Peripheral Homeostasis Accelerates Prostate Carcinoma Metastasis," Journal of Clinical Investigation, 123(10):Supplement Material, American Society for Clinical Investigation, United States, (Oct. 2013), 13 pages.

Zou, Y., et al., "MICA is a Target for Complement-Dependent Cytotoxicity With Mouse Monoclonal Antibodies and Human Alloantibodies," Human Immunology, 63(1):30-39,Elsevier/North-Holland, United States (Jan. 2002).

International Search Report and Written Opinion for Application No. PCT/US2019/023693, dated Sep. 13, 2019, 23 pages.

Paulus, H., et al., "Preparation and Biomedical Applications of Bispecific Antibodies," Behring Institute Mitteilungen 78:118-132, Behringwerke Ag, Germany (1985).

Briscoe.P, et al.,"Delivery of superoxide dismutase to pulmonary epithelium via pH-sensitive liposomes," American Journal of Physiology 268:L374-380, American Physiology Society (1995).

Alexander, A.J. and Hughes, D.E., "Monitoring of IgG Antibody Thermal Stability by Micellar Electrokinetic Capillary Chromatography and Matrix-assisted Laser Desorption/ionization Mass Spectrometry," Analytical Chemistry 67(20):3626-3632, American Chemical Society, United States (1995).

Bauer, S., et al., "Activation of NK Cells and T Cells by NKG2D, a Receptor for Stress-inducible MICA," Science 285(5428):727-729, American Association for the Advancement of Science, United States (Jul. 1999).

Berge, S.M., et al., "Pharmaceutical Salts," Journal of Pharmaceutical Sciences 66(1):1-19, Wiley, United States (Jan. 1977).

Bird, R.E., et al., "Single-chain Antigen-binding Proteins," Science 242(4877):423-426, Association for the Advancement of Science, United States (Oct. 1988).

Bloemen, P.G., et al., "Adhesion Molecules: A New Target for Immunoliposome-mediated Drug Delivery," FEBS Letters 357(2):140-144, John Wiley & Sons Ltd, England (1995).

Yeung, Y.A., et al., "Engineering Human IgG1 Affinity to Human Neonatal Fc Receptor: Impact of Affinity Improvement on Pharmacokinetics in Primates," Journal of Immunology 182(12):7663-7671, American Association of Immunologists, United States (2009).

Brennan, M., et al., "Preparation of Bispecific Antibodies by Chemical Recombination of Monoclonal Immunoglobulin G1 Fragments," Science 229(4708):81-83, American Association for the Advancement of Science, United States (Jul. 1985).

(56) References Cited

OTHER PUBLICATIONS

Yamane-Ohnuki, N., et al., "Establishment of FUT8 Knockout Chinese Hamster Ovary Cells: An Ideal Host Cell Line for Producing Completely Defucosylated Antibodies with Enhanced Antibody-Dependent Cellular Cytotoxicity," Biotechnology and Bioengineering 87(5):614-622, Wiley, United States (2004).

Brummell, D.A., et al., "Probing the Combining Site of an Anti-Carbohydrate Antibody by Saturation-Mutagenesis: Role of the Heavy-Chain CDR3 Residues," Biochemistry 32(4):1180-1187, American Chemical Society, United States (1993).

Burks, E.A., et al., "In vitro Scanning Saturation Mutagenesis of an Antibody Binding Pocket," Proceedings of the National Academy of Sciences USA 94(2):412-417, Plenum Publishing Corporation, United States (1997).

Chen, B., et al., "Influence of Histidine on the Stability and Physical Properties of a Fully Human Antibody in Aqueous and Solid Forms," Pharmaceutical Research 20(12):1952-1960, Kluwer Academic, United States (2003).

Chen, J., et al., "B Cell Development in Mice That Lack One or Both Immunoglobulin Kappa Light Chain Genes," The EMBO Journal 12(3):821-830, Wiley Blackwell, England (1993).

Chen, J., et al., "Immunoglobulin Gene Rearrangement in B Cell Deficient Mice Generated by Targeted Deletion of the JH Locus," International Immunology 5(6):647-656, Oxford University Press, England (1993).

Cheung, R.C., et al., "Epitope-specific Antibody Response to the Surface Antigen of Duck Hepatitis B Virus in Infected Ducks," Virology 176(2):546-552, Academic Press, United States (1990).

Choi, T.K., et al., "Transgenic Mice Containing a Human Heavy Chain Immunoglobulin Gene Fragment Cloned in a Yeast Artificial Chromosome," Nature Genetics 4(2):117-123, Nature Pub. Co., United States (1993).

Cox, J.P., et al., "A Directory of Human Germ-line V kappa Segments Reveals a Strong Bias in their Usage," European Journal of Immunology 24(4):827-836, Verlag Chemie GmbH, Germany (Apr. 1994).

Dall Acqua, W.F., et al., "Increasing the Affinity of a Human IgG1 for the Neonatal Fc Receptor: Biological Consequences," The Journal of Immunology 169(9):5171-5180, American Association of Immunologists, United States (Nov. 2002).

Dall'Acqua, W.F., et al., "Properties of Human IgG1s Engineered for Enhanced Binding to the Neonatal Fc Receptor (FcRn)," The Journal of Biological Chemistry 281(33):23514-23524, American Society for Biochemistry and Molecular Biology, United States (2006).

De Graaf, A.J., et al., "Nonnatural Amino Acids for Site-specific Protein Conjugation," Bioconjugate Chemistry 20(7):1281-1295, American Chemical Society, United States (2009).

Diefenbach, A., et al., "Ligands for the Murine NKG2D Receptor: Expression by Tumor Cells and Activation of NK Cells and Macrophages,"Nature Immunology, 1(2):119-126, Nature America Inc, United States (Aug. 2000).

Doubrovina, E.S.,et al., "Evasion From Nk Cell Immunity by Mhc Class I Chain-related Molecules Expressing Colon Adenocarcinoma," Journal of Immunology, 171(12):6891-6899, American Association of Immunologists, United States, (Dec. 2003).

Dranoff, G., et al., "Vaccination With Irradiated Tumor Cells Engineered to Secrete Murine Granulocyte-macrophage Colony-stimulating Factor Stimulates Potent, Specific, and Long-lasting Anti-tumor Immunity," Proceedings of the National Academy of Sciences of the United States of America 90(8):3539-3543, National Academy of Sciences, United States (1993).

Fishwild, D.M., et al., "High-Avidity Human IgG Kappa Monoclonal Antibodies from a Novel Strain of Minilocus Transgenic Mice," Nature Biotechnology 14(7):845-851, Nature America Publishing, United States (1996).

Frese, M.A. and Dierks, T., "Formylglycine Aldehyde Tag-protein Engineering Through a Novel Post-translational Modification," Chembiochem 10(3):425-427, Wiley-VCH Verlag, Germany (2009).

Fulda, S., et al., "Smac Agonists Sensitize for Apo2l/TRAIL- or Anticancer Drug-induced Apoptosis and Induce Regression of Malignant Glioma in Vivo," Nature Medicine 8(8):808-815, Nature Publishing Company, United States (2002).

Gala, F.A. and Morrison, S.L., "V Region Carbohydrate and Antibody Expression," The Journal of Immunology 172(9):5489-5494, Williams & Wilkins, United States (2004).

Gautier, A., et al., "An Engineered Protein Tag for Multiprotein Labeling in Living Cells," Chemistry & Biology 15(2):128-136, Elsevier, United States (2008).

Zhang, J., et al., "Antibody-Mediated Neutralization of Soluble MIC Significantly Enhances CTLA4 Blockade Therapy," Science Advances, 3(5):e1602133, American Association for the Advancement of Science, United States (May 2017).

Ghadially, H., et al., "MHC Class I Chain-related Protein A and B (MICA and MICB) are Predominantly Expressed Intracellularly in Tumour and Normal Tissue," British Journal of Cancer, 116(9):1208-1217, Nature Publishing Group on behalf of Cancer Research UK, England, (Apr. 2017).

Ghirlando, R., et al., "Glycosylation of Human IgG-Fc: Influences on Structure Revealed by Differential Scanning Micro-Calorimetry," Immunology Letters 68(1):47-52, Elsevier/North-Holland Biomedical Press, Netherlands (1999).

Glennie, M.J., et al., "Preparation and Performance of Bispecific F(Ab' Gamma)2 Antibody Containing Thioether-linked Fab' Gamma Fragments," Journal of Immunology 139(7):2367-2375, American Association of Immunologists, United States (1987).

Greenberg, P.D. and Riddell, S.R., "Deficient Cellular Immunity-Finding and Fixing the Defects," Science 285(5427):546-551, American Association for the Advancement of Science, United States (1999).

Groh, V., et al., "Costimulation of Cd8alphabeta T Cells by NKG2D via Engagement by Mic Induced on Virus-infected Cells," Nature immunology, 2(3):255-260, Nature America Inc, United States, (Mar. 2001).

Groh, V., et al., "Efficient Cross-priming of Tumor Antigen-specific T Cells by Dendritic Cells Sensitized With Diverse Anti-mica Opsonized Tumor Cells," Proceedings of the National Academy of Sciences of the United States of America, 102(18):6461-6466, National Academy of Sciences, United States, (May 2005).

Groh, V., et al., "Tumour-derived Soluble MIC ligands Impair expression of NKG2D and T-cell Activation," Nature, 419(6908):734-738, Nature Publishing Group, England (Oct. 2002).

Hackenberger, C.P. and Schwarzer, D., "Chemoselective Ligation and Modification Strategies for Peptides and Proteins," Angewandte Chemie 47(52):10030-10074, Wiley-VCH, Germany (2008).

Hahne, M., et al., "Melanoma Cell Expression of Fas(Apo-1/CD95) Ligand: Implications for Tumor Immune Escape," Science 274(5291):1363-1366, American Association forthe Advancement of Science, United States (1996).

Harding, F.A. and Lonberg, N., "Class Switching in Human Immunoglobulin Transgenic Mice," Annals of the New York Academy of Sciences 764:536-546, The Academy, United States (1995).

He, Y-F., et al., "Blocking Programmed Death-1 Ligand-PD-1 Interactions by Local Gene Therapy Results in Enhancement of Antitumor Effect of Secondary Lymphoid Tissue Chemokine," The Journal of Immunology 173(8):4919-4928, The American Association of Immunologists, United States (Oct. 2004).

Herbst, R.S., et al., "A Study of MPDL3280A, an Engineered PD-L1 Antibody in Patients with Locally Advanced or Metastatic Tumors," Journal of Clinical Oncology 31 (Suppl):Abstract 3000, American Society of Clinical Oncology, United States (2013).

Hinton, P.R., et al., "An Engineered Human IgG1 Antibody with Longer Serum Half-Life," Journal of Immunology 176(1):346-356, American Association of Immunologists, United States (2006).

Hinton, P.R., et al., "Engineered Human IgG Antibodies With Longer Serum Half-lives in Primates," The Journal of Biological Chemistry 279(8):6213-6216, American Society for Biochemistry and Molecular Biology, United States (2004).

Howard, M. and Ogarra, A., "Biological Properties of Interleukin 10," Immunology Today 13(6):198-200, Elsevier Science Publishers, England (1992).

(56) References Cited

OTHER PUBLICATIONS

Huston, J.S., et al., "Protein Engineering of Antibody Binding Sites: Recovery of Specific Activity in an Anti-digoxin Single-chain Fv Analogue Produced in *Escherichia coli*," Proceedings of the National Academy of Sciences USA 85(16):5879-5883, National Academy of Sciences, United States (Aug. 1988).

Hutloff, A., et al., "ICOS is an Inducible T-cell Co-stimulator Structurally and Functionally Related to CD28," Nature 397(6716):263-266, Nature Publishing Group, England (Jan. 1999).

Hyer, M.L., et al., "Synthetic Triterpenoids Cooperate With Tumor Necrosis Factor-related Apoptosis-inducing Ligand to Induce Apoptosis of Breast Cancer Cells," Cancer Research 65(11):4799-4808, American Association for Cancer Research, United States (2005).

Idusogie, E.E., et al., "Engineered Antibodies with Increased Activity to Recruit Complement," The Journal of Immunology 166(4):2571-2575, American Association of Immunologists, United States (2001).

Jefferis, R., et al., "Human Immunoglobulin Allotypes: Possible Implications for Immunogenicity," Mabs 1(4):332-338, Taylor & Francis, United States (Jul.-Aug. 2009).

Jinushi, M., et al., "Therapy-Induced Antibodies to MHC Class I Chain-Related Protein A Antagonize Immune Suppression and Stimulate Antitumor Cytotoxicity," Proceedings of the National Academy of Sciences of the United States of America, 103(24):9190-9195, National Academy of Sciences, United States, (Jun. 2006).

Jones, P.T., et al., "Replacing the Complementarity-determining Regions in a Human Antibody with those from a Mouse," Nature 321(6069):522-525, Nature Publishing Group, England (May 1986).

Kabat, E.A., et al., "Sequences of Proteins of Immunological Interest," 5th Edition, U.S. Department of Public Health and Human Services, Public Health Service, NIH publication No. 91-3242, National Institutes of Health, Bethesda (1991).

Kaiser, BK., et al., "Disulphide-isomerase-enabled Shedding of tumour-associated NKG2D ligands,"Nature, 447(7143):482-486, Nature Publishing Group, England (May 2007).

Karpovsky, B., et al., "Production of Target-specific Effector Cells Using Hetero-cross-linked Aggregates Containing Anti-target Cell and Anti-fc Gamma Receptor Antibodies," The Journal of Experimental Medicine 160(6):1686-1701, Rockefeller University Press, United States (1984).

Kaufman, R.J. and Sharp, P.A., "Amplification and Expression of Sequences Cotransfected with a Modular Dihydrofolate Reductase Complementary DNA Gene," Journal of Molecular Biology 159(4):601-621, Academic Press, Inc. Ltd., England (Aug. 1982).

Kehrl, J.H., et al., "Production of Transforming Growth Factor Beta by Human T Lymphocytes and its Potential Role in the Regulation of T Cell Growth," The Journal of Experimental Medicine 163(5):1037-1050, Rockefeller University Press, United States (1986).

Keinanen, K. and Laukkanen, M.L., "Biosynthetic Lipid-tagging of Antibodies," FEBS Letters 346(1):123-126, John Wiley & Sons Ltd, England (1994).

Killion, J.J. and Fidler, I.J., "Systemic Targeting of Liposome-encapsulated Immunomodulators to Macrophages for Treatment of Cancer Metastasis," ImmunoMethods 4(3):273-279, Academic Presss, United States (1994).

Kim, N.W., et al., "Specific Association of Human Telomerase Activity With Immortal Cells and Cancer," Science 266(5193):2011-2015, American Association for the Advancement of Science, United States (1994).

Kirkland, T.N., et al., "Analysis of the Fine Specificity and Cross-reactivity of Monoclonal Anti-lipid A Antibodies," Journal of Microbiology 137(11):3614-3619, Microbiological Society of Korea, Korea (1986).

Kobayashi, H., et al., "Tryptophan H33 Plays an Important Role in Pyrimidine (6-4) Pyrimidone Photoproduct Binding by a High-Affinity Antibody," Protein Engineering Design and Selection 12(10):879-884, Oxford University Press, United States (1999).

Koguchi, Y., et al., "Serum Immunoregulatory Proteins as Predictors of Overall Survival of Metastatic Melanoma Patients Treated With Ipilimumab," Cancer Research, 75(23):5084-5092, American Association for Cancer Research, United States (Dec. 2015).

Kohler, G. and Milstein, C., "Continuous Cultures of Fused Cells Secreting Antibody of Predefined Specificity," Nature 256(5517):495-497, Macmillan Journals Ltd., England (Aug. 1975).

Kostelny, S.A., et al., "Formation of a Bispecific Antibody by the Use of Leucine Zippers," The Journal of Immunology 148(5):1547-1553, American Association of Immunologists, United States (Mar. 1992).

Krishnamurthy, R. and Manning, M.C., "The Stability Factor: Importance in Formulation Development," Current Pharmaceutical Biotechnology 3(4):361-371, Bentham Science Publishers, Netherlands (2002).

Kugler, A., et al., , "Regression of Human Metastatic Renal Cell Carcinoma After Vaccination with Tumor Cell-Dendritic Cell Hybrids," Nature Medicine 6(3):332-336, Nature Publishing Company, United States (2000).

Kuroiwa, Y., et al., "Cloned Transchromosomic Calves Producing Human Immunoglobulin," Nature Biotechnology 20(9):889-894, Nature America Publishing, United States (2002).

Liu, G., et al., "Perturbation of NK Cell Peripheral Homeostasis Accelerates Prostate Carcinoma Metastasis," Journal of Clinical Investigation, 123(10):4410-4422, American Society for Clinical Investigation, United States, (Oct. 2013).

Liu, M.A., et al., "Heteroantibody Duplexes Target Cells for Lysis by Cytotoxic T Lymphocytes," Proceedings of the National Academy of Sciences of the United States of America 82(24):8648-8652, National Academy of Sciences, United States (1985).

Lonberg, N. and Huszar, D., "Human Antibodies from Transgenic Mice," International Reviews of Immunology 13(1):65-93, Informa Healthcare, England (1995).

Lonberg, N., et al., "Antigen-specific Human Antibodies from Mice Comprising Four Distinct Genetic Modifications," Nature 368(6474):856-859, Nature Publishing Group, United States (Apr. 1994).

Lonberg, N., "Handbook of Experimental Pharmacology," The Pharmacology of Monoclonal Antibodies 113:49-101 (1994).

Lonberg, N., "Human Antibodies from Transgenic Animals," Nature Biotechnology 23(9):1117-1125, Nature Publishing Group, United Kingdom (2005).

Marshall, R.D., "Glycoproteins," Annual Review of Biochemistry 41:673-702, Annual Reviews, United States (1972).

McCafferty, J., et al., "Phage Antibodies: Filamentous Phage Displaying Antibody Variable Domains," Nature 348(6301):552-554, Nature Publishing Group, London (Dec. 1990).

Melero, I., et al., "Monoclonal Antibodies Against the 4-1BB T-cell Activation Molecule Eradicate Established Tumors," Nature Medicine 3(6):682-685, Nature Publishing Company, United States (1997).

Meyers, E., et al., "Optical Alignments in linear space," Computer Applications in the Biosciences 4(1):11-17, Oxford University Press, England (1989).

Mimura, Y., et al., "The Influence of Glycosylation on the Thermal Stability and Effector Function Expression of Human IgG1-Fc: Properties of a Series of Truncated Glycoforms," Molecular Immunology 37(12-13):697-706, Pergamon Press, England (2000).

Mokyr, M.B., et al., "Realization of the Therapeutic Potential of CTLA-4 Blockade in Low-dose Chemotherapy-treated Tumor-bearing Mice," Cancer Research 58(23):5301-5304, American Association for Cancer Research, United States (1998).

Moldenhauer, G., et al., "Identity of HML-1 Antigen on Intestinal Intraepithelial T Cells and of B-ly7 Antigen on Hairy Cell Leukaemia," Scandinavian Journal of Immunology 32(2):77-82, Blackwell Scientific Publications, England (1990).

Morel, G.A., et al., "Monoclonal Antibodies to Bovine Serum Albumin: Affinity and Specificity Determinations," Molecular Immunology 25(1):7-15, Pergamon Press, England (1988).

Morrison, S.L., "Transfectomas Provide Novel Chimeric Antibodies," Science 229(4719):1202-1207, Association for the Advancement of Science, United States (Sep. 1985).

Mossner, E., et al., "Increasing the Efficacy of CD20 Antibody Therapy through the Engineering of a NewType II anti-CD20 Antibody with Enhanced Direct and Immune Effector Cell-Mediated B-Cell Cytotoxicity," Blood 115(22):4393-4402, American Society of Hematology, United States (2010).

(56) References Cited

OTHER PUBLICATIONS

Murray, A., et al., "Epitope Affinity Chromatography and Biophysical Studies of Monoclonal Antibodies and Recombinant Antibody Fragments," Journal of Chromatographic Science 40(6):343-349, Oxford University Press, United States (2002).

Natsume, A., et al., "Improving Effector Functions of Antibodies for Cancer Treatment: Enhancing ADCC and CDC," Drug Design, Development and Therapy 3:7-16, Dove Press Limited, New Zealand (2009).

Needleman, S.B and Wunsch, C.D, "A General Method Applicable to the Search for Similarities in the Amino Acid Sequence of Two Proteins," Journal of Molecular Biology, 48(3):443-453, Elsevier, England, (Mar. 1970).

Nestle, F.O., et al., "Vaccination of Melanoma Patients with Peptide- or Tumor Lysate-Pulsed Dendritic Cells," Nature Medicine 4(3):328-332, Nature Publishing Company, United States (1998).

Nimmerjahn, F. and Ravetch, J.V., "Divergent Immunoglobulin G Subclass Activity Through Selective Fc Receptor Binding," Science 310(5753):1510-1512, American Association for the Advancement of Science, United States (2005).

Nordstrom, J. L., et al., "Anti-Tumor Activity and Toxicokinetics Analysis of MGAH22, an Anti-HER2 Monoclonal Antibody with Enhanced Fcγ Receptor Binding Properties," Breast Cancer Research 13(6):R123, BioMed Central Ltd, England (2011).

Owais, M., et al., "Chloroquine Encapsulated in Malaria-infected Erythrocyte-specific Antibody-bearing Liposomes Effectively Controls Chloroquine-resistant Plasmodium Berghei Infections in Mice," Antimicrobial Agents and Chemotherapy 39(1):180-184, American Society for Microbiology, United States (1995).

Parekh, R.B., et al., "Association of Rheumatoid Arthritis and Primary Osteoarthritis with Changes in the Glycosylation Pattern of Total Serum IgG," Nature 316(6027):452-457, Nature Publishing Group, England (1985).

Weinberg, A.D., et al., "Engagement of the OX-40 Receptor in Vivo Enhances Antitumor Immunity," Journal of Immunology 164(4):2160-2169, American Association of Immunologists, United States (2000).

Liu, S.Y., et al., "Ongoing Clinical Trials of PD-1 and PD-L1 Inhibitors for Lung Cancer in China,"Journal of Hematology & Oncology, 10(1):136, Biomed Central, England (Jul. 2017).

Zhang, F., et al., "Structural Basis of a Novel PD-L1 Nanobody for Immune Checkpoint Blockade,"Cell Discovery, 3:17004, Nature Publishing Group, England (Mar. 2017).

Queen, C., et al., "A Humanized Antibody that Binds to the Interleukin 2 Receptor," Proceedings of the National Academy of Sciences USA 86(24):10029-10033, National Academy of Sciences, United States (Dec. 1989).

Ward, E.S., et al., "Binding Activities of a Repertoire of Single Immunoglobulin Variable Domains Secreted from *Escherichia coli*," Nature 341(6242):544-546, Nature Publishing Group, England (Oct. 1989).

Ren, H., et al., "A Biocompatible Condensation Reaction for the Labeling of Terminal Cysteine Residues on Proteins," Angewandte Chemie 48(51):9658-9662, Wiley-VCH, Germany (2009).

Restifo, N. and Sznol, M., "Cancer: Principles and Practice of Oncology," Cancer Vaccines, Chapter 61, 5th ed., pp. 3023-3043, DeVita et al. (ed.) 1997.

Ribas, A., "Anti-CTLA4 Antibody Clinical Trials in Melanoma," Update on Cancer Therapeutics 2(3):133-139, Elsevier, Ltd, England (Sep. 2007).

Richards, J.O., et al., "Optimization of Antibody Binding to FcgammaRIIa Enhances Macrophage Phagocytosis of Tumor Cells," Molecular Cancer Therapeutics 7(8):2517-2527, American Association for Cancer Research, United States (2008).

Ridge J.P., et al., "A Conditioned Dendritic Cell can be a Temporal Bridge Between a CD4+ T-helper and a T-killer Cell," Nature 393(6684):474-478, Nature Publishing Group, England (1998).

Riechmann, L., et al., "Reshaping Human Antibodies for Therapy," Nature 332(6162):323-327, Nature Publishing Group, United States (Mar. 1988).

Rosenberg, S.A., "A New Era for Cancer Immunotherapy Based on the Genes That Encode Cancer Antigens," Immunity 10(3):281-287, Cell Press, United States (1999).

Salih, HR., et al., "Cutting Edge: Down-regulation of MICA on Human Tumors by Proteolytic Shedding," Journal of Immunology, 169(8):4098-4102, American Association of Immunologists, United States, (Oct. 2002).

Sarmay, G., et al., "Mapping and Comparison of the Interaction Sites on the Fc Region of IgG Responsible for Triggering Antibody Dependent Cellular Cytotoxicity (ADCC) Through Different Types of Human Fc Gamma Receptor," Molecular Immunology 29(5):633-639, Pergamon Press, England (1992).

Schaer, D.A., et al., "Modulation of GITR for Cancer Immunotherapy," Current Opinion in Immunology 24(2):217-224, Elsevier Ltd., England (Apr. 2012).

Schreier, H., et al., "Targeting of Liposomes to Cells Expressing CD4 Using Glycosylphosphatidylinositol-anchored gp120. Influence of Liposome Composition on Intracellular Trafficking," The Journal of Biological Chemistry 269(12):9090-9098, American Society for Biochemistry and Molecular Biology, United States (1994).

Senter, P.D., "Potent Antibody Drug Conjugates for Cancer Therapy," Current Opinion in Chemical Biology 13(3):235-244, Elsevier, England (2009).

Shields, R.L., et al., "High Resolution Mapping of the Binding Site on Human IgG1 for Fc gamma RI, Fc gamma RII, Fc gamma RIII, and FcRn and Design of IgG1 Variants with Improved Binding to the Fc gamma R," The Journal of Biological Chemistry 276(9):6591-6604, American Society for Biochemistry and Molecular Biology, United States (Mar. 2001).

Shields, R.L., et al., "Lack of Fucose on Human IgG1 N-linked Oligosaccharide Improves Binding to Human Fcgamma RIII and Antibody-Dependent Cellular Toxicity," The Journal of Biological Chemistry 277(30):26733-26740, American Society for Biochemistry and Molecular Biology, United States (2002).

Smith,P., et al., "Mouse Model Recapitulating Human Fcγ Receptor Structural and Functional Diversity," Proceedings of the National Academy of Sciences of the United States of America 109(16):6181-6186, National Academy of Sciences, United States (2012).

Songsivilai, S. and Lachmann, P.J., "Bispecific Antibody: A Tool for Diagnosis and Treatment of Disease," Clinical and Experimental Immunology 79(3):315-321, Blackwell Scientific Publications, England (1990).

Spear, P., et al., "NKG2D Ligands as Therapeutic Targets," Cancer Immunology, 13: 8, Cancer Research Institute, United States (May 2013).

Spiro, R.G., "Protein Glycosylation: Nature, Distribution, Enzymatic Formation, and Disease Implications of Glycopeptide Bonds," Glycobiology 12(4):43R-56R, IRL Press at Oxford University Press, England (2002).

Stahli, C., et al., "Distinction of Epitopes by Monoclonal Antibodies.," Methods in Enzymology 92:242-253, Academic Press, United States (1983).

Stavenhagen, J.B., et al., "Fc Optimization of Therapeutic Antibodies Enhances Their Ability to Kill Tumor Cells in Vitro and Controls Tumor Expansion in Vivo via Low-affinity Activating Fcgamma Receptors," Cancer Research 67(18):8882-8890, American Association for Cancer Research, United States (2007).

Strohl, W.R., "Optimization of Fc-mediated Effector Functions of Monoclonal Antibodies," Current Opinion in Biotechnology 20(6):685-691, Elsevier, England (2009).

Sunbul, M. and Yin, J., "Site Specific Protein Labeling by Enzymatic Posttranslational Modification," Organic & Biomolecular Chemistry 7(17):3361-3371, Royal Society of Chemistry, England (2009).

Suto, R. and Srivastava, P.K., "A Mechanism for the Specific Immunogenicity of Heat Shock Protein-chaperoned Peptides," Science 269(5230):1585-1588, American Association for the Advancement of Science, United States (1995).

Takebe, T., et al., "SR Alpha Promoter: An Efficient and Versatile Mammalian Cdna Expression System Composed of the Simian Virus 40 Early Promoter and the R-U5 Segment of Human T-Cell

(56) References Cited

OTHER PUBLICATIONS

Leukemia Virus Type 1 Long Terminal Repeat," Molecular and Cell Biology 8(1):466-472, American Society for Microbiology, United States (1988).
Taki, M., et al., "Transglutaminase-mediated N- and C-terminal Fluorescein Labeling of a Protein can Support the Native Activity of the Modified Protein," Protein Engineering, Design & Selection 17(2):119-126, Oxford University Press, England (2004).
Tamura, Y., et al., "Immunotherapy of Tumors with Autologous Tumor-derived Heat Shock Protein Preparations," Science 278(5335):117-120, American Association for the Advancement of Science, United States (1997).
Tarentino, A.L., et al., "The Isolation and Structure of the Core Oligosaccharide Sequences of IgM," Biochemistry 14(25):5516-5523, American Chemical Society, United States (Dec. 1975).
Taylor, E.V., et al., , "Native Chemical Ligation: SemiSynthesis of Post-translationally Modified Proteins and Biological Probes," Protein Engineering, 22:65-96, (2009).
Taylor, L.D., et al., "A Transgenic Mouse that Expresses a Diversity of Human Sequence Heavy and Light Chain Immunoglobulins," Nucleic Acids Research 20(23):6287-6295, Oxford University Press, England (1992).
Taylor, L.D., et al., "Human Immunoglobulin Transgenes Undergo Rearrangement, Somatic Mutation and Class Switching in Mice that Lack Endogenous IgM," International Immunology 6(4):579-591, University Press, England (1994).
Tomizuka, K., et al., "Double Trans-chromosomic Mice: Maintenance of Two Individual Human Chromosome Fragments Containing Ig Heavy and kappa loci and Expression of Fully Human Antibodies," Proceedings of the National Academy of Sciences USA 97(2):722-727, National Academy of Sciences, United States (Jan. 2000).
Tomlinson, I.M., et al., "The Repertoire of Human Germline VH Sequences Reveals about Fifty Groups of VH Segments with Different Hypervariable Loops," Journal of Molecular Biology 227(3):776-798, Elsevier, Netherlands (Oct. 1992).
Tuaillon, N., et al., "Biased Utilization of DHQ52 and JH4 Gene Segments in a Human Ig Transgenic Minilocus is Independent of Antigenic Selection," The Journal of Immunology 152(6):2912-2920, Williams & Wilkins, United States (1994).
Tuaillon, N., et al., "Human Immunoglobulin Heavy-chain Minilocus Recombination in Transgenic Mice: Gene-segment Use in Mu and Gamma Transcripts," Proceedings of the National Academy of Sciences of the United States of America 90(8):3720-3724, National Academy of Sciences, United States (1993).
Umana, P., et al., "Engineered Glycoforms of an Antineuroblastoma IgG1 with Optimized Antibody-Dependent Cellular Cytotoxic Activity," Nature Biotechnology 17(2):176-180, Nature America Publishing, United States (1999).
Umezawa, F. and Eto. Y., "Liposome Targeting to Mouse Brain: Mannose as a Recognition Marker," Biochemical and Biophysical Research Communications 153(3):1038-1044, Elsevier, United States (1988).
Urlaub, G. and Chasin, L.A., "Isolation of Chinese Hamster Cell Mutants Deficient in Dihydrofolate Reductase Activity," Proceedings of the National Academy of Sciences USA 77(7):4216-4220, National Academy of Sciences, United States (Jul. 1980).
Wallick, S.C., et al., "Glycosylation of a Vh Residue of a Monoclonal Antibody Against Alpha (1—-6) Dextran Increases its Affinity for Antigen," The Journal of Experimental Medicine 168(3):1099-1109, Rockefeller University Press, United States (1988).
Wang, C., et al., "In Vitro Characterization of the Anti-PD-1 Antibody Nivolumab, BMS-936558, and in Vivo Toxicology in Non-human Primates," Cancer Immunology Research 2(9):846-856, American Association for Cancer Research, United States (Sep. 2014).

\* cited by examiner

```
      Q   V   Q   L   V   E   S   G   G   G   V   V   Q   P   G   R   S
  1   CAGGTGCAAC TGGTGGAGTC TGGGGGAGGC GTGGTCCAGC CTGGGGAGGTC
                                                        CDR1
      L   R   L   S   C   A   A   S   G   F   T   F   S   N   Y   A
 51   CCTGAGACTC TCCTGTGCAG CGTCTGGATT CACCTTCAGT AACTATGCCA

M   H   W   V   R   Q   A   P   G   E   G   L   E   W   V   A   L
101   TGCACTGGGT CCGCCAGGCT CCAGGCGAGG GGCTGGAATG GGTGGCACTT
                                CDR2
      I   W   Y   D   G   S   N   K   F   Y   G   D   S   V   K   G   R
151   ATATGGTATG ATGGAAGTAA TAAATTCTAT GGAGACTCCG TGAAGGGCCG

F   T   I   S   R   D   N   S   K   N   T   L   Y   L   Q   M
201   CTTCACCATC TCCAGAGACA ATTCCAAGAA CACGCTGTAT CTGCAAATGA

N   S   L   S   A   E   D   T   A   V   Y   Y   C   A   R   E   G
251   ACAGCCTGAG CGCCGAGGAC ACGGCTGTGT ATTACTGTGC GAGAGAGGGA
               CDR3
      S   G   H   Y   W   G   Q   G   T   L   V   T   V   S   S
301   AGTGGGCACT ACTGGGGCCA GGGAACCCTG GTCACCGTCT CCTCA
```

FIG. 1A – 19G6-MICA.36 VH1

| V-SEGMENT | FAMILY | LOCUS | RF | TGL | VBASEENTRY |
|---|---|---|---|---|---|
| V-SEGMENT | VH3 | 3-33 | | pH3v4D | DP-50/hv3019b9...+ |
| D-SEGMENT | UNDETERMINED | | | | |
| J-SEGMENT | JH4 | 4 | | | JH4b |
| INPUT | 19G6.D5.E4-VH1 | | | | |

```
3-33    Q V Q L V E S G G G V V Q P G R S L R L S C A
INPUT   - - - - - - - - - - - - - - - - - - - - - - -
                                       CDR1
3-33    A S G F T F S - S Y G M H W V R Q A P G K G L E
INPUT   - - - - - - -   N A - - - - - - - - - E - - - -
             CDR2
3-33    W V A V I W Y D G S N K Y Y A D S V K G R F T
INPUT   - - - L - - - - - - - F - - - - S - - - - - -

3-33    I S R D N S K N T L Y L Q M N S L R A E D T A
INPUT   - - - - - - - - - - - - - - - - - - - - - - -
                      CDR3
3-33    V Y Y C A R
JH4               - E G S G H Y W G Q G T L V T V S S
INPUT   - - - - - - - - - - - - - - - - - - - - - - -
```

FIG. 1B – 19G6-MICA.36 VH1

```
          A   I   Q   L   T   Q   S   P   S   S   L   S   A   S   V   G   D
  1   GCCATCCAGT TGACCCAGTC TCCATCCTCC CTGTCTGCAT CTGTAGGAGA

R   V   T   I   T   C   R   A   S   Q   G   I   S   S   A   L
 51   CAGAGTCACC ATCACTTGCC GGGCAAGTCA GGGCATCAGC AGTGCTTTAG
                                                 ─────CDR1─────

A   W   Y   Q   Q   K   P   G   K   V   P   K   S   L   I   Y   D
101   CCTGGTATCA GCAGAAACCA GGGAAAGTTC CTAAGTCCCT GATCTATGAT
      ──CDR2──

A   S   S   L   E   S   G   V   P   S   R   F   S   G   S   G   S
151   GCCTCCAGTT TGGAAAGTGG GGTCCCATCA AGGTTCAGCG GCAGTGGATC

G   T   D   F   T   L   T   I   S   S   L   Q   P   E   D   F
201   TGGGACAGAT TTCACTCTCA CCATCAGCAG CCTGCAGCCT GAAGATTTTG

A   T   Y   Y   C   Q   Q   F   N   S   Y   P   I   T   F   G   Q
251   CAACTTATTA CTGTCAACAG TTTAATAGTT ACCCGATCAC CTTCGGCCAA
                           ─────CDR3─────

G   T   R   L   E   I   K
301   GGGACACGAC TGGAGATTAA A
```

FIG. 1C – 19G6-MICA.36 VK1

FIG. 1D – 19G6-MICA.36 VK1

|           | FAMILY          | LOCUS | TGL   | VBASEENTRY |
|-----------|-----------------|-------|-------|------------|
| V-SEGMENT | VK1             | L18   | Va'+  |            |
| J-SEGMENT | JK5             | 5     |       | JK5        |
| INPUT     | 19G6.D5.E4-VK1  |       |       |            |

```
                                                              CDR1
L18     A I Q L T Q S P S S L S A S V G D R V T I T C
INPUT   - - - - - - - - - - - - - - - - - - - - - - -

CDR1
L18     R A S Q G I S S A L A W Y Q Q K P G K A P K L
INPUT   - - - - - - - - - - - - - - - - - - V - - - -

CDR2
L18     L I Y D A S S L E S G V P S R F S G S G S G T
INPUT   - - - - - - - - - - - - - - - - - - - - - - -

L18     D F T L T I S S L Q P E D F A T Y Y C
INPUT   - - - - - - - - - - - - - - - - - - -

CDR3
L18     N Y
JK5                             Q Q     I T F G Q G T R L E I K
INPUT   S - P                     - F N
```

```
       M   E   F   G   L   S   W   V   F   L   V   A   L   L   R   G   V
  1  ATGGAGTTTG GGCTGAGCTG GGTTTTCCTC GTTGCTCTTT TAAGAGGTGT

Q   C   Q   V   Q   L   V   E   S   G   G   D   V   V   Q   P
 51  CCAGTGTCAG GTGCAGCTGG TGGAGTCTGG GGGAGACGTG GTCCAGCCTG

G   R   S   L   R   L   S   C   A   A   S   G   F   T   F   S   N
101  GGAGGTCCCT GAGACTCTCC TGTGCAGCGT CTGGATTCAC CTTCAGTAAC
     CDR1
       Y   N   I   H   W   V   R   Q   A   P   G   K   G   L   E   W   V
151  TATAACATAC ACTGGGTCCG CCAGGCTCCA GGCAAGGGGC TGGAGTGGGT
                                                    CDR2
       A   V   I   R   Y   D   G   I   N   K   Y   Y   A   D   S   V
201  GGCAGTTATA AGGTATGATG GAATTAATAA ATACTATGCA GACTCCGTGA

K   G   R   F   I   I   S   R   D   N   S   K   N   T   L   Y   L
251  AGGGCCGATT CATCATCTCC AGAGACAATT CCAAGAACAC GCTGTATCTG

Q   M   N   S   L   R   A   E   D   T   A   V   Y   Y   C   A   S
301  CAAATGAACA GCCTGAGAGC CGAGGACACG GCTGTGTATT ACTGTGCGAG
                         CDR3
       G   P   P   D   A   F   N   I   W   G   Q   G   T   M   V   T
351  CGGGCCCCCT GATGCTTTTA ATATCTGGGG CCAAGGGACA ATGGTCACCG

V   S   S
401  TCTCTTCA
```

FIG. 2A – 16A5-MICA.52 VH1

FIG. 2B – 16A5-MICA.52 VH1

|  | FAMILY | LOCUS | RF | TGL | VBASEENTRY |
|---|---|---|---|---|---|
| V-SEGMENT | VH3 | 3-33 | | | DP-50/hv3019b9...+ |
| D-SEGMENT | UNDETERMINED | | | | |
| J-SEGMENT | JH3 | 3 | | pH3v4D | JH3b |
| INPUT | 16A5.C1.G2-VH1 | | | | |

```
3-33   Q V Q L V E S G G G V V Q P G R S L R L S C A
INPUT  Q V Q L V E S G G G V V Q P G R S L R L S C A
                                          CDR1
3-33   A S G F T F S   S Y G M H W V R Q A P G K G L E
INPUT  A S G F T F S   N Y G I H W V R Q A P G K G L E
              CDR2
3-33   W V A V I W   Y D G S N K Y Y A D S V K G R F T I
INPUT  W V A R I W   Y D G S I K Y Y A D S V K G R F T I
3-33   I S R D N S K N T L Y L Q M N S L R A E D T A
INPUT  I S R D N S K N T L Y L Q M N S L R A E D T A
                 CDR3
3-33   V Y Y C A R
JH3                              D       D I W G Q G T M V
INPUT  V Y Y C A R   S G P P   A F N     D I W G Q G T M V

JH3    S
INPUT  S
```

```
     M   R   V         P   A   Q   L         L   G   L         L   L   L         W   L   P   G
  1  ATGAGGGTCC        CCGCTCAGCT            CCTGGGGCTT        CTGCTGCTCT        GGCTCCCAGG

A   R   C         A   I   Q         L   T   Q   S         P   S   S             L   S   A
 51  TGCCAGATGT        GCCATCCAGT        TGACCCAGTC            TCCATCCTCC            CTGTCTGCAT
                                                                                     CDR1
     S   V   G   D     R   V   T         I   T   C             R   A   S   Q         G   I   S
101  CTGTAGGAGA        CAGAGTCACC        ATCACTTGCC            GGGCAAGTCA            GGGCATCAGC

S   A   L         A   W   Y   Q     Q   K   P             G   K   V             P   K   S   L
151  AGTGCTTTAG        CCTGGTATCA        GCAGAAACCA            GGGAAAGTTC            CTAAGTCCCT
                       CDR2
     I   Y   D         A   S   S         L   E   S   G         V   P   S             R   F   S
201  GATCTATGAT        GCCTCCAGTT        TGGAAAGTGG            GGTCCCATCA            AGGTTCAGCG

G   S   G   S     G   T   D         F   T   L             T   I   S   S         L   Q   P
251  GCAGTGGATC        TGGGACAGAT        TTCACTCTCA            CCATCAGCAG            CCTGCAGCCT

E   D   F         A   T   Y   Y     C   Q   Q             F   N   S             Y   P   I   T
301  GAAGATTTTG        CAACTTATTA        CTGTCAACAG            TTTAATAGTT            ACCCGATCAC
                                                               CDR3
     F   G   Q         G   T   R         L   E   I   K
351  CTTCGGCCAA        GGGACACGAC        TGGAGATTAA        A
```

FIG. 2C – 16A5-MICA.52 VH1

| V-SEGMENT | FAMILY | LOCUS | TGL | VBASEENTRY |
|---|---|---|---|---|
| VK1 | L18 | | | Va'+ |
| J-SEGMENT | | | | |
| JK5 | 5 | | | JK5 |

INPUT: 16A5.C1.G2-VK1

```
          A I Q L T Q S P S S L S A S V G D R V T I T C
L18
INPUT     - - - - - - - - - - - - - - - - - - - - - - -
              CDR1
L18       R A S Q G I S S A L A W Y Q Q K P A K A P K L S
INPUT     - - - - - - - - - - - - - - - - - V - - P - -
                CDR2
L18       L I Y D A S S L E S G V P S R F S G S G S G T
INPUT     - - - - - - - - - - - - - - - - - - - - - - -
L18       D F T L T I S S L Q P E D F A T Y Y C Q Q F N
INPUT     - - - - - - - - - - - - - - - - - - - Q Q F N
                                                  CDR3
L18       N Y
JK5                 I T F G Q G T R L E I K
INPUT     S - P     - - - - - - - - - - - -
```

FIG. 2D – 16A5-MICA.52 VH1

```
  1  A   I   Q   L   T   Q   S   P   S   S   L   S   A   S   V   G   D
     GCC ATC CAG TTG ACC CAG TCT CCA TCC TCC CTG TCT GCA TCT GTA GGA GAC
                                                   CDR1
 52  R   V   T   I   T   C   R   A   S   Q   G   I   S   A   L   A
     AGA GTC ACC ATC ACT TGC CGG GCA AGT CAG GGC ATT AGC AGT GCT TTA GCC
                                                                 CDR2
103  W   Y   Q   Q   K   P   G   K   A   P   K   L   L   I   Y   D   A
     TGG TAT CAG CAG AAA CCA GGG AAA GCT CCT AAG CTC CTG ATC TAT GAT GCC

154  S   S   L   E   S   G   V   P   S   R   F   S   G   S   G   S   G
     TCC AGT TTG GAA AGT GGG GTC CCA TCA AGG TTC AGC GGC AGT GGA TCT GGG

205  T   D   F   T   L   T   I   S   S   L   Q   P   E   D   F   A   T
     ACA GAT TTC ACT CTC ACC ATC AGC AGC CTG CAG CCT GAA GAT TTT GCA ACT
              CDR3
256  Y   Y   C   Q   Q   F   N   S   Y   P   F   T   F   G   P   G   T
     TAT TAC TGT CAA CAG TTT AAT AGT TAC CCA TTC ACT TTC GGC CCT GGG ACC

307  K   V   D   I   K
     AAA GTG GAT ATC AAA
```

FIG. 2E – 16A5-MICA.53 VK2

|          | FAMILY           | LOCUS | TGL  | VBASEENTRY |
|----------|------------------|-------|------|------------|
| V-SEGMENT | VK1             | L18   | Va'+ |            |
| J-SEGMENT | JK3             | 3     |      | JK3        |
| INPUT    | 16A5.C1.G2-VK2   |       |      |            |

|       | A | I | Q | L | T | Q | S | P | S | S | L | S | A | S | V | G | D | R | V | T | I | T | C |
|-------|---|---|---|---|---|---|---|---|---|---|---|---|---|---|---|---|---|---|---|---|---|---|---|
| L18   | A | I | Q | L | T | Q | S | P | S | S | L | S | A | S | V | G | D | R | V | T | I | T | C |
| INPUT | - | - | - | - | - | - | - | - | - | - | - | - | - | - | - | - | - | - | - | - | - | - | - |

CDR1

|       | R | A | S | Q | G | I | S | S | A | L | A | W | Y | Q | Q | K | P | G | K | A | P | K | L |
|-------|---|---|---|---|---|---|---|---|---|---|---|---|---|---|---|---|---|---|---|---|---|---|---|
| L18   | R | A | S | Q | G | I | S | S | A | L | A | W | Y | Q | Q | K | P | G | K | A | P | K | L |
| INPUT | - | - | - | - | - | - | - | - | - | - | - | - | - | - | - | - | - | - | - | - | - | - | - |

CDR2

|       | L | I | Y | D | A | S | S | L | E | S | G | V | P | S | R | F | S | G | S | G | S | G | T |
|-------|---|---|---|---|---|---|---|---|---|---|---|---|---|---|---|---|---|---|---|---|---|---|---|
| L18   | L | I | Y | D | A | S | S | L | E | S | G | V | P | S | R | F | S | G | S | G | S | G | T |
| INPUT | - | - | - | - | - | - | - | - | - | - | - | - | - | - | - | - | - | - | - | - | - | - | - |

|       | D | F | T | L | T | I | S | S | L | Q | P | E | D | F | A | T | Y | Y | C | Q | Q | F | N |
|-------|---|---|---|---|---|---|---|---|---|---|---|---|---|---|---|---|---|---|---|---|---|---|---|
| L18   | D | F | T | L | T | I | S | S | L | Q | P | E | D | F | A | T | Y | Y | C | Q | Q | F | N |
| INPUT | - | - | - | - | - | - | - | - | - | - | - | - | - | - | - | - | - | - | - | - | - | - | - |

CDR3

|       | N | Y |   |   |   |   |   | F | T | F | G | P | G | T | K | V | D | I | K |
|-------|---|---|---|---|---|---|---|---|---|---|---|---|---|---|---|---|---|---|---|
| L18   | N | Y |   |   |   |   |   |   |   |   |   |   |   |   |   |   |   |   |   |
| JK3   |   |   |   |   |   |   |   | F | T | F | G | P | G | T | K | V | D | I | K |
| INPUT | S | - |   |   |   |   |   | P | - | - | - | - | - | - | - | - | - | - | - |

FIG. 2F – 16A5-MICA.53 VK2

```
     M   G   S     T   A   I   L     L   A   L   L     L   A   V     L   Q   G   V
  1  ATGGGGTCAA  CCGCCATCCT  CGCCCTCCTC  CTGGCTGTTC  TCCAAGGAGT

C   A   E     V   Q   L     V   Q   S   G     A   E   V     K   K   P
 51  CTGTGCCGAG  GTGCAGCTGG  TGCAGTCTGG  AGCAGAGGTG  AAAAAGCCCG

G   E   S   L     K   I   S     C   K   G     S   G   Y   S     F   T   N
101  GGGAGTCTCT  GAAGATCTCC  TGTAAGGGTT  CTGGATACAG  TTTTACCAAC
     ──CDR1──────────────────────
     Y   W   I     G   W   V   R     Q   M   P     G   K   G     L   E   W   L
151  TACTGGATCG  GCTGGGTGCG  CCAGATGCCC  GGGAAAGGCC  TGGAGTGGTT
     ──────────
     G   I   I     H   P   G     D   S   Y   T     R   Y   S     P   S   F
201  GGGGATCATC  CATCCTGGTG  ACTCTTATAC  CAGATACAGC  CCGTCCTTCC
                                  ──CDR2──────────────────────────────────
     Q   G   Q   V     T   I   S     A   D   K     S   I   S   T     A   Y   L
251  AAGGCCAGGT  CACCATCTCA  GCCGACAAGT  CCATCAGCAC  CGCCTACCTG
     ──

Q   W   S     S   L   K   A     S   D   T     A   I   Y   Y   C   A   R
301  CAGTGGAGCA  GCCTGAAGGC  CTCGGACACC  GCCATATATT  ACTGTGCCAG
                                                    ──CDR3─────────────
     E   G   I     A   A   T     P   F   D   Y     W   G   Q     G   T   L
351  AGAGGGTATA  GCAGCAACTC  CCTTTGACTA  CTGGGGCCAG  GGAACCCTGG
     ─────────────────────────────────────────────

V   T   V   S   S
401  TCACCGTCTC  CTCA
```

FIG. 3A – 24G11-MICA.54 VH1

|  | FAMILY | LOCUS | RF | TGL | VBASEENTRY |
|---|---|---|---|---|---|
| V-SEGMENT | VH5 | 5-51 | 2 | HC2,pVx6 | DP-73/V5-51...+ |
| D-SEGMENT | D6 | 6-13 | | | D6-13/DN1 |
| J-SEGMENT | JH4 | 4 | | | JH4b |
| INPUT | 24G11.A10.E1-VH1 | | | | |

```
5-51     E V Q L V Q S G A E V K K P G E S L K I S C K
INPUT    E V Q L V Q S G A E V K K P G E S L K I S C K
                                       CDR1
5-51     G S Y S F T   S Y W I G   W V R Q M P G K G L E
INPUT    G S Y S F T   N Y W I G   W V R Q M P G K G L E
                 CDR2
5-51     W M G   I I Y P G D S D T   R Y S P S F Q G Q V T
INPUT    W M G   I I H Y P G D S D Y   R Y S P S F Q G Q V T
5-51     I S A D K S I S T A Y L Q W S S L K A S D T A
INPUT    I S A D K S I S T A Y L Q W S S L K A S D T A
                                   CDR3
5-51     M Y Y C A R
6-13                 G     I A A
JH4                        E       F D Y W G Q G T L V
INPUT    M Y Y C A R G I A A E T P F D Y W G Q G T L V

JH4      T V S S
INPUT    T V S S
```

FIG. 3B – 24G11-MICA.54 VH1

```
      M   E   A   P   A   Q   L       L   F   L       L   L   L       W   L   P   D
  1   ATGGAAGCCC CAGCTCAGCT TCTCTTCCTC CTGCTACTCT GGCTCCCAGA

T   T   G       E   I   V       L   T   Q   S       P   A   T       L   S   L
 51   TACCACCGGA GAAATTGTGT TGACACAGTC TCCAGCCACC CTGTCTTTGT
                                                              CDR1
      S   P   G   E       R   A   T       L   S   C       R   A   S   Q       S   V   S
101   CTCCAGGGGA AAGAGCCACC CTCTCCTGCA GGGCCAGTCA GAGTGTTAGC

S   Y   L   A       W   F   Q       Q   K   P       G   Q   A       P   R   L   L
151   AGCTACTTAG CCTGGTTCCA ACAGAAACCT GGCCAGGCTC CCAGGCTCCT
                              CDR2
      I   Y   D   A   S   N       R   A   T   G       I   P   A       R   F   S
201   CATCTATGAT GCATCCAACA GGGCCACTGG CATCCCAGCC AGGTTCAGTG

G   S   G   S       G   T   D       F   T   L       T   I   S   S       L   E   P
251   GCAGTGGGTC TGGGACAGAC TTCACTCTCA CCATCAGCAG CCTAGAGCCT

E   D   F       A   V   Y   Y       C   Q   Q       R   S   N   W   P   P   T
301   GAAGATTTTG CAGTTTATTA CTGTCAGCAG CGTAGCAACT GGCCTCCGAC
                                                     CDR3
      F   G   Q       G   T   K       V   E   I   K
351   GTTCGGCCAA GGGACCAAGG TGGAAATCAA A
```

FIG. 3C – 24G11-MICA.54 VK1

|  | FAMILY | LOCUS | TGL | VBASEENTRY |
|---|---|---|---|---|
| V-SEGMENT | VK3 | L6 | | Vg/38K...+ |
| J-SEGMENT | JK1 | 1 | | JK1 |
| INPUT | 24G11.A10.E1-VK1 | | | |

```
             CDR1
L6     E I V L T Q S P A T L S L S P G E R A T L S C
INPUT  - - - - - - - - - - - - - - - - - - - - - - -

CDR1
L6     R A S Q S V S S Y L A W Y Q Q K P G Q A P R L
INPUT  - - - - - - - - F - - - - - - - - - - - - - -

CDR2
L6     L I Y D A S N R A T G I P A R F S G S G S G T
INPUT  - - - - - - - - - - - - - - - - - - - - - - -

L6     D F T L T I S S L E P E D F A V Y Y C Q Q R S
INPUT  - - - - - - - - - - - - - - - - - - - - - - -

CDR3
L6     N W              T F G Q G T K V E I K
JK1
INPUT  - -  P P         - - - - - - - - - - -
```

FIG. 3D – 24G11-MICA.54 VK1

```
     M   E   L   G   L   C   W   I   F   L   V   A   I   L   E   G   V
  1  ATGGAGTTGG GGCTGTGCTG GATTTTCCTT GTTGCTATTT TAGAAGGTGT

Q   C   E   V   Q   L   V   E   S   G   G   G   L   V   Q   P
 51  CCAGTGTGAG GTGCAACTGG TGGAATCTGG GGGAGGCTTG GTACAGCCTG

G   G   S   L   R   L   S   C   A   A   S   G   F   T   F   S   T
101  GGGGGTCCCT GAGACTCTCC TGTGCAGCCT CTGGATTCAC CTTCAGTACC
                CDR1
     Y   S   M   N   W   V   R   Q   A   P   G   K   G   L   E   W   V
151  TATAGCATGA ACTGGGTCCG CCAGGCTCCA GGGAAGGGGC TGGAGTGGGT
                            CDR2
     S   Y   I   S   Y   R   S   R   T   I   Y   Y   A   D   S   V
201  TTCATATACATT AGTTATCGTA GTCGTACCAT ATACTACGCA GACTCTGTGA

K   G   R   F   T   I   S   R   D   N   A   R   N   S   L   Y   L
251  AGGGCCGATT CACCATCTCC AGAGACAATG CCAGGAACTC ACTGTATCTG

Q   M   N   S   L   R   D   E   D   T   A   V   Y   Y   C   A   R
301  CAAATGAACA GCCTGAGAGA CGAGGACACG GCTGTGTATT ACTGTGCGAG
                  CDR3
     W   G   Y   G   S   G   F   D   Y   W   G   Q   G   T   L
351  ATGGGGCTAT GGTTCGGGGG GCTTTGACTA CTGGGGCCAG GGAACCCTGG

V   T   V   S   S
401  TCACCGTCTC CTCA
```

FIG. 4A — 3F5-MICA.2 VH1

```
                                          CDR1
3-48 germline   E V Q L V E S G G G L V Q P G G S L R L S C A A S G F T F S S Y S M N W
3F5 VH          - - - - - - - - - - - - - - - - - - - - - - - - - - - - - - - T - - - -

CDR2
3-48 germline   V R Q A P G K G L E W V S Y I S S S S S T I Y Y A D S V K G R F T I S R
3F5 VH          - - - - - - - - - - - - - - - Y R - - - - - - - - - - - - - - - - - -

CDR3
3-48 germline   D N A K N S L Y L Q M N S L R D E D T A V Y Y C A R
JH4b germline                                                     - - - - - - - - - - F D Y
3F5 VH          - - - - - - - - - - - - - - - - - - - - - - - - - - W G Y G S G G F D Y JH4b germline   W G Q G T L V T V S S
3F5 VH          - - - - - - - - - - -
```

FIG. 4B – 3F5-MICA.2 VH1

```
           M   E   T   P   A   Q   L   L   F   L   L   L   L   W   L   P   D
  1        ATGGAAACCC CAGGCGCAGCT TCTCTTCCTC CTGCTACTCT GGCTCCCAGA

T   T   G   E   I   V   L   T   Q   S   P   G   T   L   S   L
 51        TACCACCGGA GAAATTGTGT TGACGCAGTC TCCAGGCACC CTGTCTTTGT
                                                        CDR1
           S   P   G   E   R   A   T   L   S   C   R   A   S   Q   S   V   S
101        CTCCAGGGGA AAGAGCCACC CTCTCCTGCA GGGCCAGTCA GAGTGTTAGC

S   S   Y   L   A   W   Y   Q   Q   K   P   G   Q   A   P   R   L
151        AGCAGCTACT TAGCCTGGTA CCAGCAGAAA CCTGGCCAGG CTCCCAGGCT
                      CDR2
           L   I   Y   G   A   S   S   R   A   T   G   I   P   D   R   F
201        CCTCATCTAT GGTGCATCCA GCAGGGCCAC TGGCATCCCA GACAGGTTCA

S   G   S   G   S   G   T   D   F   T   L   T   I   S   R   L   E
251        GTGGCAGTGG GTCTGGGACA GACTTCACTC TCACCATCAG CAGACTGGAG
                                                                    CDR3
           P   E   D   F   A   V   Y   Y   C   Q   Q   Y   G   S   S   F   T
301        CCTGAAGATT TTGCAGTGTA TTACTGTCAG CAGTATGGTA GCTCATTCAC

F   G   P   G   T   K   V   D   I   K
351        TTTCGGCCCT GGGACCAAAG TGGATATCAA A
```

FIG. 4C — 3F5-MICA.2 VK1

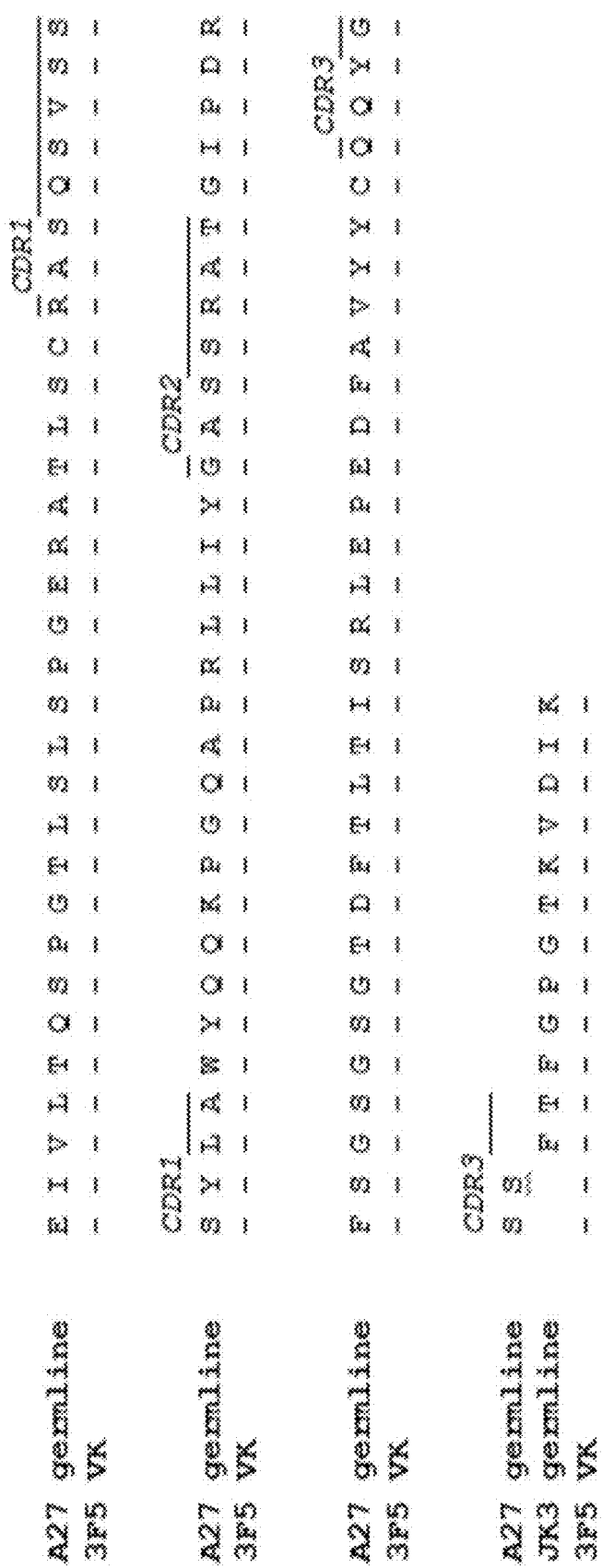
FIG. 4D – 3F5-MICA.2 VK1

```
      M   E   L   G   L   S   W       I   F   L       L   A   I       L   K   G   V
  1  ATGGAGTTGG GACTGAGCTG GATTTCCTT TTGGCTATTT TAAAAGGTGT

Q   C   E   V   Q   L       V   E   S   G       G   G   L       V   Q   P
 51  CCAGTGTGAA GTGCAGCTGG TGGAGTCTGG GGGAGGCTTG GTACAGCCTG

G   R   S   L   R   L   S       C   A   A       S   G   F   T       F   N   N
101  GCAGGTCCCT GAGACTCTCC TGTGCAGCCT CTGGATTCAC CTTTAATAAT
                    CDR1
      Y   A   M       H   W   V   R       Q   A   P       G   K   G       L   E   W   V
151  TATGCCATGC ACTGGGTCCG GCAAGCTCCA GGGAAGGGCC TGGAGTGGGT
                                              CDR2
      S       G   I       T   W   N       S   D   S   I       G   Y   A       D   S   V
201  CTCAGGTATT ACTTGGAATA GTGATAGCAT AGGCTATGCG GACTCTGTGA

K   G   R   F       T   I   S       R   D   N       A   K   N   S       L   Y   L
251  AGGGCCGATT CACCATCTCC AGAGACAACG CCAAGAACTC CCTGTATCTG

Q   M   N   S   L   R   A       E   D   T       A   L   Y       Y   C   A   K
301  CAAATGAACA GTCTGAGAGC TGAGGACACG GCCTTGTATT ACTGTGCAAA
                                        CDR3
      D   S   V   L   L   W       F   G   G   M       D   V   W       G   Q   G
351  AGATTCCGTA TTACTATGGT TCGGGGGTAT GGACGTCTGG GGCCAAGGGA

T   T   V   T   V   S   S
401  CCACGGTCAC CGTCTCCTCA
```

FIG. 5A – 71C2 VH1

```
             FAMILY    LOCUS  RF  TGL   VBASEENTRY

V-SEGMENT    VH3       3-09                 DP-31/V3-9P...+
D-SEGMENT    D3        3-10    1            D3-10/DXP'1
J-SEGMENT    JH6         6                  JH6b
INPUT        71C2.D4.C4-VH1

CDR1
3-09     E  V  Q  L  V  E  S  G  G  G  L  V  Q  P  G  R  S  L  R  L  S  C  A
INPUT    |  |  |  |  |  |  |  |  |  |  |  |  |  |  |  |  |  |  |  |  |  |  |

3-09     A  S  G  F  T  F           D  D  Y  A  M  H  W  V  R  Q  A  P  G  K  G  L  E
INPUT    |  |  |  |  |  |           |  |  |  |  |  |  |  |  |  |  |  |  |  |  |  |  |
                                        CDR2
3-09     W  V  S     G  I  S  W  N  S  G  S  I  G  Y  A  D  S  V  K  G  R  F  T
INPUT    |  |  |     |  |  |  |  |  |  |  |  |  |  |  |  |  |  |  |  |  |  |  |

3-09     I  S  R  D  N  A  K  N  S  L  Y  L  Q  M  N  S  L  R  A  E  D  T  A
INPUT    |  |  |  |  |  |  |  |  |  |  |  |  |  |  |  |  |  |  |  |  |  |  |
                           CDR3
3-09     L  Y  Y  C  A  K        
3-10                          D     
JH6                              V  L  L  W  F  G        W     Y  Y  G  M  D  V  W  G  Q  G
INPUT    |  |  |  |  |  |     S  |  |  |  |  |  |        |     |  |  |  |  |  |  |  |  |  |

JH6                                                                                           T  T  V  T  V  S  S
INPUT                                                                                         |  |  |  |  |  |  |
```

FIG. 5B — 71C2 VH1

```
      M   E   T   P   A   Q   L   L   F   L   L   L   L   W   L   P   D
  1   ATGGAAACCC CAGGCGCAGCT TCTCTTCCTC CTGCTACTCT GGCTCCCAGA

T   T   G   E   I   V   L   T   Q   S   P   G   T   L   S   L
 51   TACCACCGGA GAAATTGTGT TGACGCAGTC TCCAGGCACC CTGTCTTTGT
                                                          CDR1
      S   P   G   E   R   A   T   L   S   C   R   A   S   Q   S   V   S
101   CTCCAGGGGA AAGAGCCACC CTCTCCTGCA GGGCCAGTCA GAGTGTTAGC

S   S   Y   L   A   W   Y   Q   Q   K   P   G   Q   A   P   R   L
151   AGCAGCTACT TAGCCTGGTA CCAGCAGAAA CCTGGCCAGG CTCCCAGGCT
              CDR2
      L   I   Y   G   A   S   S   R   A   T   G   I   P   D   R   F
201   CCTCATCTAT GGTGCATCCA GCAGGGCCAC TGGCATCCCA GACAGGTTCA

S   G   S   G   S   G   T   D   F   T   L   T   I   S   R   L   E
251   GTGGCAGTGG GTCTGGGACA GACTTCACTC TCACCATCAG CAGACTGGAG
                                                          CDR3
      P   E   D   F   A   V   Y   Y   C   Q   Q   Y   G   S   S   P   P
301   CCTGAAGATT TTGCAGTGTA TTACTGTCAG CAGTATGGTA GCTCACCTCC
       Y   T   F   G   Q   G   T   K   L   E   I   K
351   GTACACTTTT GGCCAGGGGA CCAAGCTGGA GATCAAA
```

FIG. 5C – 71C2 VK1

|  | FAMILY | LOCUS | TGL | VBASEENTRY |
|---|---|---|---|---|
| V-SEGMENT | VK3 | A27 |  | DPK22/A27...+ |
| J-SEGMENT | JK2 | 2 |  | JK2 |
| INPUT | 71C2.D4.C4-VK1 |  |  |  |

|  |  |  |  |  |  |  |  |  |  |  |  |
|---|---|---|---|---|---|---|---|---|---|---|---|
| A27 | E | I | V | L | T | Q | S | P | G | T | L S L S P G E R A T L S C |
| INPUT | E | I | V | L | T | Q | S | P | G | T | L S L S P G E R A T L S C |

CDR1
| A27 | R | A | S | Q | S | V | S | S | S | Y | L | A | W | Y | Q | Q | K | P | G | Q | A | P | R |
| INPUT | R | A | S | Q | S | V | S | S | S | Y | L | A | W | Y | Q | Q | K | P | G | Q | A | P | R |

CDR2
| A27 | L | L | I | Y | G | A | S | S | R | A | T | G | I | P | D | R | F | S | G | S | G |
| INPUT | L | L | I | Y | G | A | S | S | R | A | T | G | I | P | D | R | F | S | G | S | G |

| A27 | T | D | F | T | L | T | I | S | R | L | E | P | E | D | F | A | V | Y | Y | C |
| INPUT | T | D | F | T | L | T | I | S | R | L | E | P | E | D | F | A | V | Y | Y | C |

CDR3
| A27 | G | S | S | | | | Y | | | | | | Q | Q | Y |
| JK2 | | | | | | | | T | F | G | Q | G | T | K | L | E | I | K |
| INPUT | | | P | P | | | Y | T | F | G | Q | G | T | K | L | E | I | K |

FIG. 5D – 71C2 VK1

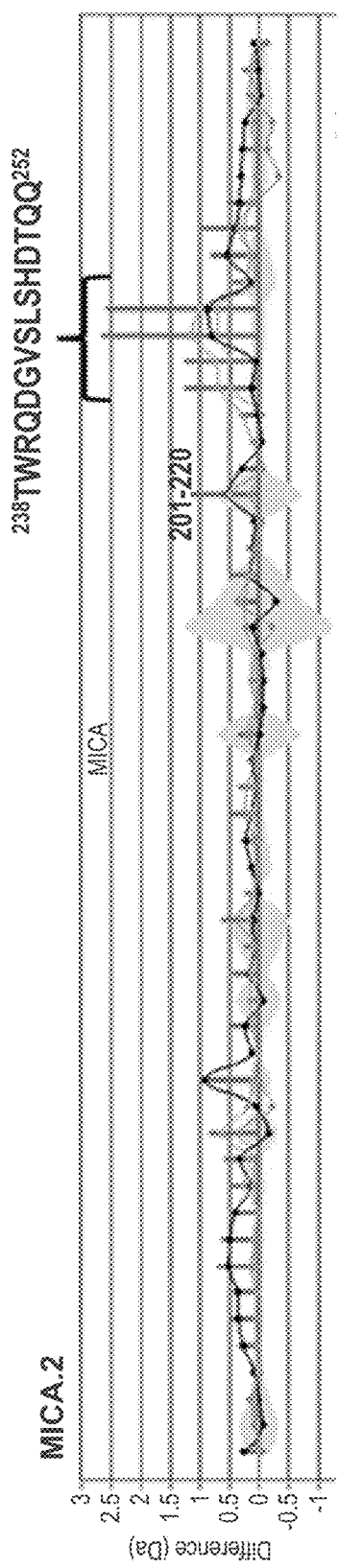
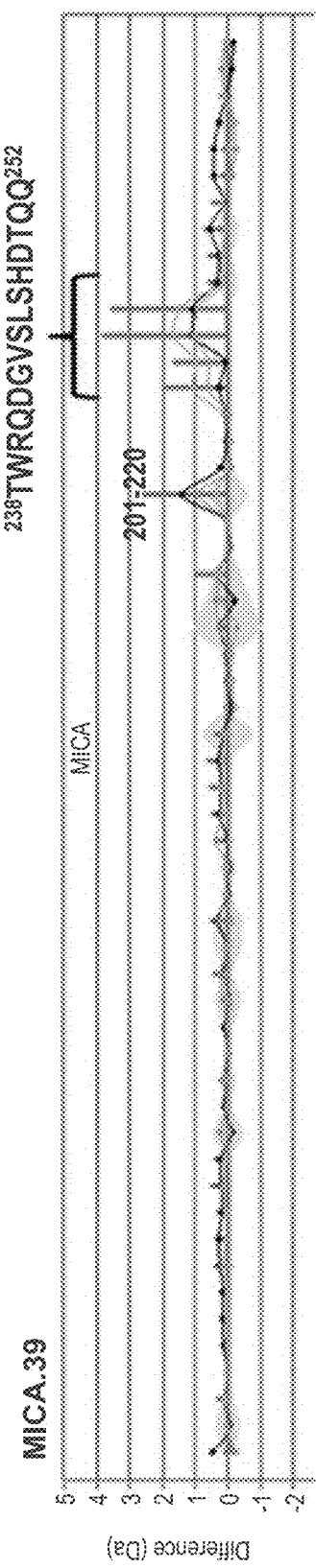
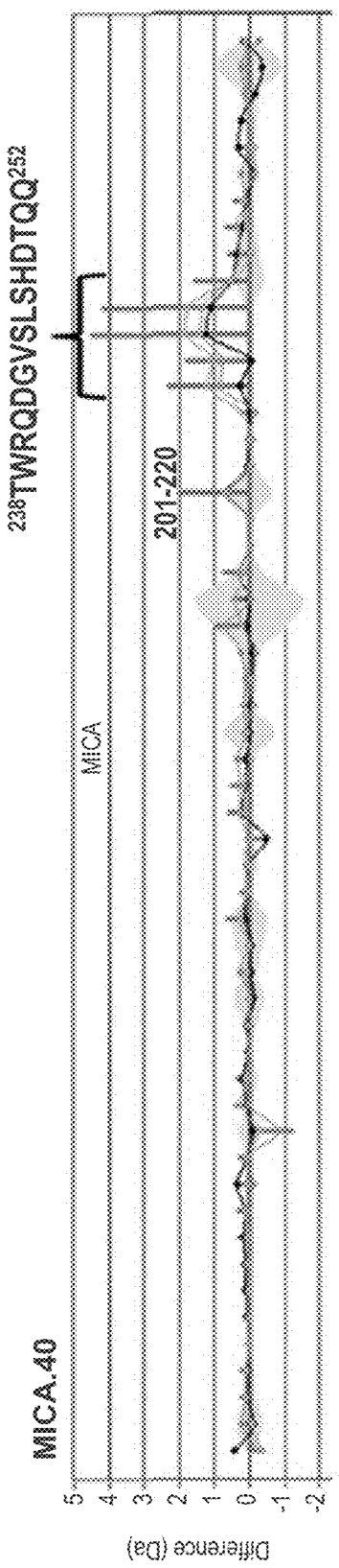
FIG. 9A
FIG. 9B
FIG. 9C

```
  1  MGLGPVFLLL  AGIFPFAPPG  AAAEPHSLRY  NLTVLSWDGS  VQSGFLAEVH  LDGQPFLRYD
 61  RQKCRAKPQG  QWAEDVLGNK  TMDRETRDLT  GNGKDLRMTL  AHIKDQKEGL  HSLQEIRVCE
121  IHEDNSTRSS  QHFYDGELF   LSQNLETEEW  TVPQSSRAQT  LAMNVRNFLK  EDAMKTKTHY
181  HAMHADCLQE  LRRYLESGVV  LRRTVPPMVN  VTRSEASEGN  ITVTCRASSF  YPRNIILTWR
241  QDGVSLSHDT  QQWGDVLPDG  NGTYQTWVAT  RICRGEEQRF  TCYMEHSGNH  STHPVPSGKV
301  LVLQSHWQTF  HVSAVAAGCC  YFCYYFLCP   LL
```

FIG. 10A

```
  1 MGLGPVFLLL AGIFPFAPPG AAAEPHSLRY NLTVLSWDGS VQSGFLAEVH LDGQPFLRYD
 61 RQKCRAKPQG QWAEDVLGNK TMDRETRDLT GNGKDLRMTL AHIKDQKEGL HSLQEIRVCE
121 IHEDNSTRSS QHFYDGELF  LSQNLETEEW TVPQSSRAQT LAMNVRNFLK EDAMKTKTHY
181 HAMHADCLQE LRRYLESGVV LRRTVPPMVN VTRSEASEGN ITVTCRASSF YPRNIILTWR
241 QDGVSLSHDT QQWGDVLPDG NGTYQTWVAT RICRGEEQRF TCYMEHSGNH STHPVPSGKV
301 LVLQSHWQTF HVSAVAAGCC YFCYYYFLCP LL
```

FIG. 10B

```
  1 MGLGPVFLLL AGIFPFAPPG AAAEPHSLRY NLTVLSWDGS VQSGFLAEVH LDGQPFLRYD
 61 RQKCRAKPQG QWAEDVLGNK TWDRETRDLT GNGKDLRMTL AHIKDQKEGL HSLQEIRVCE
121 IHEDNSTRSS QHFYYDGELF LSQNLETEEW TVPQSSRAQT LAMNVRNFLK EDAMKTKTHY
181 HAMHADCLQE LRRYLESGVV LRRTVPPMVN VTRSEASEGN ITVTCRASSF YPRNIILTWR
241 QDGVSLSHDT QQWGDVLPDG NGTYQTWVAT RICRGEEQRF TCYMEHSGNH STHPVPSGKV
301 LVLQSHWQTF HVSAVAAGCC YFCYYFLCP LL
```

FIG. 10C

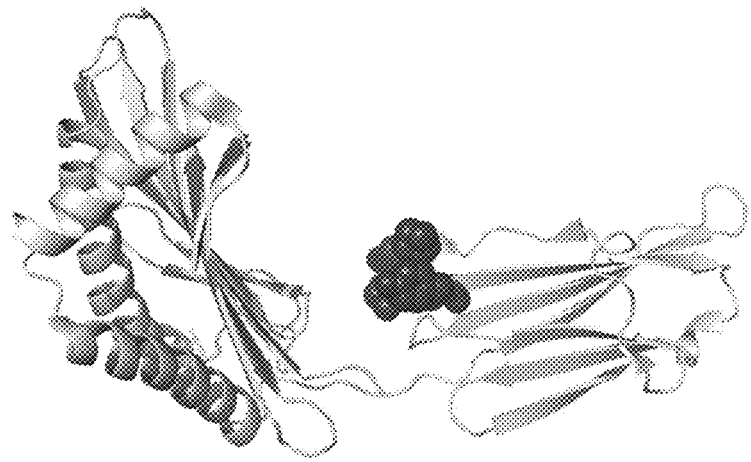
FIG. 10F 24G11
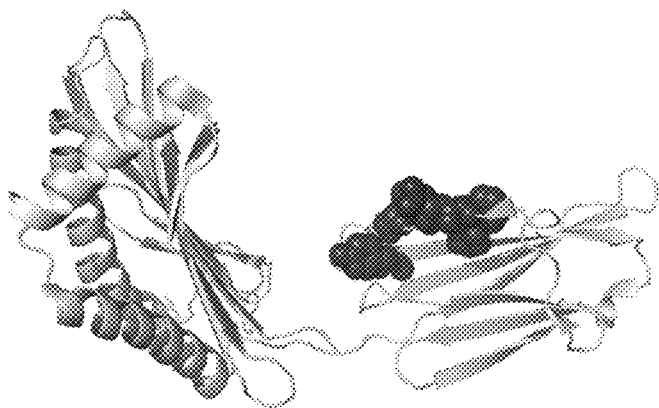
FIG. 10E MICA.36
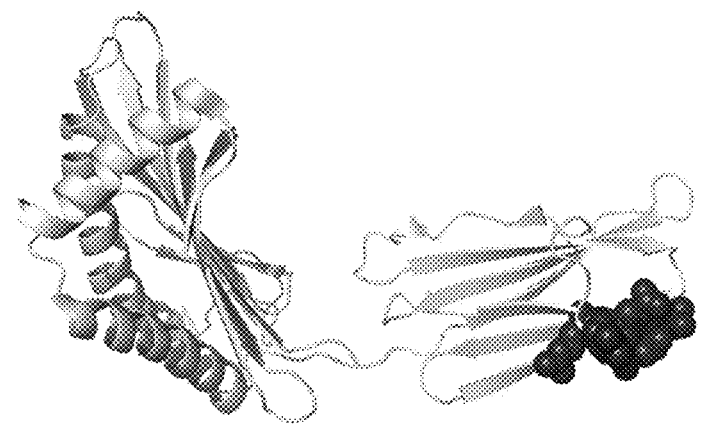
FIG. 10D MICA.2

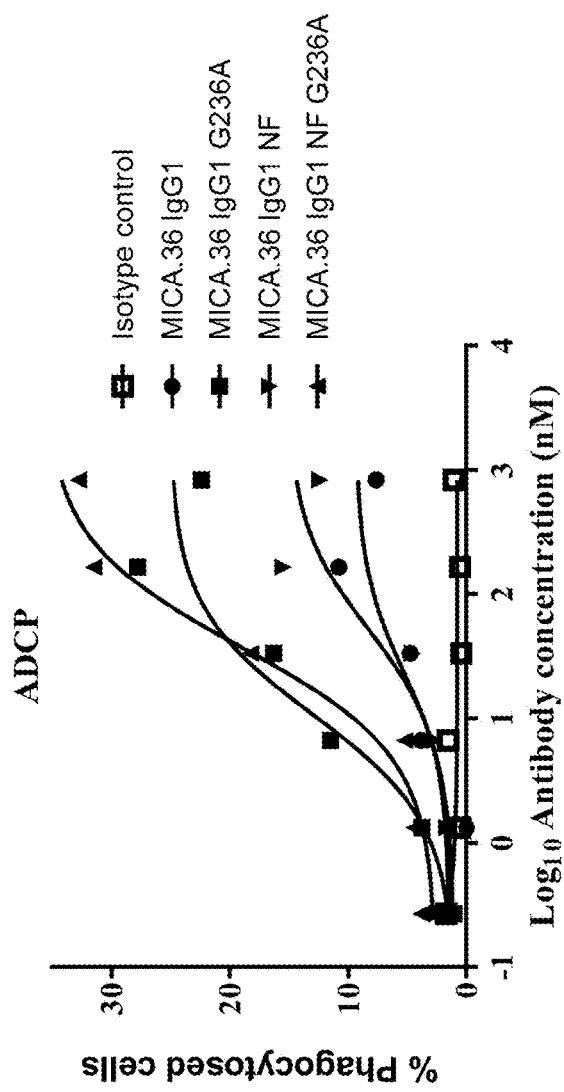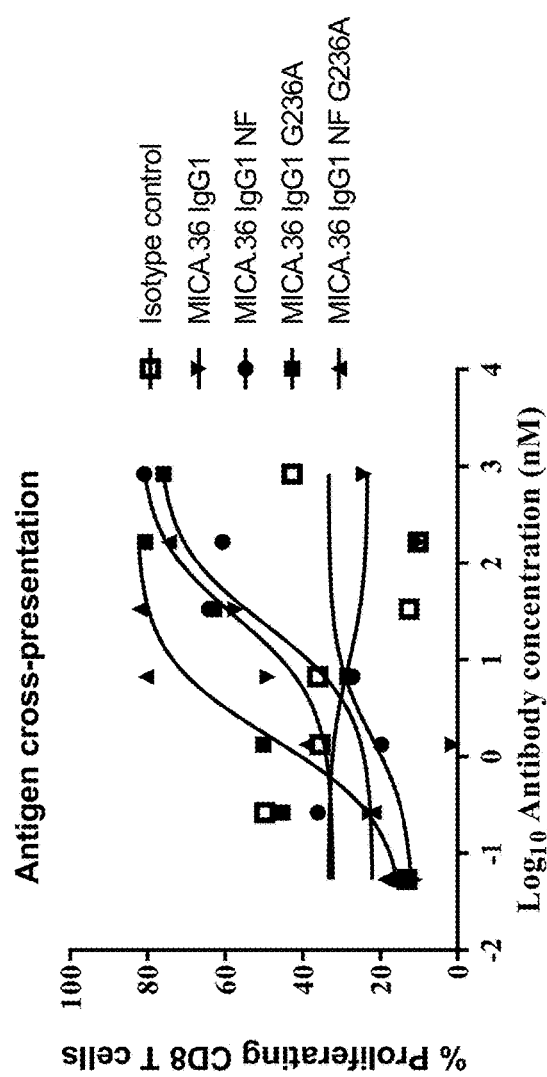
FIG. 15A
FIG. 15B

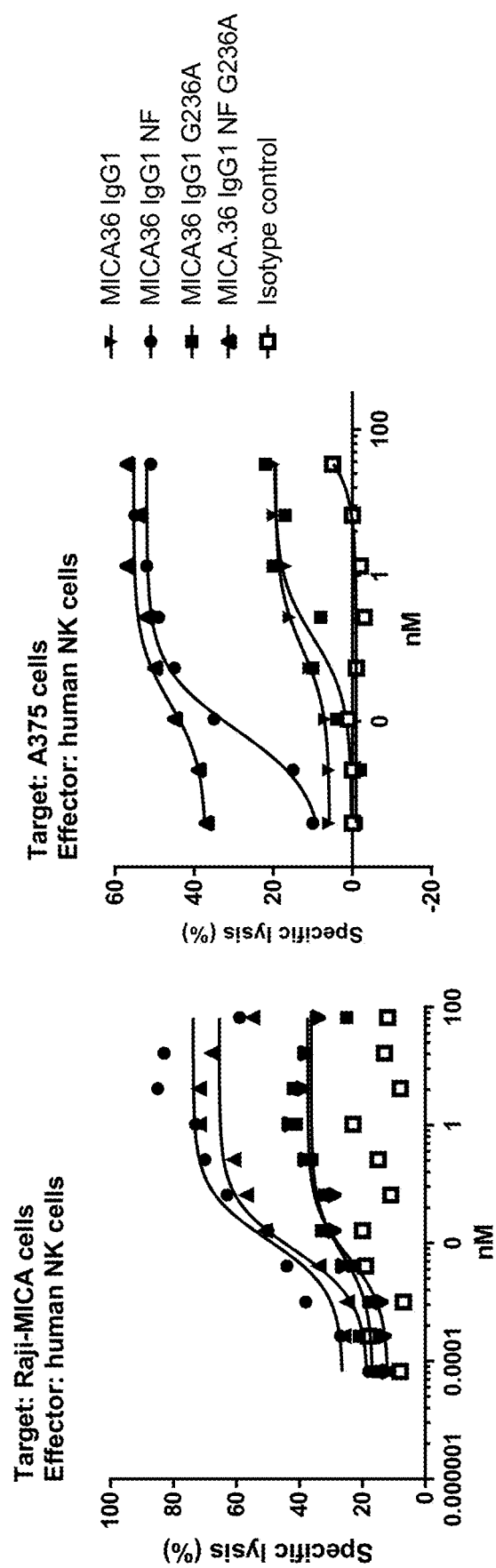

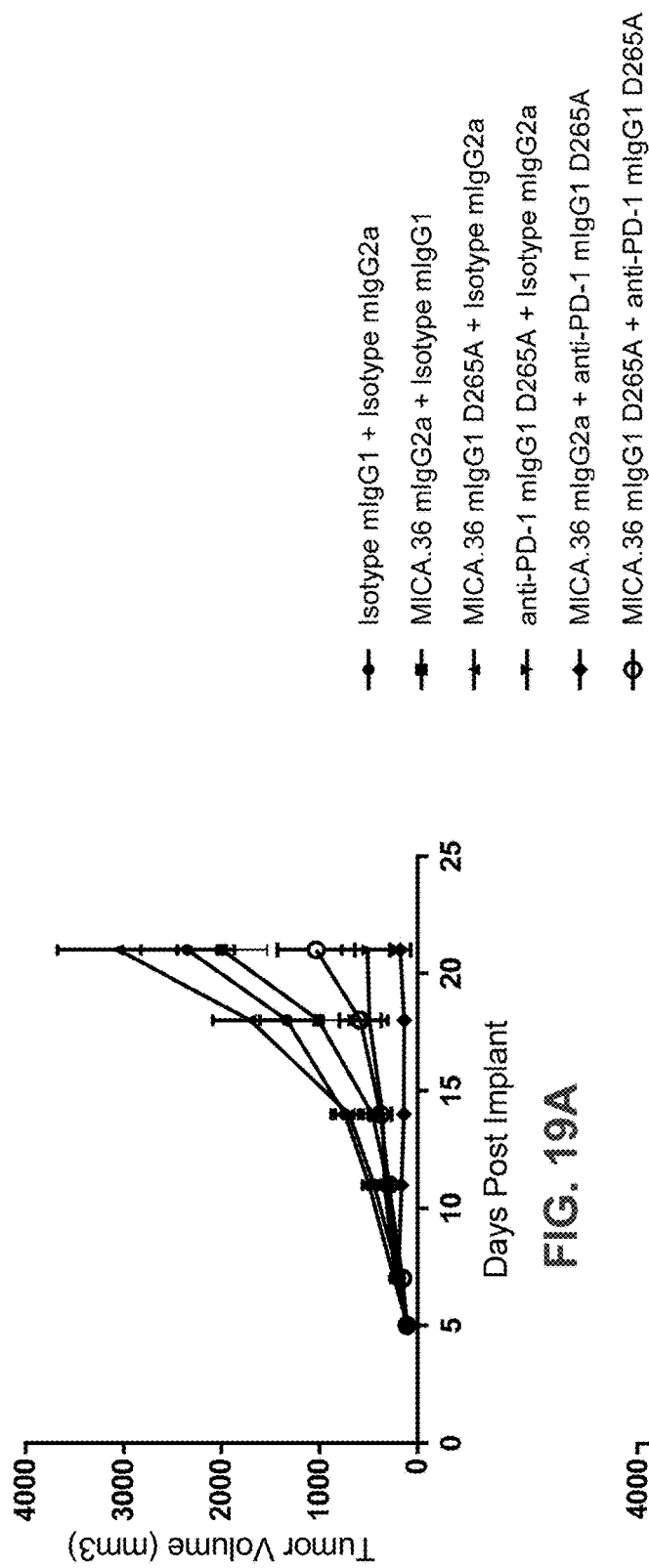
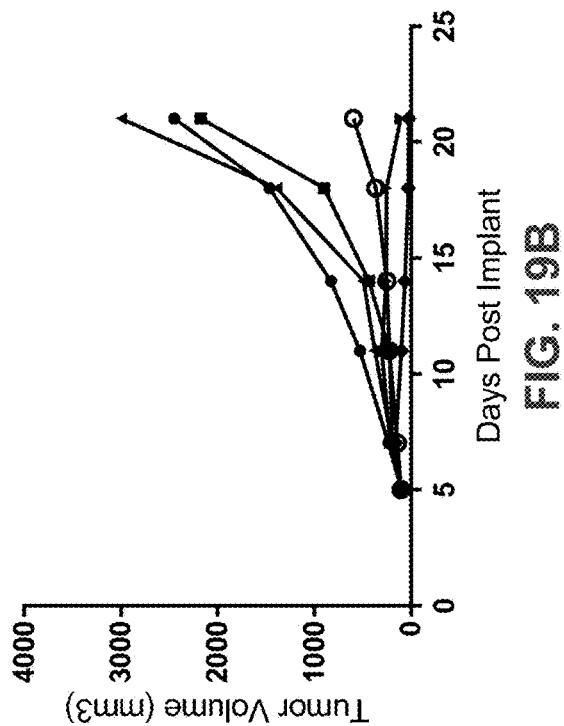
FIG. 19A
FIG. 19B

ANTIBODIES AGAINST MICA AND/OR MICB AND USES THEREOF

REFERENCE TO SEQUENCE LISTING SUBMITTED ELECTRONICALLY VIA EFS-WEB

The content of the electronically submitted sequence listing in ASCII text file (Name: 3338_101PC02_Seqlisting_ST25.txt; Size: 154,660 bytes; and Date of Creation: Mar. 18, 2019) filed with the application is herein incorporated by reference in its entirety.

BACKGROUND OF THE DISCLOSURE

Major histocompatibility complex class I chain-related A and B (MICA/B) are highly polymorphic cell surface proteins related to MHC class I glycoproteins. They contain three extracellular domains ($\alpha 1$, $\alpha 2$, and $\alpha 3$), a transmembrane region and a cytoplasmic tail, and act as ligand to stimulate an activating receptor, NKG2D, expressed on NK, $\gamma\delta$ T, CD8+$\alpha\beta$ T, and NKT cells. Normally, MICA/B are constitutively expressed at low levels on epithelial, endothelial, fibroblasts and myeloid cells. However, they are upregulated or expressed de novo in stressed conditions, such as during carcinogenesis, infections, DNA damage response and in autoimmune conditions. As such, MICA/B expression serves as a signal of cellular stress, and engagement of NKG2D by MICA/B triggers NK cells and co-stimulates T cells, resulting in immune effector functions, such as cytotoxicity and cytokine production. Bauer, Science 1999; 285: 727-9. Diefenbach et al., Nat Immunol. 2000; 1:119-26. Groh et al., Nat Immunol. 2001; 2:255-60. Tumor cells, however, have mechanisms to prevent the response mediated by NKG2D by cleaving MICA/B from the cell surface resulting both in reduction of MICA/B surface density and in generation of soluble MICA/B (sMICA/B), which downregulates NKG2D on cytotoxic effector cells. Groh et al. Nature 2002; 419:734-8. Salih, J. Immunol. 2002; 169:4098-4102. On tumor cells, the $\alpha 3$ domain of MICA/B interacts with a disulphide isomerase/chaperone, endoplasmic reticulum protein 5 (ERp5), to induce a conformational change enabling the cleavage of MICA/B by proteases including disintegrin and metalloproteinases, ADAM10 and ADAM17. Kaiser, Nature 2007; 447:482-6.

Currently, about 100 alleles of MICA encoding 79 protein variants and 40 alleles of MICB encoding 26 protein variants have been identified (European Bioinformatics Institute (EMBL-EB1) Immuno Polymorphism Database: www.ebi.ac.uk/ipd/imgt/hla/stats html (accessed on 8 Dec. 2017)). Expression of MICA/B has been reported in a wide range of tumor types, with high expression associated with poor prognosis. Spear, Cancer Immunity 2013; 13. Ghadially et al., Br. J. Cancer 2017; 116:1208-17. Since prolonged exposure to high concentrations of sMICA has been shown to reduce NKG2D activity on CD8 T and NK cells, generation of sMICA/B has been considered as a mechanism of tumor immune escape. Groh et al., Nat. Immunol. 2001; 2:255-60. Salih, J. Immunol. 2002; 169:4098-4102. sMICA/B proteins have been identified in many human tumor types including melanoma, lung, colon, ovarian, breast, prostate and myeloma. Zhang et al., Sci. Adv. 2017; 3:e1602133. Levels of sMICA correlated with poor survival in patients with metastatic melanoma treated with anti-CTLA-4 antibody, ipilimumab. Koguchi, Cancer Res. 2015; 75:5084-92. Furthermore, melanoma patients responding to ipilimumab were shown to generate therapy-induced anti-MICA/B antibodies; some of these patients experienced decreases in sMICA levels and demonstrated clinical evidence of antitumor activity. Zhang et al., Sci. Adv. 2017; 3:e1602133. Jinushi, PNAS. 2006; 103:9190-9195.

The extent to which viruses and tumors have devised mechanisms to evade detection by NKG2D indicates that therapeutic strategies to restore or enhance NKG2D-dependent activation of NK and T cells may be beneficial. Therefore, there is a need to generate and select anti-MICA/B antibodies that bind to the region proximal to ERp5 binding site on MICA/B and/or retain MICA/B at the cell surface so that it can productively engage NKG2D, leading to enhanced antitumor activity in patients.

SUMMARY OF THE DISCLOSURE

One aspect of the present disclosure is directed to an antibody that specifically binds to human MHC class I polypeptide-related sequence A (MICA) and/or human MHC class I polypeptide-related sequence B (MICB), comprising a heavy chain variable region (VH) and a light chain variable region (VL); wherein the VH comprises a VH complementarity determining region (CDR) 1, a VH-CDR2, and a VH-CDR3 and the VL comprises a VL-CDR1, a VL-CDR2, and a VL-CDR3; wherein the VH-CDR3 comprises an amino acid sequence selected from the group consisting of SEQ ID NOs: 7, 17, 27, 37, and 47. In some embodiments, the VH-CDR2 comprises an amino acid sequence selected from the group consisting of SEQ ID NOs: 6, 16, 26, 36, and 46. In some embodiments, the VH-CDR1 comprises an amino acid sequence selected from the group consisting of SEQ ID NOs: 5, 15, 25, 35, and 45. In some embodiments, the VL-CDR1 comprises an amino acid sequence selected from the group consisting of SEQ ID NOs: 8, 18, 28, 38, and 48. In some embodiments, the VL-CDR2 comprises an amino acid sequence selected from the group consisting of SEQ ID NOs: 9, 19, 29, 39, and 49. In some embodiments, the VL-CDR3 comprises an amino acid sequence selected from the group consisting of SEQ ID NOs: 10, 20, 30, 40, and 50.

In some embodiments, (a) the VH-CDR1 comprises the amino acid sequence set forth in SEQ ID NO:5, the VH-CDR2 comprises the amino acid sequence set forth in SEQ ID NO:6, the VH-CDR3 comprises the amino acid sequence set forth in SEQ ID NO:7, the VL-CDR1 comprises the amino acid sequence set forth in SEQ ID NO:8, the VL-CDR2 comprises the amino acid sequence set forth in SEQ ID NO:9, and the VL-CDR3 comprises the amino acid sequence set forth in SEQ ID NO:10; (b) the VH-CDR1 comprises the amino acid sequence set forth in SEQ ID NO:15, the VH-CDR2 comprises the amino acid sequence set forth in SEQ ID NO:16, the VH-CDR3 comprises the amino acid sequence set forth in SEQ ID NO:17, the VL-CDR1 comprises the amino acid sequence set forth in SEQ ID NO:18, the VL-CDR2 comprises the amino acid sequence set forth in SEQ ID NO:19, and the VL-CDR3 comprises the amino acid sequence set forth in SEQ ID NO:20; (c) the VH-CDR1 comprises the amino acid sequence set forth in SEQ ID NO:25, the VH-CDR2 comprises the amino acid sequence set forth in SEQ ID NO:26, the VH-CDR3 comprises the amino acid sequence set forth in SEQ ID NO:27, the VL-CDR1 comprises the amino acid sequence set forth in SEQ ID NO:28, the VL-CDR2 comprises the amino acid sequence set forth in SEQ ID NO:29, and the VL-CDR3 comprises the amino acid sequence set forth in SEQ ID NO:30; (d) the VH-CDR1 comprises the amino acid sequence set forth in SEQ ID NO:35, the VH-CDR2 comprises the amino acid sequence set forth in SEQ ID NO:36, the VH-CDR3 comprises the amino acid sequence set forth in SEQ ID NO:37, the VL-CDR1 comprises the amino acid sequence set forth in SEQ ID NO:38, the VL-CDR2 comprises the amino acid sequence set forth in SEQ ID NO:39, and the VL-CDR3 comprises the amino acid sequence set forth in SEQ ID NO:40; or (c) the VH-CDR1 comprises the amino acid sequence set forth in SEQ ID NO:45, the VH-CDR2 comprises the amino acid sequence set forth in SEQ ID NO:46, the VH-CDR3 comprises the amino acid sequence set forth in SEQ ID NO:47, the VL-CDR1 comprises the amino acid sequence set forth in SEQ ID NO:48, the VL-CDR2 comprises the amino acid sequence set forth in SEQ ID NO:49, and the VL-CDR3 comprises the amino acid sequence set forth in SEQ ID NO:50.

In some embodiments, the antibody has one or more properties selected from the group consisting of: (a) the antibody inhibits shedding of MICA by a tumor cell; (b) the antibody increases membrane bound MICA on a tumor cell; (c) the antibody reduces soluble MICA level in the serum in a patient; (d) the antibody mediates enhanced ADCC and/or ADCP; (e) the antibody mediates enhanced antigen processing and/or cross-presentation by a cell; (f) the antibody inhibits tumor growth and/or metastasis; (g) the antibody reduces tumor volume; (h) the antibody increases progression-free survival; (i) the antibody increases overall survival; and (j) any combination thereof.

In some embodiments, the VH comprises an amino acid sequence at least about 70%, at least about 80%, at least about 90%, at least about 95%, at least about 96%, at least about 97%, at least about 98%, or at least about 99% sequence identity to an amino acid sequence selected from the group consisting of SEQ ID NOs: 2, 12, 22, 32, and 42. In some embodiments, the VH comprises an amino acid sequence selected from the group consisting of SEQ ID NOs: 2, 12, 22, 32, and 42.

In some embodiments, the VL comprises an amino acid sequence at least about 70%, at least about 80%, at least about 90%, at least about 95%, at least about 96%, at least about 97%, at least about 98%, or at least about 99% sequence identity to an amino acid sequence selected from the group consisting of SEQ ID NOs: 4, 14, 24, 34, and 44. In some embodiments, the VL comprises an amino acid sequence selected from the group consisting of SEQ ID NOs: 4, 14, 24, 34, and 44.

In some embodiments, (a) the VH comprises the amino acid sequence set forth in SEQ ID NO:2 and the VL comprises the amino acid sequence set forth in SEQ ID NO:4; (b) the VH comprises the amino acid sequence set forth in SEQ ID NO:12 and the VL comprises the amino acid sequence set forth in SEQ ID NO:14; (c) the VH comprises the amino acid sequence set forth in SEQ ID NO:22 and the VL comprises the amino acid sequence set forth in SEQ ID NO:24; (d) the VH comprises the amino acid sequence set forth in SEQ ID NO:32 and the VL comprises the amino acid sequence set forth in SEQ ID NO:34; or (e) the VH comprises the amino acid sequence set forth in SEQ ID NO:42 and the VL comprises the amino acid sequence set forth in SEQ ID NO:44.

In some embodiments, (a) the antibody comprises a heavy chain comprising the amino acid sequence set forth in SEQ ID NO:58, and a light chain comprising the amino acid sequence set forth in SEQ ID NO:60; (b) the antibody comprises a heavy chain comprising the amino acid sequence set forth in SEQ ID NO:130, and a light chain comprising the amino acid sequence set forth in SEQ ID NO:60; (c) the antibody comprises a heavy chain comprising the amino acid sequence set forth in SEQ ID NO:62, and a light chain comprising the amino acid sequence set forth in SEQ ID NO:64; (d) the antibody comprises a heavy chain comprising the amino acid sequence set forth in SEQ ID NO:66, and a light chain comprising the amino acid sequence set forth in SEQ ID NO:68; or (e) the antibody comprises a heavy chain comprising the amino acid sequence set forth in SEQ ID NO:70, and a light chain comprising the amino acid sequence set forth in SEQ ID NO:72.

In some embodiments, the antibody binds an epitope on human MICA comprising one or more amino acid residues of human MICA selected from the group consisting of G254, D255, L257, Y264, W267, and any combination thereof corresponding to SEQ ID NO: 51, as determined by yeast surface display. In some embodiments, the antibody binds an epitope on human MICA comprising G254, D255, L257, Y264, and W267 corresponding to SEQ ID NO: 51, as determined by yeast surface display. In some embodiments, the antibody binds an epitope on human MICA comprising amino acid residues W150-M163 corresponding to SEQ ID NO: 51, as determined by hydrogen/deuterium exchange mass spectrometry (HDX-MS). In some embodiments, the antibody binds an epitope on human MICA comprising amino acid residues Y231-T238 corresponding to SEQ ID NO: 51, as determined by hydrogen/deuterium exchange mass spectrometry (HDX-MS). In some embodiments, the antibody binds an epitope on human MICA comprising amino acid residues D255-Q265 corresponding to SEQ ID NO: 51, as determined by hydrogen/deuterium exchange mass spectrometry (HDX-MS). In some embodiments, the epitope comprises amino acid residues W253-W267 corresponding to SEQ ID NO: 51, as determined by hydrogen/deuterium exchange mass spectrometry (HDX-MS). In some embodiments, the antibody binds an epitope on human MICA comprising L201-N220 corresponding to SEQ ID NO:51, as determined by hydrogen/deuterium exchange mass spectrometry (HDX-MS). In some embodiments, the antibody binds an epitope on human MICA comprising T238-Q252 corresponding to SEQ ID NO:51, as determined by hydrogen/deuterium exchange mass spectrometry (HDX-MS). In some embodiments, the antibody binds an epitope on human MICA comprising L201-N220 and T238-Q252 corresponding to SEQ ID NO:51, as determined by hydrogen/deuterium exchange mass spectrometry (HDX-MS). In some embodiments, the antibody binds an epitope on human MICA comprising R240, Q241, D242, V244, and R279 corresponding to SEQ ID NO:51, as determined by yeast surface display. In some embodiments, the antibody binds an epitope on human MICA comprising P258, G260, G262, and Y264 corresponding to SEQ ID NO:51, as determined by yeast surface display. In some embodiments, the antibody binds an epitope on human MICA comprising at least 1, at least 2, at least 3, at least 4, at least 5, at least 6, at least 7, at least 8, at least 9, or at least 10 residues selected from T222, T224, R226, W233, N234, H248, D249, Q251, Q252, W253, G254, D255, V256, L257, P258, D259, G260, N261, Y264, Q265, W267, and A269, as determined by X-ray co-crystallography. In some embodiments, the antibody binds an epitope on human MICA comprising at least two residues selected from T222, T224, R226, W233, N234, H248, D249, Q251, Q252, W253, G254, D255, V256, L257, P258, D259, G260, N261, Y264, Q265, W267, and A269, as determined by X-ray co-crystallography. In some embodiments, the antibody binds an epitope on human MICA comprising at least four residues selected from T222, T224, R226, W233, N234, H248, D249, Q251, Q252, W253, G254, D255, V256, L257, P258, D259, G260, N261, Y264, Q265, W267, and A269, as determined by X-ray co-crystallography. In some embodiments, the antibody binds an epitope on human MICA comprising at least six residues selected from T222, T224, R226, W233, N234, H248, D249, Q251, Q252, W253, G254, D255, V256, L257, P258, D259, G260, N261, Y264, Q265, W267, and A269, as determined by X-ray co-crystallography. In some embodiments, the antibody binds an epitope on human MICA comprising T222, T224, R226, W233, N234, H248, D249, Q251, Q252, W253, G254, D255, V256, L257, P258, D259, G260, N261, Y264, Q265, W267, and A269, as determined by X-ray co-crystallography.

In some embodiments, the antibody is selected from the group consisting of an IgG1, an IgG2, an IgG3, an IgG4 or a variant thereof. In some embodiments, the antibody is non-fucosylated. In some embodiments, the antibody comprises a constant region in the heavy chain, and wherein the constant region comprises a G to A mutation at a position that corresponds to residue 234 in SEQ ID NO: 58.

Another aspect of the present disclosure is directed to an antibody that specifically binds to human MHC class I polypeptide-related sequence A (MICA) and/or human MHC class I polypeptide-related sequence B (MICB), comprising a heavy chain variable region (VH) and a light chain variable region (VL); wherein the VH comprises a VH complementarity determining region (CDR) 1, a VH-CDR2, and a VH-CDR3 and the VL comprises a VL-CDR1, a VL-CDR2, and a VL-CDR3; wherein the VH-CDR1 comprises the amino acid sequence set forth in SEQ ID NO:5, the VH-CDR2 comprises the amino acid sequence set forth in SEQ ID NO:6, the VH-CDR3 comprises the amino acid sequence set forth in SEQ ID NO:7, the VL-CDR1 comprises the amino acid sequence set forth in SEQ ID NO:8, the VL-CDR2 comprises the amino acid sequence set forth in SEQ ID NO:9, and the VL-CDR3 comprises the amino acid sequence set forth in SEQ ID NO:10; and wherein the antibody is nonfucosylated. In some embodiments, the VH comprises the amino acid sequence set forth in SEQ ID NO:2 and the VL comprises the amino acid sequence set forth in SEQ ID NO:4. In some embodiments, the antibody comprises a constant region in the heavy chain that comprises a G to A mutation at a position that corresponds to residue 234 in SEQ ID NO: 58. In some embodiments, the antibody comprises a heavy chain comprising the amino acid sequence set forth in SEQ ID NO:58, and a light chain comprising the amino acid sequence set forth in SEQ ID NO:60. In some embodiments, the antibody comprises a heavy chain comprising the amino acid sequence set forth in SEQ ID NO:130, and a light chain comprising the amino acid sequence set forth in SEQ ID NO:60. In some embodiments, the antibody is nonfucosylated. In some embodiments, the antibody is hypofucosylated.

Some aspects of the present disclosure is directed to an antibody that specifically binds to human MHC class T polypeptide-related sequence A (MICA) and/or human MHC class T polypeptide-related sequence B (MICB), comprising a heavy chain comprising the amino acid sequence set forth in SEQ ID NO: 58, and a light chain comprising the amino acid sequence set forth in SEQ ID NO:60, wherein the antibody is nonfucosylated.

In some embodiments, the antibody is produced by a cell line that has reduced or eliminated expression of fucosyltransferase.

Some aspects of the present disclosure are directed to a polynucleotide or a set of polynucleotides encoding an antibody described herein. Other aspects of the present disclosure are directed to a vector or a set of vectors comprising the polynucleotide or set of polynucleotides. Other aspects of the present disclosure are directed to a host cell comprising the antibody, polynucleotide or set of polynucleotides, or vector.

Some aspects of the present disclosure are directed to an immunoconjugate comprising the antibody and a therapeutic agent. In some embodiments, the therapeutic agent is selected from the group consisting of a cytotoxin, a non-cytotoxic drug, a radioactive agent, a second antibody, an enzyme, an anti-neoplastic agent, and any combination thereof. In some embodiments, the cytotoxin is selected from the group consisting of dolastatin, monomethyl auristatin E (MMAE), maytansine, duocarmycin, calicheamicin, pyrrolobenzodiazepine, duocarmycin, centanamycin, SN38, doxorubicin, a derivative thereof, a synthetic analog thereof, and any combination thereof. In some embodiments, the cytotoxin comprises Cytotoxin A. In some embodiments, Some aspects of the present disclosure are directed to pharmaceutical compositions comprising the antibody, polynucleotide or set of polynucleotides, vector or set of vectors, or immunoconjugate and a pharmaceutically acceptable excipient. In some embodiments, the pharmaceutical composition comprises a second antibody. In some embodiments, the second antibody specifically binds a protein selected from the group consisting of PD-1, PD-L1, CTLA-4, LAG3, TIGIT, TIM3, NKG2a, OX40, ICOS, CD137, KIR, TGFβ, IL-10, IL-8, IL-2, CD96, VISTA, B7-H4, Fas ligand, CXCR4, mesothelin, CD27, GITR, and any combination thereof.

Some aspects of the present disclosure are directed to method of treating a cancer in a subject in need thereof, comprising administering to the subject the antibody, the polynucleotide or the set of polynucleotides, the vector or the set of vectors, the host cell, the immunoconjugate, or the pharmaceutical composition. In some embodiments, the cancer comprises a tumor. In some embodiments, the method comprises administering to the subject a second therapy. In some embodiments, the second therapy comprises an effective amount of an antibody that specifically binds a protein selected from Inducible T cell Co-Stimulator (ICOS), CD137 (4-1BB), CD134 (OX40), NKG2A, CD27, CD96, Glucocorticoid-Induced TNFR-Related protein (GITR), and Herpes Virus Entry Mediator (HVEM), Programmed Death-1 (PD-1), Programmed Death Ligand-1 (PD-L1), CTLA-4, B and T Lymphocyte Attenuator (BTLA), T cell Immunoglobulin and Mucin domain-3 (TIM-3), Lymphocyte Activation Gene-3 (LAG-3), adenosine A2a receptor (A2aR), Killer cell Lectin-like Receptor G1 (KLRG-1), Natural Killer Cell Receptor 2B4 (CD244), CD160, T cell Immunoreceptor with Ig and ITIM domains (TIGIT), and the receptor for V-domain Ig Suppressor of T cell Activation (VISTA), KIR, TGFβ, IL-10, IL-8, IL-2, B7-H4, Fas ligand, CXCR4, mesothelin, CEACAM-1, CD52, HER2, and any combination thereof. In some embodiments, the second therapy comprises an effective amount of pegylated IL-10, IL-10-Fc, or pegylated IL-2. In some embodiments, the second therapy comprises a chemotherapeutic agent for cancer, radiation, an agent that activates innate immune cells, and/or an agent that enhances survival of NK and/or CD8+ T-cells.

Other features and advantages of the instant disclosure will be apparent from the following detailed description and examples which should not be construed as limiting. The contents of all cited references, including scientific articles, newspaper reports, GenBank entries, patents and patent applications cited throughout this application are expressly incorporated herein by reference.

BRIEF DESCRIPTION OF THE DRAWINGS/FIGURES

FIGS. 1A-1D are sequence alignments of the anti-MICA/B antibody MICA.36 (19G6), heavy chain variable region (FIGS. 1A-1B; nucleotide: SEQ ID NO: 1; amino acid: SEQ ID NO: 2) and light chain variable region (FIGS. 1C-1D; nucleotide: SEQ ID NO: 3; amino acid: SEQ ID NO: 4). FIGS. 1A and 1C show the nucleotide sequences and corresponding amino acid sequences for MICA.36 (19G6), heavy chain variable region (FIG. 1A) and light chain variable region (FIG. 1C). FIGS. 1B and 1D show the germline sequences relative to the MICA.36 (19G6) ("input") sequences for the heavy chain variable region (FIG. 1B) and light chain variable region (FIG. 1D). Complementarity Determining Regions (CDRs) determined by Kabat numbering are marked by horizontal lines and labeled accordingly (FIGS. 1A-1D).

FIGS. 2A-2F are sequence alignments of the anti-MICA/B antibody MICA.52 (16A5), heavy chain variable region (FIGS. 2A-2B; nucleotide: SEQ ID NO: 11; amino acid: SEQ ID NO: 12), light chain variable region 1 (FIGS. 2C-2D; nucleotide: SEQ ID NO: 13; amino acid: SEQ ID NO: 14), and light chain variable region 2 (FIGS. 2E-2F; nucleotide: SEQ ID NO: 127; amino acid: SEQ ID NO: 128). FIGS. 2A, 2C, and 2E show the nucleotide sequences and corresponding amino acid sequences for the anti-MICA/B antibody 16A5, heavy chain variable region (FIG. 2A) and light chain variable regions 1 (MICA.52) and 2 (MICA.53) (FIGS. 2C and 2E, respectively). FIGS. 2B, 2D, and 2F show the germline sequences relative to the MICA.52 or MICA.53 (16A5) ("input") sequences for the heavy chain variable region (FIG. 2B) and light chain variable regions 1 and 2 (FIGS. 2D and 2F). Complementarity Determining Regions (CDRs) determined by Kabat numbering are marked by horizontal lines and labeled accordingly (FIGS. 2A-2F).

FIGS. 3A-3D are sequence alignments of the anti-MICA/B antibody MICA.54 (24G11), heavy chain variable region (FIGS. 3A-3B; nucleotide: SEQ ID NO: 21; amino acid: SEQ ID NO: 22) and light chain variable region (FIGS. 3C-3D; nucleotide: SEQ ID NO: 23; amino acid: SEQ ID NO: 24). FIGS. 3A and 3C show the nucleotide sequences and corresponding amino acid sequences for the anti-MICA/B antibody MICA.54 (24G11), heavy chain variable region (FIG. 3A) and light chain variable region (FIG. 3C). FIGS. 3B and 3D show the germline sequences relative to the MICA.54 (24G11) ("input") sequences for the heavy chain variable region (FIG. 3B) and light chain variable region (FIG. 3D). Complementarity Determining Regions (CDRs) determined by Kabat numbering are marked by horizontal lines and labeled accordingly (FIGS. 3A-3D).

FIGS. 4A-4D are sequence alignments of the anti-MICA/B antibody MICA.2 (3F5), heavy chain variable region (FIGS. 4A-4B; nucleotide: SEQ ID NO: 31; amino acid: SEQ ID NO: 32) and light chain variable region (FIGS. 4C-4D; nucleotide: SEQ ID NO: 33; amino acid: SEQ ID NO: 34). FIGS. 4A and 4C show the nucleotide sequences and corresponding amino acid sequences for the anti-MICA/B antibody MICA.2 (3F5), heavy chain variable region (FIG. 4A) and light chain variable region (FIG. 4B). FIGS. 4B and 4D show the germline sequences relative to the MICA.2 (3F5) ("input") sequences for the heavy chain variable region (FIG. 4B) and light chain variable region (FIG. 4D). Complementarity Determining Regions (CDRs) determined by Kabat numbering are marked by horizontal lines and labeled accordingly (FIGS. 4A-4D).

FIGS. 5A-5D are sequence alignments of the anti-MICA/B antibody 71C2, heavy chain variable region (FIGS. 5A-5B; nucleotide: SEQ ID NO: 41; amino acid: SEQ ID NO: 42) and light chain variable region (FIGS. 5C-5D; nucleotide: SEQ ID NO: 43; amino acid: SEQ ID NO: 44). FIGS. 5A and 5C show the nucleotide sequences and corresponding amino acid sequences for the anti-MICA/B antibody 71C2, heavy chain variable region (FIG. 5A) and light chain variable region (FIG. 5B). FIGS. 5B and 5D show the germline sequences relative to the 71C2 ("input") sequences for the heavy chain variable region (FIG. 5B) and light chain variable region (FIG. 5D). Complementarity Determining Regions (CDRs) determined by Kabat numbering are marked by horizontal lines and labeled accordingly (FIGS. 5A-5D).

Figures 6A, 6B, 6C:
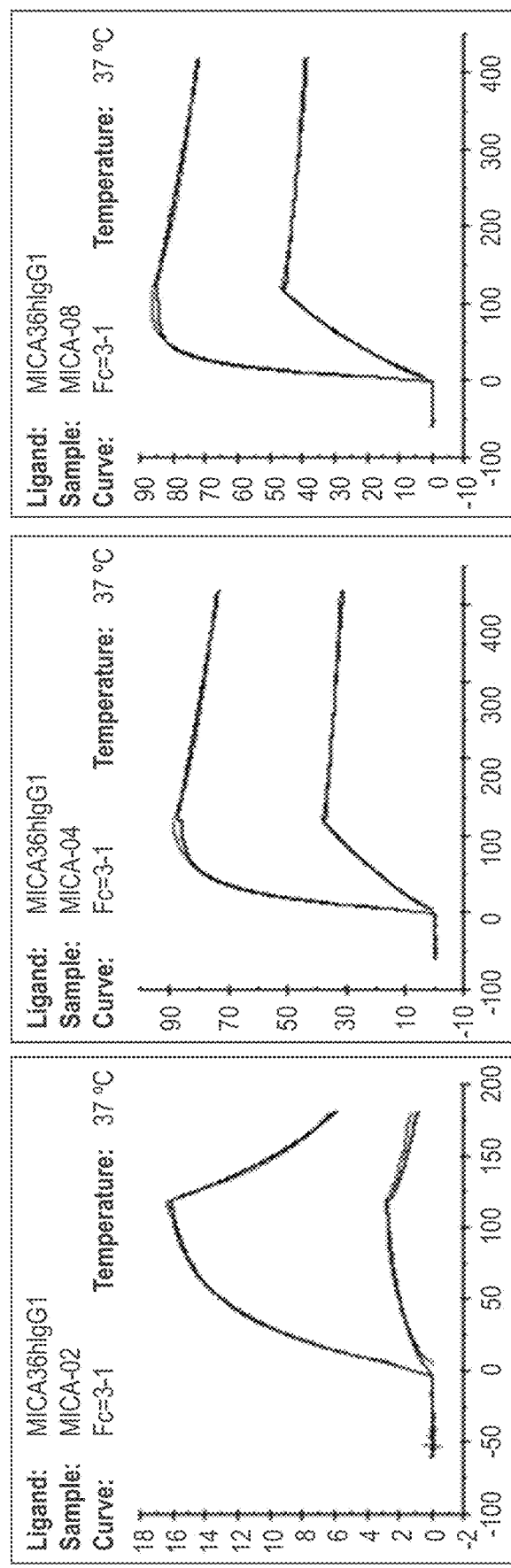
FIGS. 6A-6H are graphical representations of the binding affinity kinetics of the anti-MICA/B antibodies: MICA.36 (FIGS. 6A-6D) and MICA.38 (FIGS. 6E-6H) for the MICA alleles MICA*002 (FIGS. 6A and 6E), MICA*004 (FIGS. 6B and 6F), MICA*008 (FIGS. 6C and 6G), and MICA*009 (FIGS. 6D and 6H) as measured by surface plasmon resonance (SPR).
Figures 6D, 6E, 6F:
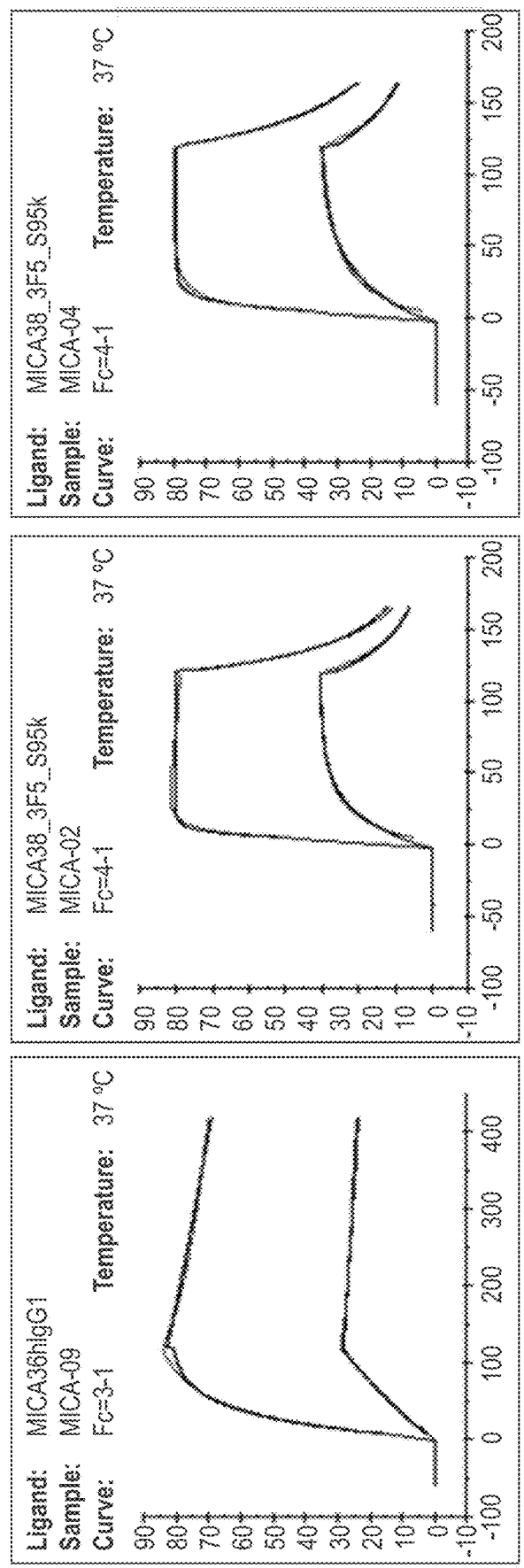
Figures 6G, 6H:
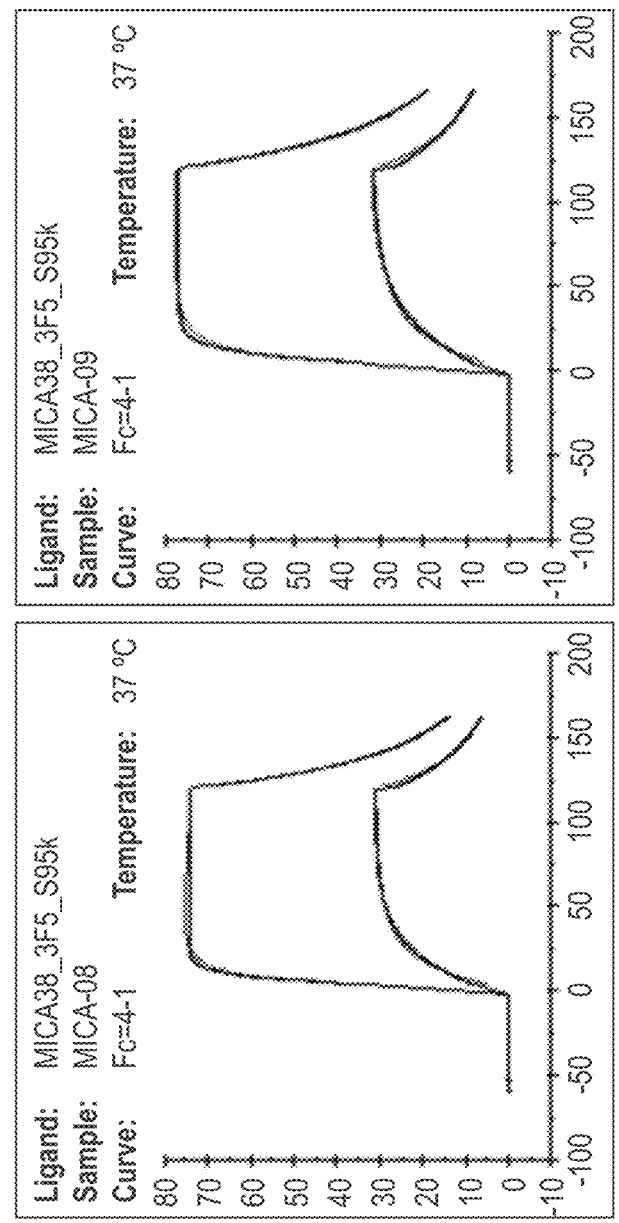
Figure 6I:
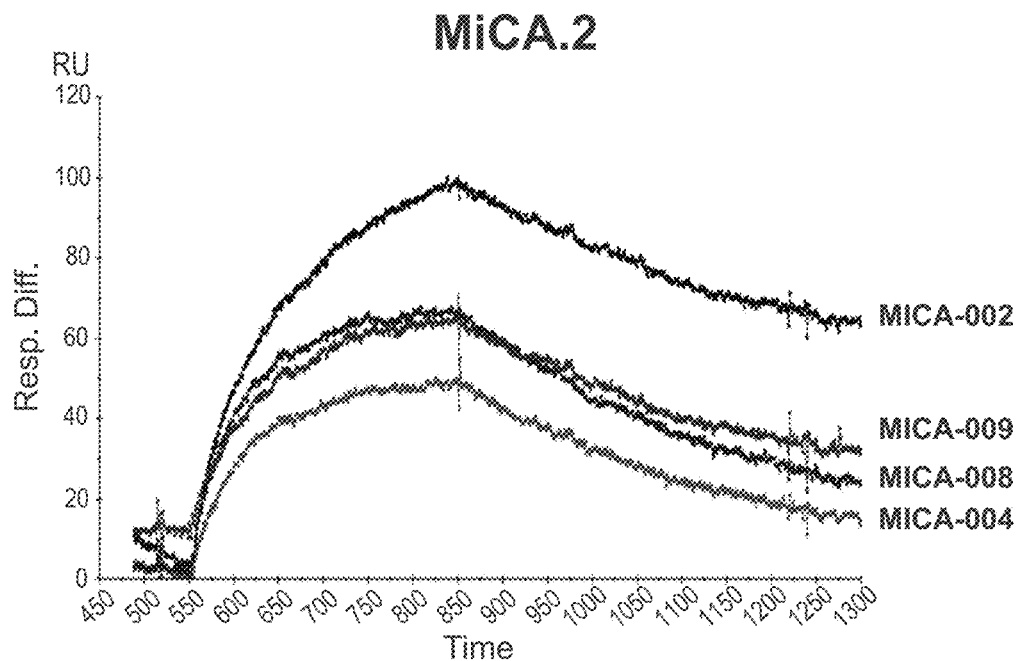
FIGS. 6I-6L are graphical representations of the binding affinity kinetics of the anti-MICA/B antibodies: MICA.2 (FIG. 6I), 16A5 (FIG. 6J), 19G6 (FIG. 6K), and 71C2 (FIG. 6L) for the MICA alleles MICA*002, MICA*004, MICA*008, and MICA*009 as measured by SPR using BIACORE® 3000 instrument.
Figure 6J:
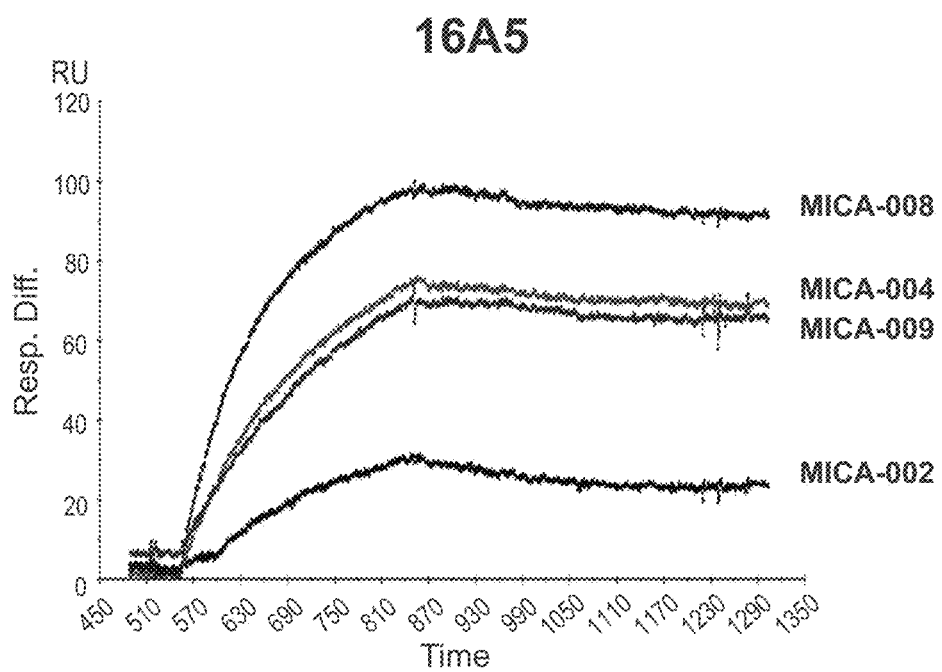
Figure 6K:
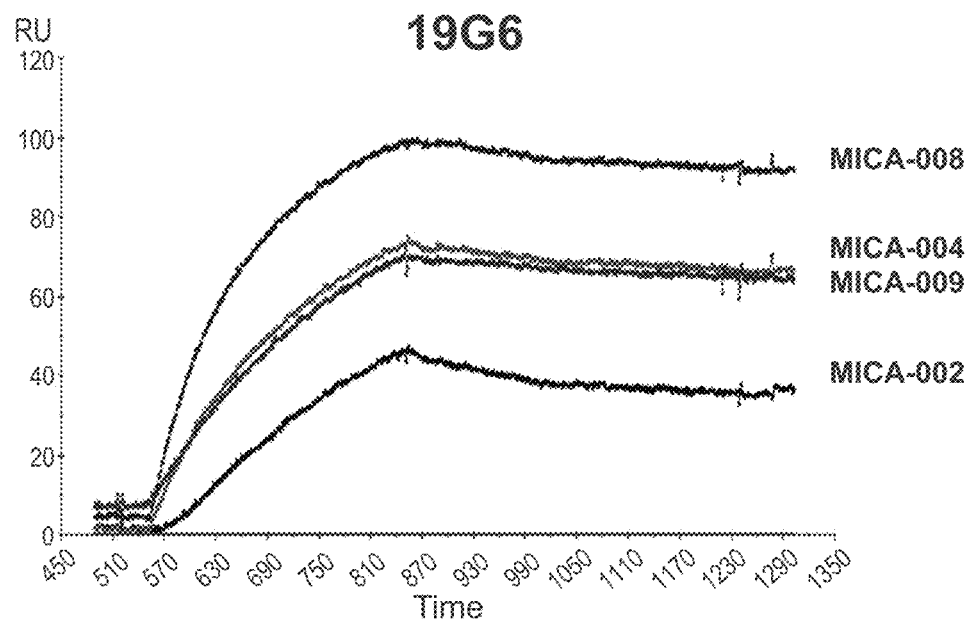
Figure 6L:
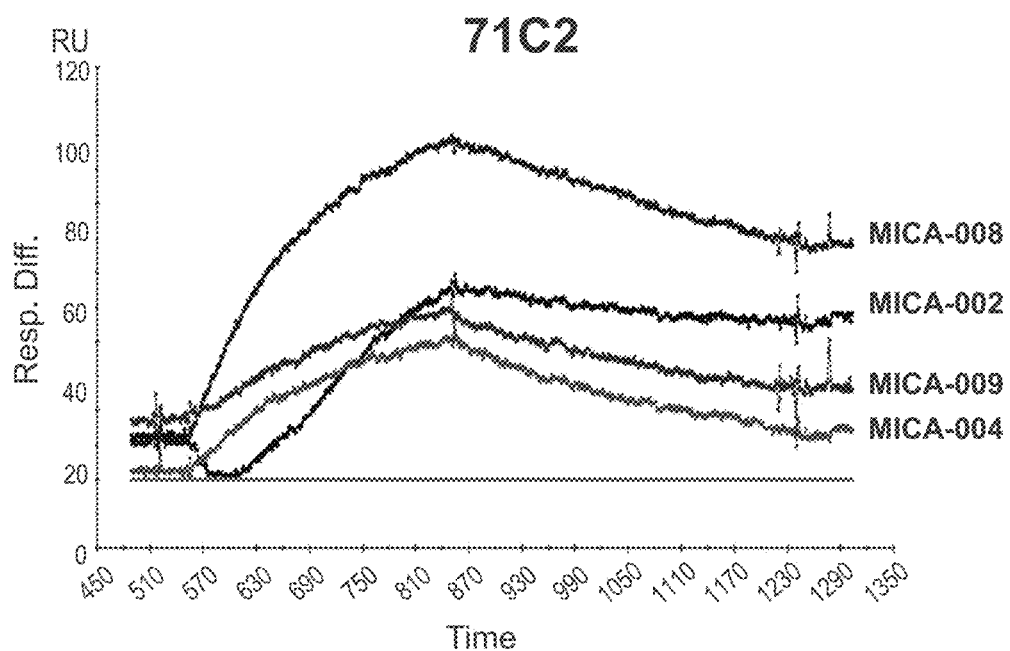
Figure 7A:
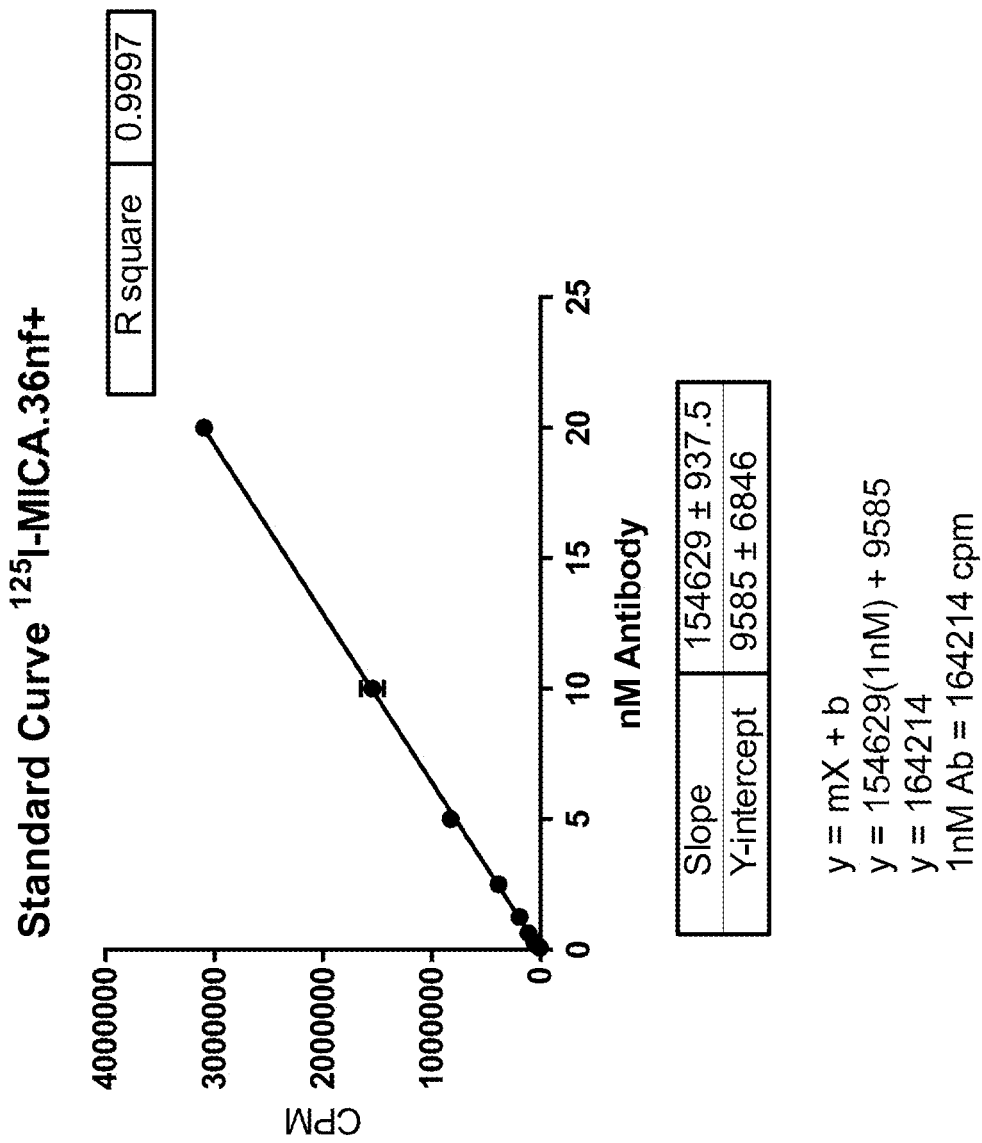
Figure 7B:
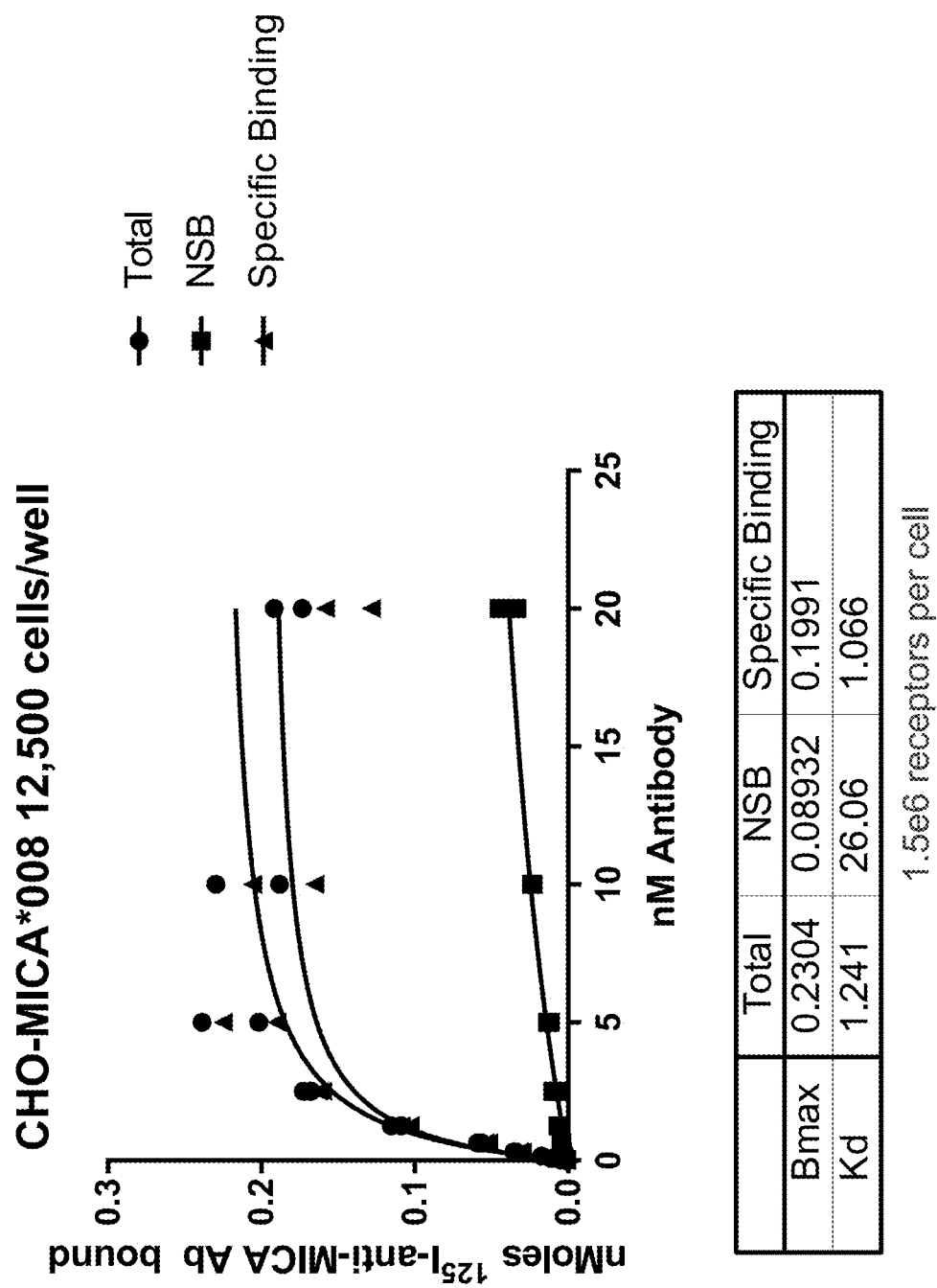
Figure 7C:
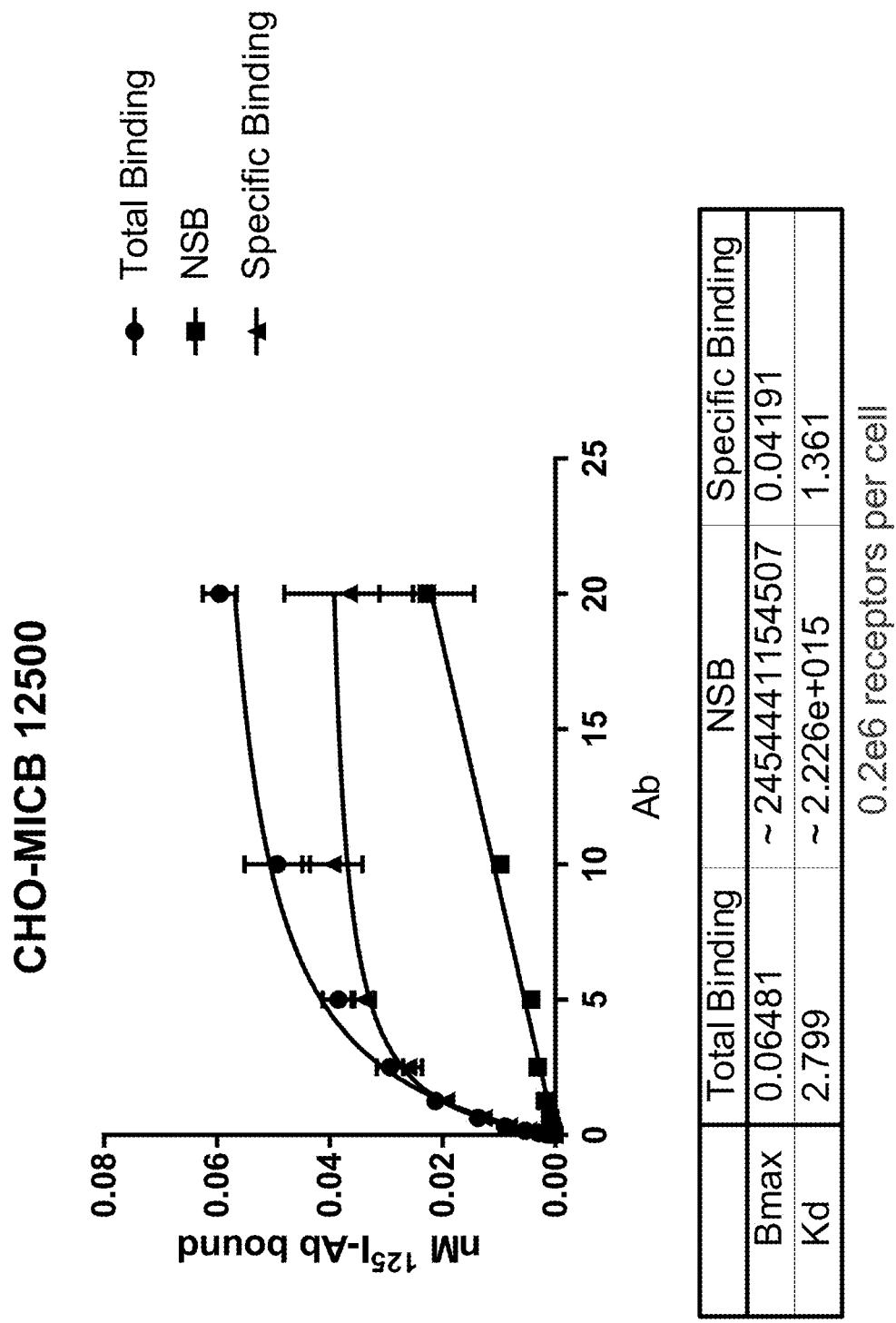
Figure 7D:
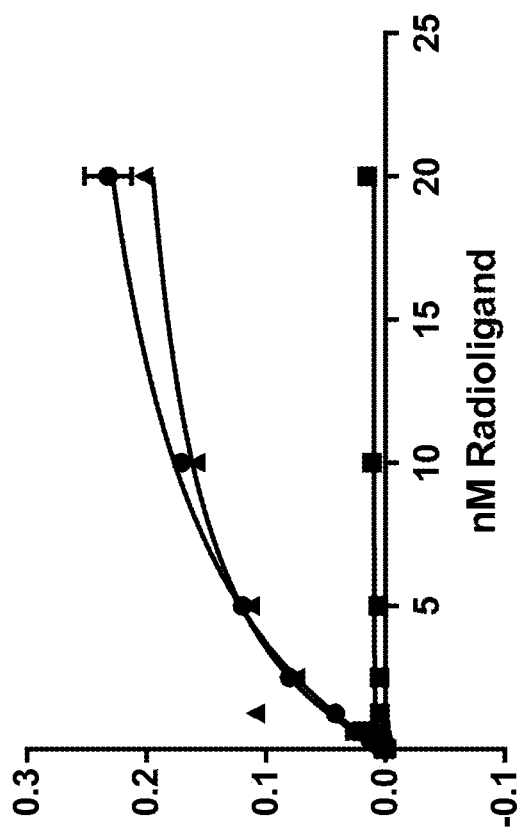
Figure 7E:
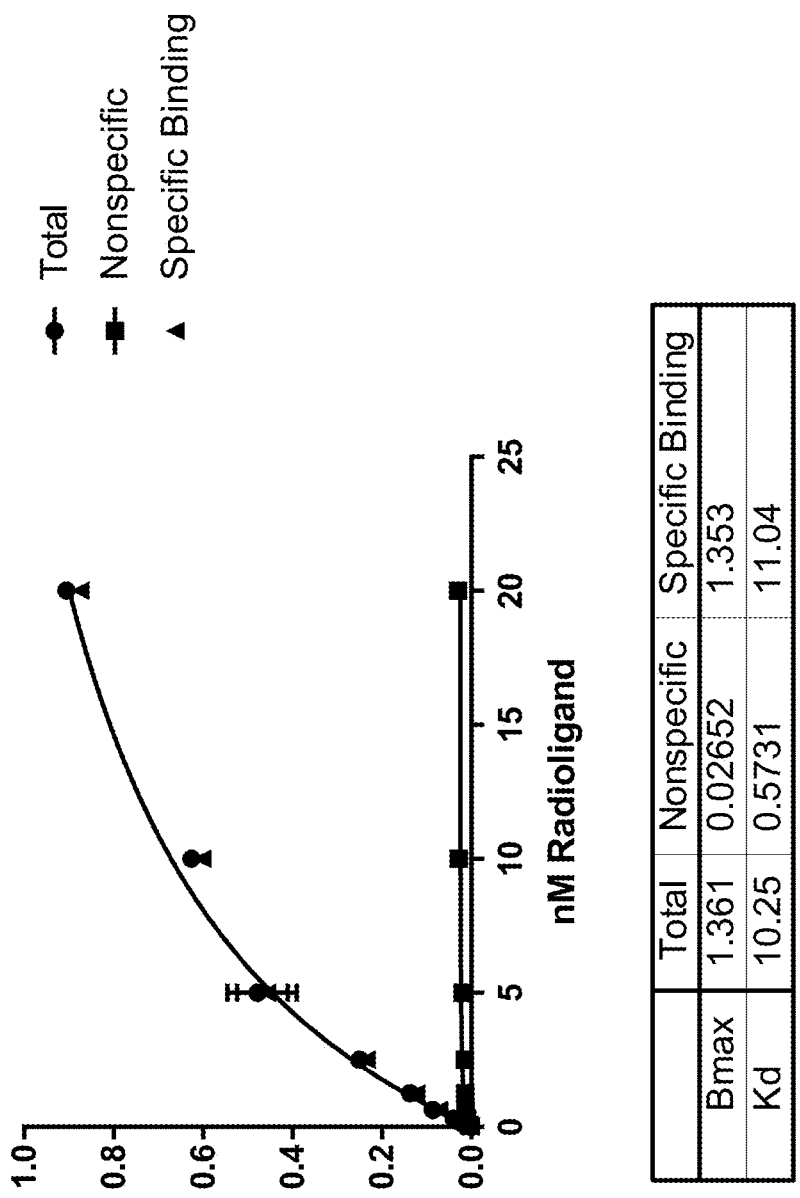
Figure 7F:
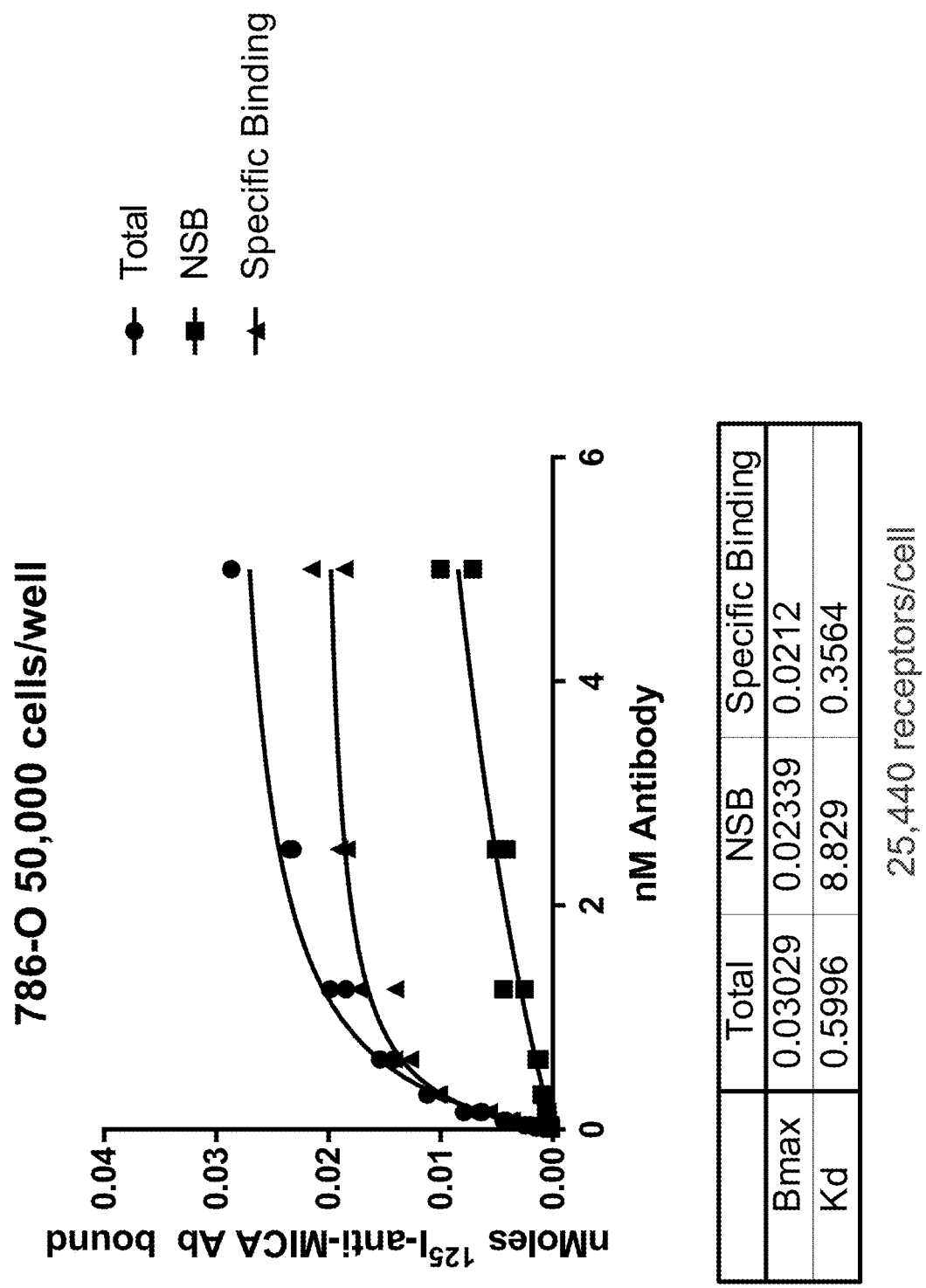
Figure 7G:
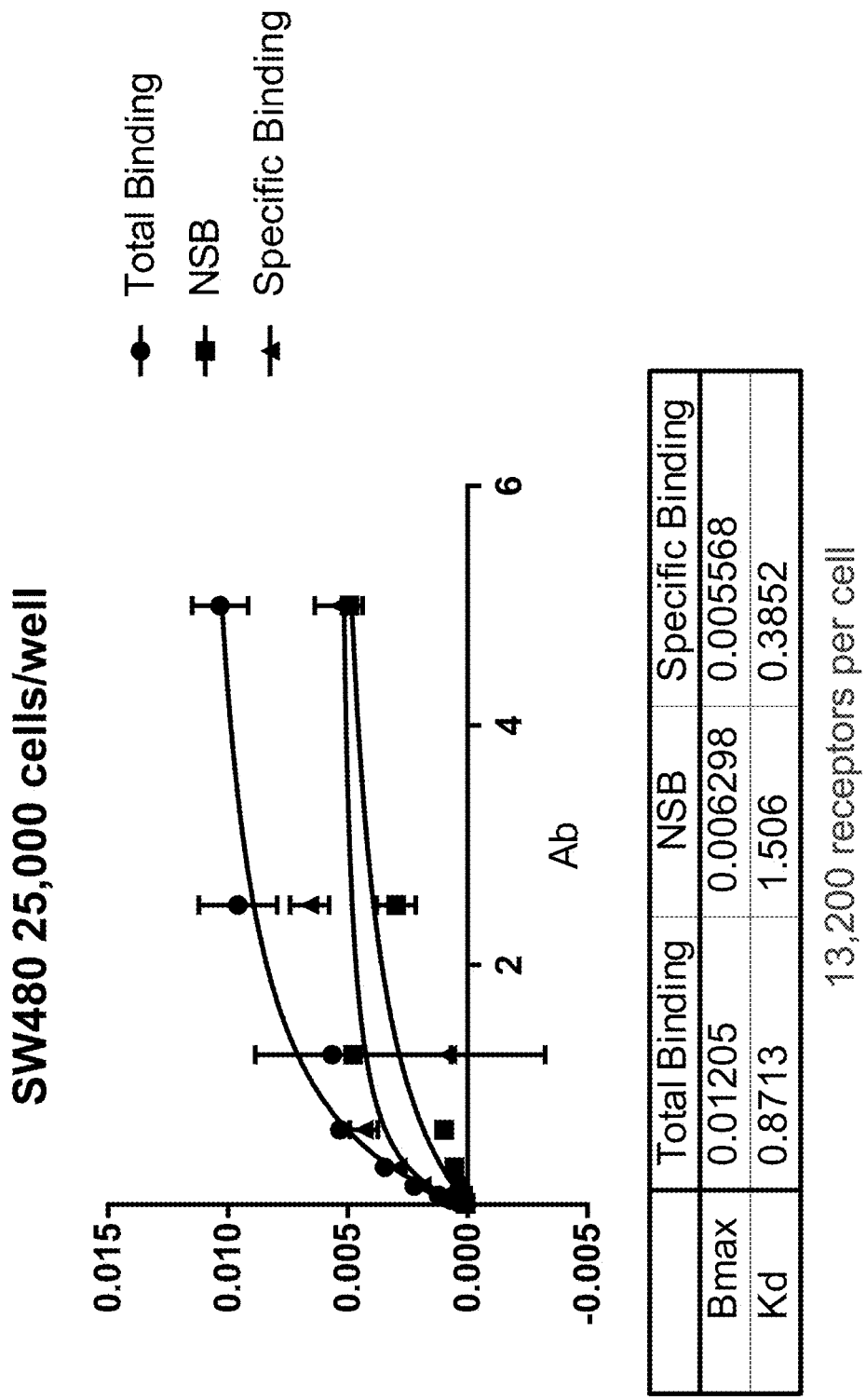

FIGS. 7A-7G are graphical representations of the specific binding activity of MICA.36 to MICA/B antigens expressed by cells in vitro, analyzed with Scatchard plots. FIG. 7A is a standard curve of titrated antibody concentration (x-axis; nM antibody) plotted against the associated counts per minute (y-axis; CPM). FIGS. 7B-7F show the specific binding, total binding, and non-specific binding (NSB) of MICA.36 to human MICA*008 (FIG. 7B), human MICB*005 (FIG. 7C), and cynomolgus monkey MICA/B (clones #4 and #6) (FIGS. 7D-7E) overexpressed in Chinese hamster ovary (CHO) cells; and human MICA/B endogenously expressed on 786-O cells (FIG. 7F) and SW480 cells (FIG. 7G).

Figures 8A, 8B:
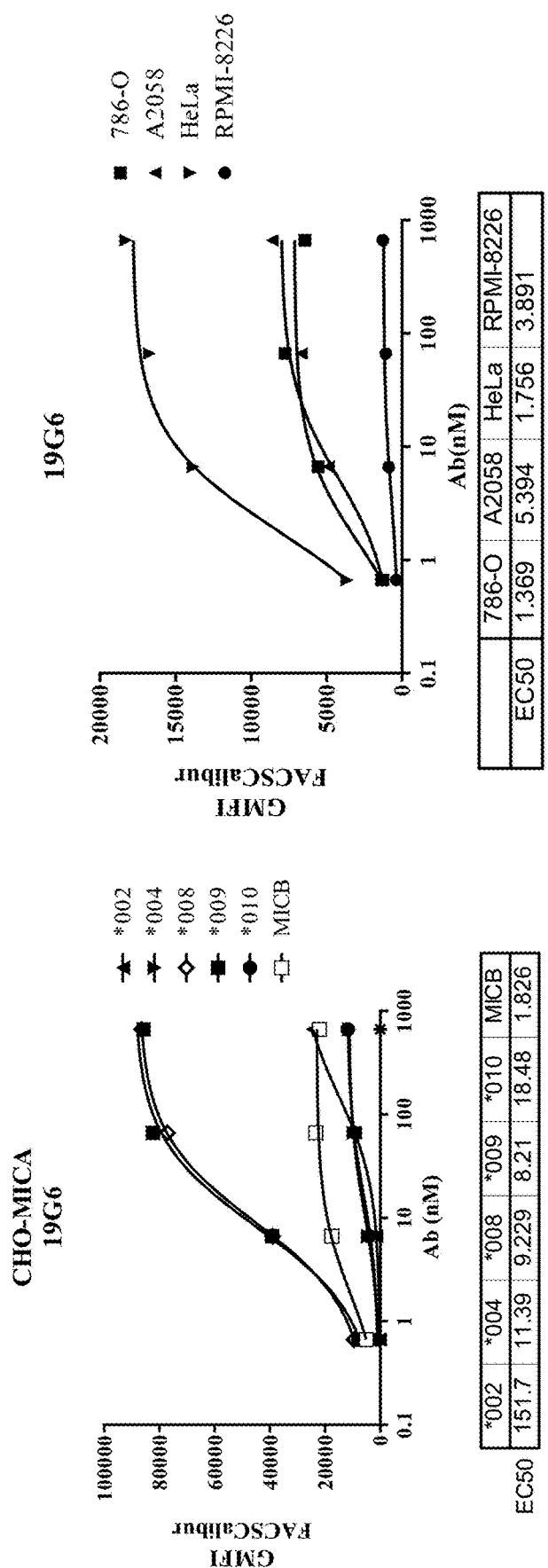
Figure 8C:
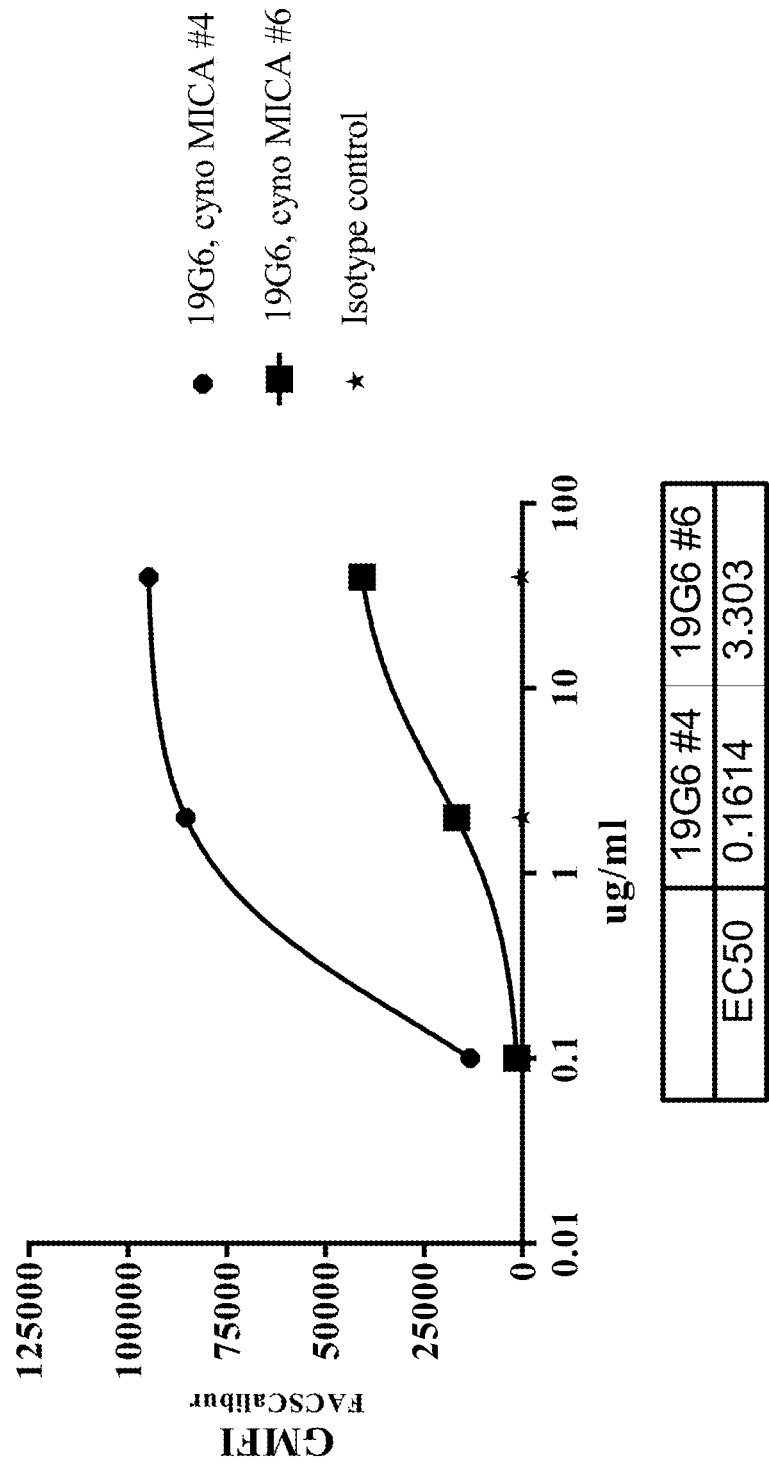
Figure 8D:
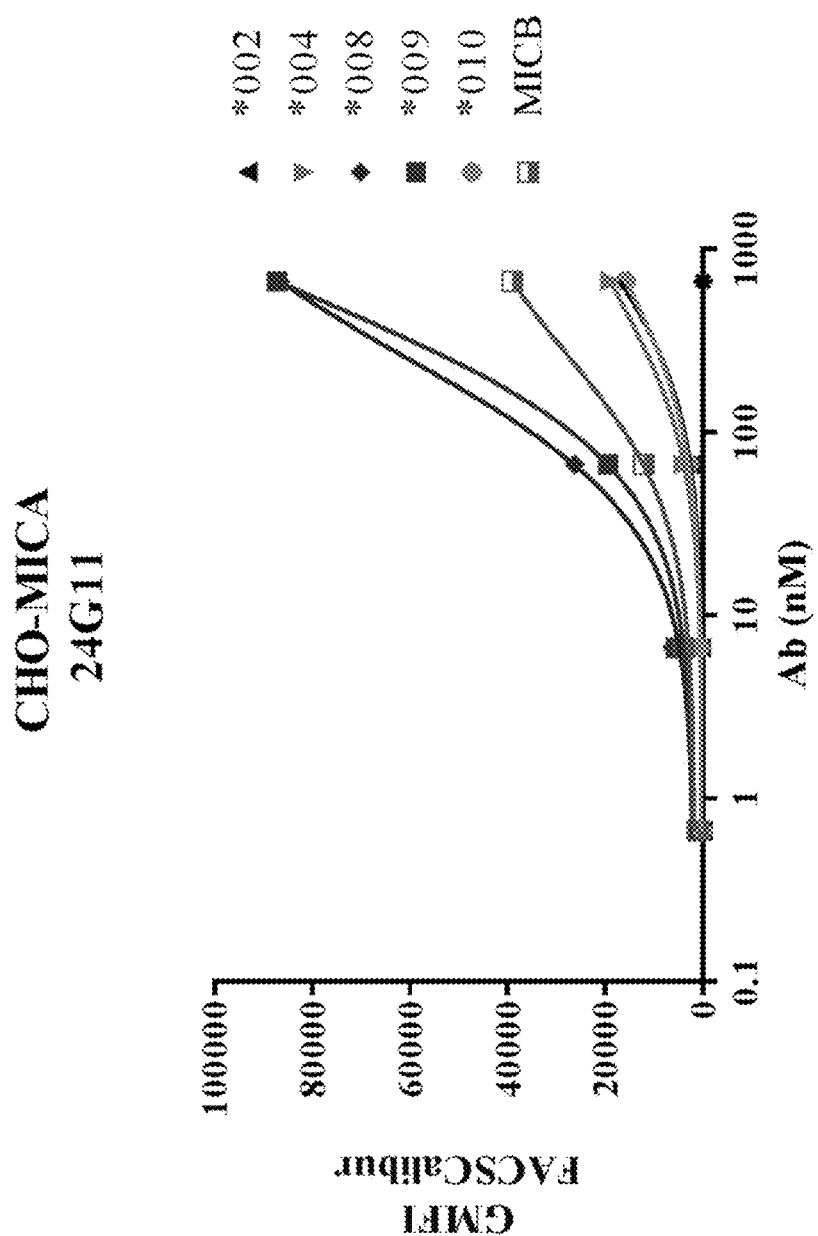
Figure 8E:
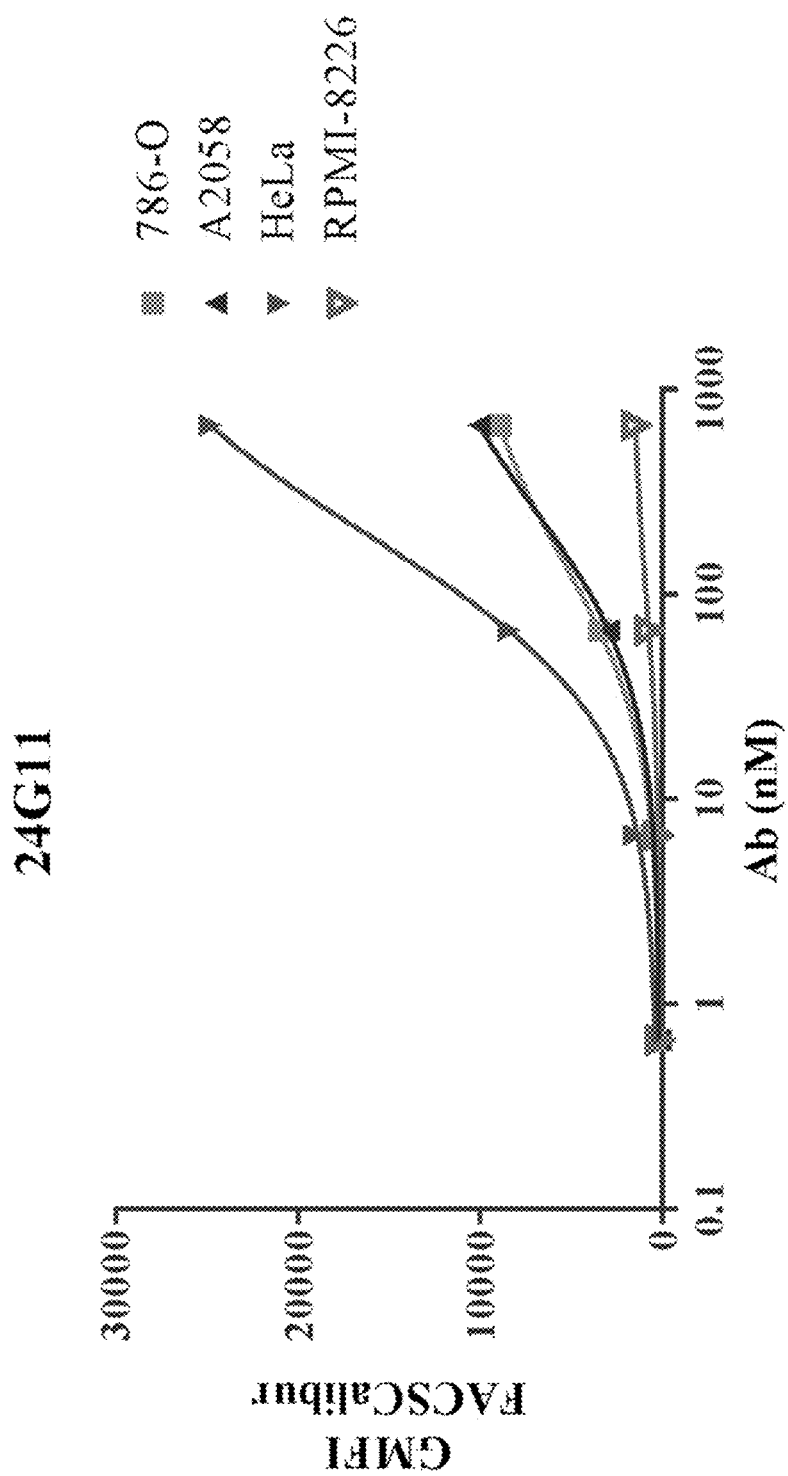
Figure 8F:
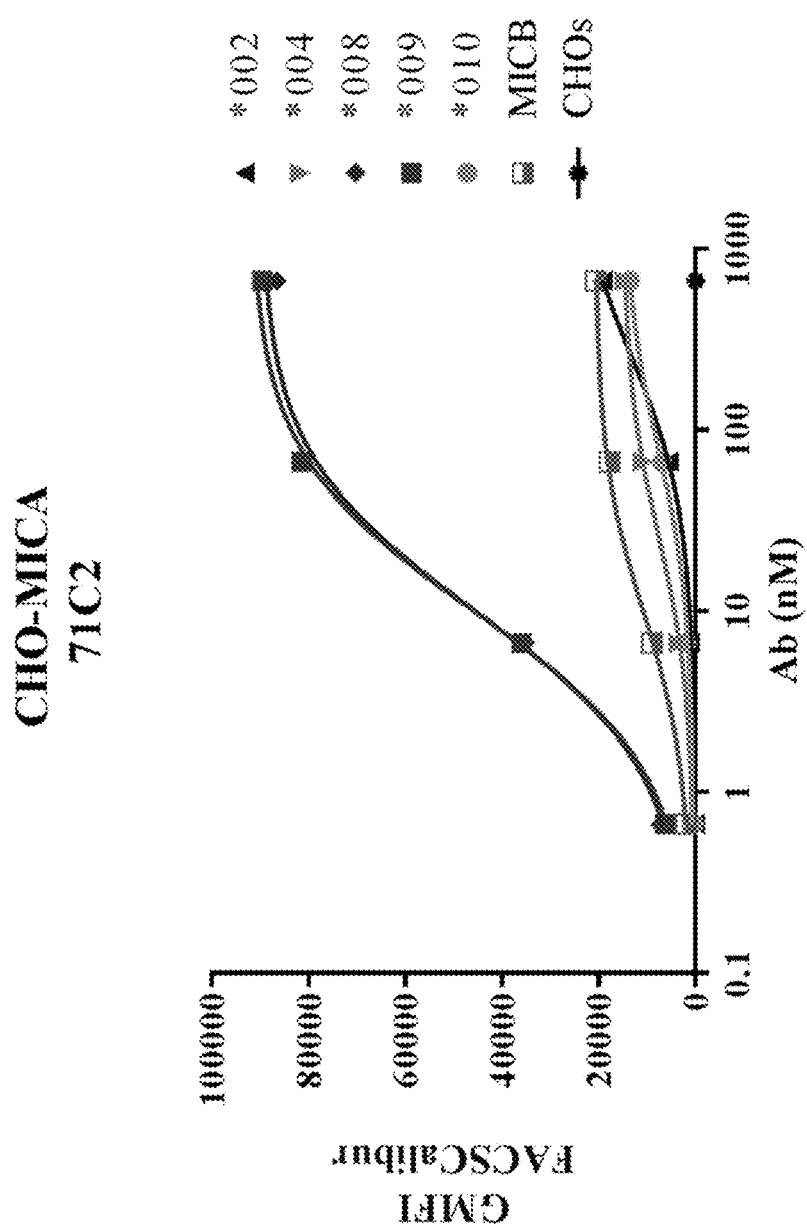
Figure 8G:
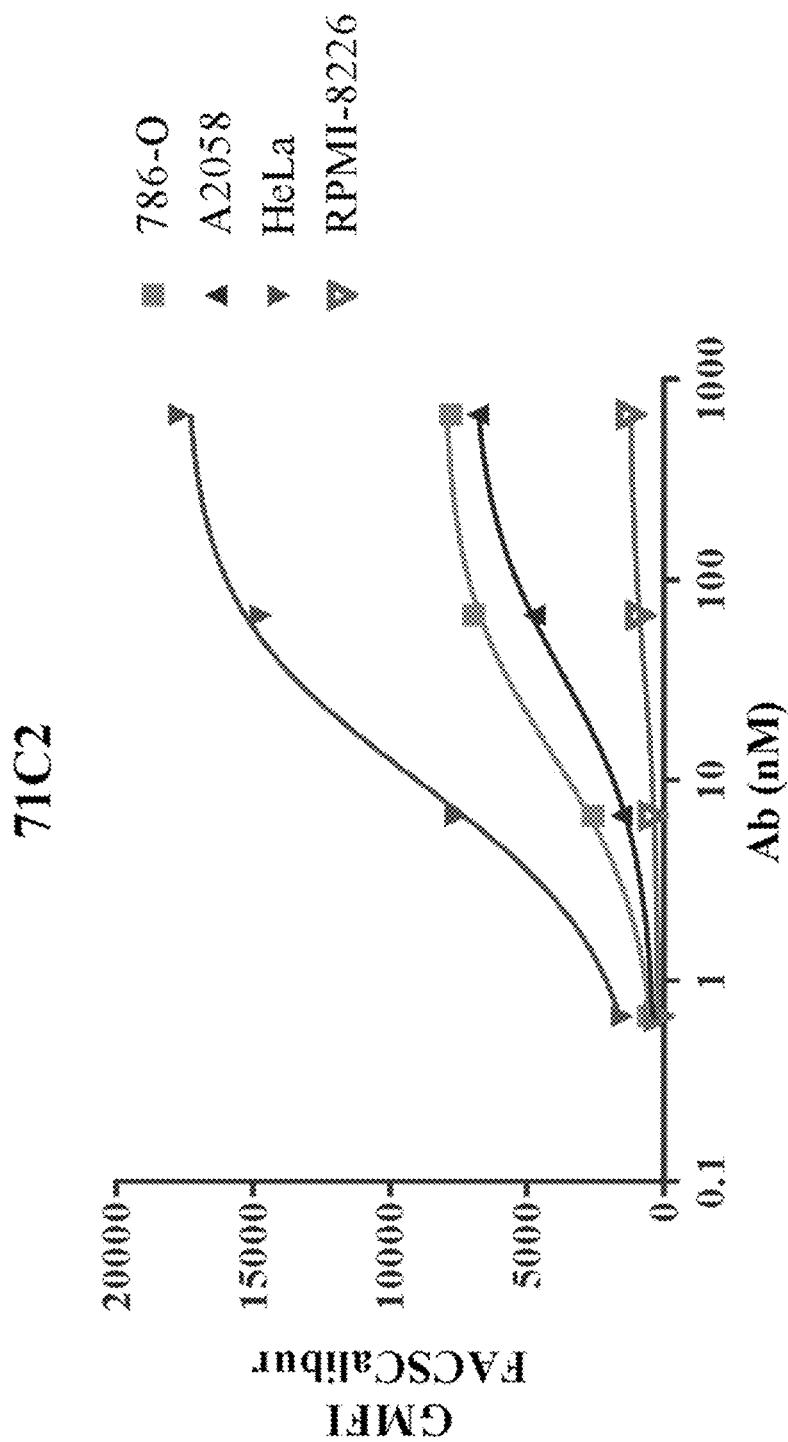
Figure 8H:
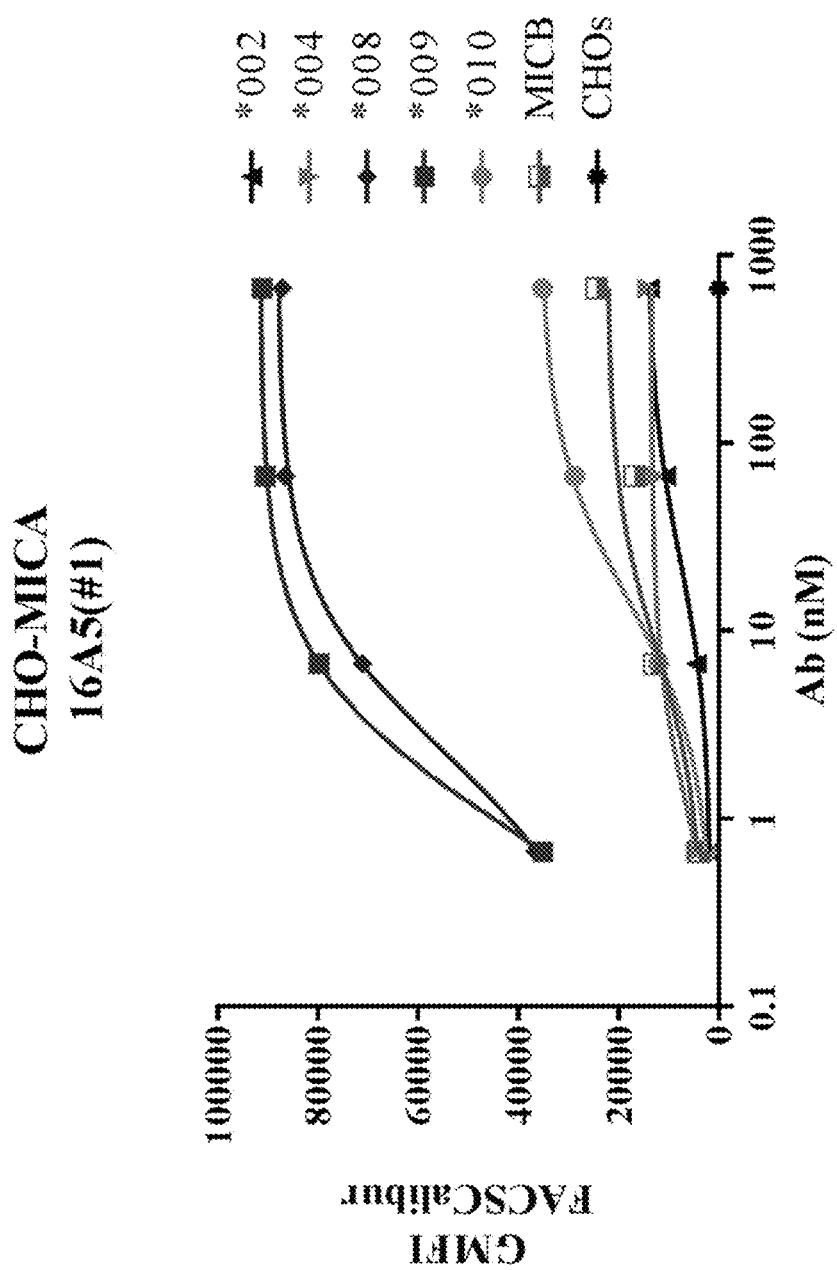
Figure 8I:
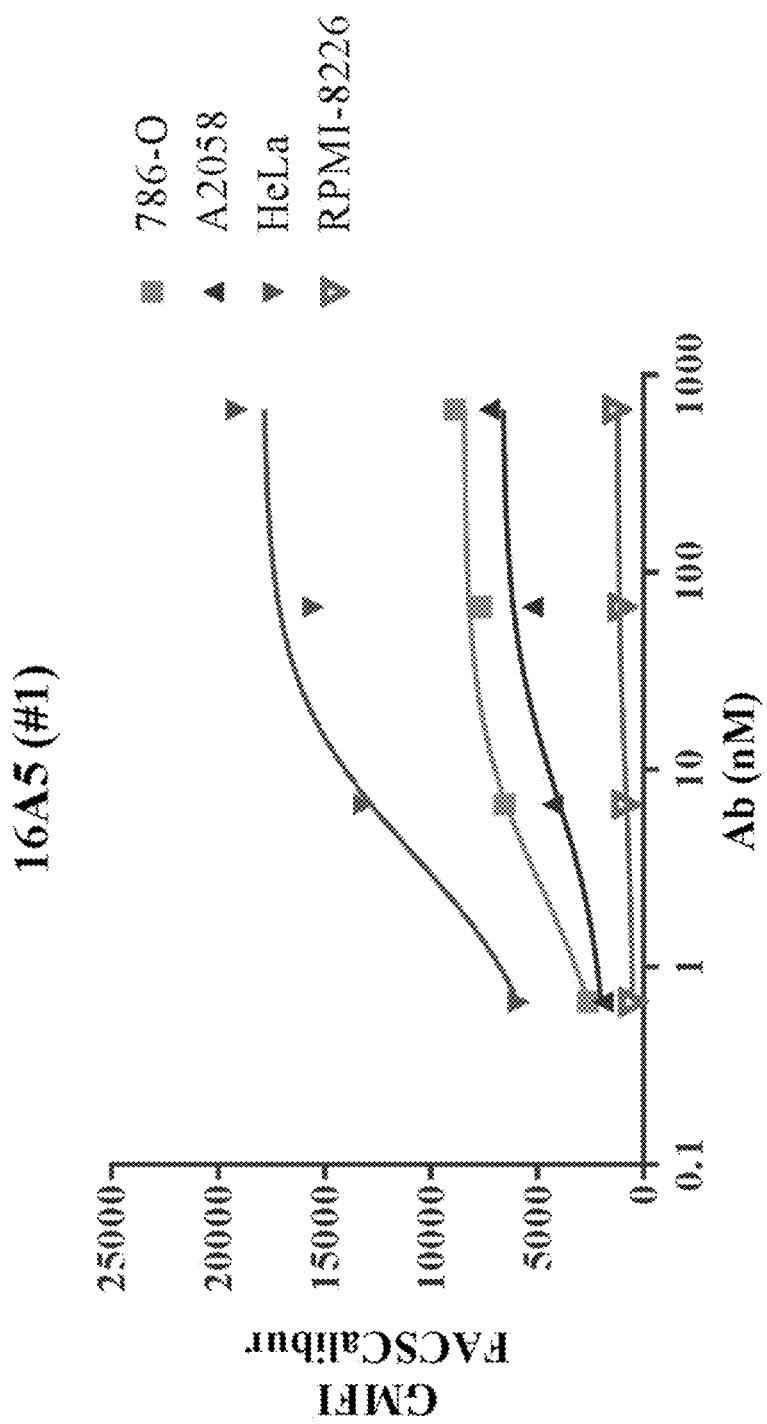
Figure 8J:
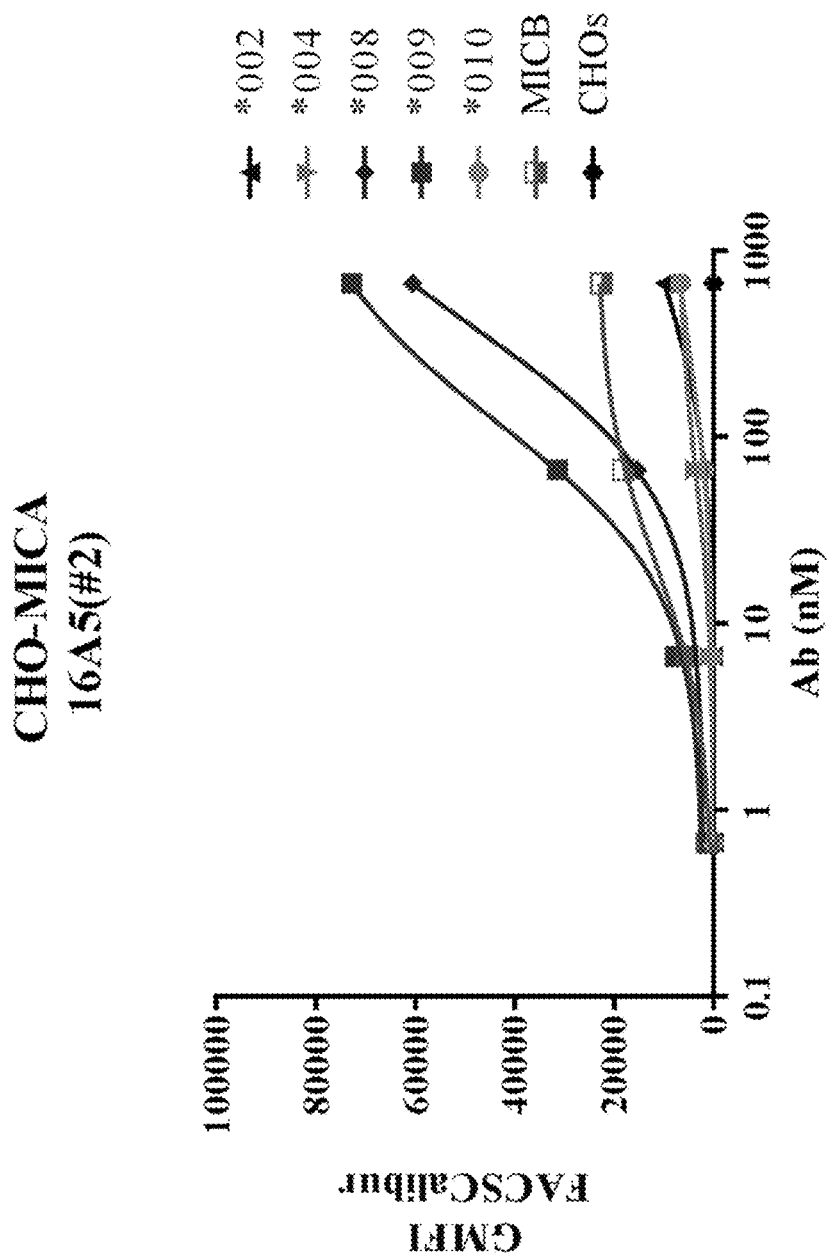
Figure 8K:
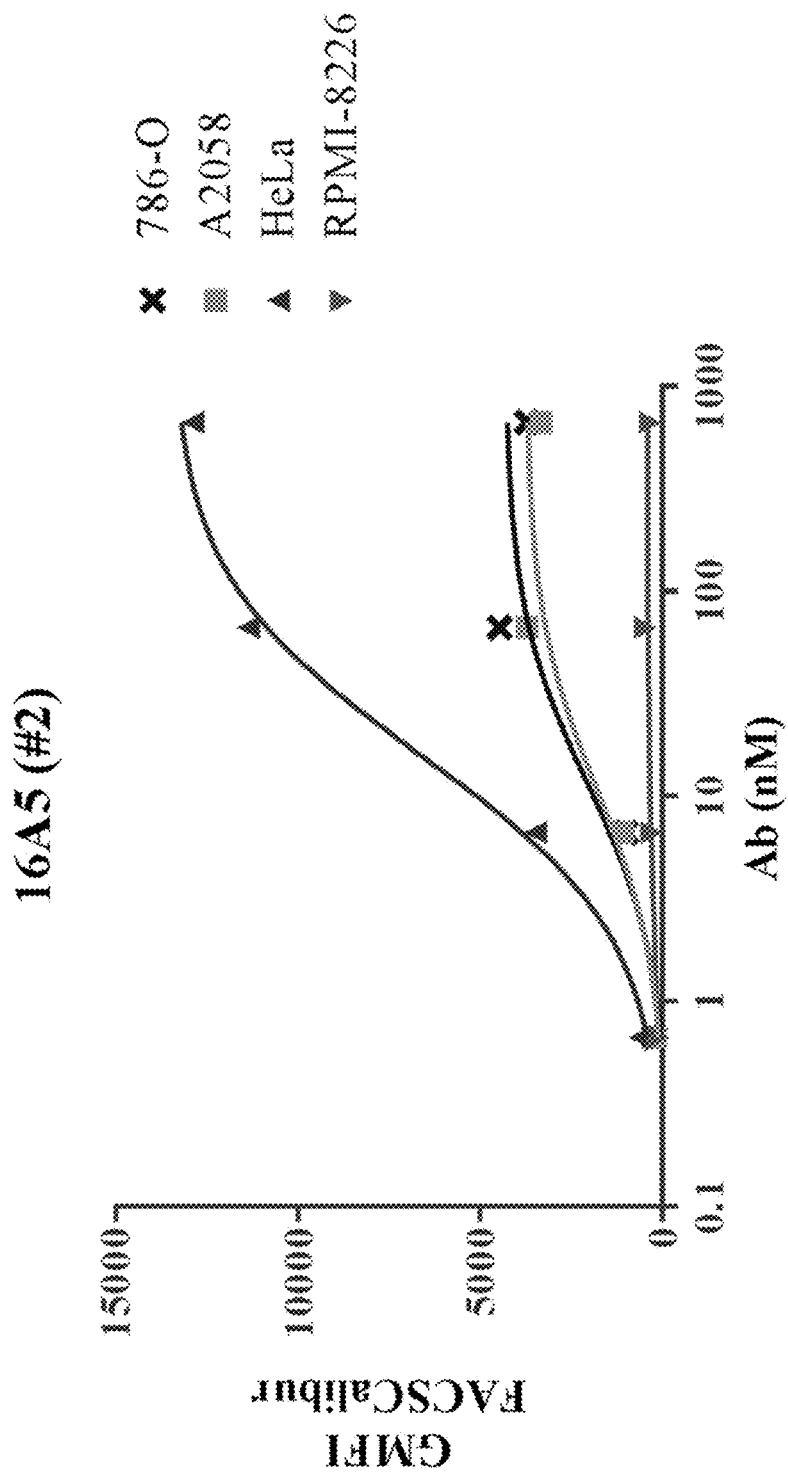
Figure 8L:
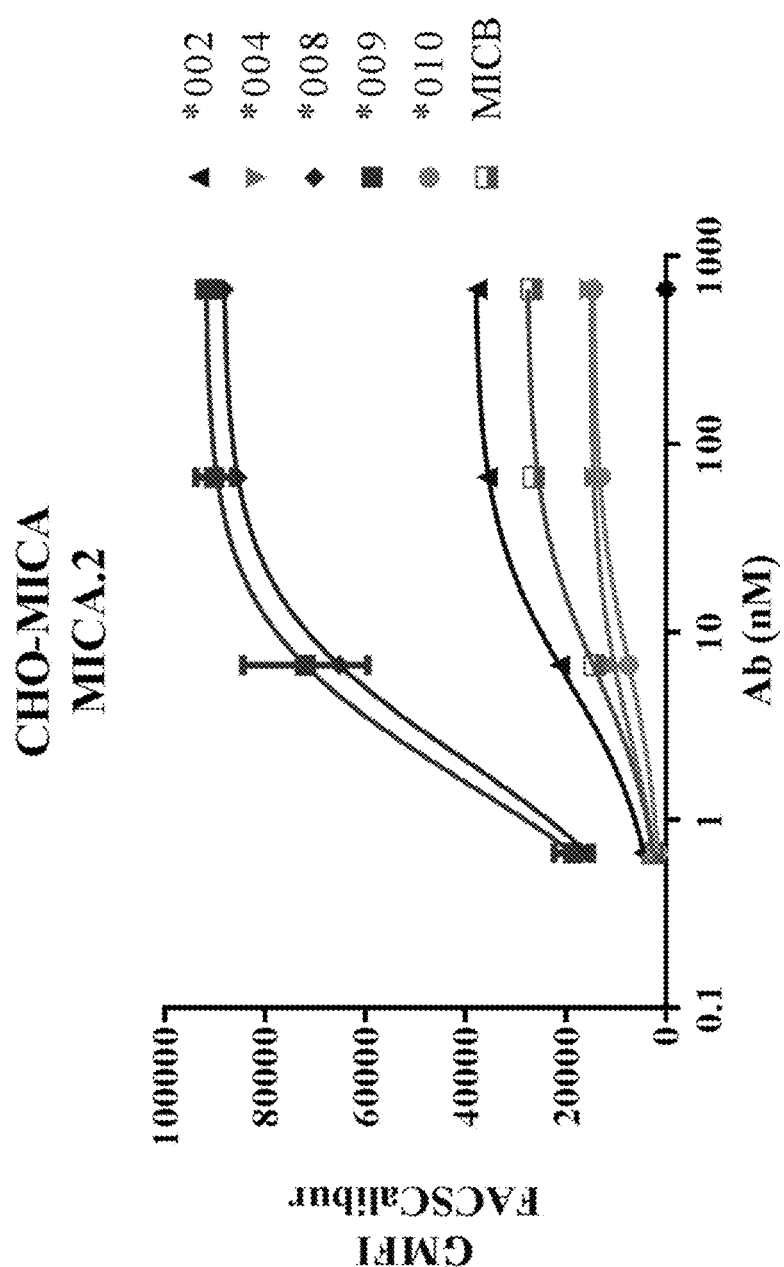
Figure 8M:
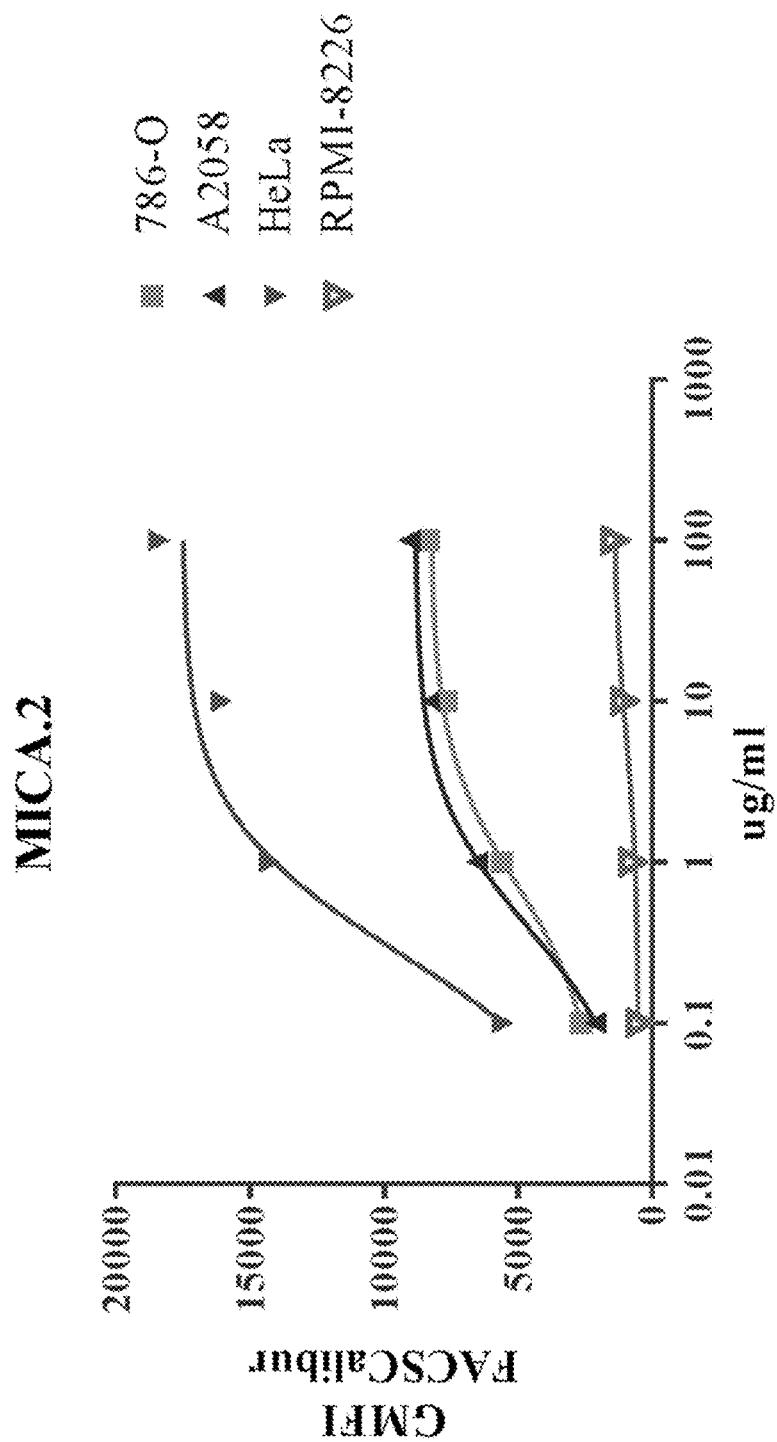
Figure 8N:
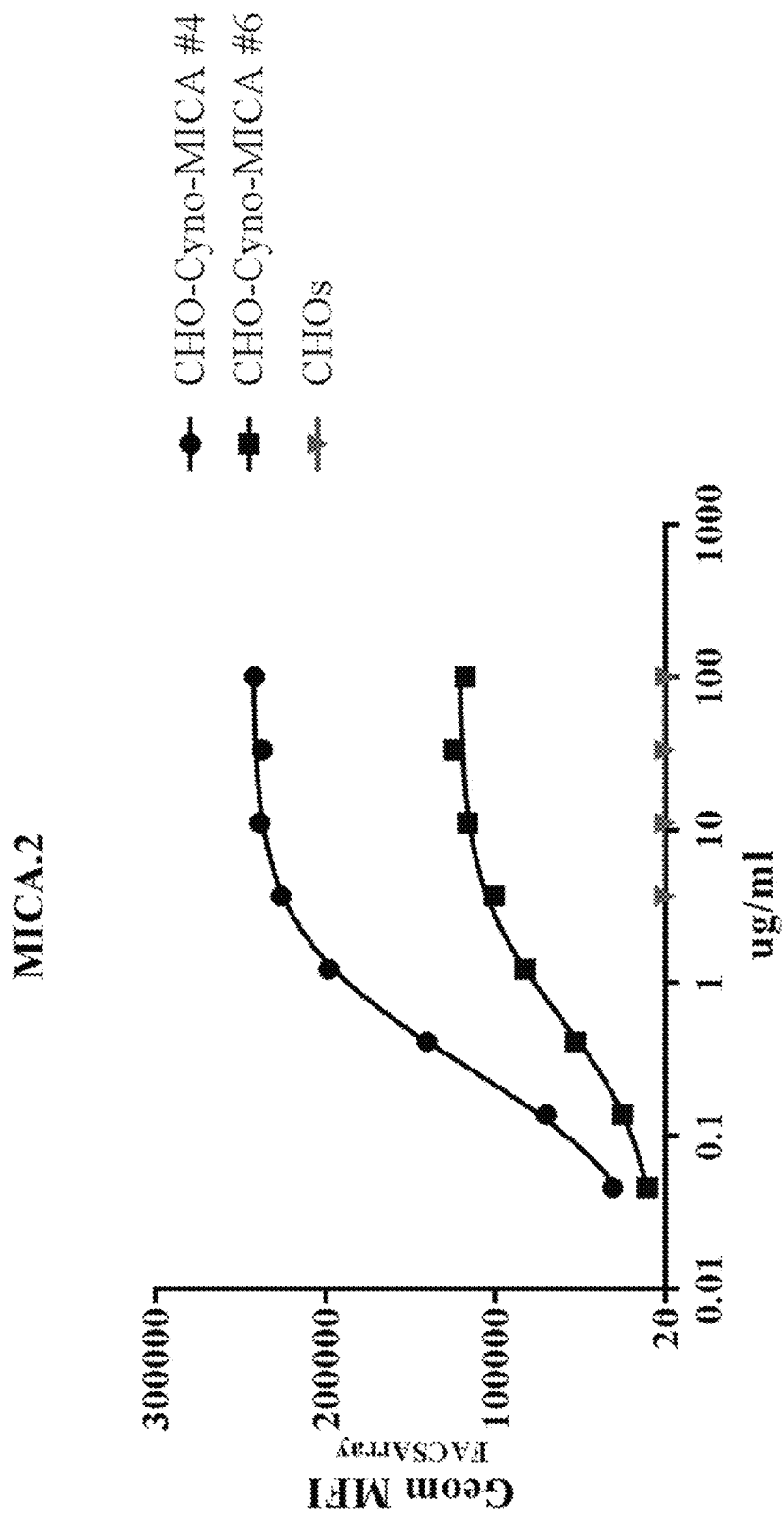

FIGS. 8A-8N show the binding affinity of MICA/B antibodies to MICA or MICB common alleles expressed on various cell lines using fluorescence activated cell sorting (FACS). FIGS. 8A, 8D, 8F, 8H, 8J, and 8L show binding of 19G6 (8A), 24G11 (FIG. 8D), 71C2 (FIG. 8F), 16A5 (FIGS. 8H and 8J, two subclones), and MICA.2 (FIG. 8L) to MICA/B antigens MICA*002 (triangles), MICA*004 (inverted triangles), MICA*008 (open diamonds), MICA*009 (filled squares), MICA*010 (filled circles), and MICB (open squares) expressed on the surface of CHO cells at increasing antibody concentrations. FIGS. 8B, 8E, 8G, 8I, 8K, and 8M show binding of 19G6 (8B), 24G11 (FIG. 8E), 71C2 (FIG. 8G), 16A5 (FIGS. 8I and 8K), and MICA.2 (FIG. 8M) to MICA-expressing 786-O (squares), A2058 (triangles), HeLa (inverted triangles), and RPMI-8226 (circles) cell lines. FIGS. 8C and 8N shows the cross-reactivity of 19G6 (FIG. 8C) and MICA.2 (FIG. 8N) to cynomolgus monkey MICA/B expressed on the surface of CHO cell clones #4 and #6 as compared to a negative control (CHO).

Figure 9D:
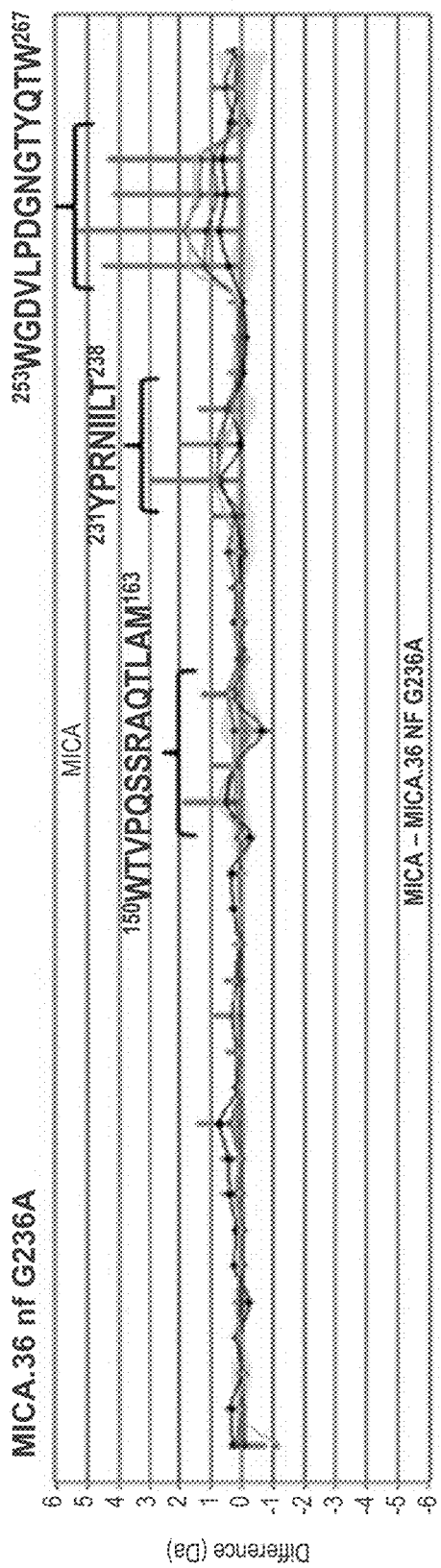
Figure 9E:
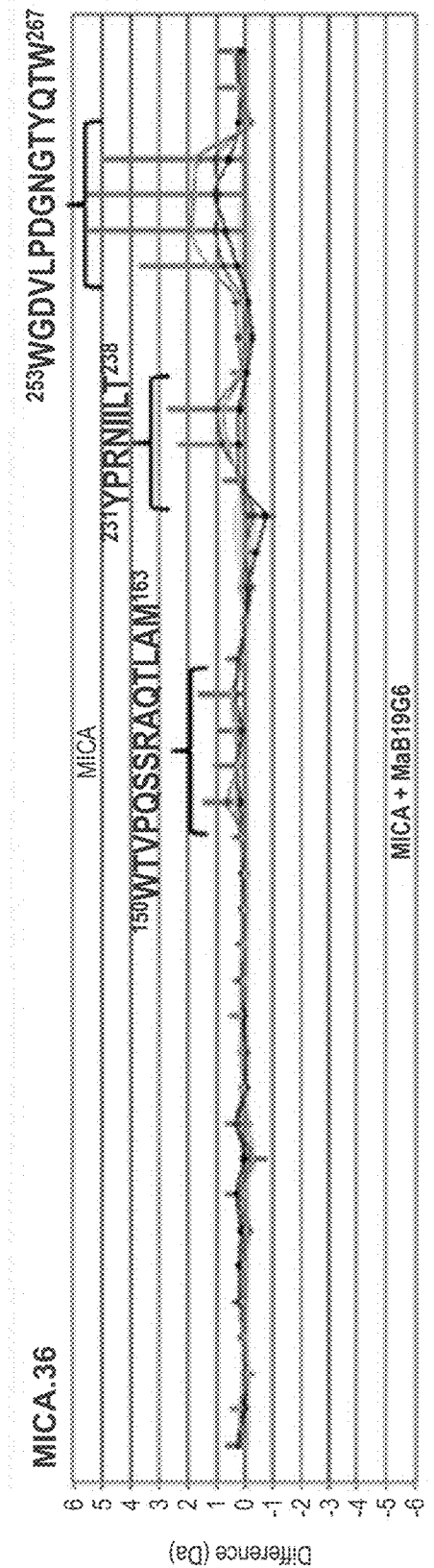

FIGS. 9A-9F show the results of epitope mapping using hydrogen/deuterium exchange (HDX) mass spectrometry (MS) for various anti-MICA/B antibodies. FIGS. 9A-9E are graphical representations of differential HDX of MICA upon the interaction of mAbs MICA.2 (FIG. 9A), MICA.39 (FIG. 9B), MICA.40 (FIG. 9C), non-fucosylated MICA.36 with Fc containing G236A (FIG. 9D), and MICA.36 (FIG. 9E) as measured using mass spectrometry. The MICA binding epitopes are also shown Region 2: $^{238}$TWRQDGVSLSHDTQQ$^{252}$ (SEQ ID NO: 57) (FIGS. 9A-9C) and Region 3: $^{253}$WGDVLPDGNGTYQTW$^{267}$ (SEQ ID NO: 55) (FIGS. 9D-9E).

Figure 9F:
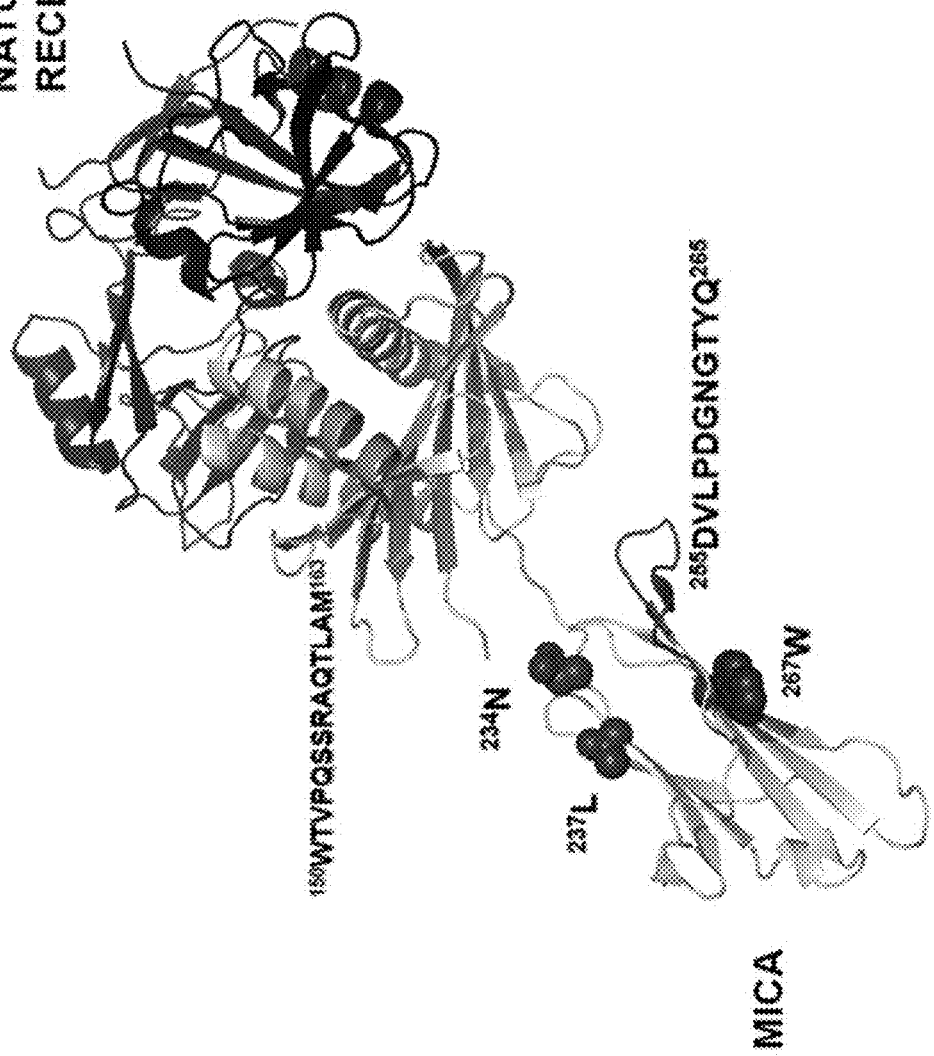
Figure 11B:
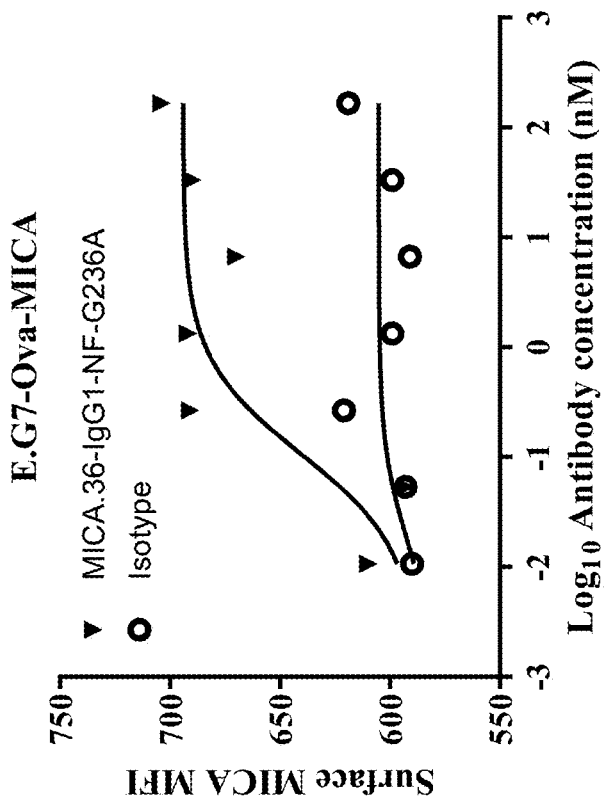
Figure 11A:
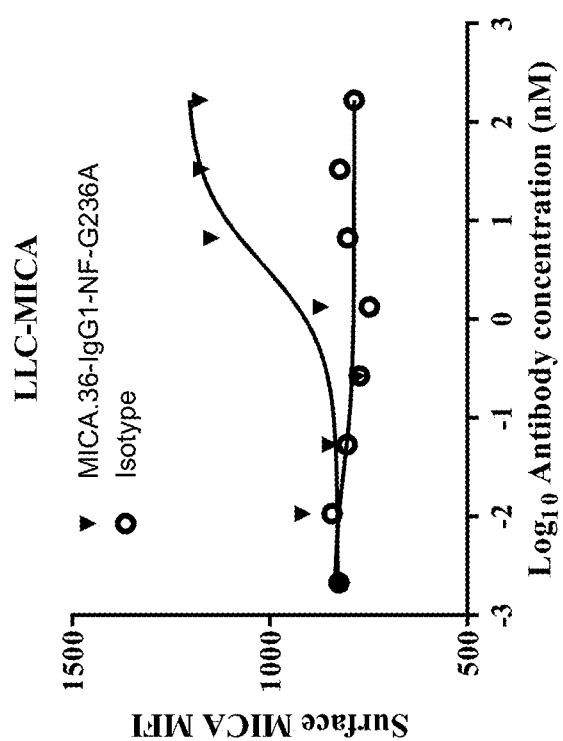
Figure 11D:
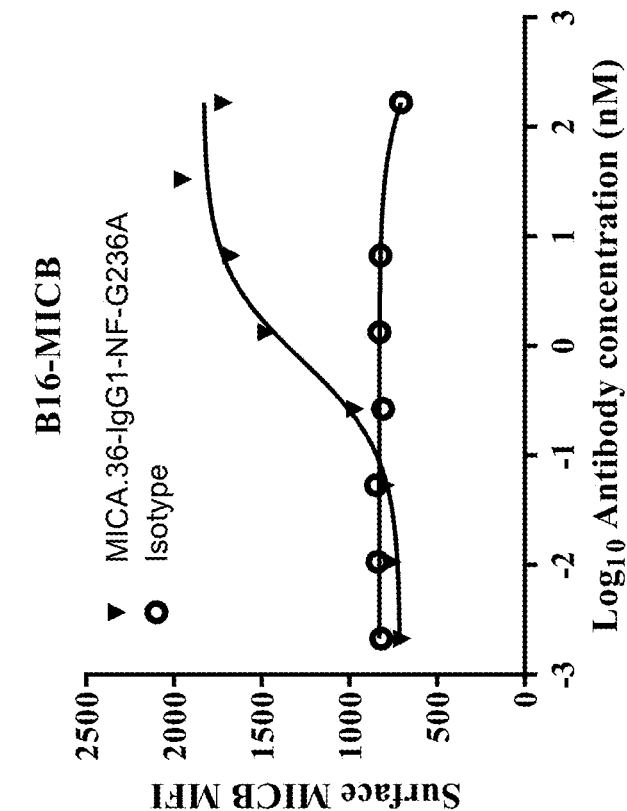
Figure 11C:
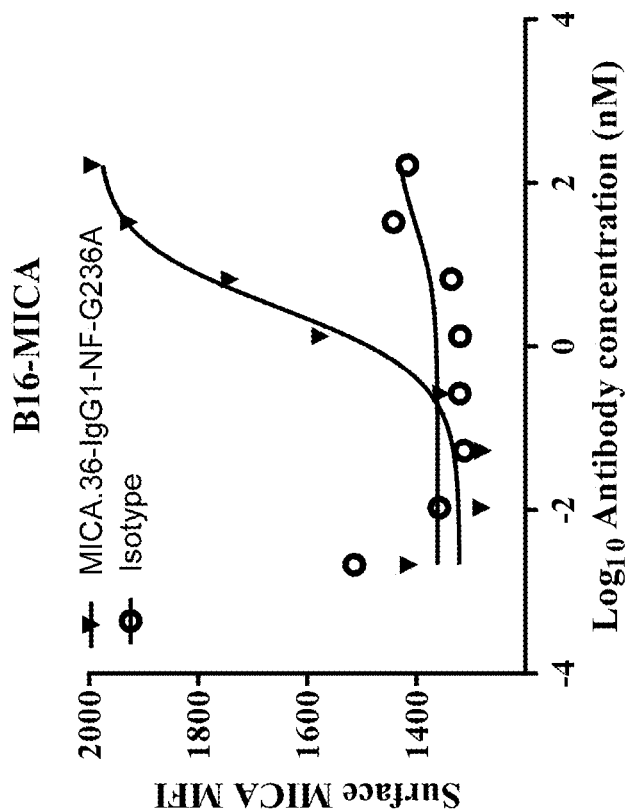
Figure 12B:
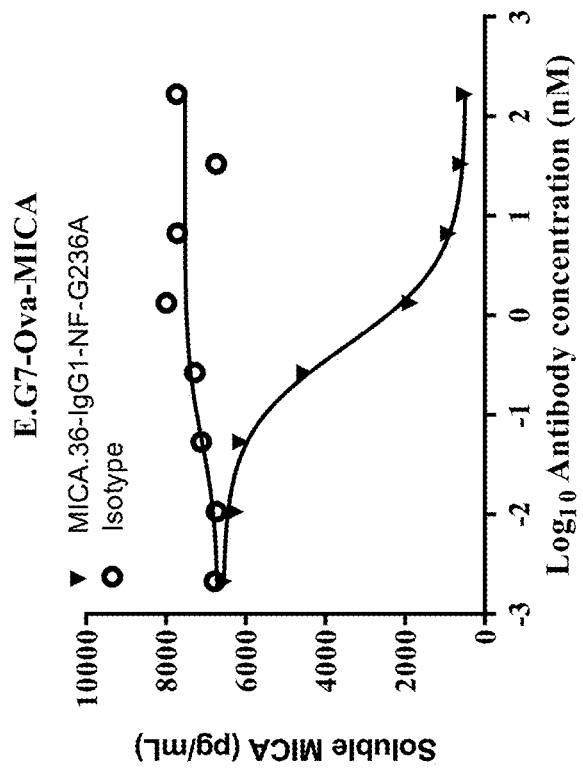
Figure 12A:
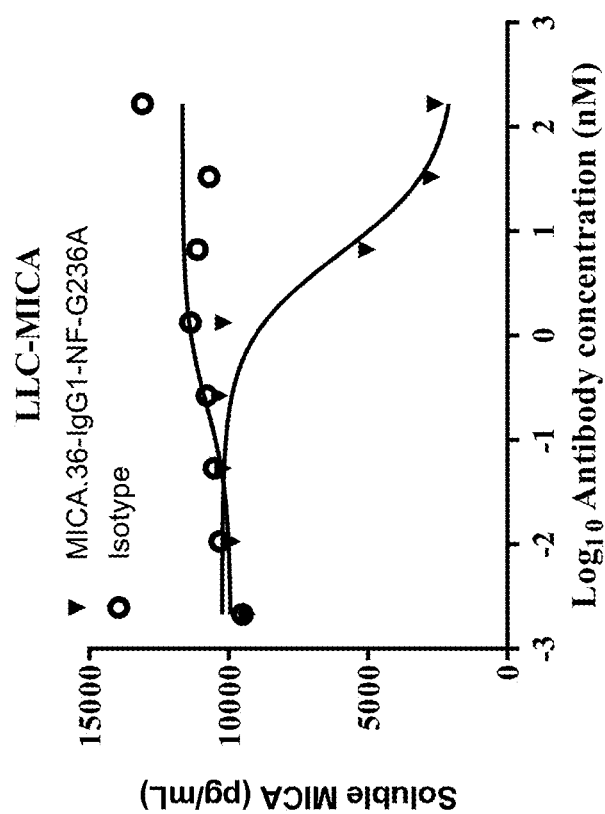
Figure 12D:
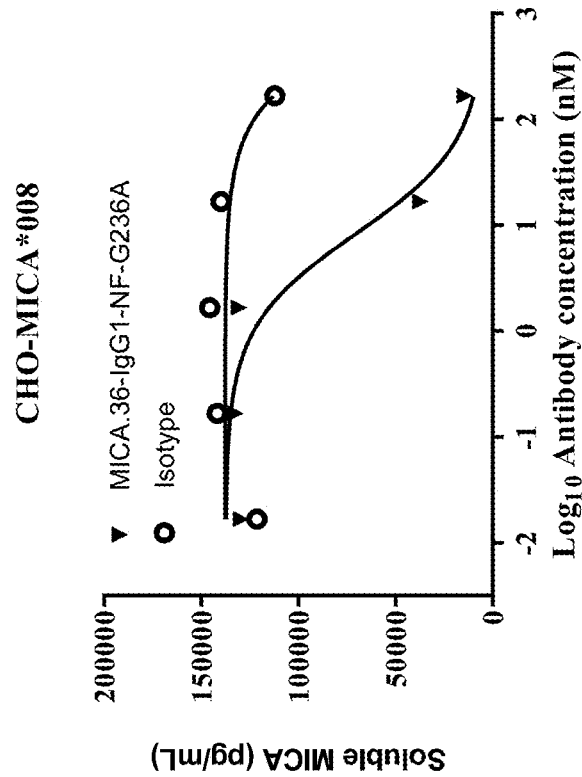
Figure 12C:
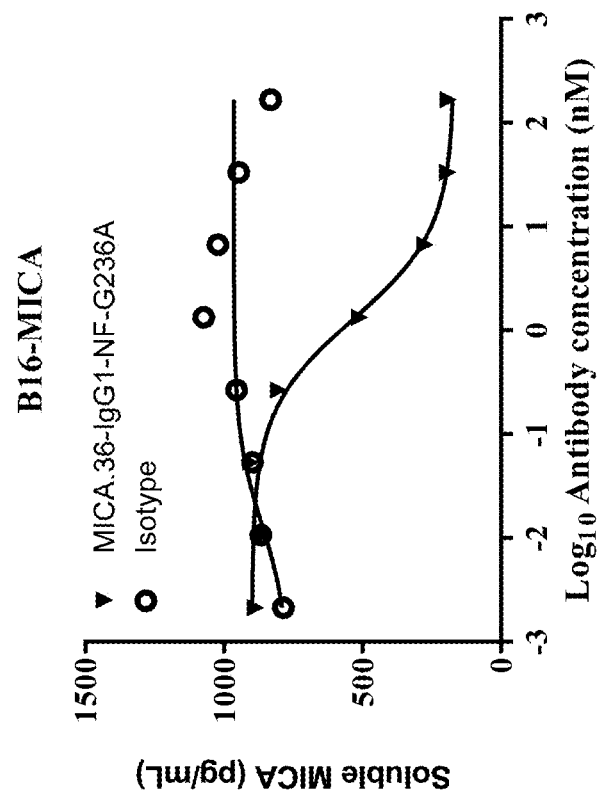
Figure 13B:
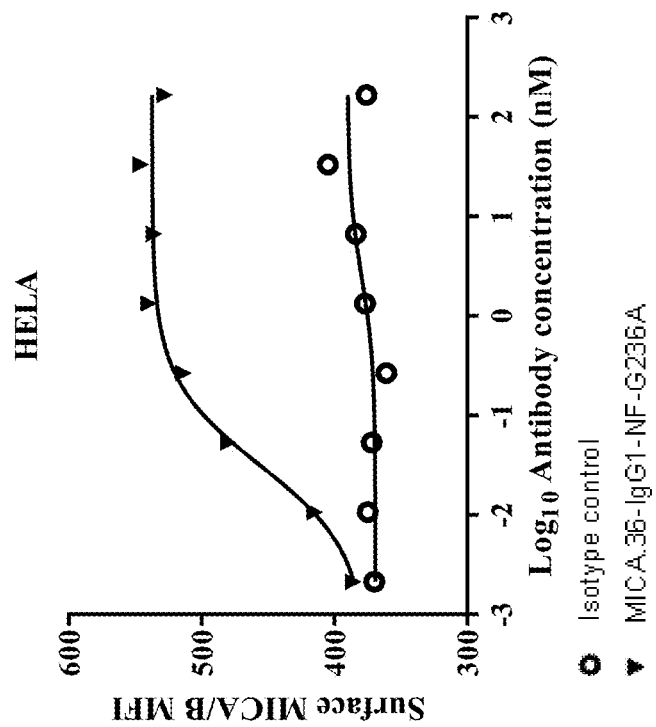
Figure 13A:
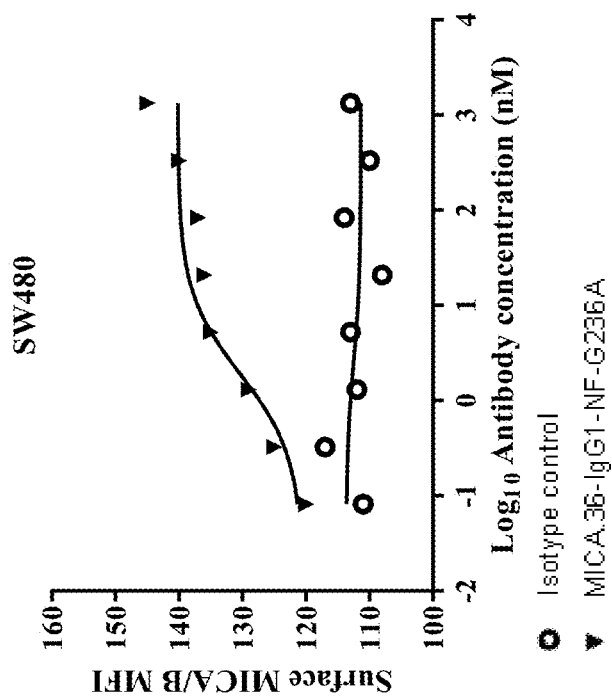
Figure 13D:
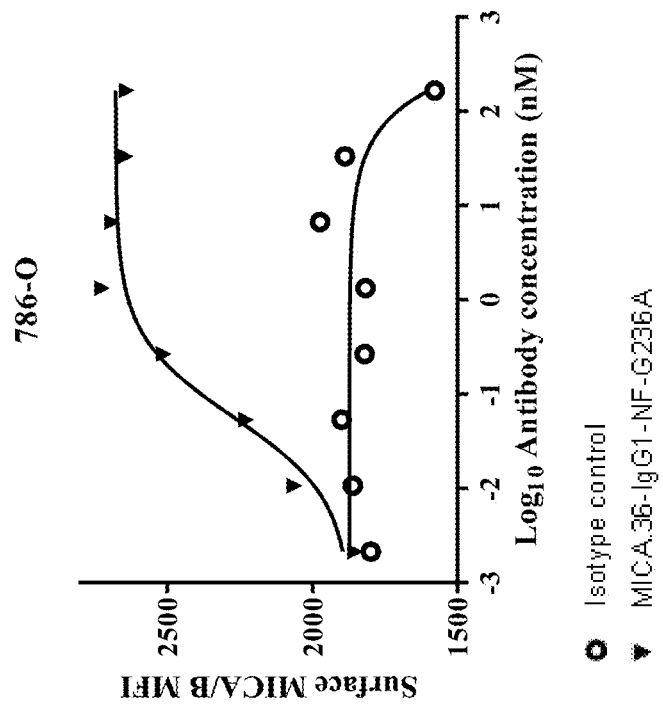
Figure 13C:
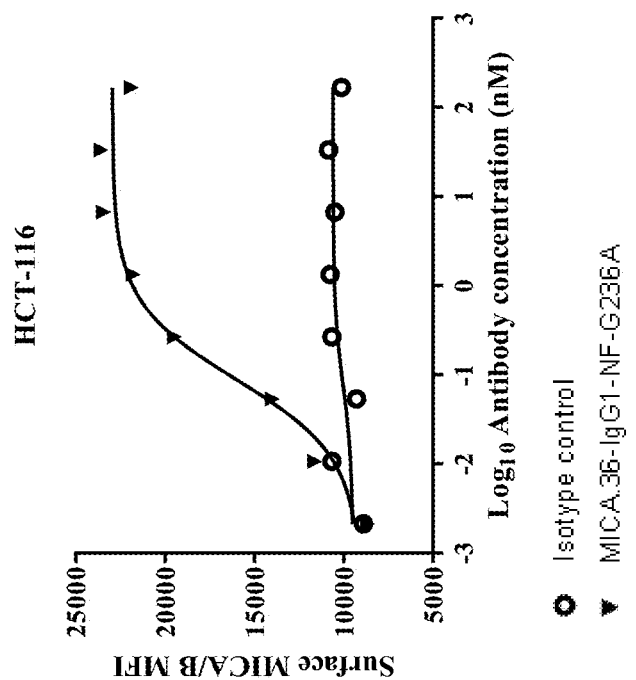
Figure 13E:
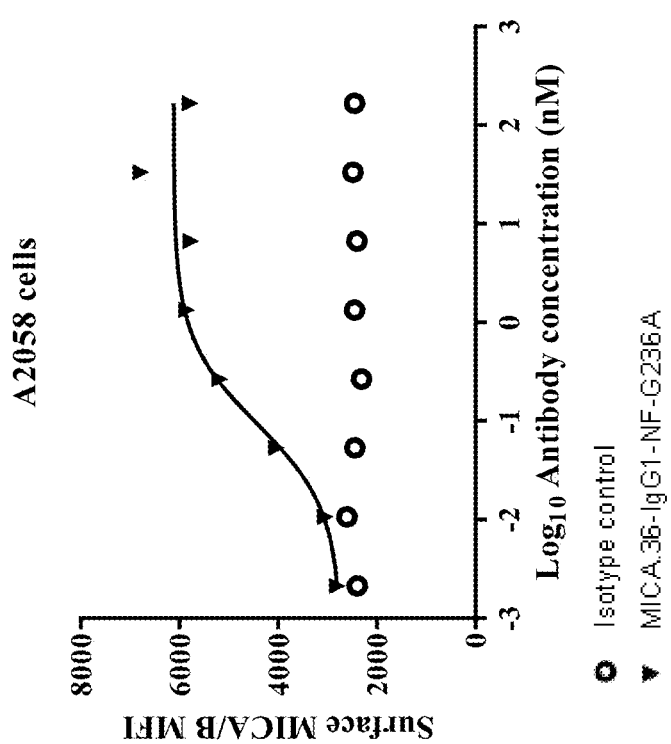

FIG. 9F is a ribbon diagram of the crystal structure of human MICA bound to natural killer cell receptor (NKG2D), wherein the mapped MICA.36 epitope is highlighted (SEQ ID NO: 57).

FIGS. 10A-10F show the results of epitope mapping using yeast display for various anti-MICA/B antibodies. FIGS. 10A-10C show the individual epitopes for MICA.36 (FIG. 10A), MICA.2 (FIG. 10B), and 24G11 (FIG. 10C). FIGS. 10D-10F show the same epitopes superimposed on ribbon diagrams of the crystal structure of MICA bound to NKG2D for MICA.2 (FIG. 10D), MICA.36 (FIG. 10E), and 24G11 (FIG. 10F).

FIGS. 11A-11D are graphical representations of surface MICA or MICB levels as measured by maximum fluorescence intensity on LLC cells (FIG. 11A), E.G7-Ova cells (FIG. 11B), and B16 cells (FIGS. 11C and 11D) ectopically expressing MICA (FIGS. 11A-11C) or MICB (FIG. 11D) following exposure to increasing concentrations of the anti-MICA/B antibody MICA.36 (non-fucosylated, G236A variant; inverted triangles) as compared to exposure to an isotype control (circles), as measured by FACS.

FIGS. 12A-12D are graphical representations of the concentration of soluble MICA/B present in the supernatant of a cell culture, as measured by ELISA, for LLC cells (FIG. 12A), E.G7-Ova cells (FIG. 12B), and B16 cells (FIG. 12C), and CHO cells (FIG. 12D) ectopically expressing MICA/B (FIGS. 12A-12C) or recombinant MICA*008 antigen (FIG. 12D) following exposure to increasing concentrations of the anti-MICA/B antibody MICA.36 (non-fucosylated, G236A variant; inverted triangles) as compared to exposure to an isotype control (circles).

FIGS. 13A-13E are graphical representations of surface MICA/B levels on the surface of human cell lines that endogenously express MICA/B. Surface localization of MICA/B was measured by maximum fluorescence intensity using FACS on the surface of SW480 cells (FIG. 13A), HeLa cells (FIG. 13B), HCT-116 cells (FIG. 13C), 786-O cells (FIG. 13D), and A2058 cells (FIG. 13E) following exposure to increasing concentrations of the anti-MICA/B antibody MICA.36 (non-fucosylated, G236A variant; inverted triangles) as compared to exposure to an isotype control (circles).

Figure 14B:
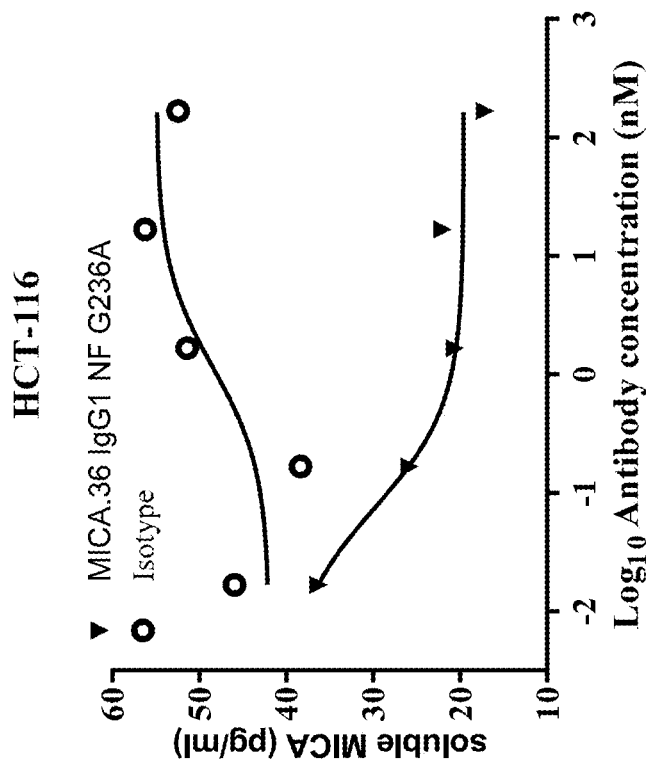
Figure 14A:
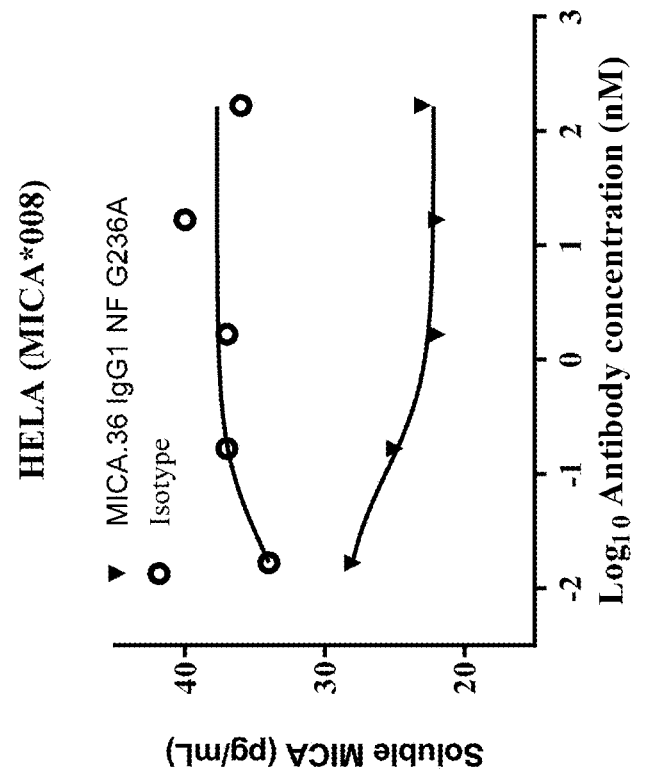
Figure 14C:
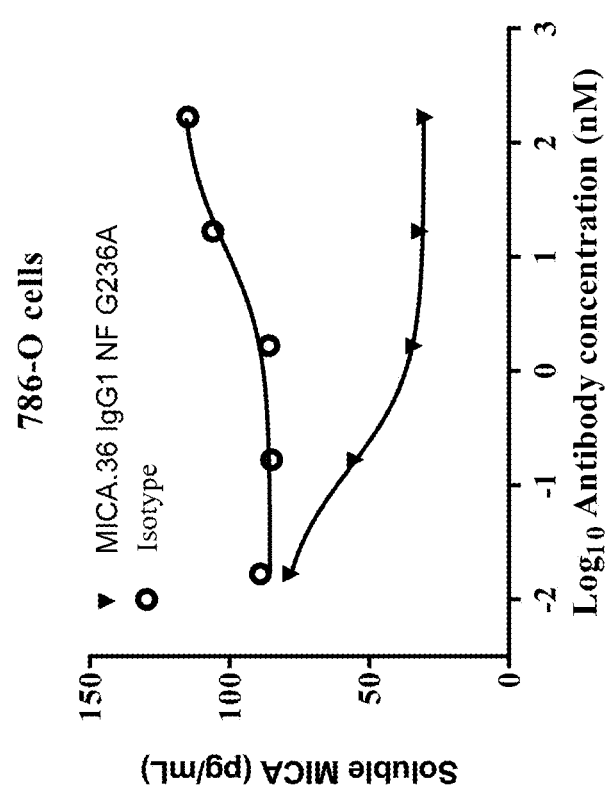

FIGS. 14A-14C are graphical representations of soluble MICA/B concentrations in the culture media of human cell lines that endogenously express MICA/B, as measured by ELISA in the media of cultured HeLa cells (FIG. 14A; expressing MICA*008), HCT-116 cells (FIG. 14B), and 786-O cells (FIG. 14C) following exposure to increasing concentrations of the anti-MICA/B antibody MICA.36 (non-fucosylated, G236A variant; inverted triangles) as compared to exposure to an isotype control (circles).

FIG. 15A is a graphical representation of the level of antibody-dependent cellular phagocytosis (ADCP) following culture with increasing concentrations of MICA.36 IgG1 (circles), MICA.36 IgG1 G236A (closed squares), MICA.36 IgG1 non-fucosylated (NF; inverted triangles), and MICA.36-IgG1-NF-G236A (triangles) or an isotype control (hIgG1, open squares). FIG. 15B is a graphical representation of antigen cross-presentation as measured by the percent of proliferating CD8 T cells following culture with increasing concentrations of MICA.36 IgG1 (inverted triangles), MICA.36 IgG1 NF (circles), MICA.36 IgG1 G236A (closed squares), MICA.36-IgG1-NF-G236A (triangles) or an isotype control (open squares).

FIGS. 16A and 16B are graphical illustrations of the percent of specific lysis of MICA/B-expressing Raji cells (FIG. 16A) and A375 cells (FIG. 16B) following exposure to increasing concentrations of MICA.36 NF G236A (triangles), MICA.36 IgG1 (inverted triangles), MICA.36 IgG1 NF (circles), MICA.36 IgG1 G236A (closed squares) or an isotype control (open squares).

Figure 17B:
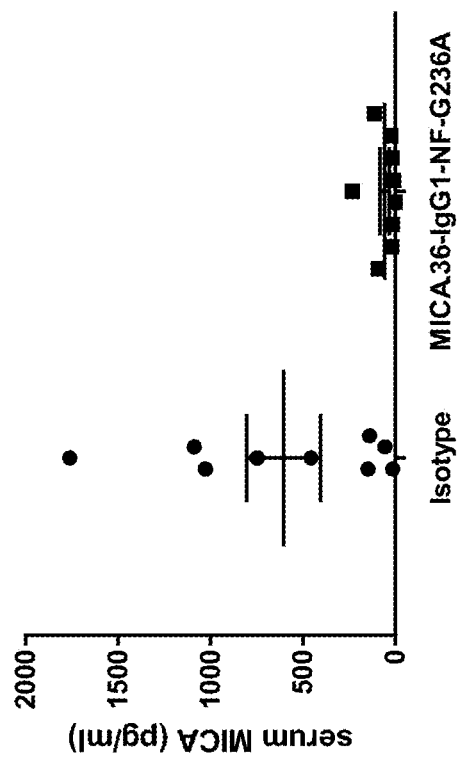
Figure 17A:
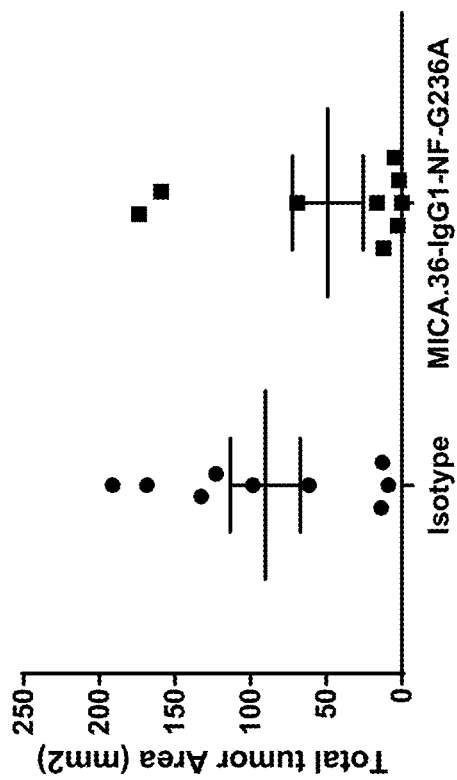

FIGS. 17A and 17B illustrate the in vivo effects of administered anti-MICA/B antibody MICA.36 NF G236A on total tumor area (FIG. 17A) and serum levels of soluble MICA/B (FIG. 17B) in mice induced to develop tumors in the lung.

Figure 18A:
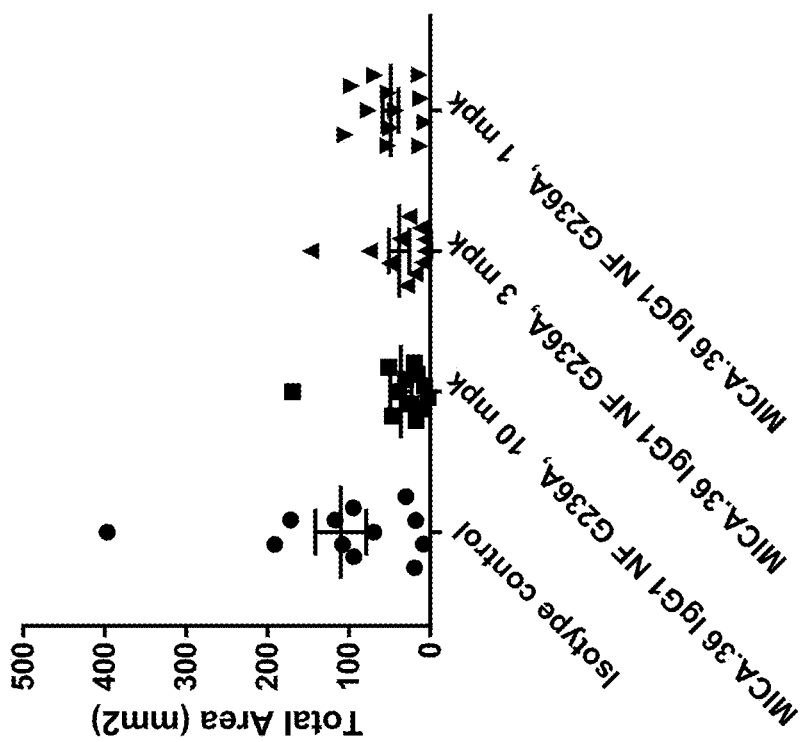
Figure 18B:
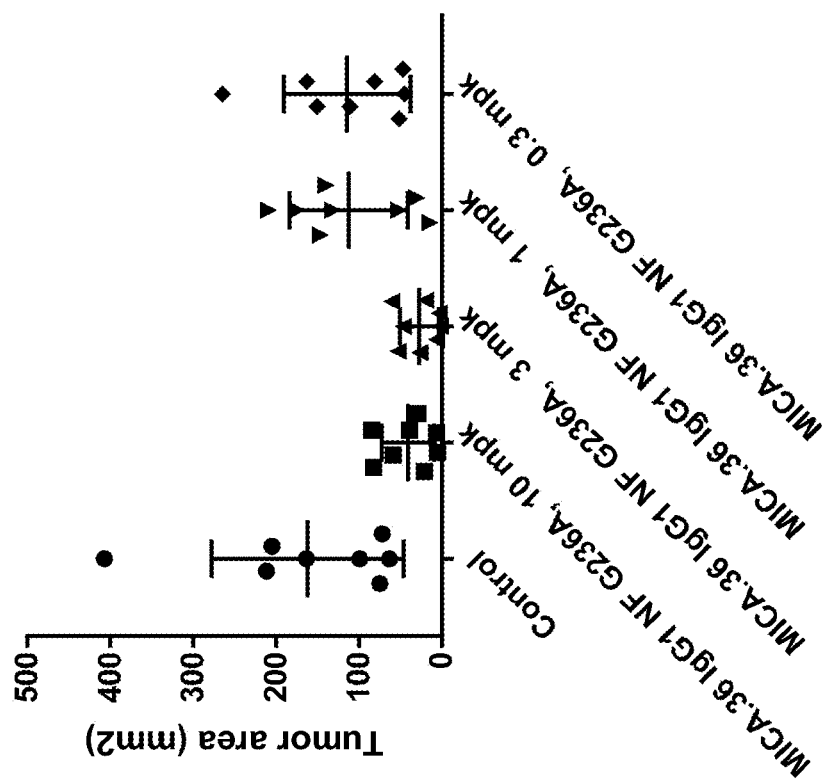

FIGS. 18A and 18B show the results of two dose escalation studies in mice induced to develop Tumors in the lung, measuring the total size of tumors following administration of varying doses (10 mg/kg (mpk), 3 mpk, 1 mpk, or 0.3 mpk) of the anti-MICA/B antibody MICA.36 NF G236A or an isotype control.

Figure 19C:
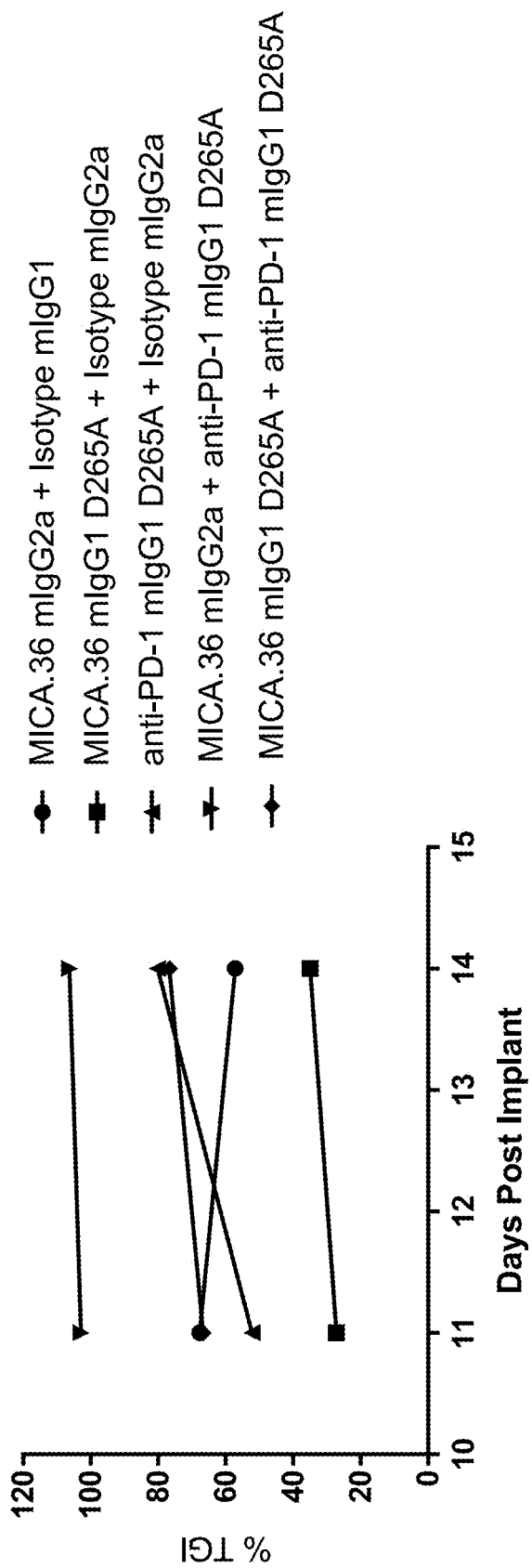
Figure 19D:
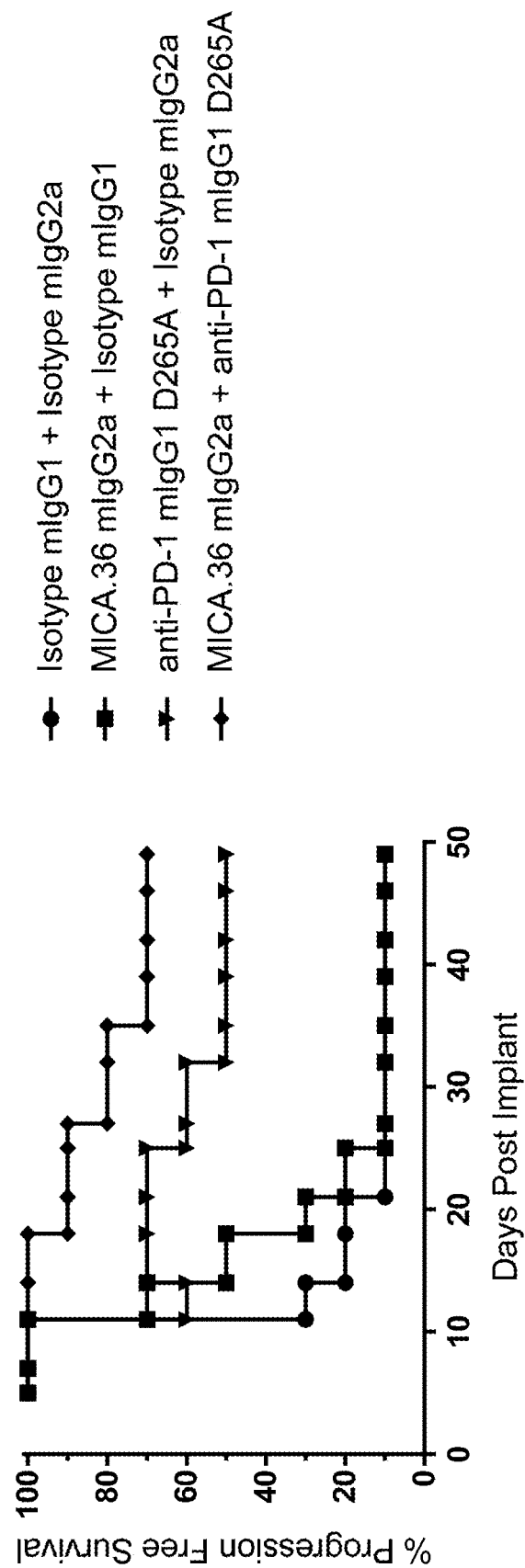
Figure 19E:
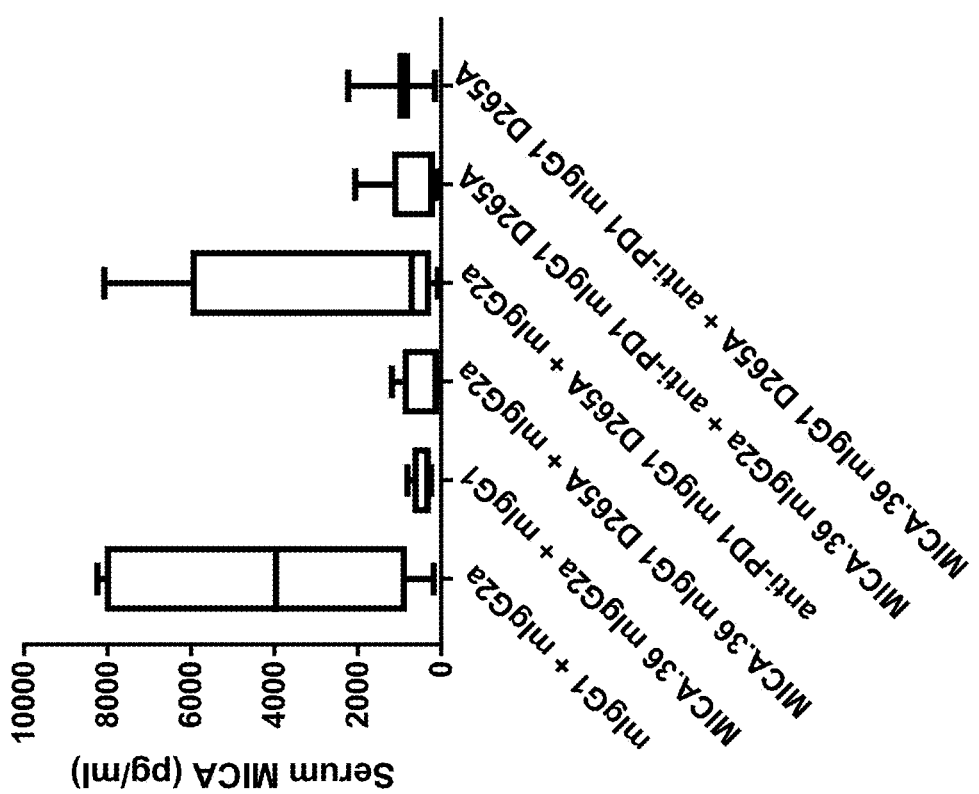

FIGS. 19A-19E show the results of administration of an anti-MICA/B antibody alone or in combination with an anti-PD-1 antibody to MICA transgenic mice presenting EG7-MICA tumors. FIGS. 19A and 19B are graphical representations of mean (FIG. 19A) and median (FIG. 19B) tumor volume in mice administered isotype control (closed circles), MICA.36 mIgG2a and isotype control mIgG1 (squares), MICA.36 mIgG1 D265A and isotype mIgG2a (triangles), anti-PD-1 mIgG1 D265A and isotype mIgG2a (inverted triangles), MICA.36 mIgG2a and anti-PD-1 mIgG1 D265A (diamonds), or MICA.36 mIgG1 D265A and anti-PD-1 mIgG1 D265A (open circles). FIG. 19C is a graphical representation of the calculated percent tumor growth inhibition (TGI %) for each treatment group: 10 mg/kg MICA.36 mIgG2a and 10 mg/kg isotype mIgG1 (circles), 10 mg/kg MICA.36 mIgG1 D265A and 10 mg/kg isotype mIgG2a (squares), 10 mg/kg anti-PD-1 mIgG1 D265A and 10 mg/kg isotype mIgG2a (triangles), 10 mg/kg MICA.36 mIgG2a and 10 mg/kg MICA.36 mIgG1 D265A (inverted triangles), and 10 mg/kg MICA.36 mIgG1 D265A and 10 mg/kg anti-PD-1 mIgG1 D265A (diamonds). FIG. 19D shows the progression free survival (PFS %) for transgenic mice presenting EG7-MICA tumors following treatment with isotype 10 mg/kg mIgG1 and 10 mg/kg isotype mIgG2a double control (circles), 10 mg/kg MICA.36 mIgG2a and 10 mg/kg isotype mIgG1 (squares), 10 mg/kg anti-PD-1 mIgG1 D265A and 10 mg/kg isotype mIgG2a (inverted triangles), or 10 mg/kg MICA.36 mIgG2a and 10 mg/kg anti-PD-1 mIgG1 D265A (diamonds). FIG. 19E shows the concentration of soluble MICA in the serum of transgenic mice with EG7-MICA tumors following treatment with an isotype control, MICA.36 mIgG2a, MICA.36 mIgG1 D265A, anti-PD-1 mIgG1 D265A, MICA.36 mIgG2a and anti-PD-1 mIgG1 D265A, or MICA.36 mIgG1 D265A and anti-PD-1 mIgG1 D265A.

Figure 20A:
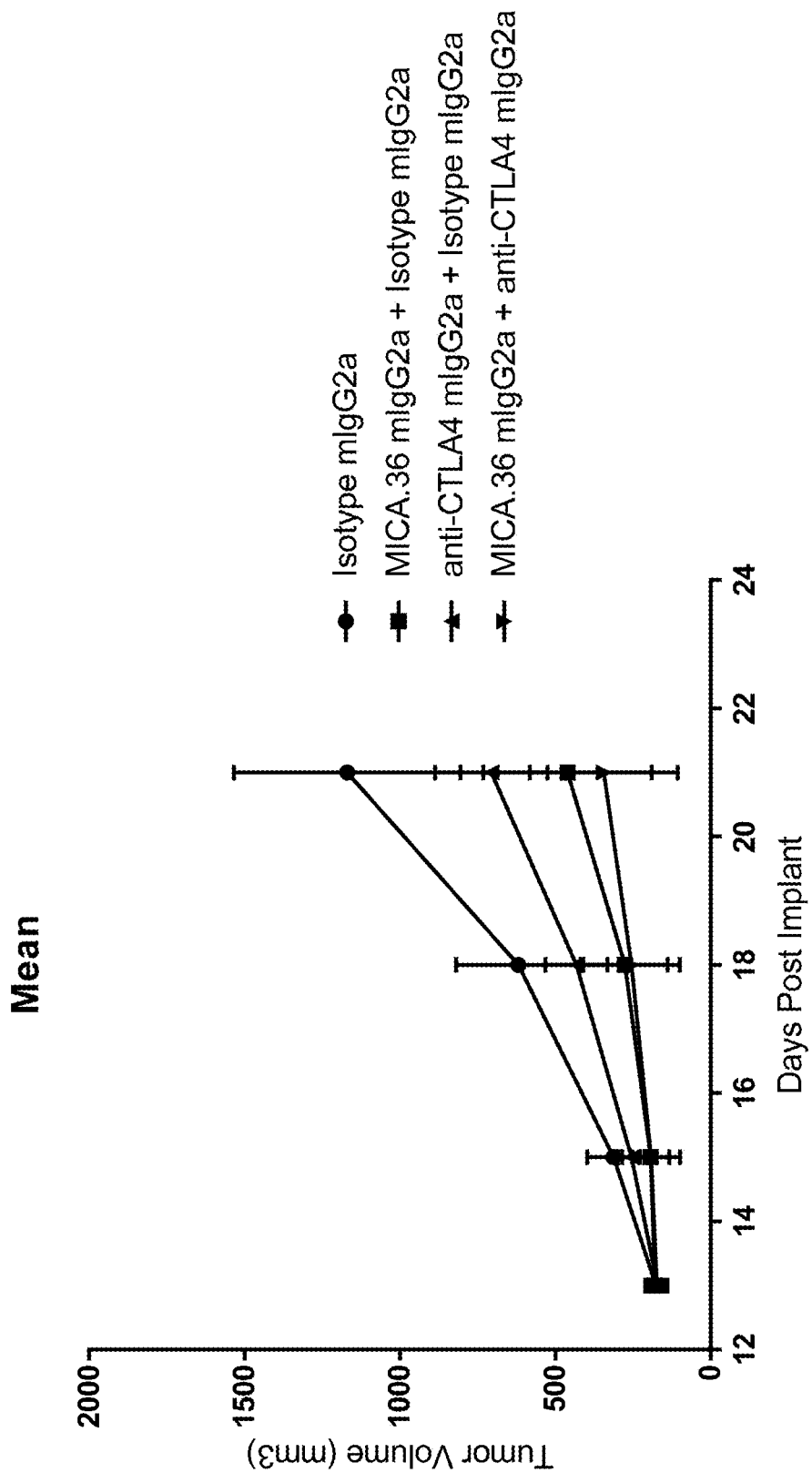
Figure 20B:
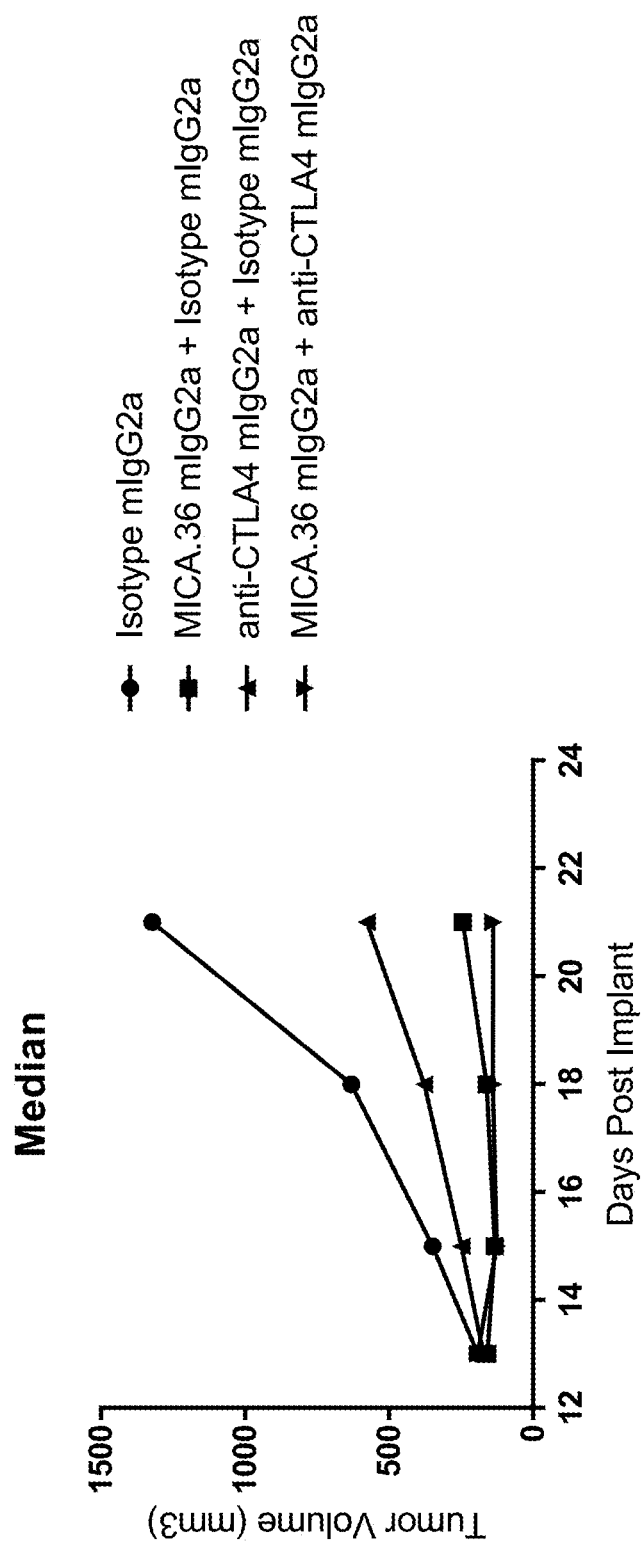
Figure 20C:
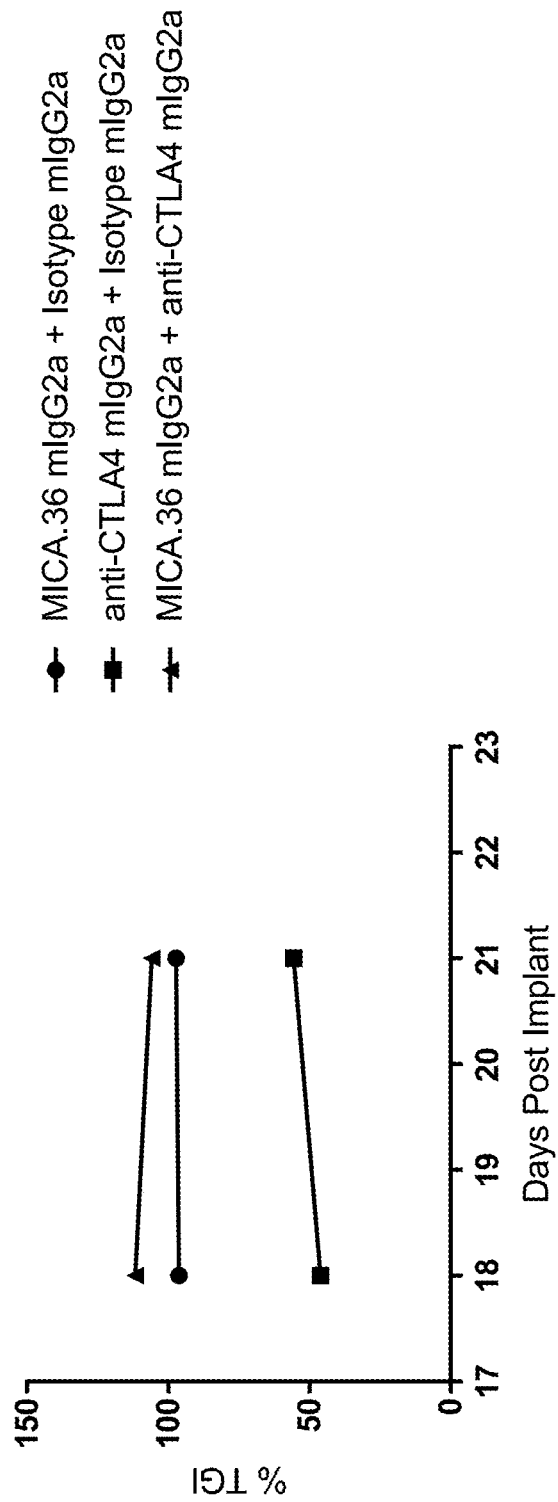
Figure 20D:
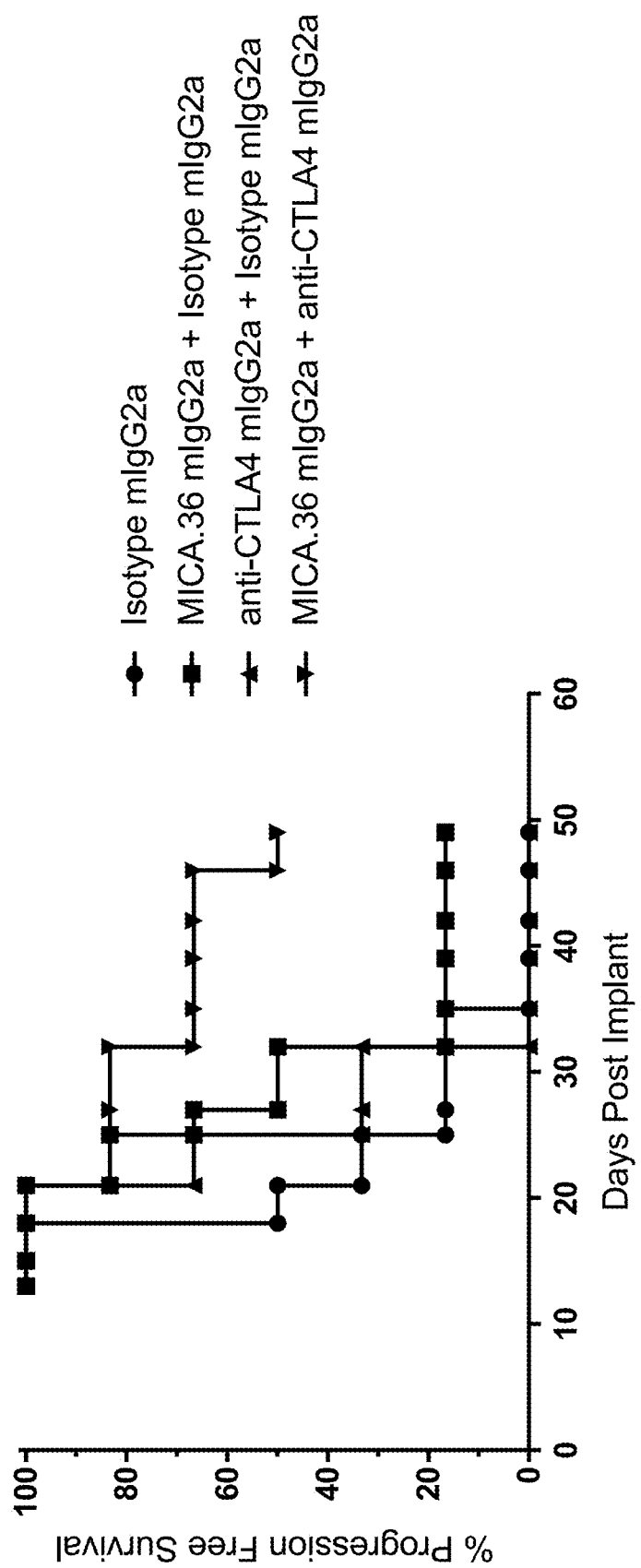

FIGS. 20A-20D show the results of the in vivo effects of anti-MICA/B antibodies in B6-MICA transgenic mice with EG7-MICA/B tumors. FIGS. 20A and 20B are graphical representations of the mean (FIG. 20A) and median (FIG. 20B) tumor volume in mice treated with 20 mg/kg isotype mIgG2a (circles), 10 mg/kg MICA.36 mIgG2a and 10 mg/kg isotype control mIgG2a (squares), 10 mg/kg anti- CTLA-4 mIgG2a and 10 mg/kg isotype mIgG2a (triangles), or 10 mg/kg MICA.36 mIgG2a and 10 mg/kg anti-CTLA-4 mIgG2a (inverted triangles). FIG. 20C shows the calculated percent tumor growth inhibition (TGI %) for each treatment group: 10 mg/kg MICA.36 mIgG2a and 10 mg/kg isotype mIgG2a (circles), 10 mg/kg anti-CTLA-4 mIgG2a and 10 mg/kg isotype mIgG2a (squares), and 10 mg/kg MICA.36 mIgG2a and 10 mg/kg anti-CTLA-4 mIgG2a (triangles). FIG. 20D shows the progression free survival (PFS %) for transgenic mice with EG7-MICA/B tumors following treatment with 20 mg/kg isotype mIgG2a (circles), 10 mg/kg MICA.36 mIgG2a and 10 mg/kg isotype control mIgG2a (squares), 10 mg/kg anti-CTLA-4 mIgG2a and 10 mg/kg isotype mIgG2a (triangles), or 10 mg/kg MICA.36 mIgG2a and 10 mg/kg anti-CTLA-4 mIgG2a (inverted triangles).

Figure 21A:
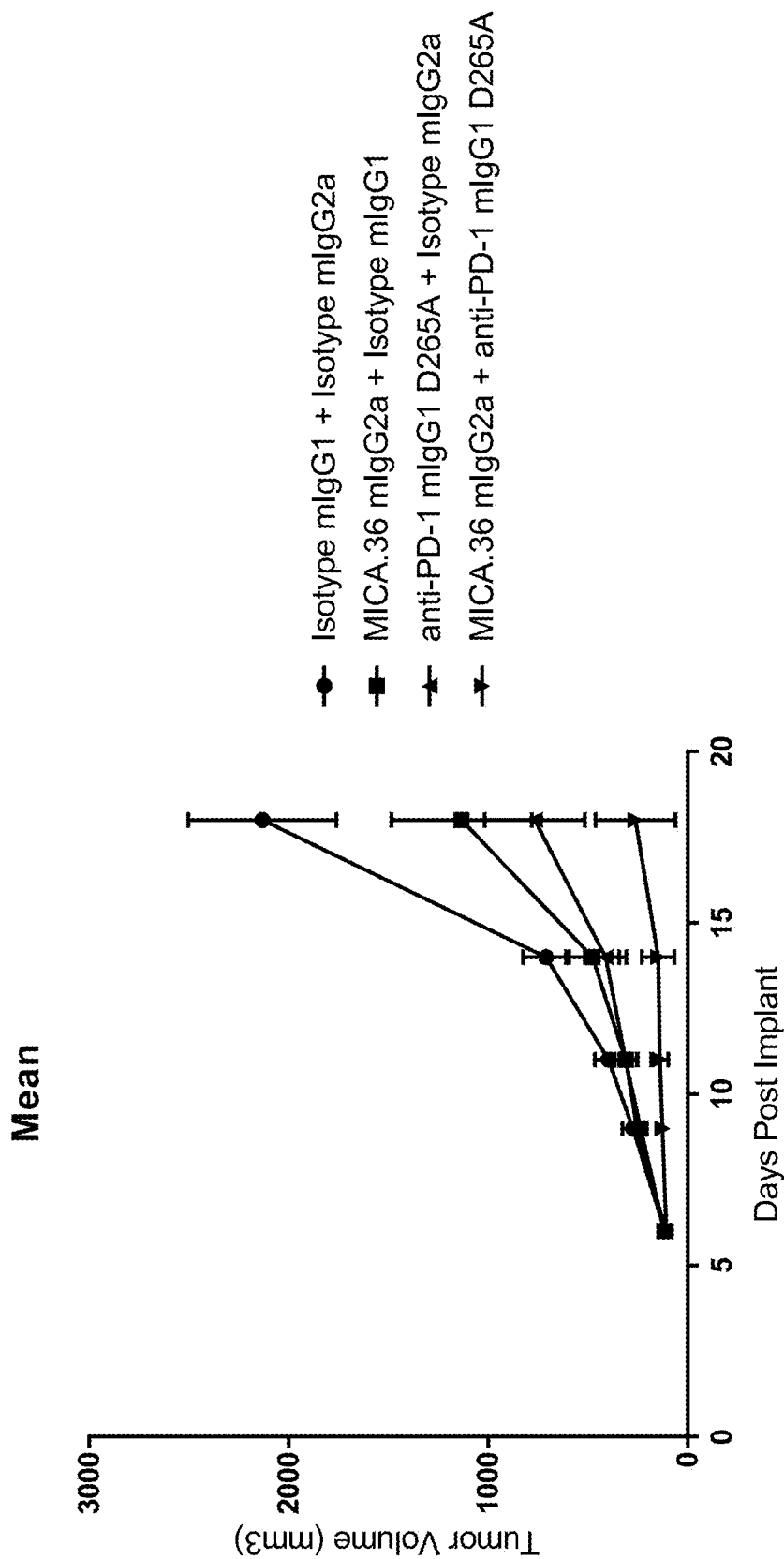
Figure 21B:
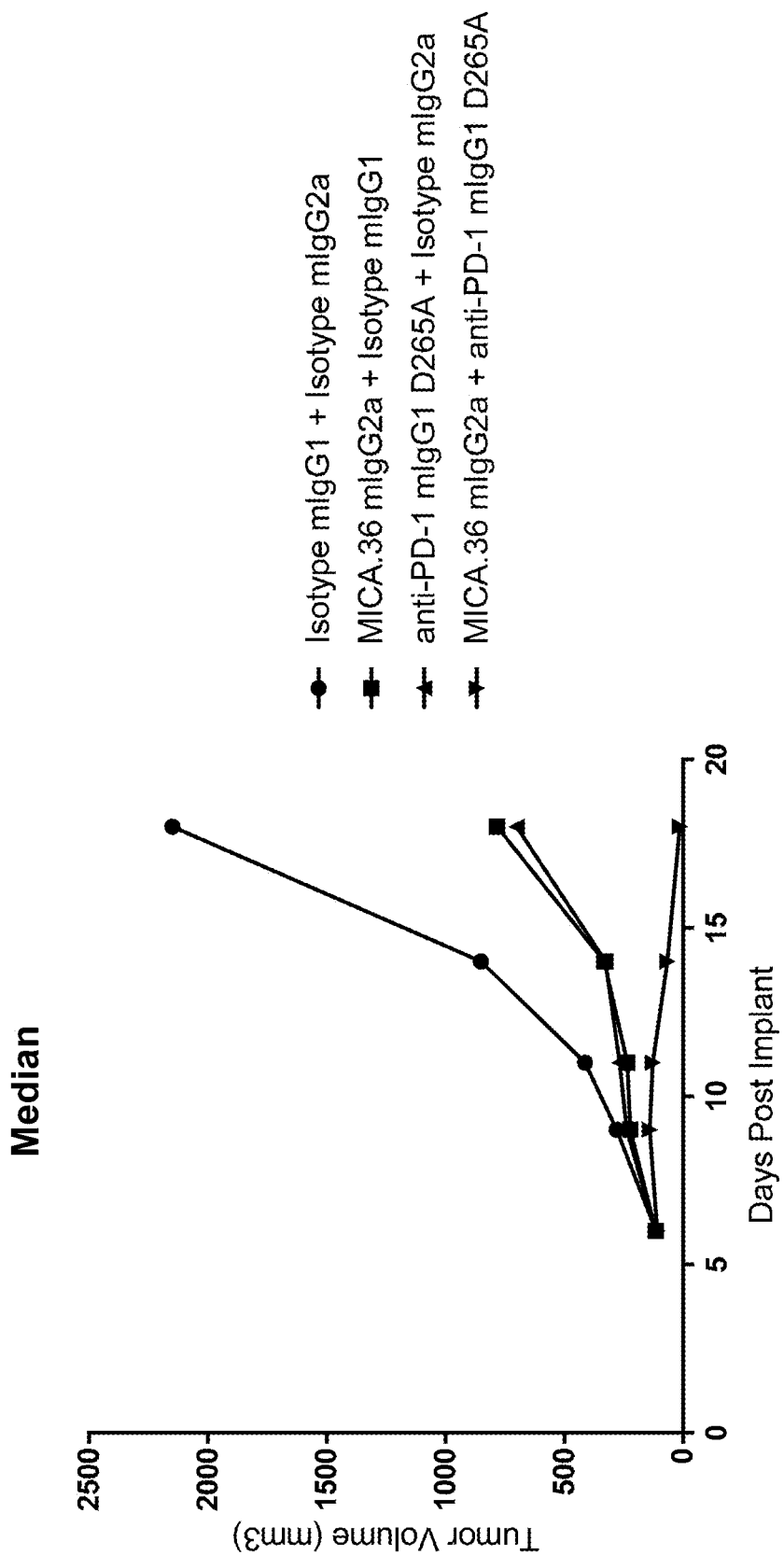
Figure 21C:
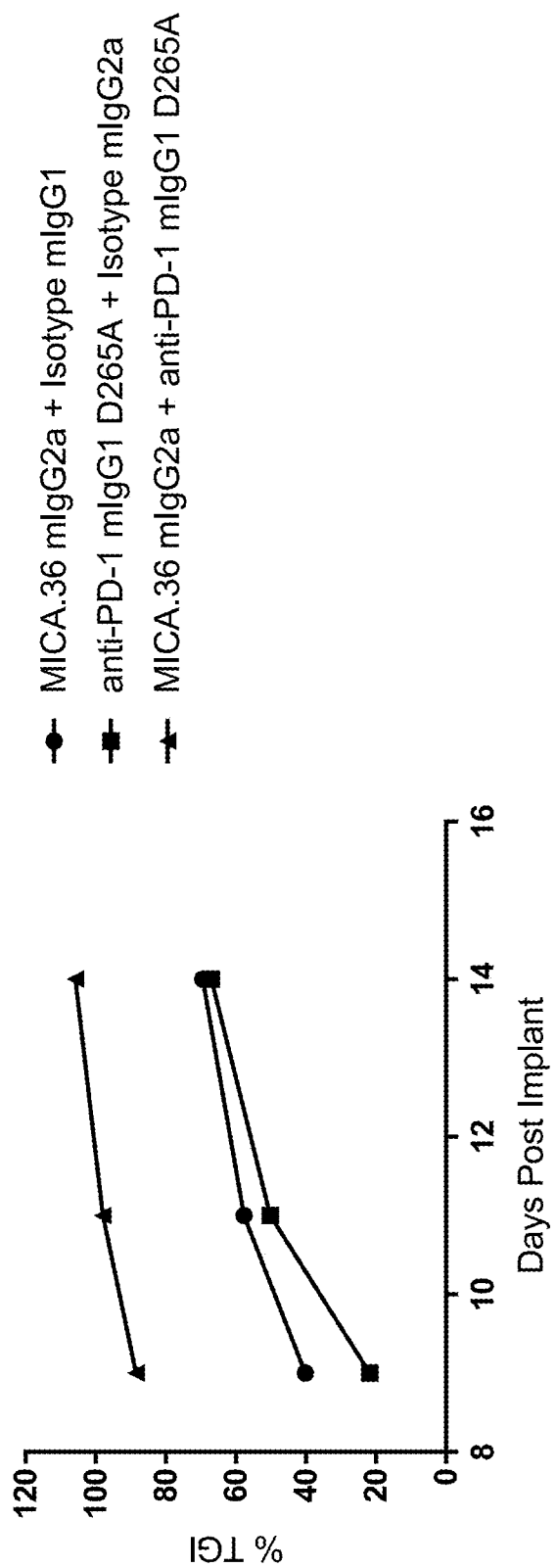
Figure 21D:
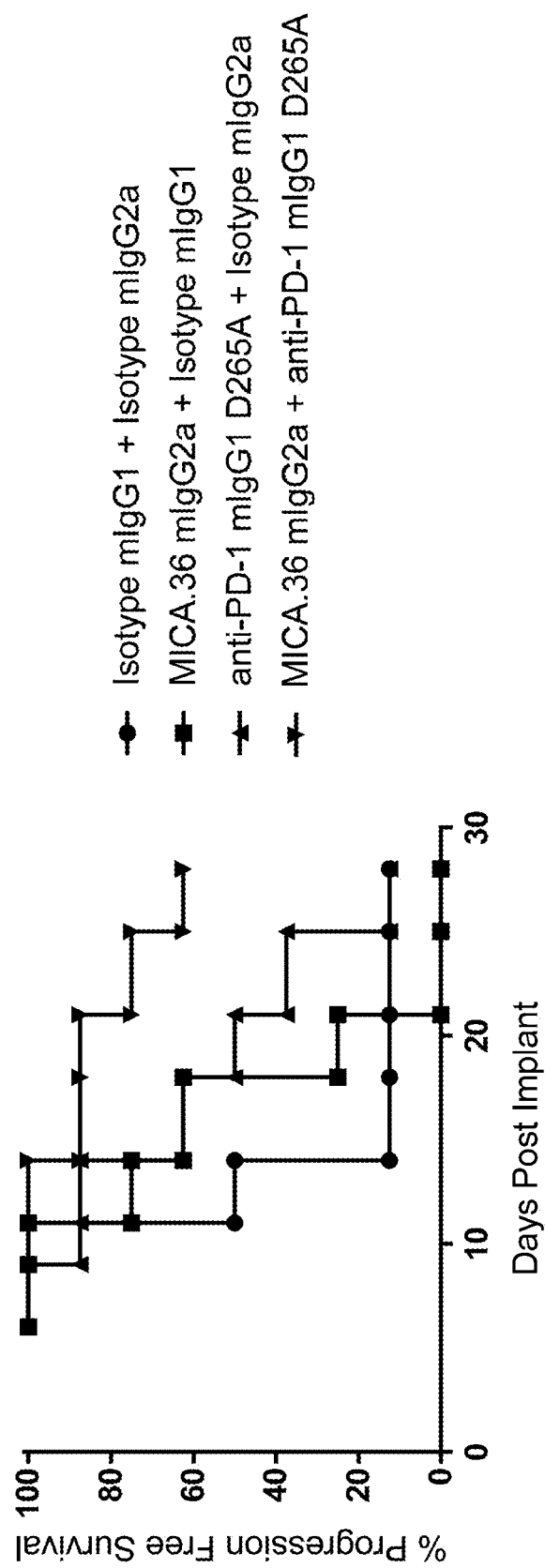

FIGS. 21A-21D show the results of the in vivo effects of anti-MICA/B antibodies in B6-MICA transgenic mice injected subcutaneously with EG7-MICA/B tumor cells. FIGS. 21A and 21B are graphical representations of the mean (FIG. 21A) and median (FIG. 21B) tumor volume in mice treated with 10 mg/kg isotype mIgG1 and 10 mg/kg isotype mIgG2a (circles), 10 mg/kg MICA.36 mIgG2a and 10 mg/kg isotype mIgG1 (squares), 10 mg/kg anti-PD-1 mIgG1 D265A and 10 mg/kg isotype mIgG2a (triangles), or 10 mg/kg MICA.36 mIgG2a and 10 mg/kg isotype mIgG2a anti-PD-1 mIgG1 (inverted triangles). FIG. 21C is a graphical representation of the calculated percent tumor growth inhibition (TGI %) for each treatment group: 10 mg/kg MICA.36 mIgG2a and 10 mg/kg isotype mIgG1 (circles), 10 mg/kg anti-PD-1 mIgG1 D265A and 10 mg/kg isotype mIgG2a (squares), and 10 mg/kg MICA.36 mIgG2a and 10 mg/kg anti-PD-1 mIgG1 D265A (triangles). FIG. 21D shows the progression free survival (PFS %) for transgenic mice injected subcutaneously with EG7-MICA tumor cells following treatment with 10 mg/kg isotype mIgG1 and 10 mg/kg isotype mIgG2a (circles), 10 mg/kg MICA.36 mIgG2a and 10 mg/kg isotype mIgG1 (squares), 10 mg/kg anti-PD-1 mIgG1 D265A and 10 mg/kg isotype mIgG2a (triangles), or 10 mg/kg MICA.36 mIgG2a and 10 mg/kg anti-PD-1 mIgG1 D265A (inverted triangles).

Figure 22C:
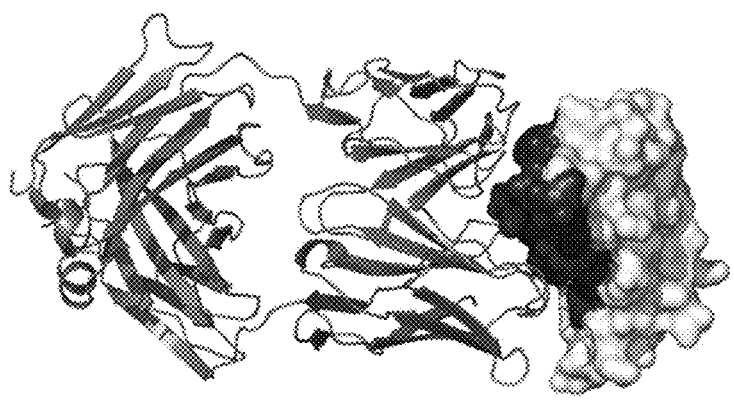
Figure 22B:
Figure 22A:
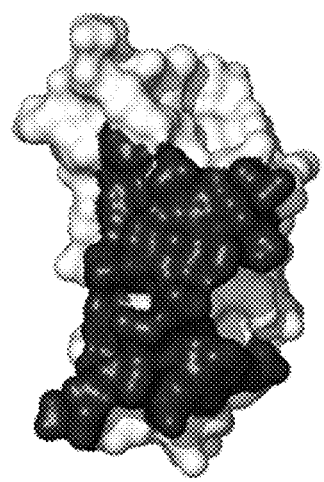

FIGS. 22A-22C show the results of epitope mapping using X-ray co-crystallography. FIG. 22A is a surface representation of the α3 domain of MICA with epitope residues shown in black, and the remaining surface residues shown in grey. FIGS. 22B and 22C show two orientations of MICA.36 Fab (ribbon representation) in complex with the α3 domain of MICA (surface representation, as shown in FIG. 22A). The MICA.36 epitope on the α3 domain of MICA is shown in black, and the remaining residues of the α3 domain of MICA are shown in grey.

Figure 23A:
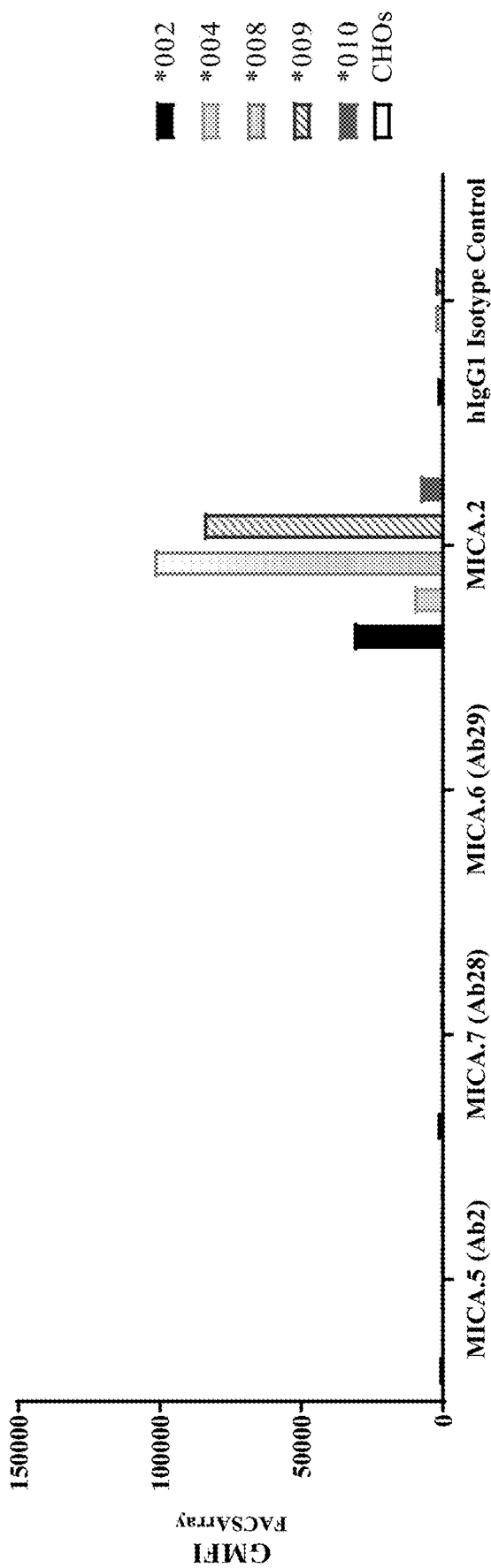
Figure 23B:
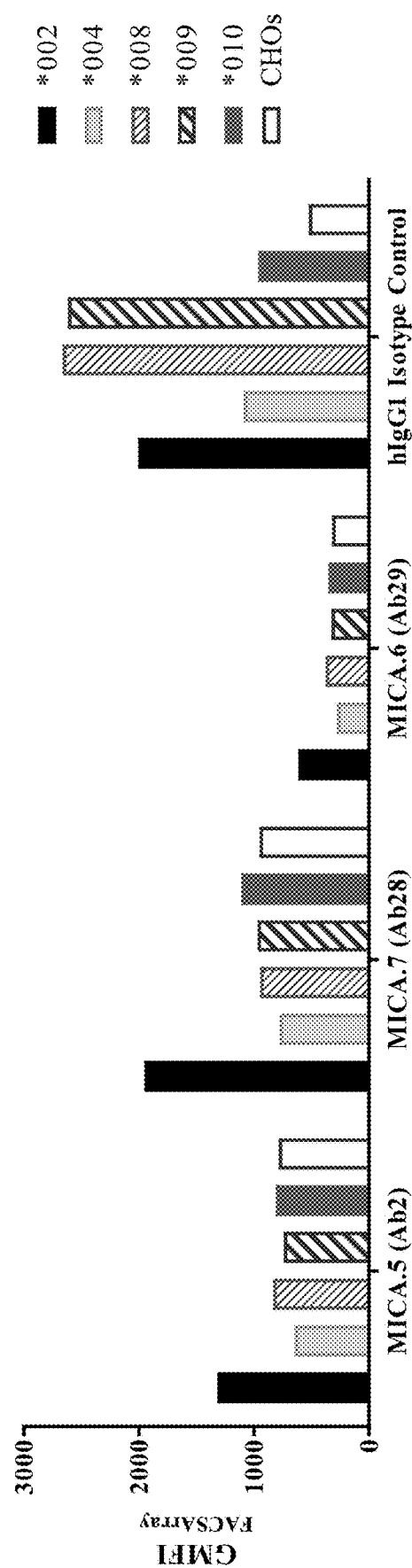

FIGS. 23A-23B show the binding affinity of anti-MICA/B antibodies to MICA common alleles expressed on CHO cells using FACS. FIG. 23B shows the same data as in FIG. 23A but with a different Y-axis for recombinant antibodies MICA.5, MICA.6 and MICA.7 and the isotype control.

Figure 24A:
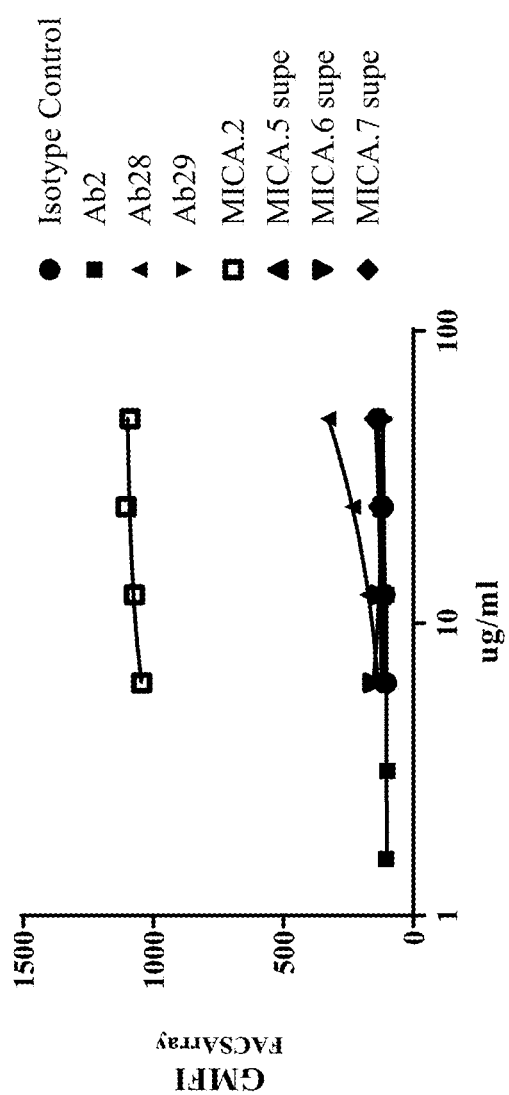
Figure 24B:
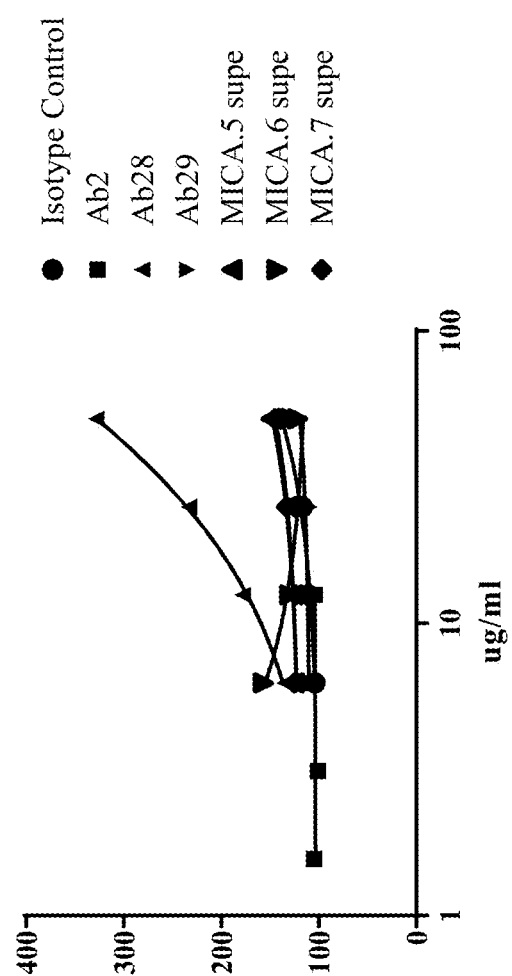

FIGS. 24A-24B show the binding affinity of anti-MICA/B antibodies to MICA endogenously expressed on RPMI-8226 cells using FACS. FIG. 24B shows the same data as in FIG. 24A but with a different Y-axis for Ab2, Ab28, Ab29, the isotype control, and the supernatants ("supe") from the CHO cell lines expressing recombinant antibodies MICA.5, MICA.6 and MICA.7.

Figure 25:
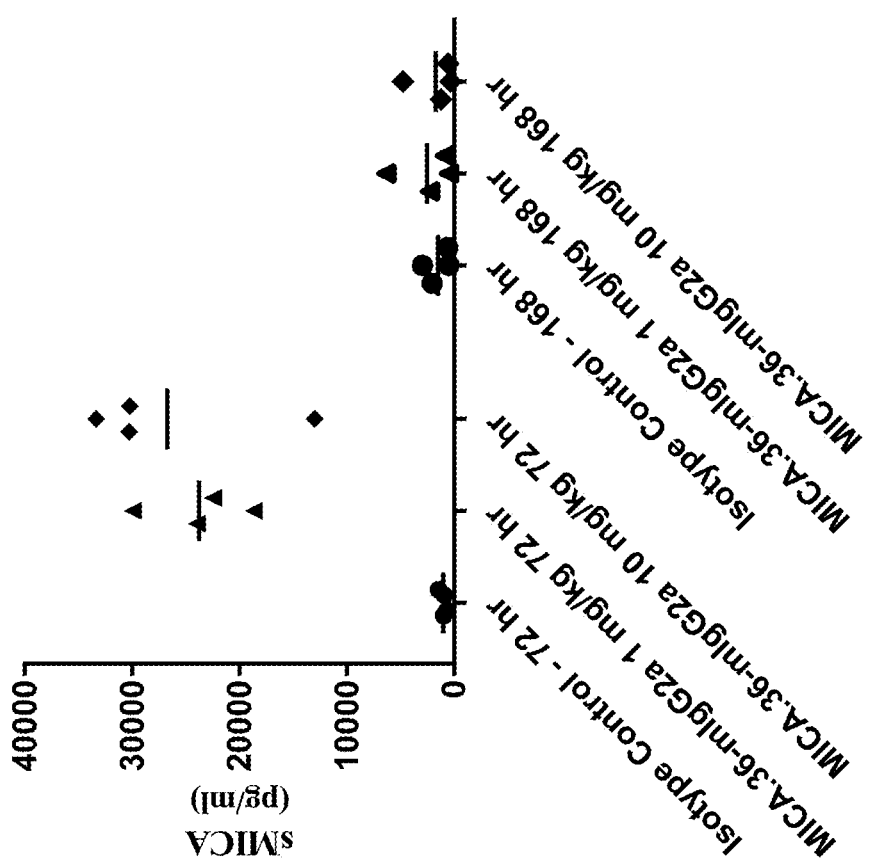

FIG. 25 shows serum levels of soluble MICA/B in B6-MICA transgenic mice 72 hours and 168 hours after dosed with antibody MICA.36-mIgG2a at 1 mg/kg or 10 mg/kg or isotype control.

Figure 26:
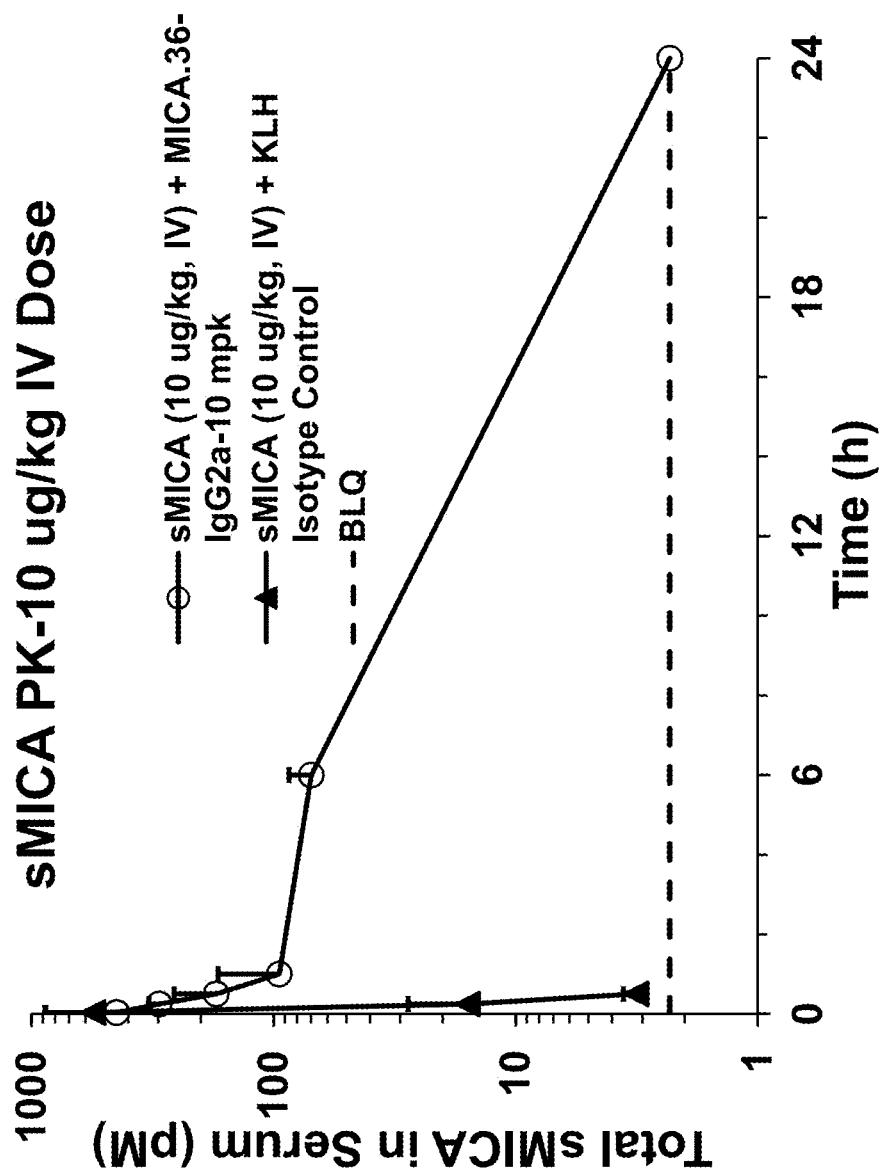

FIG. 26 shows the results of PK analysis of sMICA in B6-MICA transgenic mice after dosed with sMICA and antibody MICA.36-mIgG2a or isotype control.

DETAILED DESCRIPTION OF DISCLOSURE

The present disclosure relates to antibodies and antigen binding fragments thereof that specifically bind MHC class I polypeptide-related sequence A (MICA) and/or MHC class I polypeptide-related sequence B (MICB) ("anti-MICA/B antibodies"). In some embodiments, the MICA is human MICA. In some embodiments, the MICB is human MICB. Other aspects of the present disclosure relate to methods of treating a subject in need thereof, comprising administering to the subject an antibody or antigen binding fragment thereof that specifically binds MICA and/or MICB. In some embodiments, the subject has a cancer, and the anti-MICA/B antibody treats the cancer in the subject.

I. Terms

In order that the present description can be more readily understood, certain terms are first defined. Additional definitions are set forth throughout the detailed description.

It is to be noted that the term "a" or "an" entity refers to one or more of that entity; for example, "a nucleotide sequence," is understood to represent one or more nucleotide sequences. As such, the terms "a" (or "an"), "one or more," and "at least one" can be used interchangeably herein.

Furthermore, "and/or" where used herein is to be taken as specific disclosure of each of the two specified features or components with or without the other. Thus, the term "and/or" as used in a phrase such as "A and/or B" herein is intended to include "A and B," "A or B," "A" (alone), and "B" (alone). Likewise, the term "and/or" as used in a phrase such as "A, B, and/or C" is intended to encompass each of the following aspects: A, B, and C; A, B, or C; A or C; A or B; B or C; A and C; A and B; B and C; A (alone); B (alone); and C (alone).

It is understood that wherever aspects are described herein with the language "comprising," otherwise analogous aspects described in terms of "consisting of" and/or "consisting essentially of" are also provided.

Unless defined otherwise, all technical and scientific terms used herein have the same meaning as commonly understood by one of ordinary skill in the art to which this disclosure is related. For example, the Concise Dictionary of Biomedicine and Molecular Biology, Juo, Pei-Show, 2nd ed., 2002, CRC Press; The Dictionary of Cell and Molecular Biology, 3rd ed., 1999, Academic Press; and the Oxford Dictionary Of Biochemistry And Molecular Biology, Revised, 2000, Oxford University Press, provide one of skill with a general dictionary of many of the terms used in this disclosure.

Units, prefixes, and symbols are denoted in their Système International de Unites (SI) accepted form. Numeric ranges are inclusive of the numbers defining the range. Unless otherwise indicated, nucleotide sequences are written left to right in 5' to 3' orientation. Amino acid sequences are written left to right in amino to carboxy orientation. The headings provided herein are not limitations of the various aspects of the disclosure, which can be had by reference to the specification as a whole. Accordingly, the terms defined immediately below are more fully defined by reference to the specification in its entirety.

The term "about" is used herein to mean approximately, roughly, around, or in the regions of. When the term "about" is used in conjunction with a numerical range, it modifies that range by extending the boundaries above and below the numerical values set forth. In general, the term "about" can modify a numerical value above and below the stated value by a variance of, e.g., 10 percent, up or down (higher or lower).

The term "MEC class I polypeptide-related sequence A" or "MICA" as used herein refers to a non-classical major histocompatibility complex (MHC) class I molecule. The term "MHC class I polypeptide-related sequence B" or "MICB" as used herein refers to a non-classical major histocompatibility complex (MHC) class I molecule. The term "MICA/B" as used herein refers to MICA and/or MICB.

MICA is a naturally expressed glycosylated and polymorphic protein that is generally anchored to the cell membrane. Cleavage of membrane bound MICA by matrix metalloproteinases and ADAM proteinase releases a soluble form of MICA into the extracellular matrix. MICA is a ligand for NKG2D, which is a receptor expressed on the surface of natural killer (NK) cells, CD8 T cells, and γδ T cells. MICA expression is induced in healthy cells during stress, and MICA acts as a signal to induce NK and T cell mediated cytolysis of the cell expressing MICA. Effectively, MICA acts as a "kill me" signal for cells during stress. MICA is expressed by a variety of tumor cells.

The term "MICA" includes any variants or isoforms of MICA which are naturally expressed by cells, including but not limited to tumor cells. Accordingly, antibodies described herein may cross-react with MICA from species other than human (e.g., cynomolgus MICA). Alternatively, the antibodies may be specific for human MICA and do not exhibit any cross-reactivity with other species. MICA or any variants and isoforms thereof, can either be isolated from cells or tissues which naturally express them or be recombinantly produced using well-known techniques in the art and/or those described herein.

Human MICA (SEQ ID NO: 51) consists of 332 amino acids. At least two additional isoforms of human MICA have been identified. Isoform 1, known as MICA1 (UniProt ID No. Q29983-1; SEQ ID NO: 109) consists of 383 amino acids. Isoform 2, known as MICA2 (UniProt ID No. Q29983-2; SEQ ID NO: 88) consists of 287 amino acids. MICA2 lacks amino acid residues 109-204 relative to the amino acid sequence of MICA1.

Below are the amino acid sequences of the three known human MICA isoforms.

```
(A) Human MICA (SEQ ID NO: 51):
MGLGPVFLLLAGIFPFAPPGAAAEPHSLRYNLTVLSWDGSVQSGFLAEVH

LDGQPFLRYDRQKCRAKPQGQWAEDVLGNKTWDRETRDLTGNGKDLRMTL

AHIKDQKEGLHSLQEIRVCEIHEDNSTRSSQHFYYDGELFLSQNLETEEW

TVPQSSRAQTLAMNVRNFLKEDAMKTKTHYHAMHADCLQELRRYLESGVV

LRRTVPPMVNVTRSEASEGNITVTCRASSFYPRNIILTWRQDGVSLSHDT

QQWGDVLPDGNGTYQTWVATRICRGEEQRFTCYMEHSGNHSTHPVPSGKV

LVLQSHWQTFHVSAVAAGCCYFCYYYFLCPLL (B) Human MICA isoform 1 (UniProt ID No. Q29983-1;
SEQ ID NO: 109):
MGLGPVFLLLAGIFPFAPPGAAAEPHSLRYNLTVLSWDGSVQSGFLTEVH

LDGQPFLRCDRQKCRAKPQGQWAEDVLGNKTWDRETRDLTGNGKDLRMTL

AHIKDQKEGLHSLQEIRVCEIHEDNSTRSSQHFYYDGELFLSQNLETKEW
```

```
TMPQSSRAQTLAMNVRNFLKEDAMKTKTHYHAMHADCLQELRRYLKSGVV

LRRTVPPMVNVTRSEASEGNITVTCRASGFYPWNITLSWRQDGVSLSHDT

QQWGDVLPDGNGTYQTWVATRICQGEEQRFTCYMEHSGNHSTHPVPSGKV

LVLQSHWQTFHVSAVAAAAIFVIIIFYVRCCKKKTSAAEGPELVSLQVLD

QHPVGTSDHRDATQLGFQPLMSDLGSTGSTEGA (C) Human MICA isoform 2 (UniProt ID No. Q29983-2;
SEQ ID NO: 88):
MGLGPVFLLLAGIFPFAPPGAAAEPHSLRYNLTVLSWDGSVQSGFLTEVH

LDGQPFLRCDRQKCRAKPQGQWAEDVLGNKTWDRETRDLTGNGKDLRMTL

AHIKDQKEVPPMVNVTRSEASEGNITVTCRASGFYPWNITLSWRQDGVSL

SHDTQQWGDVLPDGNGTYQTWVATRICQGEEQRFTCYMEHSGNHSTHPVP

SGKVLVLQSHWQTFHVSAVAAAAIFVIIIFYVRCCKKKTSAAEGPELVSL

QVLDQHPVGTSDHRDATQLGFQPLMSDLGSTGSTEGA
```

The signal sequence of MICA corresponds to amino acids 1-23 (underlined). Thus, the mature isoforms of MICA, MICA1, and MICA2 consist of amino acids 24 to 332, 383, or 287, respectively. The extracellular domain of mature human MICA consists of amino acids 24-307 of SEQ ID NO: 51 and has the amino acid sequence:

```
                                        (SEQ ID NO: 89)
EPHSLRYNLTVLSWDGSVQSGFLTEVHLDGQPFLRCDRQKCRAKPQGQWA

EDVLGNKTWDRETRDLTGNGKDLRMTLAHIKDQKEGLHSLQEIRVCEIHE

DNSTRSSQHFYYDGELFLSQNLETKEWTMPQSSRAQTLAMNVRNFLKEDA

MKTKTHYHAMHADCLQELRRYLKSGVVLRRTVPPMVNVTRSEASEGNITV

TCRASGFYPWNITLSWRQDGVSLSHDTQQWGDVLPDGNGTYQTWVATRIC

QGEEQRFTCYMEHSGNHSTHPVPSGKVLVLQSHW.
```

There are a number of known MICA (MICA) alleles. In some embodiments, the MICA is MICA*002 (also referred to herein as the MICA*002 allele), which has the amino acid sequence:

```
                                        (SEQ ID NO: 110)
MGLGPVFLLLAGIFPFAPPGAAAEPHSLRYNLTVLSGDGSVQSGFLAEVH

LDGQPFLRCDRQKCRAKPQGQWAEDVLGNKTWDRETRDLTGNGKDLRMTL

AHIKDQKEGLHSLQEIRVCEIHEDNSTRSSQHFYYDGELFLSQNLETEEW

TMPQSSRAQTLAMNVRNFLKEDAMKTKTHYHAMHADCLQELRRYLKSGVV

VTRSEASEGNITVTCRASGFYPWNITLSWRLRRTVPPMVNQDGVSLSHDT

QQWGDVLPDGNGTYQTWVATRICQGEEQRFTCYMEHSGNHSTHPVPSGKV

LVLQSHWQTFHVSAVAAAAIEVIIIFYVRCCKKKTSAAEGPELVSLQVLD

QHPVGTSDHRDATQLGFQPLMSDLGSTGSTEGT.
```

In some embodiments, the MICA is MICA*004 (also referred to herein as the MICA*004 antigen), which has the amino acid sequence:

```
                                        (SEQ ID NO: 111)
MGLGPVFLLLAGIFPFAPPGAAAEPHSLRYNLTVLSWDGSVQSGFLAEVH
```

-continued
LDGQPFLRYDRQKCRAKPQGQWAEDVLGNKTWDRETRDLTGNGKDLRMTL

AHIKDQKEGLHSLQEIRVCEIHEDNSTRSSQHFYYDGELFLSQNVETEEW

TVPQSSRAQTLAMNVRNFLKEDAMKTKTHYHAMHADCLQELRRYLESSVV

LRRRVPPMVNVTRSEASEGNITVTCRASSFYPRNITLSTRQDGVSLSHDT

QQWGDVLPDGNGTYQTWVATRICQGEEQRFTCYMEHSGNHSTHPVPSGKV

LVLQSHWQTFHVSAVAAAAAAIEVIIIFYVRCCKKKTSAAEGPELVSLQV

LDQHPVGTSDHRDATQLGFQPLMSALGSTGSTEGA.

In some embodiments, the MICA is MICA*008 (also referred to herein as the MICA*008 antigen), which has the amino acid sequence:

(SEQ ID NO: 112)
MGLGPVFLLLAGIFPFAPPGAAAEPHSLRYNLTVLSWDGSVQSGFLAEVH

LDGQPFLRYDRQKCRAKPQGQWAEDVLGNKTWDRETRDLTGNGKDLRMTL

AHIKDQKEGLHSLQEIRVCEIHEDNSTRSSQHFYYDGELFLSQNLETEEW

TVPQSSRAQTLAMNVRNFLKEDAMKTKTHYHAMHADCLQELRRYLESGVV

LRRTVPPMVNVTRSEASEGNITVTCRASSFYPRNIILTWRQDGVSLSHDT

QQWGDVLPDGNGTYQTWVATRICRGEEQRFTCYMEHSGNHSTHPVPSGKV

LVLQSHWQTFHVSAVAAAAIFVIIIFYVRCC.

In some embodiments, the MICA is MICA*009 (also referred to herein as the MICA*009 antigen), which has the amino acid sequence:

(SEQ ID NO: 113)
MGLGPVFLLLAGIFPFAPPGAAAEPHSLRYNLTVLSWDGSVQSGFLAEVH

LDGQPFLRYDRQKCRAKPQGQWAEDVLGNKTWDRETRDLTGNGKDLRMTL

AHIKDQKEGLHSLQEIRVCEIHEDNSTRSSQHFYYDGELFLSQNLETEEW

TVPQSSRAQTLAMNVRNFLKEDAMKTKTHYHAMHADCLQELRRYLESSVV

LRRTVPPMVNVTRSEASEGNITVTCRASSFYPRNITLTWRQDGVSLSHDT

QQWGDVLPDGNGTYQTWVATRICQGEEQRFTCYMEHSGNHSTHPVPSGKV

LVLQSHWQTFHVSAVAAAAIEVIIIFYVRCCKKKTSAAEGPELVSLQVLD

QHPVGTSDHRDATQLGFQPLMSALGSTGSTEGT.

in some embodiments, the MICA is MICA*009 (also referred to herein as the MICA*009 antigen), which has the amino acid sequence:

(SEQ ID NO: 114)
MGLGPVFLLLAGIFPFAPPGAAAEPHSLPYNLTVLSWDGSVQSGFLAEVH

LDGQPFLRYDRQKCRAKPQGQWAEDVLGNKTWDRETRDLTGNGKDLRMTL

AHIKDQKEGLHSLQEIRVCEIHEDNSTRSSQHFYYDGELFLSQNLETEEW

TVPQSSRAQTLAMNVRNFLKEDAMKTKTHYHAMHADCLQELRRYLESSVV

LRRTVPPMVNVTRSEASEGNITVTCRASSFYPRNIILTWRQDGVSLSHDT

QQWGDVLPDGNGTYQTWVATRICRGEEQRFTCYMEHSGNHSTHPVPSGKV

LVLQSHWQTFHVSAVAAAAAIEVIIIFYVRCCKKKTSAAEGPELVSLQVL

DQHPVGTSDHRDATQLGFQPLMSALGSTGSTEGA.

There are many different alleles of human MICA known in the art, including seventy-three or more MICA alleles. See Frigoul and Lefranc, *Recent Res. Devel. Human Genet.* 3:95-145 (2005). The antibodies disclosed in the present description can bind to one or more allele of MICA. In some embodiments, the anti-MICA/B antibodies specifically bind to a single MICA allele. In some embodiments, the anti-MICA/B antibodies bind with high affinity to one or more MICA allele and with low affinity to other MICA alleles. In some embodiments, the anti-MICA/B antibodies bind to one or more MICA allele selected from the group consisting of MICA*002, MICA*004, MICA*008, and MICA*009. In some embodiments, the anti-MICA/B antibodies bind with high affinity to MICA*004, MICA*008, and MICA*009 and optionally with low affinity to MICA*002.

Cynomolgus MICA protein comprises the following amino acid sequence (including a signal sequence):

ELHSLRYNVTVLSRDGSVQSGFLAEGHLDGQLFLLYDRQKCRARPQGEWS

EDVLGAKTWDTETGDLTENGKDLRMTLAHIKGQKGGLHSLQEIKVCEIHE

DNSTGGLRHFYYDGELFLSQNLETQEWTELQSSRAQTLALNIRNFWKEDT

MKTKTHYRAVQADCLKKLQQYLESGVAVRRTAPPMVNVTHSEASEGNITV

TCRASGFYPRNIALTWRQDGVSLNHNAQQWGGILPDQNGTYQTWVATRIR

QGEEQRFACYMEHSGNHSTHPVPS (SEQ ID NO: 90; UniProt

ID No. Q2MGE0).

MICB is a naturally expressed glycosylated and polymorphic protein that is generally anchored to the cell membrane. Cleavage of membrane bound MICB releases a soluble form of MICB into the extracellular matrix. MICB is a ligand for NKG2D and acts as a signal to induce NK and T cell mediated cytolysis of the cell expressing MICB. MICB acts as a "kill me" signal for cells during stress and is expressed by a variety of tumor cells. The term "MICB" includes any variants or isoforms of MICB which are naturally expressed by cells, including but not limited to tumor cells.

Antibodies described herein may cross-react with MICB from species other than human (e.g., cynomolgus MICB). Alternatively, the antibodies may be specific for human MICB and do not exhibit any cross-reactivity with other species. MICB or any variants and isoforms thereof, can either be isolated from cells or tissues which naturally express them or be recombinantly produced using well-known techniques in the art and/or those described herein.

Human MICB (SEQ ID NO: 132) consists of 383 amino acids (UniProt ID No. Q29980), having the amino acid sequence below:

MGLGRVLLFLAVAFPFAPPAAAAEPHSLRYNLMVLSQDESVQSGFLAEGH

LDGQPFLRYDRQKRRAKPQGQWAEDVLGAKTWDTETEDLTENGQDLRRTL

THIKDQKGGLHSLQEIRVCEIHEDSSTRGSRHFYYDGELFLSQNLETQES

TVPQSSRAQTLAMNVTNFWKEDAMKTKTHYRAMQADCLQKLQRYLKSGVA

IRRTVPPMVNVTCSEVSEGNITVTCRASSFYPRNITLTWRQDGVSLSHNT

QQWGDVLPDGNGTYQTWVATRIRQGEEQRFTCYMEHSGNHGTHPVPSGKV

LVLQSQRTDFPYVSAAMPCFVIIILCVPCCKKKTSAAEGPELVSLQVLD

QHPVGTGDHRDAAQLGFQPLMSATGSTGSTEGA

Additional isoforms of human MICB have been identified. Isoform 2 of MICB (UniProt ID No. Q29980-2) has the following amino acid sequence:

(SEQ ID NO: 133)
MGLGRVLLFLAVAFPFAPPAAAAEPHSLRYNLMVLSQDESVQSGFLAEGH

LDGQPFLRYDRQKRRAKPQGQWAEDVLGAKTWDTETEDLTENGQDLRRTL

THIKDQKGVPQSSRAQTLAMNVTNFWKEDAMKTKTHYRAMQADCLQKLQR

YLKSGVAIRRTVPPMVNVTCSEVSEGNITVTCRASSFYPRNITLTWRQDG

VSLSHNTQQWGDVLPDGNGTYQTWVATRIRQGEEQRFTCYMEHSGNHGTH

PVPSGKVLVLQSQRTDFPYVSAAMPCFVIIIILCVPCCKKKTSAAEGPEL

VSLQVLDQHPVGTGDHRDAAQLGFQPLMSATGSTGSIEGA.

The term "antibody" refers, in some embodiments, to a protein comprising at least two heavy (H) chains and two light (L) chains inter-connected by disulfide bonds. Each heavy chain is comprised of a heavy chain variable region (abbreviated herein as VH) and a heavy chain constant region (abbreviated herein as CH). In some antibodies, e.g., naturally-occurring IgG antibodies, the heavy chain constant region is comprised of a hinge and three domains, CH1, CH2 and CH3. In some antibodies, e.g., naturally-occurring IgG antibodies, each light chain is comprised of a light chain variable region (abbreviated herein as VL) and a light chain constant region. The light chain constant region is comprised of one domain (abbreviated herein as CL). The VH and VL regions can be further subdivided into regions of hypervariability, termed complementarity determining regions (CDR), interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, and FR4. The variable regions of the heavy and light chains contain a binding domain that interacts with an antigen. The constant regions of the antibodies can mediate the binding of the immunoglobulin to host tissues or factors, including various cells of the immune system (e.g., effector cells) and the first component (C1q) of the classical complement system. A heavy chain may have the C-terminal lysine or not. Unless specified otherwise herein, the amino acids in the variable regions are numbered using the Kabat numbering system and those in the constant regions are numbered using the EU system.

An "IgG antibody", e.g., a human IgG1, IgG2, IgG3 and IgG4 antibody, as used herein has, in some embodiments, the structure of a naturally-occurring IgG antibody, i.e., it has the same number of heavy and light chains and disulfide bonds as a naturally-occurring IgG antibody of the same subclass. For example, an anti-MICA/B IgG1, IgG2, IgG3 or IgG4 antibody consists of two heavy chains (HCs) and two light chains (LCs), wherein the two HCs and LCs are linked by the same number and location of disulfide bridges that occur in naturally-occurring IgG1, IgG2, IgG3 and IgG4 antibodies, respectively (unless the antibody has been mutated to modify the disulfide bridges).

Antibodies typically bind specifically to their cognate antigen with high affinity, reflected by a dissociation constant ($K_D$) of $10^{-5}$ to $10^{-11}$ M or less. Any $K_D$ greater than about $10^{-4}$ M is generally considered to indicate nonspecific binding. As used herein, an antibody that "binds specifically" to an antigen refers to an antibody that binds to the antigen and substantially identical antigens with high affinity, which means having a $K_D$ of $10^{-7}$ M or less, $10^{-8}$ M or less, $5 \times 10^{-9}$ M or less, or between $10^{-8}$ M and $10^{-10}$ M or less, but does not bind with high affinity to unrelated antigens. An antigen is "substantially identical" to a given antigen if it exhibits a high degree of sequence identity to the given antigen, for example, if it exhibits at least 80%, at least 90%, at least 95%, at least 97%, or at least 99% sequence identity to the sequence of the given antigen. By way of example, an antibody that binds specifically to human MICA/B can, in some embodiments, also have cross-reactivity with MICA/B antigens from certain primate species (e.g., cynomolgus MICA/B), but cannot cross-react with MICA/B antigens from other species or with an antigen other than MICA/B.

An immunoglobulin can be from any of the commonly known isotypes, including but not limited to IgA, secretory IgA, IgG and IgM. The IgG isotype is divided in subclasses in certain species: IgG1, IgG2, IgG3 and IgG4 in humans, and IgG1, IgG2a, IgG2b and IgG3 in mice. In some embodiments, the anti-MICA/B antibodies described herein are of the IgG1 subtype. Immunoglobulins, e.g., IgG1, exist in several allotypes, which differ from each other in at most a few amino acids. "Antibody" includes, by way of example, both naturally-occurring and non-naturally-occurring antibodies; monoclonal and polyclonal antibodies; chimeric and humanized antibodies; human and nonhuman antibodies and wholly synthetic antibodies.

The term "antigen-binding portion" of an antibody, as used herein, refers to one or more fragments of an antibody that retain the ability to specifically bind to an antigen (e.g., human MICA/B). It has been shown that the antigen-binding function of an antibody can be performed by fragments of a full-length antibody. Examples of binding fragments encompassed within the term "antigen-binding portion" of an antibody, e.g., an anti-MICA/B antibody described herein, include (i) a Fab fragment (fragment from papain cleavage) or a similar monovalent fragment consisting of the $V_L$, $V_H$, LC and CH1 domains; (ii) a F(ab')2 fragment (fragment from pepsin cleavage) or a similar bivalent fragment comprising two Fab fragments linked by a disulfide bridge at the hinge region; (iii) a Fd fragment consisting of the $V_H$ and CH1 domains; (iv) a Fv fragment consisting of the $V_L$ and $V_H$ domains of a single arm of an antibody, (v) a dAb fragment (Ward et al., (1989) Nature 341:544-546), which consists of a $V_H$ domain; (vi) an isolated complementarity determining region (CDR) and (vii) a combination of two or more isolated CDRs which can optionally be joined by a synthetic linker. Furthermore, although the two domains of the Fv fragment, $V_L$ and $V_H$, are coded for by separate genes, they can be joined, using recombinant methods, by a synthetic linker that enables them to be made as a single protein chain in which the $V_L$ and $V_H$ regions pair to form monovalent molecules (known as single chain Fv (scFv); see, e.g., Bird et al. (1988) Science 242:423-426; and Huston et al. (1988) Proc. Natl. Acad. Sci. U.S.A. 85:5879-5883). Such single chain antibodies are also intended to be encompassed within the term "antigen-binding portion" of an antibody. These antibody fragments are obtained using conventional techniques known to those with skill in the art, and the fragments are screened for utility in the same manner as are intact antibodies. Antigen-binding portions can be produced by recombinant DNA techniques, or by enzymatic or chemical cleavage of intact immunoglobulins.

A "bispecific" or "bifunctional antibody" is an artificial hybrid antibody having two different heavy/light chain pairs and two different binding sites. Bispecific antibodies can be produced by a variety of methods including fusion of hybridomas or linking of Fab' fragments. See, e.g., Songsivilai & Lachmnann, *Clin Exp. Immunol.* 79:315-321 (1990); Kostelny et al., *J. Immunol.* 148, 1547-1553 (1992).

The term "monoclonal antibody," as used herein, refers to an antibody from a population of substantially homogeneous antibodies, i.e., the individual antibodies comprised in the population are substantially similar and bind the same epitope(s) (e.g., the antibodies display a single binding specificity and affinity), except for possible variants that may arise during production of the monoclonal antibody, such variants generally being present in minor amounts. The modifier "monoclonal" indicates the character of the antibody as being obtained from a substantially homogeneous population of antibodies, and is not to be construed as requiring production of the antibody by any particular method. The term "human monoclonal antibody" refers to an antibody from a population of substantially homogeneous antibodies that display(s) a single binding specificity and which has variable and optional constant regions derived from human germline immunoglobulin sequences. In some embodiments, human monoclonal antibodies are produced by a hybridoma which includes a B cell obtained from a transgenic non-human animal, e.g., a transgenic mouse, having a genome comprising a human heavy chain transgene and a light chain transgene fused to an immortalized cell.

The term "recombinant human antibody," as used herein, includes all human antibodies that are prepared, expressed, created or isolated by recombinant means, such as (a) antibodies isolated from an animal (e.g., a mouse) that is transgenic or transchromosomal for human immunoglobulin genes or a hybridoma prepared therefrom, (b) antibodies isolated from a host cell transformed to express the antibody, e.g., from a transfectoma, (c) antibodies isolated from a recombinant, combinatorial human antibody library, and (d) antibodies prepared, expressed, created or isolated by any other means that involve splicing of human immunoglobulin gene sequences to other DNA sequences. Such recombinant human antibodies comprise variable and constant regions that utilize particular human germline immunoglobulin sequences encoded by the germline genes, but include subsequent rearrangements and mutations which occur, for example, during antibody maturation. As known in the art (see, e.g., Lonberg (2005) *Nature Biotech.* 23(9): 1117-1125), the variable region contains the antigen binding domain, which is encoded by various genes that rearrange to form an antibody specific for a foreign antigen. In addition to rearrangement, the variable region can be further modified by multiple single amino acid changes (referred to as somatic mutation or hypermutation) to increase the affinity of the antibody to the foreign antigen. The constant region will change in further response to an antigen (i.e., isotype switch). Therefore, the rearranged and somatically mutated nucleic acid molecules that encode the light chain and heavy chain immunoglobulin polypeptides in response to an antigen cannot have sequence identity with the original nucleic acid molecules, but instead will be substantially identical or similar (i.e., have at least 80% identity).

A "human" antibody (HuMAb) refers to an antibody having variable regions in which both the framework and CDR regions are derived from human germline immunoglobulin sequences. Furthermore, if the antibody contains a constant region, the constant region also is derived from human germline immunoglobulin sequences. The anti-MICA/B antibodies described herein can include amino acid residues not encoded by human germline immunoglobulin sequences (e.g., mutations introduced by random or site-specific mutagenesis in vitro or by somatic mutation in vivo). However, the term "human antibody", as used herein, is not intended to include antibodies in which CDR sequences derived from the germline of another mammalian species, such as a mouse, have been grafted onto human framework sequences. The leans "human" antibodies and "fully human" antibodies are used synonymously.

A "humanized" antibody refers to an antibody in which some, most or all of the amino acids outside the CDR domains of a non-human antibody are replaced with corresponding amino acids derived from human immunoglobulins. In some embodiments of a humanized form of an antibody, some, most or all of the amino acids outside the CDR domains have been replaced with amino acids from human immunoglobulins, whereas some, most or all amino acids within one or more CDR regions are unchanged. Small additions, deletions, insertions, substitutions or modifications of amino acids are permissible as long as they do not abrogate the ability of the antibody to bind to a particular antigen. A "humanized" antibody retains an antigenic specificity similar to that of the original antibody.

A "chimeric antibody" refers to an antibody in which the variable regions are derived from one species and the constant regions are derived from another species, such as an antibody in which the variable regions are derived from a mouse antibody and the constant regions are derived from a human antibody.

As used herein, "isotype" refers to the antibody class (e.g., IgG1, IgG2, IgG3, IgG4, IgM, IgA1, IgA2, IgD, and IgE antibody) that is encoded by the heavy chain constant region genes.

"Allotype" refers to naturally-occurring variants within a specific isotype group, which variants differ in a few amino acids (see, e.g., Jefferis et al. (2009) mAbs 1:1). Anti-MICA/B antibodies described herein can be of any allotype. As used herein, antibodies referred to as "IgG1f," "IgG1.if," or "IgG1.3f" isotype are IgG1, effectorless IgG1.1, and effectorless IgG1.3 antibodies, respectively, of the allotype "f," i.e., having 214R, 356E and 358M according to the EU index as in Kabat.

The phrases "an antibody recognizing an antigen" and "an antibody specific for an antigen" are used interchangeably herein with the term "an antibody which binds specifically to an antigen."

An "isolated antibody," as used herein, is intended to refer to an antibody which is substantially free of other proteins and cellular material.

As used herein, an antibody that "binds MICA/B" is intended to refer to an antibody that interacts with MICA/B, e.g., in binding assays using CHO cells transfected with human MICA/B or MICA/B expressing tumor cells, with an $EC_{50}$ of about 25 µg/mL or less, about 23 µg/mL or less, about 20 µg/mL or less, about 15 µg/mL or less, about 10 µg/mL or less, about 5 µg/mL or less, about 3 µg/mL or less, about 2 µg/mL or less, about 1 µg/mL or less, about 0.5 µg/mL or less, about 0.45 µg/mL or less, about 0.4 µg/mL or less, about 0.35 µg/mL, or less, or about 0.3 µg/mL or less, in art-recognized methods, e.g., the FACS-based binding assays described herein. In some embodiments, the anti-MICA/B antibody binds human-MICA/B expressed on, e.g., CHO cells, with an $EC_{50}$ of about 200 nM or less, about 175 nM or less, about 160 nM or less, about 150 nM or less, about 125 nM or less, about 110 nM or less, about 100 nM or less about 80 nM or less, about 75 nM or less, about 60 nM or less, about 50 nM or less, about 40 nM or less, about 35 nM or less, about 30 nM or less, about 25 nM or less, about 20 nM or less, about 15 nM or less, about 10 nM or less, about 9 nM or less, about 8 nM or less, about 7 nM or less, about 6 nM or less, about 5 nM or less, about 4 nM or less, about 3 nM or less, about 2 nM or less, about 1.9 nM or less, about 1.8 nM or less, about 1.7 nM or less, about 1.6 nM or less, about 1.5 nM or less, about 1.4 nM or less, about 1.3 nM or less, about 1.2 nM or less, about 1.1 nM or less, about 1.0 nM or less, about 0.9 nM or less, about 0.8 nM or less, about 0.7 nM or less, about 0.6 nM or less, about 0.5 nM or less, about 0.4 nM or less, about 0.3 nM or less, about 0.2 nM or less, or about 0.1 nM or less. In certain embodiments, the anti-MICA/B antibody binds human-MICA/B expressed on, e.g., CHO cells, with an $EC_{50}$ of less than about 10 nM. In certain embodiments, the anti-MICA/B antibody binds human-MICA/B expressed on, e.g., CHO cells, with an $EC_{50}$ of less than about 5 nM. In certain embodiments, the anti-MICA/B antibody binds human-MICA/B expressed on, e.g., CHO cells, with an $EC_{50}$ of less than about 1.5 nM. In certain embodiments, the anti-MICA/B antibody binds human-MICA/B expressed on, e.g., CHO cells, with an $EC_{50}$ of about 1 nM or less. In certain embodiments, the anti-MICA/B antibody binds human-MICA/B expressed on, e.g., CHO cells, with an $EC_{50}$ of about 0.5 nM or less. In certain embodiments, the anti-MICA/B antibody binds human-MICA/B expressed on, e.g., CHO cells, with an $EC_{50}$ of about 0.3 nM or less. In certain embodiments, the anti-MICA/B antibody binds human-MICA/B expressed on, e.g., CHO cells, with an $EC_{50}$ of about 0.2 nM or less.

As used herein, an antibody that "inhibits, prevents, or reduces shedding of MICA/B" by a cell, e.g., a tumor cell, is intended to refer to an antibody that inhibits, prevents, or reduces release of soluble MICA/B from the surface of the cell. Without being bound by a mechanism, the anti-MICA/B antibodies disclosed herein reduce the amount of MICA/B that is released, e.g., by cleavage, into the plasma as soluble MICA/B. In some embodiments, the antibody increases membrane bound MICA/B on the surface of the cell. In some embodiments, the anti-MICA/B antibody increases the retention of surface MICA/B on a cell transfected with human MICA/B at a MICA/B retention $EC_{50}$ of about 10 nM or less, about 5 nM or less, about 1 nM or less, about 0.85 nM or less, about 0.8 nM or less, about 0.75 nM or less, about 0.7 nM or less, about 0.65 nM or less, about 0.6 nM or less, about 0.55 nM or less, about 0.5 nM or less, about 0.45 nM or less, about 0.4 nM or less, about 0.35 nM or less, about 0.3 nM or less, about 0.25 nM or less, about 0.2 nM or less, about 0.15 nM or less, or about 0.1 nM or less. In certain embodiments, the anti-MICA/B antibody increases retention of surface MICA/B on a cell transfected with human MICA/B by at least about 1.2 fold, at least about 1.3 fold, at least about 1.4 fold, at least about 1.5 fold, at least about 1.6 fold, at least about 1.7 fold, at least about 1.8 fold, at least about 1.9 fold, at least about 2 fold, at least about 2.1 fold, at least about 2.2 fold, at least about 2.3 fold, at least about 2.4 fold, at least about 2.5 fold, at least about 2.75 fold, at least about 3 fold, at least about 3.5 fold, at least about 4 fold, at least about 4.5 fold, at least about 5 fold, at least about 7.5 fold, at least about 10 fold, or at least about 20 fold.

In some embodiments, the anti-MICA/B antibody reduces soluble MICA/B (sMICA/B) levels in the serum of the patient. In some embodiments, the anti-MICA/B antibody reduces soluble MICA/B shed from cells transfected with human MICA/B at an $IC_{50}$ of about 10 nM or less, about 5 nM or less, about 1 nM or less, about 0.7 nM or less, about 0.6 nM or less, about 0.5 nM or less, about 0.45 nM or less, about 0.4 nM or less, about 0.35 nM or less, about 0.3 nM or less, about 0.25 nM or less, about 0.2 nM or less, about 0.19 nM or less, about 0.18 nM or less, about 0.17 nM or less, about 0.16 nM or less, about 0.15 nM or less, about 0.14 nM or less, about 0.13 nM or less, about 0.12 nM or less, about 0.11 nM or less, about 0.1 nM or less, about 0.09 nM or less, about 0.08 nM or less, about 0.07 nM or less, about 0.06 nM or less, about 0.05 nM or less, about 0.04 nM or less, about 0.03 nM or less, about 0.02 nM or less, or about 0.01 nM or less. In certain embodiments, the anti-MICA/B antibody reduces shedding of MICA/B from cells transfected with human MICA by about 0.9 fold or less, about 0.85 fold or less, about 0.8 fold or less, about 0.75 fold or less, about 0.7 fold or less, about 0.65 fold or less, about 0.6 fold or less, about 0.55 fold or less, about 0.5 fold or less, about 0.45 fold or less, about 0.4 fold or less, about 0.35 fold or less, about 0.3 fold or less, about 0.25 fold or less, about 0.2 fold or less, about 0.15 fold or less, about 0.1 fold or less, or about 0.05 or less. In certain embodiments, the anti-MICA/B antibody may reduce soluble MICA/B in the serum of a subject by, e.g., at least about 10%, at least about 20%, at least about 30%, at least about 40%, at least about 50%, at least about 60%, at least about 70%, at least about 80%, or at least about 90%.

The term "shed" or "shedding," as used herein, refers to the release of soluble MICA/B from the surface of a MICA/B expressing cell. MICA/B is expressed as a transmembrane protein, which is localized to the cell surface. Cleavage within the extracellular domain releases a portion of MICA/B into the plasma, which is referred to herein as "soluble MICA/B" or "sMICA/B."

An "effector function" refers to the interaction of an antibody Fc region with an Fc receptor or ligand, or a biochemical event that results therefrom. Exemplary "effector functions" include C1q binding, complement dependent cytotoxicity (CDC), Fc receptor binding, FcγR-mediated effector functions such as ADCC and antibody dependent cell-mediated phagocytosis (ADCP), and downregulation of a cell surface receptor (e.g., the B cell receptor; BCR). Such effector functions generally require the Fc region to be combined with a binding domain (e.g., an antibody variable domain).

An "Fc receptor" or "FcR" is a receptor that binds to the Fc region of an immunoglobulin. FcRs that bind to an IgG antibody comprise receptors of the FcγR family, including allelic variants and alternatively spliced forms of these receptors. The FcγR family consists of three activating (FcγRI, FcγRIII, and FcγRIV in mice; FcγRIA, FcγRIIA, and FcγRIIIA in humans) and one inhibitory (FcγRIIB) receptor. Various properties of human FcγRs are known in the art. The majority of innate effector cell types coexpress one or more activating FcγR and the inhibitory FcγRIIB, whereas natural killer (NK) cells selectively express one activating Fc receptor (FcγRIII in mice and FcγRIIIA in humans) but not the inhibitory FcγRIIB in mice and humans Human IgG1 binds to most human Fc receptors and is considered equivalent to murine IgG2a with respect to the types of activating Fc receptors that it binds to.

An "Fc region" (fragment crystallizable region) or "Fc domain" or "Fc" refers to the C-terminal region of the heavy chain of an antibody that mediates the binding of the immunoglobulin to host tissues or factors, including binding to Fc receptors located on various cells of the illumine system (e.g., effector cells) or to the first component (C1q) of the classical complement system. Thus, an Fc region comprises the constant region of an antibody excluding the first constant region immunoglobulin domain (e.g., CH1 or CL). In IgG, IgA and IgD antibody isotypes, the Fc region comprises two identical protein fragments, derived from the second (CH2) and third (CH3) constant domains of the antibody's two heavy chains; IgM and IgE Fc regions comprise three heavy chain constant domains (CH domains 2-4) in each polypeptide chain. For IgG, the Fc region comprises immunoglobulin domains CH2 and CH3 and the hinge between CH1 and CH2 domains Although the definition of the boundaries of the Fc region of an immunoglobulin heavy chain might vary, as defined herein, the human IgG heavy chain Fc region is defined to stretch from an amino acid residue D221 for IgG1, V222 for IgG2, L221 for IgG3 and P224 for IgG4 to the carboxy-terminus of the heavy chain, wherein the numbering is according to the EU index as in Kabat. The CH2 domain of a human IgG Fc region extends from amino acid 237 to amino acid 340, and the CH3 domain is positioned on C-terminal side of a CH2 domain in an Fc region, i.e., it extends from amino acid 341 to amino acid 447 or 446 (if the C-terminal lysine residue is absent) or 445 (if the C-terminal glycine and lysine residues are absent) of an IgG. As used herein, the Fc region can be a native sequence Fc, including any allotypic variant, or a variant Fc (e.g., a non-naturally-occurring Fc).

A "native sequence Fc region" or "native sequence Fc" comprises an amino acid sequence that is identical to the amino acid sequence of an Fc region found in nature. Native sequence human Fc regions include a native sequence human IgG1 Fc region; native sequence human IgG2 Fc region; native sequence human IgG3 Fc region; and native sequence human IgG4 Fc region as well as naturally-occurring variants thereof. Native sequence Fc include the various allotypes of Fcs (see, e.g., Jefferis el al. (2009) mAbs 1:1).

The term "epitope" or "antigenic determinant" refers to a site on an antigen (e.g., MICA) to which an immunoglobulin or antibody specifically binds, e.g., as defined by the specific method used to identify it. Epitopes can be formed both from contiguous amino acids (usually a linear epitope) or non-contiguous amino acids juxtaposed by tertiary folding of a protein (usually a conformational epitope). Epitopes formed from contiguous amino acids are typically, but not always, retained on exposure to denaturing solvents, whereas epitopes formed by tertiary folding are typically lost on treatment with denaturing solvents. An epitope typically includes at least 3, 4, 5, 6, 7, 8, 9, 10, 11, 12, 13, 14 or 15 amino acids in a unique spatial conformation. Methods for determining what epitopes are bound by a given antibody (i.e., epitope mapping) are well known in the art and include, for example, immunoblotting and immunoprecipitation assays, wherein overlapping or contiguous peptides from (e.g., from MICA) are tested for reactivity with a given antibody (e.g., anti-MICA/B antibody). Methods of determining spatial conformation of epitopes include techniques in the art and those described herein, for example, x-ray crystallography, x-ray co-crystallography, antigen mutational analysis, 2-dimensional nuclear magnetic resonance and HDX-MS (see, e.g., Epitope Mapping Protocols in Methods in Molecular Biology, Vol. 66, G. E. Morris, Ed. (1996)).

The term "epitope mapping" refers to the process of identification of the molecular determinants for antibody-antigen recognition.

The term "binds to the same epitope" with reference to two or more antibodies means that the antibodies bind to the same segment of amino acid residues, as determined by a given method. Techniques for determining whether antibodies bind to the "same epitope on MICA" with the antibodies described herein include, for example, epitope mapping methods, such as, x-ray analyses of crystals of antigen:antibody complexes which provides atomic resolution of the epitope and hydrogen/deuterium exchange mass spectrometry (HDX-MS). Other methods monitor the binding of the antibody to antigen fragments or mutated variations of the antigen where loss of binding due to a modification of an amino acid residue within the antigen sequence is often considered an indication of an epitope component. In addition, computational combinatorial methods for epitope mapping can also be used. These methods rely on the ability of the antibody of interest to affinity isolate specific short peptides from combinatorial phage display peptide libraries. Antibodies having the same VH and VL or the same CDR1, 2 and 3 sequences are expected to bind to the same epitope.

Antibodies that "compete with another antibody for binding to a target" refer to antibodies that inhibit (partially or completely) the binding of the other antibody to the target. Whether two antibodies compete with each other for binding to a target, i.e., whether and to what extent one antibody inhibits the binding of the other antibody to a target, can be determined using known competition experiments, e.g., BIACORE® surface plasmon resonance (SPR) analysis. In some embodiments, an antibody competes with, and inhibits binding of another antibody to a target by at least 50%, 60%, 70%, 80%, 90% or 100%. The level of inhibition or competition can be different depending on which antibody is the "blocking antibody" (i.e., the cold antibody that is incubated first with the target). Competition assays can be conducted as described, for example, in Ed Harlow and David Lane, Cold Spring Harb Protoc; 2006; doi: 10.1101/pdb.prot4277 or in Chapter 11 of "Using Antibodies" by Ed Harlow and David Lane, Cold Spring Harbor Laboratory Press, Cold Spring Harbor, N.Y., USA 1999. Two antibodies "cross-compete" if antibodies block each other both ways by at least 50%, i.e., regardless of whether one or the other antibody is contacted first with the antigen in the competition experiment.

Competitive binding assays for determining whether two antibodies compete or cross-compete for binding include: competition for binding to cells expressing MICA/B, e.g., by flow cytometry, such as described in the Examples. Other methods include: SPR (e.g., BIACORE®), solid phase direct or indirect radioimmunoassay (RIA), solid phase direct or indirect enzyme immunoassay (EIA), sandwich competition assay (see Stahli et al., *Methods in Enzymology* 9:242 (1983)); solid phase direct biotin-avidin EIA (see Kirkland et al., *J. Immunol.* 137:3614 (1986)); solid phase direct labeled assay, solid phase direct labeled sandwich assay (see Harlow and Lane, Antibodies: A Laboratory Manual, Cold Spring Harbor Press (1988)); solid phase direct label RIA using 1-125 label (see Morel et al., *Mol. Immunol.* 25(1):7 (1988)); solid phase direct biotin-avidin EIA (Cheung et al., *Virology* 176:546 (1990)); and direct labeled RIA. (Moldenhauer et al., *Scand. J. Immunol.* 32:77 (1990)).

As used herein, the terms "specific binding," "selective binding," "selectively binds," and "specifically binds," refer to antibody binding to an epitope on a predetermined antigen. Typically, the antibody (i) binds with an equilibrium dissociation constant ($K_D$) of approximately less than $10^{-7}$ M, such as approximately less than $10^{-8}$ M, $10^{-9}$ M or $10^{-10}$ M or even lower when determined by, e.g., surface plasmon resonance (SPR) technology in a BIACORE® 2000 instrument using the predetermined antigen, e.g., recombinant human MICA or MICB, as the analyte and the antibody as the ligand, or Scatchard analysis of binding of the antibody to antigen positive cells, and (ii) binds to the predetermined antigen with an affinity that is at least two-fold greater than its affinity for binding to a non-specific antigen (e.g., BSA, casein) other than the predetermined antigen or a closely-related antigen. Accordingly, an antibody that "specifically binds to human MICA/B" refers to an antibody that binds to soluble or cell bound human MICA/B with a $K_D$ of $10^{-7}$ M or less, such as approximately less than $10^{-8}$ M, $10^{-9}$M or $10^{-10}$ M or even lower. An antibody that "cross-reacts with cynomolgus MICA/B" refers to an antibody that binds to cynomolgus MICA/B with a $K_D$ of $10^{-7}$ M or less, such as approximately less than $10^{-8}$ M, $10^{-9}$M or $10^{-10}$ M or even lower. In some embodiments, such antibodies that do not cross-react with MICA/B from a non-human species exhibit essentially undetectable binding against these proteins in standard binding assays.

The term "$k_{assoc}$" or "$k_a$", as used herein, is intended to refer to the association rate of a particular antibody-antigen interaction, whereas the term "$k_{dis}$" or "$k_d$," as used herein, is intended to refer to the dissociation rate of a particular antibody-antigen interaction. The term "$K_D$", as used herein, is intended to refer to the dissociation constant, which is obtained from the ratio of $k_d$ to $k_a$ (i.e., $k_d/k_a$) and is expressed as a molar concentration (M). $K_D$ values for antibodies can be determined using methods well established in the art. Available methods for determining the $K_D$ of an antibody include surface plasmon resonance, a biosensor system such as a BIACORE® system or flow cytometry and Scatchard analysis.

As used herein, the term "high affinity" for an IgG antibody refers to an antibody having a $K_D$ of $10^{-8}$ M or less, $10^{-9}$ M or less, or $10^{-10}$ M or less for a target antigen. However, "high affinity" binding can vary for other antibody isotypes. For example, "high affinity" binding for an IgM isotype refers to an antibody having a $K_D$ of $10^{-10}$ M or less, or $10^{-8}$ M or less.

The term "$EC_{50}$" in the context of an in vitro or in vivo assay using an antibody or antigen binding fragment thereof, refers to the concentration of an antibody or an antigen-binding portion thereof that induces a response that is 50% of the maximal response, i.e., halfway between the maximal response and the baseline.

The term "naturally-occurring" as used herein as applied to an object refers to the fact that an object can be found in nature. For example, a polypeptide or polynucleotide sequence that is present in an organism (including viruses) that can be isolated from a source in nature and which has not been intentionally modified by man in the laboratory is naturally-occurring.

A "polypeptide" refers to a chain comprising at least two consecutively linked amino acid residues, with no upper limit on the length of the chain. One or more amino acid residues in the protein can contain a modification such as, but not limited to, glycosylation, phosphorylation or disulfide bond formation. A "protein" can comprise one or more polypeptides.

The term "nucleic acid molecule," as used herein, is intended to include DNA molecules and RNA molecules. A nucleic acid molecule can be single-stranded or double-stranded, and can be cDNA.

"Conservative amino acid substitutions" refer to substitutions of an amino acid residue with an amino acid residue having a similar side chain Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine). In some embodiments, a predicted nonessential amino acid residue in an anti-MICA/B antibody is replaced with another amino acid residue from the same side chain family. Methods of identifying nucleotide and amino acid conservative substitutions which do not eliminate antigen binding are well-known in the art (see, e.g., Brummell et al., *Biochem.* 32: 1180-1187 (1993); Kobayashi et al. *Protein Eng.* 12(10):879-884 (1999); and Burks et al. *Proc. Natl. Acad. Sci. USA* 94:412-417 (1997)).

For nucleic acids, the term "substantial homology" indicates that two nucleic acids, or designated sequences thereof, when optimally aligned and compared, are identical, with appropriate nucleotide insertions or deletions, in at least about 80% of the nucleotides, at least about 90% to 95%, or at least about 98% to 99.5% of the nucleotides. Alternatively, substantial homology exists when the segments will hybridize under selective hybridization conditions, to the complement of the strand.

For polypeptides, the term "substantial homology" indicates that two polypeptides, or designated sequences thereof, when optimally aligned and compared, are identical, with appropriate amino acid insertions or deletions, in at least about 80% of the amino acids, at least about 90% to 95%, or at least about 98% to 99.5% of the amino acids.

The percent identity between two sequences is a function of the number of identical positions shared by the sequences (i.e., % homology=# of identical positions/total # of positions×100), taking into account the number of gaps, and the length of each gap, which need to be introduced for optimal alignment of the two sequences. The comparison of sequences and determination of percent identity between two sequences can be accomplished using a mathematical algorithm, as described in the non-limiting examples below.

The percent identity between two nucleotide sequences can be determined using the GAP program in the GCG software package (available at worldwideweb.gcg.com), using a NWSgapdna.CMP matrix and a gap weight of 40, 50, 60, 70, or 80 and a length weight of 1, 2, 3, 4, 5, or 6. The percent identity between two nucleotide or amino acid sequences can also be determined using the algorithm of E. Meyers and W. Miller (*CABIOS*, 4: 11-17 (1989)) which has been incorporated into the ALIGN program (version 2.0), using a PAM120 weight residue table, a gap length penalty of 12 and a gap penalty of 4. In addition, the percent identity between two amino acid sequences can be determined using the Needleman and Wunsch (*J. Mol. Biol.* (48):444-453 (1970)) algorithm which has been incorporated into the GAP program in the GCG software package (available at www.gcg.com), using either a Blossum 62 matrix or a PAM250 matrix, and a gap weight of 16, 14, 12, 10, 8, 6, or 4 and a length weight of 1, 2, 3, 4, 5, or 6.

The nucleic acid and protein sequences described herein can further be used as a "query sequence" to perform a search against public databases to, for example, identify related sequences. Such searches can be performed using the NBLAST and XBLAST programs (version 2.0) of Altschul, et. al. (1990) *J. Mol. Biol.* 215:403-10. BLAST nucleotide searches can be performed with the NBLAST program, score=100, word length=12 to obtain nucleotide sequences homologous to the nucleic acid molecules described herein. BLAST protein searches can be performed with the XBLAST program, score=50, word length=3 to obtain amino acid sequences homologous to the protein molecules described herein. To obtain gapped alignments for comparison purposes, Gapped BLAST can be utilized as described in Altschul et al., (1997) *Nucleic Acids Res.* 25(17):3389-3402. When utilizing BLAST and Gapped BLAST programs, the default parameters of the respective programs (e.g., XBLAST and NBLAST) can be used. See worldwideweb.ncbi.nlm.nih.gov.

The nucleic acids can be present in whole cells, in a cell lysate, or in a partially purified or substantially pure form. A nucleic acid is "isolated" or "rendered substantially pure" when purified away from other cellular components or other contaminants, e.g., other cellular nucleic acids (e.g., the other parts of the chromosome) or proteins, by standard techniques, including alkaline/SDS treatment, CsCl banding, column chromatography, agarose gel electrophoresis and others well known in the art. See, F. Ausubel, et al., ed. Current Protocols in Molecular Biology, Greene Publishing and Wiley Interscience, New York (1987).

Nucleic acids, e.g., cDNA, can be mutated, in accordance with standard techniques to provide gene sequences. For coding sequences, these mutations, can affect amino acid sequence as desired. In particular, DNA sequences substantially homologous to or derived from native V, D, J, constant, switches and other such sequences described herein are contemplated (where "derived" indicates that a sequence is identical or modified from another sequence).

The term "vector," as used herein, is intended to refer to a nucleic acid molecule capable of transporting another nucleic acid to which it has been linked. One type of vector is a "plasmid," which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" (or simply, "expression vectors"). In general, expression vectors of utility in recombinant DNA techniques are often in the form of plasmids. In the present specification, "plasmid" and "vector" can be used interchangeably as the plasmid is the most commonly used form of vector. However, also included are other forms of expression vectors, such as viral vectors (e.g., replication defective retroviruses, adenoviruses and adeno-associated viruses), which serve equivalent functions.

The term "recombinant host cell" (or simply "host cell"), as used herein, is intended to refer to a cell that comprises a nucleic acid that is not naturally present in the cell, and can be a cell into which a recombinant expression vector has been introduced. It should be understood that such terms are intended to refer not only to the particular subject cell but to the progeny of such a cell. Because certain modifications can occur in succeeding generations due to either mutation or environmental influences, such progeny cannot, in fact, be identical to the parent cell, but are still included within the scope of the term "host cell" as used herein.

An "immune response" is as understood in the art, and generally refers to a biological response within a vertebrate against foreign agents or abnormal, e.g., cancerous cells, which response protects the organism against these agents and diseases caused by them. An immune response is mediated by the action of one or more cells of the immune system (for example, a T lymphocyte, B lymphocyte, natural killer (NK) cell, macrophage, eosinophil, mast cell, dendritic cell or neutrophil) and soluble macromolecules produced by any of these cells or the liver (including antibodies, cytokines, and complement) that results in selective targeting, binding to, damage to, destruction of, and/or elimination from the vertebrate's body of invading pathogens, cells or tissues infected with pathogens, cancerous or other abnormal cells, or, in cases of autoimmunity or pathological inflammation, normal human cells or tissues. An immune reaction includes, e.g., activation or inhibition of a T cell, e.g., an effector T cell, a Th cell, a CD4$^+$ cell, a CD8$^+$ T cell, or a Treg cell, or activation or inhibition of any other cell of the immune system, e.g., NK cell.

An "immunomodulator" or "immunoregulator" refers to an agent, e.g., an agent targeting a component of a signaling pathway that can be involved in modulating, regulating, or modifying an immune response. "Modulating," "regulating," or "modifying" an immune response refers to any alteration in a cell of the immune system or in the activity of such cell (e.g., an effector T cell, such as a Th1 cell). Such modulation includes stimulation or suppression of the immune system which can be manifested by an increase or decrease in the number of various cell types, an increase or decrease in the activity of these cells, or any other changes which can occur within the immune system. Both inhibitory and stimulatory immunomodulators have been identified, some of which can have enhanced function in a tumor microenvironment. In some embodiments, the immunomodulator targets a molecule on the surface of a T cell. An "immunomodulatory target" or "immunoregulatory target" is a molecule, e.g., a cell surface molecule, that is targeted for binding by, and whose activity is altered by the binding of, a substance, agent, moiety, compound or molecule. Immunomodulatory targets include, for example, receptors on the surface of a cell ("immunomodulatory receptors") and receptor ligands ("immunomodulatory ligands").

"Immunotherapy" refers to the treatment of a subject afflicted with, or at risk of contracting or suffering a recurrence of, a disease by a method comprising inducing, enhancing, suppressing or otherwise modifying the immune system or an immune response.

"Immuno stimulating therapy" or "immuno stimulatory therapy" refers to a therapy that results in increasing (inducing or enhancing) an immune response in a subject for, e.g., treating cancer.

"Potentiating an endogenous immune response" means increasing the effectiveness or potency of an existing immune response in a subject. This increase in effectiveness and potency can be achieved, for example, by overcoming mechanisms that suppress the endogenous host immune response or by stimulating mechanisms that enhance the endogenous host immune response.

"T effector" ("$T_{\textit{eff}}$") cells refers to T cells (e.g., CD4$^+$ and CD8$^+$ T cells) with cytolytic activities as well as T helper (Th) cells, e.g., Th1 cells, which cells secrete cytokines and activate and direct other immune cells, but does not include regulatory T cells (Treg cells). Certain anti-MICA/B antibodies described herein activate $T_{\textit{eff}}$ cells, e.g., CD4$^+$ and CD8$^+$ $T_{\textit{eff}}$ cells and Th1 cells.

An increased ability to stimulate an immune response or the immune system, can result from an enhanced agonist activity of T cell co-stimulatory receptors and/or an enhanced antagonist activity of inhibitory receptors. An increased ability to stimulate an immune response or the immune system can be reflected by a fold increase of the $EC_{50}$ or maximal level of activity in an assay that measures an immune response, e.g., an assay that measures changes in cytokine or chemokine release, cytolytic activity (determined directly on target cells or indirectly via detecting CD107a or granzymes) and proliferation. The ability to stimulate an immune response or the immune system activity can be enhanced by at least 10%, 30%, 50%, 75%, 2 fold, 3 fold, 5 fold or more.

As used herein, the term "linked" refers to the association of two or more molecules. The linkage can be covalent or non-covalent. The linkage also can be genetic (i.e., recombinantly fused). Such linkages can be achieved using a wide variety of art recognized techniques, such as chemical conjugation and recombinant protein production.

As used herein, "administering" refers to the physical introduction of a composition comprising a therapeutic agent to a subject, using any of the various methods and delivery systems known to those skilled in the art. Different routes of administration for the anti-MICA/B antibodies described herein include intravenous, intraperitoneal, intramuscular, subcutaneous, spinal or other parenteral routes of administration, for example by injection or infusion. The phrase "parenteral administration" as used herein means modes of administration other than enteral and topical administration, usually by injection, and includes, without limitation, intravenous, intraperitoneal, intramuscular, intraarterial, intrathecal, intralymphatic, intralesional, intracapsular, intraorbital, intracardiac, intradermal, transtracheal, subcutaneous, subcuticular, intraarticular, subcapsular, subarachnoid, intraspinal, epidural and intrasternal injection and infusion, as well as in vivo electroporation. Alternatively, an antibody described herein can be administered via a non-parenteral route, such as a topical, epidermal or mucosal route of administration, for example, intranasally, orally, vaginally, rectally, sublingually or topically Administering can also be performed, for example, once, a plurality of times, and/or over one or more extended periods.

As used herein, the term "T cell-mediated response" refers to a response mediated by T cells, including effector T cells (e.g., $CD8^+$ cells) and helper T cells (e.g., $CD4^+$ cells). T cell mediated responses include, for example, T cell cytotoxicity and proliferation.

As used herein, the term "cytotoxic T lymphocyte (CTL) response" refers to an immune response induced by cytotoxic T cells. CTL responses are mediated primarily by $CD8^+$ T cells.

As used herein, the phrase "inhibits growth of a tumor" includes any measurable decrease in the growth of a tumor, e.g., the inhibition of growth of a tumor by at least about 10%, for example, at least about 20%, at least about 30%, at least about 40%, at least about 50%, at least about 60%, at least about 70%, at least about 80%, at least about 90%, at least about 99%, or 100%. In some embodiments, inhibition of tumor growth is measured as the percent tumor growth inhibition (TGI %). TGI % can be determined by calculating the TGI at da1 "t" calculated from all treatment animals according to the formula: $[1-((T_t/T_0)/(C_t/C_0))]/[(C_t-C_0)/C_t]*100$ [Formula 1], where $T_t$=individual tumor size of treated animal at time 't', $T_0$=individual tumor size of treated animal at first measurement, $C_t$=median tumors size of control animals at time 't', $C_0$=median tumor size of control animals at first measurement.

As used herein, "cancer" refers a broad group of diseases characterized by the uncontrolled growth of abnormal cells in the body. Unregulated cell division can result in the formation of malignant tumors or cells that invade neighboring tissues and can metastasize to distant parts of the body through the lymphatic system or bloodstream.

The terms "treat," "treating," and "treatment," as used herein, refer to any type of intervention or process performed on, or administering an active agent to, the subject with the objective of reversing, alleviating, ameliorating, inhibiting, or slowing down or preventing the progression, development, severity or recurrence of a symptom, complication, condition or biochemical indicia associated with a disease or enhancing overall survival. Treatment can be of a subject having a disease or a subject who does not have a disease (e.g., for prophylaxis).

The term "effective dose" or "effective dosage" is defined as an amount sufficient to achieve or at least partially achieve a desired effect. A "therapeutically effective amount" or "therapeutically effective dosage" of a drug or therapeutic agent is any amount of the drug that, when used alone or in combination with another therapeutic agent, promotes disease regression evidenced by a decrease in severity of disease symptoms, an increase in frequency and duration of disease symptom-free periods, an increase in overall survival (the length of time from either the date of diagnosis or the start of treatment for a disease, such a cancer, that patients diagnosed with the disease are still alive), or a prevention of impairment or disability due to the disease affliction. A therapeutically effective amount or dosage of a drug includes a "prophylactically effective amount" or a "prophylactically effective dosage", which is any amount of the drug that, when administered alone or in combination with another therapeutic agent to a subject at risk of developing a disease or of suffering a recurrence of disease, inhibits the development or recurrence of the disease. The ability of a therapeutic agent to promote disease regression or inhibit the development or recurrence of the disease can be evaluated using a variety of methods known to the skilled practitioner, such as in human subjects during clinical trials, in animal model systems predictive of efficacy in humans, or by assaying the activity of the agent in in vitro assays.

By way of example, an anti-cancer agent is a drug that promotes cancer regression in a subject. In some embodiments, a therapeutically effective amount of the drug promotes cancer regression to the point of eliminating the cancer. "Promoting cancer regression" means that administering an effective amount of the drug, alone or in combination with an antineoplastic agent, results in a reduction in tumor growth or size, necrosis of the tumor, a decrease in severity of at least one disease symptom, an increase in frequency and duration of disease symptom-free periods, an increase in overall survival, a prevention of impairment or disability due to the disease affliction, or otherwise amelioration of disease symptoms in the patient. In addition, the terms "effective" and "effectiveness" with regard to a treatment includes both pharmacological effectiveness and physiological safety. Pharmacological effectiveness refers to the ability of the drug to promote cancer regression in the patient. Physiological safety refers to the level of toxicity, or other adverse physiological effects at the cellular, organ and/or organism level (adverse effects) resulting from administration of the drug.

By way of example for the treatment of tumors, a therapeutically effective amount or dosage of the drug inhibits cell growth or tumor growth by at least about 20%, by at least about 40%, by at least about 60%, or by at least about 80% relative to untreated subjects. In some embodiments, a therapeutically effective amount or dosage of the drug completely inhibits cell growth or tumor growth, i.e., inhibits cell growth or tumor growth by 100%. The ability of a compound to inhibit tumor growth can be evaluated using the assays described infra. Alternatively, this property of a composition can be evaluated by examining the ability of the compound to inhibit cell growth, such inhibition can be measured in vitro by assays known to the skilled practitioner. In some embodiments described herein, tumor regression can be observed and continue for a period of at least about 20 days, at least about 40 days, or at least about 60 days.

The term "patient" includes human and other mammalian subjects that receive either prophylactic or therapeutic treatment.

As used herein, the term "subject" includes any human or non-human animal. For example, the methods and compositions described herein can be used to treat a subject having cancer. The term "non-human animal" includes all vertebrates, e.g., mammals and non-mammals, such as non-human primates, sheep, dog, cow, chickens, amphibians, reptiles, etc.

The term "weight based" dose or dosing as referred to herein means that a dose that is administered to a patient is calculated based on the weight of the patient. For example, when a patient with 60 kg body weight requires 3 mg/kg of an anti-MICA/B antibody, one can calculate and use the appropriate amount of the anti-MICA/B antibody (i.e., 180 mg) for administration.

The use of the term "fixed dose" with regard to combinations described herein means that two or more different antibodies (e.g., anti-MICA/B antibody and a second antibody, e.g., a PD-1 or PD-L1 antibody) are present in the composition or administered separately in particular (fixed) amounts or ratios with each other. In some embodiments, the fixed dose is based on the weight (e.g., mg) of the antibodies. In some embodiments, the fixed dose is based on the concentration (e.g., mg/ml) of the antibodies. In some embodiments, the ratio of the two antibodies (e.g., anti-MICA/B and anti-PD1 or anti-PD-L1) is at least about 1:1, about 1:2, about 1:3, about 1:4, about 1:5, about 1:6, about 1:7, about 1:8, about 1:9, about 1:10, about 1:15, about 1:20, about 1:30, about 1:40, about 1:50, about 1:60, about 1:70, about 1:80, about 1:90, about 1:100, about 1:120, about 1:140, about 1:160, about 1:180, about 1:200, about 200:1, about 180:1, about 160:1, about 140:1, about 120:1, about 100:1, about 90:1, about 80:1, about 70:1, about 60:1, about 50:1, about 40:1, about 30:1, about 20:1, about 15:1, about 10:1, about 9:1, about 8:1, about 7:1, about 6:1, about 5:1, about 4:1, about 3:1, or about 2:1 mg first antibody (e.g., anti-MICA/B antibody) to mg second antibody. For example, a 2:1 ratio of an anti-MICA/B antibody and an anti-PD-1 antibody, such as nivolumab, can mean that a vial or an injection can contain about 480 mg of the anti-MICA/B antibody and 240 mg of the anti-PD-1 antibody, or about 2 mg/ml of the anti-MICA/B antibody and 1 mg/ml of the anti-PD-1 antibody.

The use of the term "flat dose" with regard to the methods and dosages described herein means a dose that is administered to a patient without regard for the weight or body surface area (BSA) of the patient. The flat dose is therefore not provided as a mg/kg dose, but rather as an absolute amount of the agent (e.g., the anti-MICA/B antibody). For example, a 60 kg person and a 100 kg person would receive the same dose of an antibody (e.g., 480 mg of an anti-MICA/B antibody).

As used herein, the terms "ug" and "uM" are used interchangeably with "μg" and "μM," respectively.

Various aspects described herein are described in further detail in the following subsections.

II. Anti-Human MICA/B Antibodies

Described herein are antibodies, e.g., fully human antibodies, which are capable of specifically binding to MI-IC class I polypeptide-related sequence AB (MICA/B), and inhibiting, preventing or reducing shedding of MICA/B by tumor cells, thereby increasing retention of MICA/B at the tumor cell surface. For example, the antibodies specifically bind human MICA/B, and more specifically, a particular domain (e g the α3 domain) within the extracellular domain of human MICA. In some embodiments, the antibodies specifically bind to MICA/B, thereby reducing the MICA/B level in serum whereas the antibodies increase the level of membrane bound MICA/B. In some embodiments, anti-MICA/B antibodies cross-react with MICA/B from one or more non-human primates, such as cynomolgus MICA/B. In some embodiments, the antibodies specifically bind to the α3 domain of human MICA/B and the α3 domain of cynomolgus MICA/B. In some embodiments, the antibodies bind to human MICA/B with high affinity.

Anti-MICA/B antibodies described herein exhibit one or more of the following functional properties:
(a) binding to membrane bound human MICA/B;
(b) binding to membrane bound cyno MICA/B;
(c) reducing soluble MICA/B level in the serum in a subject;
(d) increasing membrane bound MICA/B on a tumor cell;
(e) inhibiting, preventing, or reducing shedding of MICA/B by a tumor cell;
(f) mediating enhanced antigen processing and/or cross-presentation by a cell;
(g) mediating enhanced ADCC and/or ADCP;
(h) inhibiting tumor growth and/or metastasis;
(i) reducing tumor volume;
(j) increasing progression-free survival;
(k) increasing overall survival; and
(l) any combination thereof.

In some embodiments, anti-MICA/B antibodies described herein bind to human MICA/B with high affinity, for example, with a $K_D$ of $10^{-6}$ M or less, $10^{-7}$ M or less, $10^{-8}$ M or less, $10^{-9}$ M or less, $10^{-10}$ M or less, $10^{-11}$ M or less, $10^{-12}$ M or less, $10^{-12}$ M to $10^{-7}$ M, $10^{-11}$ M to $10^{-7}$ M, $10^{-10}$ M to $10^{-7}$ M, or $10^{-9}$ M to $10^{-7}$ M. In some embodiments, the anti-MICA/B antibody binds to human MICA/B, e.g., as determined by Surface Plasmon Resonance, e.g. using BIACORE™ (e.g., as described in the Examples), with a $K_D$ of $10^{-6}$ M or less, $10^{-7}$ M or less, $10^{-8}$ M or less, $10^{-9}$ M (1 nM) or less, $10^{-10}$ M or less, $10^{-12}$ M to $10^{-7}$ M, $10^{-11}$ M to $10^{-7}$ M, $10^{-10}$ M to $10^{-7}$ M, $10^{-9}$ M to $10^{-7}$ M, or $10^{-8}$ M to $10^{-7}$ M. In some embodiments, an anti-MICA/B antibody binds to human sMICA/B, e.g., as determined by ELISA, e.g., a MICA/B ELISA kit, e.g., ABCAM ab100592, with an $EC_{50}$ of $EC_{50}$ of 100 nM or less, 10 nM or less, 1 nM or less, 100 nM to 0.01 nM, 100 nM to 0.1 nM, 100 nM to 1 nM, or 10 nM to 1 nM, or 10 ug/mL or less, 5 ug/mL or less, 1 ug/mL or less, 0.9 ug/mL or less, 0.8 ug/mL or less, 0.7 ug/mL or less, 0.6 ug/mL or less, 0.5 ug/mL or less, 0.4 ug/mL or less, 0.3 ug/mL or less, 0.2 ug/mL or less, 0.1 ug/mL or less, 0.05 ug/mL or less, or 0.01 ug/mL or less. In some embodiments, anti-MICA/B antibodies described herein bind to cyno MICA/B, for example, with a $K_D$ of $10^{-6}$ M or less, $10^{-7}$ M or less, $10^{-8}$ M or less, $10^{-9}$ M or less, $10^{-10}$ M or less, $10^{-11}$ M or less, $10^{-12}$ M or less, $10^{-12}$ M to $10^{-7}$ M, $10^{-11}$ M to $10^{-7}$ M, $10^{-10}$ M to $10^{-7}$ M, or $10^{-9}$ M to $10^{-7}$ M. In some embodiments, an anti-MICA/B antibody binds to soluble cyno MICA/B, e.g., as determined by BIACORE™ (e.g., as described in the Examples), with a $K_D$ of $10^{-6}$ M or less, $10^{-7}$ M or less, $10^{-8}$ M or less, $10^{-9}$ M (1 nM) or less, $10^{-10}$ M or less, $10^{-12}$ M to $10^{-7}$ M, $10^{-11}$ M to $10^{-7}$ M, $10^{-10}$ M to $10^{-7}$ M, $10^{-9}$ M to $10^{-7}$ M, or $10^{-8}$ M to $10^{-7}$ M. Anti-MICA/B antibodies can bind to cynomolgus sMICA/B, e.g., with an $EC_{50}$ of 100 nM or less, 10 nM or less, 100 nM to 0.01 nM, 100 nM to 0.1 nM, 100 nM to 1 nM, or 10 nM to 1 nM, e.g., as measured by ELISA (e.g., as described in the Examples).

In some embodiments, the anti-MICA/B antibody specifically binds to human MICA/B with a $K_D$ of about $5 \times 10^{-4}$ M or less, about $1 \times 10^{-4}$ M or less, $5 \times 10^{-5}$ M or less, about $1 \times 10^{-5}$ M or less, about $1 \times 10^{-6}$ M or less, about $1 \times 10^{-7}$ M or less, or about $1 \times 10^{-8}$ M or less, wherein $K_D$ is measured by surface plasmon resonance (BIACORE®) analysis. In some embodiments, the anti-MICA/B antibody specifically binds to human MICA allele MICA*002 with a $K_D$ of about $1 \times 10^{-4}$ M or less, about $1 \times 10^{-5}$ M or less, $1 \times 10^{-6}$ M or less, about $1 \times 10^{-7}$ M or less, or about $1 \times 10^{-8}$ M or less, wherein $K_D$ is measured by surface plasmon resonance (BIACORE®) analysis. In some embodiments, the anti-MICA/B antibody specifically binds to human MICA allele MICA*004 with a $K_D$ of about $1 \times 10^{-4}$ M or less, about $1 \times 10^{-5}$ M or less, $1 \times 10^{-6}$ M or less, about $1 \times 10^{-7}$ M or less, or about $1 \times 10^{-8}$ M or less, wherein $K_D$ is measured by surface plasmon resonance (BIACORE®) analysis. In some embodiments, the anti-MICA/B antibody specifically binds to human MICA allele MICA*008 with a $K_D$ of about $1 \times 10^{-4}$ M or less, about $1 \times 10^{-5}$ M or less, $1 \times 10^{-6}$ M or less, about $1 \times 10^{-7}$ M or less, or about $1 \times 10^{-8}$ M or less, wherein $K_D$ is measured by surface plasmon resonance (BIACORE®) analysis. In some embodiments, the anti-MICA/B antibody specifically binds to human MICA allele MICA*009 with a $K_D$ of about about $1 \times 10^{-4}$ M or less, about $1 \times 10^{-5}$ M or less, $1 \times 10^{-6}$ M or less, about $1 \times 10^{-7}$ M or less, or about $1 \times 10^{-8}$ M or less, wherein $K_D$ is measured by surface plasmon resonance (BIACORE®) analysis. In some embodiments, the anti-MICA/B antibody specifically binds to human MICB allele MICB*005 with a $K_D$ of about $1 \times 10^{-4}$ M or less, about $1 \times 10^{-5}$ M or less, $1 \times 10^{-6}$ M or less, about $1 \times 10^{-7}$ M or less, or about $1 \times 10^{-8}$ M or less, wherein $K_D$ is measured by surface plasmon resonance (BIACORE®) analysis.

In some embodiments, the anti-MICA/B antibody specifically binds human MICA/B with an association constant ($k_a$) rate of at least about $1 \times 10^3$ ms$^{-1}$, at least about $5 \times 10^3$ ms$^{-1}$, at least about $1 \times 10^4$ ms$^{-1}$, at least about $5 \times 10^4$ ms$^{-1}$, at least about $1 \times 10^5$ ms$^{-1}$, at least about $5 \times 10^5$ ms$^{-1}$, or at least about $1 \times 10^6$ ms$^{-1}$, wherein $k_a$ is measured by surface plasmon resonance (BIACORE®) analysis.

In some embodiments, the anti-MICA/B antibody specifically binds human MICA/B with a dissociation constant ($k_d$) rate of about 0.1 s$^{-1}$ or less, 0.05 s$^{-1}$ or less, 0.01 s$^{-1}$ or less, $5 \times 10^{-3}$ s$^{-1}$ or less, $1 \times 10^{-3}$ s$^{-1}$ or less, $5 \times 10^{-4}$ s$^{-1}$ or less, $1 \times 10^{-4}$ s$^{-1}$ or less, $5 \times 10^{-5}$ s$^{-1}$ or less, or $1 \times 10^{-5}$ s$^{-1}$ or less, wherein $K_D$ is measured by surface plasmon resonance (BIACORE®) analysis.

In some embodiments, the anti-MICA/B antibody specifically binds to MICA/B. In some embodiments, the anti-MICA/B antibody binds MICA and MICB. In some embodiments, the anti-MICA/B antibody specifically binds the MICA*002 allele. In some embodiments, the anti-MICA/B antibody specifically binds the MICA*004 allele. In some embodiments, the anti-MICA/B antibody specifically binds the MICA*008 allele. In some embodiments, the anti-MICA/B antibody specifically binds the MICA*009 allele. In some embodiments, the anti-MICA/B antibody specifically binds the MICA*002 allele, the MICA*004 allele, the MICA*008 allele, and the MICA*009 allele. In some embodiments, the anti-MICA/B antibody binds the MICA*002 allele with a higher affinity than the MICA*004 allele, the MICA*008 allele, or the MICA*009 allele. In some embodiments, the anti-MICA/B antibody binds the MICA*004 allele with a higher affinity than the MICA*002 allele, the MICA*008 allele, or the MICA*008 allele. In some embodiments, the anti-MICA/B antibody binds the MICA*008 allele with a higher affinity than the MICA*002 allele, the MICA*004 allele, or the MICA*009 allele. In some embodiments, the anti-MICA/B antibody binds the MICA*009 allele with a higher affinity than the MICA*002 allele, the MICA*004 allele, or the MICA*008 allele.

In some embodiments, the anti-MICA/B antibody comprises a heavy chain variable region (VH) and a light chain variable region (VL); wherein the VH comprises a VH complementarity determining region (CDR) 1 (VH-CDR1), a VH-CDR2, and a VH-CDR3 and the VL comprises a VL-CDR1, a VL-CDR2, and a VL-CDR3; wherein the VH-CDR3 comprises an amino acid sequence having at least about 90%, at least about 95%, at least about 96%, at least about 97%, at least about 98%, or at least about 99% sequence identity to an amino acid sequence selected from the group consisting of SEQ ID NOs: 7, 17, 27, 37, and 47. In some embodiments, the anti-MICA/B antibody comprises a VH-CDR3 comprising an amino acid sequence selected from the group consisting of SEQ ID NOs: 7, 17, 27, 37, and 47. In one embodiment, the anti-MICA/B antibody comprises a VH-CDR3 comprising the amino acid sequence as set forth in SEQ ID NO: 7.

In some embodiments, the anti-MICA/B antibody comprises a VH-CDR2 comprising an amino acid sequence having at least about 90%, at least about 95%, at least about 96%, at least about 97%, at least about 98%, or at least about 99% sequence identity to an amino acid sequence selected from the group consisting of SEQ ID NOs: 6, 16, 26, 36, and 46. In some embodiments, the anti-MICA/B antibody comprises a VH-CDR2 comprising an amino acid sequence selected from the group consisting of SEQ ID NOs: 6, 16, 26, 36, and 46. In one embodiment, the anti-MICA/B antibody comprises a VH-CDR2 comprising the amino acid sequence as set forth in SEQ ID NO: 6.

In some embodiments, the anti-MICA/B antibody comprises a VH-CDR1 comprising an amino acid sequence having at least about 90%, at least about 95%, at least about 96%, at least about 97%, at least about 98%, or at least about 99% sequence identity to an amino acid sequence selected from the group consisting of SEQ ID NOs: 5, 15, 25, 35, and 45. In some embodiments, the anti-MICA/B antibody comprises a VH-CDR1 comprising an amino acid sequence selected from the group consisting of SEQ ID NOs: 5, 15, 25, 35, and 45. In one embodiment, the anti-MICA/B antibody comprises a VH-CDR1 comprising the amino acid sequence as set forth in SEQ ID NO: 5.

In some embodiments, the anti-MICA/B antibody comprises a VL-CDR1 comprising an amino acid sequence having at least about 90%, at least about 95%, at least about 96%, at least about 97%, at least about 98%, or at least about 99% sequence identity to an amino acid sequence selected from the group consisting of SEQ ID NOs: 8, 18, 28, 38, and 48. In some embodiments, the anti-MICA/B antibody comprises a VL-CDR1 comprising an amino acid sequence selected from the group consisting of SEQ ID NOs: 8, 18, 28, 38, and 48. In one embodiment, the anti-MICA/B antibody comprises a VL-CDR1 comprising the amino acid sequence as set forth in SEQ ID NO: 8.

In some embodiments, the anti-MICA/B antibody comprises a VL-CDR2 comprising an amino acid sequence having at least about 90%, at least about 95%, at least about 96%, at least about 97%, at least about 98%, or at least about 99% sequence identity to an amino acid sequence selected from the group consisting of SEQ ID NOs: 9, 19, 29, 39, and 49. In some embodiments, the anti-MICA/B antibody comprises a VL-CDR2 comprising an amino acid sequence selected from the group consisting of SEQ ID NOs: 9, 19, 29, 39, and 49. In one embodiment, the anti-MICA/B antibody comprises a VL-CDR2 comprising the amino acid sequence as set forth in SEQ ID NO: 9.

In some embodiments, the anti-MICA/B antibody comprises a VL-CDR3 comprising an amino acid sequence having at least about 90%, at least about 95%, at least about 96%, at least about 97%, at least about 98%, or at least about 99% sequence identity to an amino acid sequence selected from the group consisting of SEQ ID NOs: 10, 20, 30, 40, and 50. In some embodiments, the anti-MICA/B antibody comprises a VL-CDR3 comprising an amino acid sequence selected from the group consisting of SEQ ID NOs: 10, 20, 30, 40, and 50. In one embodiment, the anti-MICA/B antibody comprises a VL-CDR3 comprising the amino acid sequence set forth in SEQ ID NO: 10.

In certain embodiments, the anti-MICA/B antibody comprises a VH-CDR1 comprising the amino acid sequence set forth in SEQ ID NO:5, a VH-CDR2 comprising the amino acid sequence set forth in SEQ ID NO:6, a VH-CDR3 comprising the amino acid sequence set forth in SEQ ID NO:7, a VL-CDR1 comprising the amino acid sequence set forth in SEQ ID NO:8, a VL-CDR2 comprising the amino acid sequence set forth in SEQ ID NO:9, and a VL-CDR3 comprising the amino acid sequence set forth in SEQ ID NO:10. In some embodiments, the anti-MICA/B antibody is non-fucosylated. In some embodiments, the anti-MICA/B antibody is hypo-fucosylated. III some embodiments, the anti-MICA/B antibody cross competes for binding to human MICA/B with a reference antibody comprising a VH-CDR1 comprising the amino acid sequence set forth in SEQ ID NO:5, a VH-CDR2 comprising the amino acid sequence set forth in SEQ ID NO:6, a VH-CDR3 comprising the amino acid sequence set forth in SEQ ID NO:7, a VL-CDR1 comprising the amino acid sequence set forth in SEQ ID NO:8, a VL-CDR2 comprising the amino acid sequence set forth in SEQ ID NO:9, and a VL-CDR3 comprising the amino acid sequence set forth in SEQ ID NO:10. In some embodiments, the anti-MICA/B antibody binds to the same epitope as a reference antibody comprising a VH-CDR1 comprising the amino acid sequence set forth in SEQ ID NO:5, a VH-CDR2 comprising the amino acid sequence set forth in SEQ ID NO:6, a VH-CDR3 comprising the amino acid sequence set forth in SEQ ID NO:7, a VL-CDR1 comprising the amino acid sequence set forth in SEQ ID NO:8, a VL-CDR2 comprising the amino acid sequence set forth in SEQ ID NO:9, and a VL-CDR3 comprising the amino acid sequence set forth in SEQ ID NO:10.

In certain embodiments, the anti-MICA/B antibody comprises a VH-CDR1 comprising the amino acid sequence set forth in SEQ ID NO:15, a VH-CDR2 comprising the amino acid sequence set forth in SEQ ID NO:16, a VH-CDR3 comprising the amino acid sequence set forth in SEQ ID NO:17, a VL-CDR1 comprising the amino acid sequence set forth in SEQ ID NO:18, a VL-CDR2 comprising the amino acid sequence set forth in SEQ ID NO:19, and a VL-CDR3 comprising the amino acid sequence set forth in SEQ ID NO:20. In some embodiments, the anti-MICA/B antibody is non-fucosylated. In some embodiments, the anti-MICA/B antibody is hypo-fucosylated. In some embodiments, the anti-MICA/B antibody cross competes for binding to human MICA with a reference antibody comprising a VH-CDR1 comprising the amino acid sequence set forth in SEQ ID NO:15, a VH-CDR2 comprising the amino acid sequence set forth in SEQ ID NO:16, a VH-CDR3 comprising the amino acid sequence set forth in SEQ ID NO:17, a VL-CDR1 comprising the amino acid sequence set forth in SEQ ID NO:18, a VL-CDR2 comprising the amino acid sequence set forth in SEQ ID NO:19, and a VL-CDR3 comprising the amino acid sequence set forth in SEQ ID NO:20.

In certain embodiments, the anti-MICA/B antibody comprises a VH-CDR1 comprising the amino acid sequence set forth in SEQ ID NO:25, a VH-CDR2 comprising the amino acid sequence set forth in SEQ ID NO:26, a VH-CDR3 comprising the amino acid sequence set forth in SEQ ID NO:27, a VL-CDR1 comprising the amino acid sequence set forth in SEQ ID NO:28, a VL-CDR2 comprising the amino acid sequence set forth in SEQ ID NO:29, and a VL-CDR3 comprising the amino acid sequence set forth in SEQ ID NO:30. In some embodiments, the anti-MICA/B antibody is non-fucosylated. In some embodiments, the anti-MICA/B antibody is hypo-fucosylated. In some embodiments, the anti-MICA/B antibody cross competes for binding to human MICA with a reference antibody comprising a VH-CDR1 comprising the amino acid sequence set forth in SEQ ID NO:25, a VH-CDR2 comprising the amino acid sequence set forth in SEQ ID NO:26, a VH-CDR3 comprising the amino acid sequence set forth in SEQ ID NO:27, a VL-CDR1 comprising the amino acid sequence set forth in SEQ ID NO:28, a VL-CDR2 comprising the amino acid sequence set forth in SEQ ID NO:29, and a VL-CDR3 comprising the amino acid sequence set forth in SEQ ID NO:30.

In certain embodiments, the anti-MICA/B antibody comprises a VH-CDR1 comprising the amino acid sequence set forth in SEQ ID NO:35, a VH-CDR2 comprising the amino acid sequence set forth in SEQ ID NO:36, a VH-CDR3 comprising the amino acid sequence set forth in SEQ ID NO:37, a VL-CDR1 comprising the amino acid sequence set forth in SEQ ID NO:38, a VL-CDR2 comprising the amino acid sequence set forth in SEQ ID NO:39, and a VL-CDR3 comprising the amino acid sequence set forth in SEQ ID NO:40. In some embodiments, the anti-MICA/B antibody is non-fucosylated. In some embodiments, the anti-MICA/B antibody is hypo-fucosylated. In some embodiments, the anti-MICA/B antibody cross competes for binding to human MICA with a reference antibody comprising a VH-CDR1 comprising the amino acid sequence set forth in SEQ ID NO:35, a VH-CDR2 comprising the amino acid sequence set forth in SEQ ID NO:36, a VH-CDR3 comprising the amino acid sequence set forth in SEQ ID NO:37, a VL-CDR1 comprising the amino acid sequence set forth in SEQ ID NO:38, a VL-CDR2 comprising the amino acid sequence set forth in SEQ ID NO:39, and a VL-CDR3 comprising the amino acid sequence set forth in SEQ ID NO:40.

In certain embodiments, the anti-MICA/B antibody comprises a VH-CDR1 comprising the amino acid sequence set forth in SEQ ID NO:45, a VH-CDR2 comprising the amino acid sequence set forth in SEQ ID NO:46, a VH-CDR3 comprising the amino acid sequence set forth in SEQ ID NO:47, a VL-CDR1 comprising the amino acid sequence set forth in SEQ ID NO:48, a VL-CDR2 comprising the amino acid sequence set forth in SEQ ID NO:49, and a VL-CDR3 comprising the amino acid sequence set forth in SEQ ID NO:50. In some embodiments, the anti-MICA/B antibody is non-fucosylated. In some embodiments, the anti-MICA/B antibody is hypo-fucosylated. In some embodiments, the anti-MICA/B antibody cross competes for binding to human MICA with a reference antibody comprising a VH-CDR1 comprising the amino acid sequence set forth in SEQ ID NO:45, a VH-CDR2 comprising the amino acid sequence set forth in SEQ ID NO:46, a VH-CDR3 comprising the amino acid sequence set forth in SEQ ID NO:47, a VL-CDR1 comprising the amino acid sequence set forth in SEQ ID NO:48, a VL-CDR2 comprising the amino acid sequence set forth in SEQ ID NO:49, and a VL-CDR3 comprising the amino acid sequence set forth in SEQ ID NO:50.

In some embodiments, the anti-MICA/B antibody comprises a VH comprising an amino acid sequence having at least about 60%, at least about 65%, at least about 70%, at least about 75%, at least about 80%, at least about 85%, at least about 90%, at least about 95%, at least about 96%, at least about 97%, at least about 98%, or at least about 99% sequence identity to an amino acid sequence selected from the group consisting of SEQ ID NOs: 2, 12, 22, 32, and 42. In certain embodiments, the VH comprises an amino acid sequence selected from the group consisting of SEQ ID NOs: 2, 12, 22, 32, and 42.

In some embodiments, the anti-MICA/B antibody comprises a VL comprising an amino acid sequence having at least about 60%, at least about 65%, at least about 70%, at least about 75%, at least about 80%, at least about 85%, at least about 90%, at least about 95%, at least about 96%, at least about 97%, at least about 98%, or at least about 99% sequence identity to an amino acid sequence selected from the group consisting of SEQ ID NOs: 4, 14, 24, 34, and 44. In certain embodiments, the VL comprises an amino acid sequence selected from the group consisting of SEQ ID NOs: 4, 14, 24, 34, and 44.

In some embodiments, the anti-MICA/B antibody comprises a VH comprising an amino acid sequence having at least about 60%, at least about 65%, at least about 70%, at least about 75%, at least about 80%, at least about 85%, at least about 90%, at least about 95%, at least about 96%, at least about 97%, at least about 98%, or at least about 99% sequence identity to SEQ ID NO:2. In certain embodiments, the VH comprises the amino acid sequence set forth in SEQ ID NO:2. In some embodiments, the anti-MICA/B antibody comprises a VL comprising an amino acid sequence having at least about 60%, at least about 65%, at least about 70%, at least about 75%, at least about 80%, at least about 85%, at least about 90%, at least about 95%, at least about 96%, at least about 97%, at least about 98%, or at least about 99% sequence identity to SEQ ID NO:4. In certain embodiments, the VL comprises the amino acid sequence set forth in SEQ ID NO:4. In one embodiment, the VH comprises the amino acid sequence set forth in SEQ ID NO:2 and the VL comprises the amino acid sequence set forth in SEQ ID NO:4. In another embodiment, the anti-MICA/B antibody cross competes for binding to human MICA/B with an antibody comprising a VH comprising the amino acid sequence set forth in SEQ ID NO:2 and a VL comprising the amino acid sequence set forth in SEQ ID NO:4. In another embodiment, the VH comprises the amino acid sequence set forth in SEQ ID NO:2 and the VL comprises the amino acid sequence set forth in SEQ ID NO:4, wherein the antibody is nonfucosylated. In some embodiments, the anti-MICA/B antibody comprises a heavy chain constant region, comprising a G to A mutation at a position that corresponds to residue 234 in SEQ ID NO:58 (also referred to as "G236A" according to EU numbering).

In some embodiments, the anti-MICA/B antibody comprises a VH comprising an amino acid sequence having at least about 60%, at least about 65%, at least about 70%, at least about 75%, at least about 80%, at least about 85%, at least about 90%, at least about 95%, at least about 96%, at least about 97%, at least about 98%, or at least about 99% sequence identity to SEQ ID NO:12. In certain embodiments, the VH comprises the amino acid sequence set forth in SEQ ID NO:12. In some embodiments, the anti-MICA/B antibody comprises a VL comprising an amino acid sequence having at least about 60%, at least about 65%, at least about 70%, at least about 75%, at least about 80%, at least about 85%, at least about 90%, at least about 95%, at least about 96%, at least about 97%, at least about 98%, or at least about 99% sequence identity to SEQ ID NO:14. In certain embodiments, the VL comprises the amino acid sequence set forth in SEQ ID NO:14. In another embodiment, the VH comprises the amino acid sequence set forth in SEQ ID NO:12 and the VL comprises the amino acid sequence set forth in SEQ ID NO:14. In another embodiment, the anti-MICA/B antibody cross competes for binding to human MICA/B with an antibody comprising a VH comprising the amino acid sequence set forth in SEQ ID NO:12 and a VL comprising the amino acid sequence set forth in SEQ ID NO:14. In some embodiments, the anti-MICA/B antibody comprises a heavy chain constant region, comprising a G to A mutation at a position that corresponds to residue 234 in SEQ ID NO:58.

In some embodiments, the anti-MICA/B antibody comprises a VH comprising an amino acid sequence having at least about 60%, at least about 65%, at least about 70%, at least about 75%, at least about 80%, at least about 85%, at least about 90%, at least about 95%, at least about 96%, at least about 97%, at least about 98%, or at least about 99% sequence identity to SEQ ID NO:22. In certain embodiments, the VH comprises the amino acid sequence set forth in SEQ ID NO:22. In some embodiments, the anti-MICA/B antibody comprises a VL comprising an amino acid sequence having at least about 60%, at least about 65%, at least about 70%, at least about 75%, at least about 80%, at least about 85%, at least about 90%, at least about 95%, at least about 96%, at least about 97%, at least about 98%, or at least about 99% sequence identity to SEQ ID NO:24. In certain embodiments, the VL comprises the amino acid sequence set forth in SEQ ID NO:24. In another embodiment, the VH comprises the amino acid sequence set forth in SEQ ID NO:22 and the VL comprises the amino acid sequence set forth in SEQ ID NO:24. In another embodiment, the anti-MICA/B antibody cross competes for binding to human MICA/B with an antibody comprising a VH comprising the amino acid sequence set forth in SEQ ID NO:22 and a VL comprising the amino acid sequence set forth in SEQ ID NO:24. In some embodiments, the anti-MICA/B antibody comprises a heavy chain constant region, comprising a G to A mutation at a position that corresponds to residue 234 in SEQ ID NO:58.

In some embodiments, the anti-MICA/B antibody comprises a VH comprising an amino acid sequence having at least about 60%, at least about 65%, at least about 70%, at least about 75%, at least about 80%, at least about 85%, at least about 90%, at least about 95%, at least about 96%, at least about 97%, at least about 98%, or at least about 99% sequence identity to SEQ ID NO:32. In certain embodiments, the VH comprises the amino acid sequence set forth in SEQ ID NO:32. In some embodiments, the anti-MICA/B antibody comprises a VL comprising an amino acid sequence having at least about 60%, at least about 65%, at least about 70%, at least about 75%, at least about 80%, at least about 85%, at least about 90%, at least about 95%, at least about 96%, at least about 97%, at least about 98%, or at least about 99% sequence identity to SEQ ID NO:34. In certain embodiments, the VL comprises the amino acid sequence set forth in SEQ ID NO:34. In another embodiment, the VH comprises the amino acid sequence set forth in SEQ ID NO:32 and the VL comprises the amino acid sequence set forth in SEQ ID NO:34. In some embodiments, the VL comprises the amino acid sequence set forth in SEQ ID NO:34 having an insertion of a Ser residue between positions 95 and 96 of SEQ ID NO: 34. In some embodiments, the VL comprises the amino acid sequence set forth in SEQ ID NO:34 having an insertion of an Ala residue between positions 95 and 96 of SEQ ID NO: 34. In some embodiments, the VL comprises the amino acid sequence set forth in SEQ ID NO:34 having an insertion of a Gly residue between positions 95 and 96 of SEQ ID NO: 34. In another embodiment, the anti-MICA/B antibody cross competes for binding to human MICA/B with an antibody comprising a VH comprising the amino acid sequence set forth in SEQ ID NO:32 and a VL comprising the amino acid sequence set forth in SEQ ID NO:34. In some embodiments, the anti-MICA/B antibody comprises a heavy chain constant region, comprising a G to A mutation at a position that corresponds to residue 234 in SEQ ID NO:58.

In some embodiments, the anti-MICA/B antibody comprises a VH comprising an amino acid sequence having at least about 60%, at least about 65%, at least about 70%, at least about 75%, at least about 80%, at least about 85%, at least about 90%, at least about 95%, at least about 96%, at least about 97%, at least about 98%, or at least about 99% sequence identity to SEQ ID NO:42. In certain embodiments, the VH comprises the amino acid sequence set forth in SEQ ID NO:42. In some embodiments, the anti-MICA/B antibody comprises a VL comprising an amino acid sequence having at least about 60%, at least about 65%, at least about 70%, at least about 75%, at least about 80%, at least about 85%, at least about 90%, at least about 95%, at least about 96%, at least about 97%, at least about 98%, or at least about 99% sequence identity to SEQ ID NO:44. In certain embodiments, the VL comprises the amino acid sequence set forth in SEQ ID NO:44. In another embodiment, the VH comprises the amino acid sequence set forth in SEQ ID NO:42 and the VL comprises the amino acid sequence set forth in SEQ ID NO:44.

In another embodiment, the anti-MICA/B antibody cross competes for binding to human MICA/B with an antibody comprising a VH comprising the amino acid sequence set forth in SEQ ID NO:42 and a VL comprising the amino acid sequence set forth in SEQ ID NO:44. In some embodiments, the anti-MICA/B antibody comprises a heavy chain constant region, comprising a G to A mutation at a position that corresponds to residue 234 in SEQ ID NO:58. In some embodiments, the anti-MICA/B antibody comprises a heavy chain comprising an amino acid sequence having at least about at least about 60%, at least about 65%, at least about 70%, at least about 75%, at least about 80%, at least about 85%, at least about 90%, at least about 95%, at least about 96%, at least about 97%, at least about 98%, or at least about 99% sequence identity to an amino acid sequence selected from SEQ ID NOs: 58, 62, 66, 70, and 74. In certain embodiments, the anti-MICA/B antibody comprises a heavy chain comprising an amino acid sequence selected from SEQ ID NOs: 58, 130, 62, 66, 70, and 74. In certain embodiments, the heavy chain amino acid sequence comprises one or more deletions, substitutions, or mutations within the immunoglobulin constant region, e.g., within the CH1 domain, the CH2 domain, the CH3 domain, or the hinge region.

In some embodiments, the anti-MICA/B antibody comprises a light chain comprising an amino acid sequence having at least about at least about 60%, at least about 65%, at least about 70%, at least about 75%, at least about 80%, at least about 85%, at least about 90%, at least about 95%, at least about 96%, at least about 97%, at least about 98%, or at least about 99% sequence identity to an amino acid sequence selected from SEQ ID NOs: 60, 64, 68, 72, and 76. In certain embodiments, the anti-MICA/B antibody comprises a light chain comprising an amino acid sequence selected from SEQ ID NOs: 60, 64, 68, 72, and 76.

In some embodiments, the anti-MICA/B antibody comprises a heavy chain comprising an amino acid sequence having at least about at least about 60%, at least about 65%, at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO:58. In some embodiments, the anti-MICA/B antibody comprises a heavy chain comprising an amino acid sequence set forth in SEQ ID NO:58. In some embodiments, the anti-MICA/B antibody comprises a heavy chain comprising an amino acid sequence set forth in SEQ ID NO:130. In some embodiments, the anti-MICA/B antibody comprises a light chain comprising an amino acid sequence having at least about at least about 60%, at least about 65%, at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO:60. In some embodiments, the anti-MICA/B antibody comprises a light chain comprising an amino acid sequence set forth in SEQ ID NO:60. In one embodiment, the anti-MICA/B antibody comprises a heavy chain comprising the amino acid sequence set forth in SEQ ID NO:58 and a light chain comprising the amino acid sequence set forth in SEQ ID NO:60. In one embodiment, the anti-MICA/B antibody comprises a heavy chain comprising the amino acid sequence set forth in SEQ ID NO:130 and a light chain comprising the amino acid sequence set forth in SEQ ID NO:60. In another embodiment, the anti-MICA/B antibody comprises a heavy chain comprising the amino acid sequence set forth in SEQ ID NO:58 and a light chain comprising the amino acid sequence set forth in SEQ ID NO:60, wherein the antibody is nonfucosylated. In another embodiment, the anti-MICA/B antibody comprises a heavy chain comprising the amino acid sequence set forth in SEQ ID NO:130 and a light chain comprising the amino acid sequence set forth in SEQ ID NO:60, wherein the antibody is nonfucosylated. In another embodiment, the anti-MICA/B antibody cross competes for binding to human MICA/B with an antibody comprising a heavy chain comprising the amino acid sequence set forth in SEQ ID NO:58 and a light chain comprising the amino acid sequence set forth in SEQ ID NO:60.

In some embodiments, the anti-MICA/B antibody comprises a heavy chain comprising an amino acid sequence having at least about at least about 60%, at least about 65%, at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO:62. In some embodiments, the anti-MICA/B antibody comprises a heavy chain comprising an amino acid sequence set forth in SEQ ID NO:62. In some embodiments, the anti-MICA/B antibody comprises a light chain comprising an amino acid sequence having at least about at least about 60%, at least about 65%, at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO:64. In some embodiments, the anti-MICA/B antibody comprises a heavy chain constant region, comprising a G to A mutation at a position that corresponds to residue 234 in SEQ ID NO:58. In some embodiments, the anti-MICA/B antibody comprises a light chain comprising an amino acid sequence set forth in SEQ ID NO:64. In another embodiment, the anti-MICA/B antibody comprises a heavy chain comprising the amino acid sequence set forth in SEQ ID NO:62 and a light chain comprising the amino acid sequence set forth in SEQ ID NO:64. In another embodiment, the anti-MICA/B antibody cross competes for binding to human MICA/B with an antibody comprising a heavy chain comprising the amino acid sequence set forth in SEQ ID NO:62 and a light chain comprising the amino acid sequence set forth in SEQ ID NO:64.

In some embodiments, the anti-MICA/B antibody comprises a heavy chain comprising an amino acid sequence having at least about at least about 60%, at least about 65%, at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO:66. In some embodiments, the anti-MICA/B antibody comprises a heavy chain comprising an amino acid sequence set forth in SEQ ID NO:66. In some embodiments, the anti-MICA/B antibody comprises a light chain comprising an amino acid sequence having at least about at least about 60%, at least about 65%, at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO:68. In some embodiments, the anti-MICA/B antibody comprises a heavy chain constant region, comprising a G to A mutation at a position that corresponds to residue 234 in SEQ ID NO:58. In some embodiments, the anti-MICA/B antibody comprises a light chain comprising an amino acid sequence set forth in SEQ ID NO:68. In another embodiment, the anti-MICA/B antibody comprises a heavy chain comprising the amino acid sequence set forth in SEQ ID NO:66 and a light chain comprising the amino acid sequence set forth in SEQ ID NO:68. In another embodiment, the anti-MICA/B antibody cross competes for binding to human MICA/B with an antibody comprising a heavy chain comprising the amino acid sequence set forth in SEQ ID NO:66 and a light chain comprising the amino acid sequence set forth in SEQ ID NO:68.

In some embodiments, the anti-MICA/B antibody comprises a heavy chain comprising an amino acid sequence having at least about at least about 60%, at least about 65%, at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO:70. In some embodiments, the anti-MICA/B antibody comprises a heavy chain constant region, comprising a G to A mutation at a position that corresponds to residue 234 in SEQ ID NO:58. In some embodiments, the anti-MICA/B antibody comprises a heavy chain comprising an amino acid sequence set forth in SEQ ID NO:70. In some embodiments, the anti-MICA/B antibody comprises a light chain comprising an amino acid sequence having at least about at least about 60%, at least about 65%, at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO:72. In some embodiments, the anti-MICA/B antibody comprises a light chain comprising an amino acid sequence set forth in SEQ ID NO:72. In another embodiment, the anti-MICA/B antibody comprises a heavy chain comprising the amino acid sequence set forth in SEQ ID NO:70 and a light chain comprising the amino acid sequence set forth in SEQ ID NO:72. In another embodiment, the anti-MICA/B antibody cross competes for binding to human MICA/B with an antibody comprising a heavy chain comprising the amino acid sequence set forth in SEQ ID NO:70 and a light chain comprising the amino acid sequence set forth in SEQ ID NO:72.

In some embodiments, the anti-MICA/B antibody comprises a heavy chain comprising an amino acid sequence having at least about at least about 60%, at least about 65%, at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO:74. In some embodiments, the anti-MICA/B antibody comprises a heavy chain comprising an amino acid sequence set forth in SEQ ID NO:74. In some embodiments, the anti-MIC/B A antibody comprises a light chain comprising an amino acid sequence having at least about at least about 60%, at least about 65%, at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO:76. In some embodiments, the anti-MICA/B antibody comprises a light chain comprising an amino acid sequence set forth in SEQ ID NO:76. In another embodiment, the anti-MICA/B antibody comprises a heavy chain comprising the amino acid sequence set forth in SEQ TD NO:74 and a light chain comprising the amino acid sequence set forth in SEQ ID NO:76. In another embodiment, the anti-MICA/B antibody cross competes for binding to human MICA/B with an antibody comprising a heavy chain comprising the amino acid sequence set forth in SEQ ID NO:74 and a light chain comprising the amino acid sequence set forth in SEQ ID NO:76.

In some embodiments, the anti-MICA/B antibody described herein is selected from the group consisting of an IgG1, an IgG2, an IgG3, an IgG4 or a variant thereof. In certain embodiment, the anti-MICA/B described herein antibody is an IgG1 antibody. In some embodiments, the anti-MICA/B antibody described herein is non-fucosylated. In certain embodiments, the anti-MICA/B antibody described herein is hypofucosylated.

In some embodiments, the anti-MICA/B antibody described herein is a human antibody. In some embodiments, the anti-MICA/B antibody described herein is a humanized antibody. In some embodiments, the anti-MICA/B antibody described herein is a chimeric antibody.

In certain embodiments, the anti-MICA/B antibody described herein comprises a heavy chain constant region, comprising a G to A mutation at a position that corresponds to residue 234 in SEQ ID NO:58.

A. Human MICA/B Epitopes

In certain embodiments, the anti-MICA/B antibody binds a specific epitope on human MICA/B. The term "epitope," as used herein, includes any determinant capable being bound by an antigen binding protein, such as an antibody. An epitope is a region of an antigen that is bound by an antigen binding protein that targets that antigen, and when the antigen is a protein, includes specific amino acids that directly contact the antigen binding protein. Epitope determinants can include chemically active surface groupings of molecules such as amino acids, sugar side chains, phosphoryl or sulfonyl groups, and can have specific three dimensional structural characteristics, and/or specific charge characteristics. Generally, antibodies specific for a particular target antigen will preferentially recognize an epitope on the target antigen in a complex mixture of proteins and/or macromolecules.

In some embodiments, the epitope comprises at least one amino acid, at least two amino acids, at least three amino acids, at least four amino acids, at least five amino acids, at least six amino acids, at least seven amino acids, at least eight amino acids, at least nine amino acids, or at least ten amino acids. Where the epitope comprises more than one amino acid, the more than one amino acid can be sequential, e.g., G254 and D255, or separated by more than one amino acid that does not directly interact with the anti-MICA/B antibody or which is not required for anti-MICA/B binding, e.g., D255 and L257. In some embodiments, the epitope comprises two sequential amino acids, three sequential amino acids, four sequential amino acids, five sequential amino acids, six sequential amino acids, seven sequential amino acids, eight sequential amino acids, nine sequential amino acids, ten sequential amino acids, or more than ten sequential amino acids. In some embodiments, the epitope comprises at least two amino acids which are not sequentially location, but which are positioned in proximity when the human MICA/B is present in its three dimensional confirmation.

An epitope on an antigen, e.g., an epitope on human MICA/B that is bound by an anti-MICA/B antibody, can be identified using any method known in the art. In some embodiments, the epitope is determined using yeast surface display. In some embodiments, the epitope is determined by hydrogen/deuterium exchange mass spectrometry (HDX-MS).

In some embodiments, the anti-MICA/B antibody binds an epitope on the surface of human MICA. In some embodiments, the anti-MICA/B antibody binds an epitope within the α3 domain of human MICA.

In some embodiments, the anti-MICA/B antibody binds an epitope on human MICA located between amino acids 190 and 230 of SEQ ID NO: 51. In some embodiments, the anti-MICA/B antibody binds an epitope on human MICA located between amino acids 195 and 225 of SEQ ID NO: 51. In some embodiments, the anti-MICA/B antibody binds an epitope on human MICA located between amino acids 200 and 221 of SEQ ID NO: 51, as determined by HDX-MS. In certain embodiments, the anti-MICA/B antibody binds an epitope on human MICA comprising L201-N220 corresponding to SEQ ID NO:51, as determined by hydrogen/deuterium exchange mass spectrometry (HDX-MS). In some embodiments, the anti-MICA/B antibody binds an epitope on human MICA comprising SEQ ID NO: 56, as determined by HDX-MS.

In some embodiments, the anti-MICA/B antibody binds an epitope on human MICA located between amino acids 230 and 260 of SEQ ID NO: 51. In some embodiments, the anti-MICA/B antibody binds an epitope on human MICA located between amino acids 235 and 255 of SEQ ID NO: 51. In some embodiments, the anti-MICA/B antibody binds an epitope on human MICA located between amino acids 237 and 253 of SEQ ID NO: 51, as determined by HDX-MS. In certain embodiments, the anti-MICA/B antibody binds an epitope on human MICA comprising T238-Q252 corresponding to SEQ ID NO:51, as determined by hydrogen/deuterium exchange mass spectrometry (HDX-MS),In some embodiments, the anti-MICA/B antibody binds an epitope on human MICA comprising SEQ ID NO: 57, as determined by HDX-MS.

In certain embodiments, the anti-MICA/B antibody binds an epitope on human MICA comprising L201-N220 and T238-Q252 corresponding to SEQ ID NO:51, as determined by HDX-MS. In some embodiments, the anti-MICA/B antibody binds an epitope on human MICA comprising SEQ ID NOs: 56 and 57, as determined by HDX-MS.

In some embodiments, the anti-MICA/B antibody binds an epitope on human MICA located between amino acids 140 and 170 of SEQ ID NO: 51. In some embodiments, the anti-MICA/B antibody binds an epitope on human MICA located between amino acids 145 and 165 of SEQ ID NO: 51. In some embodiments, the anti-MICA/B antibody binds an epitope on human MICA located between amino acids 149 and 164 of SEQ ID NO: 51, as determined by HDX-MS. In some embodiments, the anti-MICA/B antibody binds an epitope on human MICA comprising SEQ ID NO: 52, as determined by HDX-MS.

In some embodiments, the anti-MICA/B antibody binds an epitope on human MICA located between amino acids 220 and 250 of SEQ ID NO: 51. In some embodiments, the anti-MICA/B antibody binds an epitope on human MICA located between amino acids 225 and 245 of SEQ ID NO: 51. In some embodiments, the anti-MICA/B antibody binds an epitope on human MICA located between amino acids 230 and 239 of SEQ ID NO: 51, as determined by HDX-MS. In some embodiments, the anti-MICA/B antibody binds an epitope on human MICA comprising SEQ ID NO: 53, as determined by HDX-MS. In certain embodiments, the anti-MICA/B antibody binds an epitope on human MICA comprising N234 and/or L237, corresponding to SEQ ID NO: 51, as determined by HDX-MS.

In some embodiments, the anti-MICA/B antibody binds an epitope on human MICA located between amino acids 245 and 275 of SEQ ID NO: 51. In some embodiments, the anti-MICA/B antibody binds an epitope on human MICA located between amino acids 250 and 270 of SEQ ID NO: 51. In some embodiments, the anti-MICA/B antibody binds an epitope on human MICA located between amino acids 252 and 268 of SEQ ID NO: 51, as determined by HDX-MS. In some embodiments, the anti-MICA/B antibody binds an epitope on human MICA comprising SEQ ID NO: 55, as determined by HDX-MS. In certain embodiments, the anti-MICA/B antibody binds an epitope on human MICA located between amino acids 254 and 266 of SEQ ID NO: 51, as determined by HDX-MS. In some embodiments, the anti-MICA/B antibody binds an epitope on human MICA comprising SEQ ID NO: 54, as determined by HDX-MS. In certain embodiments, the anti-MICA/B antibody binds an epitope on human MICA comprising amino acids D255-Q265 and W267, corresponding to SEQ ID NO: 51, as determined by HDX-MS.

In certain embodiments, the anti-MICA/B antibody binds an epitope on human MICA comprising SEQ ID NOs: 52-54, as determined by HDX-MS. In some embodiments, the anti-MICA/B antibody binds an epitope on human MICA comprising SEQ ID NOs: 52, 53, and 55, as determined by HDX-MS.

In some embodiments, the anti-MICA/B antibody binds an epitope on human MICA located between amino acids 230 and 290 of SEQ ID NO: 51, as determined by yeast surface display. In some embodiments, the anti-MICA/B antibody binds an epitope on human MICA located between amino acids 235 and 285 of SEQ ID NO: 51, as determined by yeast surface display. In some embodiments, the anti-MICA/B antibody binds an epitope on human MICA located between amino acids 239 and 280 of SEQ ID NO: 51, as determined by yeast surface display. In some embodiments, the anti-MICA/B antibody binds an epitope on human MICA located between amino acids 230 and 250 of SEQ ID NO: 51, as determined by yeast surface display. In some embodiments, the anti-MICA/B antibody binds an epitope on human MICA located between amino acids 235 and 250 of SEQ ID NO: 51, as determined by yeast surface display. In some embodiments, the anti-MICA/B antibody binds an epitope on human MICA located between amino acids 239 and 245 of SEQ ID NO: 51, as determined by yeast surface display.

In some embodiments, the anti-MICA/B antibody binds an epitope on human MICA located between amino acids 245 and 275 of SEQ ID NO: 51, as determined by yeast surface display. In some embodiments, the anti-MICA/B antibody binds an epitope on human MICA located between amino acids 250 and 270 of SEQ ID NO: 51, as determined by yeast surface display. In some embodiments, the anti-MICA/B antibody binds an epitope on human MICA located between amino acids 253 and 268 of SEQ ID NO: 51, as determined by yeast surface display. In some embodiments, the anti-MICA/B antibody binds an epitope on human MICA located between amino acids 257 and 265 of SEQ ID NO: 51, as determined by yeast surface display.

In certain embodiments, the anti-MICA/B antibody binds an epitope comprising one or more amino acid selected from the group consisting of R240, Q241, D242, V244, G254, D255, L257, P258, G260, G262, Y264, W267, and R279, corresponding to SEQ ID NO:51, as determined by yeast surface display. In some embodiments, the anti-MICA/B antibody binds an epitope comprising one or more amino acid selected from the group consisting of G254, D255, L257, Y264, and W267, corresponding to SEQ ID NO:51, as determined by yeast surface display. In certain embodiments, the anti-MICA/B antibody binds an epitope comprising amino acids G254, D255, L257, Y264, and W267, corresponding to SEQ ID NO:51, as determined by yeast surface display.

In some embodiments, the anti-MICA/B antibody binds an epitope comprising one or more amino acid selected from the group consisting of R240, Q241, D242, V244, and R279, corresponding to SEQ ID NO:51, as determined by yeast surface display. In certain embodiments, the anti-MICA/B antibody binds an epitope comprising amino acids R240, Q241, D242, V244, and R279, corresponding to SEQ ID NO:51, as determined by yeast surface display.

In some embodiments, the anti-MICA/B antibody binds an epitope comprising one or more amino acid selected from the group consisting of P258, G260, G262, and Y264, corresponding to SEQ ID NO:51, as determined by yeast surface display. In certain embodiments, the anti-MICA/B antibody binds an epitope comprising amino acids P258, G260, G262, and Y264, corresponding to SEQ ID NO:51, as determined by yeast surface display.

In certain embodiments, when the anti-MICA/B antibody is bound to human MICA, the antibody is positioned about 30 angstroms or less, 25 angstroms or less, 30 angstroms or less, about 15 angstroms or less, about 10 angstroms or less, about 9 angstroms or less, about 8 angstroms or less, about 7 angstroms or less, about 6 angstroms or less, about 5 angstroms or less, about 4 angstroms or less, about 3 angstroms or less, or about 2 angstroms or less from at least one of the following residues of human MICA: R240, Q241, D242, V244, G254, D255, L257, P258, G260, G262, Y264, W267, and R279, corresponding to SEQ ID NO:51, as determined by crystallography, e.g., using the conditions described herein. In some embodiments, when the anti-MICA/B antibody is bound to human MICA, the antibody is positioned about 10 angstroms or less from at least one of the following residues of human MICA: R240, Q241, D242, V244, G254, D255, L257, P258, G260, G262, Y264, W267, and R279, corresponding to SEQ ID NO:51, as determined by crystallography, e.g., using the conditions described herein. In some embodiments, when the anti-MICA/B antibody is bound to human MICA, the antibody is positioned about 10 angstroms or less from at least one of the following residues of human MICA: G254, D255, L257, Y264, and W267, corresponding to SEQ ID NO:51, as determined by crystallography, e.g., using the conditions described herein. In some embodiments, when the anti-MICA/B antibody is bound to human MICA, the antibody is positioned about 10 angstroms or less from at least one of the following residues of human MICA: R240, Q241, D242, V244, and R279, corresponding to SEQ ID NO:51, as determined by crystallography, e.g., using the conditions described herein. In some embodiments, when the anti-MICA/B antibody is bound to human MICA, the antibody is positioned about 10 angstroms or less from at least one of the following residues of human MICA: P258, G260, G262, and Y264, corresponding to SEQ ID NO:51, as determined by crystallography, e.g., using the conditions described herein. In certain embodiments, when the anti-MICA/B antibody is bound to human MICA, the antibody is positioned about 30 angstroms or less, 25 angstroms or less, 20 angstroms or less, about 15 angstroms or less, about 10 angstroms or less, about 9 angstroms or less, about 8 angstroms or less, about 7 angstroms or less, about 6 angstroms or less, about 5 angstroms or less, about 4 angstroms or less, about 3 angstroms or less, or about 2 angstroms or less from at least one of the following residues of human MICA: R240, Q241, D242, V244, G254, D255, L257, P258, G260, G262, Y264, W267, and R279, corresponding to SEQ ID NO:51, as determined by X-ray co-crystallography, e.g., using the conditions described herein.

In some embodiments, the anti-MICA/B antibody binds an epitope on human MICA comprising at least 1, at least 2, at least 3, at least 4, at least 5, at least 6, at least 7, at least 8, at least 9, or at least 10 residues selected from T222, T224, R226, W233, N234, H248, D249, Q251, Q252, W253, G254, D255, V256, L257, P258, D259, G260, N261, Y264, Q265, W267, and A269, as determined by X-ray co-crystallography. In some embodiments, the anti-MICA/B antibody binds an epitope on human MICA comprising at least two residues selected from T222, T224, R226, W233, N234, H248, D249, Q251, Q252, W253, G254, D255, V256, L257, P258, D259, G260, N261, Y264, Q265, W267, and A269, as determined by X-ray co-crystallography. In some embodiments, the anti-MICA/B antibody binds an epitope on human MICA comprising at least four residues selected from T222, T224, R226, W233, N234, H248, D249, Q251, Q252, W253, G254, D255, V256, L257, P258, D259, G260, N261, Y264, Q265, W267, and A269, as determined by X-ray co-crystallography. In some embodiments, the anti-MICA/B antibody binds an epitope on human MICA comprising at least six residues selected from T222, T224, R226, W233, N234, H248, D249, Q251, Q252, W253, G254, D255, V256. L257, P258, D259, G260, N261, Y264, Q265, W267, and A269, as determined by X-ray co-crystallography. In some embodiments, the anti-MICA/B antibody binds an epitope on human MICA comprising T222, T224, R226, W233, N234, H248, D249, Q251, Q252, W253, G254, D255, V256, L257, P258, D259, G260, N261, Y264, Q265, W267, and A269, as determined by X-ray co-crystallography.

A VH domain, or one or more CDRs thereof, described herein can be linked to a constant domain for forming a heavy chain, e.g., a full length heavy chain. Similarly, a VL domain, or one or more CDRs thereof, described herein can be linked to a constant domain for forming a light chain, e.g., a full length light chain. A full length heavy chain (optionally with the exception of the C-terminal lysine (K) or with the exception of the C-terminal glycine and lysine (GK), which can be absent) and full length light chain may combine to form a full length antibody.

A VH domain described herein can be fused to the constant domain of a human IgG, e.g., IgG1, IgG2, IgG3 or IgG4, which are either naturally-occurring or modified, e.g., as further described herein. For example, a VH domain can comprise the amino acid sequence of any VH domain described herein fused to a human IgG, e.g., an IgG1, constant region, such as the following wild-type human IgG1 constant domain amino acid sequence:

```
                                              (SEQ ID NO: 91)
ASTKGPSVFPLAPSSKSTSGGTAALGCLVKDYFPEPVTVSWNSGALTSGV

HTFPAVLQSSGLYSLSSVVTVPSSSLGTQTYICNVNHKPSNTKVDKKVEP

KSCDKTHTCPPCPAPELLGGPSVFLFPPKPKDTLMISRTPEVTCVVVDVS

HEDPEVKFNWYVDGVEVHNAKTKPREEQYNSTYRVVSVLTVLHQDWLNGK

EYKCKVSNKALPAPIEKTISKAKGQPREPQVYTLPPSRDELTKNQVSLTC

LVKGFYPSDIAVEWESNGQPENNYKTTPPVLDSDGSFFLYSKLTVDKSRW

QQGNVFSCSVMHEALHNHYTQKSLSLSPGK
``` or that of an allotypic variant of SEQ ID NO: 91 and have the following amino acid sequences:

```
ASTKGPSVFPLAPSSKSTSGGTAALGCLVKDYFPEPVTVSWNSGALTSGV

HTFPAVLQSSGLYSLSSVVTVPSSSLGTQTYICNVNHKPSNTKVDKRVEP

KSCDKTHTCPPCPAPELLGGPSVFLFPPKPKDTLMISRTPEVTCVVVDVS

HEDPEVKFNWYVDGVEVHNAKTKPREEQYNSTYRVVSVLTVLHQDWLNGK

EYKCKVSNKALPAPIEKTISKAKGQPREPQVYTLPPSREEMTKNQVSLTC

LVKGFYPSDIAVEWESNGQPENNYKTTPPVLDSDGSFFLYSKLTVDKSRW

QQGNVFSCSVMHEALHNHYTQKSLSLSPGK (SEQ ID NO: 92;
allotype specific amino acid residues are in bold
and underlined).
```

A VH domain of an anti-MICA/B antibody can comprise the amino acid sequence of any VH domain described herein fused to an effectorless constant region, e.g., the following effectorless human IgG1 constant domain amino acid sequences:

```
ASTKGPSVFPLAPSSKSTSGGTAALGCLVKDYFPEPVTVSWNSGALTSGV

HTFPAVLQSSGLYSLSSVVTVPSSSLGTQTYICNVNHKPSNTKVDKRVEP

KSCDKTHTCPPCPAPEAEGAPSVFLFPPKPKDTLMISRTPEVTCVVVDVS

HEDPEVKFNWYVDGVEVHNAKTKPREEQYNSTYRVVSVLTVLHQDWLNGK

EYKCKVSNKALPSSIEKTISKAKGQPREPQVYTLPPSREEMTKNQVSLTC

LVKGFYPSDIAVEWESNGQPENNYKTTPPVLDSDGSFFLYSKLTVDKSRW

QQGNVFSCSVMHEALHNHYTQKSLSLSPGK (SEQ ID NO: 93;
"IgG1.1f," comprising substitutions L234A, L235E,
G237A, A330S and P331S, which are underlined)
or

ASTKGPSVFPLAPSSKSTSGGTAALGCLVKDYFPEPVTVSWNSGALTSGV

HTFPAVLQSSGLYSLSSVVTVPSSSLGTQTYICNVNHKPSNTKVDKRVEP

KSCDKTHTCPPCPAPEAEGAPSVFLFPPKPKDTLMISRTPEVTCVVVDVS

HEDPEVKFNWYVDGVEVHNAKTKPREEQYNSTYRVVSVLTVLHQDWLNGK

EYKCKVSNKALPAPIEKTISKAKGQPREPQVYTLPPSREEMTKNQVSLTC

LVKGFYPSDIAVEWESNGQPENNYKTTPPVLDSDGSFFLYSKLTVDKSRW

QQGNVFSCSVMHEALHNHYTQKSLSLSPGK (SEQ ID NO: 94;
"IgG1.3f", comprising substitutions L234A, L235E
and G237A, which are underlined).
```

For example, an allotypic variant of IgG1 comprises K97R, D239E, and/or L241M (underlined and bolded above) as numbered in SEQ ID NOs: 91. Within the full length heavy chain constant region, e.g., MICA.36 (SEQ ID NO: 58) and according to EU numbering, these amino acid substitutions are numbered K214R, D356E, and L358M. In some embodiments, the constant region of an anti-MICA/B antibody can further comprises one or more mutations or substitutions at amino acids L117, A118, G120, A213, and P214 (underlined above) as numbered in SEQ ID NO: 92, 93, and 94, or L234, A235, G237, A330 and P331, per EU numbering. In some embodiments, the constant region of an anti-MICA/B antibody comprises one or more mutations or substitutions at amino acids L117A, A118E, G120A, A213S, and P214S of SEQ ID NO: 91, or L234A, L235E, G237A, A330S and P331S, per EU numbering. The constant region of an anti-MICA/B antibody may also comprise one or more mutations or substitutions L117A, A118E and G120A of SEQ ID NO: 91, or L234A, L235E and G237A, per EU numbering Alternatively, a VH domain of an anti-MICA/B antibody can comprise the amino acid sequence of any VH domain described herein fused to a human IgG4 constant region, e.g., the following human IgG4 amino acid sequence or variants thereof:

```
ASTKGPSVFPLAPCSRSTSESTAALGCLVKDYFPEPVTVSWNSGALTSGV

HTFPAVLQSSGLYSLSSVVTVPSSSLGTKTYTCNVDHKPSNTKVDKRVES

KYGPPCPSCPAPEFLGGPSVFLFPPKPKDTLMISRTPEVTCVVVDVSQED

PEVQFNWYVDGVEVHNAKTKPREEQFNSTYRVVSVLTVLHQDWLNGKEYK

CKVSNKGLPSSIEKTISKAKGQPREPQVYTLPPSQEEMTKNQVSLTCLVK

GFYPSDIAVEWESNGQPENNYKTTPPVLDSDGSFFLYSRLTVDKSRWQEG
```

-continued

NVFSCSVMHEALHNHYTQKSLSLSLGK (SEQ ID NO: 95, comprising S228P).

A VL domain described herein can be fused to the constant domain of a human Kappa or Lambda light chain. For example, a VL domain of an anti-MICA/B antibody can comprise the amino acid sequence of any VL domain described herein fused to the following human IgG1 kappa light chain amino acid sequence:

(SEQ ID NO: 96)
RTVAAPSVFIFPPSDEQLKSGTASVVCLLNNFYPREAKVQWKVDNALQSG
NSQESVTEQDSKDSTYSLSSTLTLSKADYEKHKVYACEVTHQGLSSPVTK
SFNRGEC

In some embodiments, the heavy chain constant region comprises a lysine or another amino acid at the C-terminus, e.g., it comprises the following last amino acids: LSPGK (SEQ ID NO: 97) in the heavy chain. In some embodiments, the heavy chain constant region is lacking one or more amino acids at the C-terminus, and has, e.g., the C-terminal sequence LSPG (SEQ ID NO: 98) or LSP (SEQ ID NO: 99).

The amino acid sequences of exemplary heavy and light chains are described herein.

Provided herein are isolated anti-human MICA/B antibodies, or antigen-binding portion thereof, comprising:

(a1) heavy and light chain sequences comprising SEQ ID NOs: 58 and 60, respectively;

(a2) heavy and light chain sequences comprising SEQ ID NOs: 130 and 60, respectively;

(a3) heavy and light chain sequences comprising SEQ ID NOs: 62 and 64, respectively;

(a4) heavy and light chain sequences comprising SEQ ID NOs: 66 and 68, respectively;

(a5) heavy and light chain sequences comprising SEQ ID NOs:70 and 72, respectively;

(a6) heavy and light chain sequences comprising SEQ ID NOs: 74 and 76, respectively;

wherein the antibody specifically binds to human MICA/B.

In some embodiments, an anti-MICA/B antibody comprises a combination of a heavy and light chain sequences set forth herein, e.g., in the preceding paragraph, wherein the antibody comprises two heavy chains and two light chains, and can further comprise at least one disulfide bond linking the two heavy chains together. The antibodies can also comprise disulfide bonds linking each of the light chains to each of the heavy chains Heavy and light chains comprising an amino acid sequence that is at least 99%, 98%, 97%, 96%, 95%, 90%, 85%, 80%, 75% or 70% identical to any of the heavy or light chains set forth herein (or their variable regions), e.g., SEQ ID NOs: 58 and 60, can be used for forming anti-human MICA/B antibodies having the desired characteristics, e.g., those further described herein. Exemplary variants are those comprising an allotypic variation, e.g., in the constant domain, and/or a mutation in the variable or constant region, such as the mutations disclosed herein. Heavy and light chains comprising an amino acid sequence that differs in at most 1-30, 1-25, 1-20, 1-15, 1-10, 1-5, 1-4, 1-3, 1-2 or 1 amino acid (by substitution, addition or deletion) from any of the heavy or light chains set forth herein (or their variable regions) can be used for forming anti-human MICA antibodies having the desired characteristics, e.g., those further described herein.

In some embodiments, an anti-MICA/B antibody comprises a heavy chain variable region from a particular germline heavy chain immunoglobulin gene and/or a light chain variable region from a particular germline light chain immunoglobulin gene.

As demonstrated herein, human antibodies specific for MICA/B have been prepared that comprise a heavy chain variable region that is the product of or derived from a human germline. Accordingly, provided herein are isolated monoclonal antibodies, or antigen-binding portions thereof, comprising a heavy chain variable region that is the product of or derived from a human VH germline gene selected from the group consisting of: 3-09, 3-10, 3-33, 3-48, 5-51, 6-13, JH3b, JH4b, JH6b, and any combination thereof, and any combination thereof.

Human antibodies specific for MICA/B have been prepared that comprise a light chain variable region that is the product of or derived from a human germline. Accordingly, provide herein are isolated monoclonal antibodies, or antigen-binding portions thereof, comprising a light chain variable region that is the product of or derived from a human VK germline gene selected from the group consisting of: A27, L6, L18, JK1, JK2, JK3, JK5, and any combination thereof, and any combination thereof.

Anti-MICA/B antibodies described herein include those comprising a heavy chain variable region that is the product of or derived from one of the above-listed human germline VH genes and also comprising a light chain variable region that is the product of or derived from one of the above-listed human germline VK genes, as shown in the Figures.

As used herein, a human antibody comprises heavy and light chain variable regions that are "the product of" or "derived from" a particular germline sequence if the variable regions of the antibody are obtained from a system that uses human germline immunoglobulin genes. Such systems include immunizing a transgenic mouse carrying human immunoglobulin genes with the antigen of interest or screening a human immunoglobulin gene library displayed on phage with the antigen of interest. A human antibody that is "the product of" or "derived from" a human germline immunoglobulin sequence can be identified as such by comparing the amino acid sequence of the human antibody to the amino acid sequences of human germline immunoglobulins and selecting the human germline immunoglobulin sequence that is closest in sequence (i.e., greatest % identity) to the sequence of the human antibody. A human antibody that is "the product of" or "derived from" a particular human germline immunoglobulin sequence can contain amino acid differences as compared to the germline sequence, due to, for example, naturally-occurring somatic mutations or intentional introduction of site-directed mutation. However, a selected human antibody typically is at least 90% identical in amino acids sequence to an amino acid sequence encoded by a human germline immunoglobulin gene and contains amino acid residues that identify the human antibody as being human when compared to the germline immunoglobulin amino acid sequences of other species (e.g., murine germline sequences). In some cases, a human antibody can be at least 95%, or even at least 96%, 97%, 98%, or 99% identical in amino acid sequence to the amino acid sequence encoded by the germline immunoglobulin gene. Typically, a human antibody derived from a particular human germline sequence will display no more than 10 amino acid differences from the amino acid sequence encoded by the human germline immunoglobulin gene. In certain cases, the human antibody can display no more than 5, or even no more than 4, 3, 2, or 1 amino acid difference from the amino acid sequence encoded by the germline immunoglobulin gene.

Anti-MICA/B antibodies can comprise a heavy chain variable region comprising CDR1, CDR2 and CDR3 sequences and a light chain variable region comprising CDR1, CDR2 and CDR3 sequences, wherein one or more of these CDR sequences comprise specified amino acid sequences based on the anti-MICA/B antibodies described herein, or conservative modifications thereof, and wherein the antibodies retain the desired functional properties of the anti-MICA/B antibodies described herein.

Conservative amino acid substitutions can be made in portions of the antibodies other than, or in addition to, the CDRs. For example, conservative amino acid modifications can be made in a framework region or in the Fc region. A variable region or a heavy or light chain can comprise 1, 2, 3, 4, 5, 1-2, 1-3, 1-4, 1-5, 1-10, 1-15, 1-20, 1-25, or 1-50 conservative amino acid substitutions relative to the anti-MICA/B antibody sequences provided herein. In some embodiments, an anti-MICA/B antibody comprises a combination of conservative and non-conservative amino acid modification.

Also provided are engineered and modified antibodies that can be prepared using an antibody having one or more of the VH and/or VL sequences disclosed herein as starting material to engineer a modified antibody, which modified antibody can have altered properties from the starting antibody. An antibody can be engineered by modifying one or more residues within one or both variable regions (i.e., VH and/or VL), for example within one or more CDR regions and/or within one or more framework regions. Additionally or alternatively, an antibody can be engineered by modifying residues within the constant region(s), for example to alter the effector function(s) of the antibody.

One type of variable region engineering that can be performed is CDR grafting. Antibodies interact with target antigens predominantly through amino acid residues that are located in the six heavy and light chain complementarity determining regions (CDRs). For this reason, the amino acid sequences within CDRs are more diverse between individual antibodies than sequences outside of CDRs. Because CDR sequences are responsible for most antibody-antigen interactions, it is possible to express recombinant antibodies that mimic the properties of specific naturally-occurring antibodies by constructing expression vectors that include CDR sequences from the specific naturally-occurring antibody grafted onto framework sequences from a different antibody with different properties (see, e.g., Riechmann L et al. (1998) *Nature* 332:323-327; Jones, P. et al. (1986) *Nature* 321:522-525: Queen, C. et al. (1989) *Proc. Natl. Acad. Sci. U.S.A.* 86: 10029-10033; U.S. Pat. No. 5,225,539 to Winter, and U.S. Pat. Nos. 5,530,101; 5,585,089; 5,693,762 and 6,180,370 to Queen et al.).

Accordingly, some embodiments described herein pertain to an isolated monoclonal antibody, or antigen binding portion thereof, comprising a heavy chain variable region comprising CDR1, CDR2, and CDR3 sequences described herein, and a light chain variable region comprising CDR1, CDR2, and CDR3 sequences described herein. Thus, such antibodies contain the VH and VL CDR sequences of monoclonal antibodies described herein yet can contain different framework sequences from these antibodies.

Such framework sequences can be obtained from public DNA databases or published references that include germline antibody gene sequences. For example, germline DNA sequences for human heavy and light chain variable region genes can be found in the "VBase" human germline sequence database (available on the Internet at www.mrc-cpe.cam.ac.uk/vbase), as well as in Kabat, E. A., et al. (1991) Sequences of Proteins of Immunological Interest, Fifth Edition, U.S. Department of Health and Human Services, NIH Publication No. 91-3242; Tomlinson. I M., et al. (1992) "The Repertoire of Human Germline $V_H$ Sequences Reveals about Fifty Groups of $V_H$ Segments with Different Hypervariable Loops" *I. Mol. Biol.* 227:776-798; and Cox, J. P. L. et al. (1994) "A Directory of Human Germ-line $V_H$ Segments Reveals a Strong Bias in their Usage" *Eur. J. Immunol.* 24:827-836; the contents of each of which are expressly incorporated herein by reference.

In some embodiments, the framework sequences for use in the anti-MICA/B antibodies described herein are those that are structurally similar to the framework sequences used by the anti-MICA/B antibodies described herein. The VH CDR1, CDR2 and CDR3 sequences, and the VL CDR1, CDR2 and CDR3 sequences, can be grafted onto framework regions that have the identical sequence as that found in the germline immunoglobulin gene from which the framework sequence derive, or the CDR sequences can be grafted onto framework regions that contain one or more mutations as compared to the germline sequences. For example, it has been found that in certain instances it is beneficial to mutate residues within the framework regions to maintain or enhance the antigen binding ability of the antibody (see, e.g., U.S. Pat. Nos. 5,530,101; 5,585,089; 5,693,762; and U.S. Pat. No. 6,180,370 to Queen et al.).

Engineered anti-MICA/B antibodies described herein include those in which modifications have been made to framework residues within VH and/or VL, e.g., to improve the properties of the antibody. Typically such framework modifications are made to decrease the immunogenicity of the antibody. For example, one approach is to "backmutate" one or more framework residues to the corresponding germline sequence. More specifically, an antibody that has undergone somatic mutation can contain framework residues that differ from the germline sequence from which the antibody is derived. Such residues can be identified by comparing the antibody framework sequences to the germline sequences from which the antibody is derived. To return the framework region sequences to their germline configuration, the somatic mutations can be "backmutated" to the germline sequence by, for example, site-directed mutagenesis or PCR-mediated mutagenesis. Such "backmutated" antibodies are also intended to be encompassed. Another type of framework modification involves mutating one or more residues within the framework region, or even within one or more CDR regions, to remove T cell epitopes to thereby reduce the potential immunogenicity of the antibody. This approach is also referred to as "deimmunization" and is described in further detail in U.S. Patent Publication No. 20030153043 by Carr et al.

Another type of variable region modification is to mutate amino acid residues within the VH and/or VL CDR1, CDR2 and/or CDR3 regions to thereby improve one or more binding properties (e.g., affinity) of the antibody of interest. Site-directed mutagenesis or PCR-mediated mutagenesis can be performed to introduce the mutation(s) and the effect on antibody binding, or other functional property of interest, can be evaluated in in vitro or in vivo assays as described herein and provided in the Examples. In some embodiments, conservative modifications (as discussed above) are introduced. The mutations can be amino acid substitutions, additions or deletions. Moreover, typically no more than one, two, three, four or five residues within a CDR region are altered.

Methionine residues in CDRs of antibodies can be oxidized, resulting in potential chemical degradation and consequent reduction in potency of the antibody. Accordingly, also provided are anti-MICA/B antibodies which have one or more methionine residues in the heavy and/or light chain CDRs replaced with amino acid residues which do not undergo oxidative degradation. In some embodiments, the methionine residues in the CDRs of antibodies MICA.36, MICA.52, MICA.54, MICA.2, and 71C2 are replaced with amino acid residues which do not undergo oxidative degradation.

Similarly, deamidation sites call be removed from anti-MICA/B antibodies, particularly in the CDRs.

Anti-MICA/B variable regions described herein can be linked (e.g., covalently linked or fused) to an Fc, e.g., an IgG1, IgG2, IgG3 or IgG4 Fc, which can be of any allotype or isoallotype, e.g., for IgG1: G1m, G1m1(a), G1m2(x), G1m3(f), G1m17(z); for IgG2: G2m, G2m23(n); for IgG3: G3m, G3m21(g1), G3m28(g5), G3m11(b0), G3m5(b1), G3m13(b3), G3m14(b4), G3m10(b5), G3m15(s), G3 m16 (t), G3m6(c3), G3 m24(c5), G3m26(u), G3 m27(v); and for K: Km, Km1, Km2, Km3 (see, e.g., Jefferies et al. (2009) mAbs 1:1).

Generally, variable regions described herein can be linked to an Fc comprising one or more modification, typically to alter one or more functional properties of the antibody, such as serum half-life, complement fixation, Fc receptor binding, antigen-dependent cellular cy toxicity, and/or antibody-dependent cellular phagocytosis. Furthermore, an antibody described herein can be chemically modified (e.g., one or more chemical moieties can be attached to the antibody) or be modified to alter its glycosylation, to alter one or more functional properties of the antibody. Each of these embodiments is described in further detail below. The numbering of residues in the Fc region is that of the EU index of Kabat.

The Fc region encompasses domains derived from the constant region of an immunoglobulin, including a fragment, analog, variant, mutant or derivative of the constant region. Suitable immunoglobulins include IgG1, IgG2, IgG3, IgG4, and other classes such as IgA, IgD, IgE and IgM, The constant region of an immunoglobulin is defined as a naturally-occurring or synthetically-produced polypeptide homologous to the immunoglobulin C-terminal region, and can include a CH1 domain, a hinge, a CH2 domain, a CH3 domain, or a CH4 domain, separately or in combination.

Ig molecules interact with multiple classes of cellular receptors. For example IgG molecules interact with three classes of Fcγ receptors (FcγR) specific for the IgG class of antibody, namely FcγRI, FcγRII, and FcγRIII. The important sequences for the binding of IgG to the FcγR receptors have been reported to be located in the CH2 and CH3 domains The serum half-life of an antibody is influenced by the ability of that antibody to bind to an Fc receptor (FcR).

In some embodiments, the Fc region is a variant Fc region, e.g., an Fc sequence that has been modified (e.g., by amino acid substitution, deletion and/or insertion) relative to a parent Fc sequence (e.g., an unmodified Fc polypeptide that is subsequently modified to generate a variant), to provide desirable structural features and/or biological activity, Generally, variants of the constant region or portions thereof, e.g., CH1, CL, hinge, CH2 or CH3 domains can comprise 1, 2, 3, 4, 5, 6, 7, 8, 9, 10 or more mutations, and/or at most 10, 9, 8, 7, 6, 5, 4, 3, 2 or 1 mutation, or 1-10 or 1-5 mutations, or comprise an amino acid sequence that is at least about 75%, 80%, 85%, 90%, 95%, 96%, 97%, 98%, or 99% identical to that of the corresponding wild-type region or domain (CH1, CL, hinge, CH2, or CH3 domain, respectively), provided that the heavy chain constant region comprising the specific variant retains the necessary biological activity.

For example, one can make modifications in the Fc region in order to generate an Fc variant that (a) mediates increased or decreased antibody-dependent cell-mediated cytotoxicity (ADCC) and/or antibody-dependent cellular phagocytosis (ADCP), (b) mediates increased or decreased complement mediated cytotoxicity (CDC), (c) has increased or decreased affinity for C1q and/or (d) has increased or decreased affinity for a Fc receptor relative to the parent Fc. Such Fc region variants will generally comprise at least one amino acid modification in the Fc region. Combining amino acid modifications is thought to be particularly desirable. For example, the variant Fc region can include two, three, four, five, etc. substitutions therein, e.g., of the specific Fc region positions identified herein.

A variant Fc region can also comprise a sequence alteration wherein amino acids involved in disulfide bond formation are removed or replaced with other amino acids. Such removal can avoid reaction with other cysteine-containing proteins present in the host cell used to produce the anti-MICA/B antibodies described herein. Even when cysteine residues are removed, single chain Fc domains can still form a dimeric Fc domain that is held together non-covalently. In some embodiments, the Fc region can be modified to make it more compatible with a selected host cell. For example, one can remove the PA sequence near the N-terminus of a typical native Fc region, which can be recognized by a digestive enzyme in *E. coli* such as proline iminopeptidase. In some embodiments, one or more glycosylation sites within the Fc domain can be removed. Residues that are typically glycosylated (e.g., asparagine) can confer cytolytic response. Such residues can be deleted or substituted with unglycosylated residues (e.g., alanine). In some embodiments, sites involved in interaction with complement, such as the C1q binding site, can be removed from the Fc region. For example, one can delete or substitute the EKK sequence of human IgG1. In some embodiments, sites that affect binding to Fc receptors can be removed, preferably sites other than salvage receptor binding sites. In some embodiments, an Fc region can be modified to remove an ADCC site. ADCC sites are known in the art; see, for example, *Molec. Immunol.* 29 (5): 633-9 (1992) with regard to ADCC sites in IgG1. Specific examples of variant Fc domains are disclosed for example, in WO 97/34631, WO 96/32478 and WO07/041635.

In some embodiments, the hinge region of Fc is modified such that the number of cysteine residues in the hinge region is altered, e.g., increased or decreased. This approach is described further in U.S. Pat. No. 5,677,425 by Bodmer et al. The number of cysteine residues in the hinge region of Fc is altered to, for example, facilitate assembly of the light and heavy chains or to increase or decrease the stability of the antibody. In some embodiments, the Fc hinge region of an antibody is mutated to decrease the biological half-life of the antibody. More specifically, one or more amino acid mutations are introduced into the CH2-CH3 domain interface region of the Fc-hinge fragment such that the antibody has impaired Slaphylococcyl protein A (SpA) binding relative to native Fc-hinge domain SpA binding. This approach is described in further detail in U.S. Pat. No. 6,165,745 by Ward et al.

In some embodiments, the Fc region is altered by replacing at least one amino acid residue with a different amino acid residue to alter the effector function(s) of the antibody. For example, one or more amino acids selected from amino acid residues 234, 235, 236, 237, 297, 318, 320, 322, 330, and/or 331 can be replaced with a different amino acid residue such that the antibody has an altered affinity for an effector ligand but retains the antigen-binding ability of the parent antibody. The effector ligand to which affinity is altered can be, for example, an Fc receptor or the C1 component of complement. This approach is described in further detail in U.S. Pat. Nos. 5,624,821 and 5,648,260, both by Winter et al.

In another example, one or more amino acids selected from amino acid residues 329, 331, and 322 can be replaced with a different amino acid residue such that the antibody has altered C1q binding and/or reduced or abolished complement dependent cytotoxicity (CDC). This approach is described in further detail in U.S. Pat. No. 6,194,551 by Idusogie et al.

In another example, one or more amino acid residues within amino acid positions 231 and 239 are altered to thereby alter the ability of the antibody to fix complement. This approach is described further in PCT Publication WO 94/29351 by Bodmer et al.

In another example, the Fc region can be modified to enhance affinity for an Fcγ and increase macrophage-mediated phagocytosis. See, e.g., Richard et al., Mo. Cancer. Ther. 7(8):2517-27 (2008), which is incorporated by reference herein in its entirety. In certain embodiments, the Fc region can be modified to increase affinity for FcγRIIa relative to inhibitory FcγRIIb. One particular point mutation, G236A (whose numbering is according to the EU index), has been identified as having increased affinity for FcγRIIa relative to inhibitory FcγRIIb. This increased affinity for FcRIIa correlated with increased macrophage-mediated phagocytosis, relative to native IgG1. In some embodiments, the Fc region of the anti-MICA/B antibody comprises one or more mutation or combination of mutations selected from G236A, I332E, S239/I332E, I332E/G236A, and S239D/I332E/G236A. Other modifications to the Fc region can increase antibody dependent cellular cytotoxicity (ADCC), e.g., by increasing affinity for activating receptors such as FcγRI and/or FcγRIIIa. For example, the G236A substitution, and combination of the G236A substitution with modifications that improve affinity for activating receptors (e.g., FcγRI and/or FcγRIIIa), for example including but not limited to substitutions at 332 and 239, provide substantially improved ADCC relative to the parent WT antibody. See U.S. Pat. No. 9,040,041, which is incorporated by reference herein in its entirety.

In another example, the Fc region can be modified to decrease antibody dependent cellular cytotoxicity (ADCC) and/or to decrease the affinity for an Fcγ receptor by modifying one or more amino acids at the following positions: 234, 235, 236, 238, 239, 240, 241, 243, 244, 245, 247, 248, 249, 252, 254, 255, 256, 258, 262, 263, 264, 265, 267, 268, 269, 270, 272, 276, 278, 280, 283, 285, 286, 289, 290, 292, 293, 294, 295, 296, 298, 299, 301, 303, 305, 307, 309, 312, 313, 315, 320, 322, 324, 325, 326, 327, 329, 330, 331, 332, 333, 334, 335, 337, 338, 340, 360, 373, 376, 378, 382, 388, 389, 398, 414, 416, 419, 430, 433, 434, 435, 436, 437, 438 or 439. Exemplary substitutions include 236A, 239D, 239E, 268D, 267E, 268E, 268F, 324T, 332D, and 332E. Exemplary variants include 239D/332E, 236A/332E, 236A/239D/332E, 268F/324T, 267E/268F, 267E/324T, and 267E/268F7324T. Other modifications for enhancing FcγR and complement interactions include but are not limited to substitutions 298A, 333A, 334A, 326A, 2471, 339D, 339Q, 280H, 290S, 298D, 298V, 243L, 292P, 300L, 396L, 3051, and 396L. These and other modifications are reviewed in Strohl, 2009, *Current Opinion in Biotechnology* 20:685-691.

Fc modifications that increase binding to an Fcγ receptor include amino acid modifications at any one or more of amino acid positions 238, 239, 248, 249, 252, 254, 255, 256, 258, 265, 267, 268, 269, 270, 272, 279, 280, 283, 285, 298, 289, 290, 292, 293, 294, 295, 296, 298, 301, 303, 305, 307, 312, 315, 324, 327, 329, 330, 335, 337, 338, 340, 360, 373, 376, 379, 382, 388, 389, 398, 414, 416, 419, 430, 434, 435, 437, 438 or 439 of the Fc region, wherein the numbering of the residues in the Fc region is that of the EU index as in Kabat (WO00/42072).

Optionally, the Fc region can comprise a non-naturally-occurring amino acid residue at additional and/or alternative positions known to one skilled in the art (see, e.g., U.S. Pat. Nos. 5,624,821; 6,277,375; 6,737,056; 6,194,551; 7,317,091; 8,101,720; 9,040,041; PCX Patent Publications WO 00/42072; WO 01/58957; WO 02/06919; WO 04/016750; WO 04/029207; WO 04/035752; WO 04/074455; WO 04/099249; WO 04/063351; WO 05/070963; WO 05/040217; WO 05/092925; and WO 06/0201 14).

The affinities and binding properties of an Fc region for its ligand can be determined by a variety of in vitro assay methods (biochemical or immunological based assays) known in the art including but not limited to, equilibrium methods (e.g., enzyme-linked immunosorbent assay (ELISA), or radioimmunoassay (RIA)), or kinetics (e.g., BTACORE® analysis), and other methods such as indirect binding assays, competitive inhibition assays, fluorescence resonance energy transfer (FRET), gel electrophoresis and chromatography (e.g., gel filtration). These and other methods can utilize a label on one or more of the components being examined and/or employ a variety of detection methods including but not limited to chromogenic, fluorescent, luminescent, or isotopic labels. A detailed description of binding affinities and kinetics can be found in Paul, W. E., ed., Fundamental immunology, 4th Ed., Lippincott-Raven, Philadelphia (1999), which focuses on antibody-immunogen interactions.

In some embodiments, the antibody is modified to increase its biological half-life. Various approaches are possible. For example, this can be done by increasing the binding affinity of the Fc region for FeRn, For example, one or more of more of following residues can be mutated: 252, 254, 256, 433, 435, 436, as described in U.S. Pat. No. 6,277,375. Specific exemplary substitutions include one or more of the following: T252L, T254S, and/or T256F. Alternatively, to increase the biological half-life, the antibody can be altered within the CH1 or CL region to contain a salvage receptor binding epitope taken from two loops of a CH2 domain of an Fc region of an IgG, as described in U.S. Pat. Nos. 5,869,046 and 6,121,022 by Presta et al. Other exemplary variants that increase binding to FcRn and/or improve pharmacokinetic properties include substitutions at positions 259, 308, 428, and 434, including for example 259I, 308F. 428L, 428M, 434S, 4341 1, 434F, 434Y. and 434X1. Other variants that increase Fc binding to FcRn include: 250E, 250Q, 428 L, 428F, 250Q/428L (Hinton et al. 2004, *J. Biol. Chem.* 279(8): 6213-6216, Hinton et al. 2006 *Journal of Immunology* 176:346-356), 256A, 272A, 286A, 305A, 307A, 307Q, 31 1A, 312A, 376A, 378Q, 380A, 382A, 434A (Shields et al., *Journal of Biological Chemistry*, 2001, 276(9):6591-6604). 252F, 252T, 252Y, 252W, 254T, 256S, 256R, 256Q, 256E, 256D. 256T, 309P, 31 1 S, 433R, 433S, 4331, 433P, 433Q, 434H, 434F, 434Y, 252Y/254T/256E, 433K/434F/436H, 308T/309P/311S (Dall Acqua et al. *Journal of Immunology, 2002, 169:5171-5180, Dall'Acqua et al., 2006, Journal of Biological Chemistry 281:23514-23524). Other modifications for modulating FcRn binding are described in Yeung et al., 2010, J Immunol, 182:7663-7671.

In some embodiments, hybrid IgG isotypes with particular biological characteristics can be used. For example, an IgG1/IgG3 hybrid variant can be constructed by substituting IgG1 positions in the CH2 and/or CH3 region with the amino acids from IgG3 at positions where the two isotypes differ. Thus a hybrid variant IgG antibody can be constructed that comprises one or more substitutions, e.g., 274Q, 276K, 300F, 339T, 356E, 358M, 384S, 392N, 397M, 422I, 435R, and 436F. In some embodiments described herein, an IgG1/IgG2 hybrid variant can be constructed by substituting IgG2 positions in the CH2 and/or CH3 region with amino acids from IgG1 at positions where the two isotypes differ. Thus a hybrid variant IgG antibody can be constructed that comprises one or more substitutions, e.g., one or more of the following amino acid substitutions: 233E, 234L, 235L, −236G (referring to an insertion of a glycine at position 236), and 327A.

Moreover, the binding sites on human IgG1 for FcγRI, FcγRII, FcγRIII and FcRn have been mapped and variants with improved binding have been described (see Shields, R. L. et al. (2001) J. Biol. Chem 276:6591-6604). Specific mutations at positions 256, 290, 298, 333, 334 and 339 were shown to improve binding to FcγRIII. Additionally, the following combination mutants were shown to improve FcγRIII binding: T256A/S298A, S298A/E333A, S298A/K224A and S298A/E333A/K334A, which has been shown to exhibit enhanced FcγRIIIa binding and ADCC activity (Shields et al., 2001). Other IgG1 variants with strongly enhanced binding to FcγRIIIa have been identified, including variants with S239D/I332E and S239D/I332E/A330L mutations which showed the greatest increase in affinity for FcγRIIIa, a decrease in FcγRIIb binding, and strong cytotoxic activity in cynomolgus monkeys (Lazar et al., 2006). Introduction of the triple mutations into antibodies such as alemtuzumab (CD52-specific), trastuzumab (HER2/neu-specific), rituximab (CD20-specific), and cetuximab (EGFR-specific) translated into greatly enhanced ADCC activity in vitro, and the S239D/I332E variant showed an enhanced capacity to deplete B cells in monkeys (Lazar et al., 2006). In addition, IgG1 mutants containing L235V, F243L, R292P, Y300L and P396L mutations which exhibited enhanced binding to FcγRIIIa and concomitantly enhanced ADCC activity in transgenic mice expressing human FcγRIIIa in models of B cell malignancies and breast cancer have been identified (Stavenhagen el al., 2007; Nordstrom el al., 2011). Other Fc mutants that can be used include: S298A/E333A/L334A, S239D/I332E, S239D/I332E/A330L, L235V/F243L/R292P/Y300L/P396L, and M428L/N434S.

Specific mutations at positions 234, 235, 236, 239, 267, 268, 293, 295, 324, 327, 328, 330, and 332 were shown to improve binding to FcγRIIa and/or reduce binding to FcγRIIb, resulting in enhanced ADCC and/or ADCP activity (Richards et al., Mol. Cancer Ther. 7(8):2517-2527; U.S. Pat. No. 9,040,041). In particular, Fc variants that selectively improve binding to one or more human activating receptors relative to FcγRIIb, or selectively improve binding to FcγRIIb relative to one or more activating receptors, may comprise a substitution selected from the group consisting of 234G, 234I, 235D, 235E, 235I, 235Y, 236A, 236S, 239D, 267D, 267E, 267Q, 268D, 268E, 293R, 295E, 324G, 324I, 327H, 328A, 328F, 328I, 330I, 330L, 330Y, 332D, and 332E. Additional substitutions that may also be combined include other substitutions that modulate FcγR affinity and complement activity, including but not limited to 298A, 298T, 326A, 326D, 326E, 326W, 326Y, 333A, 333S, 334L, and 334A (U.S. Pat. No. 6,737,056; Shields et al, Journal of Biological Chemistry, 2001, 276(9):6591-6604; U.S. Pat. No. 6,528,624; Idusogie et al., 2001, J. Immunology 166: 2571-2572). Preferred variants that may be particularly useful to combine with other Fc variants include those that comprise the substitutions 298A, 326A, 333A, and 334A. Additional substitutions that may be combined with the FcγR selective variants include 247L, 255L, 270E, 392T, 396L, and 421K (U.S. Ser. No. 10/754,922; U.S. Ser. No. 10/902,588); and 280H, 280Q, and 280Y (U.S. Ser. No. 10/370,749).

When using an IgG4 constant domain, it can include the substitution S228P, which mimics the hinge sequence in IgG1 and thereby stabilizes IgG4 molecules.

III. Nonfucosylation, Hypofucosylation and Reduced Fucosylation

In some embodiments, the glycosylation of an antibody may be modified. For example, an aglycoslated antibody can be made (i.e., the antibody lacks glycosylation). Glycosylation can be altered to, for example, increase the affinity of the antibody for antigen. Such carbohydrate modifications can be accomplished by, for example, altering one or more sites of glycosylation within the antibody sequence. For example, one or more amino acid substitutions can be made that result in elimination of one or more variable region framework glycosylation sites to thereby eliminate glycosylation at that site. Such aglycosylation can increase the affinity of the antibody for antigen. Such an approach is described in further detail in U.S. Pat. Nos. 5,714,350 and 6,350,861 by Co et al.

Glycosylation of the constant region on N297 can be prevented by mutating the N297 residue to another residue, e.g., N297A, and/or by mutating an adjacent amino acid, e.g., 298 to thereby reduce glycosylation on N297.

The interaction of antibodies with FcγRs can also be enhanced by modifying the glycan moiety attached to each Fc fragment at the N297 residue. In particular, the absence of core fucose residues enhances ADCC via improved binding of IgG to activating FcγRIIIA without altering antigen binding or CDC. Natsume el al. (2009) Drug Des. Devel. Ther. 3:7. There is convincing evidence that afucosylated tumor-specific antibodies translate into enhanced therapeutic activity in mouse models in vivo. Nimmerjahn & Ravetch (2005) Science 310:1510; Mossner et al. (2010) Blood 115:4393. Modification of antibody glycosylation can be accomplished by, for example, expressing the antibody in a host cell with altered glycosylation machinery. Cells with altered glycosylation machinery have been described in the art and can be used as host cells in which to express recombinant antibodies of this disclosure to thereby produce an antibody with altered glycosylation. For example, the cell lines Ms704, Ms705, and Ms709 lack the fucosyltransferase gene, FUT8 (α-(1,6) fucosyltransferase (see U.S. Pat. App. Publication No. 20040110704; Yamane-Ohnuki et al. (2004) Biotechnol. Bioeng. 87: 614), such that antibodies expressed in these cell lines lack fucose on their carbohydrates. As another example, EP 1176195 also describes a cell line with a functionally disrupted FUT8 gene as well as cell lines that have little or no activity for adding fucose to the N-acetylglucosamine that binds to the Fc region of the antibody, for example, the rat myeloma cell line YB2/0 (ATCC CRL 1662). PCT Publication WO 03/035835 describes a variant CHO cell line, Lec13, with reduced ability to attach fucose to Asn(297)-linked carbohydrates, also resulting in hypofucosylation of antibodies expressed in that host cell. See also Shields et al. (2002) *J. Biol. Chem.* 277:26733 Antibodies with a modified glycosylation profile can also be produced in chicken eggs, as described in PCT Publication No. WO 2006/089231. Alternatively, antibodies with a modified glycosylation profile can be produced in plant cells, such as Lonna. See e.g. U.S. Publication No. 2012/0276086. PCT Publication No. WO 99/54342 describes cell lines engineered to express glycoprotein-modifying glycosyl transferases (e.g., beta(1,4)-N-acetylglucosaminyltransferase III (GnTIII)) such that antibodies expressed in the engineered cell lines exhibit increased bisecting GlcNac structures which results in increased ADCC activity of the antibodies. See also Umaña et al. (1999) *Nat. Biotech.* 17:176. Alternatively, the fucose residues of the antibody may be cleaved off using a fucosidase enzyme. For example, the enzyme alpha-L-fucosidase removes fucosyl residues from antibodies. Tarentino et a (1975) Biochem. 14:5516. Antibodies with reduced fucosylation may also be produced in cells harboring a recombinant gene encoding an enzyme that uses GDP-6-deoxy-D-lyxo-4-hexylose as a substrate, such as GDP-6-deoxy-D-lyxo-4-hexylose reductase (RMD), as described at U.S. Pat. No. 8,642,292. Alternatively, cells may be grown in medium containing fucose analogs that block the addition of fucose residues to the N-linked glycan or a glycoprotein, such as antibody, produced by cells grown in the medium. U.S. Pat. No. 8,163,551; WO 09/135181.

Because nonfucosylated antibodies exhibit greatly enhanced ADCC and/or ADCP compared with fucosylated antibodies, antibody preparations need not be completely free of fucosylated heavy chains to be useful in the present invention. Residual levels of fucosylated heavy chains will not significantly interfere with the ADCC and/or ADCP activity of a preparation substantially of nonfucosylated heavy chains Antibodies produced in conventional CHO cells, which are fully competent to add core fucose to N-glycans, may nevertheless comprise from a few percent up to 15% nonfucosylated antibodies. Nonfucosylated antibodies may exhibit ten-fold higher affinity for CD16, and up to 30- to 100-fold enhancement of ADCC and/or ADCP activity, so even a small increase in the proportion of nonfucosylated antibodies may drastically increase the ADCC and/or ADCP activity of a preparation. Any preparation comprising more nonfucosylated antibodies than would be produced in normal CHO cells in culture may exhibit some level of enhanced ADCC and/or ADCP. Such antibody preparations are referred to herein as preparations having reduced fucosylation. Depending on the original level of nonfucosylation obtained from normal CHO cells, reduced fucosylation preparations may comprise 80%, 70%, 60% 50%, 30%, 20%, 10% and even 5% nonfucosylated antibodies. Reduced fucosylation may be functionally defined as preparations exhibiting 30%, 40%, 50%, 60%, 70%, 80%, 90%, 100%, two-fold, three-fold or greater enhancement of ADCC and/or ADCP compared with antibodies prepared in normal CHO cells, and not with reference to any fixed percentage of nonfucosylated species.

The level of nonfucosylation may be structurally defined. As used herein, "nonfucosylated" or "afucosylated" (terms used synonymously) refers to antibody preparations in which over 95% of heavy chains lack fucose, such as over 96%, over 97%. Over 98%, over 99%, or 100%. The term "hypofucosylated" refers to antibody preparations in which more than 80% and less than or equal to 95% heavy chains lack fucose, e.g. antibody preparations in which between 85 and 95%, between 80 and 85%, between 80 and 90%, between 85 and 90%, or between 90 and 95% of heavy chains lack fucose. The term "hypofucosylated or nonfucosylated" refers to antibody preparations in which 80% or more of heavy chains lack fucose. The term "reduced fucosylation" refers to antibody preparations in which between 10 and 80% of heavy chains lack fucose, such as 20-80%, 30-80%, 40-80%, 50-80%, 60-80%, 70-80%, 20-70%, 30-70%, 40-70%, 50-70%, 60-70%, 20-60%, 30-60%, 40-60%, 50-60%, 20-50%, 30-50%, 40-50%, 20-40%, 30-40%, 10-20%, 10-30%, or 20-30%.

In some embodiments, hypofucosylated or nonfucosylated anti-MICA/B antibodies may be produced in cells lacking an enzyme essential to fucosylation, such as FUT8 (e.g. U.S. Pat. No. 7,214,775), or in cells in which an exogenous enzyme partially depletes the pool of metabolic precursors for fucosylation (e.g. U.S. Pat. No. 8,642,292), or in cells cultured in the presence of a small molecule inhibitor of an enzyme involved in fucosylation (e.g. WO 09/135181).

The level of fucosylation in an antibody preparation may be determined by any method known in the art, including but not limited to gel electrophoresis, capillary electrophoresis, liquid chromatography, and mass spectrometry. In some embodiments, the level of fucosylation in an antibody preparation may be determined by hydrophilic interaction chromatography (or hydrophilic interaction liquid chromatography, HILIC). In some embodiments, to determine the level of fucosylation of an antibody preparation, samples are denatured and treated with PNGase F to cleave N-linked glycans, which are then analyzed for fucose content. LC/MS of full-length antibody chains is an alternative method to detect the level of fucosylation of an antibody preparation, but mass spectroscopy is inherently less quantitative.

In some embodiments, the anti-MICA/B antibodies described herein may have reduced fucosylation, or be hypofucosylated or nonfucosylated. In some embodiments, the anti-MICA/B antibodies described herein may have reduced fucosylation. In some embodiments, the anti-MICA/B antibodies described herein may be hypofucosylated. In some embodiments, the anti-MICA/B antibodies described herein may be nonfucosylated.

In some embodiments, the anti-MICA/B antibodies described herein may comprise i) one or more amino acid mutations to the Fc region to alter FcγR binding and optionally ii) reduced or eliminated fucosylation. In some embodiments, the anti-MICA/B antibodies described herein may comprise one or more amino acid mutations to the Fc region to alter FcγR binding and be hypofucosylated or nonfucosylated. In some embodiments, the anti-MICA/B antibodies described herein may comprise one or more amino acid mutations to the Fc region to alter FcγR binding and be nonfucosylated Another modification of the anti-MICA/B antibodies described herein is pegylation. An antibody can be pegylated to, for example, increase the biological (e.g., serum) half-life of the antibody. To pegylate an antibody, the antibody, or fragment thereof, typically is reacted with polyethylene glycol (PEG), such as a reactive ester or aldehyde derivative of PEG, under conditions in which one or more PEG groups become attached to the antibody or antibody fragment. In some embodiments, the pegylation is carried out via an acylation reaction or an alkylation reaction with a reactive PEG molecule (or an analogous reactive water-soluble polymer). As used herein, the term "polyethylene glycol" is intended to encompass any of the forms of PEG that have been used to derivatize other proteins, such as mono (C1—C10) alkoxy- or aryloxy-polyethylene glycol or polyethylene glycol-maleimide. In some embodiments, the antibody to be pegylated is an aglycosylated antibody. Methods for pegylating proteins are known in the art and can be applied to the anti-MICA/B antibodies described herein. See, for example, EP 0 154 316 by Nishimura et al. and EP 0 401 384 by Ishikawa et al.

IV. Antibody Physical Properties

Anti-MICA/B antibodies, e.g., those described herein, have some or all of the physical characteristics of the specific anti-MICA/B antibodies described herein, such as the characteristics described in the Examples.

Anti-MICA/B antibodies described herein can contain one or more glycosylation sites in either the light or heavy chain variable region. Such glycosylation sites can result in increased immunogenicity of the antibody or an alteration of the pK of the antibody due to altered antigen binding (Marshall et al., (1972) *Annu Rev Biochem* 41:673-702; Gala and Morrison (2004) *J. Immunol* 172:5489-94; Wallick et al., (1988) *J Exp Med* 168: 1099-109; Spiro (2002) *Glycobiology* 12:43R-56R; Parekh et al., (1985) *Nature* 316:452-7; Mimura et al., (2000) *Mol Immunol* 37:697-706). Glycosylation has been known to occur at motifs containing an N-X-S/T sequence. In some instances, an anti-MICA/B antibody does not contain variable region glycosylation. This can be achieved either by selecting antibodies that do not contain the glycosylation motif in the variable region or by mutating residues within the glycosylation region.

In some embodiments, the anti-MICA/B antibodies described herein do not contain asparagine isomerism sites. The deamidation of asparagine can occur on N-G or D-G sequences and result in the creation of an isoaspartic acid residue that introduces a kink into the polypeptide chain and decreases its stability (isoaspartic acid effect).

Each antibody will have a unique isoelectric point (pi), which generally falls in the pH range between 6 and 9.5. The pi for an IgG1 antibody typically falls within the pH range of 7-9.5 and the pi for an IgG4 antibody typically falls within the pH range of 6-8. There is speculation that antibodies with a pi outside the normal range can have some unfolding and instability under in vivo conditions. Thus, an anti-MICA/B antibody can contain a pi value that falls in the normal range. This can be achieved either by selecting antibodies with a pi in the normal range or by mutating charged surface residues.

Each antibody will have a characteristic melting temperature, with a higher melting temperature indicating greater overall stability in vivo (Krishnamurthy R and Maiming M C (2002) *Curr Pharm Biotechnol* 3:361-71). Generally, the $T_M i$ (the temperature of initial unfolding) can be greater than 60° C., greater than 65° C., or greater than 70° C. The melting point of an antibody can be measured using differential scanning calorimetry (Chen et al., (2003) *Pharm Res* 20: 1952-60; Ghirlando et al., (1999) *Immunol Lett* 68:47-52) or circular dichroism (Murray et al., (2002) *J. Chromatogr Sci* 40:343-9).

In some embodiments, antibodies are selected that do not degrade rapidly. Degradation of an antibody can be measured using capillary electrophoresis (CE) and MALDI-MS (Alexander A J and Hughes D E (1995) *Anal Chem* 67:3626-32).

In some embodiments, antibodies are selected that have minimal aggregation effects, which can lead to the triggering of an unwanted immune response and/or altered or unfavorable pharmacokinetic properties. Generally, antibodies are acceptable with aggregation of 25% or less, 20% or less, 15% or less, 10% or less, or 5% or less. Aggregation can be measured by several techniques, including size-exclusion column (SEC), high performance liquid chromatography (HPLC), and light scattering. In some embodiments, the antibodies display a desirable solubility, e.g., solubility that allows commercial manufacturing. In some embodiments, the solubility of the antibodies described herein was at least 10 mg/ml, at least 15 mg/ml, at least 20 mg/ml, at least 25 mg/ml, at least 30 mg/ml, at least 40 mg/ml, at least 50 mg/nil, at least 60 mg/ml, or at least 70 mg/ml, at neutral or slightly acidic pH.

In some embodiments, the antibodies described herein have higher stability than a reference antibody. In some embodiments, the antibodies described herein have a higher melting temperature than a reference antibody. In some embodiments, the antibodies described herein have a lower tendency for aggregation than a reference antibody. In some embodiments, the antibodies described herein have a higher solubility than a reference antibody. In some embodiments, the antibodies described herein have a higher rate of absorption, lower toxicity, higher biological activity and/or target selectivity, better manufacturability, and/or lower immunogenicity than a reference antibody. The reference antibody can be another antibody or fragments thereof, or conjugate thereof, that binds to MICA/B.

V. Methods of Engineering Antibodies

As discussed above, the anti-MICA/B antibodies having VH and VL sequences disclosed herein can be used to create new anti-MICA/B antibodies by modifying the VH and/or VL sequences, or the constant region(s) attached thereto. Thus, in another aspect described herein, the structural features of an anti-MICA/B antibody described herein are used to create structurally related anti-MICA/B antibodies that retain at least one functional property of the anti-MICA/B antibodies described herein, such as binding to human MICA/B and cynomolgus MICA/B. For example, one or more CDR regions of MICA.36, MICA.52, MICA.54, MICA.2, and 71C2 can be combined recombinantly with known framework regions and/or other CDRs to create additional, recombinantly-engineered, anti-MICA/B antibodies described herein, as discussed above. Other types of modifications include those described in the previous section. The starting material for the engineering method is one or more of the VH and/or VL sequences provided herein, or one or more CDR regions thereof. To create the engineered antibody, it is not necessary to actually prepare (i.e., express as a protein) an antibody having one or more of the VH and/or VL sequences provided herein, or one or more CDR regions thereof. Rather, the information contained in the sequence(s) is used as the starting material to create a "second generation" sequence(s) derived from the original sequence(s) and then the "second generation" sequence(s) is prepared and expressed as a protein.

Accordingly, provided herein are methods for preparing an anti-MICA/B antibody described herein.

The altered antibody can exhibit at least one of the functional properties set herein. The functional properties of the altered antibodies can be assessed using standard assays available in the art and/or described herein, such as those set forth in the Examples (e.g., ELISAs, FACS).

In some embodiments of the methods of engineering the anti-MICA/B antibodies described herein, mutations can be introduced randomly or selectively along all or part of an anti-MICA/B antibody coding sequence and the resulting modified anti-MICA/B antibodies can be screened for binding activity and/or other functional properties as described herein. Mutational methods have been described in the art. For example, PCT Publication WO 02/092780 by Short describes methods for creating and screening antibody mutations using saturation mutagenesis, synthetic ligation assembly, or a combination thereof. Alternatively, PCT Publication WO 03/074679 by Lazar et al. describes methods of using computational screening methods to optimize physiochemical properties of antibodies.

VI. Nucleic Acid Molecules

Another aspect described herein pertains to nucleic acid molecules that encode the anti-MICA/B antibodies described herein. The nucleic acids can be present in whole cells, in a cell lysate, or in a partially purified or substantially pure form. A nucleic acid is "isolated" or "rendered substantially pure" when purified away from other cellular components or other contaminants, e.g., other cellular nucleic acids (e.g., other chromosomal DNA, e.g., the chromosomal DNA that is linked to the isolated DNA in nature) or proteins, by standard techniques, including alkaline/SDS treatment, CsCl banding, column chromatography, restriction enzymes, agarose gel electrophoresis and others well known in the art. See, F. Ausubel, et al., ed. (1987) Current Protocols in Molecular Biology, Greene Publishing and Wiley Interscience, New York. A nucleic acid described herein can be, for example, DNA or RNA and can or cannot contain intronic sequences. In some embodiments, the nucleic acid is a cDNA molecule.

Nucleic acids described herein can be obtained using standard molecular biology techniques. For antibodies expressed by hybridomas (e.g., hybridomas prepared from transgenic mice carrying human immunoglobulin genes as described further below), cDNAs encoding the light and heavy chains of the antibody made by the hybridoma can be obtained by standard PCR amplification or cDNA cloning techniques. For antibodies obtained from an immunoglobulin gene library (e.g., using phage display techniques), nucleic acid encoding the antibody can be recovered from the library.

Some nucleic acids molecules described herein are those encoding the VH and VL sequences of the MICA.36, MICA.52, MICA.54, MICA.2, and 71C2 antibodies. Exemplary DNA sequences encoding the VH sequences of MICA.36, MICA.52, MICA.54, MICA.2, and 71C2 are set forth in SEQ ID NOs: 1, 11, 21, 31, and 41, respectively. Exemplary DNA sequences encoding the VL sequences of MICA.36, MICA.52, MICA.54, MICA.2, and 71C2 are set forth in SEQ ID NOs: 3, 13, 23, 33, and 43, respectively. Exemplary DNA sequences encoding the heavy chain sequences of MICA.36, MICA.52, MICA.54, MICA.2, and 71C2 are set forth in SEQ ID NOs: 59, 63, 67, 71, abd 75, respectively. Exemplary DNA sequences encoding the light chain sequences of MICA.36. MICA.52, MICA.54, MICA.2, and 71C2 are set forth in SEQ ID NOs: 61, 65, 69, 73, and 77.

Exemplary nucleic acids encoding the mature VH and VL domains of the MICA.36 antibody are set forth as SEQ ID NOs: 1 and 3, respectively. Exemplary nucleic acids encoding the mature heavy chains of the MICA.36 antibody is set forth as SEQ ID NOs: 59 and 131, and an exemplary nucleic acid encoding the mature light chain of the MICA.36 antibody is set forth as SEQ ID NO: 61.

Exemplary nucleic acids encoding the mature VH and VL domains of the MICA.52 antibody are set forth as SEQ ID NOs: 11 and 13, respectively. Exemplary nucleic acids encoding the mature heavy chains of the MICA.52 antibody is set forth as SEQ ID NOs: 63, and an exemplary nucleic acid encoding the mature light chain of the MICA.52 antibody is set forth as SEQ ID NO: 65.

Exemplary nucleic acids encoding the mature VH and VL domains of the MICA.54 antibody are set forth as SEQ ID NOs: 21 and 23, respectively. Exemplary nucleic acids encoding the mature heavy chains of the MICA.54 antibody is set forth as SEQ ID NOs: 67, and an exemplary nucleic acid encoding the mature light chain of the MICA.54 antibody is set forth as SEQ ID NO: 69.

Exemplary nucleic acids encoding the mature VH and VL domains of the MICA.2 antibody are set forth as SEQ ID NOs: 31 and 33, respectively. Exemplary nucleic acids encoding the mature heavy chains of the MICA.2 antibody is set forth as SEQ ID NOs: 71, and an exemplary nucleic acid encoding the mature light chain of the MICA.2 antibody is set forth as SEQ ID NO: 73.

Exemplary nucleic acids encoding the mature VH and VL domains of the 71C2 antibody are set forth as SEQ ID NOs: 41 and 43, respectively. Exemplary nucleic acids encoding the mature heavy chains of the 71C2 antibody is set forth as SEQ ID NOs: 75, and an exemplary nucleic acid encoding the mature light chain of the 71C2 antibody is set forth as SEQ ID NO: 77.

The above exemplary nucleic acids can further include a signal peptide set forth in SEQ ID NOs: 100-105. Nucleotide sequences encoding signal peptides are set forth as SEQ ID NOs: 106-107. In some embodiments, the signal peptide comprises MRAWIFFLLCLAGRALA (SEQ ID NO: 105).

The nucleic acid molecules described herein may be modified to delete specific sequences, e.g., restriction enzyme recognition sequences, or to optimize codons.

A method for making MICA.36, MICA.52, MICA.54, MICA.2, and 71C2 can comprise expressing the heavy chain and the light chains in a cell line comprising the nucleotide sequences encoding the heavy and light chains with a signal peptide, e.g., for MICA.36, SEQ ID NOs: 59 and 61, respectively, or SEQ ID Nos: 131 and 61, respectively. A method for making MICA.36, MICA.52, MICA.54, MICA.2, and 71C2 can comprise expressing the heavy chain and the light chains in a cell line comprising the nucleotide sequences encoding the heavy and light chains with a signal peptide. Host cells comprising these nucleotide sequences are encompassed herein.

Once DNA fragments encoding VH and VL segments are obtained, these DNA fragments can be further manipulated by standard recombinant DNA techniques, for example to convert the variable region genes to full-length antibody chain genes, to Fab fragment genes or to a scFv gene. In these manipulations, a VL- or VH-encoding DNA fragment is operatively linked to another DNA fragment encoding another protein, such as an antibody constant region or a flexible linker. The term "operatively linked", as used in this context, is intended to mean that the two DNA fragments are joined such that the amino acid sequences encoded by the two DNA fragments remain in-frame.

The isolated DNA encoding the VH region can be converted to a full-length heavy chain gene by operatively linking the VH-encoding DNA to another DNA molecule encoding heavy chain constant regions (hinge, CH1, CH2, and/or CH3). The sequences of human heavy chain constant region genes are known in the art (see, e.g., Kabat, E. A., et al. (1991) Sequences of Proteins of Immunological Interest, Fifth Edition, U.S. Department of Health and Human Services, NTH Publication No. 91-3242) and DNA fragments encompassing these regions can be obtained by standard PCR amplification. The heavy chain constant region can be an IgG1, IgG2, IgG3, IgG4, IgA, IgE, IgM or IgD constant region, for example, an IgG1 region. For a Fab fragment heavy chain gene, the VH-encoding DNA can be operatively linked to another DNA molecule encoding only the heavy chain CH1 constant region.

The isolated DNA encoding the VL region can be converted to a full-length light chain gene (as well as a Fab light chain gene) by operatively linking the VL-encoding DNA to another DNA molecule encoding the light chain constant region, CL. The sequences of human light chain constant region genes are known in the art (see, e.g., Kabat, E. A., et al. (1991) Sequences of Proteins of Immunological Interest, Fifth Edition, U.S. Department of Health and Human Services, NIH Publication No. 91-3242) and DNA fragments encompassing these regions can be obtained by standard PCR amplification. The light chain constant region can be a kappa or lambda constant region.

To create a scFv gene, the VH- and VL-encoding DNA fragments are operatively linked to another fragment encoding a flexible linker, e.g., encoding the amino acid sequence (Gly$_4$-Ser)$_3$, such that the VH and VL sequences can be expressed as a contiguous single-chain protein, with the VL and VH regions joined by the flexible linker (see, e.g., Bird et al., (1988) *Science* 242:423-426; Huston et al., (1988) *Proc. Natl. Acad. Sci. USA* 85:5879-5883; McCafferty et al., (1990) *Nature* 348:552-554).

Also provided herein are nucleic acid molecules encoding VH and VL sequences that are homologous to those of the MICA.36, MICA.52, MICA.54, MICA.2, and 71C2 antibodies. Exemplary nucleic acid molecules encode VH and VL sequences that are at least 70% identical, for example, at least 75%, at least 80%, at least 85%, at least 90%, at least 95%, or at least 99% identical, to nucleic acid molecules encoding the VH and VL sequences of the MICA.36, MICA.52, MICA.54, MICA.2, and 71C2 antibodies. Also provided herein are nucleic acid molecules with conservative substitutions (i.e., substitutions that do not alter the resulting amino acid sequence upon translation of nucleic acid molecule), e.g., for codon optimization.

Also provided are nucleic acids encoding the VH and/or VL regions of anti-MICA/B antibodies, such as the anti-MICA/B antibodies described herein, which nucleic acids comprise a nucleotide sequence that is at least about 75%, 80%, 85%, 90%, 95%, 96%, 97%, 98% or 99% identical to any of the nucleotide sequences encoding the VH and/or VL regions of anti-MICA/B antibodies described herein.

Also provided are nucleic acids encoding the heavy chain and/or the light chain of anti-MICA/B antibodies, such as the anti-MICA/B antibodies described herein, which nucleic acids comprise a nucleotide sequence that is at least about 75%, 80%, 85%, 90%, 95%, 96%, 97%, 98% or 99% identical to any of the nucleotide sequences encoding the heavy and/or light chains of anti-MICA/B antibodies described herein.

VII. Antibody Production

Monoclonal anti-MICA/B antibodies described herein can be produced using a variety of known techniques, such as the standard somatic cell hybridization technique described by Kohler and Milstein, *Nature* 256: 495 (1975). Although somatic cell hybridization procedures are preferred, in principle, other techniques for producing monoclonal antibodies also can be employed, e.g., viral or oncogenic transformation of B lymphocytes, phage display technique using libraries of human antibody genes.

The preferred animal system for preparing hybridomas is the murine system. Hybridoma production in the mouse is a very well-established procedure Immunization protocols and techniques for isolation of immunized splenocytes for fusion are known in the art. Fusion partners (e.g., murine myeloma cells) and fusion procedures are also known.

Chimeric or humanized anti-MICA/B antibodies described herein can be prepared based on the sequence of a murine monoclonal antibody prepared as described above. DNA encoding the heavy and light chain immunoglobulins can be obtained from the murine hybridoma of interest and engineered to contain non-murine (e.g., human) immunoglobulin sequences using standard molecular biology techniques. For example, to create a chimeric antibody, the murine variable regions can be linked to human constant regions using methods known in the art (see, e.g., U.S. Pat. No. 4,816,567 to Cabilly et al.). To create a humanized antibody, the murine CDR regions can be inserted into a human framework using methods known in the art (see, e.g., U.S. Pat. No. 5,225,539 to Winter, and U.S. Pat. Nos. 5,530,101; 5,585,089; 5,693,762 and 6,180,370 to Queen et al).

In some embodiments, the anti-MICA/B antibodies described herein are human monoclonal antibodies. Such human monoclonal antibodies directed against MICA/B can be generated using transgenic or transchromosomic mice carrying parts of the human immune system rather than the mouse system. These transgenic and transchromosomic mice include mice referred to herein as HuMAb mice and KM mice, respectively, and are collectively referred to herein as "human Ig mice."

The HUMAB-MOUSE® (Medarex, Inc.) contains human immunoglobulin gene miniloci that encode unrearranged human heavy (µ and γ) and κ light chain immunoglobulin sequences, together with targeted mutations that inactivate the endogenous µ and κ chain loci (see, e.g., Lonberg, et al., (1994) *Nature* 368(6474): 856-859). Accordingly, the mice exhibit reduced expression of mouse IgM or κ, and in response to immunization, the introduced human heavy and light chain transgenes undergo class switching and somatic mutation to generate high affinity human IgGκ monoclonal (Lonberg, N. et al. (1994), supra; reviewed in Lonberg, N. (1994) Handbook of Experimental Pharmacology 113:49-101; Lonberg, N. and Huszar, D. (1995) *Intern. Rev. Immunol.* 13: 65-93, and Harding, F. and Lonberg, N. (1995) *Ann. N.Y. Acad. Sci.* 764:536-546). The preparation and use of HuMab mice, and the genomic modifications carried by such mice, is further described in Taylor, L. et al. (1992) *Nucleic Acids Research* 20:6287-6295; Chen, J. et al., (1993) *International Immunology* 5: 647-656; Tuaillon et al. (1993) *Proc. Natl. Acad. Sci. USA* 90:3720-3724; Choi et al. (1993) *Nature Genetics* 4:117-123; Chen, J. et al. (1993) *EMBO J.* 12: 821-830; Tuaillon et al. (1994) *Immunol.* 152:2912-2920; Taylor, L. et al. (1994) *International Immunology* 6: 579-591; and Fishwild, D. et al. (1996) *Nature Biotechnology* 14: 845-851. See further, U.S. Pat. Nos. 5,545,806; 5,569,825; 5,625,126; 5,633,425; 5,789,650; 5,877,397; 5,661,016; 5,814,318; 5,874,299; and 5,770,429; all to Lonberg and Kay; U.S. Pat. No. 5,545,807 to Surani et al.; PCT Publication Nos. WO 92/03918, WO 93/12227, WO 94/25585, WO 97/13852, WO 98/24884 and WO 99/45962, all to Lonberg and Kay; and PCT Publication No. WO 01/14424 to Korman et al.

In some embodiments, the anti-MICA/B antibodies described herein are raised using a mouse that carries human immunoglobulin sequences on transgenes and transchomosomes, such as a mouse that carries a human heavy chain transgene and a human light chain transchromosome. Such mice, referred to herein as "KM mice," are described in detail in PCT Publication WO 02/43478 to Ishida et al.

Still further, alternative transgenic animal systems expressing human immunoglobulin genes are available in the art and can be used to raise anti-MICA/B antibodies described herein. For example, an alternative transgenic system referred to as the Xenomouse (Abgenix, Inc.) can be used; such mice are described in, for example, U.S. Pat. Nos. 5,939,598; 6,075,181; 6,114,598; 6, 150,584 and 6,162,963 to Kucherlapati et al.

Moreover, alternative transchromosomic animal systems expressing human immunoglobulin genes are available in the art and can be used to raise anti-MICA/B antibodies described herein. For example, mice carrying both a human heavy chain transchromosome and a human light chain tranchromosome, referred to as "TC mice" can be used; such mice are described in Tomizuka et al. (2000) *Proc. Natl. Acad. Sci. USA* 97:722-727. Furthermore, cows carrying human heavy and light chain transchromosomes have been described in the art (Kuroiwa et al. (2002) *Nature Biotechnology* 20:889-894) and can be used to raise anti-MICA/B antibodies described herein.

Additional mouse systems described in the art for raising human antibodies, e.g., human anti-MICA/B antibodies, include (i) the VELOCLMMUNE® mouse (Regeneron Pharmaceuticals, Inc.), in which the endogenous mouse heavy and light chain variable regions have been replaced, via homologous recombination, with human heavy and light chain variable regions, operatively linked to the endogenous mouse constant regions, such that chimeric antibodies (human V/mouse C) are raised in the mice, and then subsequently converted to fully human antibodies using standard recombinant DNA techniques; and (ii) the MEMO® mouse (Mems Biopharmaceuticals, Inc.), in which the mouse contains unrcarranged human heavy chain variable regions but a single rearranged human common light chain variable region. Such mice, and use thereof to raise antibodies, are described in, for example, WO 2009/15777, US 2010/0069614, WO 2011/072204, WO 2011/097603, WO 2011/163311, WO 2011/163314, WO 2012/148873, US 2012/0070861 and US 2012/0073004.

Human monoclonal anti-MICA/B antibodies described herein can also be prepared using phage display methods for screening libraries of human immunoglobulin genes. Such phage display methods for isolating human antibodies are established in the art. See for example: U.S. Pat. Nos. 5,223,409; 5,403,484; and U.S. Pat. No. 5,571,698 to Ladner et al.; U.S. Pat. Nos. 5,427,908 and 5,580,717 to Dower et al.; U.S. Pat. Nos. 5,969,108 and 6,172,197 to McCafferty et al.; and U.S. Pat. Nos. 5,885,793; 6,521,404; 6,544,731; 6,555,313; 6,582,915 and 6,593,081 to Griffiths et al.

Human monoclonal anti-MICA/B antibodies described herein can also be prepared using SCID mice into which human immune cells have been reconstituted such that a human antibody response can be generated upon immunization Such mice are described in, for example, U.S. Pat. Nos. 5,476,996 and 5,698,767 to Wilson et al.

VII.A. Immunizations

To generate fully human antibodies to MICA/B, transgenic or transchromosomal mice containing human immunoglobulin genes (e.g., HCol2. HCo7 or KM mice) can be immunized with a purified or enriched preparation of a human MICA/B antigen, e.g., MICA*002, MICA*004, MICA*008, MICA*009, MICB*005, or any combination thereof, and/or cells expressing MICA or fragment thereof, as described for other antigens, for example, by Lonbcrg et al., (1994) *Nature* 368(6474): 856-859; Fishwild et al., (1996) *Nature Biotechnology* 14: 845-851 and WO 98/24884. Alternatively, mice can be immunized with DNA encoding human MICA/B or fragment thereof. In some embodiments, the mice can be 6-16 weeks of age upon the first infusion. For example, a purified or enriched preparation (5-50 µg) of the recombinant MICA/B antigen can be used to immunize the HuMAb mice intraperitoneally. In the event that immunizations using a purified or enriched preparation of the MICA/B antigen do not result in antibodies, mice can also be immunized with cells expressing MICA/B, e.g., a cell line, to promote immune responses. Exemplary cell lines include MICA/B-overexpressing stable CHO and Raji cell lines.

Cumulative experience with various antigens has shown that the HuMAb transgenic mice respond best when initially immunized intraperitoneally (IP) or subcutaneously (SC) with antigen in Ribi's adjuvant, followed by every other week IP/SC immunizations (up to a total of 10) with antigen in Ribi's adjuvant. The immune response can be monitored over the course of the immunization protocol with plasma samples being obtained by retroorbital bleeds. The plasma can be screened by ELISA and FACS (as described below), and mice with sufficient titers of anti-MICA/B human immunoglobulin can be used for fusions. Mice can be boosted intravenously with antigen 3 days before sacrifice and removal of the spleen and lymph nodes. It is expected that 2-3 fusions for each immunization may need to be performed. Between 6 and 24 mice are typically immunized for each antigen. Usually, HCo7, HCo12, and KM strains are used. In addition, both HCo7 and HCol2 transgene can be bred together into a single mouse having two different human heavy chain transgenes (HCo7/HCo12).

VII.B. Generation of Hybridomas Producing Monoclonal Antibodies to MICA/B

To generate hybridomas producing human monoclonal anti-MICA/B antibodies described herein, splenocytes and/or lymph node cells from immunized mice can be isolated and fused to an appropriate immortalized cell line, such as a mouse myeloma cell line. The resulting hybridomas can be screened for the production of antigen-specific antibodies. For example, single cell suspensions of splenic lymphocytes from immunized mice can be fused to Sp2/0 nonsecreting mouse myeloma cells (ATCC, CRL 1581) with PEG. Cells can be plated in flat bottom microliter plate, followed by incubation in selective medium. After several weeks, cells can be cultured in medium. Individual wells can then be screened by ELISA for human monoclonal IgM and IgG antibodies. Once extensive hybridoma growth occurs, medium can be observed usually after 10-14 days. The antibody secreting hybridomas can be replaced, screened again, and if still positive for human IgG, the monoclonal antibodies can be subcloned at least twice by limiting dilution. The stable subclones can then be cultured in vitro to generate small amounts of antibody in tissue culture medium for characterization.

To purify human monoclonal antibodies, selected hybridomas can be grown in two-liter spinner-flasks for monoclonal antibody purification. Supernatants can be filtered and concentrated before affinity chromatography with protein A-SEPHAROSE™ (Pharmacia, Piscataway, N.J.). Eluted IgG can be checked by gel electrophoresis and high performance liquid chromatography to ensure purity. The buffer solution can be exchanged into PBS, and the concentration can be determined by OD280 using 1.43 extinction coefficient. The monoclonal antibodies can be aliquoted and stored.

VII.C. Generation of Transfectomas Producing Monoclonal Antibodies to MICA/B

Antibodies can be produced in a host cell transfectoma using, for example, a combination of recombinant DNA techniques and gene transfection methods as is well known in the art (Morrison, S. (1985) *Science* 229: 1202).

For example, to express antibodies, or antibody fragments thereof, DNAs encoding partial or full-length light and heavy chains, can be obtained by standard molecular biology techniques (e.g., PCR amplification or cDNA cloning using a hybridoma that expresses the antibody of interest) and the DNAs can be inserted into expression vectors such that the genes are operatively linked to transcriptional and translational control sequences. In this context, the term "operatively linked" is intended to mean that an antibody gene is ligated into a vector such that transcriptional and translational control sequences within the vector serve their intended function of regulating the transcription and translation of the antibody gene. The expression vector and expression control sequences are chosen to be compatible with the expression host cell used. The antibody light chain gene and the antibody heavy chain gene can be inserted into separate vector or both genes are inserted into the same expression vector. The antibody genes are inserted into the expression vector(s) by standard methods (e.g., ligation of complementary restriction sites on the antibody gene fragment and vector, or blunt end ligation if no restriction sites are present). The light and heavy chain variable regions of the anti-MICA/B antibodies described herein can be used to create full-length antibody genes of any antibody isotype by inserting them into expression vectors already encoding heavy chain constant and light chain constant regions of the desired isotype such that the V$_H$ segment is operatively linked to the C$_H$ segment(s) within the vector and the V$_L$ segment is operatively linked to the C$_L$ segment within the vector.

Additionally or alternatively, the recombinant expression vector can encode a signal peptide that facilitates secretion of the antibody chain from a host cell. The antibody chain gene can be cloned into the vector such that the signal peptide is linked in-frame to the amino terminus of the antibody chain gene. The signal peptide can be an immunoglobulin signal peptide or a heterologous signal peptide (i.e., a signal peptide from a non-immunoglobulin protein).

In some embodiments, the following signal peptides from human antibody heavy and light chains can be used: MDWTWRVFCLLAVAPGAHS (SEQ ID NO: 100); METPAQLLFLLLLWLPDTTG (SEQ ID NO: 101); MKHLWFFLLLVAAPRWVLS (SEQ ID NO: 102); MEFGLSWVFLVAIIKGVQC (SEQ ID NO: 103); MDMRVPAQLLGLLLWLPGARC (SEQ ID NO: 104) or MRAWIFFLLCLAGRALA (SEQ ID NO: 105). In some embodiments, a signal sequence used for expression of any one of the anti-MICA/B antibodies described herein is SEQ ID NO: 105. Heavy and light chains of anti-MICA/B antibodies can be expressed with the respective signal sequence that was linked to each chain in the hybridoma from which they were cloned. Below are the signal sequences of various anti-MICA/B antibodies as present in the hybridoma from which they were cloned, which signal sequences can be used to express the same antibody or another antibody:

In some embodiments, the heavy and light chains of the anti-MICA/B antibodies (e.g., MICA.36) can be engineered with signal sequences that differ from those present in the hybridomas from which they were cloned. Examples of such sequences include, but not limited to, the following:

(i) Nucleic acid sequence of signal sequence for the heavy chain:

(SEQ ID NO: 106)
ATGAGGGCTTGGATCTTCTTTCTGCTCTGCCTGGCCGGGAGAGCGCTCGCA (ii) Nucleic acid sequence of signal sequence for the light chain:

(SEQ ID NO: 107)
ATGAGGGCTTGGATCTTCTTTCTGCTCTGCCTGGCCGGGCGCGCCTTGGCC (iii) Amino acid sequence of signal sequence for the heavy and light chains. MRAWIFFLLCLAGRALA (SEQ ID NO: 105).

In addition to the antibody chain genes, recombinant expression vectors can carry regulatory sequences that control the expression of the antibody chain genes in a host cell. The term "regulatory sequence" is intended to include promoters, enhancers and other expression control elements (e.g., polyadenylation signals) that control the transcription or translation of the antibody chain genes. Such regulatory sequences are described, for example, in Goeddel (Gene Expression Technology. Methods in Enzymology 185, Academic Press, San Diego, Calif. (1990)). It will be appreciated by those skilled in the art that the design of the expression vector, including the selection of regulatory sequences, can depend on such factors as the choice of the host cell to be transformed, the level of expression of protein desired, etc. Preferred regulatory sequences for mammalian host cell expression include viral elements that direct high levels of protein expression in mammalian cells, such as promoters and/or enhancers derived from cytomegalovirus (CMV), Simian Virus 40 (SV40), adenovirus, (e.g., the adenovirus major late promoter (AdMLP) and polyoma. Alternatively, nonviral regulatory sequences can be used, such as the ubiquitin promoter or β-globin promoter. Still further, regulatory elements composed of sequences from different sources, such as the SRa promoter system, which contains sequences from the SV40 early promoter and the long terminal repeat of human T cell leukemia virus type 1 (Takebe, Y. et al. (1988) *Mol. Cell. Biol.* 8:466-472).

In addition to the antibody chain genes and regulatory sequences, recombinant expression vectors can carry additional sequences, such as sequences that regulate replication of the vector in host cells (e.g., origins of replication) and selectable marker genes. The selectable marker gene facilitates selection of host cells into which the vector has been introduced (see, e.g., U.S. Pat. Nos. 4,399,216, 4,634,665 and 5,179,017, all by Axel et al). For example, typically the selectable marker gene confers resistance to drugs, such as G418, hygromycin or methotrexate, on a host cell into which the vector has been introduced. Preferred selectable marker genes include the dihydrofolate reductase (DHFR) gene (for use in dhfr-host cells with methotrexate selection/amplification) and the neo gene (for G418 selection).

For expression of the light and heavy chains, the expression vector(s) encoding the heavy and light chains is transfected into a host cell by standard techniques. The various forms of the term "transfection" are intended to encompass a wide variety of techniques commonly used for the introduction of exogenous DNA into a prokaryotic or eukaryotic host cell, e.g., electroporation, calcium-phosphate precipitation, DEAE-dextran transfection and the like.

It is possible to express the anti-MICA/B antibodies described herein in either prokaryotic or eukaryotic host cells, such as mammalian cells.

Certain mammalian host cells for expressing the recombinant anti-MICA/B antibodies described herein include Chinese Hamster Ovary (CHO cells) (including dhfr-CHO cells, described in Urlaub and Chasin, (1980) *Proc. Natl. Acad. Sci. USA* 77:4216-4220, used with a DHFR selectable marker, e.g., as described in R J Kaufman and P. A. Sharp (1982) Mol. Biol. 759:601-621), NSO myeloma cells, COS cells and SP2 cells. In particular, for use with NSO myeloma cells, another expression system is the GS gene expression system disclosed in WO 87/04462, WO 89/01036 and EP 338,841. When recombinant expression vectors encoding antibody genes are introduced into mammalian host cells, the antibodies are produced by culturing the host cells for a period of time sufficient to allow for expression of the antibody in the host cells or, more preferably, secretion of the antibody into the culture medium in which the host cells are grown Antibodies can be recovered from the culture medium using standard protein purification methods.

VIII. Immunoconjugates, Antibody Derivatives and Diagnostics

Anti-MICA/B antibodies described herein can be used for diagnostic purposes, including sample testing and in vivo imaging, and for this purpose the antibody (or binding fragment thereof) can be conjugated to an appropriate detectable agent, to form an immunoconjugate. For diagnostic purposes, appropriate agents are detectable labels that include radioisotopes, for whole body imaging, and radioisotopes, enzymes, fluorescent labels and other suitable antibody tags for sample testing.

The detectable labels that can be linked to any anti-MICA/B antibody described herein can be any of the various types used currently in the field of in vitro diagnostics, including particulate labels including metal sols such as colloidal gold, isotopes such as $I^{125}$ or $Tc^{99}$ presented for instance with a peptidic chelating agent of the N2S2, $N_3S$ or $N_4$ type, chromophores including fluorescent markers, luminescent markers, phosphorescent markers and the like, as well as enzyme labels that convert a given substrate to a detectable marker, and polynucleotide tags that are revealed following amplification such as by polymerase chain reaction. Suitable enzyme labels include horseradish peroxidase, alkaline phosphatase and the like. For instance, the label can be the enzyme alkaline phosphatase, detected by measuring the presence or formation of chemiluminescence following conversion of 1,2 dioxetane substrates such as adamantyl methoxy phosphoryloxy phenyl dioxetane (AMPPD), disodium 3-(4-(methoxyspiro{1,2-dioxetane-3,2'-(5'-chloro)tricyclo{3.3.1.1 3,7}decan}-4-yl) phenyl phosphate (CSPD), as well as CDP and CDP-STAR® or other luminescent substrates well-known to those in the art, for example the chelates of suitable lanthanides such as Terbium(III) and Europium(III). The detection means is determined by the chosen label. Appearance of the label or its reaction products can be achieved using the naked eye, in the case where the label is particulate and accumulates at appropriate levels, or using instruments such as a spectrophotometer, a luminometer, a fluorimeter, and the like, all in accordance with standard practice.

In some embodiments, conjugation methods result in linkages which are substantially (or nearly) non-immunogenic, e.g., peptide- (i.e., amide-), sulfide-, (sterically hindered), disulfide-, hydrazone-, and ether linkages. These linkages are nearly non-immunogenic and show reasonable stability within serum (see e.g., Seiner, P. D., Curr. Opin. Chem. Biol. 13 (2009) 235-244; WO 2009/059278; WO 95/17886).

Depending on the biochemical nature of the moiety and the antibody, different conjugation strategies can be employed. In case the moiety is naturally-occurring or recombinant of between 50 to 500 amino acids, there are standard procedures in text books describing die chemistry for synthesis of protein conjugates, which can be easily followed by the skilled artisan (see, e.g., Hackenberger, C. P. R., and Schwarzer, D., Angew. Chem. Int. Ed. Engl. 47 (2008) 10030-10074). In some embodiments the reaction of a maleinimido moiety with a cysteine residue within the antibody or the moiety is used. This is an especially suited coupling chemistry in case e.g., a Fab or Fab'-fragment of an antibody is used. Alternatively, in some embodiments, coupling to the C-terminal end of the antibody or moiety is performed. C-terminal modification of a protein, e.g., of a Fab-fragment, can be performed as described (Sunbul. M. and Yin, J., Org. Biomol. Chem. 7 (2009) 3361-3371).

In general, site specific reaction and covalent coupling is based on transforming a natural amino acid into an amino acid with a reactivity which is orthogonal to the reactivity of the other functional groups present. For example, a specific cysteine within a rare sequence context can be enzymatically converted in an aldehyde (see Fresc, M. A., and Dicrks, T., ChemBioChem. 10 (2009) 425-427). It is also possible to obtain a desired amino acid modification by utilizing the specific enzymatic reactivity of certain enzymes with a natural amino acid in a given sequence context (see, e.g., Taki, M. et al., Prot. Eng. Des. Sel. 17 (2004) 119-126; Gautier, A. et al. Chem. Biol. 15 (2008) 128-136; and Protease-catalyzed formation of C—N bonds is used by Bordusa, F., Highlights in Bioorganic Chemistry (2004) 389-403). Site specific reaction and covalent coupling can also be achieved by the selective reaction of terminal amino acids with appropriate modifying reagents.

The reactivity of an N-terminal cysteine with benzonitrils (see Ren, H. et al., Angew. Chem. Int. Ed. Engl. 48 (2009) 9658-9662) can be used to achieve a site-specific covalent coupling.

Native chemical ligation can also rely on C-terminal cysteine residues (Taylor, E. Vogel; Imperiali, B, Nucleic Acids and Molecular Biology (2009), 22 (Protein Engineering), 65-96).

U.S. Pat. No. 6,437,095 B1 describes a conjugation method which is based on the faster reaction of a cysteine within a stretch of negatively charged amino acids with a cysteine located in a stretch of positively charged amino acids.

The moiety can also be a synthetic peptide or peptide mimic In case a polypeptide is chemically synthesized, amino acids with orthogonal chemical reactivity can be incorporated during such synthesis (see e.g., de Graaf, A. J. et al., Bioconjug. Chem. 20 (2009) 1281-1295). Since a great variety of orthogonal functional groups is at stake and can be introduced into a synthetic peptide, conjugation of such peptide to a linker is standard chemistry.

In order to obtain a mono-labeled polypeptide, the conjugate with 1:1 stoichiometry can be separated by chromatography from other conjugation side-products. This procedure can be facilitated by using a dye labeled binding pair member and a charged linker. By using this kind of labeled and highly negatively charged binding pair member, mono conjugated polypeptides are easily separated from non-labeled polypeptides and polypeptides which carry more than one linker, since the difference in charge and molecular weight can be used for separation. The fluorescent dye can be useful for purifying the complex from un-bound components, like a labeled monovalent binder.

In some embodiments the moiety attached to an anti-MICA/B antibody is selected from the group consisting of a binding moiety, a labeling moiety, and a biologically active moiety.

Anti-MICA/B antibodies described herein can also be conjugated to a therapeutic agent to form an immunoconjugate such as an antibody-drug conjugate (ADC). Suitable therapeutic agents include antimetabolites, alkylating agents, DNA minor groove binders, DNA intercalators, DNA crosslinkers, histone deacetylase inhibitors, nuclear export inhibitors, proteasome inhibitors, topoisomerase I or II inhibitors, heat shock protein inhibitors, tyrosine kinase inhibitors, antibiotics, and anti-mitotic agents. In the ADC, the antibody and therapeutic agent preferably are conjugated via a linker cleavable such as a peptidyl, disulfide, or hydrazone linker. In some embodiments, the linker is a peptidyl linker such as Val-Cit, Ala-Val, Val-Ala-Val, Lys-Lys, Pro-Val-Gly-Val-Val (SEQ ID NO: 108), Ala-Asn-Val, Val-Leu-Lys, Ala-Ala-Asn, Cit-Cit, Val-Lys, Lys, Cit, Ser, or Glu. The ADCs can be prepared as described in U.S. Pat. Nos. 7,087,600; 6,989,452; and 7,129,261; PCT Publications WO 02/096910; WO 07/038658; WO 07/051081; WO 07/059404; WO 08/083312; and WO 08/103693; U.S. Patent Publications 20060024317; 20060004081; and 20060247295.

In some embodiments, the therapeutic agent is selected from the group consisting of a cytotoxin, a non-cytotoxic drug, a radioactive agent, a second antibody, an enzyme, an anti-neoplastic agent, and any combination thereof.

In some embodiments, the immunoconjugate comprises an anti-MICA/B antibody and a cytotoxin. The cytotoxin can be selected from any cytotoxin known in the art. In some embodiments, the cytotoxin is selected from the group consisting of dolastatin, monomethyl auristatin E (MMAE), maytansine, duocarmycin, calicheamicin, pyrrolobenzodiazepine, duocarmycin, centanamycin, SN38, doxonibicin, a derivative thereof, a synthetic analog thereof, and any combination thereof. In certain embodiments, the immunoconjugate comprises an anti-MICA/B antibody and Cytotoxin A. In other embodiments, the immunoconjugate comprises an anti-MICA/B antibody and a non-cytotoxic drug.

In some embodiments, the immunoconjugate comprises an anti-MICA/B antibody and a radioactive agent. In some embodiments, the radioactive agent is a radionucleotide. In certain embodiments, the radioactive agent comprises radioactive iodine. In particular embodiments, the radioactive agent comprises 131-iodine. In other embodiments, the radioactive agent comprises the radioactive isotope Yttrium-90.

In some embodiments, the immunoconjugate comprises an anti-MICA/B antibody and a second antibody. The second antibody can be any antibody described in the present disclosure, including, but not limited to, an antibody that specifically binds a protein selected from the group consisting of PD-1, PD-L1, CTLA-4, LAG3, TIGIT, TIM3, NKG2a, OX40, ICOS, CD137, KIR, TGFβ, IL-10, IL-2, IL-8, B7-H4, Fas ligand, CXCR4, mesothelin, VISTA, CD96, CD27, GITR, and any combination thereof. In one embodiment, the immunoconjugate comprises an anti-MICA/B antibody and an anti-PD-1 antibody. In another embodiment, the immunoconjugate comprises an anti-MICA/B antibody and nivolumab.

In one embodiment, the immunoconjugate comprises an anti-MICA/B antibody and a pegylated IL-2 or pegylated IL-10.

In certain embodiments, the immunoconjugate comprises an anti-MICA/B antibody and an enzyme. In some embodiments, the enzyme comprises glucose oxidase. In some embodiments, the enzyme comprises a peroxidase. In some embodiments, the enzyme comprises myeloperoxidase. In some embodiments, the enzyme comprises glucose oxidase. In some embodiments, the enzyme comprises horseradish peroxidase.

In certain embodiments, the immunoconjugate comprises an anti-MICA/B antibody and an anti-neoplastic agent. The anti-neoplastic agent can be any such agent known in the art. In some embodiments, the anti-neoplastic agent is epirubicin. In some embodiments, the anti-neoplastic agent is a super antigen. In certain embodiments, the super antigen is staphylococcal enterotoxin A (SEA/E-120; estafenatox).

Anti-MICA/B antibodies, e.g., those described herein, can also be used for detecting MICA/B, such as human MICA/B, e.g., human MICA/B on the surface of a cell or soluble MICA/B in serum. The antibodies can be used, e.g., in an ELISA assay or in flow cytometry. In some embodiments, an anti-MICA/B antibody is contacted with cells or serum for a time appropriate for specific binding to occur, and then a reagent, e.g., an antibody that detects the anti-MICA/B antibody, is added. Exemplary assays are provided in the Examples. Exemplary methods for detecting MICA/B, e.g., surface expressed MICA/B or soluble MICA/B (sMICA/B) in a sample (serum) comprise (i) contacting a sample with an anti-MICA/B antibody, for a time sufficient for allowing specific binding of the anti-MICA/B antibody to MICA/B in the sample, and (2) contacting the sample with a detection reagent, e.g., an antibody, that specifically binds to the anti-MICA/B antibody, such as to the Fc region of the anti-MICA/B antibody, to thereby detect MICA/B bound by the anti-MICA/B antibody. Wash steps can be included after the incubation with the antibody and/or detection reagent. Anti-MICA/B antibodies for use in these methods do not have to be linked to a label or detection agents, as a separate detection agent can be used.

Other uses for anti-MICA/B antibodies, e.g., as monotherapy or combination therapy, are provided elsewhere herein, e.g., in the section pertaining to combination treatments.

IX. Bispecific Molecules

Anti-MICA/B antibodies described herein can be used for forming bispecific molecules. An anti-MICA/B antibody, or antigen-binding portions thereof, can be derivatized or linked to another functional molecule, e.g., another peptide or protein (e.g., another antibody or ligand for a receptor) to generate a bispecific molecule that binds to at least two different binding sites or target molecules. For example, an anti-MICA/B antibody can be linked to an antibody or scFv that binds specifically to any protein that can be used as potential targets for combination treatments, such as the proteins described herein (e.g., antibodies to PD-1, PD-L1, CTLA-4, LAG3, TIGIT, TIM3, NKG2a, OX40, ICOS, CD137, KIR, TGFβ, IL-10, IL-2, IL-8, B7-H4, Fas ligand, CXCR4, mesothelin, CD27, CD96, VISTA, or GITR, or pegylated IL-2 or pegylated IL-10). The antibody described herein can in fact be derived or linked to more than one other functional molecule to generate multispecific molecules that bind to more than two different binding sites and/or target molecules; such multispecific molecules are also intended to be encompassed by the term "bispecific molecule" as used herein. To create a bispecific molecule described herein, an antibody described herein can be functionally linked (e.g., by chemical coupling, genetic fusion, noncovalent association or otherwise) to one or more other binding molecules, such as another antibody, antibody fragment, peptide or binding mimetic, such that a bispecific molecule results.

Accordingly, provided herein are bispecific molecules comprising at least one first binding specificity for MICA/B and a second binding specificity for a second target epitope. In some embodiments described herein in which the bispecific molecule is multispecific, the molecule can further include a third binding specificity.

In some embodiments, the bispecific molecules described herein comprise as a binding specificity at least one antibody, or an antibody fragment thereof, including, e.g., an Fab, Fab', F(ab')2, Fv, or a single chain Fv (scFv). The antibody can also be a light chain or heavy chain dimer, or any minimal fragment thereof such as a Fv or a single chain construct as described in Ladner et al. U.S. Pat. No. 4,946,778.

While human monoclonal antibodies are preferred, other antibodies which can be employed in the bispecific molecules described herein are murine, chimeric and humanized monoclonal antibodies.

The bispecific molecules described herein can be prepared by conjugating the constituent binding specificities using methods known in the art. For example, each binding specificity of the bispecific molecule can be generated separately and then conjugated to one another. When the binding specificities are proteins or peptides, a variety of coupling or cross-linking agents can be used for covalent conjugation. Examples of cross-linking agents include protein A, carbodiimide, N-succinimidyl-S-acetyl-thioacetate (SATA), 5,5'-dithiobis(2-nitrobenzoic acid) (DTNB), o-phenylenedimaleimide (oPDM), N-succinimidyl-3-(2-pyridyldithio)propionate (SPDP), and sulfosuccinimidyl 4-(N-maleimidomethyl) cyclohaxane-1-carboxylate (sulfo-SMCC) (see, e.g., Karpovsky et al. (1984) *J. Exp. Med.* 160: 1686; Liu, M A et al. (1985) *Proc. Natl. Acad. Sci. USA* 82:8648). Other methods include those described in Paulus (1985) *Behring Ins. Hitt. No.* 78, 118-132; Brennan et al. (1985) *Science* 229:81-83), and Glennie et al. (1987) *J. Immunol.* 139: 2367-2375). Some conjugating agents are SATA and sulfo-SMCC, both available from Pierce Chemical Co. (Rockford, Ill.).

When the binding specificities are antibodies, they can be conjugated via sulfhydryl bonding of the C-terminus hinge regions of the two heavy chains In some embodiments, the hinge region is modified to contain an odd number of sulfhydryl residues, preferably one, prior to conjugation.

Alternatively, both binding specificities can be encoded in the same vector and expressed and assembled in the same host cell. This method is particularly useful where the bispecific molecule is a mAb×mAb, mAb×Fab, mAb×(scFv)$_2$, Fab×F(ab')$_2$ or ligand x Fab fusion protein. A bispecific antibody can comprise an antibody comprising an scFv at the C-terminus of each heavy chain. A bispecific molecule described herein can be a single chain molecule comprising one single chain antibody and a binding determinant, or a single chain bispecific molecule comprising two binding determinants Bispecific molecules can comprise at least two single chain molecules. Methods for preparing bispecific molecules are described for example in U.S. Pat. Nos. 5,260,203; 5,455,030; 4,881,175; 5,132,405; 5,091,513; 5,476,786; 5,013,653; 5,258,498; and 5,482,858.

Binding of the bispecific molecules to their specific targets can be confirmed using art-recognized methods, such as enzyme-linked immunosorbent assay (ELISA), radioimmunoassay (RIA), FACS analysis, bioassay (e.g., growth inhibition), or Western Blot assay. Each of these assays generally detects the presence of protein-antibody complexes of particular interest by employing a labeled reagent (e.g., an antibody) specific for the complex of interest.

X. Compositions

Further provided are compositions, e.g., a pharmaceutical compositions, containing one or a combination of anti-MICA/B antibodies or combination with antibodies to other targets, or antigen-binding portion(s) thereof, described herein, formulated together with a pharmaceutically acceptable carrier. Such compositions can include one or a combination of (e.g., two or more different) antibodies, or immunoconjugates or bispecific molecules described herein. For example, a pharmaceutical composition described herein can comprise a combination of antibodies (or immunoconjugates or bispecifics) that bind to different epitopes on the target antigen or that have complementary activities.

In some embodiments, a composition comprises an anti-MICA/B antibody at a concentration of at least 1 mg/ml, 5 mg/ml. 10 mg/ml, 50 mg/ml, 100 mg/ml, 150 mg/ml, 200 mg/ml, 1-300 mg/ml, or 100-300 mg/ml.

Pharmaceutical compositions described herein also can be administered in combination therapy, i.e., combined with other agents. For example, the combination therapy can include an anti-MICA/B antibody described herein combined with at least one other anti-cancer and/or immunomodulating, e.g., T-cell stimulating (e.g., activating) agent. Examples of therapeutic agents that can be used in combination therapy are described in greater detail below in the section on uses of the anti-MICA/B antibodies described herein.

In some embodiments, the anti-MICA/B antibody may be combined with at least one other agent selected from chemotherapy drugs, small molecule drugs and antibodies that stimulate the immune response to a given cancer. In some instances, the anti-MICA/B antibody may be combined with, for example, one or more of an anti-CTLA-4 antibody, an anti-PD-1 antibody, an anti-PD-L1 antibody, an anti-OX40 (also known as CD134, TNFRSF4, ACT35 and/or TXGP1L) antibody (e.g., BMS986178, or MDX-1803), an anti-CD137 antibody, an anti-LAG-3 antibody, an anti-GITR antibody, an anti-KIR antibody, an anti-TGFβ antibody, an anti-IL-10 antibody, a long-acting IL-10 molecule (e.g. IL-10-Fc fusion, or Pegylated IL-10, such as AM0010 of ARMO BioSciences), a long-acting IL-2 (e.g., Pegylated IL-2 molecules, such as NKTR-214 of Nektar; see U.S. Pat. No. 8,252,275, WO12/065086 and WO15/125159), an anti-VISTA antibody, an anti-CD96 antibody, an anti-IL-8 antibody, an anti-B7-H4, an anti-Fas ligand antibody, an anti-CXCR4 antibody, an anti-mesothelin antibody, an anti-CD27 antibody, or any combination thereof.

In other embodiments, the anti-MICA/B antibody may be formulated with a second antibody. In some embodiments, the second antibody specifically binds a protein selected from the group consisting of PD-1, PD-L1, CTLA-4, LAG3, TIGIT, TIM3, NKG2a, OX40, ICOS, CD137, KIR, TGFβ, IL-10, IL-2, VISTA, CD96, IL-8, B7-H4, Fas ligand, CXCR4, mesothelin, CD27. GITR, and any combination thereof.

In some embodiments, the second antibody may be an anti-PD-1 antibody. The anti-PD-1 antibody can be any antibody that binds PD-1 and inhibits the interaction of PD-1 and PD-L1. In some embodiments, the anti-PD-1 antibody is any anti-PD-1 antibody disclosed herein. In some embodiments, the second antibody may be nivolumab. In some embodiments, the second antibody may be pembrolizumab In some embodiments, the second antibody may be an anti-PD-L1 antibody. The anti-PD-L1 antibody can be any antibody that binds PD-L1 and inhibits the interaction of PD-1 and PD-L1. In some embodiments, the anti-PD-L1 antibody is any anti-PD-L1 antibody disclosed herein. In some embodiments, the second antibody may be atezolizumab In some embodiments, the second antibody may be durvalumab In some embodiments the second antibody may be avelumab.

In some embodiments, the second antibody may be an anti-CTLA-4 antibody. The anti-CTLA-4 antibody can be any antibody that binds CTLA-4 and inhibits its activity. In some embodiments, the anti-CTLA-4 antibody is any anti-CTLA-4 antibody disclosed herein. In some embodiments, the second antibody may be tremelimumab In some embodiments, the second antibody may be ipilimumab In some embodiments, the second antibody may be an anti-LAG3 antibody. The anti-LAG3 antibody can be any antibody that binds LAG-3 and inhibits its activity. In some embodiments, the anti-LAG3 antibody is any anti-LAG3 antibody disclosed herein. In some embodiments, the second antibody may be 25F7.

In some embodiments, the second antibody may be an anti-CD137 antibody. The anti-CD137 antibody can be any antibody that binds CD137 and inhibits its activity. In some embodiments, the anti-CD137 antibody is any anti-CD137 antibody disclosed herein. In some embodiments, the second antibody may be urelumab.

In some embodiments, the second antibody may be an anti-KIR antibody. The anti-KIR antibody can be any antibody that binds KIR and inhibits its activity. In some embodiments, the anti-KIR antibody is any anti-KIR antibody disclosed herein. In some embodiments, the second antibody may be lirilumab.

In some embodiments, the second antibody may be an anti-GITR antibody. The anti-GITR antibody can be any antibody that binds GITR and inhibits its activity. In some embodiments, the anti-GITR antibody is any anti-GITR antibody disclosed herein. In some embodiments, the second antibody may be MK4166. In some embodiments, the second antibody may be TRX518.

In some embodiments, the second antibody may be an anti-CD96 antibody.

In some embodiments, the second antibody may be an anti-TIM3 antibody.

In some embodiments, the second antibody may be an anti-VISTA antibody.

In some embodiments, the second antibody may be an anti-NKG2a antibody.

In some embodiments, the second antibody may be an anti-ICOS antibody.

In some embodiments, the second antibody may be an anti-OX40 antibody.

In some embodiments, the second antibody may be an anti-IL8 antibody, such as HUMAX®-IL8 (BMS-986253).

In some embodiments, the anti-MICA/B antibody may be formulated with a long-acting IL-10 molecule. In some embodiments, the anti-MICA/B antibody may be formulated with IL-10-Fc fusion molecule. In some embodiments, the anti-MICA/B antibody may be formulated with Pegylated 1L-10, such as AM0010 of ARMO BioSciences.

In some embodiments, the anti-MICA/B antibody may be formulated with a long-acting IL-2. In some embodiments, the anti-MICA/B antibody may be formulated with Pegylated IL-2 molecules, such as NKTR-214 of Nektar: see U.S. Pat. No. 8,252,275, WO12/065086 and WO15/125159.

In some embodiments, the composition of the invention further comprises a bulking agent. A bulking agent can be selected from the group consisting of NaCl, mannitol, glycine, alanine, and any combination thereof. In other embodiments, the composition of the invention comprises a stabilizing agent. The stabilizing agent can be selected from the group consisting of sucrose, trehalose, raffinose, arginine; or any combination thereof. In other embodiments, the composition of the invention comprises a surfactant. The surfactant can be selected from the group consisting of polysorbate 80 (PS80), polysorbate 20 (PS20), and any combination thereof. In certain embodiments, the composition further comprises a chelating agent. The chelating agent can be selected from the group consisting of diethylenetriaminepentaacetic acid (DTPA), ethylenediaminetetraacetic acid, nitrilotriacetic acid, and any combination thereof.

In other embodiments, the composition comprises a third antibody. In some embodiments, the third antibody is any antibody disclosed herein.

In one embodiment, the composition further comprises NaCl, mannitol, pentetic acid (DTPA), sucrose, PS80, and any combination thereof.

As used herein, "pharmaceutically acceptable carrier" includes any and all solvents, dispersion media, coatings, antibacterial and antifungal agents, isotonic and absorption delaying agents, and the like that are physiologically compatible. In some embodiments, the carrier is suitable for intravenous, intramuscular, subcutaneous, parenteral, spinal or epidermal administration (e.g., by injection or infusion). An option for subcutaneous injection is based on Halozyme Therapeutics' ENHANZE® drug-delivery technology, involving a co-formulation of an Ab with recombinant human hyaluronidase enzyme (rHuPH20) that removes traditional limitations on the volume of biologics and drugs that can be delivered subcutaneously due to the extracellular matrix (U.S. Pat. No. 7,767,429). Depending on the route of administration, the active compound, i.e., antibody, immunoconjugate, or bispecific molecule, can be coated in a material to protect the compound from the action of acids and other natural conditions that can inactivate the compound.

The pharmaceutical compounds described herein can include one or more pharmaceutically acceptable salts. A "pharmaceutically acceptable salt" refers to a salt that retains the desired biological activity of the parent compound and does not impart any undesired toxicological effects (see e.g., Berge, S. M., et al. (1977) *J. Pharm. Sci.* 66: 1-19). Examples of such salts include acid addition salts and base addition salts. Acid addition salts include those derived from nontoxic inorganic acids, such as hydrochloric, nitric, phosphoric, sulfuric, hydrobromic, hydroiodic, phosphorous and the like, as well as from nontoxic organic acids such as aliphatic mono- and dicarboxylic acids, phenyl-substituted alkanoic acids, hydroxy alkanoic acids, aromatic acids, aliphatic and aromatic sulfonic acids and the like. Base addition salts include those derived from alkaline earth metals, such as sodium, potassium, magnesium, calcium and the like, as well as from nontoxic organic amines, such as N,N'-dibenzylethylenediamine, N-methylglucamine, chloroprocaine, choline, diethanolamine, ethylenediamine, procaine and the like.

A pharmaceutical composition described herein can also include a pharmaceutically acceptable anti-oxidant. Examples of pharmaceutically acceptable antioxidants include: (1) water soluble antioxidants, such as ascorbic acid, cysteine hydrochloride, sodium bisulfate, sodium metabisulfite, sodium sulfite and the like; (2) oil-soluble antioxidants; such as ascorbyl palmitate, butylated hydroxyanisole (BHA); butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Examples of suitable aqueous and nonaqueous carriers that can be employed in the pharmaceutical compositions described herein include water, ethanol, polyols (such as glycerol, propylene glycol, polyethylene glycol, and the like), and suitable mixtures thereof, vegetable oils, such as olive oil, and injectable organic esters, such as ethyl oleate.

Proper fluidity can be maintained, for example, by the use of coating materials, such as lecithin, by the maintenance of the required particle size in the case of dispersions, and by the use of surfactants.

These compositions can also contain adjuvants such as preservatives, wetting agents, emulsifying agents and dispersing agents. Prevention of presence of microorganisms can be ensured both by sterilization procedures, supra, and by the inclusion of various antibacterial and antifungal agents, for example, paraben, chlorobutanol, phenol sorbic acid, and the like. It can also be desirable to include isotonic agents, such as sugars, sodium chloride, and the like into the compositions. In addition, prolonged absorption of the injectable pharmaceutical form can be brought about by the inclusion of agents which delay absorption such as aluminum monostearate and gelatin.

Pharmaceutically acceptable carriers include sterile aqueous solutions or dispersions and sterile powders for the extemporaneous preparation of sterile injectable solutions or dispersion. The use of such media and agents for pharmaceutically active substances is known in the art. Except insofar as any conventional media or agent is incompatible with the active compound, use thereof in the pharmaceutical compositions described herein is contemplated. A pharmaceutical composition can comprise a preservative or can be devoid of a preservative. Supplementary active compounds can be incorporated into the compositions.

Therapeutic compositions typically must be sterile and stable under the conditions of manufacture and storage. The composition can be formulated as a solution, microemulsion, liposome, or other ordered structure suitable to high drug concentration. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. In many cases, the compositions can include isotonic agents, for example, sugars, polyalcohols such as mannitol, sorbitol, or sodium chloride in the composition. Prolonged absorption of the injectable compositions can be brought about by including in the composition an agent that delays absorption, for example, monostearate salts and gelatin.

Sterile injectable solutions can be prepared by incorporating the active compound in the required amount in an appropriate solvent with one or a combination of ingredients enumerated above, as required, followed by sterilization microfiltration. Generally, dispersions are prepared by incorporating the active compound into a sterile vehicle that contains a basic dispersion medium and the required other ingredients from those enumerated herein. In the case of sterile powders for the preparation of sterile injectable solutions, some methods of preparation are vacuum drying and freeze-drying (lyophilization) that yield a powder of the active ingredient plus any additional desired ingredient from a previously sterile-filtered solution thereof.

The amount of active ingredient which can be combined with a carrier material to produce a single dosage form will vary depending upon the subject being treated, and the particular mode of administration. The amount of active ingredient which can be combined with a carrier material to produce a single dosage form will generally be that amount of the composition which produces a therapeutic effect. Generally, out of one hundred percent, this amount will range from about 0.01 percent to about ninety-nine percent of active ingredient, from about 0.1 percent to about 70 percent, or from about 1 percent to about 30 percent of active ingredient in combination with a pharmaceutically acceptable carrier.

Dosage regimens are adjusted to provide the optimum desired response (e.g., a therapeutic response). For example, a single bolus can be administered, several divided doses can be administered over time or the dose can be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the subjects to be treated; each unit contains a predetermined quantity of active compound calculated to produce the desired therapeutic effect in association with the required pharmaceutical carrier. The specification for the dosage unit forms described herein are dictated by and directly dependent on (a) the unique characteristics of the active compound and the particular therapeutic effect to be achieved, and (b) the limitations inherent in the art of compounding such an active compound for the treatment of sensitivity in individuals.

For administration of an anti-MICA/B antibody, e.g., described herein, the dosage ranges from about 0.0001 to 100 mg/kg. An anti-MICA/B antibody can be administered at a flat dose (flat dose regimen). In some embodiments, an anti-MICA/B antibody can be administered at a fixed dose with another antibody. In some embodiments, an anti-MICA/B antibody is administered at a dose based on body weight.

In some methods, two or more monoclonal antibodies with different binding specificities are administered simultaneously, in which case the dosage of each antibody administered falls within the ranges indicated. Antibody is usually administered on multiple occasions. Intervals between single dosages can be, for example, weekly, monthly, every three months or yearly. Intervals can also be irregular as indicated by measuring blood levels of antibody to the target antigen in the patient. In some methods, dosage is adjusted to achieve a plasma antibody concentration of about 1-1000 µg/ml and in some methods about 25-300 µg/ml.

An anti-MICA/B antibody can be administered with another antibody at the dosage regimen of the other antibody. For example, an anti-MICA/B antibody can be administered with an anti-PD-1 antibody, such as nivolumab (OPDIVO®), every two weeks as an i.v. infusion over 60 minutes until disease progression or unacceptable toxicity occurs. An anti-MICA/B antibody can be administered with pembrolizumab (KEYTRUDA®) every 3 weeks as an i.v. infusion over 30 minutes until disease progression or unacceptable toxicity occurs. An anti-MICA/B antibody can be administered with atezolizumab (TECENTRIQ™) every 3 weeks as an i.v. infusion over 60 or 30 minutes until disease progression or unacceptable toxicity occurs.

An antibody can be administered as a sustained release formulation, in which case less frequent administration is required. Dosage and frequency vary depending on the half-life of the antibody in the patient. In general, human antibodies show the longest half-life, followed by humanized antibodies, chimeric antibodies, and nonhuman antibodies. The dosage and frequency of administration can vary depending on whether the treatment is prophylactic or therapeutic. In prophylactic applications, a relatively low dosage is administered at relatively infrequent intervals over a long period of time. Some patients continue to receive treatment for the rest of their lives. In therapeutic applications, a relatively high dosage at relatively short intervals is sometimes required until progression of the disease is reduced or terminated, and until the patient shows partial or complete amelioration of symptoms of disease. Thereafter, the patient can be administered a prophylactic regime.

Actual dosage levels of the active ingredients in the pharmaceutical compositions described herein can be varied so as to obtain an amount of the active ingredient which is effective to achieve the desired therapeutic response for a particular patient, composition, and mode of administration, without being toxic to the patient. The selected dosage level will depend upon a variety of pharmacokinetic factors including the activity of the particular compositions described herein employed, or the ester, salt or amide thereof, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors well known in the medical arts.

A "therapeutically effective dosage" of an anti-MICA/B antibody described herein call result in a decrease in severity of disease symptoms, an increase in frequency and duration of disease symptom-free periods, or a prevention of impairment or disability due to the disease affliction. In the context of cancer, a therapeutically effective dose can result in increased survival, e.g., overall survival, and/or prevention of further deterioration of physical symptoms associated with cancer. Symptoms of cancer are well-known in the art and include, for example, unusual mole features, a change in the appearance of a mole, including asymmetry, border, color and/or diameter, a newly pigmented skin area, an abnormal mole, darkened area under nail, breast lumps, nipple changes, breast cysts, breast pain, death, weight loss, weakness, excessive fatigue, difficulty eating, loss of appetite, chronic cough, worsening breathlessness, coughing up blood, blood in the urine, blood in stool, nausea, vomiting, liver metastases, lung metastases, bone metastases, abdominal fullness, bloating, fluid in peritoneal cavity, vaginal bleeding, constipation, abdominal distension, perforation of colon, acute peritonitis (infection, fever, pain), pain, vomiting blood, heavy sweating, fever, high blood pressure, anemia, diarrhea, jaundice, dizziness, chills, muscle spasms, colon metastases, lung metastases, bladder metastases, liver metastases, bone metastases, kidney metastases, and pancreatic metastases, difficulty swallowing, and the like.

A therapeutically effective dose can prevent or delay onset of cancer, such as can be desired when early or preliminary signs of the disease are present. Laboratory tests utilized in the diagnosis of cancer include chemistries (including the measurement of MICA/B levels), hematology, serology and radiology. Accordingly, any clinical or biochemical assay that monitors any of the foregoing can be used to determine whether a particular treatment is a therapeutically effective dose for treating cancer. One of ordinary skill in the art would be able to determine such amounts based on such factors as the subject's size, the severity of the subject's symptoms, and the particular composition or route of administration selected.

A composition described herein can be administered via one or more routes of administration using one or more of a variety of methods known in the art. As will be appreciated by the skilled artisan, the route and/or mode of administration will vary depending upon the desired results. Routes of administration for the anti-MICA/B antibodies described herein can include intravenous, intramuscular, intradermal, intraperitoneal, subcutaneous, spinal or other parenteral routes of administration, for example by injection or infusion. The phrase "parenteral administration" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion.

Alternatively, an antibody described herein could potentially be administered via a non-parenteral route, such as a topical, epidermal or mucosal route of administration, for example, intranasally, orally, vaginally, rectally, sublingually or topically.

The active compounds can be prepared with carriers that will protect the compound against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known to those skilled in the art. See, e.g., Sustained and Controlled Release Drag Delivery Systems, J. R. Robinson, ed., Marcel Dekker, Inc. New York, 1978.

Therapeutic compositions can be administered with medical devices known in the art. For example, in some embodiments, a therapeutic composition described herein can be administered with a needleless hypodermic injection device, such as the devices disclosed in U.S. Pat. Nos. 5,399,163: 5,383,851; 5,312,335; 5,064,413; 4,941,880; 4,790,824; or 4,596,556. Examples of well-known implants and modules for use with anti-MICA/B antibodies described herein include: U.S. Pat. No. 4,487,603, which discloses an implantable micro-infusion pump for dispensing medication at a controlled rate; U.S. Pat. No. 4,486,194, which discloses a therapeutic device for administering medicaments through the skin; U.S. Pat. No. 4,447,233, which discloses a medication infusion pump for delivering medication at a precise infusion rate; U.S. Pat. No. 4,447,224, which discloses a variable flow implantable infusion apparatus for continuous drug delivery; U.S. Pat. No. 4,439,196, which discloses an osmotic drug delivery system having multi-chamber compartments; and U.S. Pat. No. 4,475,196, which discloses an osmotic drug delivery system. These patents are incorporated herein by reference. Many other such implants, delivery systems, and modules are known to those skilled in the art.

In some embodiments, the anti-MICA/B antibodies described herein can be formulated to ensure proper distribution in vivo. For example, the blood-brain barrier (BBB) excludes many highly hydrophilic compounds. To ensure that the therapeutic compounds described herein cross the BBB (if desired, e.g., for brain cancers), they can be formulated, for example, in liposomes. For methods of manufacturing liposomes, see, e.g., U.S. Pat. Nos. 4,522, 811; 5,374,548; and 5,399,331. The liposomes can comprise one or more moieties which are selectively transported into specific cells or organs, thus enhance targeted drug delivery (see, e.g., V. V. Ranade (1989) *J. Clin. Pharmacol.* 29:685). Exemplary targeting moieties include folate or biotin (see, e.g., U.S. Pat. No. 5,416,016 to Low et al.); mannosides (Umezawa et (1988) *Biochem. Biophys. Res. Commun.* 153: 1038); antibodies (P. G. Bloeman et al. (1995) *FEBS Lett.* 357: 140; M. Owais et al. (1995) *Antimicrob. Agents*

Chemother. 39: 180); surfactant protein A receptor (Briscoe et al. (1995) Am. J. Physiol. 1233: 134); p120 (Schreier et al. (1994) J. Biol. Chem. 269:9090); see also K. Keinanen; M. L. Laukkanen (1994) FEBS Lett. 346: 123; J. J. Killion; I. J. Fidler (1994) Immunomethods 4:273.

XI. Uses and Methods

Certain aspects of the present disclosure are directed to method of treating a subject, comprising administering to the subject an anti-MICA/B antibody disclosed herein, a polynucleotide encoding the anti-MICA/B antibody, a vector comprising the polynucleotide, a host cell comprising the polynucleotide, an immunoconjugate comprising an anti-MICA/B antibody, or any combination thereof.

Certain aspects of the present disclosure are directed to a method of treating a cancer in a subject in need thereof, comprising administering to the subject an effective dose of a composition disclosed herein (e.g., an antibody, polynucleotide, vector, host cell, immunoconjugate, or pharmaceutical composition). In other aspects, the present disclosure is directed to a method of inhibiting shedding of MICA/B by a tumor cell in a subject in need thereof, comprising administering to the subject an effective dose of a composition disclosed herein. In other aspects, the present disclosure is directed to a method of reducing shed MICA/B in the serum and/or retaining MICA/B on the cell surface in a subject in need thereof, comprising administering to the subject an effective dose of a composition disclosed herein. In other aspects, the present disclosure is directed to a method of killing a tumor cell in a subject in need thereof, comprising administering to the subject an effective dose of a composition disclosed herein. In other aspects, the present disclosure is directed to a method of reducing the size of a tumor in a subject in need thereof, comprising administering to the subject an effective dose of a composition disclosed herein. In other embodiments, the present disclosure is directed to inhibiting metastasis of a tumor in a subject in need thereof, comprising administering to the subject an effective dose of a composition disclosed herein. In some embodiments, the subject is a human.

The compositions of the present disclosure can be administered using any pharmaceutically acceptable route. In some embodiments, the composition (e.g., antibody, polynucleotide, vector, host cell, immunoconjugate, or pharmaceutical composition) is administered intravenously, intraperitoneally, intramuscularly, intraarterially, intrathecally, intralymphaticly, intralesionally, intracapsularly, intraorbitally, intracardiacly, intradermally, transtracheally, subcutaneously, subcuticularly, intraarticularly, subcapsularly, subarachnoidly, intraspinally, epidurally, intrasternally, topically, epidermally, mucosally, or any combination thereof. In some embodiments, the composition is administered intravenously. In some embodiments, the composition is administered subcutaneously.

In certain embodiments, the method reduces the size of a cancer, e.g., the size of a tumor, in the subject. In some embodiments, the size of the caner is reduced by at least about 5%, at least about 10%, at least about 15%, at least about 20%, at least about 25%, at least about 30%, at least about 35%, at least about 40%, at least about 45%, at least about 50%, at least about 60%, at least about 70%, at least about 80%, or at least about 90%.

In some embodiments, the method increases the over survival of the subject. In some embodiments, the overall survival is increased relative to the average overall survival of a subject having the same cancer but treated with a different therapy. In certain embodiments, the overall survival is increased by at least about 10%, at least about 20%, at least about 25%, at least about 50%, at least about 2 fold, at least about 3 fold, at least about 5 fold. In some embodiments, the overall survival is increased by at least about one month, at least about 2 months, at least about 3 months, at least about 4 months, at least about 5 months, at least about 6 months, at least about 7 months, at least about 8 months, at least about 9 months, at least about 10 months, at least about 1 months, at least about 12 months, at least about 15 months, at least about 18 months, at least about 21 months, at least about 2 years, at least about 3 years, at least about 4 years, at least about 5 years, or at least about 10 years.

In some embodiments, the method increases the progression free survival of the subject. In some embodiments, the overall survival is increased relative to the average progression free survival of a subject having the same cancer but treated with a different therapy. In certain embodiments, the progression free survival is increased by at least about 10%, at least about 20%, at least about 25%, at least about 50%, at least about 2 fold, at least about 3 fold, at least about 5 fold. In some embodiments, the overall survival is increased by at least about one month, at least about 2 months, at least about 3 months, at least about 4 months, at least about 5 months, at least about 6 months, at least about 7 months, at least about 8 months, at least about 9 months, at least about 10 months, at least about 1 months, at least about 12 months, at least about 15 months, at least about 18 months, at least about 21 months, at least about 2 years, at least about 3 years, at least about 4 years, at least about 5 years, or at least about 10 years.

In some embodiments, the method increases the objective response rate of the subject. In certain embodiments, the method induces a complete response in the subject. In some embodiments, the method induces a partial response in the subject.

In some embodiments, the method comprises administering an anti-MICA/B antibody (or a polynucleotide, vector, host cell, or immunoconjugate) disclosed herein and a second therapy. In some embodiments, the second therapy is administered prior to the anti-MICA/B antibody. In some embodiments, the second therapy is administered after the anti-MICA/B antibody. In some embodiments, the second therapy is administered concurrently with the anti-MICA/B antibody. In certain embodiments, the anti-MICA/B antibody and the second therapy are administered separately. In other embodiments, the anti-MICA/B antibody and the second therapy are administered in a single formulation.

The second therapy can be any other therapy known in the art. In some embodiments, the second therapy comprises an immunotherapy. In some embodiments, the second therapy comprises a chemotherapy. In some embodiments, the second therapy comprises a radiotherapy. In some embodiments, the second therapy comprises a surgery. In some embodiments, the second therapy comprises administering a second therapeutic agent.

In certain embodiments, the second therapeutic agent comprises a second antibody. In some embodiments, the second therapeutic agent comprises an effective amount of an antibody that specifically binds a protein selected from Inducible T cell Co-Stimulator (ICOS), CD137 (4-IBB), CD134 (OX40), NKG2A, CD27, Glucocorticoid-Induced TNFR-Related protein (GITR), and Herpes Vims Entry Mediator (HVEM), Programmed Death-1 (PD-1), Programmed Death Ligand-1 (PD-L1), CTLA-4, B and T Lymphocyte Attenuator (BTLA), T cell Immunoglobulin and Mucin domain-3 (TIM-3), Lymphocyte Activation Gene-3 (LAG-3), adenosine A2a receptor (A2aR), Killer cell Lectin-like Receptor G1 (KLRG-1), Natural Killer Cell Receptor 2B4 (CD244), CD160, T cell Immunoreceptor with Ig and ITIM domains (TIGIT), and the receptor for V-domain Ig Suppressor of T cell Activation (VISTA), NKG2a, KIR, TGFβ, IL-10, IL-8, B7-H4, Fas ligand, CXCR4, mesothelin, CEACAM-1, CD96, CD52, HER2, and any combination thereof.

XI.A. Anti-PD-1 Antibodies

In some embodiments, the second antibody may be an anti-PD-1 antibody. Anti-PD-1 antibodies that are known in the art can be used in the presently described compositions and methods. Various human monoclonal antibodies that bind specifically to PD-1 with high affinity have been disclosed in U.S. Pat. No. 8,008,449. Anti-PD-1 human antibodies disclosed in U.S. Pat. No. 8,008,449 have been demonstrated to exhibit one or more of the following characteristics: (a) bind to human PD-1 with a $K_D$ of $1 \times 10^{-7}$ M or less, as determined by surface plasmon resonance using a BIACORE® biosensor system; (b) do not substantially bind to human CD28, CTLA-4 or ICOS; (c) increase T-cell proliferation in a Mixed Lymphocyte Reaction (MLR) assay; (d) increase interferon-y production in an MLR assay; (e) increase IL-2 secretion in an MLR assay; (f) bind to human PD-1 and cynomolgus monkey PD-1; (g) inhibit the binding of PD-L1 and/or PD-L2 to PD-1; (h) stimulate antigen-specific memory responses; (i) stimulate antibody responses; and (j) inhibit tumor cell growth in vivo. Anti-PD-1 antibodies usable in the present invention include monoclonal antibodies that bind specifically to human PD-1 and exhibit at least one, in some embodiments, at least five, of the preceding characteristics.

Other anti-PD-1 monoclonal antibodies have been described in, for example, U.S. Pat. Nos. 6,808,710, 7,488, 802, 8,168.757 and 8,354,509. US Publication No. 2016/ 0272708, and PCT Publication Nos. WO 2012/145493, WO 2008/156712, WO 2015/112900, WO 2012/145493, WO 2015/112800, WO 2014/206107, WO 2015/35606, WO 2015/085847, WO 2014/179664, WO 2017/020291, WO 2017/020858, WO 2016/197367, WO 2017/024515, WO 2017/025051, WO 2017/123557, WO 2016/106159, WO 2014/194302, WO 2017/040790, WO 2017/133540, WO 2017/132827, WO 2017/024465, WO 2017/025016, WO 2017/106061, WO 2017/19846, WO 2017/024465, WO 2017/025016, WO 2017/132825, and WO 2017/133540 each of which is incorporated by reference in its entirety.

In some embodiments, the anti-PD-1 antibody is selected from the group consisting of nivolumab (also known as OPDIVO®, 5C4, BMS-936558, MDX-1106, and ONO-4538), pembrolizumab (Merck; also known as KEYTRUDA®, lambrolizumab, and MK-3475; see WO2008/156712), PDR001 (Novartis; see WO 2015/112900), MEDI-0680 (AstraZeneca; also known as AMP-514; see WO 2012/145493), cemiplimab (Regeneron; also known as REGN-2810; see WO 2015/112800), JS001 (TAIZHOU JUNSHI PHARMA; see Si-Yang Liu et al., *J. Hematol. Oncol.* 10:136 (2017)), BGB-A317 (Beigene; see WO 2015/35606 and US 2015/0079109), INCSHR1210 (Jiangsu Hengrui Medicine; also known as SHR-1210; see WO 2015/085847; Si-Yang Liu et al., *J. Hematol. Oncol.* 10:136 (2017)), TSR-042 (Tesaro Biopharmaceutical; also known as ANB011; see WO2014/179664), GLS-010 (Wuxi/Harbin Gloria Pharmaceuticals; also known as WBP3055; see Si-Yang Liu et al., *J. Hematol. Oncol.* 10:136 (2017)), AM-0001 (Armo), STI-1110 (Sorrento Therapeutics; see WO 2014/194302), AGEN2034 (Agenus; see WO 2017/040790), MGA012 (Macrogenics, see WO 2017/19846), and IBI308 (Innovent; see WO 2017/024465, WO 2017/025016, WO 2017/132825, and WO 2017/133540).

In one embodiment, the anti-PD-1 antibody is nivolumab. Nivolumab is a fully human IgG4 (S228P) PD-1 immune checkpoint inhibitor antibody that selectively prevents interaction with PD-1 ligands (PD-L1 and PD-L2), thereby blocking the down-regulation of antitumor T-cell functions (U.S. Pat. No. 8,008,449; Wang et al., 2014 *Cancer Immunol Res.* 2(9):846-56).

In another embodiment, the anti-PD-1 antibody is pembrolizumab. Pembrolizumab is a humanized monoclonal IgG4 (S228P) antibody directed against human cell surface receptor PD-1 (programmed death-1 or programmed cell death-1). Pembrolizumab is described, for example, in U.S. Pat. Nos. 8,354,509 and 8,900,587.

Anti-PD-1 antibodies usable in the disclosed compositions and methods also include isolated antibodies that bind specifically to human PD-1 and cross-compete for binding to human PD-1 with any anti-PD-1 antibody disclosed herein, e.g., nivolumab (see, e.g., U.S. Pat. Nos. 8,008,449 and 8,779,105; WO 2013/173223). In some embodiments, the anti-PD-1 antibody binds the same epitope as any of the anti-PD-1 antibodies described herein, e.g., nivolumab. The ability of antibodies to cross-compete for binding to an antigen indicates that these monoclonal antibodies bind to the same epitope region of the antigen and sterically hinder the binding of other cross-competing antibodies to that particular epitope region. These cross-competing antibodies are expected to have functional properties very similar those of the reference antibody, e.g., nivolumab, by virtue of their binding to the same epitope region of PD-1. Cross-competing antibodies can be readily identified based on their ability to cross-compete with nivolumab in standard PD-1 binding assays such as BIACORE® analysis, ELISA assays or flow cytometry (see, e.g., WO 2013/173223).

In certain embodiments, the antibodies that cross-compete for binding to human PD-1 with, or bind to the same epitope region of human PD-1 antibody, nivolumab, are monoclonal antibodies. For administration to human subjects, these cross-competing antibodies are chimeric antibodies, engineered antibodies, or humanized or human antibodies. Such chimeric, engineered, humanized or human monoclonal antibodies can be prepared and isolated by methods well known in the art.

Anti-PD-1 antibodies usable in the compositions and methods of the disclosed invention also include antigen-binding portions of the above antibodies. It has been amply demonstrated that the antigen-binding function of an antibody can be performed by fragments of a full-length antibody.

Anti-PD-1 antibodies suitable for use in the disclosed compositions and methods are antibodies that bind to PD-1 with high specificity and affinity, block the binding of PD-L1 and or PD-L2, and inhibit the immunosuppressive effect of the PD-1 signaling pathway. In any of the compositions or methods disclosed herein, an anti-PD-1 "antibody" includes an antigen-binding portion or fragment that binds to the PD-1 receptor and exhibits the functional properties similar to those of whole antibodies in inhibiting ligand binding and up-regulating the immune system. In certain embodiments, the anti-PD-1 antibody or antigen-binding portion thereof cross-competes with nivolumab for binding to human PD-1.

XI.B. Anti-PD-L1 Antibodies

In some embodiments, the second antibody may be an anti-PD-L1 antibody. Anti-PD-L1 antibodies that are known in the art can be used in the compositions and methods of the present disclosure. Examples of anti-PD-L1 antibodies useful in the compositions and methods of the present disclosure include the antibodies disclosed in U.S. Pat. No.

9,580,507. Anti-PD-L1 human monoclonal antibodies disclosed in U.S. Pat. No. 9,580,507 have been demonstrated to exhibit one or more of the following characteristics: (a) bind to human PD-L1 with a $K_D$ of $1 \times 10^{-7}$ M or less, as determined by surface plasmon resonance using a BIA-CORE® biosensor system; (b) increase T-cell proliferation in a Mixed Lymphocyte Reaction (MLR) assay; (c) increase interferon-γ production in an MLR assay; (d) increase IL-2 secretion in an MLR assay; (e) stimulate antibody responses; and (f) reverse the effect of T regulatory cells on T cell effector cells and/or dendritic cells. Anti-PD-L1 antibodies usable in the present invention include monoclonal antibodies that bind specifically to human PD-L1 and exhibit at least one, in some embodiments, at least five, of the preceding characteristics.

In certain embodiments, the anti-PD-L1 antibody is selected from the group consisting of BMS-936559 (also known as 12A4, MDX-1105; see, e.g., U.S. Pat. No. 7,943,743 and WO 2013/173223), atezolizumab (Roche; also known as TECENTRIQ®; MPDL3280A, RG7446; see U.S. Pat. No. 8,217,149; see, also, Herbst et al. (2013) J Chin Oncol 31(suppl):3000), durvalumab (AstraZeneca; also known as IMFINZI™, MEDI-4736; see WO 2011/066389), avelumab (Pfizer; also known as BAVENCIO®, MSB-0010718C; see WO 2013/079174), STI-1014 (Sorrento; see WO2013/181634), CX-072 (Cytoma; see WO2016/149201), KN035 (3D Med/Alphamab; see Zhang et al., *Cell Discov.* 7:3 (March 2017), LY3300054 (Eli Lilly Co.; see, e.g., WO 2017/034916), and CK-301 (Checkpoint Therapeutics; see Gorelik et al., AACR:Abstract 4606 (April 2016)).

In certain embodiments, the PD-L1 antibody is atezolizumab (TECENTRIQ®). Atezolizumab is a fully humanized IgG1 monoclonal anti-PD-L1 antibody.

In certain embodiments, the PD-L1 antibody is durvalumab (IMFINZI™). Durvalumab is a human IgG1 kappa monoclonal anti-PD-L1 antibody.

In certain embodiments, the PD-L1 antibody is avelumab (BAVENCIO®). Avelumab is a human IgG1 lambda monoclonal anti-PD-L1 antibody.

In other embodiments, the anti-PD-L1 monoclonal antibody is selected from the group consisting of 28-8, 28-1, 28-12, 29-8, 5H1, and any combination thereof.

Anti-PD-L1 antibodies usable in the disclosed compositions and methods also include isolated antibodies that bind specifically to human PD-L1 and cross-compete for binding to human PD-L1 with any anti-PD-L1 antibody disclosed herein, e.g., atezolizumab durvalumab, and/or avelumab. In some embodiments, the anti-PD-L1 antibody binds the same epitope as any of the anti-PD-L1 antibodies described herein, e.g., atezolizumab, durvalumab, and/or avelumab. The ability of antibodies to cross-compete for binding to an antigen indicates that these antibodies bind to the same epitope region of the antigen and sterically hinder the binding of other cross-competing antibodies to that particular epitope region. These cross-competing antibodies are expected to have functional properties very similar those of the reference antibody, e.g., atezolizumab and/or avelumab, by virtue of their binding to the same epitope region of PD-L1. Cross-competing antibodies can be readily identified based on their ability to cross-compete with atezolizumab and/or avelumab in standard PD-L1 binding assays such as BIACORE® analysis, ELISA assays or flow cytometry (see, e.g., WO 2013/173223).

In certain embodiments, the antibodies that cross-compete for binding to human PD-L1 with, or bind to the same epitope region of human PD-L1 antibody as, atezolizumab, durvalumab, and/or avelumab, are monoclonal antibodies. For administration to human subjects, these cross-competing antibodies are chimeric antibodies, engineered antibodies, or humanized or human antibodies. Such chimeric, engineered, humanized or human monoclonal antibodies can be prepared and isolated by methods well known in the art.

Anti-PD-L1 antibodies usable in the compositions and methods of the disclosed invention also include antigen-binding portions of the above antibodies. It has been amply demonstrated that the antigen-binding function of an antibody can be performed by fragments of a full-length antibody.

Anti-PD-L1 antibodies suitable for use in the disclosed compositions and methods are antibodies that bind to PD-L1 with high specificity and affinity, block the binding of PD-1, and inhibit the immunosuppressive effect of the PD-1 signaling pathway. In any of the compositions or methods disclosed herein, an anti-PD-L1 "antibody" includes an antigen-binding portion or fragment that binds to PD-L1 and exhibits the functional properties similar to those of whole antibodies in inhibiting receptor binding and up-regulating the immune system. In certain embodiments, the anti-PD-L1 antibody or antigen-binding portion thereof cross-competes with atezolizumab, durvalumab, and/or avelumab for binding to human PD-L1.

XI.C. Anti-CTLA-4 Antibodies

In some embodiments, the second antibody may be an anti-CTLA-4 antibody. Anti-CTLA-4 antibodies that are known in the art can be used in the compositions and methods of the present disclosure. Anti-CTLA-4 antibodies of the instant invention bind to human CTLA-4 so as to disrupt the interaction of CTLA-4 with a human B7 receptor. Because the interaction of CTLA-4 with B7 transduces a signal leading to inactivation of T-cells bearing the CTLA-4 receptor, disruption of the interaction effectively induces, enhances or prolongs the activation of such T cells, thereby inducing, enhancing or prolonging an immune response.

Human monoclonal antibodies that bind specifically to CTLA-4 with high affinity have been disclosed in U.S. Pat. No. 6,984,720. Other anti-CTLA-4 monoclonal antibodies have been described in, for example, U.S. Pat. Nos. 5,977,318, 6,051,227, 6,682,736, and 7,034,121 and International Publication Nos. WO 2012/122444, WO 2007/113648, WO 2016/196237, and WO 2000/037504, each of which is incorporated by reference herein in its entirety. The anti-CTLA-4 human monoclonal antibodies disclosed in U.S. Pat. No. 6,984,720 have been demonstrated to exhibit one or more of the following characteristics: (a) binds specifically to human CTLA-4 with a binding affinity reflected by an equilibrium association constant ($K_a$) of at least about $10^7$ $M^{-1}$, or about $10^9$ $M^{-1}$, or about $10^{10}$ $M^{-1}$ to $10^{11}$ $M^{-1}$ or higher, as determined by BIACORE® analysis: (b) a kinetic association constant ($k_a$) of at least about $10^3$, about $10^4$, or about $10^5$ $m^{-1}$ $s^{-1}$; (c) a kinetic disassociation constant ($k_d$) of at least about $10^3$, about $10^4$, or about $10^5$ $m^{-1}$ $s^{-1}$; and (d) inhibits the binding of CTLA-4 to B7-1 (CD80) and B7-2 (CD86). Anti-CTLA-4 antibodies useful for the present invention include monoclonal antibodies that bind specifically to human CTLA-4 and exhibit at least one, at least two, or at least three of the preceding characteristics.

In certain embodiments, the CTLA-4 antibody is selected from the group consisting of ipilimumab (also known as YERVOY®, MDX-010, 10D1; see U.S. Pat. No. 6,984,720), MK-1308 (Merck), AGEN-1884 (Agenus Inc.; see WO 2016/196237), and tremelimumab (AstraZeneca; also known as ticilimumab, CP-675,206; see WO 2000/037504 and Ribas, *Update Cancer Ther.* 2(3): 133-39 (2007)). In particular embodiments, the anti-CTLA-4 antibody is ipilimumab.

In particular embodiments, the CTLA-4 antibody is ipilimumab for use in the compositions and methods disclosed herein. Ipilimumab is a fully human, IgG1 monoclonal antibody that blocks the binding of CTLA-4 to its B7 ligands, thereby stimulating T cell activation and improving overall survival (OS) in patients with advanced melanoma.

In particular embodiments, the CTLA-4 antibody is tremelimumab

In particular embodiments, the CTLA-4 antibody is MK-1308.

In particular embodiments, the CTLA-4 antibody is AGEN-1884.

In some embodiments, the CTLA-4 antibody is nonfucosylated or hypofucosylated. In some embodiments, the CTLA-4 antibody exhibits enhanced ADCC and/or ADCP activity. In some embodiments, the CTLA-4 antibody is BMS-986218, as described in PCT/US18/19868.

Anti-CTLA-4 antibodies usable in the disclosed compositions and methods also include isolated antibodies that bind specifically to human CTLA-4 and cross-compete for binding to human CTLA-4 with any anti-CTLA-4 antibody disclosed herein, e.g., ipilimumab and/or tremelimumab. In some embodiments, the anti-CTLA-4 antibody binds the same epitope as any of the anti-CTLA-4 antibodies described herein, e.g., ipilimumab and/or tremelimumab The ability of antibodies to cross-compete for binding to an antigen indicates that these antibodies bind to the same epitope region of the antigen and sterically hinder the binding of other cross-competing antibodies to that particular epitope region. These cross-competing antibodies are expected to have functional properties very similar those of the reference antibody, e g ipilimumab and/or tremelimumab, by virtue of their binding to the same epitope region of CTLA-4. Cross-competing antibodies can be readily identified based on their ability to cross-compete with ipilimumab and/or tremelimumab in standard CTLA-4 binding assays such as BIACORE® analysis, ELISA assays or flow cytometry (see, e.g., WO 2013/173223).

In certain embodiments, the antibodies that cross-compete for binding to human CTLA-4 with, or bind to the same epitope region of human CTLA-4 antibody as, ipilimumab and/or tremelimumab, are monoclonal antibodies. For administration to human subjects, these cross-competing antibodies are chimeric antibodies, engineered antibodies, or humanized or human antibodies. Such chimeric, engineered, humanized or human monoclonal antibodies can be prepared and isolated by methods well known in the art.

Anti-CTLA-4 antibodies usable in the compositions and methods of the disclosed invention also include antigen-binding portions of the above antibodies. It has been amply demonstrated that the antigen-binding function of an antibody can be performed by fragments of a full-length antibody.

Anti-CTLA-4 antibodies suitable for use in the disclosed methods or compositions are antibodies that bind to CTLA-4 with high specificity and affinity, block the activity of CTLA-4, and disrupt the interaction of CTLA-4 with a human B7 receptor. In any of the compositions or methods disclosed herein, an anti-CTLA-4 "antibody" includes an antigen-binding portion or fragment that binds to CTLA-4 and exhibits the functional properties similar to those of whole antibodies in inhibiting the interaction of CTLA-4 with a human B7 receptor and up-regulating the immune system. In certain embodiments, the anti-CTLA-4 antibody or antigen-binding portion thereof cross-competes with ipilimumab and/or tremelimumab for binding to human CTLA-4.

XI.D. Anti-LAG-3 Antibodies

In some embodiments, the second antibody may be an anti-LAG-3 antibody. Anti-LAG-3 antibodies of the instant disclosure bind to human LAG-3. Antibodies that bind to LAG-3 have been disclosed in Int'l Publ. No. WO/2015/042246 and U.S. Publ. Nos. 2014/0093511 and 2011/0150892.

An exemplary LAG-3 antibody useful in the present disclosure is 25F7 (described in U.S. Publ. No. 2011/0150892). An additional exemplary LAG-3 antibody useful in the present disclosure is BMS-986016. In one embodiment, an anti-LAG-3 antibody useful for the composition cross-competes with 25F7 or BMS-986016. In another embodiment, an anti-LAG-3 antibody useful for the composition binds to the same epitope as 25F7 or BMS-986016. In other embodiments, an anti-LAG-3 antibody comprises six CDRs of 25F7 or BMS-986016.

XI.E. Anti-CD137 Antibodies

In some embodiments, the second antibody may be an anti-CD137 antibody. Anti-CD137 antibodies specifically bind to and activate CD137-expressing immune cells, stimulating an immune response, in particular a cytotoxic T cell response, against tumor cells. Antibodies that bind to CD137 have been disclosed in U.S. Publ. No. 2005/0095244 and U.S. Pat. Nos. 7,288,638, 6,887,673, 7,214,493, 6,303,121, 6,569,997, 6,905,685, 6,355,476, 6,362,325, 6,974,863, and 6,210,669.

In some embodiments, the anti-CD137 antibody is urelumab (BMS-663513), described in U.S. Pat. No. 7,288,638 (20H4.9-IgG4 [10C7 or BMS-663513]). In some embodiments, the anti-CD137 antibody is BMS-663031 (20H4.9-IgG1), described in U.S. Pat. No. 7,288,638. In some embodiments, the anti-CD137 antibody is 4E9 or BMS-554271, described in U.S. Pat. No. 6,887,673. In some embodiments, the anti-CD137 antibody is an antibody disclosed in U.S. Pat. Nos. 7,214,493; 6,303,121; 6,569,997; 6,905,685; or 6,355,476. In some embodiments, the anti-CD137 antibody is 1D8 or BMS-469492; 3H3 or BMS-469497; or 3E1, described in U.S. Pat. No. 6,362,325. In some embodiments, the anti-CD137 antibody is an antibody disclosed in issued U.S. Pat. No. 6,974,863 (such as 53A2). In some embodiments, the anti-CD137 antibody is an antibody disclosed in issued U.S. Pat. No. 6,210,669 (such as 1D8, 3B8, or 3E1). In some embodiments, the antibody is Pfizer's PF-05082566 (PF-2566). In other embodiments, an anti-CD137 antibody useful for the invention cross-competes with the anti-CD137 antibodies disclosed herein. In some embodiments, an anti-CD137 antibody binds to the same epitope as the anti-CD137 antibody disclosed herein. In other embodiments, an anti-CD137 antibody useful in the disclosure comprises six CDRs of the anti-CD137 antibodies disclosed herein.

XI.F. Anti-KIR Antibodies

In some embodiments, the second antibody may be an anti-KIR3 antibody. Antibodies that bind specifically to KIR block the interaction between Killer-cell immunoglobulin-like receptors (KIR) on NK cells with their ligands. Blocking these receptors facilitates activation of NK cells and, potentially, destruction of tumor cells by the latter. Examples of anti-KIR antibodies have been disclosed in Intl Publ. Nos. WO/2014/055648, WO 2005/003168, WO 2005/009465, WO 2006/072625, WO 2006/072626, WO 2007/042573, WO 2008/084106, WO 2010/065939, WO 2012/071411 and WO/2012/160448.

One anti-KIR antibody useful in the present disclosure is lirilumab (also referred to as BMS-986015, IPH2102, or the S241P variant of 1-7F9), first described in Int'l Publ. No. WO 2008/084106. An additional anti-KIR antibody useful in the present disclosure is 1-7F9 (also referred to as IPH2101), described in Int'l Publ. No. WO 2006/003179. In one embodiment, an anti-KIR antibody for the present composition cross competes for binding to KIR with lirilumab or I-7F9. In another embodiment, an anti-KIR antibody binds to the same epitope as lirilumab or I-7F9. In other embodiments, an anti-KIR antibody comprises six CDRs of lirilumab or I-7F9.)

XI.G. Anti-GITR Antibodies

In some embodiments, the second antibody may be an anti-GITR antibody. Anti-GITR antibodies may be any anti-GITR antibody that binds specifically to human GITR target and activates the glucocorticoid-induced tumor necrosis factor receptor (GITR). GITR is a member of the TNF receptor superfamily that is expressed on the surface of multiple types of immune cells, including regulatory T cells, effector T cells, B cells, natural killer (NK) cells, and activated dendritic cells ("anti-GITR agonist antibodies"). Specifically, GITR activation increases the proliferation and function of effector T cells, as well as abrogating the suppression induced by activated T regulatory cells. In addition, GITR stimulation promotes anti-tumor immunity by increasing the activity of other immune cells such as NK cells, antigen presenting cells, and B cells. Examples of anti-GITR antibodies have been disclosed in Int'l Publ. Nos. WO/2015/031667, WO2015/184,099, WO2015/026,684, WO11/028683 and WO/2006/105021, U.S. Pat. Nos. 7,812,135 and 8,388,967 and U.S. Publ. Nos. 2009/0136494, 2014/0220002, 2013/0183321 and 2014/0348841.

In one embodiment, an anti-GITR antibody useful in the present disclosure is TRX518 (described in, for example, Schaer et al. *Curr Opin Immunol.* (2012) April; 24(2): 217-224, and WO/2006/105021). In another embodiment, the anti-GITR antibody is selected from MK4166, MK1248, and antibodies described in WO11/028683 and U.S. Pat. No. 8,709,424, and comprising, e.g., a VH chain comprising SEQ ID NO: 104 and a VL chain comprising SEQ ID NO: 105 (wherein the SEQ ID NOs are from WO11/028683 or U.S. Pat. No. 8,709,424). In certain embodiments, an anti-GITR antibody is an anti-GITR antibody that is disclosed in WO2015/031667, e.g., an antibody comprising VH CDRs 1-3 comprising SEQ ID NOs: 31, 71 and 63 of WO2015/031667, respectively, and VL CDRs 1-3 comprising SEQ ID NOs: 5, 14 and 30 of WO2015/031667. In certain embodiments, an anti-GITR antibody is an anti-GITR antibody that is disclosed in WO2015/184099, e.g., antibody Hum231 #1 or Hum231 #2, or the CDRs thereof, or a derivative thereof (e.g., pab1967, pab1975 or pab1979). In certain embodiments, an anti-GITR antibody is an anti-GITR antibody that is disclosed in JP2008278814, WO09/009116, WO2013/039954, US20140072566, US20140072565, US20140065152, or WO2015/026684, or is INBRX-110 (INHIBRx), LKZ-145 (Novartis), or MEDI-1873 (MedImmune). In certain embodiments, an anti-GITR antibody is an anti-GITR antibody that is described in PCT/US2015/033991 (e.g., an antibody comprising the variable regions of 28F3, 18E10 or 19D3). For example, an anti-GITR antibody may be an antibody comprising the following VH and VL chains or the CDRs thereof:

```
VH:
                                     (SEQ ID NO: 78)
QVQLVESGGGVVQPGRSLRLSCAASGFTFSSYGMHWVRQAPGKGLEWVAV
IWYEGSNKYYADSVKGRFTISRDNSKNTLYLQMNSLRAEDTAVYYCARGG
SMVRGDYYYGMDVWGQGTTVTVS,
and VL:
                                     (SEQ ID NO: 79)
AIQLTQSPSSLSASVGDRVTITCRASQGISSALAWYQQKPGKAPKLLIYD
ASSLESGVPSRFSGSGSGTDFTLTISSLQPEDFATYYCQQFNSYPYTFGQ
GTKLEIK;
or VH:
                                     (SEQ ID NO: 80)
QVQLVESGGGVVQPGRSLRLSCAASGFTFSSYGFHWVRQAPGKGLEWVAV
IWYAGSNKFYADSVKGRFTISRDNSKNTLYLQMNSLRAEDTAVYYCARGG
QLDYYYYVMDVWGQGTTVTVSS,
and VL:
                                     (SEQ ID NO: 81)
DIQMTQSPSSLSASVGDRVTITCRASQGISSWLAWYQQKPEKAPKSLIYA
ASSLQSGVPSRFSGSGSGTDFTLTISSLQPEDFATYYCQQYNSYPYTFGQ
GTKLEIK;
or VH:
                                     (SEQ ID NO: 82)
VQLVESGGGVVQPGRSLRLSCAASGFTFSSYGMHWVRQAPGKGLEWVAVI
WYAGSNKYYADSVKGRFTISRDNSKNTLYLQMNSLRAEDTAVYYCARGGR
IAVAFYYSMDVWGQGTTVTVSS,
and VL:
                                     (SEQ ID NO: 83)
DIQMTQSPSSLSASVGDRVTITCRASQGISSWLAWYQQKPEKAPKSLIYA
ASSLQSGVPSRFSGSGSGTDFTLTISSLQPEDFATYYCQQYNSYPYTFGQ
GTKLEIK.
```

In certain embodiments, an antibody comprising a pair of the above VH and VL light chains, or their CDRs, comprises a heavy chain constant region of an IgG1 isotype, either wild type or mutated, e.g., to be effectorless. In one embodiment, an anti-GITR antibody comprises the following heavy and light chains amino acid sequences:

```
heavy chain:
                                     (SEQ ID NO: 84)
QVQLVESGGGVVQPGRSLRLSCAASGFTFSSYGMHWVRQAPGKGLEWVAV

IWYEGSNKYYADSVKGRFTISRDNSKNTLYLQMNSLRAEDTAVYYCARGG

SMVRGDYYYGMDVWGQGTTVTVSSASTKGPSVFPLAPCSRSTSESTAALG

CLVKDYFPEPVTVSWNSGALTSGVHTFPAVLQSSGLYSLSSVVTVPSSNF

GTQTYTCNVDHKPSNTKVDKTVERKCCVECPPCPAPPVAGPSVFLFPPKP

KDTLMISRTPEVTCVVVDVSHEDPEVQFNWYVDGVEVHNAKTKPREEQFN

STFRVVSVLTVVHQDWLNGKEYKCKVSNKGLPAPIEKTISKTKGQPREPQ

VYTLPPSREEMTKNQVSLTCLVKGFYPSDIAVEWESNGQPENNYKTTPPM

LDSDGSFFLYSKLTVDKSRWQQGNVFSCSVMHEALHNHYTQKSLSLSPG,
and light chain:
                                     (SEQ ID NO: 85)
AIQLTQSPSSLSASVGDRVTITCRASQGISSALAWYQQKPGKAPKLLIYD

ASSLESGVPSRFSGSGSGTDFTLTISSLQPEDFATYYCQQFNSYPYTFGQ

GTKLEIKRTVAAPSVFIFPPSDEQLKSGTASVVCLLNNFYPREAKVQWKV

DNALQSGNSQESVTEQDSKDSTYSLSSTLTLSKADYEKHKVYACEVTHQG
```

-continued

```
LSSPVTKSFNRGEC,
or heavy chain:
                                        (SEQ ID NO: 86)
qvqlvesgggvvqpgrslrlscaasgftfssygmhwvrqapgkglewvav iwyegsnkyyadsvkgrftisrdnskntlylqmnslraedtavyycargg smvrgdyyygmdvwgqgttvtvssastkgpsvfplapssksts ggtaalg clvkdyfpepvtvswnsgaltsgyhtfpavlqssglyslssvvtvpsssl gtqtyicnvnhkpsntkvdkrvepkscdkthtcppcpapeaegapsvflf ppkpkdtlmisrtpevtcvwdvshedpevkfnwyvdgvevhnaktkpree qynstyrvvsyltvlhqdwhigkeykckvsnkalpssiektiskakgqpr epqvytlppsreemtknqvsltclvkgfypsdiavewesngqpennyktt ppvldsdgsfflyskltvdksrwqqgnvfscsvmhealhnhytqkslsls pg,
and light chain:
                                        (SEQ ID NO: 87)
AIQLTQSPSSLSASVGDRVTITCRASQGISSALAWYQQKPGKAPKLLIYD

ASSLESGVPSRFSGSGSGTDFTLTISSLQPEDFATYYCQQFNSYPYTFGQ

GTKLEIKRTVAAPSVFIFPPSDEQLKSGTASVVCLLNNFYPREAKVQWKV

DNALQSGNSQESVTEQDSKDSTYSLSSTLTLSKADYEKHKVYACEVTHQG

LSSPVTKSFNRGEC.
```

In certain embodiments, the anti-GITR antibody cross-competes with an anti-GITR antibody described herein, e.g., TRX518, MK4166 or an antibody comprising a VH domain and a VL domain amino acid sequence described herein. In some embodiments, the anti-GITR antibody binds the same epitope as that of an anti-GITR antibody described herein, e.g., TRX518, MK4166 or an antibody comprising a VH domain and a VL domain amino acid sequence described herein. In certain embodiments, the anti-GITR antibody comprises the six CDRs of TRX518, MK4166 or those of an antibody comprising a VH domain and a VL domain amino acid sequence described herein.

XI.H. Anti-TIM3 Antibodies

In some embodiments, the second antibody may be an anti-TIM3 antibody. In some embodiments, the anti-TIM3 antibody may be selected from the anti-TIM3 antibodies disclosed in Int'l Publ. Nos. WO2018013818, WO/2015/117002 (e.g., MGB453, Novartis), WO/2016/161270 (e.g., TSR-022, Tesaro/AnaptysBio), WO2011155607, WO2016/144803 (e.g., STI-600, Sorrento Therapeutics), WO2016/071448, WO17055399; WO17055404, WO17178493, WO18036561, WO18039020 (e.g., Ly-3221367, Eli Lilly), WO2017205721, WO17079112; WO17079115; WO17079116, WO11159877, WO13006490, WO2016068802 WO2016068803, WO2016/111947, WO/2017/031242.

XI.I Anti-OX40 Antibodies

In some embodiments, the second antibody may be an anti-OX40 (also known as CD134, TNFRSF4, ACT35 and/or TXGP1L) antibody. In some embodiments, the anti-OX40 antibody may be BMS-986178 (Bristol-Myers Squibb Company), described in Int'l Publ. No. WO20160196228. In some embodiments, the anti-OX40 antibody may be selected from the anti-OX40 antibodies described in Int'l Publ. Nos. WO95012673, WO199942585, WO14148895, WO15153513, WO15153514, WO13038191, WO16057667, WO03106498, WO12027328, WO13028231, WO16200836, WO 17063162, WO17134292, WO 17096179, WO 17096281, and WO 17096182.

XI.J. Anti-NKG2A Antibodies

In some embodiments, the second antibody may be an anti-NKG2A antibody. NKG2A is a member of the C-type lectin receptor family that is expressed on natural killer (NK) cells and a subset of T lymphocytes. Specifically, NKG2A primarily expressed on tumor infiltrating innate immune effector NK cells, as well as on some CD8+ T cells. Its natural ligand human leukocyte antigen E (HLA-E) is expressed on solid and hematologic tumors. NKG2A is an inhibitory receptor that blinds HLA-E.

In some embodiments, the anti-NKG2A antibody may be BMS-986315, a human monoclonal antibody that blocks the interaction of NKG2A to its ligand HLA-E, thus allowing activation of an anti-tumor immune response. In some embodiments, the anti-NKG2A antibody may be a checkpoint inhibitor that activates T cells, NK cells, and/or tumor-infiltrating immune cells. In some embodiments, the anti-NKG2A antibody may be selected from the anti-NKG2A antibodies described in, for example, WO 2006/070286 (Innate Pharma S.A.; University of Genova); U.S. Pat. No. 8,993,319 (Innate Pharma S.A.; University of Genova); WO 2007/042573 (Innate Pharma S/A; Novo Nordisk A/S; University of Genova); U.S. Pat. No. 9,447,185 (Innate Pharma S/A; Novo Nordisk A/S; University of Genova); WO 2008/009545 (Novo Nordisk A/S); U.S. Pat. Nos. 8,206,709; 8,901,283; 9,683,041 (Novo Nordisk A/S); WO 2009/092805 (Novo Nordisk A/S); U.S. Pat. Nos. 8,796,427 and 9,422,368 (Novo Nordisk A/S); WO 2016/134371 (Ohio State Innovation Foundation); WO 2016/032334 (Janssen); WO 2016/041947 (Innate); WO 2016/041945 (Academisch Ziekenhuis Leiden H.O.D.N. LUMC); WO 2016/041947 (Innate Pharma); and WO 2016/041945 (Innate Pharma).

XI.K. Anti-ICOS Antibodies

In some embodiments, the second antibody may be an anti-ICOS antibody. ICOS is an illumine checkpoint protein that is a member of the CD28-superfamily. ICOS is a 55-60 kDa type I transmembrane protein that is expressed on T cells after T cell activation and co-stimulates T-cell activation after binding its ligand, ICOS-L (B7H2). ICOS is also known as inducible T-cell co-stimulator, CVID1, AILIM, inducible costimulator, CD278, activation-inducible lymphocyte immunomediatory molecule, and CD278 antigen.

In some embodiments, the anti-ICOS antibody may be BMS-986226, a humanized IgG monoclonal antibody that binds to and stimulates human ICOS. In some embodiments, the anti-ICOS antibody may be selected from anti-ICOS antibodies described in, for example, WO 2016/154177 (Jounce Therapeutics, Inc.), WO 2008/137915 (MedImmune), WO 2012/131004 (INSERM, French National Institute of Health and Medical Research), EP3147297 (INSERM, French National Institute of Health and Medical Research), WO 2011/041613 (Memorial Sloan Kettering Cancer Center), EP 2482849 (Memorial Sloan Kettering Cancer Center), WO 1999/15553 (Robert Koch Institute), U.S. Pat. Nos. 7,259,247 and 7,722,872 (Robert Kotch Institute); WO 1998/038216 (Japan Tobacco Inc.), U.S. Pat. Nos. 7,045,615; 7,112,655, and 8,389,690 (Japan Tobacco Inc.), U.S. Pat. Nos. 9,738,718 and 9,771,424 (GlaxoSmithKline), and WO 2017/220988 (Kymab Limited).

XI.L. Anti-TIGIT Antibodies

In some embodiments, the second antibody may be an anti-TIGIT antibody. In some embodiments, the anti-TIGIT antibody may be BMS-986207. In some embodiments, the anti-TIGIT antibody may be done 22G2, as described in WO 2016/106302. In some embodiments, the anti-TIGIT antibody may be MTIG7192A/RG6058/RO7092284, or clone 4.1D3, as described in WO 2017/053748. In some embodiments, the anti-TIGIT antibody may be selected from the anti-TIGIT antibodies described in, for example, WO 2016/106302 (Bristol-Myers Squibb Company) and WO 2017/053748 (Genentech).

XI.M. Additional Anti-Cancer Agents

In some embodiments, the anti-MICA/B antibody may be used in combination with an anti-IL-10 antibody. In some embodiments, the anti-MICA/B antibody may be used in combination with a long-acting IL-10 molecule. In some embodiments, the long-acting IL-10 molecule may be an IL-10-Fc fusion molecule. In some embodiments, the long-acting IL-10 molecule may be a Pegylated IL-10, such as AM0010 (ARMO BioSciences).

In some embodiments, the anti-MICA/B antibody may be used in combination with an anti-IL-2 antibody. In some embodiments, the anti-MICA/B antibody may be used in combination with a long-acting IL-2 molecule. In some embodiments, the long-acting IL-2 may be a Pegylated IL-2, such as NKTR-214 (Nektar; see U.S. Pat. No. 8,252,275, WO12/065086 and WO15/125159).

In some embodiments, the anti-MICA/B antibody may be used in combination with an anti-VISTA antibody.

In some embodiments, the anti-MICA/B antibody may be used in combination with an anti-CD96 antibody.

In some embodiments, the anti-MICA/B antibody may be used in combination with an anti-IL-8 antibody, e.g., with HuMax®-IL8.

In some embodiments, the anti-MICA/B antibody may be used in combination with an anti-TGFβ antibody.

In some other embodiments, the anti-MICA/B antibody may be used in combination with an anti-B7-H4 antibody. In certain embodiments, the anti-B7-H4 antibody is an anti-B7-H4 disclosed in Intl Publ. No. WO/2009/073533.

In certain embodiments, the anti-MICA/B antibody may be used in combination with an anti-Fas ligand antibody. In certain embodiments, the anti-Fas ligand antibody is an anti-Fas ligand disclosed in Int'l Publ. No. WO/2009/073533.

In some embodiments, the anti-MICA/B antibody may be used in combination with an anti-CXCR4 antibody. In certain embodiments, the anti-CXCR4 antibody is an anti-CXCR4 disclosed in U.S. Publ. No. 2014/0322208 (e.g., Ulocuplumab (BMS-936564)).

In some embodiments, the anti-MICA/B antibody may be used in combination with an anti-mesothelin antibody. In certain embodiments, the anti-mesothelin antibody is an anti-mesothelin disclosed in U.S. Pat. No. 8,399,623.

In some embodiments, the anti-MICA/B antibody may be used in combination with an anti-HER2 antibody. In certain embodiments, the anti-HER2 antibody is HERCEPTIN® (U.S. Pat. No. 5,821,337), trastuzumab, or ado-trastuzumab emtansine (Kadcyla, e.g., WO/2001/000244).

In embodiments, the anti-MICA/B antibody may be used in combination with an anti-CD27 antibody. In embodiments, the anti-CD-27 antibody is Varlilumab (also known as "CDX-1127" and "1F5"), which is a human IgG1 antibody that is an agonist for human CD27 as disclosed in, for example, U.S. Pat. No. 9,169,325.

In some embodiments, the anti-MICA/B antibody may be used in combination with an anti-CD73 antibody. In certain embodiments, the anti-CD73 antibody is CD73.4.IgG2C219S.IgG1.1f.

In certain embodiments, the second therapy comprises administering a chemotherapeutic agent. In some embodiments, the chemotherapeutic agent induces MICA/B expression on tumor cells. In some embodiments, the chemotherapeutic agent is selected from a proteasome inhibitor, an immunomodulatory drug (IMiD), a Bet inhibitor, and any combination thereof. In some embodiments, the proteasome inhibitor is selected from bortezomib, ixazomib, carfilzomib, oprozomib and marizomib. In certain embodiments, the proteasome inhibitor comprises bortezomib.

In some embodiments, the second therapy comprises a radiotherapy. Any radiotherapy known in the art can be used as the second therapy.

In some embodiments, the second therapy comprises administering an agent that activates innate immune cells. In some embodiments, the agent that activates innate immune cells comprises an NLRP3 agonist. In some embodiments, the NLRP3 agonist comprises monosodium urate monohydrate (MSU) and/or the vaccine adjuvant alum. In some embodiments, the agent that activates innate immune cells is a toll like receptor 7 (TLR7) agonist. In some embodiments, the TLR7 agonist comprises imiquimod (R837), GS-9620 (see Tsai et al., J. Virology doi:10.1128/JVI.02166-16 (Feb. 8, 2017)), ORN R-2336 (Miltenyl Biotec), or any combination thereof.

In some embodiments, the second therapy comprises administering an agent that enhances the survival of natural killer (NK) cells, $CD8^+$ T cells, or both. In some embodiments, the agent comprises IL-2. In certain embodiments, the agent comprises pegylated IL-2.

In certain embodiments, the second therapy comprises administering an agent selected from the group consisting of doxorubicin (ADRIAMYCIN®), cisplatin, carboplatin, bleomycin sulfate, carmustine, chlorambucil (LEUKERAN®), cyclophosphamide (CYTOXAN®; NEOSAR®), lenalidomide (REVLIMID®), bortezomib (VELCADE®), dexamethasone, mitoxantrone, etoposide, cytarabine, bendamustine (TREANDA®), rituximab (RITUXAN®), ifosfamide, vincristine (ONCOVIN®), fludarabine (FLUDARA®), thalidomide (THALOMID®), alemtuzumab (CAMPATH®), ofatumumab (ARZERRA®), everolimus (AFINITOR®, ZORTRESS®), carfilzomib (KYPROLIS™), and any combination thereof.

XI.N. Cancer

Anti-MICA/B antibodies can enhance the immune response to cancerous cells in a patient having cancer. Provided herein are methods for treating a subject having cancer, comprising administering to the subject an anti-MICA/B antibody described herein, such that the subject is treated, e.g., such that growth of cancerous tumors is inhibited or reduced and/or that the tumors regress and/or that prolonged survival is achieved. An anti-MICA/B antibody can be used alone to inhibit the growth of cancerous tumors. Alternatively, an anti-MICA/B antibody can be used in conjunction with another agent, e.g., another immunogenic agent, a standard cancer treatment, or another antibody, as described below.

Accordingly, provided herein are methods of treating cancer, e.g., by inhibiting growth of tumor cells, in a subject, comprising administering to the subject a therapeutically effective amount of an anti-MICA/B antibody described herein, e.g., MICA.36, MICA.52, MICA.54, MICA.2, and 71C2 having a wild type IgG constant region or a constant region variant having altered effector function, or antigen-binding portion thereof. The antibody can be a human anti-MICA/B antibody (such as any of the human anti-human MICA/B antibodies described herein). Cancers whose growth can be inhibited using the antibodies of the disclosure include cancers typically responsive to immunotherapy and those that are not typically responsive to immunotherapy. Cancers that can be treated also include MICA/B positive cancers. Cancers can be cancers with solid tumors or hematolotical malignancies (liquid tumors). Non-limiting examples of cancers for treatment include squamous cell carcinoma, small-cell lung cancer, non-small cell lung cancer, squamous non-small cell lung cancer (NSCLC), non-squamous NSCLC, glioma, gastrointestinal cancer, renal cancer (e.g., clear cell carcinoma), ovarian cancer, liver cancer, colorectal cancer, endometrial cancer, kidney cancer (e.g., renal cell carcinoma (RCC)), prostate cancer (e.g., hormone refractory prostate adenocarcinoma), thyroid cancer, neuroblastoma, pancreatic cancer, glioblastoma (glioblastoma multiforme), cervical cancer, stomach cancer, bladder cancer, hepatoma, breast cancer, colon carcinoma, and head and neck cancer (or carcinoma), gastric cancer, germ cell tumor, pediatric sarcoma, sinonasal natural killer, melanoma (e.g., metastatic malignant melanoma, such as cutaneous or intraocular malignant melanoma), bone cancer, skin cancer, uterine cancer, cancer of the anal region, testicular cancer, carcinoma of the fallopian tubes, carcinoma of the endometrium, carcinoma of the cervix, carcinoma of the vagina, carcinoma of the vulva, cancer of the esophagus, cancer of the small intestine, cancer of the endocrine system, cancer of the parathyroid gland, cancer of the adrenal gland, sarcoma of soft tissue, cancer of the urethra, cancer of the penis, rectal cancer, solid tumors of childhood, cancer of the ureter, carcinoma of the renal pelvis, neoplasm of the central nervous system (CNS), primary CNS lymphoma, tumor angiogenesis, spinal axis tumor, brain cancer, brain stem glioma, pituitary adenoma, Kaposi's sarcoma, epidermoid cancer, squamous cell cancer, environmentally-induced cancers including those induced by asbestos, virus-related cancers or cancers of viral origin (e.g., human papilloma virus (HPV-related or -originating tumors)); and any combinations of said cancers.

Non-limiting examples of cancers for treatment include hematological malignancies derived from either of the two major blood cell lineages, i.e., the myeloid cell line (which produces granulocytes, erythrocytes, thrombocytes, macrophages and mast cells) or lymphoid cell line (which produces B, T, NK and plasma cells), such as all types of leukemias, lymphomas, and myelomas, e.g., acute, chronic, lymphocytic and/or myelogenous leukemias, such as acute leukemia (ALL), acute myelogenous leukemia (AML), chronic lymphocytic leukemia (CLL), and chronic myelogenous leukemia (CML), undifferentiated AML (MO), myeloblastic leukemia (M1), myeloblastic leukemia (M2; with cell maturation), promyelocytic leukemia (M3 or M3 variant [M3V]), myelomonocytic leukemia (M4 or M4 variant with eosinophilia [M4E]), monocytic leukemia (M5), erythroleukemia (M6), megakaryoblastic leukemia (M7), isolated granulocytic sarcoma, and chloroma; lymphomas, such as Hodgkin's lymphoma (HL), non-Hodgkin's lymphoma (NHL), B cell hematologic malignancy, e.g., B-cell lymphomas, T-cell lymphomas, lymphoplasmacytoid lymphoma, monocytoid B-cell lymphoma, mucosa-associated lymphoid tissue (MALT) lymphoma, anaplastic (e.g., Ki 1+) large-cell lymphoma, adult T-cell lymphoma/leukemia, mantle cell lymphoma, angio immunoblastic T-cell lymphoma, angiocentric lymphoma, intestinal T-cell lymphoma, primary mediastinal B-cell lymphoma, precursor T-lymphoblastic lymphoma, T-lymphoblastic; and lymphoma/leukaemia (T-Lbly/T-ALL), peripheral T-cell lymphoma, lymphoblastic lymphoma, post-transplantation lymphoproliferative disorder, true histiocytic lymphoma, primary central nervous system lymphoma, primary effusion lymphoma, B cell lymphoma, lymphoblastic lymphoma (LBL), hematopoictic tumors of lymphoid lineage, acute lymphoblastic leukemia, diffuse large B-cell lymphoma, Burkitt's lymphoma, follicular lymphoma, diffuse histiocytic lymphoma (DHL), immunoblastic large cell lymphoma, precursor B-lymphoblastic lymphoma, cutaneous T-cell lymphoma (CTLC) (also called mycosis fungoides or Sezary syndrome), and lymphoplasmacytoid lymphoma (LPL) with Waldenstrom's macroglobulinemia; myelomas, such as IgG myeloma, light chain myeloma, nonsecretory myeloma, smoldering myeloma (also called indolent myeloma), solitary plasmacytoma, and multiple myelomas, chronic lymphocytic leukemia (CLL), hairy cell lymphoma; hematopoietic tumors of myeloid lineage, tumors of mesenchymal origin, including fibrosarcoma and rhabdomyoscarcoma; seminoma, teratocarcinoma, tumors of the central and peripheral nervous, including astrocytoma, schwannomas; tumors of mesenchymal origin, including fibrosarcoma, rhabdomyoscaroma, and osteosarcoma; and other tumors, including melanoma, xeroderma pigmentosum, keratoacanthoma, seminoma, thyroid follicular cancer and teratocarcinoma, hematopoietic tumors of lymphoid lineage, for example T-cell and B-cell tumors, including but not limited to T-cell disorders such as T-prolymphocytic leukemia (T-PLL), including of the small cell and cerebriform cell type; large granular lymphocyte leukemia (LGL) of the T-cell type; a/d T-NHL hepatosplenic lymphoma; peripheral/post-thymic T cell lymphoma (pleomorphic and immunoblastic subtypes); angiocentric (nasal) T-cell lymphoma; and any combinations of said cancers.

The methods described herein can also be used for treatment of metastatic cancers, unresectable, refractory cancers (e.g., cancers refractory to previous immunotherapy, e.g., with a blocking CTLA-4 or PD-1 antibody), and/or recurrent cancers.

In some embodiments, the subject has a cancer selected from non-small cell lung cancer (NSCLC), head and neck squamous cell carcinoma (HNSCC), melanoma, bladder cancer, pancreatic cancer, gastric cancer, colon cancer, renal cell carcinoma (RCC), small-cell lung cancer (SCLC), mesothelioma, hepatocellular carcinoma, prostate cancer, multiple myeloma, and combinations of said cancers.

In some embodiments, the subject has a cancer selected from non-small cell lung cancer (NSCLC), head and neck squamous cell carcinoma (HNSCC), melanoma, bladder cancer, pancreatic cancer, gastric cancer, colon cancer, and combinations of said cancers.

In some embodiments, an anti-MICA/B antibody is administered to patients having a cancer that exhibited an inadequate response to, or progressed on, a prior treatment, e.g., a prior treatment with an immuno-oncology or immunotherapy drug, or patients having a cancer that is refractory or resistant, either intrinsically refractory or resistant (e.g., refractory to a PD-1 pathway antagonist), or a wherein the resistance or refractory state is acquired. For example, subjects who are not responsive or not sufficiently responsive to a first therapy or who see disease progression following treatment, e.g., anti-PD-1 treatment, can be treated by administration of an anti-MICA/B antibody alone or in combination with another therapy (e.g., with an anti-PD-1 therapy).

In some embodiments, an anti-MICA/B antibody is administered to patients who have not previously received (i.e., been treated with) an immuno-oncology agent, e.g., a PD-1 pathway antagonist.

In some embodiments, a method of treating cancer in a subject comprises first determining whether the subject is MICA/B positive, e.g., has tumor cells that express MICA/B, and if the subject has MICA/B positive cancer, then administering to the subject an anti-MICA/B antibody, e.g., described herein. A method of treating a subject having cancer with an anti-MICA/B antibody may comprise administering to a subject who has cancer cells that express MICA/B, a therapeutically effective amount of a MICA/B antibody. Also provided herein are methods for predicting whether a subject will respond to treatment with an anti-MICA/B antibody, wherein the methods comprise determining the level of MICA/B in cancer cells of the patient, and if cancer cells of the subject are MICA/B positive, then the subject is likely to respond to a treatment with a MICA/B antibody.

In some embodiments, a method of treating cancer in a subject comprises first determining whether the subject is PD-L1 or PD-1 positive, e.g., has tumor cells or TILs that express PD-L1 or PD-1, and if the subject has PD-L1 or PD-1 positive cancer or TIL cells, then administering to the subject an anti-MICA/B antibody (and optionally a PD-1 or PD-L1 antagonist), e.g., described herein. A method of treating a subject having cancer with an anti-MICA/B antibody (and optionally a PD-1 or PD-L1 antagonist) may comprise administering to a subject who has cancer cells or TIL cells that express PD-L1 or PD-1, a therapeutically effective amount of an anti-MICA/B antibody (and optionally a PD-1 or PD-L1 antagonist). Also provided herein are methods for predicting whether a subject will respond to treatment with an anti-MICA/B antibody (and optionally a PD-1 or PD-L1 antagonist), wherein the methods comprise determining the level of PD-L1 or PD-1 in cancer or TIL cells of the patient, and if cancer or TIL cells of the subject are PD-L1 or PD-1 positive, then the subject is likely to respond to a treatment with a MICA antibody (and optionally a PD-1 or PD-L1 antagonist).

An anti-MICA/B antibody can be administered with a standard of care treatment. An anti-MICA/B antibody can be administered as a maintenance therapy, e.g., a therapy that is intended to prevent the occurrence or recurrence of tumors.

An anti-MICA/B antibody can be administered with another treatment, e.g., radiation, surgery, or chemotherapy. For example, anti-MICA/B antibody adjunctive therapy can be administered when there is a risk that micrometastases can be present and/or in order to reduce the risk of a relapse.

An anti-MICA/B antibody can be administered as a monotherapy, or as the only immuno stimulating therapy. Antibodies to MICA/B, e.g., the anti-MICA/B, can also be combined with an immunogenic agent, such as cancerous cells, purified tumor antigens (including recombinant proteins, peptides, and carbohydrate molecules), cells, and cells transfected with genes encoding immune stimulating cytokines (He et al., (2004) *J. Immunol.* 173:4919-28). Non-limiting examples of tumor vaccines that can be used include peptides of melanoma antigens, such as peptides of gp100, MAGE antigens, Trp-2, MART1 and/or tyrosinase, or tumor cells transfected to express the cytokine GM-CSF (discussed further below).

In humans, some tumors have been shown to be immunogenic such as melanomas. By lowering the threshold of T cell activation by reducing the level of soluble MICA/B in plasma, the tumor responses in the host can be activated, allowing treatment of non-immunogenic tumors or those having limited immunogenicity.

An anti-MICA/B antibody, e.g., an anti-MICA/B antibody described herein, can be combined with a vaccination protocol. Many experimental strategies for vaccination against tumors have been devised (see Rosenberg, S., 2000, Development of Cancer Vaccines, ASCO Educational Book Spring: 60-62; Logothetis, C, 2000, ASCO Educational Book Spring: 300-302; Khayat, D. 2000, ASCO Educational Book Spring: 414-428; Foon, K. 2000, ASCO Educational Book Spring: 730-738; see also Rcstifo, N. and Sznol, M., Cancer Vaccines, Ch. 61, pp. 3023-3043 in DeVita et al. (eds.), 1997, Cancer: Principles and Practice of Oncology, Fifth Edition). In one of these strategies, a vaccine is prepared using autologous or allogeneic tumor cells. These cellular vaccines have been shown to be most effective when the tumor cells are transduced to express GM-CSF. GM-CSF has been shown to be a potent activator of antigen presentation for tumor vaccination (Dranoff et al. (1993) *Proc. Natl. Acad. Sci U.S.A.* 90: 3539-43).

The study of gene expression and large scale gene expression patterns in various tumors has led to the definition of so called tumor specific antigens (Rosenberg, S A (1999) *Immunity* 10: 281-7). In many cases, these tumor specific antigens are differentiation antigens expressed in the tumors and in the cell from which the tumor arose, for example melanocyte antigens gp100, MAGE antigens, and Trp-2. More importantly, many of these antigens can be shown to be the targets of tumor specific T cells found in the host. Anti-MICA/B antibody treatment can be used in conjunction with a collection of recombinant proteins and/or peptides expressed in a tumor in order to generate an immune response to these proteins. These proteins are normally viewed by the immune system as self-antigens and are therefore tolerant to them. The tumor antigen can include the protein telomerase, which is required for the synthesis of telomeres of chromosomes and which is expressed in more than 85% of human cancers and in only a limited number of somatic tissues (Kim et al. (1994) Science 266: 2011-2013). Tumor antigen can also be "nco-antigcns" expressed in cancer cells because of somatic mutations that alter protein sequence or create fusion proteins between two unrelated sequences (i.e., bcr-abl in the Philadelphia chromosome), or idiotype from B cell tumors.

Other tumor vaccines can include the proteins from viruses implicated in human cancers such a Human Papilloma Viruses (HPV), Hepatitis Viruses (HBV and HCV) and Kaposi's Herpes Sarcoma. Virus (KHSV). Another form of tumor specific antigen, which can be used in conjunction with administration of an anti-MICA/B antibody, is purified heat shock proteins (HSP) isolated from the tumor tissue itself. These heat shock proteins contain fragments of proteins from the tumor cells and these HSPs are highly efficient at delivery to antigen presenting cells for eliciting tumor immunity (Suot & Srivastava (1995) *Science* 269: 1585-1588; Tamura et al. (1997) *Science* 278: 117-120).

Dendritic cells (DC) are potent antigen presenting cells that can be used to prime antigen-specific responses. DCs can be produced ex vivo and loaded with various protein and peptide antigens as well as tumor cell extracts (Nestle et al. (1998) *Nature Medicine* 4: 328-332). DCs can also be transduced by genetic means to express these tumor antigens as well. DCs have also been fused directly to tumor cells for the purposes of immunization (Kugler et al. (2000) *Nature Medicine* 6:332-336). As a method of vaccination, DC immunization can be effectively combined with administration of an anti-MICA/B antibody to activate more potent anti-tumor responses.

Administration of an anti-MICA/B antibody can also be combined with standard cancer treatments (e.g., surgery, radiation, and chemotherapy) Administration of an anti-MICA/B antibody can be effectively combined with chemotherapeutic regimes. In these instances, it can be possible to reduce the dose of chemotherapeutic reagent administered (Mokyr et al. (1998) *Cancer Research* 58: 5301-5304). An example of such a combination is an anti-MICA/B antibody in combination with decarbazine for the treatment of melanoma. Another example of such a combination is an anti-MICA/B antibody in combination with interleukin-2 (IL-2), e.g. pegyalated IL-2, for the treatment of melanoma. The scientific rationale behind the combined use of an anti-MICA/B antibody and chemotherapy is that cell death, that is a consequence of the cytotoxic action of most chemotherapeutic compounds, should result in increased levels of tumor antigen in the antigen presentation pathway. Other combination therapies that can result in synergy with administration of an anti-MICA/B antibody through cell death are radiation, surgery, and hormone deprivation. Each of these protocols creates a source of tumor antigen in the host. Angiogenesis inhibitors can also be combined with administration of an anti-MICA/B antibody. Inhibition of angiogenesis leads to tumor cell death which can feed tumor antigen into host antigen presentation pathways.

The anti-MICA/B antibodies described herein call also be used in combination with bispecific antibodies that target Fcα or Fcγ receptor-expressing effectors cells to tumor cells (see, e.g., U.S. Pat. Nos. 5,922,845 and 5,837,243). Bispecific antibodies can be used to target two separate antigens. For example anti-Fc receptor/anti-tumor antigen (e.g., Her-2/neu) bispecific antibodies have been used to target macrophages to sites of tumor. This targeting can more effectively activate tumor specific responses. The T cell arm of these responses would be augmented by the action of the anti-MICA/B antibody. Alternatively, antigen can be delivered directly to DCs by the use of bispecific antibodies which bind to tumor antigen and a dendritic cell specific cell surface marker.

Tumors evade host immune surveillance by a large variety of mechanisms. Many of these mechanisms can be overcome by the inactivation of proteins which are expressed by the tumors and which are immunosuppressive. These include among others TGF-β (Kehrl et al. (1986) *J. Exp. Med.* 163: 1037-1050), IL-10 (Howard & O'Garra (1992) *Immunology Today* 13: 198-200), and Fas ligand (Halme et al. (1996) *Science* 274: 1363-1365). Antibodies to each of these entities can be used in combination with anti-MICA/B antibodies to counteract the effects of the immunosuppressive agent and favor tumor immune responses by the host.

Other antibodies which activate host immune responsiveness can be used in combination with anti-MICA/B antibodies. These include molecules on the surface of dendritic cells which activate DC function and antigen presentation. Anti-CD40 antibodies are able to substitute effectively for T cell helper activity (Ridge et al. (1998) *Nature* 393: 474-478) and can be used in conjunction with anti-MICA/B antibodies. Activating antibodies to T cell costimulatory molecules such as CTLA-4 (e.g., U.S. Pat. No. 5,811,097), OX-40 (Weinberg et al. (2000) *Immunol* 164: 2160-2169), 4-IBB (Melero et at (1997) *Nature Medicine* 3: 682-685 (1997), and ICOS (Hutloff et al. (1999) *Nature* 397: 262-266) can also provide for increased levels of T cell activation. Inhibitors of PD1 or PD-L1 can also be used in conjunction with an anti-MICA/B antibody. Other combination are provided elsewhere herein.

Bone marrow transplantation is currently being used to treat a variety of tumors of hematopoietic origin. While graft versus host disease is a consequence of this treatment, therapeutic benefit can be obtained from graft vs. tumor responses. MICA/B inhibition can be used to increase the effectiveness of the donor engrafted tumor specific T cells.

There are also several experimental treatment protocols that involve ex vivo activation and expansion of antigen specific T cells and adoptive transfer of these cells into recipients in order to stimulate antigen-specific T cells against tumor (Greenberg & Riddell (1999) *Science* 285: 546-51). These methods can also be used to activate T cell responses to infectious agents such as CMV. Ex vivo activation in the presence of anti-MICA/B antibodies can increase the frequency and activity of the adoptively transferred T cells.

XI.O. Infectious Diseases

Methods described herein can also be used to treat patients that have been exposed to particular toxins or pathogens. Accordingly, another aspect described herein provides a method of treating an infectious disease in a subject comprising administering to the subject an anti-MICA/B antibody such that the subject is treated for the infectious disease.

Similar to its application to tumors as discussed above, anti-MICA/B antibodies can be administered alone, or as an adjuvant, in combination with vaccines, to stimulate the immune response to pathogens, toxins, and self-antigens. Examples of pathogens for which this therapeutic approach can be particularly useful, include pathogens for which there is currently no effective vaccine, or pathogens for which conventional vaccines are less than completely effective. These include, but are not limited to HIV, Hepatitis (A, B, & C), Influenza, Herpes, Giardia, Malaria, Leishmania, Staphylococcus aureus, Pseudomonas aeruginosa. Anti-MICA/B antibodies can be useful against established infections by agents such as HIV that present altered antigens over the course of the infections. These novel epitopes are recognized as foreign at the time of anti-human MICA/B antibody administration, thus provoking a strong T cell response.

XI.P Combination Therapies

In addition to the combinations therapies provided above, anti-MICA/B antibodies, e.g., those described herein, can also be used in combination therapy, e.g., for treating cancer, as described below.

Provided herein are methods of combination therapy in which an anti-MICA/B antibody is coadministered with one or more additional agents, e.g., small molecule drugs, antibodies or antigen binding portions thereof, that are effective in stimulating immune responses to thereby further enhance, stimulate or upregulate immune responses in a subject.

Generally, an anti-MICA/B antibody, e.g., described herein, can be combined with (i) an agonist of a stimulatory (e.g., co-stimulatory) molecule (e.g., receptor or ligand) and/or (ii) an antagonist of an inhibitory signal or molecule (e.g., receptor or ligand) on immune cells, such as T cells, both of which result in amplifying immune responses, such as antigen-specific T cell responses. In some aspects, an immuno-oncology agent is (i) an agonist of a stimulatory (including a co-stimulatory) molecule (e.g., receptor or ligand) or (ii) an antagonist of an inhibitory (including a co-inhibitory) molecule (e.g., receptor or ligand) on cells, e.g., those inhibiting T cell activation or those involved in innate immunity, e.g., NK cells, and wherein the immuno-oncology agent enhances innate immunity Such immuno-oncology agents are often referred to as immune checkpoint regulators, e.g., immune checkpoint inhibitor or immune checkpoint stimulator.

In some embodiments, an anti-MICA/B antibody is administered with an agent that targets a stimulatory or inhibitory molecule that is a member of the immunoglobulin super family (IgSF). For example, anti-MICA/B antibodies, e.g., described herein, can be administered to a subject with an agent that targets a member of the IgSF family to increase an immune response. For example, an anti-MICA/B antibody can be administered with an agent that targets (or binds specifically to) a member of the B7 family of membrane-bound ligands that includes B7-1, B7-2, B7-H1 (PD-L1), B7-DC (PD-L2), B7-H2 (1COS-L), B7-H3, B7-H4, B7-H5 (VISTA), and B7-H6 or a co-stimulatory or co-inhibitory receptor or ligand binding specifically to a B7 family member.

An anti-MICA/B antibody can also be administered with an agent that targets a member of the TNF and TNFR family of molecules (ligands or receptors), such as CD40 and CD40L, OX-40, OX-40L, CD70, CD27L, CD30, CD30L, 4-1BBL, CD137, TRAIL/Apo2-L, TRAILR1/DR4, TRAILR2/DR5, TRAILR3, TRAILR4, OPG, RANK, RANKL, TWEAKR/Fn 14, TWEAK, BAFFR, EDAR, XEDAR, TACI, APRIL, BCMA, LTpR, LIGHT, DcR3, HVEM, VEGI/TL1A, TRAMP/DR3, EDA1, EDA2, TNFR1, Lymphotoxin a/TNFp, TNFR2, TNFa, LTpR, Lymphotoxin a FAS, FASL, RELT, DR6, TROY, and NGFR (see, e.g., Tansey (2009) *Drug Discovery Today* 00: 1).

T cell responses can be stimulated by a combination of anti-MICA/B antibodies having the variable regions of, e.g., MICA.36, MICA.52, MICA.54, MICA.2, and 71C2, and one or more of the following agents:

(1) An antagonist (inhibitor or blocking agent) of a protein that inhibits T cell activation (e.g., immune checkpoint inhibitors), such as CTLA-4, PD-1, PD-L1, PD-L2, GITR, and LAG-3, Galectin 9, CEACAM-1, BTLA, CD69, Galectin-1, TIG1T, CD113, GPR56, VISTA, B7-H3, B7-H4, 2B4, CD48, GARP, PD1H, LA1R1, TIM-1, TIM-3, and TIM-4; and/or (2) An agonist of a protein that stimulates T cell activation, such as B7-1, B7-2, CD28, 4-1BB (CD137), 4-1BBL, GITR, ICOS, ICOS-L, OX40, OX40L, CD70, CD27, CD40, DR3 and CD28H.

Exemplary agents that modulate one of the above proteins and can be combined with anti-MICA/B antibodies, e.g., those described herein, for treating cancer, include: YER-VOY® (ipilimumab) or Tremelimumab (to CTLA-4), galiximab (to B7.1), BMS-936558 (to PD-1), MK-34'75 (to PD-1), atezolizumab (TECENTRIQ®), AMP224 (to B7DC), BMS-936559 (to B7-H1), MPDL3280A (to B7-H1), MEDI-570 (to ICOS), AMG557 (to B7H2), MGA271 (to B7H3), IMP321 (to LAG-3), BMS-663513 (to CD137), PF-05082566 (to CD137), CDX-1127 (to CD27), anti-OX40 (Providence Health Services), huMAbOX40L (to OX40L), Atacicept (to TACI), CP-870893 (to CD40), Lucatumumab (to CD40), Dacetuzumab (to CD40), Muromonab-CD3 (to CD3); anti-GITR antibodies MK4166, TRX518, Medi1873, INBRX-110, LK2-145, GWN-323, GITRL-Fc, or any combination thereof.

Other molecules that can be combined with anti-MICA/B antibodies for the treatment of cancer include antagonists of inhibitory receptors on NK cells or agonists of activating receptors on NK cells. For example, anti-MICA/B antibodies can be combined with antagonists of KIR (e.g., lirilumab).

T cell activation is also regulated by soluble cytokines, and anti-MICA/B antibodies can be administered to a subject, e.g., having cancer, with antagonists of cytokines that inhibit T cell activation or agonists of cytokines that stimulate T cell activation.

In some embodiments, anti-MICA/B antibodies can be used in combination with (i) antagonists (or inhibitors or blocking agents) of proteins of the IgSF family or B7 family or the TNF family that inhibit T cell activation or antagonists of cytokines that inhibit T cell activation (e.g., IL-6, IL-10, TGF-β, VEGF; "immunosuppressive cytokines") and/or (ii) agonists of stimulatory receptors of the IgSF family, B7 family or the TNF family or of cytokines that stimulate T cell activation, for stimulating an immune response, e.g., for treating proliferative diseases, such as cancer.

Yet other agents for combination therapies include agents that inhibit or deplete macrophages or monocytes, including but not limited to CSF-1R antagonists such as CSF-1R antagonist antibodies including RG7155 (WO11/70024, WO11/107553, WO11/131407, WO13/87699, WO13/119716, WO13/132044) or FPA-008 (WO11/140249; WO13169264; WO14/036357).

Anti-MICA/B antibodies can also be administered with agents that inhibit TGF-β signaling.

Additional agents that can be combined with an anti-MICA/B antibody include agents that enhance tumor antigen presentation, e.g., dendritic cell vaccines, GM-CSF secreting cellular vaccines, CpG oligonucleotides, and imiquimod, or therapies that enhance the immunogenicity of tumor cells (e.g., anthracyclines).

Yet other therapies that can be combined with an anti-MICA/B antibody include therapies that deplete or block Treg cells, e.g., an agent that specifically binds to CD25.

Another therapy that can be combined with an anti-MICA/B antibody is a therapy that inhibits a metabolic enzyme such as indoleamine dioxigenase (IDO), dioxigenase, arginase, or nitric oxide synthetase. Suitable IDO antagonists include, for example, INCB-024360 (WO2006/122150, WO07/75598, WO08/36653, WO08/36642), indoximod, NLG-919 (WO09/73620, WO09/1156652, WO11/56652, WO12/142237) or F001287.

Another class of agents that can be used with an anti-MICA/B antibody includes agents that inhibit the formation of adenosine, e.g., CD73 inhibitors, or inhibit the adenosine A2A receptor.

Other therapies that can be combined with an anti-MICA/B antibody for treating cancer include therapies that reverse/prevent T cell anergy or exhaustion and therapies that trigger an innate immune activation and/or inflammation at a tumor site.

An anti-MICA/B antibody can be combined with more than one immuno-oncology agent, and can be, e.g., combined with a combinatorial approach that targets multiple elements of the immune pathway, such as one or more of the following: a therapy that enhances tumor antigen presentation (e.g., dendritic cell vaccine, GM-CSF secreting cellular vaccines, CpG oligonucleotides, imiquimod); a therapy that inhibits negative immune regulation e.g., by inhibiting CTLA-4 and/or PD1/PD-L1/PD-L2 pathway and/or depleting or blocking Tregs or other immune suppressing cells; a therapy that stimulates positive immune regulation, e.g., with agonists that stimulate the CD-137, OX-40, and/or CD40 or GITR pathway and/or stimulate T cell effector function; a therapy that increases systemically the frequency of anti-tumor T cells; a therapy that depletes or inhibits Tregs, such as Tregs in the tumor, e.g., using an antagonist of CD25 (e.g., daclizumab) or by ex vivo anti-CD25 bead depletion; a therapy that impacts the function of suppressor myeloid cells in the tumor; a therapy that enhances immunogenicity of tumor cells (e.g., anthracyclines); adoptive T cell or NK cell transfer including genetically modified cells, e.g., cells modified by chimeric antigen receptors (CAR-T therapy); a therapy that inhibits a metabolic enzyme such as indoleamine dioxigenase (IDO), dioxigenase, arginase, or nitric oxide synthetase; a therapy that reverses/prevents T cell anergy or exhaustion; a therapy that triggers an innate immune activation and/or inflammation at a tumor site; administration of immune stimulatory cytokines; or blocking of immuno repressive cytokines.

Anti-MICA/B antibodies described herein can be used together with one or more of agonistic agents that ligate positive costimulatory receptors, blocking agents that attenuate signaling through inhibitory receptors; antagonists, and one or more agents that increase systemically the frequency of anti-tumor T cells, agents that overcome distinct immune suppressive pathways within the tumor microenvironment (e.g., block inhibitory receptor engagement (e.g., PD-L1/PD-1 interactions), deplete or inhibit Tregs (e.g., using an anti-CD25 monoclonal antibody (e.g., daclizumab) or by ex vivo anti-CD25 bead depletion), inhibit metabolic enzymes such as IDO, or reverse/prevent T cell anergy or exhaustion) and agents that trigger innate immune activation and/or inflammation at tumor sites.

In some embodiments, an anti-MICA/B antibody is administered to a subject together with a BRAF inhibitor if the subject is BRAF V600 mutation positive.

In some embodiments, the anti-MICA/B antibody is administered to a subject together with an antibody that specifically binds PD-1, PD-L1, CTLA-4, LAG3, TIGIT, TIM3, NKG2a, OX40, ICOS, CD137, KIR, TGFβ, IL-10, IL-8, IL-2, B7-H4, Fas ligand, CXCR4, mesothelin, CD27, VISTA, CD96, GITR or any combination thereof.

The anti-MICA/B antibodies and combination therapies described herein can also be used in conjunction with other well-known therapies that are selected for their particular usefulness against the indication being treated (e.g., cancer). Combinations of the anti-MICA/B antibodies described herein can be used sequentially with known pharmaceutically acceptable agent(s).

For example, the anti-MICA/B antibodies and combination therapies described herein can be used in combination (e.g., simultaneously or separately) with an additional treatment, such as irradiation and/or chemotherapy, e.g., using camptothecin (CPT-11), 5-fluorouracil (5-FU), cisplatin, doxorubicin, irinotecan, paclitaxel, gemcitabine, cisplatin, paclitaxel, carboplatin-paclitaxel (Taxol), doxombicin, or camptothecin+apo21/TRAIL (a 6× combo)), one or more proteasome inhibitors (e.g., bortezomib or MG132), one or more Bcl-2 inhibitors (e.g., BH3I-2' (bcl-xl inhibitor), indoleamine dioxygenase-1 inhibitor (e.g., INCB24360, indoximod, NLG-919, or F001287), AT-101 (R-(−)-gossypol derivative), ABT-263 (small molecule), GX-15-070 (obatoclax), or MCL-1 (myeloid leukemia cell differentiation protein-1) antagonists), iAP (inhibitor of apoptosis protein) antagonists (e.g., smac7, smac4, small molecule smac mimetic, synthetic smac peptides (see Fulda et al., *Nat Med* 2002; 8:808-15), ISIS23722 (LY2181308), or AEG-35156 (GEM-640)), HDAC (histone deacetylase) inhibitors, anti-CD20 antibodies (e.g., rituximab), angiogenesis inhibitors (e.g., bevacizumab), anti-angiogenic agents targeting VEGF and VEGFR (e.g., Avastin), synthetic triterpenoids (see Hyer et al, *Cancer Research* 2005; 65:4799-808), c-FLIP (cellular FLICE-inhibitory protein) modulators (e.g., natural and synthetic ligands of PPARy (peroxisome proliferator-activated receptor γ), 5809354 or 5569100), kinase inhibitors (e.g., Sorafenib), Trastuzumab, Cetuximab, Temsirolimus, mTOR inhibitors such as rapamycin and temsirolimus, Bortezomib, JAK2 inhibitors, HSP90 inhibitors, PI3K-AKT inhibitors, Lenalildomide, GSK3P inhibitors, IAP inhibitors and/or genotoxic drugs.

The anti-MICA/B antibodies and combination therapies described herein can further be used in combination with one or more anti-proliferative cytotoxic agents. Classes of compounds that can be used as anti-proliferative cytotoxic agents include, but are not limited to, the following:

Alkylating agents (including, without limitation, nitrogen mustards, ethylenimine derivatives, alkyl sulfonates, nitrosoureas and triazenes): Uracil mustard, Chlormethine, Cyclophosphamide (CYTOXAN®) fosfamide, Melphalan, Chlorambucil, Pipobroman, Triethylenemelamine, Triethylenethiophosphoramine, Busulfan, Carmustine, Lomustine, Streptozocin, Dacarbazine, and Temozolomide.

Antimetabolites (including, without limitation, folic acid antagonists, pyrimidine analogs, purine analogs and adenosine deaminase inhibitors): Methotrexate, 5-Fluorouracil, Floxuridine, Cytarabine, 6-Mercaptopurine, 6-Thioguanine, Fludarabine phosphate, Pentostatin, and Gemcitabine.

Suitable anti-proliferative agents for combining with anti-MICA/B antibodies, without limitation, taxanes, paclitaxel (paclitaxel is commercially available as TAXOL™), docetaxel, discodermolide (DDM), dictyostatin (DCT), Peloruside A, epothilones, epothilone A, epothilone B, epothilone C, epothilone D, epothilone E, epothilone F, furanoepothilone D, desoxyepothilone B1, [17]-dehydrodesoxyepothilone B, [18]dehydrodesoxyepothilones B, C12,13-cyclopropyl-epothilone A, C6-C8 bridged epothilone A, trans-9,10-dehydroepothilone D, cis-9,10-dehydroepothilone D, 16-desmethylepothilone B, epothilone BIO, discodermolide, patupilone (EPO-906), KOS-862, KOS-1584, ZK-EPO, ABJ-789, XAA296A (Discodermolide), TZT-1027 (soblidotin), ILX-651 (tasidotin hydrochloride), Halichondrin B, Eribulin mesylate (E-7389), Hemiasterlin (HTI-286), E-7974, Cyrptophycins, LY-355703, Maytansinoid immunoconjugates (DM-1), MKC-1, ABT-751, T1-38067, T-900607, SB-715992 (ispinesib), SB-743921, MK-0731, STA-5312, cleutherobin, 17beta-acetoxy-2-ethoxy-6-oxo-B-homo-estra-1,3,5(10)-trien-3-ol, cyclostreptin, isolaulimalide, laulimalide, 4-epi-7-dehydroxy-14,16-didemethyl-(+)-discodermolides, and cryptothilone 1, in addition to other microtubuline stabilizing agents known in the art.

In cases where it is desirable to render aberrantly proliferative cells quiescent in conjunction with or prior to treatment with anti-MICA/B antibodies described herein, hormones and steroids (including synthetic analogs), such as 17a-Ethinylestradiol, Diethylstilbestrol, Testosterone, Prednisone, Fluoxymesterone, Dromostanolone propionate, Testolactone, Megestrolacetate, Methylprednisolone, Methyltestosterone, Prednisolone, Triamcinolone, Chlorotrianisene, Hydroxyprogesterone, Aminoglutethimide. Estramustine, Medroxyprogesteroneacetate, Leuprolide, Flutamide, Toremifene, ZOLADEX®, can also be administered to the patient. When employing the methods or compositions described herein, other agents used in the modulation of tumor growth or metastasis in a clinical setting, such as antimimetics, can also be administered as desired.

In some embodiments, the combination of the anti-MICA/B antibody and a second agent discussed herein can be administered concurrently as a single composition in a pharmaceutically acceptable carrier, or concurrently as separate compositions with the anti-MICA/B antibody and the second agent in a pharmaceutically acceptable carrier. In some embodiments, the combination of the anti-MICA/B antibody and the second agent can be administered sequentially The administration of the two agents can start at times that are, e.g., 30 minutes, 60 minutes, 90 minutes, 120 minutes, 3 hours, 6 hours, 12 hours, 24 hours, 36 hours, 48 hours, 3 days, 5 days, 7 days, or one or more weeks apart, or administration of the second agent can start, e.g., 30 minutes, 60 minutes, 90 minutes, 120 minutes, 3 hours, 6 hours, 12 hours, 24 hours, 36 hours, 48 hours, 3 days, 5 days, 7 days, or one or more weeks after the first agent has been administered.

In some embodiments, an anti-neoplastic antibody that can be combined with an anti-MICA/B antibody and/or a second agent includes RITUXAN® (rituximab), HERCEPTIN® (trastuzumab), BEXXAR® (tositumomab), ZEVALIN® (ibritumomab), CAMPATH® (alemtuzumab), LYMPHOCIDE® (eprtuzumab), AVASTIN® (bevacizumab), and TARCEVA® (erlotinib), or any combination thereof. In some embodiments, the second antibody useful for the combination therapy with an anti-MICA/B antibody can be an antibody drug conjugate.

In some embodiments, an anti-MICA/B antibody alone or in combination with another agent is used concurrently or sequentially with bone marrow transplantation to treat a variety of tumors of hematopoietic origin.

Provided herein are methods for altering an adverse event associated with treatment of a hyperproliferative disease (e.g., cancer) with an immuno stimulatory agent, comprising administering an anti-MICA/13 antibody with or without a second agent, to a subject. For example, the methods described herein provide for a method of reducing the incidence of immuno stimulatory therapeutic antibody-induced colitis or diarrhea by administering a non-absorbable steroid to the patient. As used herein, a "non-absorbable steroid" is a glucocorticoid that exhibits extensive first pass metabolism such that, following metabolism in the liver, the bioavailability of the steroid is low, i.e., less than about 20%. In some embodiments described herein, the non-absorbable steroid is budesonide. Budesonide is a locally-acting glucocorticosteroid, which is extensively metabolized, primarily by the liver, following oral administration. ENTOCORT EC® (Astra-Zeneca) is a pH- and time-dependent oral formulation of budesonide developed to optimize drug delivery to the ileum and throughout the colon. ENTOCORT EC® is approved in the U.S. for the treatment of mild to moderate Crohn's disease involving the ileum and/or ascending colon. In some embodiments, an anti-MICA/B antibody in conjunction with a non-absorbable steroid can be further combined with a salicylate. Salicylates include 5-ASA agents such as, for example: sulfasalazine (AZULFIDINE®, Pharmacia & Up John); olsalazine (DJPENTUM®, Pharmacia & Up John); balsalazide (COLAZAL®, Salix Pharmaceuticals, Inc.); and mesalamine (ASACOL®, Procter & Gamble Pharmaceuticals; PENTASA®, Shire US; CANASA®, Axcan Scandipharm, Inc.; ROWASA®, Solvay).

TABLE 1

Sequences.

| SEQ ID | Description | Sequences |
|---|---|---|
| 1 | 19G6-MICA.36 VH1 | CAGGTGCAACTGGTGGAGTCTGGGGGAGGCGTGGTCCAGCCTGGGAGGTCCCTGAGACT CTCCTGTGCAGCGTCTGGATTCACCTTCAGTAACTATGCCATGCACTGGGTCCGCCAGGCTCCAG GCGAGGGGCTGGAATGGGTGGCACTTATATGGTATGATGGAAGTAATAAATTCTATGGAGACTCC GTGAAGGGCCGCTTCACCATCTCCAGAGACAATTCCAAGAACACGCTGTATCTGCAAATGAACAG CCTGAGCGCCGAGGACACGGCTGTGTATTACTGTGCGAGAGAGGGAAGTGGGCACTACTGGGGCC AGGGAACCCTGGTCACCGTCTCCTCA |
| 2 | 19G6-MICA.36 VH1 | QVQLVESGGGVVQPGRSLRLSCAASGFTFSNYAMHWVRQAPGEGLEWVALIWYDGSNKF YGDSVKGRFTISRDNSKNTLYLQMNSLSAEDTAVYYCAREGSGHYWGQGTLVTVSS |
| 3 | 19G6-MICA.36 VK1 | GCCATCCAGTTGACCCAGTCTCCATCCTCCCTGTCTGCATCTGTAGGAGACAGAGTCAC CATCACTTGCCGGGCAAGTCAGGGCATCAGCAGTGCTTTAGCCTGGTATCAGCAGAAACCAGGGA AAGTTCCTAAGTCCCTGATCTATGATGCCTCCAGTTTGGAAAGTGGGGTCCCATCAAGGTTCAGC GGCAGTGGATCTGGGACAGATTTCACTCTCACCATCAGCAGCCTGCAGCCTGAAGATTTTGCAAC TTATTACTGTCAACAGTTTAATAGTTACCCGATCACCTTCGGCCA AGGGACACGACTGGAGATTAAA |
| 4 | 19G6-MICA.36 VK1 | ATQLTQSPSSLSASVGDRVTITCRASQGISSALAWYQQKPGKVPKSLIYDASSLESGVP SRFSGSGSGTDFTLTISSLQPEDFATYYCQQFNSYPITFGQGTRLEIK |
| 5 | 19G6-MICA.36 VH1_CDR1 | NYAMH |
| 6 | 19G6-MICA.36 VH1_CDR2 | LIWYDGSNKFYGDSVKG |
| 7 | 19G6-MICA.36 VH1_CDR3 | EGSGHY |
| 8 | 19G6-MICA.36 VK1_CDR1 | RASQGISSALA |

TABLE 1-continued

Sequences.

| SEQ ID | Description | Sequences |
|---|---|---|
| 9 | 19G6-MICA.36 VK1_CDR2 | DASSLES |
| 10 | 19G6-MICA.36 VK1_CDR3 | QQFNSYPIT |
| 11 | 16A5-MICA.52 VH1 | ATGGAGTTTGGGCTGAGCTGGGTTTTCCTCGTTGCTCTTTTAAGAGGTGTCCAGTGTCA<br>GGTGCAGCTGGTGGAGTCTGGGGGAGACGTGGTCCAGCCTGGGAGGTCCCTGAGACTCTC<br>CTGTGCAGCGTCTGGATTCACCTTCAGTAACTATAACATACACTGGGTCCGCCAGGCTCCAGGCA<br>AGGGGCTGGAGTGGGTGGCAGTTATAAGGTATGATGGAATTAATAAATACTATGCAGACTCCGTG<br>AAGGGCCGATTCATCATCTCCAGAGACAATTCCAAGAACACGCTGTATCTGCAAATGAACAGCCT<br>GAGAGCCGAGGACACGGCTGTGTATTACTGTGCGAGCGGGCCCCCTGATGCTTTTAATATCTGGG<br>GCCAAGGGACAATGGTCACCGTCTCTTCA |
| 12 | 16A5-MICA.52 VH1 | MEFGLSWVFLVALLRGVQCQVQLVESGGDVVQPGRSLRLSCAASGFTFSNYNIHWVRQA<br>PGKGLEWVAVIRYDGINKYYADSVKGRFIISRDNSKNTLYLQMNSLRAEDTAVYYCASGP<br>PDAFNIWGQGTMVTVSS |
| 13 | 16A5-MICA.52 VK1 | ATGAGGGTCCCCGCTCAGCTCCTGGGGCTTCTGCTGCTCTGGCTCCCAGGTGCCAGATG<br>TGCCATCCAGTTGACCCAGTCTCCATCCTCCCTGTCTGCATCTGTAGGAGACAGAGTCACCATCA<br>CTTGCCGGGCAAGTCAGGGCATCAGCAGTGCTTTAGCCTGGTATCAGCAGAAACCAGGGAAAGTT<br>CCTAAGTCCCTGATCTATGATGCCTCCAGTTTGGAAAGTGGGGTCCCATCAAGGTTCAGCGGCAG<br>TGGATCTGGGACAGATTTCACTCTCACCATCAGCAGCCTGCAGCCTGAAGATTTTGCAACTTATT<br>ACTGTCAACAGTTTAATAGTTACCCGATCACCTTCGGCCAAGGGACACGACTGGAGATTAAA |
| 14 | 16A5-MICA.52 VK1 | MRVPAQLLGLLLLWLPGARCAIQLTQSPSSLSASVGDRVTITCRASQGISSALAWYQQK<br>PGKVPKSLIYDASSLESGVPSRFSGSGSGTDFTLTISSLQPEDFATYYCQQFNSYPITFGQGTRL<br>EIK |
| 127 | 16A5-MICA.52 VK2 | ATGGACATGAGGGTCCCCGCTCAGCTCCTGGGGCTTCTGCTGCTCTGGCTCCCAGGTGC<br>CAGATGTGCCATCCAGTTGACCCAGTCTCCATCCTCCCTGTCTGCATCTGTAGGAGACAG<br>AGTCACCATCACTTGCCGGGCAAGTCAGGGCATTAGCAGTGCTTTAGCCTGGTATCAGCA<br>GAAACCAGGGAAAGCTCCTAAGCTCCTGATCTATGATGCCTCCAGTTTGGAAAGTGGGGT<br>CCCATCAAGGTTCAGCGGCAGTGGATCTGGGACAGATTTCACTCTCACCATCAGCAGCCT<br>GCAGCCTGAAGATTTTGCAACTTATTACTGTCAACAGTTTAATAGTTACCCATTCACTTTT<br>CGGCCCTGGGACCAAAGTGGATATCAAA |
| 128 | 16A5-MICA.5 VK2 | MDMRVPAQLLGLLLLWLPGARCAIQLTQSPSSLSASVGDRVTITCRASQGISSALAWYQ<br>QKPGKAPKLLIYDASSLESGVPSRFSGSGSGTDFTLTISSLQPEDFATYYCQQFNSYPFTFGPGT<br>KVDIK |
| 15 | 16A5-MICA.52 VH1_CDR1 | NYNIH |
| 16 | 16A5-MICA.52 VH1_CDR2 | VIRYDGINKYYADSVKG |
| 17 | 16A5-MICA.52 VH1_CDR3 | GPPDAFNI |
| 18 | 16A5-MICA.52 VK1_CDR1 | RASQGISSALA |
| 19 | 16A5-MICA.52 VK1_CDR2 | DASSLES |
| 20 | 16A5-MICA.52 VK1_CDR3 | QQFNSYPIT |
| 21 | 24G11-MICA.54 VH1 | ATGGGGTCAACCGCCATCCTCGCCCTCCTCCTGGCTGTTCTCCAAGGAGTCTGTGCCGA<br>GGTGCAGCTGGTGCAGTCTGGAGCAGAGGTGAAAAAGCCCGGGGAGTCTCTGAAGATCTC<br>CTGTAAGGGTTCTGGATACAGTTTTACCAACTACTGGATCGGCTGGGTGCGCCAGATGCC<br>CGGGAAAGGCCTGGAGTGGTTGGGGATCATCCATCCTGGTGACTCTTATACCAGATACAG<br>CCCGTCCTTCCAAGGCCAGGTCACCATCTCAGCCGACAAGTCCATCAGCACCGCCTACCT<br>GCAGTGGAGCAGCCTGAAGGCCTCGGACACCGCCATATATTACTGTGCGAGAGAGGGTAT<br>AGCAGCAACTCCCTTTGACTACTGGGGCCAGGGAACCCTGGTCACCGTCTCCTCA |

TABLE 1-continued

Sequences.

| SEQ ID | Description | Sequences |
|---|---|---|
| 22 | 24G11-MICA.54 VH1 | MGSTAILALLLAVLQGVCAEVQLVQSGAEVKKPGESLKISCKGSGYSFTNYWIGWVRQM PGKGLEWLGITHPGDSYTRYSPSFQGQVTISADKSISTAYLQWSSLKASDTAIYYCAREG IAATPFDYWGQGTLVTVSS |
| 23 | 24G11-MICA.54 VK1 | ATGGAAGCCCCAGCTCAGCTTCTCTTCCTCCTGCTACTCTGGCTCCCAGATACCACCGG AGAAATTGTGTTGACACAGTCTCCAGCCACCCTGTCTTTGTCTCCAGGGGAAAGAGCCAC CCTCTCCTGCAGGGCCAGTCAGAGTGTTAGCAGCTACTTAGCCTGGTTCCAACAGAAACC TGGCCAGGCTCCCAGGCTCCTCATCTATGATGCATCCAACAGGGCCACTGGCATCCCAGC CAGGTTCAGTGGCAGTGGGTCTGGGACAGACTTCACTCTCACCATCAGCAGCCTAGAGCC TGAAGATTTTGCAGTTTATTACTGTCAGCAGCGTAGCAACTGGCCTCCGACGTTCGGCCA AGGGACCAAGGTGGAAATCAAA |
| 24 | 24G11-MICA.54 VK1 | MEAPAQLLFLLLLWLPDTTGEIVLTQSPATLSLSPGERATLSCRASQSVSSYLAWFQQK PGQAPRLLIYDASNRATGIPARFSGSGSGTDFTLTISSLEPEDFAVYYCQQRSNWPPTFG QGTKVEIK |
| 25 | 24G11-MICA.54 VH1_CDR1 | NYWIG |
| 26 | 24G11-MICA.54 VH1_CDR2 | IIHPGDSYTRYSPSFQG |
| 27 | 24G11-MICA.54 VH1_CDR3 | EGIAATPFDY |
| 28 | 24G11-MICA.54 VK1_CDR1 | RASQSVSSYLA |
| 29 | 24G11-MICA.54 VK1_CDR2 | DASNRAT |
| 30 | 24G11-MICA.54 VK1_CDR3 | QQRSNWPPT |
| 31 | 3F5-MICA.2 VH1 | ATGGAGTTGGGGCTGTGCTGGATTTTCCTTGTTGCTATTTTAGAAGGTGTCCAGTGTGAGGTGCA ACTGGTGGAATCTGGGGGAGGCTTGGTACAGCCTGGGGGTCCCTGAGACTCTCCTGTGCAGCCT CTGGATTCACCTTCAGTACCTATAGCATGAACTGGGTCCGCCAGGCTCCAGGGAAGGGGCTGGAG TGGGTTTCATACATTAGTTATCGTAGTCGTACCATATACTACGCAGACTCTGTGAAGGGCCGATT CACCATCTCCAGAGACAATGCCAGGAACTCACTGTATCTGCAAATGAACAGCCTGAGAGACGAGG ACACGGCTGTGTATTACTGTGCGAGATGGGGCTATGGTTCGGGGGGCTTTGACTACTGGGGCCAG GGAACCCTGGTCACCGTCTCCTCA |
| 32 | 3F5-MICA.2 VH1 | MELGLCWIFLVAILEGVQCEVQLVESGGGLVQPGGSLRLSCAASGFTFSTYSMNWVRQAPGKGLE WVSYISYRSRTIYYADSVKGRFTISRDNARNSLYLQMNSLRDEDTAVYYCARWGYGSGGFDYWGQ GTLVTVSS |
| 33 | 3F5-MICA.2 VK1 | ATGGAAACCCCAGCGCAGCTTCTCTTCCTCCTGCTACTCTGGCTCCCAGATACCACCGGAGAAAT TGTGTTGACGCAGTCTCCAGGCACCCTGTCTTTGTCTCCAGGGGAAAGAGCCACCCTCTCCTGCA GGGCCAGTCAGAGTGTTAGCAGCAGCTACTTAGCCTGGTACCAGCAGAAACCTGGCCAGGCTCCC AGGCTCCTCATCTATGGTGCATCCAGCAGGGCCACTGGCATCCCAGACAGGTTCAGTGGCAGTGG GTCTGGGACAGACTTCACTCTCACCATCAGCAGACTGGAGCCTGAAGATTTTGCAGTGTATTACT GTCAGCAGTATGGTAGCTCATTCACTTTCGGCCCTGGGACCAAAGTGGATATCAAA |
| 34 | 3F5-MICA.2 VK1 | METPAQLLFLLLLWLPDTTGEIVLTQSPGTLSLSPGERATLSCRASQSVSSSYLAWYQQKPGQAP RLLIYGASSRATGIPDRFSGSGSGTDFTLTISRLEPEDFAVYYCQQYGSSFTFGPGTKVDIK |
| 35 | 3F5-MICA.2 VH1_CDR1 | TYSMN |
| 36 | 3F5-MICA.2 VH1_CDR2 | YISYRSRTIYYADSVKG |
| 37 | 3F5-MICA.2 VH1_CDR3 | WGYGSGGFDY |
| 38 | 3F5-MICA.2 VK1_CDR1 | RASQSVSSSYLA |
| 39 | 3F5-MICA.2 VK1_CDR2 | GASSRAT |

TABLE 1-continued

Sequences.

| SEQ ID | Description | Sequences |
|---|---|---|
| 40 | 3F5-MICA.2 VK1_CDR3 | QQYGSSFT |
| 41 | 71C2 VH1 | ATGGAGTTGGGACTGAGCTGGATTTTCCTTTTGGCTATTTTAAAAGGTGTCCAGTGTGA<br>AGTGCAGCTGGTGGAGTCTGGGGGAGGCTTGGTACAGCCTGGCAGGTCCCTGAGACTCTC<br>CTGTGCAGCCTCTGGATTCACCTTTAATAATTATGCCATGCACTGGGTCCGGCAAGCTCC<br>AGGGAAGGGCCTGGAGTGGGTCTCAGGTATTACTTGGAATAGTGATAGCATAGGCTATGC<br>GGACTCTGTGAAGGGCCGATTCACCATCTCCAGAGACAACGCCAAGAACTCCCTGTATCT<br>GCAAATGAACAGTCTGAGAGCTGAGGACACGGCCTTGTATTACTGTGCAAAGATTCCGT<br>ATTACTATGGTTCGGGGGTATGGACGTCTGGGGCCAAGGGACCACGGTCACCGTCTCCTC A |
| 42 | 71C2 VH1 | MELGLSWIFLLAILKGVQCEVQLVESGGGLVQPGRSLRLSCAASGFTFNNYAMHWVRQA<br>PGKGLEWVSGITWNSDSIGYADSVKGRFTISRDNAKNSLYLQMNSLRAEDTALYYCAKDS<br>VLLWFGGMDVWGQGTTVTVSS |
| 43 | 71C2 VK1 | ATGGAAACCCCAGCGCAGCTTCTCTTCCTCCTGCTACTCTGGCTCCCAGATACCACCGG<br>AGAAATTGTGTTGACGCAGTCTCCAGGCACCCTGTCTTTGTCTCAGGGGAAAGAGCCAC<br>CCTCTCCTGCAGGGCCAGTCAGAGTGTTAGCAGCAGCTACTTAGCCTGGTACCAGCAGAA<br>ACCTGGCCAGGCTCCCAGGCTCCTCATCTATGGTGCATCCAGCAGGGCCACTGGCATCCC<br>AGACAGGTTCAGTGGCAGTGGGTCTGGGACAGACTTCACTCTCACCATCAGCAGACTGGA<br>GCCTGAAGATTTTGCAGTGTATTACTGTCAGCAGTATGGTAGCTCACCTCCGTACACTTTT<br>TGGCCAGGGGACCAAGCTGGAGATCAAA |
| 44 | 71C2 VK1 | METPAQLLFLLLLWLPDTTGEIVLTQSPGTLSLSPGERATLSCRASQSVSSSYLAWYQQ<br>KPGQAPRLLIYGASSRATGIPDRFSGSGSGTDFTLTISRLEPEDFAVYYCQQYGSSPPYT<br>FGQGTKLEIK |
| 45 | 71C2 VH1_CDR1 | NYAMH |
| 46 | 71C2 VH1_CDR2 | GITWNSDSIGYADSVKG |
| 47 | 71C2 VH1_CDR3 | DSVLLWFGGMDV |
| 48 | 71C2 VK1_CDR1 | RASQSVSSSYLA |
| 49 | 71C2 VK1_CDR2 | GASSRAT |
| 50 | 71C2 VK1_CDR3 | QQYGSSPPYT |
| 58 | 19G6-MICA.36 G236A Heavy Chain AA | QVQLVESGGGVVQPGRSLRLSCAASGFTFSNYAMHWVRQAPGEGLEWVALIWYDGSNKFYGDSVK<br>GRFTISRDNSKNTLYLQMNSLSAEDTAVYYCAREGSGHYWGQGTLVTVSSASTKGPSVFPLAPSS<br>KSTSGGTAALGCLVKDYFPEPVTVSWNSGALTSGVHTFPAVLQSSGLYSLSSVVTVPSSSLGTQT<br>YICNVNHKPSNTKVDKRVEPKSCDKTHTCPPCPAPELLAGPSVFLFPPKPKDTLMISRTPEVTCV<br>VVDVSHEDPEVKFNWYVDGVEVHNAKTKPREEQYNSTYRVVSVLTVLHQDWLNGKEYKCKVSNKA<br>LPAPIEKTISKAKGQPREPQVYTLPPSREEMTKNQVSLTCLVKGFYPSDIAVEWESNGQPENNYK<br>TTPPVLDSDGSFFLYSKLTVDKSRWQQGNVFSCSVMHEALHNHYTQKSLSLSPG |
| 59 | 19G6-MICA.36 G236A Heavy Chain NT | caggtgcaactggtggagtctgggggaggcgtggtccagcctggagggtccctgagactctcctg<br>tgcagcgtctggattcaccttcagtaactatgccatgcactgggtccgccaggctccaggcgagg<br>ggctggaatgggtggcacttatatggtatgatggaagtaataaattctatggagactccgtgaag<br>ggccgcttcaccatctccagagacaattccaagaacacgctgtatctgcaaatgaacagcctgag<br>cgccgaggacacggctgtgtattactgtgcgagagagggaagtgggcactactggggccagggaa<br>ccctggtcaccgtctcctcagctagcaccaagggcccatcggtcttccccctggcacccctcc<br>aagagcacctctgggggcacagcggccctgggctgcctggtcaaggactacttccccgaaccggt<br>gacggtgtcgtggaactcaggcgccctgaccagcggcgtgcacaccttcccggctgtcctacagt<br>cctcaggactctactccctcagcagcgtggtgaccgtgccctccagcagcttgggcacccagacc<br>tacatctgcaacgtgaatcacaagcccagcaacaccaaggtggacaagagagttgagcccaaatc<br>ttgtgacaaaactcacacatgcccaccgtgcccagcacctgaactcctggcgggaccgtcagtct<br>tcctcttccccccaaaacccaaggacaccctcatgatctcccggacccctgaggtcacatgcgtg<br>gtggtggacgtgagccacgaagaccctgaggtcaagttcaactggtacgtggacggcgtggaggt<br>gcataatgccaagacaaagccgcgggaggagcagtacaacagcacgtaccgtgtggtcagcgtcc<br>tcaccgtcctgcaccaggactggctgaatggcaaggagtacaagtgcaaggtctccaacaaagcc<br>ctcccagcccccatcgagaaaaccatctccaaagccaaagggcagccccgagaaccacaggtgta<br>caccctgcccccatcccgggaggagatgaccaagaaccaggtcagcctgacctgcctggtcaaag<br>gcttctatcccagcgacatcgccgtggagtgggagagcaatgggcagccggagaacaactacaag<br>accacgcctcccgtgctggactccgacggctccttcttcctctatagcaagctcaccgtggacaa<br>gagcaggtggcagcaggggaacgtcttctcatgctccgtgatgcatgaggctctgcacaaccact<br>acacgcagaagagcctctccctgtcccggggt |

TABLE 1-continued

Sequences.

| SEQ ID | Description | Sequences |
|---|---|---|
| 60 | 19G6-MICA.36 Light Chain AA | aiqltgspsslsasvgdrvtitcrasqgissalawyqqkpgkvpksliydasslesgvpsrfsgs gsgtdftltisslqpedfatyycqqfnsypitfgqgtrleikrtvaapsvfifppsdeqlksgta svvcllnnfypreakvqwkvdnalqsgnsqesvteqdskdstyslsstltlskadyekhkvyace vthqglsspvtksfnrgec |
| 61 | 19G6-MICA.36 Light Chain NT | gccatccagttgacccagtctccatcctccctgtctgcatctgtaggagacagagtcaccatcac ttgccgggcaagtcagggcatcagcagtgctttagcctggtatcagcagaaaccagggaaagttc ctaagtccctgatctatgatgcctccagtttggaaagtggggtcccatcaaggttcagcggcagt ggatctgggacagatttcactctcaccatcagcagcctgcagcctgaagattttgcaacttatta ctgtcaacagtttaatagttacccgatcaccttcggccaagggacacgactggagattaaacgta cggtggctgcaccatctgtcttcatcttcccgccatctgatgagcagttgaaatctggaactgcc tctgttgtgtgcctgctgaataacttctatcccagagaggccaaagtacagtggaaggtggataa cgccctccaatcgggtaactcccaggagagtgtcacagagcaggacagcaaggacagcacctaca gcctcagcagcaccctgacgctgagcaaagcagactacgagaaacacaaagtctacgcctgcgaa gtcacccatcagggcctgagctcgcccgtcacaaagagcttcaacaggggagagtgt |
| 62 | 16A5-MICA.52 Heavy Chain AA | QVQLVESGGDVVQPGRSLRLSCAASGFTFSNYNIHWVRQAPGKGLEWVAVIRYDGINKYYADSVK GRFIISRDNSKNTLYLQMNSLRAEDTAVYYCASGPPDAFNIWGQGTMVTVSSASTKGPSVFPLAP SSKSTSGGTAALGCLVKDYFPEPVTVSWNSGALTSGVHTFPAVLQSSGLYSLSSVVTVPSSSLGT QTYICNVNHKPSNTKVDKRVEPKSCDKTHTCPPCPAPELLGGPSVFLFPPKPKDTLMISRTPEVT CVVVDVSHEDPEVKFNWYVDGVEVHNAKTKPREEQYNSTYRVVSVLTVLHQDWLNGKEYKCKVSN KALPAPIEKTISKAKGQPREPQVYTLPPSREEMTKNQVSLTCLVKGFYPSDIAVEWESNGQPENN YKTTPPVLDSDGSFFLYSKLTVDKSRWQQGNVFSCSVMHEALHNHYTQKSLSLSPG |
| 63 | 16A5-MICA.52 Heavy Chain NT | caggtgcagctggtggagtctgggggagacgtggtccagcctggggaggtccctgagactctcctg tgcagcgtctggattcaccttcagtaactataacatacactgggtccgccaggctccaggcaagg ggctggagtgggtggcagttataaggtatgatggaattaataaatactatgcagactccgtgaag ggccgattcatcatctccagagacaattccaagaacacgctgtatctgcaaatgaacagcctgag agccgaggacacggctgtgtattactgtgcgagcgggccccctgatgcttttaatatctggggcc aagggacaatggtcaccgtctcttcagctagcaccaagggcccatcggtcttccccctggcaccc tcctccaagagcacctctgggggcacagcggccctgggctgcctggtcaaggactacttccccga accggtgacggtgtcgtggaactcaggcgccctgaccagcggcgtgcacaccttcccggctgtcc tacagtcctcaggactctactccctcagcagcgtggtgaccgtgccctccagcagcttgggcacc cagacctacatctgcaacgtaatcacaagcccagcaacaccaaggtggacaagagagttgagcc caaatcttgtgacaaaactcacacatgcccaccgtgcccagcacctgaactcctgggggaccgt cagtcttcctcttccccccaaaacccaaggacaccctcatgatctcccggacccctgaggtcaca tgcgtggtggtggacgtgagccacgaagaccctgaggtcaagttcaactggtacgtggacggcgt ggaggtgcataatgccaagacaaagccgcgggaggagcagtacaacagcacgtaccgtgtggtca gcgtcctcaccgtcctgcaccaggactggctgaatggcaaggagtacaagtgcaaggtctccaac aaagcccttcccagccccatcgagaaaaccatctccaaagccaaagggcagccccgagaaccaca ggtgtacaccctgcccccatcccgggaggagatgaccaagaaccaggtcagcctgacctgcctgg tcaaaggcttctatcccagcgacatcgccgtggagtgggagagcaatgggcagccggagaacaac tacaagaccacgcctcccgtgctggactccgacggctccttcttcctctatagcaagctcaccgt ggacaagagcaggtggcagcaggggaacgtcttctcatgctccgtgatgcatgaggctctgcaca accactacacgcagaagagcctctccctgtccccgggt |
| 64 | 16A5-MICA.52 Light Chain AA | AIQLTQSPSSLSASVGDRVTITCRASQGISSALAWYQQKPGKVPKSLIYDASSLESGVPSRFSGS GSGTDFTLTISSLQPEDFATYYCQQFNSYPITFGQGTRLEIKRTVAAPSVFIFPPSDEQLKSGTA SVVCLLNNFYPREAKVQWKVDNALQSGNSQESVTEQDSKDSTYSLSSTLTLSKADYEKHKVYACE VTHQGLSSPVTKSFNRGEC |
| 65 | 16A5-MICA.52 Light Chain NT | gccatccagttgacccagtctccatcctccctgtctgcatctgtaggagacagagtcaccatcac ttgccgggcaagtcagggcatcagcagtgctttagcctggtatcagcagaaaccagggaaagttc ctaagtccctgatctatgatgcctccagtttggaaagtggggtcccatcaaggttcagcggcagt ggatctgggacagatttcactctcaccatcagcagcctgcagcctgaagattttgcaacttatta ctgtcaacagtttaatagttacccgatcaccttcggccaagggacacgactggagattaaacgta cggtggctgcaccatctgtcttcatcttcccgccatctgatgagcagttgaaatctggaactgcc tctgttgtgtgcctgctgaataacttctatcccagagaggccaaagtacagtggaaggtggataa cgccctccaatcgggtaactcccaggagagtgtcacagagcaggacagcaaggacagcacctaca gcctcagcagcaccctgacgctgagcaaagcagactacgagaaacacaaagtctacgcctgcgaa gtcacccatcagggcctgagctcgcccgtcacaaagagcttcaacaggggagagtgt |
| 66 | 24G11-MICA.54 Heavy Chain AA | EVQLVQSGAEVKKPGESLKISCKGSGYSFTNYWIGWVRQMPGKGLEWLGIIHPGDSYTRYSPSFQ GQVTISADKSISTAYLQWSSLKASDTAIYYCAREGIAATPFDYWGQGTLVTVSSASTKGPSVFPL APSSKSTSGGTAALGCLVKDYFPEPVTVSWNSGALTSGVHTFPAVLQSSGLYSLSSVVTVPSSSL GTQTYICNVNHKPSNTKVDKRVEPKSCDKTHTCPPCPAPELLGGPSVFLFPPKPKDTLMISRTPE VTCVVVDVSHEDPEVKFNWYVDGVEVHNAKTKPREEQYNSTYRVVSVLTVLHQDWLNGKEYKCKV SNKALPAPIEKTISKAKGQPREPQVYTLPPSREEMTKNQVSLTCLVKGFYPSDIAVEWESNGQPE NNYKTTPPVLDSDGSFFLYSKLTVDKSRWQQGNVFSCSVMHEALHNHYTQKSLSLSPG |
| 67 | 24G11-MICA.54 Heavy Chain NT | gaggtgcagctggtgcagtctggagcagaggtgaaaaagcccggggagtctctgaagatctcctg taaggggttctggatacagttttaccaactactggatcggctgggtgcgccagatgcccgggaaag gcctggagtggttggggatcatccatcctggtgactcttataccagatacagcccgtccttccaa ggccaggtcaccatctcagccgacaagtccatcagcaccgcctacctgcagtggagcagcctgaa |

TABLE 1-continued

Sequences.

| SEQ ID | Description | Sequences |
|---|---|---|
| | | ggcctcggacaccgccatatattactgtgcgagagagggtatagcagcaactcccttgactact<br>ggggccaggaaccctggtcaccgtctcctcagctagcaccaagggcccatcggtcttccccctg<br>gcaccctcctccaagagcacctctgggggcacagcggccctgggctgcctggtcaaggactactt<br>ccccgaaccggtgacggtgtcgtggaactcaggcgccctgaccagcggcgtgcacaccttcccgg<br>ctgtcctacagtcctcaggactctactccctcagcagcgtggtgaccgtgccctccagcagcttg<br>ggcacccagacctacatctgcaacgtgaatcacaagcccagcaacaccaaggtggacaagagagt<br>tgagcccaaatcttgtgacaaaactcacacatgcccaccgtgcccagcacctgaactcctggggg<br>gaccgtcagtcttcctcttccccccaaaacccaaggacaccctcatgatctcccggacccctgag<br>gtcacatgcgtggtggtggacgtgagccacgaagaccctgaggtcaagttcaactggtacgtgga<br>cggcgtggaggtgcataatgccaagacaaagccgcgggaggagcagtacaacagcacgtaccgtg<br>tggtcagcgtcctcaccgtcctgcaccaggactggctgaatggcaaggagtacaagtgcaaggtc<br>tccaacaaagcctcccagcccccatcgagaaaaccatctccaaagccaaagggcagccccgaga<br>accacaggtgtacaccctgcccccatcccgggaggagatgaccaagaaccaggtcagcctgacct<br>gcctggtcaaaggcttctatcccagcgacatcgccgtggagtgggagagcaatgggcagccggag<br>aacaactacaagaccacgcctcccgtgctggactccgacggctccttcttcctctatagcaagct<br>caccgtggacaagagcaggtggcagcaggggaacgtcttctcatgctccgtgatgcatgaggctc<br>tgcacaaccactacacgcagaagagcctctccctgtccccgggt |
| 68 | 24G11-MICA.54 Light Chain AA | EIVLTQSPATLSLSPGERATLSCRASQSVSSYLAWFQQKPGQAPRLLIYDASNRATGIPARFSGS<br>GSGTDFTLTISSLEPEDFAVYYCQQRSNWPPTFGQGTKVEIKRTVAAPSVFIFPPSDEQLKSGTA<br>SVVCLLNNFYPREAKVQWKVDNALQSGNSQESVTEQDSKDSTYSLSSTLTLSKADYEKHKVYACE<br>VTHQGLSSPVTKSFNRGEC |
| 69 | 24G11-MICA.54 Light Chain NT | gaaattgtgttgacacagtctccagccaccctgtctttgtctccaggggaaagagccac<br>cctctcctgcagggccagtcagagtgttagcagctacttagcctggttccaacagaaac<br>ctggccaggctcccaggctcctcatctatgatgcatccaacagggccactggcatccca<br>gccaggttcagtggcagtgggtctgggacagacttcactctcaccatcagcagcctaga<br>gcctgaagattttgcagtttattactgtcagcagcgtagcaactggcctccgacgttcg<br>gccaagggaccaaggtggaaatcaaacgtacggtggctgcaccatctgtcttcatcttc<br>ccgccatctgatgagcagttgaaatctggaactgcctctgttgtgtgcctgctgaataa<br>cttctatcccagagaggccaaagtacagtggaaggtggataacgccctccaatcggta<br>actcccaggagagtgtcacagagcaggacagcaaggacagcacctacagcctcagcagc<br>accctgacgctgagcaaagcagactacgagaaacacaaagtctacgcctgcgaagtcac<br>ccatcagggcctgagctcgcccgtcacaaagagcttcaacaggggagagtgt |
| 70 | 3F5-MICA.2 Heavy Chain AA | evqlvesgggglvqpggslrlscaasgftfstysmnwvrqapgkglewvsyisyrsrtiy<br>yadsvkgrftisrdnarnslylqmnslrdedtavyycarwgygsggfdywgqgtlvtvs<br>sastkgpsvflplapsskstsggtaalgclvkdyfpepvtvswnsgaltsgvhtfpavlq<br>ssglyslssvvtvpsselgtqtyicnvnhkpentkvdkrvepkscdkthtcppcpapel<br>lggpsvflfppkpkdtlmisrtpevtcvvvdvshedpevkfnwyvdgvevhnaktkpre<br>eqynstyrvvsvltvlhqdwlngkeykckvsnkalpapiektiskakgqprepqvytlp<br>psreemtknqvsltclvkgfypsdiavewesngqpennykttppvldsdgsfflyskltv<br>vdksrwqqgnvfscsvmhealhnhytqkslslspg |
| 71 | 3F5-MICA.2 Heavy Chain NT | gaggtgcaactggtggaatctgggggaggcttggtacagcctggggggtccctgagact<br>ctcctgtgcagcctctggattcaccttcagtacctatagcatgaactgggtccgccagg<br>ctccagggaaggggctggagtgggtttcatacattagttatcgtagtcgtaccatatac<br>tacgcagactctgtgaagggccgattcaccatctccagagacaatgccaggaactcact<br>gtatctgcaaatgaacagcctgagagacgaggacacggctgtgtattactgtgcgagat<br>gggctatggttcggggggctttgactactggggccagggaaccctggtcaccgtctcc<br>tcagctagcaccaagggcccatcggtcttccccctggcaccctcctccaagagcacctc<br>tgggggcacagcggccctgggctgcctggtcaaggactacttccccgaaccggtgacgg<br>tgtcgtggaactcaggcgccctgaccagcggcgtgcacaccttcccggctgtcctacag<br>tcctcaggactctactccctcagcagcgtggtgaccgtgccctccagcagcttgggcac<br>ccagacctacatctgcaacgtgaatcacaagcccagcaacaccaaggtggacaagagag<br>ttgagcccaaatcttgtgacaaaactcacacatgcccaccgtgcccagcacctgaactc<br>ctgggggaccgtcagtcttcctcttccccccaaaacccaaggacaccctcatgatctc<br>ccggacccctgaggtcacatgcgtggtggtggacgtgagccacgaagaccctgaggtca<br>agttcaactggtacgtggacggcgtggaggtgcataatgccaagacaaagccgcgggag<br>gagcagtacaacagcacgtaccgtgtggtcagcgtcctcaccgtcctgcaccaggactg<br>gctgaatggcaaggagtacaagtgcaaggtctccaacaaagcctcccagcccccatcg<br>agaaaaccatctccaaagccaaagggcagccccgagaaccacaggtgtacaccctgccc<br>ccatcccgggaggagatgaccaagaaccaggtcagcctgacctgcctggtcaaaggctt<br>ctatcccagcgacatcgccgtggagtgggagagcaatgggcagccggagaacaactaca<br>agaccacgcctcccgtgctggactccgacggctccttcttcctctatagcaagctcacc<br>gtggacaagagcaggtggcagcaggggaacgtcttctcatgctccgtgatgcatgaggc<br>tctgcacaaccactacacgcagaagagcctctccctgtccccgggt |
| 72 | 3F5-MICA.2 Light Chain AA | eivltqspgtlslspgeratlscrasqsvsssylawyqqkpgqaprlliygassratgi<br>pdrfsgsgsgtdftltisrlepedfavyycqqygssftfgpgtkvdikrtvaapsvfif<br>ppsdeqlksgtasvvcllnnfypreakvqwkvdnalqsgnsqesvteqdskdstyslss<br>tltlskadyekhkvyacevthqglsspvtksfnrgec |
| 73 | 3F5-MICA.2 Light Chain | gaaattgtgttgacgcagtctccaggcaccctgtctttgtctccaggggaaagagccac<br>cctctcctgcagggccagtcagagtgttagcagcagctacttagcctggtaccagcaga |

TABLE 1-continued

Sequences.

| SEQ ID | Description | Sequences |
|---|---|---|
| | NT | aacctggccaggctcccaggctcctcatctatggtgcatccagcagggccactggcatc ccagacaggttcagtggcagtgggtctgggacagacttcactctcaccatcagcagact ggagcctgaagattttgcagtgtattactgtcagcagtatggtagctcattcactttcg gccctgggaccaaagtggatatcaaacgtacggtggctgcaccatctgtcttcatcttc ccgccatctgatgagcagttgaaatctggaactgcctctgttgtgtgcctgctgaataa cttctatcccagagaggccaaagtacagtggaaggtggataacgccctccaatcgggta actcccaggagagtgtcacagagcaggacagcaaggacagcacctacagcctcagcagc accctgacgctgagcaaagcagactacgagaaacacaaagtctacgcctgcgaagtcac ccatcagggcctgagctcgcccgtcacaaagagcttcaacaggggagagtgt |
| 51 | Human MICA | MGLGPVFLLLAGIFPFAPPGAAAEPHSLRYNLTVLSWDGSVQSGFLAEVHLDGQPFLRY DRQKCRAKPQGQWAEDVLGNKTWDRETRDLTGNGKDLRMTLAHIKDQKEGLHSLQEIRV CEIHEDNSTRSSQHFYYDGELFLSQNLETEEWTVPQSSRAQTLAMNVRNFLKEDAMKTK THYHAMHADCLQELRRYLESGVVLRRTVPPMVNVTRSEASEGNITVTCRASSFYPRNII LTWRQDGVSLSHDTQQWGDVLPDGNGTYQTWVATRICRGEEQRFTCYMEHSGNHSTHPV PSGKVLVLQSHWQTFHVSAVAAGCCYFCYYYFLCPLL |
| 109 | MICA1 (MICA Variant) | MGLGPVFLLLAGIFPFAPPGAAAEPHSLRYNLTVLSWDGSVQSGFLTEVHLDGQPFLRC DRQKCRAKPQGQWAEDVLGNKTWDRETRDLTGNGKDLRMTLAHIKDQKEGLHSLQEIRV CEIHEDNSTRSSQHFYYDGELFLSQNLETKEEWTMPQSSRAQTLAMNVRNFLKEDAMKTK THYHAMHADCLQELRRYLKSGVVLRRTVPPMVNVTRSEASEGNITVTCRASGFYPWNIT LSWRQDGVSLSHDTQQWGDVLPDGNGTYQTWVATRICQGEEQRFTCYMEHSGNHSTHPV PSGKVLVLQSHWQTFHVSAVAAAAIFVIIIFYVRCCKKKTSAAEGPELVSLQVLDQHPV GTSDHRDATQLGFQPLMSDLGSTGSTEGA |
| 110 | MICA*002 | MGLGPVFLLLAGIFPFAPPGAAAEPHSLRYNLTVLSGDGSVQSGFLAEVHLDGQPFLRC DRQKCRAKPQGQWAEDVLGNKTWDRETRDLTGNGKDLRMTLAHIKDQKEGLHSLQEIRV CEIHEDNSTRSSQHFYYDGELFLSQNLETEEWTMPQSSRAQTLAMNVRNFLKEDAMKTK THYHAMHADCLQELRRYLKSGVVLRRTVPPMVNVTRSEASEGNITVTCRASGFYPWNIT LSWRQDGVSLSHDTQQWGDVLPDGNGTYQTWVATRICQGEEQRFTCYMEHSGNHSTHPV PSGKVLVLQSHWQTFHVSAVAAAAIFVIIIFYVRCCKKKTSAAEGPELVSLQVLDQHPV GTSDHRDATQLGFQPLMSDLGSTGSTEGT |
| 111 | MICA*004 | MGLGPVFLLLAGIFPFAPPGAAAEPHSLRYNLTVLSWDGSVQSGFLAEVHLDGQPFLRY DRQKCRAKPQGQWAEDVLGNKTWDRETRDLTGNGKDLRMTLAHIKDQKEGLHSLQEIRV CEIHEDNSTRSSQHFYYDGELFLSQNVETEEWTVPQSSRAQTLAMNVRNFLKEDAMKTK THYHAMHADCLQELRRYLESSVVLRRRVPPMVNVTRSEASEGNITVTCRASSFYPRNIT LSTRQDGVSLSHDTQQWGDVLPDGNGTYQTWVATRICQGEEQRFTCYMEHSGNHSTHPV PSGKVLVLQSHWQTFHVSAVAAAAAAIFVIIIFYVRCCKKKTSAAEGPELVSLQVLDQH PVGTSDHRDATQLGFQPLMSALGSTGSTEGA |
| 112 | MICA*008 | MGLGPVFLLLAGIFPFAPPGAAAEPHSLRYNLTVLSWDGSVQSGFLAEVHLDGQPFLRY DRQKCRAKPQGQWAEDVLGNKTWDRETRDLTGNGKDLRMTLAHIKDQKEGLHSLQEIRV CEIHEDNSTRSSQHFYYDGELFLSQNLETEEWTVPQSSRAQTLAMNVRNFLKEDAMKTK THYHAMHADCLQELRRYLESGVVLRRTVPPMVNVTRSEASEGNITVTCRASSFYPRNII LTWRQDGVSLSHDTQQWGDVLPDGNGTYQTWVATRICRGEEQRFTCYMEHSGNHSTHPV PSGKVLVLQSHWQTFHVSAVAAAAIFVIIIFYVRCC |
| 113 | MICA*009 | MGLGPVFLLLAGIFPFAPPGAAAEPHSLRYNLTVLSWDGSVQSGFLAEVHLDGQPFLRY DRQKCRAKPQGQWAEDVLGNKTWDRETRDLTGNGKDLRMTLAHIKDQKEGLHSLQEIRV CEIHEDNSTRSSQHFYYDGELFLSQNLETEEWTVPQSSRAQTLAMNVRNFLKEDAMKTK THYHAMHADCLQELRRYLESSVVLRRTVPPMVNVTRSEASEGNITVTCRASSFYPRNIT LTWRQDGVSLSHDTQQWGDVLPDGNGTYQTWVATRICQGEEQRFTCYMEHSGNHSTHPV PSGKVLVLQSHWQTFHVSAVAAAAIFVIIIFYVRCCKKKTSAAEGPELVSLQVLDQHPV GTSDHRDATQLGFQPLMSALGSTGSTEGT |
| 114 | MICA*010 | MGLGPVFLLLAGIFPFAPPGAAAEPHSLPYNLTVLSWDGSVQSGFLAEVHLDGQPFLRY DRQKCRAKPQGQWAEDVLGNKTWDRETRDLTGNGKDLRMTLAHIKDQKEGLHSLQEIRV CEIHEDNSTRSSQHFYYDGELFLSQNLETEEWTVPQSSRAQTLAMNVRNFLKEDAMKTK THYHAMHADCLQELRRYLESSVVLRRTVPPMVNVTRSEASEGNITVTCRASSFYPRNII LTWRQDGVSLSHDTQQWGDVLPDGNGTYQTWVATRICRGEEQRFTCYMEHSGNHSTHPV PSGKVLVLQSHWQTFHVSAVAAAAAIFVIIIFYVRCCKKKTSAAEGPELVSLQVLDQHP VGTSDHRDATQLGFQPLMSALGSTGSTEGA |
| 115 | MICA.20 VH | EVQLVESGGGLVQPGGSLRLSCAASGFTFSTYSMNWVRQAPGKGLEWVSYISYRSRTIY YADSVKGRFTISRDNARNSLYLQMNSLRDEDTAVYYCARWGYGSGGFDYWGQGTLVTVS S |
| 116 | MICA.20 VL | EIVLTQSPGTLSLSPGERATLSCRASQSVSSSYLAWYQQKPGQAPRLLIYGASSRATGI PDRFSGSGSGTDFTLTISRLEPEDFAVYYCQQYGSSPWTFGQGTKVEIK |
| 117 | MICA.21 VH | EVQLVESGGGLVQPGGSLRLSCAASGFTFSTYSMNWVRQAPGKGLEWVSYISYRSRTIY YADSVKGRFTISRDNARNSLYLQMNSLRDEDTAVYYCARWGYGSGGFDYWGQGTLVTVS S |

TABLE 1-continued

Sequences.

| SEQ ID | Description | Sequences |
|---|---|---|
| 118 | MICA.21 VL | EIVLTQSPGTLSLSPGERATLSCRASQSVSSSYLAWYQQKPGQAPRLLIYGASSRATGI PDRFSGSGSGTDFTLTISRLEPEDFAVYYCQQYGSSPYTFGQGTKLEIK |
| 119 | MICA.22 VH | EVQLVESGGGLVQPGGSLRLSCAASGFTFSTYSMNWVRQAPGKGLEWVSYISYRSRTIY YADSVKGRFTISRDNARNSLYLQMNSLRDEDTAVYYCARWGYGSGGFDYWGQGTLVTVSS |
| 120 | MICA.22 VL | EIVLTQSPGTLSLSPGERATLSCRASQSVSSSYLAWYQQKPGQAPRLLIYGASSRATGI PDRFSGSGSGTDFTLTISRLEPEDFAVYYCQQYGSSPFTFGPGTKVDIK |
| 121 | MICA.38 VH | EVQLVESGGGLVQPGGSLRLSCAASGFTFSTYSMNWVRQAPGKGLEWVSYISYRSRTIY YADSVKGRFTISRDNARNSLYLQMNSLRDEDTAVYYCARWGYGSGGFDYWGQGTLVTVSS |
| 122 | MICA.38 VL | EIVLTQSPGTLSLSPGERATLSCRASQSVSSSYLAWYQQKPGQAPRLLIYGASSRATGI PDRFSGSGSGTDFTLTISRLEPEDFAVYYCQQYGSSSFTFGPGTKVDIK |
| 127 | 16A5-MICA.52 VK2 NT | atggacatgagggtccccgctcagctcctggggcttctgctgctctggctcccaggtgc cagatgtgccatccagttgacccagtctccatcctccctgtctgcatctgtaggagacag agtcaccatcacttgccgggcaagtcagggcattagcagtgcttagcctggtatcagca gaaaccagggaaagctcctaagctcctgatctatgatgcctccagtttggaaagtggggt cccatcaaggttcagcggcagtggatctgggacagatttcactctcaccatcagcagcct gcagcctgaagattttgcaacttattactgtcaacagtttaatagttacccattcacttt cggccctgggaccaaagtggatatcaaa |
| 128 | 16A5-MICA.52 VK2 AA | MDMRVPAQLLGLLLLWLPGARCATQLTQSPSSLSASVGDRVTITCRASQGISSALAQ QKPGKAPKLLIYDASSLESGVPSRFSGSGSGTDFTLTISSLQPEDFATYYCQQFNSYPFT FGPGTKVDIK |
| 130 | 19G6-MICA.36 Heavy Chain AA (236G) | QVQLVESGGGVVQPGRSLRLSCAASGFTFSNYAMHWVRQAPGEGLEWVALIWYDGSNKFYGDSVK GRFTISRDNSKNTLYLQMNSLSAEDTAVYYCAREGSGHYWGQGTLVTVSSASTKGPSVFPLAPSS KSTSGGTAALGCLVKDYFPEPVTVSWNSGALTSGVHTFPAVLQSSGLYSLSSVVTVPSSSLGTQT YICNVNHKPSNTKVDKRVEPKSCDKTHTCPPCPAPELLGGPSVFLFPPKPKDTLMISRTPEVTCV VVDVSHEDPEVKFNWYVDGVEVHNAKTKPREEQYNSTYRVVSVLTVLHQDWLNGKEYKCKVSNKA LPAPIEKTISKAKGQPREPQVYTLPPSREEMTKNQVSLTCLVKGFYPSDIAVEWESNGQPENNYK TTPPVLDSDGSFFLYSKLTVDKSRWQQGNVFSCSVMHEALHNHYTQKSLSLSPG |
| 131 | 19G6-MICA.36 Heavy Chain NT (236G) | caggtgcaactggtggagtctgggggaggcgtggtccagcctggagggtccctgagact ctcctgtgcagcgtctggattcaccttcagtaactatgccatgcactgggtccgccagg ctccaggcgaggggctggaatgggtggcacttatatggtatgatggaagtaataaattc tatggagactccgtgaagggccgcttcaccatctccagagacaattccaagaacacgct gtatctgcaaatgaacagcctgagcgccgaggacacggctgtgtattactgtgcgagag agggaagtgggcactactggggccagggaaccctggtcaccgtctcctcagctagcacc aagggcccatcggtcttccccctggcaccctcctccaagagcacctctgggggcacagc ggccctgggctgcctggtcaaggactacttccccgaaccggtgacggtgtcgtggaact caggcgccctgaccagcggcgtgcacaccttcccggctgtcctacagtcctcaggactc tactccctcagcagcgtggtgaccgtgccctccagcagcttgggcacccagacctacat ctgcaacgtgaatcacaagcccagcaacaccaaggtggacaagagagttgagcccaaat cttgtgacaaaactcacacatgcccaccgtgcccagcacctgaactcctggggggaccg tcagtcttcctcttccccccaaaacccaaggacaccctcatgatctcccggacccctga ggtcacatgcgtggtggtggacgtgagccacgaagaccctgaggtcaagttcaactggt acgtggacggcgtggaggtgcataatgccaagacaaagccgcgggaggagcagtacaac agcacgtaccgtgtggtcagcgtcctcaccgtcctgcaccaggactggctgaatggcaa ggagtacaagtgcaaggtctccaacaaagccctcccagcccccatcgagaaaaccatct ccaaagccaaagggcagccccgagaaccacaggtgtacaccctgcccccatcccgggag gagatgaccaagaaccaggtcagcctgacctgcctggtcaaaggcttctatcccagcga catcgccgtggagtgggagagcaatgggcagccggagaacaactacaagaccacgcctc ccgtgctggactccgacggctccttcttcctctatagcaagctcaccgtggacaagagc aggtggcagcaggggaacgtcttctcatgctccgtgatgcatgaggctctgcacaacca ctacacgcagaagagcctctccctgtccccgggt |

The practice of the present disclosure will employ, unless otherwise indicated, conventional techniques of cell biology, cell culture, molecular biology, transgenic biology, microbiology, recombinant DNA, and immunology, which are within the skill of the art. Such techniques are explained fully in the literature. See, for example, Sambrook et al., ed. (1989) Molecular Cloning A Laboratory Manual (2nd ed.; Cold Spring Harbor Laboratory Press); Sambrook et al., ed. (1992) Molecular Cloning: A Laboratory Manual, (Cold Springs Harbor Laboratory, NY); D. N. Glover ed., (1985) DNA Cloning, Volumes I and II; Gail, ed. (1984) Oligonucleotide Synthesis; Mullis et al. U.S. Pat. No. 4,683,195; Hames and Higgins, eds. (1984) Nucleic Acid Hybridization; Hames and Higgins, eds. (1984) Transcription And Translation; Freshney (1987) Culture Of Animal Cells (Alan R. Liss, Inc.); Immobilized Cells And Enzymes (IRL Press) (1986); Perbal (1984) A Practical Guide To Molecular Cloning; the treatise, Methods In Enzymology (Academic Press, Inc., N.Y.); Miller and Calos eds. (1987) Gene Transfer Vectors For Mammalian Cells, (Cold Spring Harbor Laboratory); Wu et al., eds., Methods In Enzymology, Vols. 154 and 155; Mayer and Walker, eds. (1987) Immunochemical Methods In Cell And Molecular Biology (Academic Press, London); Weir and Blackwell, eds., (1986) Handbook Of Experimental Immunology, Volumes I-IV; Manipulating the Mouse Embryo, Cold Spring Harbor Laboratory Press, Cold Spring Harbor, N.Y., (1986);); Crooks, Antisense drug Technology: Principles, strategies and applications, 2$^{nd}$ Ed. CRC Press (2007) and in Ausubel et at (1989) Current Protocols in Molecular Biology (John Wiley and Sons, Baltimore, Md.).

The following examples are offered by way of illustration and not by way of limitation.

EXAMPLES

Example 1. Antibody Generation and Screening

Human IgG transgenic (Hco7:01 [PK] (BALB/c)) mice were immunized with CHO cells transfected with full-length human MICA/B. Spleen cells from the immunized mouse were fused to the SP2/0 fusion partner. Hybridoma supernatants were first screened for the presence of human IgG antibodies using an HTRF assay. Antigen specificity was then determined by binding in ELISA to hMICA, followed by FACS assays with CHO cells expressing various alleles of human MICA/B. These FACS-positive mAbs were subjected to further characterization for affinity and performance in functional assays. Hybridoma 3F5, 16A5, 71C2, 19G6, and 24G11 were representative antibody clones.

Example 2. Recombinant Expression of MICA/B Antibodies

Anti-MICA/B antibodies described herein can be expressed using cloning and recombinant expression techniques commonly available in the art. For example, total RNA was prepared from hybridoma clone 3F5 and VH and VK cDNAs were prepared. Variable regions of the heavy (VH) and light (VL) chains of the antibody were cloned and sequenced (FIGS. 4A and 4C, respectively). The 3F5 VH sequence (SEQ ID NO: 31) was cloned into vector pICOFSCpurG which contains the osteonectin signal sequence and the human IgG.1f constant region, generating plasmid pICOFSCpurG(MICA.2). The 3F5 VL sequence (SEQ ID NO: 33) was cloned into vector pICOFSCneoK which contains the osteonectin signal sequence and the human kappa constant region, generating plasmid pICOFSCneoK(MICA.2). Plasmids pICOFSCpurG (MICA.2) and pICOFSCneoK(MICA.2) were co-transfected into CHO-S cells and stable clones were selected and screened for recombinant expression. The recombinant antibody of 3F5 is referred to as "MICA.2." Mutations in the VL, e.g. CDR3, of MICA.2 were made to improve solubility of the antibody. Such mutants of MICA.2 include MICA.20 (VH: SEQ ID NO:115; VL: SEQ ID NO:116), MICA.21 (VH: SEQ ID NO:117; VL: SEQ ID NO:118), MICA.22 (VH: SEQ ID NO:119; VL: SEQ ID NO:120), MICA.38 (VH: SEQ ID NO:121; VL: SEQ ID NO:122), MICA.39 (VH: SEQ ID NO:123; VL: SEQ ID NO:124) and MICA 40 (VH: SEQ ID NO:125; VL: SEQ ID NO:126). These mutants contain mutations or insertions at or about position 96 in the VL of MICA.2.

Antibodies comprising the CDRs and/or variable domains of hybridoma antibodies 19G6 (MICA.36; see FIGS. 1A and 1C for VH and VL, respectively), 16A5 (MICA.52 (FIGS. 2A and 2C for VH and VL, respectively) and MICA.53), and 24G11 (MICA.54; see FIGS. 3A and 3C for VH and VL, respectively) were also expressed recombinantly in host cells. Recombinant antibodies are referred to herein with the names such as MICA.36 (19G6), MICA.52 and MICA.53 (16A5), and MICA.54 (24G11). When referring to any of these recombinant antibodies by their names, no specific constant region is referred to, i.e., antibodies MICA.2, MICA.20, MICA.21, MICA.22, MICA.36, MICA.38, MICA.39 and MICA.40, MICA.52. MICA.53, and MICA.54 may have any desired constant region. A G236A mutation (by EU numbering) was made in the heavy chain constant region of MICA.36 to create antibody MICA.36-G236A. Non-fucosylated anti-MICA/B antibody MICA.36-IgG1-NF-G236A was expressed by cloning the MICA.36-G236A sequences into the FUT8-knock-out CHO cells (POTELLIGENT® Cells) available from BioWa, Inc. (Princeton, N.J.).

Example 3. Binding Affinity of Anti-MICA/B Antibodies to Human MICA Alleles Determined by Surface Plasmon Resonance Kinetics and affinity of anti-MICA/B antibodies towards human MICA alleles were determined on a BIACORE T200® instrument at 37° C. with pH 7.4 running buffer (0.01 M HEPES pH 7.4, 0.15 M NaCl, 0.05% v/v Surfactant P20, 1 mg/mL BSA). Anti-MICA/B antibodies were captured to u-human Fc surfaces. MICA allele antigens were injected at high and low nanomolar concentrations (500 nM and 50 nM, except indicated otherwise). The results for antibodies M1CA.36 and MICA.38 (MICA.2 with a Ser inserted between residues 95 and 96 in the light chain) are shown in Table 2 below. Kinetic fits of MICA alleles of the MICA.36 and MICA.38 antibodies are shown in FIGS. 6A-6H.

TABLE 2

Antibody affinity for MICA alleles by SPR.

| Antibody | MICA Allele (antigen) | ka (1/Ms) | kd (1/s) | KD (nM) |
|---|---|---|---|---|
| MICA.36hIgG1 | MICA*002 | 2.86E+04 | 1.61E−02 | >250 (>½ highest analyte conc) |
|  | MICA*004 | 4.62E+04* | 6.37E−04* | 6.2-13.8 |
|  |  | 9.52E+04 | 5.91E−04 |  |
|  | MICA*008 | 1.20E+05* | 6.06E−04* | 4.0-5.1 |
|  |  | 1.40E+05 | 5.65E−04 |  |
|  | MICA*009 | 5.41E+04* | 6.42E−04* | 8.6-11.9 |
|  |  | 7.01E+04 | 6.03E−04 |  |
| MICA.38_3F5_S95k | MICA*002 | 1.03E+06 | 1.27E−01 | 123 |
|  | MICA*004 | 4.10E+05 | 4.26E−02 | 104 |
|  | MICA*008 | 6.00E+05 | 7.80E−02 | 130 |
|  | MICA*009 | 3.97E+05 | 5.02E−02 | 126 |

*These results were obtained using 100 nM and 10 nM antigen concentrations.

Kinetics and affinity of anti-MICA/B antibodies MICA.2, 19G6, 16A5, and 71C2 towards human MICA alleles (hu-MICA-his allele *002, *004, *008, and *009) were also determined on a BIACORE 3000® instrument using the following conditions:

Running Buffer: HES-EP running buffer
Chip: CM5 Protein G Chip Fc1: Blank. Fc2-4: ~200Rus
Ab: 5 ug/mL, 10 uL@10 uL/min
Ag binding: 5 min association, 7 min dissociation @ 25 uL/min,
Regeneration: Glycine 1.7, 10 uL@100 uL/min followed by 60s wash by HES-EP The results of the BIACORE® analysis are shown in Table 3 below. Kinetic fits of MICA alleles of MICA.2, 19G6, 16A5, and 71C2 are shown in FIGS. 6I-6L.

TABLE 3

Antibody affinity for MICA alleles by SPR

| Antibody | MICA Allele (antigen) | KD (nM) | ka (1/Ms) | kd (1/s) |
|---|---|---|---|---|
| MICA.2 | MICA*002 | 27.5 | 3.80 | 10.4 |
|  | MICA*004 | 54.6 | 5.21 | 28.4 |
|  | MICA*008 | 40.5 | 6.09 | 24.6 |
|  | MICA*009 | 61.5 | 3.77 | 23.2 |
| 19G6 | MICA*002 | 219 | 0.37 | 8.14 |
|  | MICA*004 | 9.78 | 2.34 | 2.28 |
|  | MICA*008 | 5.23 | 3.58 | 1.87 |
|  | MICA*009 | 13.7 | 1.57 | 2.15 |
| 16A5 | MICA*002 | 147 | 0.71 | 10.4 |
|  | MICA*004 | 6.89 | 2.50 | 1.72 |
|  | MICA*008 | 4.55 | 3.79 | 1.72 |
|  | MICA*009 | 12.9 | 1.66 | 2.15 |
| 71C2 | MICA*002 | 3010 | 0.03 | 11.6 |
|  | MICA*004 | 262 | 1.15 | 30.3 |
|  | MICA*008 | 39.9 | 2.72 | 10.9 |
|  | MICA*009 | 1400 | 0.23 | 32.5 |

Example 4. Binding Affinity of Anti-MICA/B Antibodies for Human and Cyno MICA/B Determined by Scatchard Analysis The MICA.36 antibody was radioiodinated with $^{125}$I-Na (1 mCi; PerkinElmer Catalog NEZ033H001 MC) using IODO-GEN® solid phase iodination reagent (1,3,4,6-tetrachloro-3a-6a-diphenylglycouril; Pierce, Catalog 28601). Excess iodide was removed using a desalting column (Pierce, Catalog 43243). Fractions of labeled antibody were collected and analyzed for radioactivity on a Wizard 1470 gamma counter. The $^{125}$I-MICA.36 antibody concentration in each fraction was calculated with the Qubit fluorometer from Invitrogen. Radiopurity was established by thin layer chromatography of peak protein and radioactive fractions (Pinestar Technology, Catalog 151-005).

Radio-iodinated MICA.36 antibody binding to human MICA/B endogenously expressed on 786-0 and SW480 cells, as well as human MICA-, human MICB- or cyno MICA/B-transduced CHO cells was demonstrated by incubating cells with a titration of $^{125}$I-MICA.36. Nonspecific binding was determined by binding in the presence of a titration of a 100 fold molar excess of unlabeled antibody and was subtracted from total counts per minute (CPM) to calculate specific binding. A linear standard curve of $^{125}$I-MICA.36 concentration versus CPM was used to extrapolate specific activity, maximal nM bound $^{125}$I-MICA.36 and thereby calculate receptor number per cell.

Specific activity of the iodinated MICA.36 was determined by plotting antibody titrations against the associated CPMs in a standard curve (FIG. 7A). The specific activity was calculated to be 164,214 CPM in 1 nM of $^{125}$I-MICA.36. The number of receptors per cell was calculated by the following equation: (Bmax)×(Avogadro's number)×(Assay Volume)/# of cells per well.

The results show that the MICA.36 antibody has an affinity of about 1-2 nM for overexpressed human MICA*008 (FIG. 7B) and MICB*005 (FIG. 7C) on CHO cells, an affinity of about 5-11 nM for overexpressed cyno MICA/B (FIGS. 7D and 7E), and an affinity of about 0.4 nM for human MICA/B endogenously expressed on 786-0 (FIG. 7F) and SW480 (FIG. 7G) cells.

Example 5. Binding of Anti-MICA/B Antibodies to Cell Surface Human MICA/B and Cross-Reactivity to Cynomolgus MICA/B Molecules in Flow Cytometry Serial dilutions of MICA.36-IgG1-NF-G236A mAb were incubated with CHO cells transduced with human MICA/B common alleles or human tumor cell lines that endogenously express MICA/B. Cells were then washed twice, and cell bound antibodies were detected using a secondary anti-human antibody conjugated with a fluorophore. Flow cytometric analyses were performed using a FACSCantoII or FACS Fortessa X-20 flow cytometer. The geometric mean fluorescence intensity of MICA.36-IgG1-NF-G236A mAb bound to cells was determined using FlowJo analysis software. Dose-response curves were generated and EC50s calculated using Prism software.

To measure cross-reactivity to Cynomolgus ("cyno") MICA/B Molecules, serial dilutions of MICA.36-IgG1-NF-G236A mAb were incubated with CHO cells transfected with two cyno MICA/B clones. Cell-bound antibody was detected using a secondary anti-human antibody conjugated with a fluorophore. Flow cytometric analyses were performed using a Fortessa X-20. After gating on FSC-SSC-7AAD parameters to exclude debris and dead cells, the mean fluorescence intensity of MICA.36-IgG1-NF-G236A mAb was determined using FlowJo analysis software.

In a flow cytometry experiment, the titration of 19G6 mAb on CHO cells ectopically expressing human MICA/B common alleles showed 19G6 bound well to native human MICA/B molecules. Data is shown in FIGS. 8A and 8B.

Cross-reactivity of 19G6 to cynomolgus monkey MICA/B was demonstrated by the binding of 19G6 to two cyno MICA/B clones transfected into CHO cells. In flow cytometry experiments, 19G6 bound well to CHO-cyno MICA clone #4 and CHO-cyno MICA clone #6. Data from one representative experiment is shown in FIG. 8C. The EC50 was 1.08 nM for cyno clone #4 and 22.02 nM for cyno clone #6, indicating that 19G6 binds cyno MICA/B with similar potency to human MICA/B.

MICA.36-IgG1-NF-G236A bound to endogenously expressed MICA/B on a variety of human tumor cell lines (FIG. 8B). EC50 values for binding to human tumor cell lines expressing MICA alleles (in parenthesis) 786-0 (*008), HeLa (*008), A2058 (*008/*018), and RPMI-8226 were 1.37 nM, 1.76 nM, 5.4 nM, and 3.90 nM, respectively.

Other anti-MICA/B antibodies, e.g., 24G11, 71C2, 16A5 (#1 and #2 are derived from two hybridoma lines from the same clone), were tested using similar method (Tables 4 and 5 below) (FIG. 8D-8H)

TABLE 4

EC50 (nM) of anti-MICA/B antibodies for common human MICA/B alleles and cyno MICA/B

| Ab | *002 | *004 | *008 | *009 | *010 | MICB | cyno#4 | cyno#6 |
|---|---|---|---|---|---|---|---|---|
| MICA.2 | 5.367 | 2.938 | 2.138 | 1.56 | 6.912 | 5.996 | 1.967 | 4.011 |
| 24G11 | 1065 | 517.5 | 247.7 | 496.9 | 722.5 | 262.2 | 394.5 | 330.6 |
| 71C2 | 264.3 | 26.21 | 10.03 | 10.15 | 80.01 | 9.813 | 23.43 | 231.7 |
| 19G6 | 151.7 | 11.39 | 9.229 | 8.21 | 18.48 | 1.826 | 1.076 | 22.02 |
| 16A5 (#1) | 25.32 | 1.043 | 2.219 | 0.9019 | 15.15 | 8.159 | 0.856 | 9.256 |
| 16A5 (#2)* | 613.6 | 65.25 | 394.6 | 122.1 | 246.5 | 21.62 | 2.384 | 13.77 |

TABLE 5

EC50 (nM) of anti-MICA/B antibodies for MICA/B endogenously expressed on human tumor cell lines

| | FACS EC50 (nM) | | | |
|---|---|---|---|---|
| Ab | 786-O | A2058 | HeLa | RPMI-8226 |
| MICA.2 | 4.951 | 2.609 | 1.738 | 41.89 |
| 24G11 | 146.7 | 260.7 | 192.3 | 103.9 |
| 71C2 | 13.75 | 33.54 | 10.15 | 36.92 |
| 19G6 | 1.369 | 5.394 | 1.756 | 3.891 |
| 16A5 (#1) | 2.484 | 7.685 | 3.761 | 7.998 |
| 16A5 (#2) | 11.63 | 10.95 | 16.2 | 2.442 |

Example 6. Binning of Anti-MICA/B Antibodies

The binning experiments were performed on an Octet HTX instrument at 25° C. in HEPES buffered saline (10 mM HEPES pH 7.4, 150 mM NaCl, 0.05% v/v surfactant P20, and 1 mg/mL BSA). Anti-MICA/B antibodies and NKG2D-mFc were captured on anti-Fc tips and remaining capture sites were blocked with an excess of negative control IgG. Recombinant soluble MICA (allele 8) was bound and subsequent binding ("sandwiching") of anti-MICA/B antibodies was tested.

The tested antibodies fell into two non-overlapping epitope bins. Members of each bin cannot simultaneously bind to MICA (indicating overlapping epitopes), but members of different bins can.

Results of the binning experiments are presented in Table 6. Antibodies MICA.2, MICA.38, MICA.39, and MICA.40 were in the same epitope bin. Antibodies 24G11 (MICA.54) and MICA.36 formed a second, non-overlapping bin. These antibodies do not block NKD2D binding to MICA.

TABLE 6

Binning of Anti-MICA/B antibodies.

| Ligand (Ab) | MICA.2 | MICA.38 | MICA.39 | MICA.40 | 24G11 | MICA.36 |
|---|---|---|---|---|---|---|
| MICA.2 | 0 | 0 | 0 | 0 | 1 | 1 |
| MICA.38 | 0 | 0 | 0 | 0 | | 1 |
| MICA.39 | 0 | 0 | 0 | 0 | | 1 |
| MICA.40 | 0 | 0 | 0 | 0 | | 1 |
| 24G11 | 1 | 1 | 1 | 1 | 0 | 0 |
| MICA.36 | 1 | 1 | 1 | 1 | 0 | 0 |

("0" = no simultaneous binding; "1" = simultaneous binding)

Example 7. Epitope Mapping by HDX

Hydrogen/deuterium exchange mass spectrometry (HDX-MS), under both normal and high-resolution modes, was utilized to probe binding epitopes of MICA with mAbs MICA.2, MICA.39, MICA.40, MICA.36 NF G236A and MICA.36.

HDX-MS probes protein conformation and conformational dynamics in solution by monitoring the rate and extent of deuterium exchange of backbone amide hydrogen atoms. The level of HDX depends on the solvent accessibility of backbone amide hydrogen atoms and the protein hydrogen bonds. The mass increase of the protein upon HDX can be precisely measured by MS. When this technique is paired with enzymatic digestion, structure features at the peptide level can be resolved, enabling differentiation of surface exposed peptides from those folded inside. The addition of gas-phase fragmentation for the selected peptide regions by MS provides high resolution HDX information at the amino acid level. Typically, the deuterium labeling and subsequent quenching experiments are performed, followed by enzymatic digestion, peptide separation, and MS analysis.

Prior to epitope mapping experiments, non-deuterated experiments were carried out to generate a list of common peptides for recombinant full length extracellular domain (ECD) of human MICA-His tag (Allele 08, 15 µM), generated in-house, and protein complex of MICA and mAb (1:1 molar ratio). In the HDX-MS experiment, 5 µL of each sample (MICA or MICA with mAb) was diluted into 55 µL of $D_2O$ buffer (10 mM phosphate buffer, $D_2O$, pH 7.0) to start the labeling reactions. The reactions were carried out for different periods of time: 20 sec, 1 min, 10 min and 240 min. By the end of each labeling reaction period, the reaction was quenched by adding quenching buffer (1M PEEP in 8 M Urea, pH 2.5, 1:1, v/v) and 50 µL of quenched sample was injected into Waters HDX-MS system for analysis. The deuterium uptake levels of common peptic peptides were monitored in the absence/presence of MICA/B mAbs. For the high resolution HDX experiments, differential HDX was monitored between MICA and MICA with Fab of the MICA.36 antibody, and the peptide regions in MICA showing significant HDX reduction upon Fab of the MICA.36 antibody binding were further fragmented by MS/MS. The deuterium uptake levels of amino acid residues were monitored in the absence/presence of Fab of MICA.36.

The HDX-MS data analysis on MICA.2 (FIG. 9A), MICA.39 (FIG. 9B), and MICA.40 (FIG. 9C) in MICA indicates that all three mAbs have identical binding epitopes comprised of two regions of MICA:

Region 1:
$^{201}$LRRTVPPMVNVTRSEASEGN$^{220}$ (SEQ ID NO: 56)

Region 2:
$^{238}$TWRQDGVSLSHDTQQ$^{252}$ (SEQ ID NO: 57)

Based on relative deuterium uptake differences, region 2 has the most significant changes in deuterium uptake.

The HDX-MS data analysis on MICA.36 NF G236A and MICA.36 in MICA indicates that both molecules have identical epitopes, which are comprised of three regions of MICA (FIGS. 9D and 9E). The removal of fucose and G236A mutation have no impact on binding epitope.

Region 1:
$^{150}$WTVPQSSRAQTLAM$^{163}$ (SEQ ID NO: 52)

Region 2:
$^{231}$YPRNIILT$^{238}$ (SEQ ID NO: 53)

Region 3:
$^{253}$WGDVLPDGNGTYQTW$^{267}$ (SEQ ID NO: 55)

Based on relative deuterium uptake differences, three peptide regions can be ranked as region 3>2>1 with region 3 having the most significant changes in deuterium uptake.

This HDX study indicates that stabilizing variants of MICA.2 (MICA.39 and MICA.40) retained identical epitope maps to MICA.2. The binding epitope of MICA.36 on MICA was characterized to contain discontinuous binding regions as: $^{150}$WTVPQSSRAQTLAM$^{163}$ (SEQ ID NO: 52), $^{231}$YPRNIILT$^{238}$ (SEQ ID NO: 53) and $^{213}$WGDVLPDGNGTYQTW$^{267}$ (SEQ ID NO: 55), and the removal of fucose and G236A mutation have no impact on binding epitope.

In high-resolution HDX experiments using MICA.36 Fab, MICA.36 epitope regions 2 and 3 were selected, based on the levels of HDX reduction, for gas-phase fragmentation. The high-resolution HDX results allow the refinement of epitopes to:

Region 1:
$^{150}$WTVPQSSRAQTLAM$^{163}$ (SEQ ID NO: 52)

Region 2:
$^{234}$N, $^{237}$L

Region 3:
$^{255}$DVLPDGNGTYQ$^{265}$, $^{267}$W (SEQ ID NO: 54)

FIG. 9F shows these residues superimposed on the crystal structure of MICA bound to NKG2D.

Example 8. Epitope Mapping by Yeast Display

Library of MICA-ECD clones were generated using Genemorph 11 mutagenesis kit. This library of mutant MICA-ECD molecules were displayed on the surface of *S. cerevisiae* under a galactose-inducible promoter, using a C-terminal myc-Aga1 fusion. Galactose-induced yeast cells were labeled first with 100 nM human-anti-MICA/B antibodies and 100 nM mouse-anti-myc antibody 9E10. Cells were then labeled with PE-conjugated goat-anti-human and ALEXA-633™ conjugated goat-anti-mouse antibodies. To isolate populations of the library that block antibody-antigen interaction, labeled cells that showed good binding to anti-myc antibody, but reduced binding to anti-MICA/B antibodies were sorted using fluorescence-activated cell sorting. The sorted cell populations were then grown and enriched for by another round of labeling and sorting, as described above. DNA was isolated from the second round of sorted cells and the starting library. DNA samples were prepared for NGS sequencing using Nextera XT library preparation kit, multiplexed and sequenced using Miseq NGS sequencing. Resulting DNA sequence reads were analyzed to identify sequences found in the sorted populations that are especially enriched over the starting library. These enriched mutations were mapped on the structure of MICA-NKG2D complex (PDB ID: 1HYR) and showed well-defined patches on the protein surface (FIGS. 10D-10F). MICA.36, MICA.2 and 24G11 (MICA.54) antibodies bound to α3 domain of MICA. The epitopes were as follows: MICA.36: G254, D255, L257, Y264, W267 (FIG. 10A) MICA.2: R240, Q241, D242, V244, R279 (FIG. 10B) 24G11: P258, G260, G262, Y264 (FIG. 10C)

Example 9. Retention of Surface MICA and Reduction of Soluble MICA (sMICA) In Vitro by Anti-MICA/B Antibody Non-human cell lines that ectopically express MICA/B were cultured for 48 hours with MICA.36-IgG1-NF-G236A or isotype control. After culture, cells were collected and surface MICA/B level was measured by staining with anti-MICA/B antibody clone 6D4. The supernatant was collected and soluble MICA (sMICA) level was measured using a MICA ELISA kit (Abeam ab100592). MICA.36-TgG1-NF-G236A increased the surface MICA level on cells, measured by flow cytometry (FIGS. 11A-11D), and reduced the amount of sMICA in culture supernatant, quantified by ELISA (FIG. 12A-12D), as compared to the isotype control (IgG1 NF).

In addition, human cell lines that endogenously express MICA were cultured for 48 hours with MICA.36-IgG1-NF-G236A or isotype control. After culture, cells were collected and surface MICA/B level was measured by staining with anti-MICA/B antibody clone 6D4. MICA.36-IgG1-NF-G236A increased the surface MICA level on cells, measured by flow cytometry (FIGS. 13A-13E), and reduced the amount of sMICA in culture supernatant, quantified by ELISA (FIG. 14A-14C). Thus, MICA.36-IgG1-NF-G236A retains MICA/B on the tumor cell surface and leads to reduction in sMICA/B. MICA retention EC50 (nM) and reduction in sMICA IC50 (nM) are shown in Table 7:

TABLE 7

Retention of surface MICA and reduction of sMICA

| Cell line | MICA allele | Binding EC50 (nM) | MICA retention EC50 (nM) | Fold increase in surface MICA | Reduction in sMICA EC50 (nM) | % decrease in sMICA |
|---|---|---|---|---|---|---|
| 786-O | 008 | 1.37 | 0.057 | 1.47 | 0.14 | 66 |
| HELA | 008 | 1.76 | 0.032 | 1.43 | 0.10 | 32 |
| A2058 | 008/018 | 5.4 | 0.093 | 2.41 | | 15 |
| HCT116 | 001/009 | 0.37 | 0.043 | 1.98 | 0.075 | 62 |

Example 10: MICA.36-IgG1-NF-G236A Showed Enhanced Affinity for CD16a and CD32a MICA.36-IgG1-NF-G236A, a nonfucosylated (NF) human IgG1 antibody containing an engineered mutation in the heavy chain, G236A, showed higher affinity for CD16a (FcγRIIIa) and CD32a (FcγRIIa) than native IgG1. The binding of human FcγRs to MICA.36-IgG1-NF-G236A was studied by surface plasmon resonance (SPR) and compared to MICA.36 antibodies with wild type human IgG1, IgG1f-G236A and IgG1f-NF isotypes, as well as non-MICA binding control human IgG1 and NF antibodies. For these studies, protein A was immobilized on flow cells 1-4 of the CM5 sensor chip using standard ethyl (dimethylaminopropyl) carbodiimide (EDC)/N-hydroxysuccinimide (NHS) chemistry, with ethanolamine blocking, in a running buffer of 10 nM HEPES pH 7.4, 150 mM NaCl, 3 mM EDTA, 0.05% surfactant p20, to a density of ~3000 RU. Antibodies at 3 µg/mL were captured on the protein A surface to a density of ~200-400 RU, and the binding of FcγR analytes was tested in miming buffer consisting of 10 mM NaPO4, 130 mM NaCl, 0.05% p20, buffer (PBS-T) pH 7.1 at 25° C., using 120 s association time and 180 s dissociation time at a flow rate of 30 µL/min To determine the kinetics and affinity of binding, an FcγR concentration series (3:1 dilution) from 1 µM down to 0.15 nM (CD64 proteins) or 10 µM down to 1.5 nM (all other FcγRs) was tested. The kinetic data were fit to either a 1:1 Langmuir model or to a steady-state model using BIACORE® T200 evaluation software.

Table 8 shows enhanced binding affinities of MICA.36-IgG1-NF-G236A to human CD16a and CD32a alleles, as measured by SPR.

TABLE 8

Surface Plasmon Resonance Affinity Values for Human FcγRs

| Antibody | hCD16a-V158 | hCD16a-F158 | hCD32a-H131 | hCD32a-R131 |
|---|---|---|---|---|
| MICA.36-IgG1-NF-G236A | 31 | 420 | 140 | 220 |
| MICA.36 IgG1 | 360 | >5000 | 780 | 1300 |
| MICA.36 IgG1 NF | 8 | 140 | 730 | 770 |
| MICA.36 IgG1 G236A | 850 | >5000 | 130 | 260 |
| Control IgG1 | 480 | >5000 | 1000 | 1700 |
| Control IgG1 NF | 9.1 | 170 | 860 | 860 |

Example 11: MICA.36-IgG1-NF-G236A Mediated Enhanced Antibody Dependent Cellular Phagocytosis (ADCP) and Antigen Cross Presentation Dendritic cells (DCs) have the capacity to engulf tumor cells, process and present tumor antigen, and prime tumor-specific T cell responses. It has been shown that opsonization of MICA/B expressing tumor cell lines with anti-MICA/B antibody can enhance cross-presentation of tumor antigen by dendritic cells and subsequent priming of antigen specific CD8+ T cells (Groh, V.; PNAS 2005; 102:6461-6). The antibody MICA.36-IgG1-NF-G236A was assessed for to ADCP and antigen cross presentation. Bone marrow derived dendritic cells (BMDC), from human Fc transgenic mice (a mouse strain where all mouse FcγRs were deleted and human FcγRs, encoded as transgenes, were inserted, resulting in recapitulation of human FcγR expression) (Smith, P., et al., 2013, Proc Natl Acad Sci USA.; 109:6181-6) were used as effectors. To make BMDC, bone marrow were isolated from human Fc transgenic mice and cultured in vitro with mGM-CSF (10 ng/ml) and mIL-4 (5 ng/ml) and half of the media was changed on day 2 and day 4. BMDCs were harvested on day 5. Typically, over 80% of total cells were CD11c positive by flow cytometry staining, indicating good BMDC induction. B16.F10 melanoma cells transduced with MICB, GFP and Ova, referred to as B16.F10-MICB-GFP-ova cells, were used as target cells.

For ADCP assay, B16.F10-MICB-GFP-ova cells were opsonized with MICA.36 Abs for 30 minutes at 4C. Cells were then irradiated to halt growth, and incubated with BMDC for 24 hours, after which the culture was stained with anti-mouse CD11c antibody and phagocytosis was assessed by flow cytometry. Phagocytosis were calculated as the percentage of CD11c+GFP+ cells out of total CD11c+ dendritic cells. Enhanced ADCP was observed with the G236A variants of the antibody (MICA.36-IgG1-NF-G236A and MICA.36 IgG1 G236A) compared to IgG1 or IgG1 NF variants of MICA.36 (FIG. 15A). An EC50 of 10.7 nM was measured for MICA.36-IgG1-NF-G236A when BMDCs from human FcγR transgenic mice were used as effectors, and B16-MTCB-GFP-Ova cells were used as target cells.

For antigen cross-presentation assay, proliferation of OT-I CD8+ T cells specific to the ova antigen is an indicator of how efficient BMDCs process and cross-present the ova antigen from the B16.F10-MICB-GFP-ova cell to CD8+ T cells.

To measure antigen cross-presentation, B16.F10-MICB-GFP-ova cells were opsonized with the MICA.36 antibody for 30 minutes at 4° C. Cells were then irradiated to halt growth, and incubated with BMDC for 24 hours. Then CD8+ T cells purified from spleens of OT-1 mice (C57BL/6-Tg(TcraTcrb)1100Mjb/J, The Jackson Laboratory) were labeled with Cell Trace Violet and added to the culture for 4 days. Then proliferation was assessed by flow cytometry. Proliferation was calculated as die percentage of CD8+ T cells with Cell Trace Violet dilution out of total CD8+ T cells. Proliferation of OT-I CD8+ T cells serves as an indicator of how efficient BMDCs processed and cross-presented the Ova peptide to CD8+ T cells. Enhanced OT-I CD8+ T cell proliferation was observed with MICA.36-IgG1-NF-G236A with EC50 of 1.6 nM (FIG. 15A).

Example 12: MICA.36-IgG1-NF-G236A Mediated Enhanced Antibody-Dependent Cell-Mediated Cytotoxicity (ADCC)

The ability of anti-MICA/B antibodies to mediate ADCC activity were tested using human NK cells as effectors and Raji cells ectopically expressing MICA*009, or A375 melanoma cells endogenously expressing MICA, as the target cells.

Target cells were plated at 5,000 cells/well (A375) or 10,000 cells/well (Raji-MICA) in 96-well white flat-bottom (A375) or V-bottom (Raji-MICA) plates. An equal volume of titrated test or control antibodies were added to the target cells and incubated at 37° C. for 2 days.

On the following day, PBMCs were purified from heparinized whole blood samples by density gradient centrifugation and washed with PBS supplemented with 2% FBS (HyClone). NK cells were isolated from PBMCs by negative selection using a magnetic bead-based separation kit (Miltenyi Biotec). Purified NK cells were resuspended at $1 \times 10^6$ cells/mL in MYELOCULT™ (Stemcell Technologies) media supplemented with 500 IU/mL IL-2 and incubated overnight at 37° C.

After overnight incubation, activated NK effector cells were washed twice in ADCC assay media (RPMI-1640 with L-glutamine, phenol red-free supplemented with 10% ultralow IgG FBS) and the concentration was adjusted to $5 \times 10^5$ cells/mL. Target cells incubated with test antibodies were washed and resuspended in 100 uL of media. Activated NK effector cells were then added (100 µL/well) to result in a final effector cell-to-target cell ratio (E:T) of 10:1. The plate was then placed in a humidified 37° C. incubator for 4 hours.

For adherent A375 cells, NK cell containing supernatant was removed and target cells washed with media before addition of 100 uL of media. CellTiter-Glo reagent (Promega) was prepared and equilibrated at room temperature before 100 uL/well was added to target cells. Luminescence was detected on an Envision plate reader with the signal proportional to viable cell number. The percentage of specific cell lysis was calculated using the formula [100−((luminescence of Sample−luminescence of maximal killing)/(luminescence of spontaneous lysis−luminescence of maximal killing)*100)].

For suspension Raji-MICA cells, target and effector cells were stained for CD3 and CD56 (Biolegend), with eBioscience Fixable Viability Dye (Invitrogen), and fluorescence read by a LSRFortessa flow cytometer (BD Biosciences). NK cells (CD3−, CD56+) were excluded and remaining cells were assessed for cell death (FVD+). The percentage of specific cell lysis was calculated using the formula [Percent sample cell death−percent spontaneous cell death].

Target cells alone provided the control of spontaneous lysis, while target cells lysed with 100 µL/well of 5% TWEEN-20™ lysis buffer represented maximal killing in the assay. Percentage of target cell lysis was plotted for each antibody using Prism v7 software from GraphPad Inc.

Enhanced ADCC was observed with the NF variants of the antibody (MICA.36-IgG1-NF-G236A and MICA.36 IgG1 NF) compared to IgG1 or IgG1 G236A variants of MICA.36 (FIGS. 16A and 16B).

Example 13: Efficacy Study in B16.F10-MICA Lung Metastasis Model

Human MICA/B is recognized by the murine NKG2D receptor, which enabled testing of anti-MICA/B antibody in fully immunocompetent mouse models. Full-length MICA protein was ectopically expressed in the murine B16F10 melanoma, MC38 colon adenocarcinoma, and EG7-ova thymoma cell lines, and the activity of the MICA.36 antibody with either human Fc (IgG1 NF G236A, IgG1 NF or IgG1) or mouse Fc (IgG2a or IgG1-D265A) was evaluated using human FcγR-Tg mice and wild type mouse strains (expressing murine FcγRs), respectively.

At day 0, mice (C57BL/6 huFcγR transgenic mice) were given an intravenous (IV) injection of 2000 µL B16.F10-MICA cells (B16.F10 melanoma cells transduced with MICA) into the lateral tail vein at a concentration of $2 \times 10^6$ cells/mL. At day 3 and day 8, animals were given an intraperitoneal (IP) injection of MICA.36-IgG1-NF-G236A at 5 mg/kg. At day 14, lungs were harvest for measurement of B16.F10-MICA cell tumor metastasis. A human IgG1 non-fucosylated mAb (in-house) served as the isotype control.

Briefly, lungs were photographed with the presence of a metric scaled ruler positioned on the same horizontal plane as the lungs. Using ImageJ software, the images were scaled, adjustments were made for color balance, threshold was set and the region of interest was selected. A determination of metastasis particle size and count was performed. Analysis was made by the cumulative area ($mm^2$) of metastases in a given surface area or by total counts of metastases in a given surface area.

At day 14, serum was collected and stored at −20° C. before measuring sMICA using a ELISA kit (Abeam ab100592).

MICA.36 antibodies with IgG1 NF isotype (MICA.36-IgG1-NF-G236A and MICA.36 IgG1 NF) were effective in reducing the total tumor area formed by B16F10-MICA tumor cells as well as the sMICA level in the serum of the mice compared to the isotype control (see FIGS. 17A and 17B).

Example 14: Dose Escalation Studies in B16.F10-MICA Lung Metastasis Model

At day 0, mice (C57BL/6 huFcγR transgenic mice) were given an intravenous (IV) injection of 100 µL B16.F10-MICA cells into the lateral tail vein at a concentration of $1 \times 10^7$ cells/mL. At day 1, animals were given an intraperitoneal (IP) injection of antibody at specified concentrations. At day 14, lungs were harvest for measurement of metastasis. A human IgG1 non-fucosylated mAb (BMS) served as the isotype control.

Briefly, lungs were photographed with the presence of a metric scaled ruler positioned on the same horizontal plane as the lungs. Using ImageJ software, the images were scaled, adjustments were made for color balance, threshold was set and the region of interest was selected. A determination of metastasis particle size and count was performed. Analysis was made by the cumulative area ($mm^2$) of metastases in a given surface area or by total counts of metastases in a given surface area.

Results from two separate studies showed reduction of the total tumor area in the mice administered with MICA.36-IgG1-NF-G236A (MICA.36 NF G236A), compared to the isotype control (3 mg/kg) (FIGS. 18A and 18B).

Example 15: Efficacy of MICA.36-IgG1-NF-G236A (MICA.36 NF G236A) in MICA Transgenic Mice with EG7-MICA Tumors To evaluate the therapeutic efficacy of anti-MICA/B antibody in MICA tolerant mice, transgenic mice were generated in which human MICA *009 was expressed in the prostate gland of C57BL/6 mice under the control of the probasin promoter (MICA transgenic(Tg) mice) (Liu, G. et al., 2013; J. Clin. Invest. 123, 4410-22). MICA-Tg male mice were able to tolerate growth of MC38 cells ectopically expressing MICA (MC38-MICA), whereas the same tumor implanted in C57BL6 or human FcγR-Tg mice, or MICA-Tg female mice were largely rejected. Accordingly, following MC38-MICA implantation, male MICA-Tg mice showed lower production of autoantibodies against human MICA compared to wild type C57BL6 or human FcγR-Tg mice. Together, these results suggest that MICA-Tg mice are tolerant to MICA protein and MICA expressing tumors.

The efficacy of anti-MICA/B antibodies was evaluated using subcutaneous (SubQ) implantation of EG7, an EL4 thymoma cell line expressing high levels of MICA and the peptide ovalbumin. MICA.36 antibody with either Fc functional (MICA.36-mg2a which has a mouse Fc that is most similar to IgG1 NF) or Fc inert (MICA.36-mg1-D265A which has a mutation in mIgG1 that abrogates binding to mouse CD16) were tested alone or in combination with anti-PD-1 antibody.

The day of tumor implantation was designated as day 0 in the study. B6.F10-MICA transgenic mice were given a SubQ injection of 100 µl EG7-MICA tumor cells at a concentration of $5 \times 10^7$ cells/mL ($5 \times 10^6$ cells/mouse). Five days after implantation, the mice were randomized and dosing was initiated. The mice were given an intraperitoneal (IP) injection of specified antibody (antibodies) at a dose volume of 10 mL/kg each antibody once every 3 days for a total of 3 doses. The following antibodies were tested in various combinations: Anti-mouse PD-1 mIgG1 with D265A Fc mutation, Anti-Human MICA.36 mIgG2a, Anti-Human MICA.36 mIgG1 with D265A Fc mutation, and isotype controls mIgG1 (MOPC-21, BioXCell) and mIgG2a mAb (C1.18.4, BioXCell).

Tumor response was determined by measurement of tumors with a caliper twice a week, until the tumors reached a predetermined "target" size of 1 cm$^3$ (FIGS. 19A and 19B). Tumor volumes [mm$^3$] were estimated from the formula: Tumor volume [mm$^3$]=(length [mm]×width [mm]$^2$)/2.

Percent tumor growth inhibition (TGI %) for each treatment group was determined by calculating the median individual TGI of that group (FIG. 19C). Individual TGI at day-'t' calculated from all treatment animals was determined by the formula:

$$[1-((T_t/T_0)/(C_t/C_0))]/[(C_t-C_0)/C_t]*100 \quad \text{[Formula 1]}$$

Where $T_t$=individual tumor size of treated animal at time 't', $T_0$=individual tumor size of treated animal at first measurement, $C_t$=median tumors size of control animals at time 't', $C_0$=median tumor size of control animals at first measurement.

Animals considered 'progression free' at time T have tumor sizes (mm$^3$) that are less than 4 times their initial measurement (FIG. 19D).

Serum was collected at day 11. Serum level of sMICA was measured using the Meso Scale Discovery (MSD) platform (FIG. 19E). MICA.38 was used as a capture antibody and MICA.2 was used as a detection antibody. MICA.36 antibodies reduced sMICA in the serum compared to isotype control (FIG. 19E).

While in this study, MICA.36-mg2a did not exhibit much single agent activity, in another study the antibody showed effect on tumor growth inhibition (Example 16). Combined MICA.36-mg2a/anti-PD-1 treatment, however, enhanced tumor regression and extended survival compared with single antibody treatment (FIGS. 19C and 19D). 70% of mice were tumor free (TF) following combination treatment, whereas 10% and 50% were TF following individual administration of MICA.36-mg2a and anti-PD-1 antibodies, respectively. Consistent with observations in lung metastasis models, MICA.36 antibodies, alone or in combination with anti-PD-1 antibody, led to a significant reduction in serum sMICA (FIG. 19E). Enhanced antitumor activity with MICA.36-mg2a/anti-PD-1 combination treatment was associated with increased infiltration of T and NK cells into the tumor, as well as increased level of Ki67 and activation marker expression on T and NK cells in tumor draining lymph nodes. MICA.36 Fc inert (MICA.36-mg1-D265A) was not active either as a single agent or in combination with anti-PD-1 antibody (although led to reduction in serum sMICA).

Example 16: In Vivo Studies in B6-MICA Transgenic Mice

In this experiment, B6-MICA transgenic mice were given a subcutaneous (SubQ) injection of 100 EG7-MICA tumor cells. Six days after implantation, the mice were randomized and dosing was initiated. The mice were given a combination of antibodies Anti-mouse CTLA4 mIgG2a, Anti-Human MICA.36 mIgG2a, and isotype control mIgG2a mAb (C1.18.4, BioXCell), at a dose volume of 10 mL/kg of each antibody once every 3 days for a total of 3 doses, as described in Example 15.

The MICA.36 antibody reduced tumor volume and increased TGI alone and in combination with the anti-CTLA4 antibody (FIGS. 20A-20C). The MICA.36 and anti-CTLA4 antibody combination showed extended progression-free survival compared with single antibody treatment (FIG. 20D).

Example 17: In Vivo Studies in B6-MICA Transgenic Mice

B6-MICA transgenic mice were given a subcutaneous (SubQ) injection of 100 µl EG7-MICA tumor cells and treated with the following antibodies as described in Example 16 (dose volume of 10 mL/kg of each antibody once every 3 days for a total of 3 doses): Anti-mouse PD-1 mIgG1 with D265A Fc mutation, Anti-Human MICA.36 mIgG2a, and isotype controls mIgG1 (MOPC-21, BioXCell), mIgG2a mAb (C1.18.4, BioXCell).

The MICA.36 antibody reduced tumor volume and increased TGI alone and in combination with the anti-PD-1 antibody (FIGS. 21A-21C). The MICA.36 and anti-PD-1 antibody combination prolonged progression-free survival (FIG. 21D).

Example 18. Solubility of Anti-MICA/B Antibodies

The MICA.2 and MICA.36 antibodies were expressed in CHO cells by recombinant methods. A 1 mL frozen vial of MICA.36 CHO clone or MICA.2 CHO clone was thawed for a scale-up production. The cell culture was incubated in CD CHO medium supplemented with 8 mM glutamine, 1×HT, and 500 ug/mL G418 in an incubator with set point at 37° C. and 8% $CO_2$. Cells were initially grown in a 250 mL shake flask at 100 mL working volume and scaled up to 2L in two 3L Corning Fernbach flasks for batch production. The culture were incubated for 10 days during the production stage and harvested when viability dropped below 40%.

The culture was clarified and filtered with a 0.8/0.2 um sterile filter, and submitted for downstream processing.

Cell culture supernatant was applied to Protein A affinity chromatography column pre-equilibrated with PBS at pH 7.5. The column was washed with PBS (5 column volumes). The antibody was elated using 0.1M citrate buffer at pH 3. The antibody containing fraction was immediately neutralized with 2 M Tris buffer at pH 8.5 to bring the final pH to 7.2. The antibody was then dialyzed against PBS or histidine sucrose buffer. The antibody was stored in 4-8° C.

The MICA.2 antibody showed poor solubility. It showed turbidity during the elution and neutralization steps, and considerable precipitation during the dialysis and storage even at low concentration (<2 mg/ml) at 4-8° C. Duc to the precipitation, there was considerable material loss. The maximum solubility of the MICA.2 antibody was 2 mg/ml at neutral or slightly acidic pH. Formulation efforts could not increase the solubility of the MICA.2 antibody to more than 15 mg/ml which will not be acceptable for manufacturing purposes.

The MICA.36 antibody showed no turbidity during all the steps of purification and storage at concentrations of 7.88 mg/ml at 4° C. It does not precipitate during storage in aqueous buffer at neutral or slightly acidic pH even at concentrations above 7 mg/ml. The MICA.36-NF-G236A antibody, a variant of the MICA.36 antibody, was stable for 3 months at 40° C. at 50 mg/ml concentration.

Therefore, the MICA.36 and MICA.36-NF-G236A antibodies have superior solubility properties compared to the MICA.2 antibody.

Example 19. Epitope Mapping by X-Ray Co-Crystallography

Protein Expression and Purification:

The ECD of MICA*02 was cloned into the pVL1393 vector with an N-terminal honey bee melittin signal peptide and a C-terminal $His_6$ tag and expressed in T.ni cells (EXPRESSION SYSTEMS). The MICA.36 heavy chain and light chains were individually cloned in the pTT5 vector with an N-terminal osteonectin signal peptide. The heavy chain was also fused to a C-terminal $His_6$ tag. The MICA.36 Fab was expressed in Expi293 suspension cells. The MICA ECD and MICA.36 Fab were purified using Ni SEPHAROSE™ resin.

Crystallization and Structure Determination:

The MICA.36:MICA ECD complex was formed at a molar ratio of 1.2:1 and the complex was purified from unbound Fab by gel filtration in 50 mM NaCl, 10 mM Tris pH 8. Crystals were grown by sitting-drop vapor diffusion at 20° C. by mixing 0.2 μL concentrated protein sample (22 mg/mL) with 0.2 μL mother liquor (0.2 M sodium tartrate dibasic dehydrate, 30% PEG MME 550). The crystals were flash-cooled in liquid nitrogen and diffraction data were collected to 3.6 Å on the IMCA-CAT 17-ID beamline at the Advanced Photon Source. The dataset was processed in the $P6_5$ space group using XDS and the structure was determined by molecular replacement with Phaser using the Fab constant domain from PDB ID 4NM4, the CDR-trimmed Fab variable domain from PDB ID 1HEZ, and the MICA α3 domain from PDB ID 1HYR. The MICA α1-α2 domain could not be found by molecular replacement. One copy of the MICA α3:MICA.36 Fab complex was found in the asymmetric unit and was refined using Phenix and built using COOT.

Structural Analysis:

Solvent accessible surface area on MICA buried upon Fab binding was calculated using AREAIMOL with probe radius of 1.4Å. The MICA residues buried upon MICA.36 binding were: T222, T224, R226, W233, N234, H248, D249, Q251, Q252, W253, G254, D255, V256. L257, P258, D259, G260, N261, Y264, Q265, W267, and A269 (FIGS. 22A-22C).

Example 20. Comparative Studies on Binding to MICA

MICA.2 was compared to anti-MICA antibodies Ab2 (CM24002 Ab2) and Ab29 (CM33322 Ab29), which are disclosed in International Patent Application Publication WO2013/049517, as well as Ab28 (CM33322 Ab28), which is disclosed in International Patent Application Publication WO2015085210, for binding to cells expressing MICA.

Antibodies Ab2, Ab28 and Ab29 were also expressed in CHO cells by recombinant methods (MICA.5, MICA.7 and MICA.6, respectively). CHO cells transduced with MICA alleles 002, 004, 008,009, 010 were plated at 100,000 cells/well. Cells were incubated with purified anti-MICA/B antibodies for 30 minutes. Binding of the antibodies to the cells was detected using a secondary anti-human F(ab')2 antibody conjugated to a fluorophore. Flow cytometric analyses were performed using a FACSCantoII cytometer. The geometric mean fluorescence intensity of the antibodies bound to cells was determined using FlowJo analysis software. MICA.2 showed significantly stronger binding to all the CHO cell lines expressing various MICA alleles than MICA.5, MICA.7, and MICA.6 (FIGS. 23A and 23B).

The antibodies were also tested for binding to human RPMI-8226 cells. The cells were plated at 100,000 cells/well and incubated with anti-MICA/B antibodies for 30 minutes. The binding of the antibodies was detected using a secondary anti human F(ab')2 antibody conjugated to a fluorophore. Flow cytometric analyses were performed using a FACSCantoII cytometer. The geometric mean fluorescence intensity of the antibodies bound to cells was determined using FlowJo analysis software. MICA.1 and MICA.2 showed significantly stronger binding to RPM:I-8226 cells than Ab2, Ab28, and Ab29 and the supernatants ("supe") from CHO cell lines expressing their recombinant counterparts MICA.5, MICA.7, and MICA.6 (FIGS. 24A and 24B).

Example 21. Serum sMICA Measurement

B6-MICA transgenic mice were given a subcutaneous (SubQ) injection of 100 ul EG7-MICA cells at a concentration of 5e7 cells/mL (5e6 cells/mouse). The day of tumor implantation was designated as day 0 Animals were given an intraperitoneal (IP) injection of specified antibody at a dose volume of 10 mL/kg on day 5. Serum samples were collected on day 8 and 12 (72 and 168 hours after antibody dosing) for sMICA measurement.

A qualified ligand binding assay on Meso Scale Discovery (MSD) platform was used to measure total soluble MICA (sMICA) in EG7-MICA mouse serum. Briefly, a MSD gold 96-well streptavidin plate was coated with a biotinylated capture MICA antibody (MICA.1-bioin) first. The plate was then incubated with samples and allowed capture of sMICA on the plate. A ruthenylated detection MICA antibody (MICA.2-Ru) was added to complete the sandwich immunoassay. The total sMICA assay detected both recombinant and endogenous MICA forms in the presence of the MICA.36-mIgG2a. The assay read out was electrochemiluminescent (ECL). ECL was obtained after adding Read Buffer and read the plate on an MSD SECTOR instrument. The resulted ECL is a quantitative measure of the amount of sMICA that is present in the sample. 72 hours after antibody dosing, mice treated with MICA.36-mIgG2a at 1 mg/kg and 10 mg/kg had increased amount of sMICA in their serum; such an increase was not observed 168 hours after antibody dosing (FIG. 25).

Example 22, sMICA Pharmacokinetics (PK) Study

To measure IV PK, sMICA *009 was evaluated at 0.1 and 10 ug/kg doses in B6-MICA transgenic mice (non tumor bearing) in the presence and absence of the MICA.36-mIgG2a antibody. First, 10 mpk (10 mg/kg) dose of either MICA.36-mIgG2a antibody or KLH isotype control were administered via the intraperitoneal route (IP). Next, sMICA*009 was administered as an IV bolus injection 72 h post dosing of the MICA.36-mIgG2a antibody. Serum samples for PK analysis were collected at 2 min, 15 min, 30 min, 1 h, 6 h, 24 h, 72 h, 168 h, and 336 h post sMICA dosing to the mice. Non-compartmental PK analysis was used for estimating the PK parameters of sMICA and MICA.36-mIgG2a antibody. The levels of sMICA in 0.1 µg/kg dosed animals were below level of quantitation (BLQ). The T1/2 of 10 ug/kg sMICA when given alone is 0.07 h, but sMICA half-life is significantly longer in the presence of MICA.36-mIgG2a (3.5 h) (FIG. 26), likely due to a longer $T_{1/2}$ of sMICA-mAb complex relative to that of sMICA. The PK of MICA.36-mIgG2a is consistent with previous studies and was not impacted by sMICA dosing.

The foregoing description of the specific embodiments will so fully reveal the general nature of the invention that others can, by applying knowledge within the skill of the art, readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims All publications, patents, and patent applications disclosed herein are incorporated by reference to the same extent as if each individual publication, patent or patent application was specifically and individually indicated to be incorporated by reference.

This application claims the benefit of U.S. Provisional Application Nos. 62/647,556, filed Mar. 23, 2018, and 62/667,170, filed May 4, 2018, which are incorporated by reference herein in their entireties.

The invention claimed is:

1. An antibody that specifically binds to human WIC class I polypeptide-related sequence A (MICA) and/or human WIC class I polypeptide-related sequence B (MICB), comprising a heavy chain variable region (VH) and a light chain variable region (VL); wherein the VH comprises a VH complementarity determining region (CDR) 1, a VH-CDR2, and a VH-CDR3 and the VL comprises a VL-CDR1, a VL-CDR2, and a VL-CDR3; wherein the VH-CDR1 comprises the amino acid sequence set forth in SEQ ID NO:5, the VH-CDR2 comprises the amino acid sequence set forth in SEQ ID NO:6, the VH-CDR3 comprises the amino acid sequence set forth in SEQ ID NO:7, the VL-CDR1 comprises the amino acid sequence set forth in SEQ ID NO:8, the VL-CDR2 comprises the amino acid sequence set forth in SEQ ID NO:9, and the VL-CDR3 comprises the amino acid sequence set forth in SEQ ID NO:10.

2. The antibody of claim 1, wherein the antibody has one or more properties selected from the group consisting of:
   (a) the antibody inhibits shedding of human MICA by a tumor cell;
   (b) the antibody increases membrane bound human MICA on a tumor cell;
   (c) the antibody reduces soluble human MICA level in the serum in a patient;
   (d) the antibody mediates enhanced ADCC and/or ADCP;
   (e) the antibody mediates enhanced antigen processing and/or cross-presentation by a cell;
   (f) the antibody inhibits tumor growth and/or metastasis;
   (g) the antibody reduces tumor volume;
   (h) the antibody increases progression-free survival;
   (i) the antibody increases overall survival; and
   (j) any combination thereof.

3. The antibody of claim 1, wherein the VH comprises the amino acid sequence set forth in SEQ ID NO:2 and the VL comprises the amino acid sequence set forth in SEQ ID NO:4.

4. The antibody of claim 1, wherein:
the antibody comprises a heavy chain comprising the amino acid sequence set forth in SEQ ID NO:58, and a light chain comprising the amino acid sequence set forth in SEQ ID NO:60.

5. The antibody of claim 1, wherein the antibody binds an epitope on human MICA, wherein the epitope comprises:
   (a) one or more amino acid residues of human MICA selected from the group consisting of G254, D255, L257, Y264, W267, and any combination thereof corresponding to SEQ ID NO: 51, as determined by yeast surface display;
   (b) amino acid residues G254, D255, L257, Y264, and W267 corresponding to SEQ ID NO: 51, as determined by yeast surface display
   (c) amino acid residues W150-M163 corresponding to SEQ ID NO: 51, as determined by hydrogen/deuterium exchange mass spectrometry (HDX-MS);
   (d) amino acid residues Y231-T238 corresponding to SEQ ID NO: 51, as determined by HDX-MS;
   (e) amino acid residues D255-Q265 corresponding to SEQ ID NO: 51, as determined by HDX-MS;
   (f) amino acid residues W253-W267 corresponding to SEQ ID NO: 51, as determined by HDX-MS;
   (g) amino acid residues L201-N220 corresponding to SEQ ID NO:51, as determined by HDX-MS;
   (h) amino acid residues T238-Q252 corresponding to SEQ ID NO:51, as determined by HDX-MS;

(i) amino acid residues L201-N220 and T238-Q252 corresponding to SEQ ID NO:51, as determined by HDX-MS;
(j) amino acid residues R240, Q241, D242, V244, and R279 corresponding to SEQ ID NO:51, as determined by yeast surface display;
(k) amino acid residues P258, G260, G262, and Y264 corresponding to SEQ ID NO:51, as determined by yeast surface display; or
(l) any combination thereof.

6. The antibody of claim 1, wherein the antibody specifically binds human MICA with a $K_D$ of between about $10^{-8}$ M and $10^{-10}$ M, wherein $K_D$ is measured by surface plasmon resonance analysis.

7. The antibody of claim 1, wherein the antibody is an IgG1, an IgG2, an IgG3, an IgG4 or a variant thereof.

8. The antibody of claim 1, which is non-fucosylated or hypo-fucosylated.

9. The antibody of claim 1, wherein the antibody comprises a constant region in the heavy chain, and wherein the constant region comprises a alanine (A) at the position that corresponds to residue 234 in SEQ ID NO: 58.

10. The antibody of claim 1, wherein the antibody is a human antibody, a humanized antibody, or a chimeric antibody.

11. An immunoconjugate comprising the antibody of claim 1 and a therapeutic agent.

12. A pharmaceutical composition comprising the antibody of claim 1.

13. An isolated antibody that specifically binds to human MICA comprising a heavy chain variable region (VH) and a light chain variable region (VL), wherein:
(a) the VH comprises the amino acid sequence set forth in SEQ ID NO: 2; and
(b) the VL comprises the amino acid sequence set forth in SEQ ID NO: 4, and wherein the antibody is IgG1.

14. The antibody of claim 13, wherein the antibody is not fucosylated.

15. An isolated antibody that specifically binds to human MICA comprising a heavy chain variable region (VH), a light chain variable region (VL), and a constant region, wherein:
(a) the VH comprises the amino acid sequence set forth in SEQ ID NO: 2; and
(b) the VL comprises the amino acid sequence set forth in SEQ ID NO: 4, and wherein the constant region comprises alanine (A) at the position that corresponds to residue 234 in SEQ ID NO: 58.

16. A polynucleotide or a set of polynucleotides encoding the antibody of claim 1.

17. A vector or a set of vectors comprising the polynucleotide or the set of polynucleotides of claim 16.

18. A host cell comprising the polynucleotide or the set of polynucleotides of claim 16.

19. A method of preparing an antibody comprising expressing the polynucleotide or the set of polynucleotides of claim 16 in a host cell under suitable conditions.

* * * * *

SEQUENCE LISTING

```
<160> NUMBER OF SEQ ID NOS: 133

<210> SEQ ID NO 1
<211> LENGTH: 345
<212> TYPE: DNA
<213> ORGANISM: artificial sequence
<220> FEATURE:
<223> OTHER INFORMATION: 19G6-MICA.36 VH1

<400> SEQUENCE: 1
caggtgcaac tggtggagtc tgggggaggc gtggtccagc ctgggaggtc cctgagactc     60
tcctgtgcag cgtctggatt caccttcagt aactatgcca tgcactgggt ccgccaggct    120
ccaggcgagg ggctggaatg ggtggcactt atatggtatg atggaagtaa taaattctat    180
ggagactccg tgaagggccg cttcaccatc tccagagaca attccaagaa cacgctgtat    240
ctgcaaatga acagcctgag cgccgaggac acggctgtgt attactgtgc gagagaggga    300
agtgggcact actggggcca gggaaccctg gtcaccgtct cctca                    345

<210> SEQ ID NO 2
<211> LENGTH: 115
<212> TYPE: PRT
<213> ORGANISM: artificial sequence
<220> FEATURE:
<223> OTHER INFORMATION: 19G6-MICA.36 VH1

<400> SEQUENCE: 2

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Asn Tyr
            20                  25                  30
```

Ala Met His Trp Val Arg Gln Ala Pro Gly Glu Gly Leu Glu Trp Val
            35                  40                  45

Ala Leu Ile Trp Tyr Asp Gly Ser Asn Lys Phe Tyr Gly Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Ser Ala Glu Asp Thr Ala Val Tyr Tyr Cys
                 85                  90                  95

Ala Arg Glu Gly Ser Gly His Tyr Trp Gly Gln Gly Thr Leu Val Thr
                100                 105                 110

Val Ser Ser
        115

<210> SEQ ID NO 3
<211> LENGTH: 321
<212> TYPE: DNA
<213> ORGANISM: artificial sequence
<220> FEATURE:
<223> OTHER INFORMATION: 19G6-MICA.36 VK1

<400> SEQUENCE: 3
gccatccagt tgacccagtc tccatcctcc ctgtctgcat ctgtaggaga cagagtcacc      60
atcacttgcc gggcaagtca gggcatcagc agtgctttag cctggtatca gcagaaacca    120
gggaaagttc ctaagtccct gatctatgat gcctccagtt tggaaagtgg ggtcccatca    180
aggttcagcg gcagtggatc tgggacagat ttcactctca ccatcagcag cctgcagcct    240
gaagattttg caacttatta ctgtcaacag tttaatagtt acccgatcac cttcggccaa    300
gggacacgac tggagattaa a                                              321

<210> SEQ ID NO 4
<211> LENGTH: 107
<212> TYPE: PRT
<213> ORGANISM: artificial sequence
<220> FEATURE:
<223> OTHER INFORMATION: 19G6-MICA.36 VK1

<400> SEQUENCE: 4

Ala Ile Gln Leu Thr Gln Ser Pro Ser Ser Leu Ser Ala Ser Val Gly
 1               5                  10                  15

Asp Arg Val Thr Ile Thr Cys Arg Ala Ser Gln Gly Ile Ser Ser Ala
                 20                  25                  30

Leu Ala Trp Tyr Gln Gln Lys Pro Gly Lys Val Pro Lys Ser Leu Ile
             35                  40                  45

Tyr Asp Ala Ser Ser Leu Glu Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Phe Asn Ser Tyr Pro Ile
                 85                  90                  95

Thr Phe Gly Gln Gly Thr Arg Leu Glu Ile Lys
                100                 105

<210> SEQ ID NO 5
<211> LENGTH: 5
<212> TYPE: PRT
<213> ORGANISM: artificial sequence
<220> FEATURE:
<223> OTHER INFORMATION: 19G6-MICA.36 VH1_CDR1

```
<400> SEQUENCE: 5

Asn Tyr Ala Met His
1               5

<210> SEQ ID NO 6
<211> LENGTH: 17
<212> TYPE: PRT
<213> ORGANISM: artificial sequence
<220> FEATURE:
<223> OTHER INFORMATION: 19G6-MICA.36 VH1_CDR2

<400> SEQUENCE: 6

Leu Ile Trp Tyr Asp Gly Ser Asn Lys Phe Tyr Gly Asp Ser Val Lys
1               5                   10                  15

Gly

<210> SEQ ID NO 7
<211> LENGTH: 6
<212> TYPE: PRT
<213> ORGANISM: artificial sequence
<220> FEATURE:
<223> OTHER INFORMATION: 19G6-MICA.36 VH1_CDR3

<400> SEQUENCE: 7

Glu Gly Ser Gly His Tyr
1               5

<210> SEQ ID NO 8
<211> LENGTH: 11
<212> TYPE: PRT
<213> ORGANISM: artificial sequence
<220> FEATURE:
<223> OTHER INFORMATION: 19G6-MICA.36 VK1_CDR1

<400> SEQUENCE: 8

Arg Ala Ser Gln Gly Ile Ser Ser Ala Leu Ala
1               5                   10

<210> SEQ ID NO 9
<211> LENGTH: 7
<212> TYPE: PRT
<213> ORGANISM: artificial sequence
<220> FEATURE:
<223> OTHER INFORMATION: 19G6-MICA.36 VK1_CDR2

<400> SEQUENCE: 9

Asp Ala Ser Ser Leu Glu Ser
1               5

<210> SEQ ID NO 10
<211> LENGTH: 9
<212> TYPE: PRT
<213> ORGANISM: artificial sequence
<220> FEATURE:
<223> OTHER INFORMATION: 19G6-MICA.36 VK1_CDR3

<400> SEQUENCE: 10

Gln Gln Phe Asn Ser Tyr Pro Ile Thr
1               5

<210> SEQ ID NO 11
<211> LENGTH: 408
<212> TYPE: DNA
<213> ORGANISM: artificial sequence
<220> FEATURE:
<223> OTHER INFORMATION: 16A5-MICA.52 VH1
```

<400> SEQUENCE: 11

```
atggagtttg gctgagctg ggttttcctc gttgctcttt taagaggtgt ccagtgtcag        60
gtgcagctgg tggagtctgg gggagacgtg gtccagcctg gaggtccct gagactctcc       120 tgtgcagcgt ctggattcac cttcagtaac tataacatac actgggtccg ccaggctcca      180
ggcaaggggc tggagtgggt ggcagttata aggtatgatg gaattaataa atactatgca      240
gactccgtga agggccgatt catcatctcc agagacaatt ccaagaacac gctgtatctg      300
caaatgaaca gcctgagagc cgaggacacg gctgtgtatt actgtgcgag cgggccccct      360
gatgctttta atatctgggg ccaagggaca atggtcaccg tctcttca                   408
```

<210> SEQ ID NO 12
<211> LENGTH: 136
<212> TYPE: PRT
<213> ORGANISM: artificial sequence
<220> FEATURE:
<223> OTHER INFORMATION: 16A5-MICA.52 VH1

<400> SEQUENCE: 12

```
Met Glu Phe Gly Leu Ser Trp Val Phe Leu Val Ala Leu Leu Arg Gly
1               5                   10                  15

Val Gln Cys Gln Val Gln Leu Val Glu Ser Gly Gly Asp Val Val Gln
            20                  25                  30

Pro Gly Arg Ser Leu Arg Leu Ser Cys Ala Ala Ser Gly Phe Thr Phe
        35                  40                  45

Ser Asn Tyr Asn Ile His Trp Val Arg Gln Ala Pro Gly Lys Gly Leu
    50                  55                  60

Glu Trp Val Ala Val Ile Arg Tyr Asp Gly Ile Asn Lys Tyr Tyr Ala
65                  70                  75                  80

Asp Ser Val Lys Gly Arg Phe Ile Ile Ser Arg Asp Asn Ser Lys Asn
                85                  90                  95

Thr Leu Tyr Leu Gln Met Asn Ser Leu Arg Ala Glu Asp Thr Ala Val
            100                 105                 110

Tyr Tyr Cys Ala Ser Gly Pro Pro Asp Ala Phe Asn Ile Trp Gly Gln
        115                 120                 125

Gly Thr Met Val Thr Val Ser Ser
    130                 135
```

<210> SEQ ID NO 13
<211> LENGTH: 381
<212> TYPE: DNA
<213> ORGANISM: artificial sequence
<220> FEATURE:
<223> OTHER INFORMATION: 16A5-MICA.52 VK1

<400> SEQUENCE: 13

```
atgagggtcc ccgctcagct cctggggctt ctgctgctct ggctcccagg tgccagatgt        60
gccatccagt tgacccagtc tccatcctcc ctgtctgcat ctgtaggaga cagagtcacc       120
atcacttgcc gggcaagtca gggcatcagc agtgctttag cctggtatca gcagaaacca      180
gggaaagttc ctaagtccct gatctatgat gcctccagtt ggaaagtgg gtcccatca       240 aggttcagcg gcagtggatc tgggacagat ttcactctca ccatcagcag cctgcagcct      300
gaagattttg caacttatta ctgtcaacag tttaatagtt acccgatcac cttcggccaa      360
gggacacgac tggagattaa a                                                381
```

```
<210> SEQ ID NO 14
<211> LENGTH: 127
<212> TYPE: PRT
<213> ORGANISM: artificial sequence
<220> FEATURE:
<223> OTHER INFORMATION: 16A5-MICA.52 VK1

<400> SEQUENCE: 14

Met Arg Val Pro Ala Gln Leu Leu Gly Leu Leu Leu Leu Trp Leu Pro
1               5                   10                  15

Gly Ala Arg Cys Ala Ile Gln Leu Thr Gln Ser Pro Ser Ser Leu Ser
            20                  25                  30

Ala Ser Val Gly Asp Arg Val Thr Ile Thr Cys Arg Ala Ser Gln Gly
        35                  40                  45

Ile Ser Ser Ala Leu Ala Trp Tyr Gln Gln Lys Pro Gly Lys Val Pro
    50                  55                  60

Lys Ser Leu Ile Tyr Asp Ala Ser Ser Leu Glu Ser Gly Val Pro Ser
65                  70                  75                  80

Arg Phe Ser Gly Ser Gly Ser Gly Thr Asp Phe Thr Leu Thr Ile Ser
                85                  90                  95

Ser Leu Gln Pro Glu Asp Phe Ala Thr Tyr Tyr Cys Gln Gln Phe Asn
            100                 105                 110

Ser Tyr Pro Ile Thr Phe Gly Gln Gly Thr Arg Leu Glu Ile Lys
        115                 120                 125

<210> SEQ ID NO 15
<211> LENGTH: 5
<212> TYPE: PRT
<213> ORGANISM: artificial sequence
<220> FEATURE:
<223> OTHER INFORMATION: 16A5-MICA.52 VH1_CDR1

<400> SEQUENCE: 15

Asn Tyr Asn Ile His
1               5

<210> SEQ ID NO 16
<211> LENGTH: 17
<212> TYPE: PRT
<213> ORGANISM: artificial sequence
<220> FEATURE:
<223> OTHER INFORMATION: 16A5-MICA.52 VH1_CDR2

<400> SEQUENCE: 16

Val Ile Arg Tyr Asp Gly Ile Asn Lys Tyr Tyr Ala Asp Ser Val Lys
1               5                   10                  15

Gly

<210> SEQ ID NO 17
<211> LENGTH: 8
<212> TYPE: PRT
<213> ORGANISM: artificial sequence
<220> FEATURE:
<223> OTHER INFORMATION: 16A5-MICA.52 VH1_CDR3

<400> SEQUENCE: 17

Gly Pro Pro Asp Ala Phe Asn Ile
1               5

<210> SEQ ID NO 18
<211> LENGTH: 11
<212> TYPE: PRT
<213> ORGANISM: artificial sequence
```

```
<220> FEATURE:
<223> OTHER INFORMATION: 16A5-MICA.52 VK1_CDR1

<400> SEQUENCE: 18

Arg Ala Ser Gln Gly Ile Ser Ser Ala Leu Ala
1               5                   10

<210> SEQ ID NO 19
<211> LENGTH: 7
<212> TYPE: PRT
<213> ORGANISM: artificial sequence
<220> FEATURE:
<223> OTHER INFORMATION: 16A5-MICA.52 VK1_CDR2

<400> SEQUENCE: 19

Asp Ala Ser Ser Leu Glu Ser
1               5

<210> SEQ ID NO 20
<211> LENGTH: 9
<212> TYPE: PRT
<213> ORGANISM: artificial sequence
<220> FEATURE:
<223> OTHER INFORMATION: 16A5-MICA.52 VK1_CDR3

<400> SEQUENCE: 20

Gln Gln Phe Asn Ser Tyr Pro Ile Thr
1               5

<210> SEQ ID NO 21
<211> LENGTH: 414
<212> TYPE: DNA
<213> ORGANISM: artificial sequence
<220> FEATURE:
<223> OTHER INFORMATION: 24G11-MICA.54 VH1

<400> SEQUENCE: 21
atggggtcaa ccgccatcct cgccctcctc ctggctgttc tccaaggagt ctgtgccgag     60
gtgcagctgg tgcagtctgg agcagaggtg aaaaagcccg gggagtctct gaagatctcc    120
tgtaagggtt ctggatacag ttttaccaac tactggatcg gctgggtgcg ccagatgccc    180
gggaaaggcc tggagtggtt ggggatcatc catcctggtg actcttatac cagatacagc    240
ccgtccttcc aaggccaggt caccatctca gccgacaagt ccatcagcac cgcctacctg    300
cagtggagca gcctgaaggc ctcggacacc gccatatatt actgtgcgag agagggtata    360
gcagcaactc cctttgacta ctggggccag ggaaccctgg tcaccgtctc ctca          414

<210> SEQ ID NO 22
<211> LENGTH: 138
<212> TYPE: PRT
<213> ORGANISM: artificial sequence
<220> FEATURE:
<223> OTHER INFORMATION: 24G11-MICA.54 VH1

<400> SEQUENCE: 22

Met Gly Ser Thr Ala Ile Leu Ala Leu Leu Leu Ala Val Leu Gln Gly
1               5                   10                  15

Val Cys Ala Glu Val Gln Leu Val Gln Ser Gly Ala Glu Val Lys Lys
            20                  25                  30

Pro Gly Glu Ser Leu Lys Ile Ser Cys Lys Gly Ser Gly Tyr Ser Phe
        35                  40                  45

Thr Asn Tyr Trp Ile Gly Trp Val Arg Gln Met Pro Gly Lys Gly Leu
    50                  55                  60
```

Glu Trp Leu Gly Ile Ile His Pro Gly Asp Ser Tyr Thr Arg Tyr Ser
65                  70                  75                  80

Pro Ser Phe Gln Gly Gln Val Thr Ile Ser Ala Asp Lys Ser Ile Ser
                85                  90                  95

Thr Ala Tyr Leu Gln Trp Ser Ser Leu Lys Ala Ser Asp Thr Ala Ile
            100                 105                 110

Tyr Tyr Cys Ala Arg Glu Gly Ile Ala Ala Thr Pro Phe Asp Tyr Trp
        115                 120                 125

Gly Gln Gly Thr Leu Val Thr Val Ser Ser
130                 135

<210> SEQ ID NO 23
<211> LENGTH: 381
<212> TYPE: DNA
<213> ORGANISM: artificial sequence
<220> FEATURE:
<223> OTHER INFORMATION: 24G11-MICA.54 VK1

<400> SEQUENCE: 23
atggaagccc cagctcagct tctcttcctc ctgctactct ggctcccaga taccaccgga      60
gaaattgtgt tgacacagtc tccagccacc ctgtctttgt ctccagggga aagagccacc     120
ctctcctgca gggccagtca gagtgttagc agctacttag cctggttcca acagaaacct     180
ggccaggctc ccaggctcct catctatgat gcatccaaca gggccactgg catcccagcc     240
aggttcagtg gcagtgggtc tgggacagac ttcactctca ccatcagcag cctagagcct     300
gaagattttg cagtttatta ctgtcagcag cgtagcaact ggcctccgac gttcggccaa     360
gggaccaagg tggaaatcaa a                                                381

<210> SEQ ID NO 24
<211> LENGTH: 127
<212> TYPE: PRT
<213> ORGANISM: artificial sequence
<220> FEATURE:
<223> OTHER INFORMATION: 24G11-MICA.54 VK1

<400> SEQUENCE: 24

Met Glu Ala Pro Ala Gln Leu Leu Phe Leu Leu Leu Leu Trp Leu Pro
1               5                   10                  15

Asp Thr Thr Gly Glu Ile Val Leu Thr Gln Ser Pro Ala Thr Leu Ser
            20                  25                  30

Leu Ser Pro Gly Glu Arg Ala Thr Leu Ser Cys Arg Ala Ser Gln Ser
        35                  40                  45

Val Ser Ser Tyr Leu Ala Trp Phe Gln Gln Lys Pro Gly Gln Ala Pro
    50                  55                  60

Arg Leu Leu Ile Tyr Asp Ala Ser Asn Arg Ala Thr Gly Ile Pro Ala
65                  70                  75                  80

Arg Phe Ser Gly Ser Gly Ser Gly Thr Asp Phe Thr Leu Thr Ile Ser
                85                  90                  95

Ser Leu Glu Pro Glu Asp Phe Ala Val Tyr Tyr Cys Gln Gln Arg Ser
            100                 105                 110

Asn Trp Pro Pro Thr Phe Gly Gln Gly Thr Lys Val Glu Ile Lys
        115                 120                 125

<210> SEQ ID NO 25
<211> LENGTH: 5
<212> TYPE: PRT
<213> ORGANISM: artificial sequence

```
<220> FEATURE:
<223> OTHER INFORMATION: 24G11-MICA.54 VH1_CDR1

<400> SEQUENCE: 25

Asn Tyr Trp Ile Gly
1               5

<210> SEQ ID NO 26
<211> LENGTH: 17
<212> TYPE: PRT
<213> ORGANISM: artificial sequence
<220> FEATURE:
<223> OTHER INFORMATION: 24G11-MICA.54 VH1_CDR2

<400> SEQUENCE: 26

Ile Ile His Pro Gly Asp Ser Tyr Thr Arg Tyr Ser Pro Ser Phe Gln
1               5                   10                  15
Gly

<210> SEQ ID NO 27
<211> LENGTH: 10
<212> TYPE: PRT
<213> ORGANISM: artificial sequence
<220> FEATURE:
<223> OTHER INFORMATION: 24G11-MICA.54 VH1_CDR3

<400> SEQUENCE: 27

Glu Gly Ile Ala Ala Thr Pro Phe Asp Tyr
1               5                   10

<210> SEQ ID NO 28
<211> LENGTH: 11
<212> TYPE: PRT
<213> ORGANISM: artificial sequence
<220> FEATURE:
<223> OTHER INFORMATION: 24G11-MICA.54 VK1_CDR1

<400> SEQUENCE: 28

Arg Ala Ser Gln Ser Val Ser Ser Tyr Leu Ala
1               5                   10

<210> SEQ ID NO 29
<211> LENGTH: 7
<212> TYPE: PRT
<213> ORGANISM: artificial sequence
<220> FEATURE:
<223> OTHER INFORMATION: 24G11-MICA.54 VK1_CDR2

<400> SEQUENCE: 29

Asp Ala Ser Asn Arg Ala Thr
1               5

<210> SEQ ID NO 30
<211> LENGTH: 9
<212> TYPE: PRT
<213> ORGANISM: artificial sequence
<220> FEATURE:
<223> OTHER INFORMATION: 24G11-MICA.54 VK1_CDR3

<400> SEQUENCE: 30

Gln Gln Arg Ser Asn Trp Pro Pro Thr
1               5

<210> SEQ ID NO 31
<211> LENGTH: 414
<212> TYPE: DNA
```

<213> ORGANISM: artificial sequence
<220> FEATURE:
<223> OTHER INFORMATION: 3F5-MICA.2 VH1

<400> SEQUENCE: 31

```
atggagttgg ggctgtgctg gattttcctt gttgctattt tagaaggtgt ccagtgtgag    60
gtgcaactgg tggaatctgg gggaggcttg gtacagcctg gggggtccct gagactctcc   120
tgtgcagcct ctggattcac cttcagtacc tatagcatga actgggtccg ccaggctcca   180
gggaaggggc tggagtgggt tcatacatt agttatcgta gtcgtaccat atactacgca    240
gactctgtga aggccgatt caccatctcc agagacaatg ccaggaactc actgtatctg    300
caaatgaaca gcctgagaga cgaggacacg gctgtgtatt actgtgcgag atggggctat   360
ggttcggggg gctttgacta ctggggccag ggaaccctgg tcaccgtctc ctca         414
```

<210> SEQ ID NO 32
<211> LENGTH: 138
<212> TYPE: PRT
<213> ORGANISM: artificial sequence
<220> FEATURE:
<223> OTHER INFORMATION: 3F5-MICA.2 VH1

<400> SEQUENCE: 32

```
Met Glu Leu Gly Leu Cys Trp Ile Phe Leu Val Ala Ile Leu Glu Gly
1               5                   10                  15
Val Gln Cys Glu Val Gln Leu Val Glu Ser Gly Gly Gly Leu Val Gln
            20                  25                  30
Pro Gly Gly Ser Leu Arg Leu Ser Cys Ala Ala Ser Gly Phe Thr Phe
        35                  40                  45
Ser Thr Tyr Ser Met Asn Trp Val Arg Gln Ala Pro Gly Lys Gly Leu
    50                  55                  60
Glu Trp Val Ser Tyr Ile Ser Tyr Arg Ser Arg Thr Ile Tyr Tyr Ala
65                  70                  75                  80
Asp Ser Val Lys Gly Arg Phe Thr Ile Ser Arg Asp Asn Ala Arg Asn
                85                  90                  95
Ser Leu Tyr Leu Gln Met Asn Ser Leu Arg Asp Glu Asp Thr Ala Val
            100                 105                 110
Tyr Tyr Cys Ala Arg Trp Gly Tyr Gly Ser Gly Gly Phe Asp Tyr Trp
        115                 120                 125
Gly Gln Gly Thr Leu Val Thr Val Ser Ser
    130                 135
```

<210> SEQ ID NO 33
<211> LENGTH: 381
<212> TYPE: DNA
<213> ORGANISM: artificial sequence
<220> FEATURE:
<223> OTHER INFORMATION: 3F5-MICA.2 VK1

<400> SEQUENCE: 33

```
atggaaaccc cagcgcagct tctcttcctc ctgctactct ggctcccaga taccaccgga    60
gaaattgtgt tgacgcagtc tccaggcacc ctgtctttgt ctccagggga aagagccacc   120
ctctcctgca gggccagtca gagtgttagc agcagctact tagcctggta ccagcagaaa   180
cctggccagg ctcccaggct cctcatctat ggtgcatcca gcagggccac tggcatccca   240
gacaggttca gtggcagtgg gtctgggaca gacttcactc tcaccatcag cagactggag   300
cctgaagatt ttgcagtgta ttactgtcag cagtatggta gctcattcac tttcggccct   360
```
gggaccaaag tggatatcaa a 381

<210> SEQ ID NO 34
<211> LENGTH: 127
<212> TYPE: PRT
<213> ORGANISM: artificial sequence
<220> FEATURE:
<223> OTHER INFORMATION: 3F5-MICA.2 VK1

<400> SEQUENCE: 34

Met Glu Thr Pro Ala Gln Leu Leu Phe Leu Leu Leu Leu Trp Leu Pro
1               5                   10                  15

Asp Thr Thr Gly Glu Ile Val Leu Thr Gln Ser Pro Gly Thr Leu Ser
            20                  25                  30

Leu Ser Pro Gly Glu Arg Ala Thr Leu Ser Cys Arg Ala Ser Gln Ser
        35                  40                  45

Val Ser Ser Ser Tyr Leu Ala Trp Tyr Gln Gln Lys Pro Gly Gln Ala
    50                  55                  60

Pro Arg Leu Leu Ile Tyr Gly Ala Ser Ser Arg Ala Thr Gly Ile Pro
65                  70                  75                  80

Asp Arg Phe Ser Gly Ser Gly Ser Gly Thr Asp Phe Thr Leu Thr Ile
                85                  90                  95

Ser Arg Leu Glu Pro Glu Asp Phe Ala Val Tyr Tyr Cys Gln Gln Tyr
            100                 105                 110

Gly Ser Ser Phe Thr Phe Gly Pro Gly Thr Lys Val Asp Ile Lys
        115                 120                 125

<210> SEQ ID NO 35
<211> LENGTH: 5
<212> TYPE: PRT
<213> ORGANISM: artificial sequence
<220> FEATURE:
<223> OTHER INFORMATION: 3F5-MICA.2 VH1_CDR1

<400> SEQUENCE: 35

Thr Tyr Ser Met Asn
1               5

<210> SEQ ID NO 36
<211> LENGTH: 17
<212> TYPE: PRT
<213> ORGANISM: artificial sequence
<220> FEATURE:
<223> OTHER INFORMATION: 3F5-MICA.2 VH1_CDR2

<400> SEQUENCE: 36

Tyr Ile Ser Tyr Arg Ser Arg Thr Ile Tyr Tyr Ala Asp Ser Val Lys
1               5                   10                  15

Gly

<210> SEQ ID NO 37
<211> LENGTH: 10
<212> TYPE: PRT
<213> ORGANISM: artificial sequence
<220> FEATURE:
<223> OTHER INFORMATION: 3F5-MICA.2 VH1_CDR3

<400> SEQUENCE: 37

Trp Gly Tyr Gly Ser Gly Gly Phe Asp Tyr
1               5                   10

<210> SEQ ID NO 38

<210> SEQ ID NO 38
<211> LENGTH: 12
<212> TYPE: PRT
<213> ORGANISM: artificial sequence
<220> FEATURE:
<223> OTHER INFORMATION: 3F5-MICA.2 VK1_CDR1

<400> SEQUENCE: 38

Arg Ala Ser Gln Ser Val Ser Ser Ser Tyr Leu Ala
1               5                   10

<210> SEQ ID NO 39
<211> LENGTH: 7
<212> TYPE: PRT
<213> ORGANISM: artificial sequence
<220> FEATURE:
<223> OTHER INFORMATION: 3F5-MICA.2 VK1_CDR2

<400> SEQUENCE: 39

Gly Ala Ser Ser Arg Ala Thr
1               5

<210> SEQ ID NO 40
<211> LENGTH: 8
<212> TYPE: PRT
<213> ORGANISM: artificial sequence
<220> FEATURE:
<223> OTHER INFORMATION: 3F5-MICA.2 VK1_CDR3

<400> SEQUENCE: 40

Gln Gln Tyr Gly Ser Ser Phe Thr
1               5

<210> SEQ ID NO 41
<211> LENGTH: 420
<212> TYPE: DNA
<213> ORGANISM: artificial sequence
<220> FEATURE:
<223> OTHER INFORMATION: 71C2 VH1

<400> SEQUENCE: 41

```
atggagttgg gactgagctg gattttcctt ttggctattt taaaaggtgt ccagtgtgaa      60
gtgcagctgg tggagtctgg gggaggcttg gtacagcctg gcaggtccct gagactctcc     120
tgtgcagcct ctggattcac ctttaataat tatgccatgc actgggtccg gcaagctcca     180
gggaagggcc tggagtgggt ctcaggtatt acttggaata gtgatagcat aggctatgcg     240
gactctgtga aggccgatt caccatctcc agagacaacg ccaagaactc cctgtatctg     300
caaatgaaca gtctgagagc tgaggacacg gccttgtatt actgtgcaaa agattccgta     360
ttactatggt tcgggggtat ggacgtctgg ggccaaggga ccacggtcac cgtctcctca     420
```

<210> SEQ ID NO 42
<211> LENGTH: 140
<212> TYPE: PRT
<213> ORGANISM: artificial sequence
<220> FEATURE:
<223> OTHER INFORMATION: 71C2 VH1

<400> SEQUENCE: 42

Met Glu Leu Gly Leu Ser Trp Ile Phe Leu Leu Ala Ile Leu Lys Gly
1               5                   10                  15

Val Gln Cys Glu Val Gln Leu Val Glu Ser Gly Gly Gly Leu Val Gln
                20                  25                  30

Pro Gly Arg Ser Leu Arg Leu Ser Cys Ala Ala Ser Gly Phe Thr Phe
            35                  40                  45

```
Asn Asn Tyr Ala Met His Trp Val Arg Gln Ala Pro Gly Lys Gly Leu
         50                  55                  60

Glu Trp Val Ser Gly Ile Thr Trp Asn Ser Asp Ser Ile Gly Tyr Ala
 65                  70                  75                  80

Asp Ser Val Lys Gly Arg Phe Thr Ile Ser Arg Asp Asn Ala Lys Asn
                 85                  90                  95

Ser Leu Tyr Leu Gln Met Asn Ser Leu Arg Ala Glu Asp Thr Ala Leu
                100                 105                 110

Tyr Tyr Cys Ala Lys Asp Ser Val Leu Leu Trp Phe Gly Gly Met Asp
            115                 120                 125

Val Trp Gly Gln Gly Thr Thr Val Thr Val Ser Ser
130                 135                 140
```

<210> SEQ ID NO 43
<211> LENGTH: 387
<212> TYPE: DNA
<213> ORGANISM: artificial sequence
<220> FEATURE:
<223> OTHER INFORMATION: 71C2 VK1

<400> SEQUENCE: 43

```
atggaaaccc cagcgcagct tctcttcctc ctgctactct ggctcccaga taccaccgga      60
gaaattgtgt tgacgcagtc tccaggcacc ctgtctttgt ctccagggga aagagccacc     120
ctctcctgca gggccagtca gagtgttagc agcagctact tagcctggta ccagcagaaa     180
cctggccagg ctcccaggct cctcatctat ggtgcatcca gcagggccac tggcatccca     240
gacaggttca gtggcagtgg gtctgggaca gacttcactc tcaccatcag cagactggag     300
cctgaagatt ttgcagtgta ttactgtcag cagtatggta gctcacctcc gtacactttt     360
ggccagggga ccaagctgga gatcaaa                                         387
```

<210> SEQ ID NO 44
<211> LENGTH: 129
<212> TYPE: PRT
<213> ORGANISM: artificial sequence
<220> FEATURE:
<223> OTHER INFORMATION: 71C2 VK1

<400> SEQUENCE: 44

```
Met Glu Thr Pro Ala Gln Leu Leu Phe Leu Leu Leu Leu Trp Leu Pro
 1               5                  10                  15

Asp Thr Thr Gly Glu Ile Val Leu Thr Gln Ser Pro Gly Thr Leu Ser
             20                  25                  30

Leu Ser Pro Gly Glu Arg Ala Thr Leu Ser Cys Arg Ala Ser Gln Ser
         35                  40                  45

Val Ser Ser Tyr Leu Ala Trp Tyr Gln Gln Lys Pro Gly Gln Ala
     50                  55                  60

Pro Arg Leu Leu Ile Tyr Gly Ala Ser Ser Arg Ala Thr Gly Ile Pro
 65                  70                  75                  80

Asp Arg Phe Ser Gly Ser Gly Ser Gly Thr Asp Phe Thr Leu Thr Ile
                 85                  90                  95

Ser Arg Leu Glu Pro Glu Asp Phe Ala Val Tyr Tyr Cys Gln Gln Tyr
                100                 105                 110

Gly Ser Ser Pro Pro Tyr Thr Phe Gly Gln Gly Thr Lys Leu Glu Ile
            115                 120                 125

Lys
```

```
<210> SEQ ID NO 45
<211> LENGTH: 5
<212> TYPE: PRT
<213> ORGANISM: artificial sequence
<220> FEATURE:
<223> OTHER INFORMATION: 71C2 VH1_CDR1

<400> SEQUENCE: 45

Asn Tyr Ala Met His
1               5

<210> SEQ ID NO 46
<211> LENGTH: 17
<212> TYPE: PRT
<213> ORGANISM: artificial sequence
<220> FEATURE:
<223> OTHER INFORMATION: 71C2 VH1_CDR2

<400> SEQUENCE: 46

Gly Ile Thr Trp Asn Ser Asp Ser Ile Gly Tyr Ala Asp Ser Val Lys
1               5                   10                  15

Gly

<210> SEQ ID NO 47
<211> LENGTH: 12
<212> TYPE: PRT
<213> ORGANISM: artificial sequence
<220> FEATURE:
<223> OTHER INFORMATION: 71C2 VH1_CDR3

<400> SEQUENCE: 47

Asp Ser Val Leu Leu Trp Phe Gly Gly Met Asp Val
1               5                   10

<210> SEQ ID NO 48
<211> LENGTH: 12
<212> TYPE: PRT
<213> ORGANISM: artificial sequence
<220> FEATURE:
<223> OTHER INFORMATION: 71C2 VK1_CDR1

<400> SEQUENCE: 48

Arg Ala Ser Gln Ser Val Ser Ser Ser Tyr Leu Ala
1               5                   10

<210> SEQ ID NO 49
<211> LENGTH: 7
<212> TYPE: PRT
<213> ORGANISM: artificial sequence
<220> FEATURE:
<223> OTHER INFORMATION: 71C2 VK1_CDR2

<400> SEQUENCE: 49

Gly Ala Ser Ser Arg Ala Thr
1               5

<210> SEQ ID NO 50
<211> LENGTH: 10
<212> TYPE: PRT
<213> ORGANISM: artificial sequence
<220> FEATURE:
<223> OTHER INFORMATION: 71C2 VK1_CDR3

<400> SEQUENCE: 50

Gln Gln Tyr Gly Ser Ser Pro Pro Tyr Thr
1               5                   10
```

```
<210> SEQ ID NO 51
<211> LENGTH: 332
<212> TYPE: PRT
<213> ORGANISM: artificial sequence
<220> FEATURE:
<223> OTHER INFORMATION: human MICA aa sequence

<400> SEQUENCE: 51

Met Gly Leu Gly Pro Val Phe Leu Leu Leu Ala Gly Ile Phe Pro Phe
1               5                   10                  15

Ala Pro Pro Gly Ala Ala Glu Pro His Ser Leu Arg Tyr Asn Leu
            20                  25                  30

Thr Val Leu Ser Trp Asp Gly Ser Val Gln Ser Gly Phe Leu Ala Glu
        35                  40                  45

Val His Leu Asp Gly Gln Pro Phe Leu Arg Tyr Asp Arg Gln Lys Cys
    50                  55                  60

Arg Ala Lys Pro Gln Gly Gln Trp Ala Glu Asp Val Leu Gly Asn Lys
65                  70                  75                  80

Thr Trp Asp Arg Glu Thr Arg Asp Leu Thr Gly Asn Gly Lys Asp Leu
                85                  90                  95

Arg Met Thr Leu Ala His Ile Lys Asp Gln Lys Glu Gly Leu His Ser
            100                 105                 110

Leu Gln Glu Ile Arg Val Cys Glu Ile His Glu Asp Asn Ser Thr Arg
        115                 120                 125

Ser Ser Gln His Phe Tyr Tyr Asp Gly Glu Leu Phe Leu Ser Gln Asn
    130                 135                 140

Leu Glu Thr Glu Glu Trp Thr Val Pro Gln Ser Ser Arg Ala Gln Thr
145                 150                 155                 160

Leu Ala Met Asn Val Arg Asn Phe Leu Lys Glu Asp Ala Met Lys Thr
                165                 170                 175

Lys Thr His Tyr His Ala Met His Ala Asp Cys Leu Gln Glu Leu Arg
            180                 185                 190

Arg Tyr Leu Glu Ser Gly Val Val Leu Arg Arg Thr Val Pro Pro Met
        195                 200                 205

Val Asn Val Thr Arg Ser Glu Ala Ser Glu Gly Asn Ile Thr Val Thr
    210                 215                 220

Cys Arg Ala Ser Ser Phe Tyr Pro Arg Asn Ile Ile Leu Thr Trp Arg
225                 230                 235                 240

Gln Asp Gly Val Ser Leu Ser His Asp Thr Gln Gln Trp Gly Asp Val
                245                 250                 255

Leu Pro Asp Gly Asn Gly Thr Tyr Gln Thr Trp Val Ala Thr Arg Ile
            260                 265                 270

Cys Arg Gly Glu Glu Gln Arg Phe Thr Cys Tyr Met Glu His Ser Gly
        275                 280                 285

Asn His Ser Thr His Pro Val Pro Ser Gly Lys Val Leu Val Leu Gln
    290                 295                 300

Ser His Trp Gln Thr Phe His Val Ser Ala Val Ala Ala Gly Cys Cys
305                 310                 315                 320

Tyr Phe Cys Tyr Tyr Tyr Phe Leu Cys Pro Leu Leu
                325                 330

<210> SEQ ID NO 52
<211> LENGTH: 14
<212> TYPE: PRT
<213> ORGANISM: artificial sequence
```

```
<220> FEATURE:
<223> OTHER INFORMATION: MICA.36 NF G236A Epitope Region 1

<400> SEQUENCE: 52

Trp Thr Val Pro Gln Ser Ser Arg Ala Gln Thr Leu Ala Met
1               5                   10

<210> SEQ ID NO 53
<211> LENGTH: 8
<212> TYPE: PRT
<213> ORGANISM: artificial sequence
<220> FEATURE:
<223> OTHER INFORMATION: MICA.36 NF G236A Epitope Region 2

<400> SEQUENCE: 53

Tyr Pro Arg Asn Ile Ile Leu Thr
1               5

<210> SEQ ID NO 54
<211> LENGTH: 11
<212> TYPE: PRT
<213> ORGANISM: artificial sequence
<220> FEATURE:
<223> OTHER INFORMATION: MICA.36 NF G236A Epitope Region 3.1

<400> SEQUENCE: 54

Asp Val Leu Pro Asp Gly Asn Gly Thr Tyr Gln
1               5                   10

<210> SEQ ID NO 55
<211> LENGTH: 15
<212> TYPE: PRT
<213> ORGANISM: artificial sequence
<220> FEATURE:
<223> OTHER INFORMATION: MICA.36 NF G236A Epitope Region 3.2

<400> SEQUENCE: 55

Trp Gly Asp Val Leu Pro Asp Gly Asn Gly Thr Tyr Gln Thr Trp
1               5                   10                  15

<210> SEQ ID NO 56
<211> LENGTH: 20
<212> TYPE: PRT
<213> ORGANISM: artificial sequence
<220> FEATURE:
<223> OTHER INFORMATION: MICA.2 Epitope Region 1

<400> SEQUENCE: 56

Leu Arg Arg Thr Val Pro Pro Met Val Asn Val Thr Arg Ser Glu Ala
1               5                   10                  15

Ser Glu Gly Asn
            20

<210> SEQ ID NO 57
<211> LENGTH: 15
<212> TYPE: PRT
<213> ORGANISM: artificial sequence
<220> FEATURE:
<223> OTHER INFORMATION: MICA.2 Epitope Region 2

<400> SEQUENCE: 57

Thr Trp Arg Gln Asp Gly Val Ser Leu Ser His Asp Thr Gln Gln
1               5                   10                  15

<210> SEQ ID NO 58
<211> LENGTH: 444
```

```
<212> TYPE: PRT
<213> ORGANISM: artificial sequence
<220> FEATURE:
<223> OTHER INFORMATION: 19G6-MICA.36 Heavy Chain AA

<400> SEQUENCE: 58

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Asn Tyr
                20                  25                  30

Ala Met His Trp Val Arg Gln Ala Pro Gly Glu Gly Leu Glu Trp Val
            35                  40                  45

Ala Leu Ile Trp Tyr Asp Gly Ser Asn Lys Phe Tyr Gly Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Ser Ala Glu Asp Thr Ala Val Tyr Tyr Cys
                85                  90                  95

Ala Arg Glu Gly Ser Gly His Tyr Trp Gly Gln Gly Thr Leu Val Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Arg Val Glu Pro Lys Ser Cys Asp Lys Thr His Thr Cys
210                 215                 220

Pro Pro Cys Pro Ala Pro Glu Leu Leu Ala Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Lys
            260                 265                 270

Phe Asn Trp Tyr Val Asp Gly Val Glu Val His Asn Ala Lys Thr Lys
        275                 280                 285

Pro Arg Glu Glu Gln Tyr Asn Ser Thr Tyr Arg Val Val Ser Val Leu
290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Arg Glu Glu Met Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
370                 375                 380
```

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
            405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly
            435                 440

<210> SEQ ID NO 59
<211> LENGTH: 1332
<212> TYPE: DNA
<213> ORGANISM: artificial sequence
<220> FEATURE:
<223> OTHER INFORMATION: 19G6-MICA.36 Heavy Chain NT

<400> SEQUENCE: 59

```
caggtgcaac tggtggagtc tgggggaggc gtggtccagc ctggggaggtc cctgagactc     60 tcctgtgcag cgtctggatt caccttcagt aactatgcca tgcactgggt ccgccaggct    120
ccaggcgagg ggctggaatg ggtggcactt atatggtatg atggaagtaa taaattctat    180
ggagactccg tgaagggccg cttcaccatc tccagagaca attccaagaa cacgctgtat    240
ctgcaaatga acagcctgag cgccgaggac acggctgtgt attactgtgc gagagggga    300 agtgggcact actggggcca gggaaccctg gtcaccgtct cctcagctag caccaagggc    360
ccatcggtct tccccctggc accctcctcc aagagcacct ctgggggcac agcggccctg    420
ggctgcctgg tcaaggacta cttccccgaa ccggtgacgg tgtcgtggaa ctcaggcgcc    480
ctgaccagcg gcgtgcacac cttcccggct gtcctacagt cctcaggact ctactccctc    540
agcagcgtgg tgaccgtgcc ctccagcagc ttgggcaccc agacctacat ctgcaacgtg    600
aatcacaagc ccagcaacac caaggtggac aagagagttg agcccaaatc ttgtgacaaa    660
actcacacat gcccaccgtg cccagcacct gaactcctgg cgggaccgtc agtcttcctc    720
ttccccccaa aacccaagga caccctcatg atctcccgga cccctgaggt cacatgcgtg    780
gtggtggacg tgagccacga agaccctgag gtcaagttca actggtacgt ggacggcgtg    840
gaggtgcata atgccaagac aaagccgcgg gaggagcagt acaacagcac gtaccgtgtg    900
gtcagcgtcc tcaccgtcct gcaccaggac tggctgaatg gcaaggagta caagtgcaag    960
gtctccaaca aagccctccc agcccccatc gagaaaacca tctccaaagc caaagggcag   1020
ccccgagaac cacaggtgta caccctgccc ccatcccggg aggagatgac caagaaccag   1080
gtcagcctga cctgcctggt caaaggcttc tatcccagcg acatcgccgt ggagtgggag   1140
agcaatgggc agccggagaa caactacaag accacgcctc ccgtgctgga ctccgacggc   1200
tccttcttcc tctatagcaa gctcaccgtg gacaagagca ggtggcagca ggggaacgtc   1260
ttctcatgct ccgtgatgca tgaggctctg cacaaccact acacgcagaa gagcctctcc   1320
ctgtccccgg gt                                                       1332
```

<210> SEQ ID NO 60
<211> LENGTH: 214
<212> TYPE: PRT
<213> ORGANISM: artificial sequence
<220> FEATURE:
<223> OTHER INFORMATION: 19G6-MICA.36 Light Chain AA

<400> SEQUENCE: 60

Ala Ile Gln Leu Thr Gln Ser Pro Ser Ser Leu Ser Ala Ser Val Gly

```
  1               5                  10                 15
Asp Arg Val Thr Ile Thr Cys Arg Ala Ser Gln Gly Ile Ser Ser Ala
             20                  25                 30

Leu Ala Trp Tyr Gln Gln Lys Pro Gly Lys Val Pro Lys Ser Leu Ile
         35                  40                 45

Tyr Asp Ala Ser Ser Leu Glu Ser Gly Val Pro Ser Arg Phe Ser Gly
     50                  55                 60

Ser Gly Ser Gly Thr Asp Phe Thr Leu Thr Ile Ser Ser Leu Gln Pro
 65                  70                 75                 80

Glu Asp Phe Ala Thr Tyr Tyr Cys Gln Gln Phe Asn Ser Tyr Pro Ile
                 85                 90                 95

Thr Phe Gly Gln Gly Thr Arg Leu Glu Ile Lys Arg Thr Val Ala Ala
             100                 105                110

Pro Ser Val Phe Ile Phe Pro Pro Ser Asp Glu Gln Leu Lys Ser Gly
         115                 120                 125

Thr Ala Ser Val Val Cys Leu Leu Asn Asn Phe Tyr Pro Arg Glu Ala
     130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 61
<211> LENGTH: 642
<212> TYPE: DNA
<213> ORGANISM: artificial sequence
<220> FEATURE:
<223> OTHER INFORMATION: 19G6-MICA.36 Light Chain NT

<400> SEQUENCE: 61

```
gccatccagt tgacccagtc tccatcctcc ctgtctgcat ctgtaggaga cagagtcacc    60
atcacttgcc gggcaagtca gggcatcagc agtgctttag cctggtatca gcagaaacca   120
gggaaagttc ctaagtccct gatctatgat gcctccagtt tggaaagtgg ggtcccatca   180
aggttcagcg gcagtggatc tgggacagat ttcactctca ccatcagcag cctgcagcct   240
gaagattttg caacttatta ctgtcaacag tttaatagtt acccgatcac cttcggccaa   300
gggacacgac tggagattaa acgtacggtg gctgcaccat ctgtcttcat cttcccgcca   360
tctgatgagc agttgaaatc tggaactgcc tctgttgtgt gcctgctgaa taacttctat   420
cccagagagg ccaaagtaca gtggaaggtg gataacgccc tccaatcggg taactcccag   480
gagagtgtca cagagcagga cagcaaggac agcacctaca gcctcagcag cacctgacg   540
ctgagcaaag cagactacga gaaacacaaa gtctacgcct gcgaagtcac ccatcagggc   600
ctgagctcgc ccgtcacaaa gagcttcaac agggagagt gt                       642
```

<210> SEQ ID NO 62
<211> LENGTH: 446
<212> TYPE: PRT
<213> ORGANISM: artificial sequence
<220> FEATURE:

<223> OTHER INFORMATION: 16A5-MICA.52 Heavy Chain AA

<400> SEQUENCE: 62

```
Gln Val Gln Leu Val Glu Ser Gly Gly Asp Val Val Gln Pro Gly Arg
1               5                   10                  15

Ser Leu Arg Leu Ser Cys Ala Ala Ser Gly Phe Thr Phe Ser Asn Tyr
            20                  25                  30

Asn Ile His Trp Val Arg Gln Ala Pro Gly Lys Gly Leu Glu Trp Val
        35                  40                  45

Ala Val Ile Arg Tyr Asp Gly Ile Asn Lys Tyr Tyr Ala Asp Ser Val
    50                  55                  60

Lys Gly Arg Phe Ile Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ser Gly Pro Pro Asp Ala Phe Asn Ile Trp Gly Gln Gly Thr Met
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
    195                 200                 205

Thr Lys Val Asp Lys Arg Val Glu Pro Lys Ser Cys Asp Lys Thr His
210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400
```

Asp Gly Ser Phe Phe Leu Tyr Ser Lys Leu Thr Val Asp Lys Ser Arg
            405                 410                 415

Trp Gln Gln Gly Asn Val Phe Ser Cys Ser Val Met His Glu Ala Leu
        420                 425                 430

His Asn His Tyr Thr Gln Lys Ser Leu Ser Leu Ser Pro Gly
        435                 440                 445

<210> SEQ ID NO 63
<211> LENGTH: 1338
<212> TYPE: DNA
<213> ORGANISM: artificial sequence
<220> FEATURE:
<223> OTHER INFORMATION: 16A5-MICA.52 Heavy Chain NT

<400> SEQUENCE: 63

| | | | | |
|---|---|---|---|---|
| caggtgcagc | tggtggagtc | tgggggagac | gtggtccagc | ctgggaggtc | cctgagactc | 60 |
| tcctgtgcag | cgtctggatt | caccttcagt | aactataaca | tacactgggt | ccgccaggct | 120 |
| ccaggcaagg | ggctggagtg | ggtggcagtt | ataaggtatg | atggaattaa | taaatactat | 180 |
| gcagactccg | tgaagggccg | attcatcatc | tccagagaca | attccaagaa | cacgctgtat | 240 |
| ctgcaaatga | acagcctgag | agccgaggac | acggctgtgt | attactgtgc | gagcgggccc | 300 |
| cctgatgctt | ttaatatctg | gggccaaggg | acaatggtca | ccgtctcttc | agctagcacc | 360 |
| aagggcccat | cggtcttccc | cctggcaccc | tcctccaaga | gcacctctgg | gggcacagcg | 420 |
| gccctgggct | gcctggtcaa | ggactacttc | cccgaaccgg | tgacggtgtc | gtggaactca | 480 |
| ggcgccctga | ccagcggcgt | gcacaccttc | ccggctgtcc | tacagtcctc | aggactctac | 540 |
| tccctcagca | gcgtggtgac | cgtgccctcc | agcagcttgg | gcacccagac | ctacatctgc | 600 |
| aacgtgaatc | acaagcccag | caacaccaag | gtggacaaga | gagttgagcc | caaatcttgt | 660 |
| gacaaaactc | acacatgccc | accgtgccca | gcacctgaac | tcctgggggg | accgtcagtc | 720 |
| ttcctcttcc | ccccaaaacc | caaggacacc | ctcatgatct | cccggacccc | tgaggtcaca | 780 |
| tgcgtggtgg | tggacgtgag | ccacgaagac | cctgaggtca | agttcaactg | gtacgtggac | 840 |
| ggcgtggagg | tgcataatgc | caagacaaag | ccgcggagg | agcagtacaa | cagcacgtac | 900 |
| cgtgtggtca | gcgtcctcac | cgtcctgcac | caggactggc | tgaatggcaa | ggagtacaag | 960 |
| tgcaaggtct | ccaacaaagc | cctcccagcc | cccatcgaga | aaaccatctc | caaagccaaa | 1020 |
| gggcagcccc | gagaaccaca | ggtgtacacc | ctgcccccat | cccgggagga | gatgaccaag | 1080 |
| aaccaggtca | gcctgacctg | cctggtcaaa | ggcttctatc | ccagcgacat | cgccgtggag | 1140 |
| tgggagagca | atgggcagcc | ggagaacaac | tacaagacca | cgcctcccgt | gctggactcc | 1200 |
| gacggctcct | tcttcctcta | tagcaagctc | accgtggaca | agagcaggtg | gcagcagggg | 1260 |
| aacgtcttct | catgctccgt | gatgcatgag | gctctgcaca | accactacac | gcagaagagc | 1320 |
| ctctccctgt | ccccgggt | | | | | 1338 |

<210> SEQ ID NO 64
<211> LENGTH: 214
<212> TYPE: PRT
<213> ORGANISM: artificial sequence
<220> FEATURE:
<223> OTHER INFORMATION: 16A5-MICA.52 Light Chain AA

<400> SEQUENCE: 64

Ala Ile Gln Leu Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Ala

```
                   20                  25                  30
Leu Ala Trp Tyr Gln Gln Lys Pro Gly Lys Val Pro Lys Ser Leu Ile
            35                  40                  45

Tyr Asp Ala Ser Ser Leu Glu Ser Gly Val Pro Ser Arg Phe Ser Gly
        50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Phe Asn Ser Tyr Pro Ile
                85                  90                  95

Thr Phe Gly Gln Gly Thr Arg Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 65
<211> LENGTH: 642
<212> TYPE: DNA
<213> ORGANISM: artificial sequence
<220> FEATURE:
<223> OTHER INFORMATION: 16A5-MICA.52 Light Chain NT

<400> SEQUENCE: 65
gccatccagt tgacccagtc tccatcctcc ctgtctgcat ctgtaggaga cagagtcacc       60
atcacttgcc gggcaagtca gggcatcagc agtgctttag cctggtatca gcagaaacca      120
gggaaagttc ctaagtccct gatctatgat gcctccagtt tggaaagtgg ggtcccatca      180
aggttcagcg gcagtggatc tgggacagat ttcactctca ccatcagcag cctgcagcct      240
gaagattttg caacttatta ctgtcaacag tttaatagtt acccgatcac cttcggccaa      300
gggacacgac tggagattaa acgtacggtg gctgcaccat ctgtcttcat cttcccgcca      360
tctgatgagc agttgaaatc tggaactgcc tctgttgtgt gcctgctgaa taacttctat      420
cccagagagg ccaaagtaca gtggaaggtg gataacgccc tccaatcggg taactcccag      480
gagagtgtca cagagcagga cagcaaggac agcacctaca gcctcagcag caccctgacg      540
ctgagcaaag cagactacga aaacacaaa gtctacgcct gcgaagtcac ccatcagggc      600
ctgagctcgc ccgtcacaaa gagcttcaac aggggagagt gt                         642

<210> SEQ ID NO 66
<211> LENGTH: 448
<212> TYPE: PRT
<213> ORGANISM: artificial sequence
<220> FEATURE:
<223> OTHER INFORMATION: 24G11-MICA.54 Heavy Chain AA

<400> SEQUENCE: 66
```

-continued

```
Glu Val Gln Leu Val Gln Ser Gly Ala Glu Val Lys Pro Gly Glu
1               5                   10                  15

Ser Leu Lys Ile Ser Cys Lys Gly Ser Gly Tyr Ser Phe Thr Asn Tyr
            20                  25                  30

Trp Ile Gly Trp Val Arg Gln Met Pro Gly Lys Gly Leu Glu Trp Leu
        35                  40                  45

Gly Ile Ile His Pro Gly Asp Ser Tyr Thr Arg Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Ile Tyr Tyr Cys
                85                  90                  95

Ala Arg Glu Gly Ile Ala Ala Thr Pro Phe Asp Tyr Trp Gly Gln Gly
                100                 105                 110

Thr Leu Val Thr Val Ser Ser Ala Ser Thr Lys Gly Pro Ser Val Phe
            115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
                180                 185                 190

Ser Ser Leu Gly Thr Gln Thr Tyr Ile Cys Asn Val Asn His Lys Pro
            195                 200                 205

Ser Asn Thr Lys Val Asp Lys Arg Val Glu Pro Lys Ser Cys Asp Lys
210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
                260                 265                 270

Pro Glu Val Lys Phe Asn Trp Tyr Val Asp Gly Val Glu Val His Asn
            275                 280                 285

Ala Lys Thr Lys Pro Arg Glu Glu Gln Tyr Asn Ser Thr Tyr Arg Val
            290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
            355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415
```

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

<210> SEQ ID NO 67
<211> LENGTH: 1344
<212> TYPE: DNA
<213> ORGANISM: artificial sequence
<220> FEATURE:
<223> OTHER INFORMATION: 24G11-MICA.54 Heavy Chain NT

<400> SEQUENCE: 67

| | |
|---|---|
| gaggtgcagc tggtgcagtc tggagcagag gtgaaaaagc ccggggagtc tctgaagatc | 60 |
| tcctgtaagg gttctggata cagttttacc aactactgga tcggctgggt gcgccagatg | 120 |
| cccgggaaag gcctggagtg gttggggatc atccatcctg gtgactctta taccagatac | 180 |
| agcccgtcct tccaaggcca ggtcaccatc tcagccgaca gtccatcag caccgcctac | 240 |
| ctgcagtgga gcagcctgaa ggcctcggac accgccatat attactgtgc gagagagggt | 300 |
| atagcagcaa ctcccttga ctactggggc cagggaaccc tggtcaccgt ctcctcagct | 360 |
| agcaccaagg gcccatcggt cttccccctg caccctcct ccaagagcac ctctgggggc | 420 |
| acagcggccc tgggctgcct ggtcaaggac tacttccccg aaccggtgac ggtgtcgtgg | 480 |
| aactcaggcg ccctgaccag cggcgtgcac accttcccgg ctgtcctaca gtcctcagga | 540 |
| ctctactccc tcagcagcgt ggtgaccgtg ccctccagca gcttgggcac ccagacctac | 600 |
| atctgcaacg tgaatcacaa gcccagcaac accaaggtgg acaagagagt tgagcccaaa | 660 |
| tcttgtgaca aaactcacac atgcccaccg tgcccagcac ctgaactcct ggggggaccg | 720 |
| tcagtcttcc tcttccccc aaaacccaag gacaccctca tgatctcccg gacccctgag | 780 |
| gtcacatgcg tggtggtgga cgtgagccac gaagaccctg aggtcaagtt caactggtac | 840 |
| gtggacggcg tggaggtgca taatgccaag acaaagccgc gggaggagca gtacaacagc | 900 |
| acgtaccgtg tggtcagcgt cctcaccgtc ctgcaccagg actggctgaa tggcaaggag | 960 |
| tacaagtgca aggtctccaa caaagccctc ccagccccca tcgagaaaac catctccaaa | 1020 |
| gccaaagggc agccccgaga accacaggtg tacaccctgc cccatcccg ggaggagatg | 1080 |
| accaagaacc aggtcagcct gacctgcctg gtcaaaggct tctatcccag cgacatcgcc | 1140 |
| gtggagtggg agagcaatgg gcagccggag aacaactaca agaccacgcc tcccgtgctg | 1200 |
| gactccgacg gctccttctt cctctatagc aagctcaccg tggacaagag caggtggcag | 1260 |
| caggggaacg tcttctcatg ctccgtgatg catgaggctc tgcacaacca ctacacgcag | 1320 |
| aagagcctct ccctgtcccc gggt | 1344 |

<210> SEQ ID NO 68
<211> LENGTH: 214
<212> TYPE: PRT
<213> ORGANISM: artificial sequence
<220> FEATURE:
<223> OTHER INFORMATION: 24G11-MICA.54 Light Chain AA

<400> SEQUENCE: 68

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Phe Gln Gln Lys Pro Gly Gln Ala Pro Arg Leu Leu Ile

```
            35                  40                  45
Tyr Asp Ala Ser Asn Arg Ala Thr Gly Ile Pro Ala Arg Phe Ser Gly
 50                  55                  60

Ser Gly Ser Gly Thr Asp Phe Thr Leu Thr Ile Ser Ser Leu Glu Pro
 65                  70                  75                  80

Glu Asp Phe Ala Val Tyr Tyr Cys Gln Gln Arg Ser Asn Trp Pro Pro
                 85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 69
<211> LENGTH: 642
<212> TYPE: DNA
<213> ORGANISM: artificial sequence
<220> FEATURE:
<223> OTHER INFORMATION: 24G11-MICA.54 Light Chain NT

<400> SEQUENCE: 69

```
gaaattgtgt tgacacagtc tccagccacc ctgtctttgt ctccagggga aagagccacc      60
ctctcctgca gggccagtca gagtgttagc agctacttag cctggttcca acagaaacct    120
ggccaggctc ccaggctcct catctatgat gcatccaaca gggccactgg catcccagcc    180
aggttcagtg gcagtgggtc tgggacagac ttcactctca ccatcagcag cctagagcct    240
gaagattttg cagtttatta ctgtcagcag cgtagcaact ggcctccgac gttcggccaa    300
gggaccaagg tggaaatcaa acgtacggtg gctgcaccat ctgtcttcat cttcccgcca    360
tctgatgagc agttgaaatc tggaactgcc tctgttgtgt gcctgctgaa taacttctat    420
cccagagagg ccaaagtaca gtggaaggtg gataacgccc tccaatcggg taactcccag    480
gagagtgtca cagagcagga cagcaaggac agcacctaca gcctcagcag caccctgacg    540
ctgagcaaag cagactacga gaaacacaaa gtctacgcct gcgaagtcac ccatcagggc    600
ctgagctcgc ccgtcacaaa gagcttcaac aggggagagt gt                       642
```

<210> SEQ ID NO 70
<211> LENGTH: 448
<212> TYPE: PRT
<213> ORGANISM: artificial sequence
<220> FEATURE:
<223> OTHER INFORMATION: 3F5-MICA.2 Heavy Chain AA

<400> SEQUENCE: 70

```
Glu Val Gln Leu Val Glu Ser Gly Gly Gly Leu Val Gln Pro Gly Gly
 1               5                  10                  15
```

```
Ser Leu Arg Leu Ser Cys Ala Ala Ser Gly Phe Thr Phe Ser Thr Tyr
            20                  25                  30

Ser Met Asn Trp Val Arg Gln Ala Pro Gly Lys Gly Leu Glu Trp Val
        35                  40                  45

Ser Tyr Ile Ser Tyr Arg Ser Arg Thr Ile Tyr Tyr Ala Asp Ser Val
50                      55                  60

Lys Gly Arg Phe Thr Ile Ser Arg Asp Asn Ala Arg Asn Ser Leu Tyr
65                  70                  75                  80

Leu Gln Met Asn Ser Leu Arg Asp Glu Asp Thr Ala Val Tyr Tyr Cys
                85                  90                  95

Ala Arg Trp Gly Tyr Gly Ser Gly Gly Phe Asp Tyr Trp Gly Gln Gly
            100                 105                 110

Thr Leu Val Thr Val Ser Ser Ala Ser Thr Lys Gly Pro Ser Val Phe
            115                 120                 125

Pro Leu Ala Pro Ser Ser Lys Ser Thr Ser Gly Gly Thr Ala Ala Leu
            130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
            195                 200                 205

Ser Asn Thr Lys Val Asp Lys Arg Val Glu Pro Lys Ser Cys Asp Lys
            210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
            275                 280                 285

Ala Lys Thr Lys Pro Arg Glu Glu Gln Tyr Asn Ser Thr Tyr Arg Val
290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
            355                 360                 365

Cys Leu Val Lys Gly Phe Tyr Pro Ser Asp Ile Ala Val Glu Trp Glu
            370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430
```

```
Ala Leu His Asn His Tyr Thr Gln Lys Ser Leu Ser Leu Ser Pro Gly
            435                 440                 445
```

<210> SEQ ID NO 71
<211> LENGTH: 1344
<212> TYPE: DNA
<213> ORGANISM: artificial sequence
<220> FEATURE:
<223> OTHER INFORMATION: 3F5-MICA.2 Heavy Chain NT

<400> SEQUENCE: 71

```
gaggtgcaac tggtggaatc tgggggaggc ttggtacagc ctggggggtc cctgagactc      60
tcctgtgcag cctctggatt caccttcagt acctatagca tgaactgggt ccgccaggct     120
ccagggaagg gctggagtg ggtttcatac attagttatc gtagtcgtac catatactac     180
gcagactctg tgaagggccg attcaccatc tccagagaca tgccaggaa ctcactgtat     240
ctgcaaatga acagcctgag agacgaggac acggctgtgt attactgtgc gagatggggc     300
tatggttcgg ggggctttga ctactggggc caggaaccc tggtcaccgt ctcctcagct     360
agcaccaagg gcccatcggt cttccccctg gcaccctcct ccaagagcac ctctggggc     420
acagcggccc tgggctgcct ggtcaaggac tacttccccg aaccggtgac ggtgtcgtgg     480
aactcaggcg ccctgaccag cggcgtgcac accttcccgg ctgtcctaca gtcctcagga     540
ctctactccc tcagcagcgt ggtgaccgtg ccctccagca gcttgggcac ccagacctac     600
atctgcaacg tgaatcacaa gcccagcaac accaaggtgg acaagagagt tgagcccaaa     660
tcttgtgaca aaactcacac atgcccaccg tgcccagcac ctgaactcct ggggggaccg     720
tcagtcttcc tcttccccc aaaacccaag gacaccctca tgatctcccg gacccctgag     780
gtcacatgcg tggtggtgga cgtgagccac gaagaccctg aggtcaagtt caactggtac     840
gtggacggcg tggaggtgca taatgccaag acaaagccgc gggaggagca gtacaacagc     900
acgtaccgtg tggtcagcgt cctcaccgtc ctgcaccagg actggctgaa tggcaaggag     960
tacaagtgca aggtctccaa caaagccctc ccagccccca tcgagaaaac catctccaaa    1020
gccaaagggc agccccgaga accacaggtg tacaccctgc ccccatcccg ggaggagatg    1080
accaagaacc aggtcagcct gacctgcctg gtcaaaggct tctatcccag cgacatcgcc    1140
gtggagtggg agagcaatgg gcagccggag aacaactaca agaccacgcc tcccgtgctg    1200
gactccgacg gctccttctt cctctatagc aagctcaccg tggacaagag caggtggcag    1260
caggggaacg tcttctcatg ctccgtgatg catgaggctc tgcacaacca ctacacgcag    1320
aagagcctct ccctgtcccc gggt                                            1344
```

<210> SEQ ID NO 72
<211> LENGTH: 214
<212> TYPE: PRT
<213> ORGANISM: artificial sequence
<220> FEATURE:
<223> OTHER INFORMATION: 3F5-MICA.2 Light Chain AA

<400> SEQUENCE: 72

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
```

```
            50                  55                  60
Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Gln Tyr Gly Ser Ser Phe
                 85                  90                  95

Thr Phe Gly Pro Gly Thr Lys Val Asp Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
            130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Cys
    210
```

```
<210> SEQ ID NO 73
<211> LENGTH: 642
<212> TYPE: DNA
<213> ORGANISM: artificial sequence
<220> FEATURE:
<223> OTHER INFORMATION: 3F5-MICA.2 Light Chain NT

<400> SEQUENCE: 73
gaaattgtgt tgacgcagtc tccaggcacc ctgtctttgt ctccagggga aagagccacc      60
ctctcctgca gggccagtca gagtgttagc agcagctact tagcctggta ccagcagaaa     120
cctggccagg ctcccaggct cctcatctat ggtgcatcca gcagggccac tggcatccca     180
gacaggttca gtggcagtgg gtctgggaca gacttcactc tcaccatcag cagactggag     240
cctgaagatt ttgcagtgta ttactgtcag cagtatggta gctcattcac tttcggccct     300
gggaccaaag tggatatcaa acgtacggtg gctgcaccat ctgtcttcat cttcccgcca     360
tctgatgagc agttgaaatc tggaactgcc tctgttgtgt gcctgctgaa taacttctat     420
cccagagagg ccaaagtaca gtggaaggtg gataacgccc tccaatcggg taactcccag     480
gagagtgtca cagagcagga cagcaaggac agcacctaca gcctcagcag caccctgacg     540
ctgagcaaag cagactacga gaaacacaaa gtctacgcct gcgaagtcac ccatcagggc     600
ctgagctcgc ccgtcacaaa gagcttcaac aggggagagt gt                       642

<210> SEQ ID NO 74

<400> SEQUENCE: 74

000

<210> SEQ ID NO 75

<400> SEQUENCE: 75

000
```

<210> SEQ ID NO 76

<400> SEQUENCE: 76

000

<210> SEQ ID NO 77

<400> SEQUENCE: 77

000

<210> SEQ ID NO 78
<211> LENGTH: 123
<212> TYPE: PRT
<213> ORGANISM: artificial sequence
<220> FEATURE:
<223> OTHER INFORMATION: GITR VH

<400> SEQUENCE: 78

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Trp Tyr Glu Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Ser Met Val Arg Gly Asp Tyr Tyr Tyr Gly Met Asp
            100                 105                 110

Val Trp Gly Gln Gly Thr Thr Val Thr Val Ser
        115                 120

<210> SEQ ID NO 79
<211> LENGTH: 107
<212> TYPE: PRT
<213> ORGANISM: artificial sequence
<220> FEATURE:
<223> OTHER INFORMATION: GITR VL

<400> SEQUENCE: 79

Ala Ile Gln Leu Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Ala
            20                  25                  30

Leu Ala Trp Tyr Gln Gln Lys Pro Gly Lys Ala Pro Lys Leu Leu Ile
        35                  40                  45

Tyr Asp Ala Ser Ser Leu Glu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Phe Asn Ser Tyr Pro Tyr
                85                  90                  95

Thr Phe Gly Gln Gly Thr Lys Leu Glu Ile Lys
            100                 105

<210> SEQ ID NO 80
<211> LENGTH: 123
<212> TYPE: PRT
<213> ORGANISM: artificial sequence
<220> FEATURE:
<223> OTHER INFORMATION: GITR VH

<400> SEQUENCE: 80

```
Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Phe His Trp Val Arg Gln Ala Pro Gly Lys Gly Leu Glu Trp Val
        35                  40                  45

Ala Val Ile Trp Tyr Ala Gly Ser Asn Lys Phe Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Gln Leu Asp Tyr Tyr Tyr Tyr Tyr Val Met Asp Val
            100                 105                 110

Trp Gly Gln Gly Thr Thr Val Thr Val Ser Ser
        115                 120
```

<210> SEQ ID NO 81
<211> LENGTH: 107
<212> TYPE: PRT
<213> ORGANISM: artificial sequence
<220> FEATURE:
<223> OTHER INFORMATION: GITR VL

<400> SEQUENCE: 81

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Glu Lys Ala Pro Lys Ser Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Tyr Pro Tyr
                85                  90                  95

Thr Phe Gly Gln Gly Thr Lys Leu Glu Ile Lys
            100                 105
```

<210> SEQ ID NO 82
<211> LENGTH: 122
<212> TYPE: PRT
<213> ORGANISM: artificial sequence
<220> FEATURE:
<223> OTHER INFORMATION: GITR VH

<400> SEQUENCE: 82

```
Val Gln Leu Val Glu Ser Gly Gly Gly Val Val Gln Pro Gly Arg Ser
1               5                   10                  15

Leu Arg Leu Ser Cys Ala Ala Ser Gly Phe Thr Phe Ser Ser Tyr Gly
            20                  25                  30
```

```
Met His Trp Val Arg Gln Ala Pro Gly Lys Gly Leu Glu Trp Val Ala
            35                  40                  45

Val Ile Trp Tyr Ala Gly Ser Asn Lys Tyr Tyr Ala Asp Ser Val Lys
 50                  55                  60

Gly Arg Phe Thr Ile Ser Arg Asp Asn Ser Lys Asn Thr Leu Tyr Leu
 65                  70                  75                  80

Gln Met Asn Ser Leu Arg Ala Glu Asp Thr Ala Val Tyr Tyr Cys Ala
            85                  90                  95

Arg Gly Gly Arg Ile Ala Val Ala Phe Tyr Tyr Ser Met Asp Val Trp
            100                 105                 110

Gly Gln Gly Thr Thr Val Thr Val Ser Ser
            115                 120
```

<210> SEQ ID NO 83
<211> LENGTH: 107
<212> TYPE: PRT
<213> ORGANISM: artificial sequence
<220> FEATURE:
<223> OTHER INFORMATION: GITR VL

<400> SEQUENCE: 83

```
Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Gly Ile Ser Ser Trp
            20                  25                  30

Leu Ala Trp Tyr Gln Gln Lys Pro Glu Lys Ala Pro Lys Ser Leu Ile
            35                  40                  45

Tyr Ala Ala Ser Ser Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Tyr Asn Ser Tyr Pro Tyr
            85                  90                  95

Thr Phe Gly Gln Gly Thr Lys Leu Glu Ile Lys
            100                 105
```

<210> SEQ ID NO 84
<211> LENGTH: 449
<212> TYPE: PRT
<213> ORGANISM: artificial sequence
<220> FEATURE:
<223> OTHER INFORMATION: GITR Heavy Chain

<400> SEQUENCE: 84

```
Gln Val Gln Leu Val Glu Ser Gly Gly Gly Val Val Gln Pro Gly Arg
 1               5                  10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
            35                  40                  45

Ala Val Ile Trp Tyr Glu Gly Ser Asn Lys Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
            85                  90                  95

Ala Arg Gly Gly Ser Met Val Arg Gly Asp Tyr Tyr Tyr Gly Met Asp
```

```
                100             105                 110
Val Trp Gly Gln Gly Thr Thr Val Thr Val Ser Ser Ala Ser Thr Lys
            115                 120             125

Gly Pro Ser Val Phe Pro Leu Ala Pro Cys Ser Arg Ser Thr Ser Glu
            130                 135             140

Ser Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Asn Phe Gly Thr Gln Thr Tyr Thr Cys Asn
            195                 200                 205

Val Asp His Lys Pro Ser Asn Thr Lys Val Asp Lys Thr Val Glu Arg
            210                 215                 220

Lys Cys Cys Val Glu Cys Pro Pro Cys Pro Ala Pro Pro Val Ala Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
                260                 265                 270

Asp Pro Glu Val Gln Phe Asn Trp Tyr Val Asp Gly Val Glu Val His
                275                 280                 285

Asn Ala Lys Thr Lys Pro Arg Glu Glu Gln Phe Asn Ser Thr Phe Arg
            290                 295                 300

Val Val Ser Val Leu Thr Val Val His Gln Asp Trp Leu Asn Gly Lys
305                 310                 315                 320

Glu Tyr Lys Cys Lys Val Ser Asn Lys Gly Leu Pro Ala Pro Ile Glu
                325                 330                 335

Lys Thr Ile Ser Lys Thr Lys Gly Gln Pro Arg Glu Pro Gln Val Tyr
                340                 345                 350

Thr Leu Pro Pro Ser Arg Glu Glu Met Thr Lys Asn Gln Val Ser Leu
            355                 360                 365

Thr Cys Leu Val Lys Gly Phe Tyr Pro Ser Asp Ile Ala Val Glu Trp
            370                 375                 380

Glu Ser Asn Gly Gln Pro Glu Asn Asn Tyr Lys Thr Thr Pro Pro Met
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
                420                 425                 430

Glu Ala Leu His Asn His Tyr Thr Gln Lys Ser Leu Ser Leu Ser Pro
            435                 440                 445

Gly

<210> SEQ ID NO 85
<211> LENGTH: 214
<212> TYPE: PRT
<213> ORGANISM: artificial sequence
<220> FEATURE:
<223> OTHER INFORMATION: GITR Light Chain

<400> SEQUENCE: 85

Ala Ile Gln Leu Thr Gln Ser Pro Ser Ser Leu Ser Ala Ser Val Gly
1               5                   10                  15
```

Asp Arg Val Thr Ile Thr Cys Arg Ala Ser Gln Gly Ile Ser Ser Ala
            20                  25                  30

Leu Ala Trp Tyr Gln Gln Lys Pro Gly Lys Ala Pro Lys Leu Leu Ile
        35                  40                  45

Tyr Asp Ala Ser Ser Leu Glu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Phe Asn Ser Tyr Pro Tyr
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 86
<211> LENGTH: 453
<212> TYPE: PRT
<213> ORGANISM: artificial sequence
<220> FEATURE:
<223> OTHER INFORMATION: GITR Heavy Chain

<400> SEQUENCE: 86

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Trp Tyr Glu Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Ser Met Val Arg Gly Asp Tyr Tyr Tyr Gly Met Asp
            100                 105                 110

Val Trp Gly Gln Gly Thr Thr Val Thr Val Ser Ser Ala Ser Thr Lys
        115                 120                 125

Gly Pro Ser Val Phe Pro Leu Ala Pro Ser Ser Lys Ser Thr Ser Gly
    130                 135                 140

Gly Thr Ala Ala Leu Gly Cys Leu Val Lys Asp Tyr Phe Pro Glu Pro
145                 150                 155                 160

```
Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Ser Leu Gly Thr Gln Thr Tyr Ile Cys Asn
        195                 200                 205

Val Asn His Lys Pro Ser Asn Thr Lys Val Asp Lys Arg Val Glu Pro
    210                 215                 220

Lys Ser Cys Asp Lys Thr His Thr Cys Pro Pro Cys Pro Ala Pro Glu
225                 230                 235                 240

Ala Glu Gly Ala Pro Ser Val Phe Leu Phe Pro Pro Lys Pro Lys Asp
                245                 250                 255

Thr Leu Met Ile Ser Arg Thr Pro Glu Val Thr Cys Val Val Val Asp
            260                 265                 270

Val Ser His Glu Asp Pro Glu Val Lys Phe Asn Trp Tyr Val Asp Gly
        275                 280                 285

Val Glu Val His Asn Ala Lys Thr Lys Pro Arg Glu Glu Gln Tyr Asn
    290                 295                 300

Ser Thr Tyr Arg Val Val Ser Val Leu Thr Val Leu His Gln Asp Trp
305                 310                 315                 320

Leu Asn Gly Lys Glu Tyr Lys Cys Lys Val Ser Asn Lys Ala Leu Pro
                325                 330                 335

Ser Ser Ile Glu Lys Thr Ile Ser Lys Ala Lys Gly Gln Pro Arg Glu
            340                 345                 350

Pro Gln Val Tyr Thr Leu Pro Pro Ser Arg Glu Glu Met Thr Lys Asn
        355                 360                 365

Gln Val Ser Leu Thr Cys Leu Val Lys Gly Phe Tyr Pro Ser Asp Ile
    370                 375                 380

Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Phe Leu Tyr Ser Lys
                405                 410                 415

Leu Thr Val Asp Lys Ser Arg Trp Gln Gln Gly Asn Val Phe Ser Cys
            420                 425                 430

Ser Val Met His Glu Ala Leu His Asn His Tyr Thr Gln Lys Ser Leu
        435                 440                 445

Ser Leu Ser Pro Gly
    450

<210> SEQ ID NO 87
<211> LENGTH: 214
<212> TYPE: PRT
<213> ORGANISM: artificial sequence
<220> FEATURE:
<223> OTHER INFORMATION: GITR Light Chain

<400> SEQUENCE: 87

Ala Ile Gln Leu Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Ala
            20                  25                  30

Leu Ala Trp Tyr Gln Gln Lys Pro Gly Lys Ala Pro Lys Leu Leu Ile
        35                  40                  45

Tyr Asp Ala Ser Ser Leu Glu Ser Gly Val Pro Ser Arg Phe Ser Gly
    50                  55                  60
```

```
Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Phe Asn Ser Tyr Pro Tyr
                 85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 88
<211> LENGTH: 287
<212> TYPE: PRT
<213> ORGANISM: artificial sequence
<220> FEATURE:
<223> OTHER INFORMATION: Human MICA Isoform 2 (MICA2)

<400> SEQUENCE: 88

```
Met Gly Leu Gly Pro Val Phe Leu Leu Leu Ala Gly Ile Phe Pro Phe
  1               5                  10                  15

Ala Pro Pro Gly Ala Ala Ala Glu Pro His Ser Leu Arg Tyr Asn Leu
                 20                  25                  30

Thr Val Leu Ser Trp Asp Gly Ser Val Gln Ser Gly Phe Leu Thr Glu
             35                  40                  45

Val His Leu Asp Gly Gln Pro Phe Leu Arg Cys Asp Arg Gln Lys Cys
 50                  55                  60

Arg Ala Lys Pro Gln Gly Gln Trp Ala Glu Asp Val Leu Gly Asn Lys
 65                  70                  75                  80

Thr Trp Asp Arg Glu Thr Arg Asp Leu Thr Gly Asn Gly Lys Asp Leu
                 85                  90                  95

Arg Met Thr Leu Ala His Ile Lys Asp Gln Lys Glu Val Pro Pro Met
            100                 105                 110

Val Asn Val Thr Arg Ser Glu Ala Ser Glu Gly Asn Ile Thr Val Thr
        115                 120                 125

Cys Arg Ala Ser Gly Phe Tyr Pro Trp Asn Ile Thr Leu Ser Trp Arg
    130                 135                 140

Gln Asp Gly Val Ser Leu Ser His Asp Thr Gln Gln Trp Gly Asp Val
145                 150                 155                 160

Leu Pro Asp Gly Asn Gly Thr Tyr Gln Thr Trp Val Ala Thr Arg Ile
                165                 170                 175

Cys Gln Gly Glu Glu Gln Arg Phe Thr Cys Tyr Met Glu His Ser Gly
            180                 185                 190

Asn His Ser Thr His Pro Val Pro Ser Gly Lys Val Leu Val Leu Gln
        195                 200                 205
```

Ser His Trp Gln Thr Phe His Val Ser Ala Val Ala Ala Ala Ile
    210                 215                 220

Phe Val Ile Ile Ile Phe Tyr Val Arg Cys Cys Lys Lys Lys Thr Ser
225                 230                 235                 240

Ala Ala Glu Gly Pro Glu Leu Val Ser Leu Gln Val Leu Asp Gln His
                245                 250                 255

Pro Val Gly Thr Ser Asp His Arg Asp Ala Thr Gln Leu Gly Phe Gln
            260                 265                 270

Pro Leu Met Ser Asp Leu Gly Ser Thr Gly Ser Thr Glu Gly Ala
            275                 280                 285

<210> SEQ ID NO 89
<211> LENGTH: 284
<212> TYPE: PRT
<213> ORGANISM: artificial sequence
<220> FEATURE:
<223> OTHER INFORMATION: MICA EC Domain

<400> SEQUENCE: 89

Glu Pro His Ser Leu Arg Tyr Asn Leu Thr Val Leu Ser Trp Asp Gly
1               5                   10                  15

Ser Val Gln Ser Gly Phe Leu Thr Glu Val His Leu Asp Gly Gln Pro
            20                  25                  30

Phe Leu Arg Cys Asp Arg Gln Lys Cys Arg Ala Lys Pro Gln Gly Gln
        35                  40                  45

Trp Ala Glu Asp Val Leu Gly Asn Lys Thr Trp Asp Arg Glu Thr Arg
50                  55                  60

Asp Leu Thr Gly Asn Gly Lys Asp Leu Arg Met Thr Leu Ala His Ile
65                  70                  75                  80

Lys Asp Gln Lys Glu Gly Leu His Ser Leu Gln Glu Ile Arg Val Cys
                85                  90                  95

Glu Ile His Glu Asp Asn Ser Thr Arg Ser Ser Gln His Phe Tyr Tyr
            100                 105                 110

Asp Gly Glu Leu Phe Leu Ser Gln Asn Leu Glu Thr Lys Glu Trp Thr
        115                 120                 125

Met Pro Gln Ser Ser Arg Ala Gln Thr Leu Ala Met Asn Val Arg Asn
130                 135                 140

Phe Leu Lys Glu Asp Ala Met Lys Thr Lys Thr His Tyr His Ala Met
145                 150                 155                 160

His Ala Asp Cys Leu Gln Glu Leu Arg Arg Tyr Leu Lys Ser Gly Val
                165                 170                 175

Val Leu Arg Arg Thr Val Pro Pro Met Val Asn Val Thr Arg Ser Glu
            180                 185                 190

Ala Ser Glu Gly Asn Ile Thr Val Thr Cys Arg Ala Ser Gly Phe Tyr
        195                 200                 205

Pro Trp Asn Ile Thr Leu Ser Trp Arg Gln Asp Gly Val Ser Leu Ser
210                 215                 220

His Asp Thr Gln Gln Trp Gly Asp Val Leu Pro Asp Gly Asn Gly Thr
225                 230                 235                 240

Tyr Gln Thr Trp Val Ala Thr Arg Ile Cys Gln Gly Glu Glu Gln Arg
                245                 250                 255

Phe Thr Cys Tyr Met Glu His Ser Gly Asn His Ser Thr His Pro Val
            260                 265                 270

Pro Ser Gly Lys Val Leu Val Leu Gln Ser His Trp
        275                 280

<210> SEQ ID NO 90
<211> LENGTH: 274
<212> TYPE: PRT
<213> ORGANISM: artificial sequence
<220> FEATURE:
<223> OTHER INFORMATION: Cynomolgus monkey MICA (partial) UniProt-Q2MGE0

<400> SEQUENCE: 90

Glu Leu His Ser Leu Arg Tyr Asn Val Thr Val Leu Ser Arg Asp Gly
1               5                   10                  15

Ser Val Gln Ser Gly Phe Leu Ala Glu Gly His Leu Asp Gly Gln Leu
            20                  25                  30

Phe Leu Leu Tyr Asp Arg Gln Lys Cys Arg Ala Arg Pro Gln Gly Glu
        35                  40                  45

Trp Ser Glu Asp Val Leu Gly Ala Lys Thr Trp Asp Thr Glu Thr Gly
50                  55                  60

Asp Leu Thr Glu Asn Gly Lys Asp Leu Arg Met Thr Leu Ala His Ile
65                  70                  75                  80

Lys Gly Gln Lys Gly Gly Leu His Ser Leu Gln Glu Ile Lys Val Cys
                85                  90                  95

Glu Ile His Glu Asp Asn Ser Thr Gly Gly Leu Arg His Phe Tyr Tyr
            100                 105                 110

Asp Gly Glu Leu Phe Leu Ser Gln Asn Leu Glu Thr Gln Glu Trp Thr
        115                 120                 125

Glu Leu Gln Ser Ser Arg Ala Gln Thr Leu Ala Leu Asn Ile Arg Asn
130                 135                 140

Phe Trp Lys Glu Asp Thr Met Lys Thr Lys Thr His Tyr Arg Ala Val
145                 150                 155                 160

Gln Ala Asp Cys Leu Lys Lys Leu Gln Gln Tyr Leu Glu Ser Gly Val
                165                 170                 175

Ala Val Arg Arg Thr Ala Pro Pro Met Val Asn Val Thr His Ser Glu
            180                 185                 190

Ala Ser Glu Gly Asn Ile Thr Val Thr Cys Arg Ala Ser Gly Phe Tyr
        195                 200                 205

Pro Arg Asn Ile Ala Leu Thr Trp Arg Gln Asp Gly Val Ser Leu Asn
210                 215                 220

His Asn Ala Gln Gln Trp Gly Gly Ile Leu Pro Asp Gln Asn Gly Thr
225                 230                 235                 240

Tyr Gln Thr Trp Val Ala Thr Arg Ile Arg Gln Gly Glu Glu Gln Arg
                245                 250                 255

Phe Ala Cys Tyr Met Glu His Ser Gly Asn His Ser Thr His Pro Val
            260                 265                 270

Pro Ser

<210> SEQ ID NO 91
<211> LENGTH: 330
<212> TYPE: PRT
<213> ORGANISM: artificial sequence
<220> FEATURE:
<223> OTHER INFORMATION: Wild-type human IgG

<400> SEQUENCE: 91

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

```
Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Leu Gly Thr Gln Thr
 65              70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
            115                 120                 125

Lys Pro Lys Asp Thr Leu Met Ile Ser Arg Thr Pro Glu Val Thr Cys
            130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
            210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
        290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 92
<211> LENGTH: 330
<212> TYPE: PRT
<213> ORGANISM: artificial sequence
<220> FEATURE:
<223> OTHER INFORMATION: Allotypic variant of human IgG

<400> SEQUENCE: 92

Ala Ser Thr Lys Gly Pro Ser Val Phe Pro Leu Ala Pro Ser Ser Lys
 1               5                  10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60
```

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
            85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
            115                 120                 125

Lys Pro Lys Asp Thr Leu Met Ile Ser Arg Thr Pro Glu Val Thr Cys
            130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
            165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
            210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
            245                 250                 255

Pro Ser Asp Ile Ala Val Glu Trp Ser Asn Gly Gln Pro Glu Asn
            260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
            290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
            325                 330

<210> SEQ ID NO 93
<211> LENGTH: 330
<212> TYPE: PRT
<213> ORGANISM: artificial sequence
<220> FEATURE:
<223> OTHER INFORMATION: IgG1.1f - effectorless human IgG1 constant
      domain

<400> SEQUENCE: 93

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
            50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys

```
            85                  90                  95
Arg Val Glu Pro Lys Ser Cys Asp Lys Thr His Thr Cys Pro Pro Cys
            100                 105                 110

Pro Ala Pro Glu Ala Glu Gly Ala Pro Ser Val Phe Leu Phe Pro Pro
            115                 120                 125

Lys Pro Lys Asp Thr Leu Met Ile Ser Arg Thr Pro Glu Val Thr Cys
        130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
            195                 200                 205

Lys Ala Leu Pro Ser Ser Ile Glu Lys Thr Ile Ser Lys Ala Lys Gly
        210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
        290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 94
<211> LENGTH: 330
<212> TYPE: PRT
<213> ORGANISM: artificial sequence
<220> FEATURE:
<223> OTHER INFORMATION: IgG1.3f - effectorless human IgG1 constant
      domain

<400> SEQUENCE: 94

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110
```

```
Pro Ala Pro Glu Ala Glu Gly Ala Pro Ser Val Phe Leu Phe Pro Pro
            115                 120                 125
Lys Pro Lys Asp Thr Leu Met Ile Ser Arg Thr Pro Glu Val Thr Cys
130                 135                 140
Val Val Asp Val Ser His Glu Asp Pro Glu Val Lys Phe Asn Trp
145                 150                 155                 160
Tyr Val Asp Gly Val Glu Val His Asn Ala Lys Thr Lys Pro Arg Glu
                165                 170                 175
Glu Gln Tyr Asn Ser Thr Tyr Arg Val Val Ser Val Leu Thr Val Leu
            180                 185                 190
His Gln Asp Trp Leu Asn Gly Lys Glu Tyr Lys Cys Lys Val Ser Asn
        195                 200                 205
Lys Ala Leu Pro Ala Pro Ile Glu Lys Thr Ile Ser Lys Ala Lys Gly
210                 215                 220
Gln Pro Arg Glu Pro Gln Val Tyr Thr Leu Pro Pro Ser Arg Glu Glu
225                 230                 235                 240
Met Thr Lys Asn Gln Val Ser Leu Thr Cys Leu Val Lys Gly Phe Tyr
                245                 250                 255
Pro Ser Asp Ile Ala Val Glu Trp Glu Ser Asn Gly Gln Pro Glu Asn
            260                 265                 270
Asn Tyr Lys Thr Thr Pro Pro Val Leu Asp Ser Asp Gly Ser Phe Phe
        275                 280                 285
Leu Tyr Ser Lys Leu Thr Val Asp Lys Ser Arg Trp Gln Gln Gly Asn
    290                 295                 300
Val Phe Ser Cys Ser Val Met His Glu Ala Leu His Asn His Tyr Thr
305                 310                 315                 320
Gln Lys Ser Leu Ser Leu Ser Pro Gly Lys
                325                 330

<210> SEQ ID NO 95
<211> LENGTH: 327
<212> TYPE: PRT
<213> ORGANISM: artificial sequence
<220> FEATURE:
<223> OTHER INFORMATION: human IgG4

<400> SEQUENCE: 95

Ala Ser Thr Lys Gly Pro Ser Val Phe Pro Leu Ala Pro Cys Ser Arg
1               5                   10                  15
Ser Thr Ser Glu Ser Thr Ala Ala Leu Gly Cys Leu Val Lys Asp Tyr
            20                  25                  30
Phe Pro Glu Pro Val Thr Val Ser Trp Asn Ser Gly Ala Leu Thr Ser
        35                  40                  45
Gly Val His Thr Phe Pro Ala Val Leu Gln Ser Ser Gly Leu Tyr Ser
    50                  55                  60
Leu Ser Ser Val Val Thr Val Pro Ser Ser Ser Leu Gly Thr Lys Thr
65                  70                  75                  80
Tyr Thr Cys Asn Val Asp His Lys Pro Ser Asn Thr Lys Val Asp Lys
                85                  90                  95
Arg Val Glu Ser Lys Tyr Gly Pro Pro Cys Pro Ser Cys Pro Ala Pro
            100                 105                 110
Glu Phe Leu Gly Gly Pro Ser Val Phe Leu Phe Pro Pro Lys Pro Lys
        115                 120                 125
Asp Thr Leu Met Ile Ser Arg Thr Pro Glu Val Thr Cys Val Val Val
    130                 135                 140
```

```
Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
                260                 265                 270

Thr Thr Pro Pro Val Leu Asp Ser Asp Gly Ser Phe Phe Leu Tyr Ser
            275                 280                 285

Arg Leu Thr Val Asp Lys Ser Arg Trp Gln Glu Gly Asn Val Phe Ser
        290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 96
<211> LENGTH: 107
<212> TYPE: PRT
<213> ORGANISM: artificial sequence
<220> FEATURE:
<223> OTHER INFORMATION: Human IgG1 kappa light chain

<400> SEQUENCE: 96

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 97
<211> LENGTH: 5
<212> TYPE: PRT
<213> ORGANISM: artificial sequence
<220> FEATURE:
<223> OTHER INFORMATION: heavy chain constant region C-terminus

<400> SEQUENCE: 97

Leu Ser Pro Gly Lys
1               5
```

<210> SEQ ID NO 98
<211> LENGTH: 4
<212> TYPE: PRT
<213> ORGANISM: artificial sequence
<220> FEATURE:
<223> OTHER INFORMATION: heavy chain constant region C-terminus

<400> SEQUENCE: 98

Leu Ser Pro Gly
1

<210> SEQ ID NO 99
<211> LENGTH: 3
<212> TYPE: PRT
<213> ORGANISM: artificial sequence
<220> FEATURE:
<223> OTHER INFORMATION: heavy chain constant region C-terminus

<400> SEQUENCE: 99

Leu Ser Pro
1

<210> SEQ ID NO 100
<211> LENGTH: 19
<212> TYPE: PRT
<213> ORGANISM: artificial sequence
<220> FEATURE:
<223> OTHER INFORMATION: signal peptide

<400> SEQUENCE: 100

Met Asp Trp Thr Trp Arg Val Phe Cys Leu Leu Ala Val Ala Pro Gly
1               5                   10                  15

Ala His Ser

<210> SEQ ID NO 101
<211> LENGTH: 20
<212> TYPE: PRT
<213> ORGANISM: artificial sequence
<220> FEATURE:
<223> OTHER INFORMATION: signal peptide

<400> SEQUENCE: 101

Met Glu Thr Pro Ala Gln Leu Leu Phe Leu Leu Leu Leu Trp Leu Pro
1               5                   10                  15

Asp Thr Thr Gly
            20

<210> SEQ ID NO 102
<211> LENGTH: 19
<212> TYPE: PRT
<213> ORGANISM: artificial sequence
<220> FEATURE:
<223> OTHER INFORMATION: signal peptide

<400> SEQUENCE: 102

Met Lys His Leu Trp Phe Phe Leu Leu Leu Val Ala Ala Pro Arg Trp
1               5                   10                  15

Val Leu Ser

<210> SEQ ID NO 103
<211> LENGTH: 19
<212> TYPE: PRT
<213> ORGANISM: artificial sequence
<220> FEATURE:

<223> OTHER INFORMATION: signal peptide

<400> SEQUENCE: 103

Met Glu Phe Gly Leu Ser Trp Val Phe Leu Val Ala Ile Ile Lys Gly
1               5                   10                  15

Val Gln Cys

<210> SEQ ID NO 104
<211> LENGTH: 21
<212> TYPE: PRT
<213> ORGANISM: artificial sequence
<220> FEATURE:
<223> OTHER INFORMATION: signal peptide

<400> SEQUENCE: 104

Met Asp Met Arg Val Pro Ala Gln Leu Leu Gly Leu Leu Leu Trp Leu
1               5                   10                  15

Pro Gly Ala Arg Cys
            20

<210> SEQ ID NO 105
<211> LENGTH: 17
<212> TYPE: PRT
<213> ORGANISM: artificial sequence
<220> FEATURE:
<223> OTHER INFORMATION: signal peptide

<400> SEQUENCE: 105

Met Arg Ala Trp Ile Phe Phe Leu Leu Cys Leu Ala Gly Arg Ala Leu
1               5                   10                  15

Ala

<210> SEQ ID NO 106
<211> LENGTH: 51
<212> TYPE: PRT
<213> ORGANISM: artificial sequence
<220> FEATURE:
<223> OTHER INFORMATION: signal peptide

<400> SEQUENCE: 106

Ala Thr Gly Ala Gly Gly Gly Cys Thr Thr Gly Gly Ala Thr Cys Thr
1               5                   10                  15

Thr Cys Thr Thr Thr Cys Thr Gly Cys Thr Cys Thr Gly Cys Cys Thr
                20                  25                  30

Gly Gly Cys Cys Gly Gly Gly Ala Gly Ala Gly Cys Gly Cys Thr Cys
            35                  40                  45

Gly Cys Ala
    50

<210> SEQ ID NO 107
<211> LENGTH: 51
<212> TYPE: PRT
<213> ORGANISM: artificial sequence
<220> FEATURE:
<223> OTHER INFORMATION: signal peptide

<400> SEQUENCE: 107

Ala Thr Gly Ala Gly Gly Gly Cys Thr Thr Gly Gly Ala Thr Cys Thr
1               5                   10                  15

Thr Cys Thr Thr Thr Cys Thr Gly Cys Thr Cys Thr Gly Cys Cys Thr
                20                  25                  30

Gly Gly Cys Cys Gly Gly Gly Cys Gly Cys Gly Cys Thr Thr Gly

```
                      35                  40                  45

Gly Cys Cys
    50

<210> SEQ ID NO 108
<211> LENGTH: 5
<212> TYPE: PRT
<213> ORGANISM: artificial sequence
<220> FEATURE:
<223> OTHER INFORMATION: Linker

<400> SEQUENCE: 108

Pro Val Gly Val Val
1               5

<210> SEQ ID NO 109
<211> LENGTH: 383
<212> TYPE: PRT
<213> ORGANISM: artificial sequence
<220> FEATURE:
<223> OTHER INFORMATION: MICA1 (MICA Variant)

<400> SEQUENCE: 109

Met Gly Leu Gly Pro Val Phe Leu Leu Ala Gly Ile Phe Pro Phe
1               5                   10                  15

Ala Pro Pro Gly Ala Ala Ala Glu Pro His Ser Leu Arg Tyr Asn Leu
                20                  25                  30

Thr Val Leu Ser Trp Asp Gly Ser Val Gln Ser Gly Phe Leu Thr Glu
            35                  40                  45

Val His Leu Asp Gly Gln Pro Phe Leu Arg Cys Asp Arg Gln Lys Cys
        50                  55                  60

Arg Ala Lys Pro Gln Gly Gln Trp Ala Glu Asp Val Leu Gly Asn Lys
65                  70                  75                  80

Thr Trp Asp Arg Glu Thr Arg Asp Leu Thr Gly Asn Gly Lys Asp Leu
                85                  90                  95

Arg Met Thr Leu Ala His Ile Lys Asp Gln Lys Glu Gly Leu His Ser
                100                 105                 110

Leu Gln Glu Ile Arg Val Cys Glu Ile His Glu Asp Asn Ser Thr Arg
            115                 120                 125

Ser Ser Gln His Phe Tyr Tyr Asp Gly Glu Leu Phe Leu Ser Gln Asn
        130                 135                 140

Leu Glu Thr Lys Glu Trp Thr Met Pro Gln Ser Ser Arg Ala Gln Thr
145                 150                 155                 160

Leu Ala Met Asn Val Arg Asn Phe Leu Lys Glu Asp Ala Met Lys Thr
                165                 170                 175

Lys Thr His Tyr His Ala Met His Ala Asp Cys Leu Gln Glu Leu Arg
                180                 185                 190

Arg Tyr Leu Lys Ser Gly Val Val Leu Arg Arg Thr Val Pro Pro Met
            195                 200                 205

Val Asn Val Thr Arg Ser Glu Ala Ser Glu Gly Asn Ile Thr Val Thr
        210                 215                 220

Cys Arg Ala Ser Gly Phe Tyr Pro Trp Asn Ile Thr Leu Ser Trp Arg
225                 230                 235                 240

Gln Asp Gly Val Ser Leu Ser His Asp Thr Gln Gln Trp Gly Asp Val
                245                 250                 255

Leu Pro Asp Gly Asn Gly Thr Tyr Gln Thr Trp Val Ala Thr Arg Ile
                260                 265                 270
```

Cys Gln Gly Glu Glu Gln Arg Phe Thr Cys Tyr Met Glu His Ser Gly
                275                 280                 285

Asn His Ser Thr His Pro Val Pro Ser Gly Lys Val Leu Val Leu Gln
            290                 295                 300

Ser His Trp Gln Thr Phe His Val Ser Ala Val Ala Ala Ala Ile
305                 310                 315                 320

Phe Val Ile Ile Ile Phe Tyr Val Arg Cys Cys Lys Lys Thr Ser
                325                 330                 335

Ala Ala Glu Gly Pro Glu Leu Val Ser Leu Gln Val Leu Asp Gln His
            340                 345                 350

Pro Val Gly Thr Ser Asp His Arg Asp Ala Thr Gln Leu Gly Phe Gln
            355                 360                 365

Pro Leu Met Ser Asp Leu Gly Ser Thr Gly Ser Thr Glu Gly Ala
            370                 375                 380

<210> SEQ ID NO 110
<211> LENGTH: 383
<212> TYPE: PRT
<213> ORGANISM: artificial sequence
<220> FEATURE:
<223> OTHER INFORMATION: MICA*002

<400> SEQUENCE: 110

Met Gly Leu Gly Pro Val Phe Leu Leu Leu Ala Gly Ile Phe Pro Phe
1               5                   10                  15

Ala Pro Pro Gly Ala Ala Ala Glu Pro His Ser Leu Arg Tyr Asn Leu
                20                  25                  30

Thr Val Leu Ser Gly Asp Gly Ser Val Gln Ser Gly Phe Leu Ala Glu
            35                  40                  45

Val His Leu Asp Gly Gln Pro Phe Leu Arg Cys Asp Arg Gln Lys Cys
        50                  55                  60

Arg Ala Lys Pro Gln Gly Gln Trp Ala Glu Asp Val Leu Gly Asn Lys
65                  70                  75                  80

Thr Trp Asp Arg Glu Thr Arg Asp Leu Thr Gly Asn Gly Lys Asp Leu
                85                  90                  95

Arg Met Thr Leu Ala His Ile Lys Asp Gln Lys Glu Gly Leu His Ser
                100                 105                 110

Leu Gln Glu Ile Arg Val Cys Glu Ile His Glu Asp Asn Ser Thr Arg
            115                 120                 125

Ser Ser Gln His Phe Tyr Tyr Asp Gly Glu Leu Phe Leu Ser Gln Asn
    130                 135                 140

Leu Glu Thr Glu Glu Trp Thr Met Pro Gln Ser Ser Arg Ala Gln Thr
145                 150                 155                 160

Leu Ala Met Asn Val Arg Asn Phe Leu Lys Glu Asp Ala Met Lys Thr
                165                 170                 175

Lys Thr His Tyr His Ala Met His Ala Asp Cys Leu Gln Glu Leu Arg
                180                 185                 190

Arg Tyr Leu Lys Ser Gly Val Val Leu Arg Arg Thr Val Pro Pro Met
            195                 200                 205

Val Asn Val Thr Arg Ser Glu Ala Ser Glu Gly Asn Ile Thr Val Thr
    210                 215                 220

Cys Arg Ala Ser Gly Phe Tyr Pro Trp Asn Ile Thr Leu Ser Trp Arg
225                 230                 235                 240

Gln Asp Gly Val Ser Leu Ser His Asp Thr Gln Gln Trp Gly Asp Val
                245                 250                 255

-continued

```
Leu Pro Asp Gly Asn Gly Thr Tyr Gln Thr Trp Val Ala Thr Arg Ile
            260                 265                 270

Cys Gln Gly Glu Glu Gln Arg Phe Thr Cys Tyr Met Glu His Ser Gly
        275                 280                 285

Asn His Ser Thr His Pro Val Pro Ser Gly Lys Val Leu Val Leu Gln
    290                 295                 300

Ser His Trp Gln Thr Phe His Val Ser Ala Val Ala Ala Ala Ala Ile
305                 310                 315                 320

Phe Val Ile Ile Ile Phe Tyr Val Arg Cys Cys Lys Lys Lys Thr Ser
                325                 330                 335

Ala Ala Glu Gly Pro Glu Leu Val Ser Leu Gln Val Leu Asp Gln His
            340                 345                 350

Pro Val Gly Thr Ser Asp His Arg Asp Ala Thr Gln Leu Gly Phe Gln
        355                 360                 365

Pro Leu Met Ser Asp Leu Gly Ser Thr Gly Ser Thr Glu Gly Thr
    370                 375                 380
```

<210> SEQ ID NO 111
<211> LENGTH: 385
<212> TYPE: PRT
<213> ORGANISM: artificial sequence
<220> FEATURE:
<223> OTHER INFORMATION: MICA*004

<400> SEQUENCE: 111

```
Met Gly Leu Gly Pro Val Phe Leu Leu Leu Ala Gly Ile Phe Pro Phe
1               5                   10                  15

Ala Pro Pro Gly Ala Ala Ala Glu Pro His Ser Leu Arg Tyr Asn Leu
            20                  25                  30

Thr Val Leu Ser Trp Asp Gly Ser Val Gln Ser Gly Phe Leu Ala Glu
        35                  40                  45

Val His Leu Asp Gly Gln Pro Phe Leu Arg Tyr Asp Arg Gln Lys Cys
    50                  55                  60

Arg Ala Lys Pro Gln Gly Gln Trp Ala Glu Asp Val Leu Gly Asn Lys
65                  70                  75                  80

Thr Trp Asp Arg Glu Thr Arg Asp Leu Thr Gly Asn Gly Lys Asp Leu
                85                  90                  95

Arg Met Thr Leu Ala His Ile Lys Asp Gln Lys Glu Gly Leu His Ser
            100                 105                 110

Leu Gln Glu Ile Arg Val Cys Glu Ile His Glu Asp Asn Ser Thr Arg
        115                 120                 125

Ser Ser Gln His Phe Tyr Tyr Asp Gly Glu Leu Phe Leu Ser Gln Asn
    130                 135                 140

Val Glu Thr Glu Glu Trp Thr Val Pro Gln Ser Ser Arg Ala Gln Thr
145                 150                 155                 160

Leu Ala Met Asn Val Arg Asn Phe Leu Lys Glu Asp Ala Met Lys Thr
                165                 170                 175

Lys Thr His Tyr His Ala Met His Ala Asp Cys Leu Gln Glu Leu Arg
            180                 185                 190

Arg Tyr Leu Glu Ser Ser Val Val Leu Arg Arg Val Pro Pro Met
        195                 200                 205

Val Asn Val Thr Arg Ser Glu Ala Ser Glu Gly Asn Ile Thr Val Thr
    210                 215                 220

Cys Arg Ala Ser Ser Phe Tyr Pro Arg Asn Ile Thr Leu Ser Thr Arg
225                 230                 235                 240
```

```
Gln Asp Gly Val Ser Leu Ser His Asp Thr Gln Gln Trp Gly Asp Val
                245                 250                 255

Leu Pro Asp Gly Asn Gly Thr Tyr Gln Thr Trp Val Ala Thr Arg Ile
            260                 265                 270

Cys Gln Gly Glu Glu Gln Arg Phe Thr Cys Tyr Met Glu His Ser Gly
        275                 280                 285

Asn His Ser Thr His Pro Val Pro Ser Gly Lys Val Leu Val Leu Gln
    290                 295                 300

Ser His Trp Gln Thr Phe His Val Ser Ala Val Ala Ala Ala Ala Ala
305                 310                 315                 320

Ala Ile Phe Val Ile Ile Ile Phe Tyr Val Arg Cys Cys Lys Lys Lys
                325                 330                 335

Thr Ser Ala Ala Glu Gly Pro Glu Leu Val Ser Leu Gln Val Leu Asp
            340                 345                 350

Gln His Pro Val Gly Thr Ser Asp His Arg Asp Ala Thr Gln Leu Gly
        355                 360                 365

Phe Gln Pro Leu Met Ser Ala Leu Gly Ser Thr Gly Ser Thr Glu Gly
    370                 375                 380

Ala
385

<210> SEQ ID NO 112
<211> LENGTH: 331
<212> TYPE: PRT
<213> ORGANISM: artificial sequence
<220> FEATURE:
<223> OTHER INFORMATION: MICA*008

<400> SEQUENCE: 112

Met Gly Leu Gly Pro Val Phe Leu Leu Leu Ala Gly Ile Phe Pro Phe
1               5                   10                  15

Ala Pro Pro Gly Ala Ala Ala Glu Pro His Ser Leu Arg Tyr Asn Leu
            20                  25                  30

Thr Val Leu Ser Trp Asp Gly Ser Val Gln Ser Gly Phe Leu Ala Glu
        35                  40                  45

Val His Leu Asp Gly Gln Pro Phe Leu Arg Tyr Asp Arg Gln Lys Cys
    50                  55                  60

Arg Ala Lys Pro Gln Gly Gln Trp Ala Glu Asp Val Leu Gly Asn Lys
65                  70                  75                  80

Thr Trp Asp Arg Glu Thr Arg Asp Leu Thr Gly Asn Gly Lys Asp Leu
                85                  90                  95

Arg Met Thr Leu Ala His Ile Lys Asp Gln Lys Glu Gly Leu His Ser
            100                 105                 110

Leu Gln Glu Ile Arg Val Cys Glu Ile His Glu Asp Asn Ser Thr Arg
        115                 120                 125

Ser Ser Gln His Phe Tyr Tyr Asp Gly Glu Leu Phe Leu Ser Gln Asn
    130                 135                 140

Leu Glu Thr Glu Glu Trp Thr Val Pro Gln Ser Ser Arg Ala Gln Thr
145                 150                 155                 160

Leu Ala Met Asn Val Arg Asn Phe Leu Lys Glu Asp Ala Met Lys Thr
                165                 170                 175

Lys Thr His Tyr His Ala Met His Ala Asp Cys Leu Gln Glu Leu Arg
            180                 185                 190

Arg Tyr Leu Glu Ser Gly Val Val Leu Arg Arg Thr Val Pro Pro Met
        195                 200                 205
```

Val Asn Val Thr Arg Ser Glu Ala Ser Glu Gly Asn Ile Thr Val Thr
210                 215                 220

Cys Arg Ala Ser Ser Phe Tyr Pro Arg Asn Ile Ile Leu Thr Trp Arg
225                 230                 235                 240

Gln Asp Gly Val Ser Leu Ser His Asp Thr Gln Gln Trp Gly Asp Val
            245                 250                 255

Leu Pro Asp Gly Asn Gly Thr Tyr Gln Thr Trp Val Ala Thr Arg Ile
            260                 265                 270

Cys Arg Gly Glu Glu Gln Arg Phe Thr Cys Tyr Met Glu His Ser Gly
            275                 280                 285

Asn His Ser Thr His Pro Val Pro Ser Gly Lys Val Leu Val Leu Gln
290                 295                 300

Ser His Trp Gln Thr Phe His Val Ser Ala Val Ala Ala Ala Ala Ile
305                 310                 315                 320

Phe Val Ile Ile Ile Phe Tyr Val Arg Cys Cys
            325                 330

<210> SEQ ID NO 113
<211> LENGTH: 383
<212> TYPE: PRT
<213> ORGANISM: artificial sequence
<220> FEATURE:
<223> OTHER INFORMATION: MICA*009

<400> SEQUENCE: 113

Met Gly Leu Gly Pro Val Phe Leu Leu Leu Ala Gly Ile Phe Pro Phe
1               5                   10                  15

Ala Pro Pro Gly Ala Ala Ala Glu Pro His Ser Leu Arg Tyr Asn Leu
            20                  25                  30

Thr Val Leu Ser Trp Asp Gly Ser Val Gln Ser Gly Phe Leu Ala Glu
        35                  40                  45

Val His Leu Asp Gly Gln Pro Phe Leu Arg Tyr Asp Arg Gln Lys Cys
    50                  55                  60

Arg Ala Lys Pro Gln Gly Gln Trp Ala Glu Asp Val Leu Gly Asn Lys
65                  70                  75                  80

Thr Trp Asp Arg Glu Thr Arg Asp Leu Thr Gly Asn Gly Lys Asp Leu
                85                  90                  95

Arg Met Thr Leu Ala His Ile Lys Asp Gln Lys Glu Gly Leu His Ser
            100                 105                 110

Leu Gln Glu Ile Arg Val Cys Glu Ile His Glu Asp Asn Ser Thr Arg
        115                 120                 125

Ser Ser Gln His Phe Tyr Tyr Asp Gly Glu Leu Phe Leu Ser Gln Asn
    130                 135                 140

Leu Glu Thr Glu Glu Trp Thr Val Pro Gln Ser Ser Arg Ala Gln Thr
145                 150                 155                 160

Leu Ala Met Asn Val Arg Asn Phe Leu Lys Glu Asp Ala Met Lys Thr
                165                 170                 175

Lys Thr His Tyr His Ala Met His Ala Asp Cys Leu Gln Glu Leu Arg
            180                 185                 190

Arg Tyr Leu Glu Ser Ser Val Val Leu Arg Arg Thr Val Pro Pro Met
        195                 200                 205

Val Asn Val Thr Arg Ser Glu Ala Ser Glu Gly Asn Ile Thr Val Thr
    210                 215                 220

Cys Arg Ala Ser Ser Phe Tyr Pro Arg Asn Ile Thr Leu Thr Trp Arg
225                 230                 235                 240

```
Gln Asp Gly Val Ser Leu Ser His Asp Thr Gln Gln Trp Gly Asp Val
                245                 250                 255

Leu Pro Asp Gly Asn Gly Thr Tyr Gln Thr Trp Val Ala Thr Arg Ile
            260                 265                 270

Cys Gln Gly Glu Glu Gln Arg Phe Thr Cys Tyr Met Glu His Ser Gly
        275                 280                 285

Asn His Ser Thr His Pro Val Pro Ser Gly Lys Val Leu Val Leu Gln
    290                 295                 300

Ser His Trp Gln Thr Phe His Val Ser Ala Val Ala Ala Ala Ala Ile
305                 310                 315                 320

Phe Val Ile Ile Ile Phe Tyr Val Arg Cys Cys Lys Lys Lys Thr Ser
                325                 330                 335

Ala Ala Glu Gly Pro Glu Leu Val Ser Leu Gln Val Leu Asp Gln His
            340                 345                 350

Pro Val Gly Thr Ser Asp His Arg Asp Ala Thr Gln Leu Gly Phe Gln
        355                 360                 365

Pro Leu Met Ser Ala Leu Gly Ser Thr Gly Ser Thr Glu Gly Thr
    370                 375                 380
```

<210> SEQ ID NO 114
<211> LENGTH: 384
<212> TYPE: PRT
<213> ORGANISM: artificial sequence
<220> FEATURE:
<223> OTHER INFORMATION: MICA*010

<400> SEQUENCE: 114

```
Met Gly Leu Gly Pro Val Phe Leu Leu Leu Ala Gly Ile Phe Pro Phe
1               5                   10                  15

Ala Pro Pro Gly Ala Ala Ala Glu Pro His Ser Leu Pro Tyr Asn Leu
                20                  25                  30

Thr Val Leu Ser Trp Asp Gly Ser Val Gln Ser Gly Phe Leu Ala Glu
            35                  40                  45

Val His Leu Asp Gly Gln Pro Phe Leu Arg Tyr Asp Arg Gln Lys Cys
        50                  55                  60

Arg Ala Lys Pro Gln Gly Gln Trp Ala Glu Asp Val Leu Gly Asn Lys
65                  70                  75                  80

Thr Trp Asp Arg Glu Thr Arg Asp Leu Thr Gly Asn Gly Lys Asp Leu
                85                  90                  95

Arg Met Thr Leu Ala His Ile Lys Asp Gln Lys Glu Gly Leu His Ser
            100                 105                 110

Leu Gln Glu Ile Arg Val Cys Glu Ile His Glu Asp Asn Ser Thr Arg
        115                 120                 125

Ser Ser Gln His Phe Tyr Tyr Asp Gly Glu Leu Phe Leu Ser Gln Asn
    130                 135                 140

Leu Glu Thr Glu Glu Trp Thr Val Pro Gln Ser Ser Arg Ala Gln Thr
145                 150                 155                 160

Leu Ala Met Asn Val Arg Asn Phe Leu Lys Glu Asp Ala Met Lys Thr
                165                 170                 175

Lys Thr His Tyr His Ala Met His Ala Asp Cys Leu Gln Glu Leu Arg
            180                 185                 190

Arg Tyr Leu Glu Ser Ser Val Val Leu Arg Arg Thr Val Pro Pro Met
        195                 200                 205

Val Asn Val Thr Arg Ser Glu Ala Ser Glu Gly Asn Ile Thr Val Thr
    210                 215                 220
```

```
Cys Arg Ala Ser Ser Phe Tyr Pro Arg Asn Ile Ile Leu Thr Trp Arg
225                 230                 235                 240

Gln Asp Gly Val Ser Leu Ser His Asp Thr Gln Gln Trp Gly Asp Val
            245                 250                 255

Leu Pro Asp Gly Asn Gly Thr Tyr Gln Thr Trp Val Ala Thr Arg Ile
        260                 265                 270

Cys Arg Gly Glu Glu Gln Arg Phe Thr Cys Tyr Met Glu His Ser Gly
    275                 280                 285

Asn His Ser Thr His Pro Val Pro Ser Gly Lys Val Leu Val Leu Gln
290                 295                 300

Ser His Trp Gln Thr Phe His Val Ser Ala Val Ala Ala Ala Ala Ala
305                 310                 315                 320

Ile Phe Val Ile Ile Ile Phe Tyr Val Arg Cys Cys Lys Lys Lys Thr
            325                 330                 335

Ser Ala Ala Glu Gly Pro Glu Leu Val Ser Leu Gln Val Leu Asp Gln
            340                 345                 350

His Pro Val Gly Thr Ser Asp His Arg Asp Ala Thr Gln Leu Gly Phe
        355                 360                 365

Gln Pro Leu Met Ser Ala Leu Gly Ser Thr Gly Ser Thr Glu Gly Ala
        370                 375                 380
```

<210> SEQ ID NO 115
<211> LENGTH: 119
<212> TYPE: PRT
<213> ORGANISM: artificial sequence
<220> FEATURE:
<223> OTHER INFORMATION: MICA.20 VH

<400> SEQUENCE: 115

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Ser Met Asn Trp Val Arg Gln Ala Pro Gly Lys Gly Leu Glu Trp Val
        35                  40                  45

Ser Tyr Ile Ser Tyr Arg Ser Arg Thr Ile Tyr Tyr Ala Asp Ser Val
    50                  55                  60

Lys Gly Arg Phe Thr Ile Ser Arg Asp Asn Ala Arg Asn Ser Leu Tyr
65                  70                  75                  80

Leu Gln Met Asn Ser Leu Arg Asp Glu Asp Thr Ala Val Tyr Tyr Cys
            85                  90                  95

Ala Arg Trp Gly Tyr Gly Ser Gly Gly Phe Asp Tyr Trp Gly Gln Gly
        100                 105                 110

Thr Leu Val Thr Val Ser Ser
        115
```

<210> SEQ ID NO 116
<211> LENGTH: 108
<212> TYPE: PRT
<213> ORGANISM: artificial sequence
<220> FEATURE:
<223> OTHER INFORMATION: MICA.20 VL

<400> SEQUENCE: 116

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30
```

Tyr Leu Ala Trp Tyr Gln Gln Lys Pro Gly Gln Ala Pro Arg Leu Leu
            35                  40                  45

Ile Tyr Gly Ala Ser Ser Arg Ala Thr Gly Ile Pro Asp Arg Phe Ser
 50                  55                  60

Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Gln Tyr Gly Ser Ser Pro
                 85                  90                  95

Trp Thr Phe Gly Gln Gly Thr Lys Val Glu Ile Lys
             100                 105

<210> SEQ ID NO 117
<211> LENGTH: 119
<212> TYPE: PRT
<213> ORGANISM: artificial sequence
<220> FEATURE:
<223> OTHER INFORMATION: MICA.21 VH

<400> SEQUENCE: 117

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ser Thr Tyr
                 20                  25                  30

Ser Met Asn Trp Val Arg Gln Ala Pro Gly Lys Gly Leu Glu Trp Val
             35                  40                  45

Ser Tyr Ile Ser Tyr Arg Ser Arg Thr Ile Tyr Tyr Ala Asp Ser Val
 50                  55                  60

Lys Gly Arg Phe Thr Ile Ser Arg Asp Asn Ala Arg Asn Ser Leu Tyr
 65                  70                  75                  80

Leu Gln Met Asn Ser Leu Arg Asp Glu Asp Thr Ala Val Tyr Tyr Cys
                 85                  90                  95

Ala Arg Trp Gly Tyr Gly Ser Gly Gly Phe Asp Tyr Trp Gly Gln Gly
             100                 105                 110

Thr Leu Val Thr Val Ser Ser
         115

<210> SEQ ID NO 118
<211> LENGTH: 108
<212> TYPE: PRT
<213> ORGANISM: artificial sequence
<220> FEATURE:
<223> OTHER INFORMATION: MICA.21 VL

<400> SEQUENCE: 118

Glu Ile Val Leu Thr Gln Ser Pro Gly Thr Leu Ser Leu Ser Pro Gly
 1               5                  10                  15

Glu Arg Ala Thr Leu Ser Cys Arg Ala Ser Gln Ser Val Ser Ser Ser
                 20                  25                  30

Tyr Leu Ala Trp Tyr Gln Gln Lys Pro Gly Gln Ala Pro Arg Leu Leu
             35                  40                  45

Ile Tyr Gly Ala Ser Ser Arg Ala Thr Gly Ile Pro Asp Arg Phe Ser
 50                  55                  60

Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Gln Tyr Gly Ser Ser Pro
                 85                  90                  95

Tyr Thr Phe Gly Gln Gly Thr Lys Leu Glu Ile Lys

-continued

```
                100                 105

<210> SEQ ID NO 119
<211> LENGTH: 119
<212> TYPE: PRT
<213> ORGANISM: artificial sequence
<220> FEATURE:
<223> OTHER INFORMATION: MICA.22 VH

<400> SEQUENCE: 119

Glu Val Gln Leu Val Glu Ser Gly Gly Gly Leu Val Gln Pro Gly Gly
1               5                  10                  15

Ser Leu Arg Leu Ser Cys Ala Ala Ser Gly Phe Thr Phe Ser Thr Tyr
            20                  25                  30

Ser Met Asn Trp Val Arg Gln Ala Pro Gly Lys Gly Leu Glu Trp Val
        35                  40                  45

Ser Tyr Ile Ser Tyr Arg Ser Arg Thr Ile Tyr Tyr Ala Asp Ser Val
    50                  55                  60

Lys Gly Arg Phe Thr Ile Ser Arg Asp Asn Ala Arg Asn Ser Leu Tyr
65                  70                  75                  80

Leu Gln Met Asn Ser Leu Arg Asp Glu Asp Thr Ala Val Tyr Tyr Cys
                85                  90                  95

Ala Arg Trp Gly Tyr Gly Ser Gly Gly Phe Asp Tyr Trp Gly Gln Gly
            100                 105                 110

Thr Leu Val Thr Val Ser Ser
        115

<210> SEQ ID NO 120
<211> LENGTH: 108
<212> TYPE: PRT
<213> ORGANISM: artificial sequence
<220> FEATURE:
<223> OTHER INFORMATION: MICA.22 VL

<400> SEQUENCE: 120

Glu Ile Val Leu Thr Gln Ser Pro Gly Thr Leu Ser Leu Ser Pro Gly
1               5                  10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Phe Thr Phe Gly Pro Gly Thr Lys Val Asp Ile Lys
            100                 105

<210> SEQ ID NO 121
<211> LENGTH: 119
<212> TYPE: PRT
<213> ORGANISM: artificial sequence
<220> FEATURE:
<223> OTHER INFORMATION: MICA.38 VH

<400> SEQUENCE: 121

Glu Val Gln Leu Val Glu Ser Gly Gly Gly Leu Val Gln Pro Gly Gly
1               5                  10                  15
```

Ser Leu Arg Leu Ser Cys Ala Ala Ser Gly Phe Thr Phe Ser Thr Tyr
            20                  25                  30

Ser Met Asn Trp Val Arg Gln Ala Pro Gly Lys Gly Leu Glu Trp Val
        35                  40                  45

Ser Tyr Ile Ser Tyr Arg Ser Arg Thr Ile Tyr Tyr Ala Asp Ser Val
50                  55                  60

Lys Gly Arg Phe Thr Ile Ser Arg Asp Asn Ala Arg Asn Ser Leu Tyr
65                  70                  75                  80

Leu Gln Met Asn Ser Leu Arg Asp Glu Asp Thr Ala Val Tyr Tyr Cys
                85                  90                  95

Ala Arg Trp Gly Tyr Gly Ser Gly Phe Asp Tyr Trp Gly Gln Gly
            100                 105                 110

Thr Leu Val Thr Val Ser Ser
            115

<210> SEQ ID NO 122
<211> LENGTH: 108
<212> TYPE: PRT
<213> ORGANISM: artificial sequence
<220> FEATURE:
<223> OTHER INFORMATION: MICA.38 VL

<400> SEQUENCE: 122

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Ser
                85                  90                  95

Phe Thr Phe Gly Pro Gly Thr Lys Val Asp Ile Lys
            100                 105

<210> SEQ ID NO 123

<400> SEQUENCE: 123

000

<210> SEQ ID NO 124

<400> SEQUENCE: 124

000

<210> SEQ ID NO 125

<400> SEQUENCE: 125

000

<210> SEQ ID NO 126

<400> SEQUENCE: 126

-continued

```
000
```

<210> SEQ ID NO 127
<211> LENGTH: 387
<212> TYPE: PRT
<213> ORGANISM: artificial sequence
<220> FEATURE:
<223> OTHER INFORMATION: 16A5-MICA.52 VK2

<400> SEQUENCE: 127

```
Ala Thr Gly Gly Ala Cys Ala Thr Gly Ala Gly Gly Thr Cys Cys
1               5                   10                  15

Cys Cys Gly Cys Thr Cys Ala Gly Cys Thr Cys Thr Gly Gly Gly
                20                  25                  30

Gly Cys Thr Thr Cys Thr Gly Cys Thr Gly Cys Thr Cys Thr Gly Gly
            35                  40                  45

Cys Thr Cys Cys Cys Ala Gly Gly Thr Gly Cys Cys Ala Gly Ala Thr
        50                  55                  60

Gly Thr Gly Cys Cys Ala Thr Cys Cys Ala Gly Thr Thr Gly Ala Cys
65                  70                  75                  80

Cys Cys Ala Gly Thr Cys Thr Cys Cys Ala Thr Cys Cys Thr Cys Cys
                85                  90                  95

Cys Thr Gly Thr Cys Thr Gly Cys Ala Thr Cys Thr Gly Thr Ala Gly
                100                 105                 110

Gly Ala Gly Ala Cys Ala Gly Ala Gly Thr Cys Ala Cys Cys Ala Thr
            115                 120                 125

Cys Ala Cys Thr Thr Gly Cys Cys Gly Gly Gly Cys Ala Ala Gly Thr
        130                 135                 140

Cys Ala Gly Gly Gly Cys Ala Thr Thr Ala Gly Cys Ala Gly Thr Gly
145                 150                 155                 160

Cys Thr Thr Thr Ala Gly Cys Cys Thr Gly Gly Thr Ala Thr Cys Ala
                165                 170                 175

Gly Cys Ala Gly Ala Ala Ala Cys Cys Ala Gly Gly Gly Ala Ala Ala
            180                 185                 190

Gly Cys Thr Cys Cys Thr Ala Ala Gly Cys Thr Cys Cys Thr Gly Ala
        195                 200                 205

Thr Cys Thr Ala Thr Gly Ala Thr Gly Cys Cys Thr Cys Cys Ala Gly
        210                 215                 220

Thr Thr Thr Gly Gly Ala Ala Ala Gly Thr Gly Gly Gly Gly Thr Cys
225                 230                 235                 240

Cys Cys Ala Thr Cys Ala Ala Gly Gly Thr Thr Cys Ala Gly Cys Gly
                245                 250                 255

Gly Cys Ala Gly Thr Gly Gly Ala Thr Cys Thr Gly Gly Gly Ala Cys
            260                 265                 270

Ala Gly Ala Thr Thr Thr Cys Ala Cys Thr Cys Thr Cys Ala Cys Cys
        275                 280                 285

Ala Thr Cys Ala Gly Cys Ala Gly Cys Cys Thr Gly Cys Ala Gly Cys
        290                 295                 300

Cys Thr Gly Ala Ala Gly Ala Thr Thr Thr Gly Cys Ala Ala Cys
305                 310                 315                 320

Thr Thr Ala Thr Thr Ala Cys Thr Gly Thr Cys Ala Ala Cys Ala Gly
                325                 330                 335

Thr Thr Thr Ala Ala Thr Ala Gly Thr Thr Ala Cys Cys Cys Ala Thr
            340                 345                 350

Thr Cys Ala Cys Thr Thr Thr Cys Gly Gly Cys Cys Cys Thr Gly Gly
```

<210> SEQ ID NO 128
<211> LENGTH: 129
<212> TYPE: PRT
<213> ORGANISM: artificial sequence
<220> FEATURE:
<223> OTHER INFORMATION: 16A5-MICA.52 VK2

<400> SEQUENCE: 128

```
Met Asp Met Arg Val Pro Ala Gln Leu Leu Gly Leu Leu Leu Leu Trp
1               5                   10                  15

Leu Pro Gly Ala Arg Cys Ala Ile Gln Leu Thr Gln Ser Pro Ser Ser
            20                  25                  30

Leu Ser Ala Ser Val Gly Asp Arg Val Thr Ile Thr Cys Arg Ala Ser
        35                  40                  45

Gln Gly Ile Ser Ser Ala Leu Ala Trp Tyr Gln Gln Lys Pro Gly Lys
    50                  55                  60

Ala Pro Lys Leu Leu Ile Tyr Asp Ala Ser Ser Leu Glu Ser Gly Val
65                  70                  75                  80

Pro Ser Arg Phe Ser Gly Ser Gly Ser Gly Thr Asp Phe Thr Leu Thr
                85                  90                  95

Ile Ser Ser Leu Gln Pro Glu Asp Phe Ala Thr Tyr Tyr Cys Gln Gln
            100                 105                 110

Phe Asn Ser Tyr Pro Phe Thr Phe Gly Pro Gly Thr Lys Val Asp Ile
        115                 120                 125

Lys
```

<210> SEQ ID NO 129

<400> SEQUENCE: 129

000

<210> SEQ ID NO 130
<211> LENGTH: 444
<212> TYPE: PRT
<213> ORGANISM: Artificial Sequence
<220> FEATURE:
<223> OTHER INFORMATION: 19G6-MICA.36 Heavy Chain AA (236G)

<400> SEQUENCE: 130

```
Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Asn Tyr
            20                  25                  30

Ala Met His Trp Val Arg Gln Ala Pro Gly Glu Gly Leu Glu Trp Val
        35                  40                  45

Ala Leu Ile Trp Tyr Asp Gly Ser Asn Lys Tyr Tyr Gly Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Ser Ala Glu Asp Thr Ala Val Tyr Tyr Cys
                85                  90                  95
```

Ala Arg Glu Gly Ser Gly His Tyr Trp Gly Gln Gly Thr Leu Val Thr
            100                 105                 110

Val Ser Ser Ala Ser Thr Lys Gly Pro Ser Val Phe Pro Leu Ala Pro
            115                 120                 125

Ser Ser Lys Ser Thr Ser Gly Gly Thr Ala Ala Leu Gly Cys Leu Val
            130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
            195                 200                 205

Val Asp Lys Arg Val Glu Pro Lys Ser Cys Asp Lys Thr His Thr Cys
210                 215                 220

Pro Pro Cys Pro Ala Pro Glu Leu Leu Gly Gly Pro Ser Val Phe Leu
225                 230                 235                 240

Phe Pro Pro Lys Pro Lys Asp Thr Leu Met Ile Ser Arg Thr Pro Glu
            245                 250                 255

Val Thr Cys Val Val Val Asp Val Ser His Glu Asp Pro Glu Val Lys
            260                 265                 270

Phe Asn Trp Tyr Val Asp Gly Val Glu Val His Asn Ala Lys Thr Lys
            275                 280                 285

Pro Arg Glu Glu Gln Tyr Asn Ser Thr Tyr Arg Val Val Ser Val Leu
290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
            325                 330                 335

Ala Lys Gly Gln Pro Arg Glu Pro Gln Val Tyr Thr Leu Pro Pro Ser
            340                 345                 350

Arg Glu Glu Met Thr Lys Asn Gln Val Ser Leu Thr Cys Leu Val Lys
            355                 360                 365

Gly Phe Tyr Pro Ser Asp Ile Ala Val Glu Trp Glu Ser Asn Gly Gln
370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
            405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly
            435                 440

<210> SEQ ID NO 131
<211> LENGTH: 1332
<212> TYPE: DNA
<213> ORGANISM: Artificial Sequence
<220> FEATURE:
<223> OTHER INFORMATION: 19G6-MICA.36 Heavy Chain NT (236G)

<400> SEQUENCE: 131
caggtgcaac tggtggagtc tgggggaggc gtggtccagc ctggggaggtc cctgagactc    60 tcctgtgcag cgtctggatt caccttcagt aactatgcca tgcactgggt ccgccaggct   120

```
ccaggcgagg ggctggaatg ggtggcactt atatggtatg atggaagtaa taaattctat      180
ggagactccg tgaagggccg cttcaccatc tccagagaca attccaagaa cacgctgtat      240
ctgcaaatga acagcctgag cgccgaggac acggctgtgt attactgtgc gagagaggga      300
agtgggcact actggggcca gggaaccctg gtcaccgtct cctcagctag caccaagggc      360
ccatcggtct tccccctggc accctcctcc aagagcacct ctgggggcac agcggccctg      420
ggctgcctgg tcaaggacta cttccccgaa ccggtgacgg tgtcgtggaa ctcaggcgcc      480
ctgaccagcg gcgtgcacac cttccggct gtcctacagt cctcaggact ctactccctc      540
agcagcgtgg tgaccgtgcc ctccagcagc ttgggcaccc agacctacat ctgcaacgtg      600
aatcacaagc ccagcaacac caaggtggac aagagagttg agcccaaatc ttgtgacaaa      660
actcacacat gcccaccgtg cccagcacct gaactcctgg ggggaccgtc agtcttcctc      720
ttccccccaa aacccaagga caccctcatg atctcccgga cccctgaggt cacatgcgtg      780
gtggtggacg tgagccacga agaccctgag gtcaagttca actggtacgt ggacggcgtg      840
gaggtgcata atgccaagac aaagccgcgg gaggagcagt acaacagcac gtaccgtgtg      900
gtcagcgtcc tcaccgtcct gcaccaggac tggctgaatg gcaaggagta caagtgcaag      960
gtctccaaca aagccctccc agcccccatc gagaaaacca tctccaaagc caaagggcag     1020
ccccgagaac cacaggtgta caccctgccc ccatcccggg aggagatgac caagaaccag     1080
gtcagcctga cctgcctggt caaaggcttc tatcccagcg acatcgccgt ggagtgggag     1140
agcaatgggc agccggagaa caactacaag accacgcctc ccgtgctgga ctccgacggc     1200
tccttcttcc tctatagcaa gctcaccgtg gacaagagca ggtggcagca ggggaacgtc     1260
ttctcatgct ccgtgatgca tgaggctctg cacaaccact acacgcagaa gagcctctcc     1320
ctgtccccgg gt                                                         1332
```

<210> SEQ ID NO 132
<211> LENGTH: 383
<212> TYPE: PRT
<213> ORGANISM: Homo sapiens

<400> SEQUENCE: 132

```
Met Gly Leu Gly Arg Val Leu Phe Leu Ala Val Ala Phe Pro Phe
1               5                   10                  15

Ala Pro Pro Ala Ala Ala Glu Pro His Ser Leu Arg Tyr Asn Leu
                20                  25                  30

Met Val Leu Ser Gln Asp Glu Ser Val Gln Ser Gly Phe Leu Ala Glu
            35                  40                  45

Gly His Leu Asp Gly Gln Pro Phe Leu Arg Tyr Asp Arg Gln Lys Arg
        50                  55                  60

Arg Ala Lys Pro Gln Gly Gln Trp Ala Glu Asp Val Leu Gly Ala Lys
65                  70                  75                  80

Thr Trp Asp Thr Glu Thr Glu Asp Leu Thr Glu Asn Gly Gln Asp Leu
                85                  90                  95

Arg Arg Thr Leu Thr His Ile Lys Asp Gln Lys Gly Gly Leu His Ser
            100                 105                 110

Leu Gln Glu Ile Arg Val Cys Glu Ile His Glu Asp Ser Ser Thr Arg
        115                 120                 125

Gly Ser Arg His Phe Tyr Tyr Asp Gly Glu Leu Phe Leu Ser Gln Asn
    130                 135                 140

Leu Glu Thr Gln Glu Ser Thr Val Pro Gln Ser Ser Arg Ala Gln Thr
```

```
                145                 150                 155                 160
Leu Ala Met Asn Val Thr Asn Phe Trp Lys Glu Asp Ala Met Lys Thr
                165                 170                 175

Lys Thr His Tyr Arg Ala Met Gln Ala Asp Cys Leu Gln Lys Leu Gln
                180                 185                 190

Arg Tyr Leu Lys Ser Gly Val Ala Ile Arg Arg Thr Val Pro Pro Met
                195                 200                 205

Val Asn Val Thr Cys Ser Glu Val Ser Glu Gly Asn Ile Thr Val Thr
                210                 215                 220

Cys Arg Ala Ser Ser Phe Tyr Pro Arg Asn Ile Thr Leu Thr Trp Arg
225                 230                 235                 240

Gln Asp Gly Val Ser Leu Ser His Asn Thr Gln Gln Trp Gly Asp Val
                245                 250                 255

Leu Pro Asp Gly Asn Gly Thr Tyr Gln Thr Trp Val Ala Thr Arg Ile
                260                 265                 270

Arg Gln Gly Glu Glu Gln Arg Phe Thr Cys Tyr Met Glu His Ser Gly
                275                 280                 285

Asn His Gly Thr His Pro Val Pro Ser Gly Lys Val Leu Val Leu Gln
                290                 295                 300

Ser Gln Arg Thr Asp Phe Pro Tyr Val Ser Ala Ala Met Pro Cys Phe
305                 310                 315                 320

Val Ile Ile Ile Ile Leu Cys Val Pro Cys Cys Lys Lys Lys Thr Ser
                325                 330                 335

Ala Ala Glu Gly Pro Glu Leu Val Ser Leu Gln Val Leu Asp Gln His
                340                 345                 350

Pro Val Gly Thr Gly Asp His Arg Asp Ala Ala Gln Leu Gly Phe Gln
                355                 360                 365

Pro Leu Met Ser Ala Thr Gly Ser Thr Gly Ser Thr Glu Gly Ala
                370                 375                 380

<210> SEQ ID NO 133
<211> LENGTH: 340
<212> TYPE: PRT
<213> ORGANISM: Homo sapiens

<400> SEQUENCE: 133

Met Gly Leu Gly Arg Val Leu Leu Phe Leu Ala Val Ala Phe Pro Phe
1               5                   10                  15

Ala Pro Pro Ala Ala Ala Glu Pro His Ser Leu Arg Tyr Asn Leu
                20                  25                  30

Met Val Leu Ser Gln Asp Glu Ser Val Gln Ser Gly Phe Leu Ala Glu
                35                  40                  45

Gly His Leu Asp Gly Gln Pro Phe Leu Arg Tyr Asp Arg Gln Lys Arg
            50                  55                  60

Arg Ala Lys Pro Gln Gly Gln Trp Ala Glu Asp Val Leu Gly Ala Lys
65                  70                  75                  80

Thr Trp Asp Thr Glu Thr Glu Asp Leu Thr Glu Asn Gly Gln Asp Leu
                85                  90                  95

Arg Arg Thr Leu Thr His Ile Lys Asp Gln Lys Gly Val Pro Gln Ser
                100                 105                 110

Ser Arg Ala Gln Thr Leu Ala Met Asn Val Thr Asn Phe Trp Lys Glu
                115                 120                 125

Asp Ala Met Lys Thr Lys Thr His Tyr Arg Ala Met Gln Ala Asp Cys
                130                 135                 140
```

-continued

```
Leu Gln Lys Leu Gln Arg Tyr Leu Lys Ser Gly Val Ala Ile Arg Arg
145                 150                 155                 160

Thr Val Pro Pro Met Val Asn Val Thr Cys Ser Glu Val Ser Glu Gly
                165                 170                 175

Asn Ile Thr Val Thr Cys Arg Ala Ser Ser Phe Tyr Pro Arg Asn Ile
            180                 185                 190

Thr Leu Thr Trp Arg Gln Asp Gly Val Ser Leu Ser His Asn Thr Gln
        195                 200                 205

Gln Trp Gly Asp Val Leu Pro Asp Gly Asn Gly Thr Tyr Gln Thr Trp
    210                 215                 220

Val Ala Thr Arg Ile Arg Gln Gly Glu Glu Gln Arg Phe Thr Cys Tyr
225                 230                 235                 240

Met Glu His Ser Gly Asn His Gly Thr His Pro Val Pro Ser Gly Lys
                245                 250                 255

Val Leu Val Leu Gln Ser Gln Arg Thr Asp Phe Pro Tyr Val Ser Ala
            260                 265                 270

Ala Met Pro Cys Phe Val Ile Ile Ile Ile Leu Cys Val Pro Cys Cys
        275                 280                 285

Lys Lys Lys Thr Ser Ala Ala Glu Gly Pro Glu Leu Val Ser Leu Gln
    290                 295                 300

Val Leu Asp Gln His Pro Val Gly Thr Gly Asp His Arg Asp Ala Ala
305                 310                 315                 320

Gln Leu Gly Phe Gln Pro Leu Met Ser Ala Thr Gly Ser Thr Gly Ser
                325                 330                 335

Thr Glu Gly Ala
            340
```